(12) United States Patent
Tonks et al.

(10) Patent No.: US 9,074,002 B2
(45) Date of Patent: Jul. 7, 2015

(54) PTP1B INHIBITORS

(75) Inventors: Nicholas Tonks, Huntington, NY (US); Aftabul Haque, Stony Brook, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 323 days.

(21) Appl. No.: 13/266,430

(22) PCT Filed: Apr. 27, 2010

(86) PCT No.: PCT/US2010/001251
§ 371 (c)(1),
(2), (4) Date: Mar. 9, 2012

(87) PCT Pub. No.: WO2010/126590
PCT Pub. Date: Nov. 4, 2010

(65) Prior Publication Data
US 2012/0164673 A1 Jun. 28, 2012
US 2013/0029366 A9 Jan. 31, 2013

Related U.S. Application Data

(60) Provisional application No. 61/173,178, filed on Apr. 27, 2009.

(51) Int. Cl.
G01N 33/53 (2006.01)
G01N 33/573 (2006.01)
C07K 16/00 (2006.01)
C07K 16/40 (2006.01)
A61K 39/00 (2006.01)

(52) U.S. Cl.
CPC ........... *C07K 16/40* (2013.01); *A61K 2039/505* (2013.01); *C07K 2317/622* (2013.01); *C07K 2317/80* (2013.01); *G01N 33/573* (2013.01); *G01N 2333/9121* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,225,539 A | 7/1993 | Winter | |
| 5,585,089 A | 12/1996 | Queen et al. | |
| 5,693,762 A | 12/1997 | Queen et al. | |
| 5,859,205 A | 1/1999 | Adair et al. | |
| 7,973,142 B2 * | 7/2011 | Rotello et al. | 530/388.26 |
| 2003/0215899 A1 * | 11/2003 | Meng et al. | 435/21 |

FOREIGN PATENT DOCUMENTS

| | | |
|---|---|---|
| WO | WO 99/46268 A1 | 9/1999 |
| WO | WO 2004/087905 A2 | 10/2004 |
| WO | WO 2005/019446 A2 | 3/2005 |

OTHER PUBLICATIONS

Paul, Fundamental Immunology, 3rd Edition, 1993, pp. 292-295, under the heading "Fv Structure and Diversity in Three Dimensions".*
Rudikoff et al Proc. Natl. Acad. Sci.USA, 79(6):1979-1983, Mar. 1982.*
Colman P. M. Research in Immunology, 145:33-36, 1994.*
Barrios et al J Molecular Recognition 17: 332-338, 2004.*
MacCallum et al Mol. Biol 262: 732-745, 1996.*
Andersen et al., A genomic perspective on protein tyrosine phosphatases: gene structure, pseudogenes, and genetic disease linkage. FASEB J. Jan. 2004;18(1):8-30.
Andersen et al., Structural and evolutionary relationships among protein tyrosine phosphatase domains. Mol Cell Biol. Nov. 2001;21(21):7117-36.
Biocca et al., Intracellular immunization: antibody targeting to subcellular compartments. Trends Cell Biol. Jun. 1995;5(6):248-52.
Brautigan et al., Serine phosphorylation of protein tyrosine phosphatase (PTP1B) in HeLa cells in response to analogues of cAMP or diacylglycerol plus okadaic acid. Mol Cell Biochem. Nov. 1993;127-128:121-9.
Cheng et al., Structure-based maximal affinity model predicts small-molecule druggability. Nat Biotechnol. Jan. 2007;25(1):71-5.
Dadke et al., Phosphorylation and activation of protein tyrosine phosphatase (PTP) 1B by insulin receptor. Mol Cell Biochem. May 2001;221(1-2):147-54.
Elchebly et al., Increased insulin sensitivity and obesity resistance in mice lacking the protein tyrosine phosphatase-1B gene. Science. Mar. 5, 1999;283(5407):1544-8.
Flint et al., Multi-site phosphorylation of the protein tyrosine phosphatase, PTP1B: identification of cell cycle regulated and phorbol ester stimulated sites of phosphorylation. EMBO J. May 1993;12(5):1937-46.
Klaman et al., Increased energy expenditure, decreased adiposity, and tissue-specific insulin sensitivity in protein-tyrosine phosphatase 1B-deficient mice. Mol Cell Biol. Aug. 2000;20(15):5479-89.
Lamontagne et al., Protein tyrosine phosphatase 1B antagonizes signalling by oncoprotein tyrosine kinase p210 bcr-abl in vivo. Mol Cell Biol, May 1998;18(5):2965-75.
Lamontagne et al., Protein tyrosine phosphatase PTP1B suppresses p210 bcr-abl-induced transformation of rat-1 fibroblasts and promotes differentiation of K562 cells. Proc Natl Acad Sci U S A. Nov. 24, 1998;95(24):14094-9.
McGuire et al., Abnormal regulation of protein tyrosine phosphatase activities in skeletal muscle of insulin-resistant humans. Diabetes. Jul. 1991;40(7):939-42.

(Continued)

*Primary Examiner* — Shulamith H Shafer
(74) *Attorney, Agent, or Firm* — Wolf, Greenfield & Sacks, P.C.

(57) ABSTRACT

Described herein are agents, including antibodies, antibody fragments, polypeptides and organic small molecules, that bind reversibly inactive PTP1B (designated herein in the alternative as PTP1B-SN or PTP1B-OX) and stabilize it (stabilize PTP1B-OX) in such a manner that they inhibit reactivation of reversibly oxidized, inactive PTP1B by reduction (by reducing agent) and have no substantial direct inhibitory effect on phosphatase activity/PTP1B activity (for example, as detectable in assays in vitro).

8 Claims, 25 Drawing Sheets

(56) References Cited

OTHER PUBLICATIONS

Myerovitch et al., Hepatic Phosphotyrosine Phosphatase Activity and Its Alterations in Diabetic Rats. J Clin Invest. 1989;84:976-83.
Myers et al., TYK2 and JAK2 are substrates of protein-tyrosine phosphatase 1B. J Biol Chem. Dec. 21, 2001;276(51):47771-4. Epub Nov. 1, 2001.
Salmeen et al., Redox regulation of protein tyrosine phosphatase 1B involves a sulphenyl-amide intermediate. Nature. Jun. 12, 2003;423(6941):769-73.
Sredy et al., Insulin resistance is associated with abnormal dephosphorylation of a synthetic phosphopeptide corresponding to the major autophosphorylation sites of the insulin receptor. Metabolism. Aug. 1995;44(8):1074-81.
Tonks et al., A brake becomes an accelerator: PTP1B—a new therapeutic target for breast cancer. Cancer Cell. Mar. 2007;11(3):214-6.
Tonks et al., Combinatorial control of the specificity of protein tyrosine phosphatases. Curr Opin Cell Biol, Apr. 2001;13(2):182-95.
Tonks, PTP1B: from the sidelines to the front lines! FEBS Lett. Jul. 3, 2003;546(1):140-8.

\* cited by examiner

FIGURE 6 - PANEL 1

```
              1         10        20                  30        40        50
:Fv1       MKKTAIAIAVALAGFATVAQAALTQ........PSSV...SANPGETVKITCSGGVGQ......WYGWYQ
:Fv16      MKKTAIAIAVALAGFATVAQAALTQ........PSSV...SANLGETVKITCSGGGSYAG.SYYYGWYQ
:Fv26      MKKTAIAIAVALAGFATVAQAALTQ........PSSV...SANPGETVGITCSGGGSY......YGWYQ
:Fv2       MKKTAIAIAVALAGFATVAQAALTQ........PSSV...SANPGGTVKITCSGGGS......YYGWYQ
:Fv8       MKKTAIAIAVALAGFATVAQAALTQ........PSSV...SANPGETVKITCSGGGS....SSYYGWYQ
:Fv17      MKKTAIAIAVALAGFATVAQAALTQ........PSSV...SANPGETVKITCSGGYS......YYGWYQ
:Fv39      MKKTAIAIAVALAGFATVAQAALTQ........PSSV...SANPGETVKITCSGGGS....D.YYGWYQ
:Fv14      MKKTAIAIAVALAGFATVAQAALTQ........PSSV...SANPGETVKITCSGGYS......GYGWFR
:Fv49      MKKTAIAIAVALAGFATVAQAALTQ........PSSV...SANPGETVEITCSGGGG......SYGWFQ
:Fv6       MKKTAIAIAVALAGFATVAQAALTQ........PSSV...SANPGDTVKITCSG...S....IRYYGWYQ
:Fv12      MKKTAIAIAVALAGFATVAQAALTQ........PSSV...SANPGEAVKITCSGGGS....SSYYGWYQ
:Fv21      MKKTAIAIAVALAGFATVAQAALTQ........PSSV...SANPGGTVKITCSGSSG.....SYYGWYQ
cFv34      MKKTAIAIAVALAGFATVAQAALTQ........PSSV...SANPGGTVEITCSGSSG.....SH.GWYQ
cFv13      MKKTAIAIAVALAGFATVAQAALSR........PR.C...QQTWGGTVKITCSGGDS....SYG..WYQ
cFv47      MKKTAIAIAVALAGFATVAQAALSR........PR.C...QQTWGGTVKITCSGGDG....SYG..WYQ
cFv19      MKKTAIAIAVALAGFATVAQAALSR........PR.C...QQTWGGTVEITCSGGSN....NYGYGWYQ
cFv22      MKKTAIAIAVALAGFATVAQAA...........V......SANPGDTVKITCSGD.....SNNYGWYQ
cFv53      MKKTAIAIAVALAGFATVAQAAL..........V......SANPGEIVKITCSGN......SSYYGWYQ
cFv27      MKKTAIAIAVALAGFATVAQAALSR........PR.C...QQTWGGTVKITCSGS......NSYYGWYQ
cFv40      MKKTAIAIAVALAGFATVAQAALSR........PR.C...QQTWGGIVKLTCSGG......SGSCGWYQ
cFv41      MKKTAIAIAVALAGFATVAQAALSR........PR.C...QQTWGGTVKITCSGG......SSYYGWYQ
cFv42      MKKTAIAIAVALAGFATVAQAALTQ........PSSV...SANPGETVEITCSGGGS....SSNYGWHQ
cFv48      MKKTAIAIAVALAGFATVAQAALTQ........PSSV...SANPGETVKITCSEGGR....SSYYGWYQ
cFv60      MKKTAIAIAVALAGFATVAQAALTQ........PSSV...SANPGAIVKITCSEGGR....SSYYGWYQ
cFv43      MKKTAIAIAVALAGFATVAQAALTQ........PSSV...SANPGETVKITCSGGGS....SSYYGWYQ
cFv58      MKKTAIAIAVALAGFATVAQAALTQ........PSSV...SANPGDTVKITCSGGGS....SSYYGWYQ
cFv56      MKKTAIAIAVALAGFATVAQAALTQ........PSSV...SANPGETVKITCSGGGS....SSYYGWYQ
cFv59      MKKTAIAIAVALAGFATVAQAALTQ........PSSV...SANPGEIFKITCSGGGSY.AGSYYYGWYQ
cFv50      MKKTAIAIAVALAGFATVAQAALTQ........PSSV...SANPGDTVEITCSGG......YSNYGWYQ
cFv52      MKKTAIAIAVALAGFATVAQAALTQ........PSSV...SANPGDPVEITCSGS......SGSYGWYQ
cFv121     MKKTAIAIAVALAGFATVAQAALTQ........PSSV...SANLGGTVKITCSGG......SSYYGWYQ
cFv123     MKKTAIAIAVALAGFATVAQAALTQ........PSSV...SANLGGTVKITCSGG......SSYYGWYQ
cFv51      MKKTAIAIAVALAGFATVAQAAL..........V......SANPGGTVKITCSGGSNSAGSYYYGWYQ
cFv104     MKKTAIAIAVALAGFATVAQAALTQ........PSSV...SANLGGTVEITCSGSGG....SYGYYGWYQ
cFv20      MKKTAIAIAVALAGFATVAQAALTQ........PSSV...SANLGGIVEITCSGSSG.....SYGWYQ
cFv25      MKKTAIAIAVALAGFATVAQAALTP........PSSV...SANLGAPVEITCSGSSG.....NYGWFQ
cFv55      MKKTAIAIAVALAGFATVAQAAL..........V......SANLGGTVEITCSGSSG.....NYGWFQ
cFv32      MKKTAIAIAVALAGFATVAQAALTQ........PSSV...SANLGGTFKITCSGSSG.....SYAWYQ
cFv134     MKKTAIAIAVALAGFATVAQAALTQ........PSSV...SANLGGTVKITCSGSSG.....SYGWYQ
cFv119     MKKTAIAIAVALAGFATVAQAALTQ........PSSV...SANLGGTVKITCSGSSG.....SYGWYQ
cFv46      MKKTAIAIAVALAGFATVAQAALTQ........PSSV...SANLGGTVKITCSGSSG.....SYGWYQ
cFv65      MKKTAIAIAVALAGFATVAQAALSR........PRC....QQTWGGTVKITCSGSSG.....SYGWYQ
cFv73      MKKTAIAIAVALAGFATVAQAALSR........PRC....QQTWGGTVKITCSGSSG.....SYGWYQ
cFv90      MKKTAIAIAVALAGFATVAQAALSR........PRC....QQTWGGTVKITCSGSSG.....SYGWYQ
cFv68      MKKTAIAIAVALAGFATVAQAALTQ........PSSV...SASPGETVKITCSGGSG.....SYGWYR
scFv74     MKKTAIAIAVALAGFATVAQAALTQ........PSSV...SASPGETVKITCSGSSG.....SYGWYQ
scFv70     MKKTAIAIAVALAGFATVAQAALTQ........PSSV...SASLGGIVEITCSGSSG.....TYGWYQ
scFv92     MKKTAIAIAVALAGFATVAQAALTQ........PSSV...SASLGTFLEITCSGSSG.....TYGWYQ
scFv83     MKKTAIAIAVALAGFATVAQAALTQ........PSSV...SANLGGPFEITCSGSSG.....SYGWYQ
scFv72     MKKTAIAIAVALAGFATVAQAALTQ........PSSV...SANPGETVKITCSGSSG.....SYGWYQ
scFv102    MKKTAIAIAVALAGFATVAQAALTQ........PSSV...SANPGETVKITCSGSSG.....SYGWYQ
scFv86     MKKTAIAIAVALAGFATVAQAALGP........DSAVLGVSKPGEALVKTTCSGGGG.....SYGWYQ
scFv84     MKKTAIAIAVALAGFATVAQAAL.............. ....KITCSGSSG.....SYAWYQ
scFv80     MKKTAIAIAVALAGFATVAQAALSR........PRC....QQTWGGPVKITCSGSSG.....SYGWYQ
scFv105    MKKTAIAIAVALAGFATVAQAALTQ........PSSV...SANPGEAVKITCSGSSG.....SYGWYQ
scFv112    MKKTAIAIAVALAGFATVAQAALTQ........PSSV...SANLGGTVKITCSGSSG.....SYGWYQ
scFv118    MKKTAIAIAVALAGFATVAQAALTQ........PSSV...SANLGGTVEITCSGSSG.....SYGWYQ
scFv124    MKKTAIAIAVALAGFATVAQAALTQ........PSSV...SANLGGTVKITCSGSSG.....SYGWYQ
scFv115    MKKTAIAIAVALAGFATVAQAALTQ........PSSV...SANPGETVEITCSGSSG.....SYGWYQ
scFv82     MKKTAIAIAVALAGFATVAQAALTQ........PSSV...SANLG.APKITCSGGGG.....SYGWYQ
scFv3      MKKTAIAIAVALAGFATVAQAAV................STNPGDTVKITCSG..G...NSWYGWFQ
scFv30     MKKTAIAIAVALAGFATVAQAAV................SANPGETVKITCSG...G...GGSYGWYQ
scFv23     MKKTAIAIAVALAGFATVAQAAV................SANLGGTVEITCSG...G...GSYYGWYQ
scFv7      MKKTAIAIAVALAGFATVAQAAV................SASLEGTVEITCSG...G...SGSYGWFQ
scFv35     MKKTAIAIAVALAGFATVAQAAV................SANPGDTVEITCSG..S....SGSYGWYQ
scFv5      MKKTAIAIAVALAGFATVAQAAV................SANPGGTVKITCSG..S....SGRYGWYQ
scFv24     MKKTAIAIAVALAGFATVAQAAV................SASPGDTVKITCSGGNS....SYGYGWYQ
scFv33     MKKTAIAIAVALAGFATVAQAAV................SANPGDTVKITCSG...G....YSGYGWYQ
scFv66     MKKTAIAIAVALAGFATVAQAALSR........PRC....QQTWGGTVEITCSGSSG....DYGYSWHQ
scFv38     MKKTAIAIAVALAGFATVAQAALTQ........PSSVS..ANPGETVKITCSGGSS......YGWYQ
scFv54     MKKTAIAIAVALAGFATVAQAALTQ........PSSVS..ANPGETVKITCSGGSYS.....YGWYQ
```

FIGURE 6 - PANEL 2

```
              60         70         80         90        100        110
cFv1      QKSPGSAPVTLIYESNQRPSNIPSRFSGSLSGSTATLTITGVQPEDEAVYFCGGYD..G.N..S..GIF
cFv16     QKAPGSAPVTLIYDNTNRPSNIPSRFSGSTSGSTNTLTITGVQADDEAVYFCGSVD..S.S..S..GVF
cFv26     QKSPGSAPVTLIYENDMRPSNIPSRFSGSTSGSTSTLTITGVQAEDEAVYFCGSYD..S.S..NYVGEF
cFv2      QKSPGSAPVTVIYDNTNRPSNIPSRFSGSKSGSTGTLTITGVQADDEAVYYCGSTD....S..SADGVF
cFv8      QKSPGSAPVTLIYESNERPSNIPSRFSGSESGSTGTLTITGVRAEDEAVYYCGSAD....S..SNAGIF
cFv17     QKTPGSAPVTLIYDNTNRPSDIPSRFSGSKSGSTATLTITGVQVEDEAMYFCGSYE..G.S..TYVGIF
cFv39     QKSPGSAPVTLIYENDKRPSNIPSRFSGSKSGSTATLTITGVQADDEAVYFCGNAD......TITGIF
cFv14     QKAPGSAPVTLIYANTNRPSDIPSRFSGSASGSTGTLTITGVQADDEAVYFCGSAD....S..TY.GIF
cFv49     QKSPGSAPVTLIYNNNNRPSDIPSRFSGSESGSTLTLTITGVQAEDEAVYFCGTRD....S..SYAGIF
cFv6      QKSPGSAPVTLIYDDKRPSDIPSRFSGSASGSTATLTITGVQADDEAIYFCGTAD..STS..SGAGIF
cFv12     QKSPGSAPVTVIYWDDERPSNIPSRFSGSTSGSTGTLTITGVQAEDEAVYFCGGYD..S....SGDGIF
cFv21     QKSPGSAPVTVIYDNDKRPSDVPSRFSGSKSGPTATLTITGVQAEDEAVYFCGS....RDN..SYVGIF
cFv34     QKSPGSAPVTVIYDNTNRPSDIPSRFSGSLSGSTATLTITGVQAEDEAVYYCGSFDTNSDS..GYVGIF
cFv13     QKSPGSAPVTLIYDNTNRPSDIPSRFSGSKSGSTGTLTITGVQAEDEAVYYCGNAD..SSS....TAAF
cFv47     QKSPGSAPVTVIYDNTNRPSDIPSRFSGSKSGSTGTLTITGVQAEDEAVYYCGNAD..SSG....AAAF
cFv19     QKSPGSAPVTLIYSNDNRPSDIPSRFSGSTSGSTSTLTITGVQAEDEAVYYCGSYD..SSN...DSGIF
cFv22     QKSPGSAPVTVIYDNTNRPSNIPSRFSGSKSGSTATLTITGVQADDEAVYFCGSFD..SST...DIF
cFv53     QKAPGSAPVTVIYDNNKRPSDIPSRFSGSKSGSTGTLTITGVQAEDEAVYFCGNGA..T........F
cFv27     QKAPGSAPVTLIYDDTNRPSDIPSRFSGSKSGSTATLTITGVQAEDEAVYFCGGFD..SSS....DSGF
cFv40     QKSPGSAPVTLIYDNDKRPSDIPSRFSGSTSGSTHTLTITGVQAEDEAIYFCGSED..SST...YASGF
scFv41    QKSPGSAPVTLIYENNNRPSDIPSRFSGSASGSTATLTITGVQAEDGAVYFCGSED..S.T...YVGIF
scFv42    QKSPGSAPVTVIYDNTNRPPNIPSRFSGSLSGSTGTLTITGVQAEDEAVYYCGGHD..SST...YAGIF
scFv48    QKSPGSAPVTVIYDSSKRPSDIPSRFSGSKSGSTGTLTITGVQAEDEAVYYCGSTD..SST...SAAIF
scFv60    QKAPGSAPVTVIYDSSSRPSDIPSRFSGSKSGSTGTLTITGVQAEDEAVYYCGSTD..SST...SAAIF
scFv43    QKSPDSAPVTLIYESNKRPSNIPSRFSGSTSGSTSTLTITGVQADDEAVYFCGSAD..SS....YVGIF
scFv58    QRSPGSAPVTLIYSNDKRPSDIPPRFSGSLSGSTATLTITGVQAEDEAVYYCGGYD..SS....YVGIF
scFv56    QKSPGSAPVTVIYESNKRPSGIPSRFSGSKSGSTHTLTITGVQAEDEAVYYCGAYD..GSS...YTGIF
scFv59    QKAPGSAPVTVIYDNTNRPSNIPSRFSGSKSGSTATLTITGVRADDSAVYYCASTD..SSS....TGIF
scFv50    QKSPGSAPVTVIYGSTSRPSDIPSRFSGSESGSTGTLTITGVQAEDEAVYFCGNAD..SS....YVGLF
scFv52    QKAPSSAPVTVIYSNDKRPSDIPSRFSGSASGSTATLTITGVQAEDEAVYYCGSFD..SSA...GYGGIF
scFv121   QKSPGSAPVTLIYENNNRPSDIPSRFSGSASGSTATLTITGVQAEDGAVYFCGSED..ST....YVGGIF
scFv123   QKSPGSAPVTLIYENNNRPSDIPSRFSGSASGSTAPLTITGVQAEDGAVYFCGSED..ST....YVGIF
scFv51    QKPPGSAPVTVIHNNNKRPSDIPSRFSGSKSGSTGTLTITGVQVDDEAVYYCGSRD..SS....YIGTF
scFv104   QKAPGSAPVTVIYDNTNRPSNIPSRFSGSASGSTGTLTITGVRAEDEAVYFCGGYD..SSN...TDAF
scFv20    QKSPGSAPVTVIYYNDKRPSNIPSRFSGSGSGSTNTLTIAGVRAEDEAVYYCGNED..SS.....GAAF
scFv25    QKSPGSAPVTVIYSNDKRPSDIPSRFSGSLSGSTGTLTITGVRAEDEAVYYCGSID..NTY..VGTGAF
scFv55    QKSPGSAPVTVIYSNDKRPSDIPSRFSGSLSGSTGTLTITGVRAEDEAVYYCGSID..NTY..VGTGAF
scFv32    QKSPGSAPVTVIYWNDKRPSNIPSRFSGSALSGSTATLTITGVQAEDEAVYFCGSAD..SSG.....AIF
scFv134   QKSPGSAPVTVIYWNDKRPSNIPSRFSGALSGSTATLTITGVQAEDEAVYFCGSAD..SSG.....AIF
scFv119   QKSPGSAPVTVIYRNDKRPSNIPSRFSGALSGSTATLTITGVQAEDEAVYFCGSAD..SSG.....AIF
scFv46    QKSPGSAPVTVIYWNDKRPSNIPSRFSGALSGSTATLTITGVQAEDEAVYFCGSAD..SSG.....AIF
scFv65    QKSPGSAPVTLIYESDKRPSDIPSRFSGSKSGSTGTLTITGVQADDEAVYFCGGYD..SSA.....GIF
scFv73    QKSPGSAPVTLIYESDKRPSDIPSRFSGSKSGSTGTLTITGVQADDEAVYFCGGYD..SSA.....GIF
scFv90    QKSPGSAPVTVIYQNDKRPSDIPSRFSGSTSGSTATLTITGVQADDEAVYFCGGYD..SSA.....GIF
scFv68    HKSPGSAPVTVIYYNDKRPSDIPSRFSGSKSGSTSTLTITGVQAEDEADYYCGSYN..SNA..GYVGIF
scFv74    QKSPGSAPVTVIYYNDKRPSDIPSRFSGSKSGSTSTLTITGVQAEDEAVYYCGSYD..SSA..GYVGIF
scFv70    QKSPGSAPVTVIYQNGKRPSNIPSRFSGSKSGSTATLTITGVQADDEAVYFCGGYD..SST...YVGIF
scFv92    QKSPGSAPVTVIYQNGKRPSNIPSRFSGSKSGSTATLTITGVQADDEAVYFCGGYD..SST...YVGIF
scFv83    QKSPGSAPVTLIYNNNNRPSDIPPRFSGSKSGSTGTLAITGVQAEDEAVYFCGGYE..GST...STGIF
scFv72    QKSPGSAPVSLIYSNDKRPSDIPSRFSGSKSGSTGTLTITGVQAEDEAVYYCGGWD..SYV......GIF
scFv102   QESPGSAPVTVIYYNDKRPSDIPSRFSGSASGSTATLTIAGVRAEDEAVYFCGSWD..SST...SAGIF
scFv86    QKSPGSAPVTVIYYNDKRPSDIPSRFSGSKSGSTGTLTITGVQAEDEAVYFCGSYD..SST...DTGIF
scFv84    QKSPGSAPVTLIYESDKRPSDIPSRFSGSKSGSTGTLTITGVQADDEAVYFCGGYD..SSA.....GIF
scFv80    QKSPGSAPVTVIYYNDQRPSDIPSRFSGSKSGSTGTLTITGVQAEDEAVYYCGGYD...ST...YVGIF
scFv105   QKSPGSAPVTVIYYNDKRPSDIPSRFSGSTSGSTSTLTITGVQAEDEAVYFCGGYD..SN...YLGIF
scFv112   QKSPGSAPVTVIYYNDQRPSDIPSRFSGSKSGSTGTLTITGVQAEDEAVYYCGGYD...ST...YVGIF
scFv118   QKSPGGAPVTVIYYNDKRPSDIPSRFSGSKSGSTATLTITGVQAEDEAVYYCGSYD..SSS...YVGIF
scFv124   QKSPGSAPVTVIYYNDQRPSDIPSRFSGSKSGSTGTLTITGVHAEDEAVYYCGGYN..ST...YVGIF
scFv115   QKPPGSAPVTVIYYNDKRPSDIPSRFSGSKSGSTGTLTITGVQAEDEAVYYCGGYG...ST...YLGIF
scFv82    QKSPGSAPVTLIYYNDKRPSDIPSRFSGSKSGSTATLTITGVQANDEAVYFCGSYE..GST...YSGIF
scFv3     QKSPGSAPVTVIYGNDERPSDIPSRFSGSESGSTATLTITGVRAEDEAVYYCGSGD.NS.G..A..GIF
scFv30    QKAPGSAPVTLIYDNTNRPSNIPSRFSGSESGSTATLTITGVRAEDEAAYYCGSAD.SS.D..A..GIF
scFv23    QKSPGSAPVTVIYANTNGPSDIPSRFSGSTSGSTATLTITGVQADDEAVYSCGSYD.SS.Y..V..GIF
scFv7     QKAPGSAPVTLIYDNTNRPSNIPSRFSGSKSGSTATLTITGVQADDEAIYYCGSWD.SSTD..A..A.F
scFv35    QKSPGSAPVTVIYANTNRPSDIPSRFSGSKSGSTATLTITGVRAEDEAVYYCGGYD.SSTD..A..GIF
scFv5     QKSPGSAPVTVIYYNDKRPSDIPSRFSGSASGSTATLTITGVQAEDEAVYFCGSYE.VNIH..E..GIF
scFv24    QKSPGSAPVSVIYYNDERPSDIPSRFSGSASGSTATLTITGVQADDEAVYYCGNAD.SSTY..A..GIF
scFv33    QKSPGSAPVTVIYSNNQRPSDIPSRFSGSTSGSTNTLTITGVQVEDEAIYFCGGYD.CSTG..SVKASF
scFv66    QKSPGSAPVTVIYESTKRPSNIPSRFSGSTSGSTGTLTITGVQVEDEAVYFCGGYD....G..STDAIF
scFv38    QKSPGSAPVTVIYYNDKRPSDIPSRFSGALSGSTATLTITGVQAEDEAVYFCGSGDSSTV.....AGIF
scFv54    QKSPGSAPVTVIYSSDKRPSDIPSRFSGSKSGSTSTLTITGVQAEDEAVYYCGSRDSSYV......GIF
```

FIGURE 6 - PANEL 3

```
cFv100   MKKTAIAIAVALAGFATVAQAALTQ........PSSVS...ANPGETVKITCSG.SSD.A....YGWYQ
cFv131   MKKTAIAIAVALAGFATVAQAALTQ........PSSVS...ANLGGTVEITCSGGSSS.Y....YGWYQ
cFv110   MKKTAIAIAVALAGFATVAQAALTQ........PSSVS...ANLGGTVKLTCSGGSSY.G....YSWHQ
cFv97    MKKTAIAIAVALAGFATVAQAALTQ........PSSVS...ANPGETVKITCSGGSYN.A....YGWYQ
cFv98    MKKTAIAIAVALAGFATVAQAALTQ........PSSVS...ANPGETVKITCSGGGSY.VGSYYYGWYQ
cFv45    MKKTAIAIAVALAGFATVAQAALTQ........PSSVS...ANPGGTVKITCSGSSSA.YG...YGWYQ
cFv62    MKKTAIAIAVALAGFATVAQAALTQ........PSSVS...ANPGGTVKITCSGSSSA.YG...YGWYQ
cFv67    MKKTAIAIAVALAGFATVAQAALTQ........PSSVS...ANPGGTVKITCSGSSSA.YG...YGWYQ
cFv114   MKKTAIAIAVALAGFATVAQAALTQ........PSSVS...ANPGGTVKITCSGSSSA.YG...YGWYQ
cFv85    MKKTAIAIAVALAGFATVAQAALTQ........PSSVS...ANPRTLLKITCSGSSSA.YG...YGWYQ
cFv111   MKKTAIAIAVALAGFATVAQAALTQ........PSSVS...ANPGETVKLTCSGDSSD.YG...YGWYQ
cFv106   MKKTAIAIAVALAGFATVAQAALTQ........PSSVS...ANPGETVKITCSGDSSD.YG...YGWYQ
cFv64    MKKTAIAIAVALAGFATVAQAALTQ........PSSVS...ANPGDPLKITCSGDSSG.YG...YGWYQ
cFv113   MKKTAIAIAVALAGFATVAQAALTQ........PSSVS...ANPGETVKITCSGDSSG.YG...YGWYQ
cFv120   MKKTAIAIAVALAGFATVAQAALTQ........PSSVS...ANPGETVKLTCSGDSSD.YG...YGWYQ
cFv57    MKKTAIAIAVALAGFATVAQAALTQ........PSSVS...ANPGAFNKITCSGSSSA.YG...YGWNQ
cFv95    MKKTAIAIAVALAGFATVAQAALTQ........PSSVS...ANPGETVEITCSGGGGS.YG.....WFQ
cFv69    MKKTAIAIAVALAGFATVAQAALTQ........PSSVS...ANPGETVKITCSGGGSS.NN...YGWHQ
cFv77    MKKTAIAIAVALAGFATVAQAALTQ........PSSVS...ANPGDPFKITCSGGGSS.NN...YGWHQ
cFv93    MKKTAIAIAVALAGFATVAQAALTQ........PSSVS...ANPGALFKITCSGGGSS.NN...YGWHQ
cFv71    MKKTAIAIAVALAGFATVAQAALTQ........PSSVS...ANPGETVKITCSGGGSS.NN...YGWHQ
cFv61    MKKTAIAIAVALAGFATVAQAALTQ........PSSVS...ANPGETVKITCSGGGSY.AGSYYYGWYQ
cFv108   MKKTAIAIAVALAGFATVAQAALTQ........PSSVS...ANPGETVKITCSGGGSY.AGSYYYGWYQ
cFv96    MKKTAIAIAVALAGFATVAQAALPGVRHRDPGGPDSAVLGVSKPRRNDKITCSGGGSY.AGSYYYGWYQ
cFv117   MKKTAIAIAVALAGFATVAQAALTQ........PSSVS...ANPGETVKITCSGGGSY.AGSYYYGWYQ
scFv87   MKKTAIAIAVALAGFATVAQAALSR........PRVS...ANPGDPVKITCSGGGSY.AGSYYYGWYQ
scFv15   MKKTAIAIAVALAGFATVAQAALSR........PRC....QQTQEHTVKITCSGGVG.....QWYGWYQ
scFv37   MKKTAIAIAVALAGFATVAQAALTQ........PSSV...SANLGDTVKITCSGGGGY.AGSYYYGWYQ
scFv44   MKKTAIAIAVALAGFATVAQAALTQ........PSSV...SANLGETVKITCSGGGSY.AGCYYYSWYD
scFv4    MKKTAIAIAVALAGFATVAQAA...
scFv28   MKKTAIAIAVALAGFATVAQAA...
scFv9    MKKTAIAIAVALAGFATVAQAA...
scFv10   MKKTAIAIAVALAGFATVAQAA...
scFv29   MKKTAIAIAVALAGFATVAQAA...
scFv31   MKKTAIAIAVALAGFATVAQAA...
scFv11   MKKTAIAIAVALAGFATVAQAA...
scFv18   MKKTAIAIAVALAGFATVAQAA...
scFv36   MKKTAIAIAVALAGFATVAQAALSR........PRC....QQTLGGTVKITCSGSNG......SYDWCH
scFv88   ...........................................................GSSGSYGWYQ
scFv63   .............................................................SNNYGWHQ
scFv91   ........................................................................
scFv79   ........................LSRPRCQQTWGGTVKITCSGSSG......GYGWYR
scFv81   ........................ALTQPSSVSANPGGTVKITCSGSSS....AYGYGWYQ
scFv89   ........................ALTQPSSVSANPGDTVKITCSGDSS....DYGYGWYQ
scFv75   ........................................................................
```

FIGURE 6 - PANEL 4

```
scFv100  QKSPGSAPVTLIYDNTNRPPDIPSRFSGALSGSTSTLTITGVRAEDEAVYYCGSADITYI......GIF
scFv131  QKSPGSAPVTVIYWNDKRPSDIPSRFSGSESGSPATLTITGVRAEDEAVYFCGSGDSSGT......GIF
scFv110  QKSPGSAPVTVIYSNDKRPSDIPSRFSGSASGSTATLTITGVQVEDEAVYFCGSYDSSSI.....AGIF
scFv97   QKSPAGAPVTLIYDNTNRPSNIPSRFSGSKSGSTHTLTITGVQADDEAVYFCGGYDSNADD......GIF
scFv98   QKSPVSAPVTLIYESTKRPSNIPSRFSGSTSGSMGTLTITGVQAEDEAVYFCGSFDSSSSVSDTADIF
scFv45   QKSPGSAPVTVIYNNNKRPSNIPSRFSGSKSGSTGTLTITGVQAEDEAVYFCGSEDSSTD......AIF
scFv62   QKSPGSAPVTVIYNNNKRPSNIPSRFSGSKSGSTGTLTITGVQAEDEAVYFCGSEDSSTD......AIF
scFv67   QKSPGSAPVTVIYNNNKRPSNIPSRFSGSKSGSTGTLTITGVQAEDEAVYFCGSEDSSTD......AIF
scFv114  QKSPGSAPVTVIYNNNKRPSNIPSRFSGSKSGSTGTLTITGVQAEDEAVYFCGSEDSSTD......AIF
scFv85   QKSPGSAPVTVIYNNNKRPSNIPSRFSGSKSGSTGTLTITGVQAEDEAVYFCGSEDSSTD......AIF
scFv111  QKSPGSAPVTVIYNNNKRPSDIPSRFSGSKSGSTGTLTISGVQAEDEAVYFCGSEDSNTD......AIF
scFv106  QKSPGSAPVTVTYSNNQRPPNIPSRFSGSASGSTATLTITGVQVEDEAVYYCGSEDSTTD......AVF
scFv64   QKSPGSAPVTVIYNNNKRPSDIPSRFSGSKSGSTGTLTITGVQAEDEAVYFCGSEDSNTD......AVF
scFv113  QKSPGSAPVTVIYNNNKRPSDIPSRFSGSKSGSTGTLTITGVQAEDEAVYFCGSEDSNTD......AVF
scFv120  QKSPGSAPVTVIYNNNKRPSDIPSRFSGSKSGSTGTLTISGVQAEDEAVYFCGSEDSNSD......AIF
scFv57   QKSPGSAPVTVIYNNNKRPSNIPSRFSGSKSGSTGTLTITGDQDEDEDFYFCGSEYSSTD......AIF
scFv95   QKSPGSAPVTVIYESTKRPSNIPSRFSGSGSGSTLTITGVQAEDEAVYYCGGYDGSSD......AIF
scFv69   QKAPGSAPVTVIYDNTNRPSNIPSRFSGSKSSSTHTLTITGVQAEDEAVYYCESADSSS.......SIF
scFv77   QKAPGSAPVTVIYDNTNRPSNIPSRFSGSKSSSTHTLTITGVQAEDEAVYYCESADSSS.......SIF
scFv93   QKAPGSAPVTVIYDNTNRPSNIPSRFSGSKSSSTHTLTITGVQAEDEAVYYCESADSSS.......SIF
scFv71   QKAPGSAPVTVIYDNTNRPSNIPSRFSGSKSSSTHTLTITGVQAEDEAVYYCESADSSS.......SIF
scFv61   QKAPGSAPVTLIYDNTNRPSNIPSRFSGSLSGSTGTLTITGVRAEDEAVYYCGSFDSSTDG..GYAAIF
scFv108  QKAPGSAPVTLIYDNTNRPSNIPSRFSGSLSGSPGTLAITGVRAEDEAVYYCGSFHSSTDG..GYAAIF
scFv96   QKAPGSAPVTLIYDNTNRPSNIPSRFSGSLSGSTGTLTITGVRAEDEAVYYCGSFDSSTDG..GYAAIF
scFv117  QKAPGSAPVTLIYDNTNRPSNIPSRFSGSLSGSTGTLTITGVRAEDEAVYYCGSFDSSTDS..GYAAIF
scFv87   QKAPGSAPVTVIYDNNQRPSNIPSRFSGSLSGSTGTLTITGVRAEDEAVYYCGSFDSSTDS..GYAAIF
scFv15   QKSPGSAPVTLIYESNQRPSNIPSRFSGSLSGSTATLTITGVQPEDEAVYFCGGYDGNS.......GIF
scFv37   HNAAGGAPVTLIYDNTIITPSDIPSRFSGSTSGSTNALTINGVQA.DYAVYFCGSVNCSS.......GVF
scFv44   HTAAGVVPVTLI.DSTIPSSYFRSRFCCSASGSINALTINEDPA.YYAVYFCGSVDVFG.......GVF
scFv4    .........VIYDNDKRPSDVPSRFSGSKSGPTATLTITGVQAEDEAVYFCGSRDNS.YV.....GIF
scFv28   .........VIYSNDERPSDIPSRFSGSTSGSTSTLTITGVQADDEAVYFCGSADSSTYA.....GIF
scFv9    .........VIYGNDERPSDIPSRFSGSESGSTATLTITGVRAEDEAVYYCGSGDNS.GA.....GIF
scFv10   .........VIYANTDRPSDIPSRFSGSKSGSTATLTITGVRAEDEAVYFCGSGDSS..T.....GIF
scFv29   .........VIYDNTNRPSNIPSRFSGSKSGSTGTLTITGVQAEDEAVYYCGSTDSSAD......GVF
scFv31   .........VIYDNTNRPSNIPSRFSGSLSGSTNTLTITGVQAEDEAVYFCGGYDSSTDS.....GMF
scFv11   .........VIYYNDKRPSNIPSRFSGSGSGSTNTLTIAGVRAEDEAVYYCGNEDSS..G.....AAF
scFv18   .........VIYYNDKRPSDIPSRFSGSKSGSTATLTITGVRAEDEAVYYCGSADST..D.....AVF
scFv36   QKTSAGAAAAVIIYDNNKTSYIPSSLFCASSCSPATLLIIGVVADDDDVDYCGSANDNSSV....VIV
scFv88   QKSPGSAPVTVIYYNDKRPSDIPSRFSGSTSGSTATLTITGVQAEDEAVYFCGGYDSNYI.....GIF
scFv63   QKAPGSAPVTVIYDNTNRPSNIPSRFSGSKSSSTHTLTITGVQAEDEAVYYCESADSSS.......SIF
scFv91   ..........IYDNTNRPSNIPSRFSGSKSSSTHTLTITGVQAEDEAVYYCESADSSS.......SIF
scFv79   HKSPGTAPVPLIYNNDNRPSDIPSRFSGSKSGSTSTLTITGVQVQDEDDYFCGGYNKNTYA....DIF
scFv81   QKSPGSAPVTVIYNNNKRPSNIPSRFSGSKSGSTGTLTITGVQAEDEAVYFCGSEDSSTD......AIF
scFv89   QKSPGSAPVTVTYSNNQRPSDIPSRFSGSASGSTATLTITGVQVEDEAVYYCGSEDSTTD......AVF
scFv75   .....RAPVTLIYNNNNRPSDIPPRFSGSKSGSTGTLAITGVQAEDEAVYFCGGYEGSTST.....GIF
```

FIGURE 7 - PANEL 1

```
            120        130              140       150       160       170
scFv1    GAGTTLTVLGQSSRSSA..............VTLDESGGGLQTPGRALSLVCKASGFTFSSYDMGWVRQAPG
scFv16   GAGTTLTVLGQSSRSSA..............VTLDESGGGLQTPGGALSLVCKASGFTFSSFDMFWVRQAPG
scFv26   GAGTTLTVLGQSSRSSA..............VTLDESGGGLQTPGGALSLVCKASGFTFSSFDMFWVRQAPG
scFv2    GAGTTLTVLGQSSRSSA..............VTLDESGGGLQTPGGGLSLVCKGSGFTFSSFDMFWVRQAPG
scFv8    GAGTTLTVLGQSSRSST..............VTLDESGGGLQTPGGALSLVCKASGFTFSSFNMGWVRQAPG
scFv17   GAGTTLTVLGQSSRSSA..............VTLDESGGGLQTPGGALSLVCKASGFTFSSYDMAWVRQAPG
scFv39   GAGTTLTVLGQSSRSST..............VTLDESGGGLQTPGGALSLVCKASGFTFSSYTMAWVRQAPG
scFv14   GAGTTLTVLGQSSRSSA..............VTLDESGGGLQTPGGALSLVCRASGFTFSDYGMEWVRQAPG
scFv49   GAGTTLTVLGQSSRSSA..............VTLDESGGGLQTPGGALSLVCKGSGFTFSDYSMMWVRQAPG
scFv6    GAGTTLTVLGQSSRSST..............VTLDESGGGLQTPGGALSLVCKGSGFTFSSFNMFWVRQAPG
scFv12   GAGTTLTVLGQSSRSSSGGGSSGGGGSAVTLDESGGGLQTPGRALSLVCKASGFTFSGYNMGWVRQAPG
scFv21   GAGTTLTVLGQSSRSSA..............VTLDESGGGLQTPGGALSLVCKASGFTFSSYDMFWVRQAPG
scFv34   GARTTLTVLGQSSRSST..............ETLDDSGGGLQTPGGALSLVCNASGFTFISYDMFWVRQAPG
scFv13   GAGTTLTVLGQSSRSST..............VTLDESGGGLQTPGGALSLVCKASGFTFSSYAMGWVRQAPG
scFv47   GAGTTLTVLGQSSRSSA..............VTLDESGGGLQTPGGALSLGCEASGFTFSSYAMGWVRQAPG
scFv19   GAGTTLTVLSQSSRSSA..............VTLDESGGGLQTPGGGLSLVCKASGFTFSTFNMFWVRQAPG
scFv22   GAGTTLTVLGQSSRSST..............VTLDESGGGLQTPGRALSLVCKASGFTFSSFNMGWVRQAPG
scFv53   GAGTTLTVLGQSSRSST..............VTLDESGGGLQTPGRALSLVCKASGFTFSSFNMGWVRQAPG
scFv27   GAGTTLTVLGQSSRSST..............VTLDESGGGLQTPGGALSLVCKASGFTFSSFNMGWVRQAPG
scFv40   GAGTTLTVLGQSSRSSA..............VTLDESGGGLQTPGRALSLVCKASGFTFSSFNMGWVRQAPG
scFv41   GAGTTLTVLGQSSRSSA..............VTLDESGGGLQTPGRALSLVCKASGFTFSSFNMGWVRQAPG
scFv42   GAGTTLTVLGQSSRSSA..............VTLDESGGGLQTPGRALSLVCKASGFTFSSFNMGWVRQAPG
scFv48   GAGTTLTVLGQSSRSST..............VTLDESGGGLQTPGRALSLVCKASGFTFSSFNMGWVRQAPG
scFv60   GAGTTLTVLGQSSRSST..............VTLDESGGGLQTPGGALSLVCKASGFTFSSFNMGWVRQAPG
scFv43   GAGTTLTVLGQSSRSSA..............VTLDESGGGLQTPGGALSLVCKASGFTFSSFNMGWVRQAPG
scFv58   GAGTTLTVLGQSSRSST..............VTLDESGGGLQTPGRALSLVCKASGFTFSSFNMGWVRQAPG
scFv56   GAGTTLTVLGQSSRSST..............VTLDESGGGLQTPGRALSLVCKASGFTFSSFNMGWVRQAPG
scFv59   GAGTTLTVLGQSSRSSA..............VTLDESGGGLQTPGRALSLVCKASGFTFSSFNMGWVRQAPG
scFv50   GAGTTLTVLGQSSRSST..............VTLDESGGGLQTPGGALSLVCKASGFTFSSFNMGWVRQAPG
scFv52   GAGTTLTVLGQSSRSST..............VTLDESGGGLQTPGRALSLVCKASGFTFSSFNMGWVRQAPG
scFv121  GAGTTLTVLGQSSRSSA..............VTLDESGGGLQTPGRALSLVCKASGFTFSSFNMGWVRQAPG
scFv123  GAGTTLTVLGQSSRSSA..............VTLDESGGGLQTPGRALSLVCKASGFTFSSFNMGWVRQAPG
scFv51   GAGTTLTVLGQSSRSSA..............VTLDESGGGLQTPGRALSLACKASGFTFSSFNMGWVRQAPG
scFv104  GAGTTLTVLGQSSRSST..............VTLDESGGGLQTPGRALSLVCKASGFTFSSYTMGWVRQAPG
scFv20   GAGTTLTVLGQSSRSSA..............VTLDESGGGLQTPGGGLSLVCKASGFTFSDYDMFWVRQAPS
scFv25   GAGTTLTVLGQSSRSSA..............VTLDESGAGLQTPGRALSLVCKGSGFTFSSFYMFWVRQAPG
scFv55   GAGTTLTVLGQSSRSST..............VTLDESGGGLQTPGRALSLVCKGSGFTFSSFYMFWVRQAPG
scFv32   GAGTTLTVLGQSSRSST..............VTLDESGGGLQTPGGGLSLVCKGSGFAFSNYGMGWMRQAPG
scFv134  GAGTTLTVLGQSSRSST..............VTLDESGGGLQTPGGGLSLVCKGSGFAFSNYGMGWMRQAPG
scFv119  GAGTTLTALGQSSRSST..............VTLEESGGGLHTPGGGLILLCKGSGVSFCNYGMGWMRRDPG
scFv46   GAGTTLTVLGQSSRSST..............VTLDESGGGLQTPGGGLSLVCKGSGFAFSNYGMGWMRQAPG
scFv65   GAGTTLTVLGQSSRSSA..............VTLDESGGGLQTPGGGLSLVCKASGFDFSSYGMGWMRQAPG
scFv73   GAGTTLTVLGQSSRSSA..............VTLDESGGGLHTPGGALSLVCKASGFDFSSYGMGWMRQAPG
scFv90   GAGTTLTVLGQSSRSSA..............VTLDESGGGLQTPGGALSLVCKASGFS.SSHGMGWMRQAPG
scFv68   GAGTTLTVLGQSSRSST..............VTLDESGGGLQTPGGGLSLVCKASGFTFSSYGMGWMRQAPG
scFv74   GAGTTLTVLGQSSRSST..............VTLDESGGGLQTPGGGLSLVCKASGFTFSSYGMGWMRQAPG
scFv70   GAGTTLTVLGQSSRSSA..............VTLDESGGGLQTPGGALSLVCKASGFDFSSYGMGWMRQAPG
scFv92   GAGTTLTVLGQSSRSSA..............VTLDESGGGLQTPGGALSLVCKASGFDFSSYGMGWMRQAPG
scFv83   GAGTTLTVLGQSSRSSA..............VTLDESGGGLQTPGGALSLVCKASGFDFSSYGMGWMRQAPG
scFv72   GAGTTLTVLGQSSRSSA..............VTLDESGGGLQTPGGGLSLVCKASGFS.SSHGMGWMRQAPG
scFv102  GAGTALTVLGQSSRSSA..............VTLDESGGGLQTPGGGLSLVCKASGFS.SSHGMGWMRQAPG
scFv86   GAGTTLTVLGQSSRSST..............VTLDESGGGLQTPGGALSLVCKASGFIFSSHGMGWMRQAPG
scFv84   GAGTTLTVLGQSSRSSA..............VTLDESGGGLQTPGGALSLVCKASGFDFSSYGMGWMRQAPG
scFv80   GAGTTLTVLGQSSRSSA..............VTLDESGGGLQTPRGALSLVCKASGFTFSSYSMAWVRQAPG
scFv105  GAGTTLTVLGQSSRSSA..............VTLDESGGGLQTPRGALSLVCKASGFTFSSYSMAWVRQAPG
scFv112  GAGTTLTVLGQSSRSSA..............VTLDESGGGLQTPRGALSLVCKASGFTFSSYSMAWVRQAPG
scFv118  GVGTTLTVLGQSSRSSA..............VTLDESGGGLQTPRGALSLVCKASGFTFSSYSMAWVRQAPG
scFv124  GAGTTLTVLGQSSRSSA..............VTLDESGGGLHTPRGALSLICKASGFTFSSYSMAWVQQAPG
scFv115  GAGTTLTVLGQSSRSSA..............VTLDESGGGLQMPGGGLSLVCKASGFTFSSYAMGWVRQAPG
scFv82   GAGTTLTVLGQSSRSST..............VTLDESGGGLQTPGGGLSLVCKASGFS.SSHGMGWMRQAPG
scFv3    GAGTTLTVLGQSSRSSA..............VTLDESGGGLQTPGGALSLVCKASGFTFSSNGMAWVRQAPG
scFv30   GAGTTLTVLGQSSRSSA..............VTLDESGGGLQTPRRALSLVCKASGFTFSDYGMAWVRQAPG
scFv23   GAGTTLTVLGQSSRSST..............VTLDESGGGLQTPGGALSLVCKASGFTFNSYALEWVRQAPG
scFv7    GAGTTLTVLGQSSRSST..............VTLDESGGGLQTPGGGLSLVCKASGFTFSDYGMGWVRQAPG
scFv35   GAGTTLTVLGQSSRSSA..............VTLDESGGGLQTPGGGLSLVCKASGFTFSDYGMGWMRQAPG
scFv5    GAGTSLTVLGQSSRSST..............VTLDESGGGLQTPGRALSLVCKASGFTFSSNGMYWVRQAPG
scFv24   GAGTTLTVLGQSSRSSA..............VTLDESGGGLQTPGGGLSLVCKASGFDFSSTNAMGWVRQAPG
scFv33   GAGTTLTVLGQSSRSSA..............VTLDESGGGLQTPGGTLSLVCKGSGFTFSSHGMGWVRQAPG
scFv66   GAGTTLTVLGQSSRSSA..............VTLDESGGGLQMPGGGLSLVCKASGFDFSSSEMQWVRQAPG
scFv38   GAGTTLTVLGQSSRSSA..............VTLDESGGGLQTPGGTLSLVCKASGFDFSSYGMHWVRQEPG
scFv54   GAGTTLTVLGQSSRSST..............VTLDESGGGLQTPGGALSLVCEASGFTFSSYEMQWVRQAPG
```

FIGURE 7 - PANEL 2

```
              180        190        200        210        220        230
cFv1     KGLEWVAYINSGSGSSTYYGTAVKGRASISRDNGQSTVRLQLNNLRVEDTGTYFCAKGASGYYSSS...
cFv16    KGLEYVAEI.SDTGSSTYYGAAVKGRATISRDNGQSTVRLQLNNLRAEDTGTYFCAKSHSGYGWST...
cFv26    KGLEYVAEI.SDTGSSTYYGAAVKGRATISRDNGQSTVRLQLNNLRAEDTGTYFCAKSHSGYGWST...
cFv2     KGLEWVAGI.RNDGSDTAYGAAVKGRATISKDNGQSTVRLQLNNLRAEDTGTYYCAKA.AGYCYVY...
cFv8     KGLEFVAGI.DNTGSFTHYGAAVKGRATISRDDGQSTVRLQLDNLRAEDTGTYYCAKA.SGYYSG...
cFv17    KGLEFVAGI..DIGSYTGYGAAVKGRATISRDNGQSTVRLQLNNLRAEDTGTYYCAKA.AGSYYYS...
cFv39    KGLEWVAGI.NDGGSYTNYGPAVQGRATISRDNGQSTVRLQLNNLRAEDTAIYYCAKS.AGGYYYS...
cFv14    KGLEWVAGI.DDDGSTTFYAPAVKGRATISRDDGQSTVRLQLNNLRAEDTATYYCAKS.AGRGWN....
cFv49    KGLEWVAGI.SSNGSTTRYGSAVKGRATISRDNGQSTVRLQLNNLRAEDTGTYYCAKT.TGVNSY....
cFv6     KGLEWVAGIYSSGGGETNYGAAVKGRATISRDNGQSTVRLQLNNLRAEDTGTYYCAKESADVGCPF...
cFv12    KGLEWVGGI.SGSGRYTEYGAAVKGRATISRDNGQSTVRLQLNNLRAEDTGTYFCAKAAVSDYCGG...
cFv21    KGLEFVAQI.NSAGSYTNYGSAVKGRATISRDDGQSTVRLQLNNLRAEDTGIYFCAKSASGYYYSG...
cFv34    KGLEFVTQI.NSAGSYTNYGSAVNGRATISRNDGQITVRLQLNDLTADDTGIYFCAESASGYDYSG...
cFv13    KGLEYVAAI.SSAGSTTNYGAAVKGRATISRDNGQSTVRLQLNNLRAEDTATYFCAKAAGSGYYVWS..
cFv47    KGLEYVATI.SSAGSNTNYGAAVKGRATISRDNGQSTVRLQLNNLEDDDTATYFCAEAAGNGYYVWS..
cFv19    KGLEFVAGI.SITGGWTGYGAAVKGRATISRDNGQSTVRLQLNNLRAEDTGTYYCAKPAAWSCY..R..
cFv22    KGLEYVASI.SSSGSYTAYGSAVKGRATISRDNGQSTVRLQLNNLRAEDTATYYCAKAAGSAYYYTAVT
cFv53    KGLEYVASI.SSSGSYTAYGSAVKGRATISRDNGQSTVRLQLNNLRAEDTATYYCAKAAGSAYYYTAVT
cFv27    KGLEYVASI.SSSGSYTAYGSAVKGRATISRDNGQSTVRLQLNNLRAEDTATYYCAKAAGSAYYYTAVT
cFv40    KGLEYVASI.SSSGSYTAYGSAVKGRATISRDNGQSTVRLQLNNLRAEDTATYYCAKAAGSAYYYTAVT
cFv41    KGLEYVASI.SSSGSYTAYGSAVKGRATISRDNGQSTVRLQLNNLGAEDTATYYCAKAAGNAYYYTAVT
cFv42    KGLEYVASI.SSSGSYTAYGSAVKGRATISRDNGQSTVRLQLNNLRAEDTATYYCAKAAGSAYYYTAVT
cFv48    KGLEYVASI.SSSGSYTAYGSAVKGRATISRDNGQSTVRLQLNNLRAEDTATYYCAKAAGSAYYYTAVT
cFv60    KGLEYVASI.SSSGSYTAYGSAVKGRATISRDNGQSTVRLQLNNLRAEDTATYYCAKAAGSAYYYTAVT
cFv43    KGLEYVASI.SSSGSYTAYGSAVKGRATISRDNGQSTVRLQLNNLRAEDTATYYCAKAAGSAYYYTAVT
cFv58    KGLEYVASI.SSSGSYTAYGSAVKGRATISRDNGQSTVRLQLNNLRAEDTATYYCAKAAGSAYYYTAVT
cFv56    KGLEYVASI.SSSGSYTAYGSAVKGRATISRDNGQSTVRLQLNNLRAEDTATYYCAKAAGSAYYYTAVT
cFv59    KGLEYVASI.SSSGSYTAYGSAVKGRATISRDNGQSTVRLQLNNLRAEDTATYYCAKAAGSAYYYTAVT
cFv50    KGLEYVASI.SSSGSYTAYGSAVKGRATISRDNGQSTVRLQLNNLRAEDTATYYCAKAAGSAYYYTAAT
cFv52    KGLEYVASI.SSSGSYTAYGSAVKGRATISRDNGQSTVRLQLNNLRAEDTATYYCAKAAGSAYYYTAVT
cFv121   KGLEYVASI.SSSGSYTAYGSAVKGRATISRDNGQSTVRLQLNNLRAEDTATYYCAKAAGSAYYYTAVT
cFv123   KGLEYVASI.SSSGSYTAYGSAVKGRATISRDNGQSTVRLQLNNLRAEDTATYYCAKAAGSAYYYTAVT
cFv51    KGLEYVASI.SSSGSYTAYGSAVKGRATISRDNGQSTVRLQLNNLRAEDTATYYCAKAAGSAYYYTAVT
scFv104  KGLEFVAGI.GNTGRYTGYGSAVKGRATISRDNGQSTVRLQLNNLRAEDTGTYYCTKCAYGYYYSWG..
scFv20   KGLEFVAAI.TSSGTGTKYGASAVKGRATISKDNGQRTVRLQLNSLGAEDTGTYYCARSDADSTTWS...
scFv25   KGLEFVACI.SSSGSSTRYGVVVKGRATISRDNGQSTVRLRLNNLRADDTGTYYCARG....TSSG...
scFv55   KGLEFVASI.SSSGSSTRYGVVVKGRATISRDNGQSTVRLRLNNLRAEDTGTYYCARG....TSSG...
scFv32   KGLEYVAGI..STGSYTDYGSAVKGRATISRDNGQSTVRLQLNNLRAEDAAIYFCAKT.AGSGYGCGS
scFv134  KGLEYVAGI..STGSYTDYGPAVKGRATISRDNGQSTVRLQLNNLRAEDAAIYFCART...AGSGYGCGS
scFv119  GGLEYVAGI..STGSYTYYGPAVKGRGTVSRDNGQSTMRLQLNHLRAEDETIYFCART..DASSHGCGS
scFv46   KGLEYVAGI..STGSYTDYGPAVKGRATISRDNGQSTVRLQLNNLRAEDAAIYFCAK............
scFv65   KGLEFVAAI.RKDGSYTAYGAAVDGRATISRDDGQSTVRLQLGNLRAEDTATYFCAKT..NSYNSA...
scFv73   KGLEFVAAI.RKDGSYTAYGAAVDGRATISRDDGQSTVRLQLGNLRAEDTATYFCAKT..NSYNSA...
scFv90   KGLEFVAGI.RSDGSSTAYGAAVDGRATISRDDGQSTVRLQLNNLRAEDTATYFCAKT..NSYNSA...
scFv68   KGLEFVAAI.RKDGRSTAYGAAVDGRATISRDDGQSTLRLQLGNLRAEDTATYFCAKT..NSYDSA...
scFv74   KGLEFVAGI.RKDGSSTAYGAAVDGRATISRDDGQSTLRLQLGNLRAEDTGTYFCAKT..NSYNSA...
scFv70   KGLEFVAAI.RKDGSYTAYGAAVDGRATISRDDGQSTVRLQLGNLRAEDTATYFCAKT..NSYNSA...
scFv92   KGLEFVAGI.RKDGSYTAYGAAVDGRATISRDDGQSTVRLQLGNLRAEDTATYFCAKT..NSYNSA...
scFv83   KGLEFVAAI.RKDGSYTAYGAAVDGRATISRDDGQSTVRLQLGNLRAEDTATYFCAKT..NSYNSA...
scFv72   KGLEFVAGI.RSDGSSTAYGAAVDGRATITRDDGQSTVLQLNNLRAEDTATYFCAKT..NSYNSA...
scFv102  KGLEFVAGI.RSDGSSTAYGAAVDGRATITRDDGQSTVLQLNNLRAEDTATYFCAKT..NSYNSA...
scFv86   KGLEFVAAI.SKDGTATYYGPAVKGRATISRDDGQTTVRLQLGNLRAEDTATYFCAKT..KYYNSA...
scFv84   KGLEFVAAI.RKDGSYTAYGAAVDGRATISRDDGQSTVRLQLGNLRAEDTATYFCAKT..NSYNSA...
scFv80   KGLEFVAGI.QNDGSITDYGSAVDGRATISRDDGQSTVRLQLNNLRTEDTATYYCAK...TTVADG...
scFv105  KGLEFVAGI.QNDGSITDYGSAVDGRATISRDDGQSTVRLQLNNLRTEDTATYYCAK...TTVADG...
scFv112  KGLEFVAGI.QNDGSITDYGSAVDGRATISRDDGQSTVRLQLNNLRTEDTATYYCAK...TTVADG...
scFv118  KGLEFVAGI.QNDGSITDYGSAVDGRATISRDDGQSTVRLQLNNLRTEDTATYYCAK...TTVADG...
scFv124  KGLEFVPGI.LNDGSITDYGSADDGRATISRDDGQSTVRLHLINLRTEDTATYYCAK...TTVADG...
scFv115  KGLEFVAGI.LNDGSITDYGSAVKGRATISRDDGQSTVRLQLSNLRTEDTATYYCAK...TTVGDG...
scFv82   KGLEFVAGI.RSDGSSTAYGAAVDGRATITRDDGQSTVLQLNNLRAEDTATYFCAKN..TTVADG...
scFv3    KGLEWVAGI.SSSGSYTNYGSAVKGRATISRDNGQSTVRLQLNNLRAEDTATYYCAKS.SYAYYGFG..
scFv30   KGLEWVAGI.GSSGSYTDYGSAVKGRATISRDNGQSTVRLQLNNLRAEDTATYYCAKD.IGSVYGCGWW
scFv23   KGLEWVAGI.SGDGSYRHYGSAVKGRATISRDSGQSTVRLQLNNLRAEDTGTYYCAKS.TGSGAGWG..
scFv7    KGLEFVAGI.GNTGSYTYYGSAVKGRATISRDNGQSTVRLQLNNLRAEDTGIYFCAKS.TDYWT..Y..
scFv35   KGLEWVAGI.DNTGSSTGYGAAVKGRATISRDNRQSTVRLQLNNLRAEDTGIYFCAKT.AGSGGWW..
scFv5    KGLEFVAGI.SSSGSYTNYAPAVKGRATISRDNGQSTVRLQLNNLRAEDTGTYYCAKG.ASSYSW....
scFv24   KGLEWVAGI.SGSGSSTWYATAVKGRATISRDNGQSTVRLQLNNLRAEDTGTYYCTKY.VGDYYWYI..
scFv33   KGLEWVAGI..YSGSSTYYGAAVKGRATISRDNGQSTVRLQLNNLRAEDTATYFCTRG.GG........
scFv66   KGLQWVGII..SSSGSTYYGAAVKGRATISRDNQSAVRLQLNNLRAEDTGTYYCTKTTAYAH.......
scFv38   KGLEWVAGISRTGS.FTYYGAAVKGRAAISRDNGSTVRLQLNNLRAEDTGTYYCAKG..GSDCSYRC
scFv54   KGLEFVAAISSDGS.YTNYGAAVQGRATISRDNGQSTVRLQLSNLRAEDTATYYCARS...PGGYTWW..
```

FIGURE 7 - PANEL 3

```
              240       250       260       270       280
scFv1     .IGAGEIDAWGHGTEVIVSSTSGQAGQHHHHHHGAYPYDVPDYAS
scFv16    ...AGDIDAWGHGTEVIVSSTSGQAGQHHHHHHGAYPYDVPDYAS
scFv26    ...AGDIDAWGHGTEVIVSSTSGQAGQHHHHHHGAYPYDVPDYAS
scFv2     .SCAGSIDAWGHGTEVIVSSTSGQAGQHHHHHHGAYPYDVPDYAS
scFv8     .VNAGSIDAWGHGTEVIVSSTSGQAGQHHHHHHGAYPYDVPDYAS
scFv17    .GAAGSIDAWGHGTEVIVSSTSGQAGQHHHHHHGAYPYDVPDYAS
scFv39    .GAAGTIDAWGHGTEVIVSSTSGQAGQHHHHHHGAYPYDVPDYAS
scFv14    ..VAGWIDAWGHGTEVIVSSTSGQAGQHHHHHHGAYPYDVPDYAS
scFv49    ..DVPAIDAWGHGTEVIVSSTSGQAGQHHHHHHGAYPYDVPDYAS
scFv6     ..TAGCIDTWGHGTEVIVSSTSGQAGQHHHHHHGAYPYDVPDYAS
scFv12    .GCAGDIDAWGHGTEVIVSSTSGQAGQHHHHHHGAYPYDVPDYAS
scFv21    .SDAGDIDAWGHGTEVIVSSTSGQAGQHHHHHHGAYPYDVPDYAS
scFv34    .SDAGDINAWGHGTEVVVSSTSGQAGQHHHHHHGAYPYDVPDYAS
scFv13    .AIAGDIDAWGHGTEVIVSSTSGQAGQHHHHHHGAYPYDVPDYAS
scFv47    .AIAGDIDAWGHGTDVIVSSTSGQAGQHHHHHHGAYPYDVPDYAS
scFv19    .GCGGEFDAWGHGTEVIVSSTSGQAGQHHHHHHGAYPYDVPDYAS
scFv22    PAFAGSIDAWGHGTEVIVSSTSGQAGQHHHHHHGAYPYDVPDYAS
scFv53    PAFAGSIDAWGHGTEVIVSSTSGQAGQHHHHHHGAYPYDVPDYAS
scFv27    PAFAGSIDAWGHGTEVIVSSTSGQAGQHHHHHHGAYPYDVPDYAS
scFv40    PAFAGSIDAWGHGTEVIVPSTSGQAGQHHHHHHGAYPYDVPDYAS
scFv41    PAFAGSIDAWGHGTEVIVPSTSGQAGQHHHHHHGAYPYDVPDYAS
scFv42    PAFAGSIDAWGHGTEVIVSSTSGQAGQHHHHHHGAYPYDVPDYAS
scFv48    PAFAGSIDAWGHGTEVIVSSTSGQAGQHHHHHHGAYPYDVPDYAS
scFv60    PAFAGSIDAWGHGTEVIVSSTSGQAGQHHHHHHGAYPYDVPDYAS
scFv43    PAFAGSIDAWGHGTEVIVSSTSGQAGQHHHHHHGAYPYDVPDYAS
scFv58    PAFAGSIDAWGHGTEVIVSSTSGQAGQHHHHHHGAYPYDVPDYAS
scFv56    PAFAGSIDAWGHGTEVIVSSTSGQAGQHHHHHHGAYPYDVPDYA.
scFv59    PAFAGSIDAWGHGTEVIVSSTSGQAGQHHHHHHGAYPYDVPDYAS
scFv50    PAFAGSIDAWGHGTEVIVSSTSGQAGQHHHHHHGAYPYDVPDYAS
scFv52    PAFAGSIDAWGHGTEVIVSSTSGQAGQHHHHHHGAYPYDVPDYAS
scFv121   PAFAGSIDAWGHGTEVIVSSTSGQAGQHHHHHHGAYPYDVPDYAS
scFv123   PAFAGSIDACGHGTEVIVSSTSGQAGQHHHHHHGAYPYDVPDYAS
scFv51    PAFAGSIDAWGHGTEVIVSSTSGQAGQHHHHHHGAYPYDVPDYAS
scFv104   .NIAGSIDAWGHGTEVIVSSTSGQAGQHHHHHHGAYPYDVPDYAS
scFv20    ...AGEIDAWGHGTEVIVSSTSGQAGQHHHHHHGAYPYDVPDYAS
scFv25    ...ANTIDAWGHGTEVIVSSTSGQAGQHHHHHHGAYPYDVPDYAS
scFv55    ...ANTIDAWGHGTEVIVSSTSGQAGQHHHHHHGAYPYDVPDYAS
scFv32    GTDLGSIDAWGHGTEVIVSSTSGQAGQHHHHHHGAYPYDVPDYAS
scFv134   GTDLGSIDAWGHGTEVIVSSTSGQAGQHHHHHHGAYPYDVPDYAS
scFv119   GTDLGSIDAWGHGTEVLLSSTSGQAGQHHHHHHGAYPYDVPDYAS
scFv46    ..........GHGTEIIVSSTSGQAGQHHHHHHGAYPYDVPDYAS
scFv65    GI......IDAWGHGTEVIVSSTSGQAGQHHHHHHGAYPYDVPDYAS
scFv73    GI......IDAWGHGTEVIVSSTSGQAGQHHHHHHGAYPYDVPDYAS
scFv90    GI......IDAWGPGTEVIVSSTSGQAGQHHHHHHGAYPYDVPDYAS
scFv68    GI......IDAWGHGTEVIVSSTSGQAGQHHHHHHGAYPYDVPDYAS
scFv74    GI......IDAWGHGTEVIVSSTSGQAGQHHHHHHGAYPYDVPDYAS
scFv70    GI......IDAWGHGTEVIVSSTSGQAGQHHHHHHGAYPYDVPDYAS
scFv92    GI......IDAWGHGTEVIVSSTSGQAGQHHHHHHGAYPYDVPDYAS
scFv83    GI......IDAWGHGTEVIVSSTSGQAGQHHHHHHGAYPYDVPDYAS
scFv72    GI......IDAWGHGTEVIVSSTSGQAGQHHHHHHGAYPYDVPDYAS
scFv102   GI......IDAWGHGTEVIVSSTSGQAGQHHHHHHGAYPYDVPDYAS
scFv86    GI......IDAWGHGTEVIVSSTSGQAGQHHHHHHGAYPYDVPDYAS
scFv84    GI......IDAWGHGTEVIVSSTSGQAGQHHHHHHGAYPYDVPDYAS
scFv80    VIGAYGIDAWGHGTEVIVSSTSGQAGQHHHHHHGAYPYDVPDYAS
scFv105   VIGAYGIDAWGHGTEVIVSSTSGQAGQHHHHHHGAYPYDVPDYAS
scFv112   VIGAYGIDAWGHGTEVIVSSTSGQAGQHHHHHHGAYPYDVPDYAS
scFv118   VIGAYGIDAWGHGTEVIVSSTSGQAGQHHHHHHGAYPYDVPDYAS
scFv124   VIGAYGIDAWGHGTEVIVSSTSGQAGQHHHHHHGAYPYDVPDYAS
scFv115   VIGAYAIDAWGHGTEVIVSSTSGQAGQHHHHHHGAYPYDVPDYAS
scFv82    VIGAYGIDAWGHGTEVIVSSTSGQAGQHHHHHHGAYPYDVPDYAS
scFv3     ...APFIDAWGHGTEVIVSSTSGQAGQHHHHHHGAYPYDVPDYAS
scFv30    ACSAGSIDAWGHGTEVIVSSTSGQAGQHHHHHHGAYPYDVPDYAS
scFv23    ...ASNIDAWGHGTEVIVSSTSGQAGQHHHHHHGAYPYDVPDYAS
scFv7     ...AGTIDAWGHGTEVIVSSTSGQAGQHHHHHHGAYPYDVPDYAS
scFv35    ...SDWIDAWGHGTEVIVSSTSGQAGQHHHHHHGAYPYDVPDYAS
scFv5     ..DGGSIDAWGHGTEVIVSSTSGQAGQHHHHHHGAYPYDVPDYAS
scFv24    ..DAGSIDAWGHGTEVIVSSTSGQAGQHHHHHHGAYPYDVPDYAS
scFv33    ...AGRIDTWGHGTEVIVSSTSGQAGQHHHHHHGAYPYDVPDYAS
scFv66    ......DIDAWGHGTEVIVSSTSGQAGQHHHHHHGAYPYDVPDYAS
scFv38    DYSAGNIDGWGHGTEVIVSSTSGQAGQHHHHHHGAYPYDVPDYAS
scFv54    PGAAGGIDAWGHGTEVIVSSTSGQAGQHHHHHHGAYPYDVPDYAS
```

FIGURE 7 - PANEL 4

```
scFv100   GAGTTLTVLGQSSRSST...........VTLDESGGGLQTPGGGLSLVCKASGFTFSSHTMQWVRQAPG
scFv131   GAGTTLTVLGQSSRSSA...........VTLDESGGGLQTPGGGLSLVCKASGFSFSDYTMNWVRQAPG
scFv110   GAGTTLTVLGQSSRFST...........VTLDESGGGLQTPGGGLSLVCKASGFTFSSYGMAWVRQAPG
scFv97    GAGTTLTVLGQSSRSST...........VTLDESGGGLQTPGGTLSLVCKASGFTFSSYAMNWMRQAPG
scFv98    GAGTTLTVLGQSSRSST...........VTLDESGGGLQTPGGALSLVCKASGFTFNSYALEWVRQAPG
scFv45    GAGTTLTVLGQSSRSST...........VTLDESGGGLQAPGGALSLVCKASGFTFSSYDMGWIRQAPG
scFv62    GAGTTLTVLGQSSRSSA...........VTLDESGGGLQTPGGALSLVCKASGFTFSSYDMGWVRQAPG
scFv67    GAGTTLTVLGQSSRSSA...........VTLDESGGGLQTPGGALSLVCKASGFTFSSYDMGWVRQAPG
scFv114   GAGTTLTVLGQSSRSSA...........VTLDESGGGLQTPGGALSLVCKASGFTFSSYDMGWVRQAPG
scFv85    GAGTTLTVLGQSSRSSA...........VTLDESGGGLQTPGGALSLVCKASGFTFSSYDMGWVRQAPG
scFv111   GAGTTLTVLGQSSRSSA...........VTLDESGGGLQTPGGALSLVCEASGFTFSSYDMGWIRQAPG
scFv106   GAGTTLTVLGQSSRSSA...........MTLDESGGGLQTPGGALSLVCKASGFTFSSYDMGWVRQAPG
scFv64    GAGTTLTVLGQSSRSST...........VTLDESGGGLQTPGGTLSLACKASGFTFSGYDMGWVRQAPG
scFv113   GAGTTLTVLGQSSRSST...........VTLDESGGGLQTPGGTLSLACKASGFTFSGYDMGWVRQAPG
scFv120   GAGTTLTVLGQSSRSSA...........VTLDEYGGGLQTPGGALSLVCEASGFTFSSYDMLRIPHAPG
scFv57    GAGTTLTVLCQSSTSST...........VTLDESGGGLQAPGGALSLVCKASGFTFSSYDMGWIPQAPG
scFv95    GAGTTLTVLGQSSRSST...........VTLDESGGGLQTPGGALSLVCKASGFTFSSHDMGWVRQAPG
scFv69    GAGTTLTVLGQSSRSSA...........VTLDESGGGLQTPGGTLSLVCKASGFTFSSFNMFWVRQAPG
scFv77    GAGTTLTVLGQSSRSSA...........VTLDESGGGLQTPGGTLSLVCKASGFTFSSFNMFWVRQAPG
scFv93    GAGTTLTVLGQSSRSST...........VTLDESGGGLQTPGGALSLVCKASGFTFSSFNMFWVRQAPG
scFv71    GAGTTLTVLGQSSRSSA...........VTLDESGGGLQTPGGTLSLVCKASGFTFSSFNMFWVRQAPG
scFv61    GAGTTLTVLGQSSRSSA...........VTLDESGGGLQTPGGGLSLVCKASEFTFSSYAMEWVRQAPG
scFv108   GAGTTLTVLGQTSRSSA...........VTLDESGGGLQTPGGGLSLLCKASEFTSISYAMEWVRQAPG
scFv96    GAGTTLTVLGQSSRSSA...........VTLDESGGGLQTPGGGLSLVCKASEFTFSSYAMEWVRQAPG
scFv117   GAGTTLTVLGQSSRSSA...........VTLDESGGGLQTPGGALSLVCRASGITFSTYAMEWVRQAPG
scFv87    GAGTTLTVLGQSSRSSA...........VTLDESGGGLQTPGGGLSLVCKASGFTFSSYAMEWVRQAPG
scFv15    GAGTTLTVLGQSSRSSA...........VTLDESGGGLQTPGGALSLVCKASGFTFSSYDMGWVRQAPG
scFv37    GAGTTLTVLCHSSTSSD...........VTLDHSRGGLQTPGGSLSLVCNASGFTFSSFHMFWVRQAPG
scFv44    GASTTLTAPGSSSISSD...........ETLDDSGSGLRTPGRALNVFCFASGFFFMIFELFGVRQAPG
scFv4     GAGTTLTVLGQSSRSSA...........VTLDESGGGLQTPGGALSLVCKASGFTFSSYDMFWVRQAPG
scFv28    GAGTTLTVLGQSSRSSA...........VTLDESGGGLQTPGGALSLVCKASGFTFSSFNMFWVRQAPG
scFv9     GAGTTLTVLGQSSRSSA...........VTLDESGGGLQTPGGALSLVCKASGFTFSSNGMAWVRQAPG
scFv10    GAGTTLTVLGQSSRSSA...........VTLDESGGGLQTPGGTLSLVCKGSGFTFSSVNMFWVRQAPG
scFv29    GAGTTLTVLGQSSRSSA...........VTLDESGGGLQTPGGGLSLVCKGSGFTFSSFDMFWVRQAPG
scFv31    GAGTTLTVLGQSSRSSA...........VTLDESGGGLQTPGGGLSLVCKASGFTFSSYDMAWVRQEPS
scFv11    GAGTTLTVLGQSSRSSA...........VTLDESGGGLQTPGGGLSLVCKASGFTFSDYDMFWVRQAPS
scFv18    GAGTTLTVLGQSSRSSA...........VTLDESGGGLQTPGGGLSLVCKASGFTFSDYDMFWVRQAPS
scFv36    GATTTMIVRRSSSSSSA...........MMEDEGGGLLTTRGGLLILCCAASGFIFSYYEMLWLHPAPG
scFv88    GAGTTLTVLGQSSRSSA...........VTLDESGGGLQTPRGALSLVCKASGFTFSSYSMAWVRQAPG
scFv63    GAGTTLTVLGQSSRSSA...........VTLDESGGGLQTPGGTLSLVCKASGFTFSSFNMFWVRQAPG
scFv91    GAGTTLTVLGQSSRSSA...........VTLDESGGGLQTPGGTLSLVCKASGFTFSSFNMFWVRQAPG
scFv79    GAGTTLTVLRQSSTSSA...........VTMDDYGGGLLTTGGALILLCWASGF.PTFHGLDWMRQAPA
scFv81    GAGTTLTVLGQSSRSST...........VTLDESGGGLQAPGGALSLVCKASGFTFSSYDMGWIRQAPG
scFv89    GAGTTLTVLGQSSRSSA...........VTLDESGGGLQTPGGALSLVCKASGFTFSSYDMGWVRQAPG
scFv75    GAGTTLTVLGQSSRSSA...........VTLDESGGGLQTPGGALSLVCKASGFDFSSYGMGWMRQAPG
```

FIGURE 7 - PANEL 5

```
scFv100   KGLEWVAEISADGSYTTYYGAAVKGRATISRDNGQSTVRLQLNNLRAEDTATYFCAKS..GYGGAGW..
scFv131   KGLEWVGQISSDNGRYTTYGAAVKGRATISRDDGQSTVRLQLNNLKAEDTATYYCAKE..SDGDYNG..
scFv110   KGLEWLAGIYRDDD.STYYAPAVKGRATISRDNGQSTVRLQLNNLRTEDTATYYCAKE..SASGGW...
scFv97    KGLEWVAGIYSDGR.YTNYGAAVKGRATISRDNGQSSVRLQLNNLRAEDTATYYCTKS..ADSD..Y..
scFv98    KGLEWVAGISGDGS.FTHYGSAVKGRATISRDNGQSTVRLHLNNLRAEDTATYYCAKS..TGSGAGW..
scFv45    KGLEYVAGITDNGR.YASYGSAVDGRATISRDNGQSSVRLQLNNLRAEDTGTYYCARD..DGSGW....
scFv62    KGLEYVAGITNDGR.YASYGSAVDGRATISRDNGQSTVRLQLNNLRAEDTGTYYCARD..DGSGW....
scFv67    KGLEYVAGITNDGR.YASYGSAVDGRATISRDNGQSTVRLQLNNLRAEDTGTYYCARD..DGSGW....
scFv114   KGLEYVAGITNDGR.YASYGSAVDGRATISRDNGQSTVRLQLNNLRAEDTGTYYCARD..DGSGW....
scFv85    KGLEYVAGITNDGR.YASYGSAVDGRATISRDNGQSTVRLQLNNLRAEDTGTYYCARN..DGSGW....
scFv111   KGLEYVAGITSNGR.YASYGSAVDGRATISRDNGQSTVRLQLNNLRAEDTGTYYCARD..DGSGW....
scFv106   KGLEYVAGITNDGR.YASYGSAVDGRATISRDNGQSTVRLQLNNLRAEDTGTYYCARD..DGSGW....
scFv64    KGLEYVAGITSDGR.YASYGSAVDGRAAIWRDNGQSTVRLQLKNLRTEDTATYYCARN..DGSGW....
scFv113   KGLEYVAGITSDGR.YASYGSAVDGRAAIWRDNGQSTVRLQLKNLRTEDTATYYCARD..DGSGW....
scFv120   KGLEYVAGLTSNGR.YASYGSAVDGRATISRDNGQSTWRLHLNNLGAEDTGPYYCAGY..DGSGW....
scFv57    KGLEYVAGITDNGI.YASYGSAVDGRATISRDNRQSSVKLQLNNLKADDTGTYYCARD..DGSGW....
scFv95    KGLEYVAGITDDGR.YASYGPAVDGRATISRDNGQSTVRLQLKNLRAEDTATYYCARD..DGSGW....
scFv69    KGLEFVAGIGNTGR.STGYGSAVKGRATISRDNGQSTVRLQLNNLRAEDTGTYYCAKA..YGD......
scFv77    KGLEFVAGIGNTGR.STGYGSAVKGRATISRDNGQSTVRLQLNNLRAEDTGTYYCAKA..YGD......
scFv93    KGLEFVAGIGNTGG.STGYGSAVKGRATISRDNGQSTVRLQLNNLRAEDTGTYYCAKA..YGD......
scFv71    KGLEFVAGIGNTGR.STGYGSAVKGRATISRDNGQSTVRLQLNNLRAEDTGTYYCAKA...L.......
scFv61    KGLEWVAYINSDGS.STWYAPAVKGRATISRDNGQSTVRLQLNSLRAEDTATYYCTRG.....S.....
scFv108   KGLEWVAYINSDGS.STWHAPAVKGRATISRDNGQSTVRLQLNSLRAEDTATYYCTIC.....S.....
scFv96    KGLEWVAYINSDGS.STWYAPAVKGRATISRDNGQSTVRLQLNSLRAEDTATYYCTRG.....S.....
scFv117   KGLEFVAVVNAAGS..TYYGAAVKGRATISRDNGQSTVRLQLNNLRAEDTGTYYCTRG.....S.....
scFv87    KGLEWVAYINSDGS.STWYATAVKGRATISRDNGQSTVRLQLNNLRGEDTATYFCAKT..KYYN.....
scFv15    KGLEWVAYINSGSSTYYGTAVKGRASISRDNGQSTVRLQLNNLRVEDTGTYFCAKGASGYY.......
scFv37    EGLEYVAEI.TDTGSSTYYGAAVKGRATISRDNGQSTVRLQLNNLMADDTGTYFCAKSHSGYGWST...
scFv44    WVLEYIADV.SDTGNSTYYRAAVNVRAAISRNNGQMTLRLLLNDHTADDTCTYFCGYCHSDYCWST...
scFv4     KGLEFVAQI.NSAGSYTYGTAVKGRATISRDDGQSTVRLQLNNLRAEDTGIYFCAKSASGYYYSG...
scFv28    RGLEFVAGI.TSSGGSTYYGTAVKGRATISRDNGQSTVRMQLNNLRAEDTGTYFCARGAYDYYFYW...
scFv9     KGLEWVAGI.SSSGSYTNYGSAVKGRATISRDNGQSTVRLQLNNLRAEDTATYYCAKSSYAYYGFG...
scFv10    KGLEWVAGI.YSSGSSTHYGAAVKGRATISRDNGQSTVRLQLNNLRAEDTGIYYCAKDA.GCYTSG...
scFv29    KGLEWVAGI.RNDGSDTAYGAAVKGRATISKDNGQSTVRLQLNNLRAEDTGTYYCAKAAG.YCYVY...
scFv31    KGLEFVASI.SNTGSDTSYAPAVKGRATISRDNGQSTVRLQLNNLRAEDTATYYCAKSAGSYYWNA...
scFv11    KGLEFVAAI.TSSGTGTKYGAAVKGRATISKDNGQRTVRLQLNSLGAEDTGTYYCARSDADSTTWS...
scFv18    KGLEFVAAI.TSSGTGTKYGAAVKGRATISKDNGQSTVRLQLNSLRAEDTGTYYCARSDADSTTWS...
scFv36    EVQDFVTII.SGGGNYTYYGSAVDGGAIISRDDGKRMLMLQLNILEDDDTGFYPCADGASGYYYGG...
scFv88    KGLEFVAGI.QNDGSITDYGSAVDGRATISRDDGQSTVRLQLNNLRTEDTATYYCAKTTVADGVI....
scFv63    KGLEFVAGI.GNTGRSTGYGSAVDGRATISRDNGQSTVRLQLNNLRAEDTGTYYCAQAYGDS:......
scFv91    KGLEFVAGI.GNTGRSTGYGSAVKGRATISRDNGQSTVRLQLNNLRAEDTGTYYCAKAYGDS.......
scFv79    TGLEFVAGI.RSDGDSTAYGAAVDGHATVSRDNGQSTMRLQLNILRAEDDATYFCA.............
scFv81    KGLEYVAGI.TDNGTYASYGS................................................
scFv89    KGLEFVAGI.TNDGRYASYGSAVDGRATISRDNGQSTVRLQLNNPQG......................
scFv75    KGLEFVAAI.KKDGSYTAYGAAVDGRATISRDDGQSTVRLQLGNLRAEDTAP.................
```

FIGURE 7 - PANEL 6

```
scFv100    ..GAGLIDAWGHGTEVIVSSTSGQAGQHHHHHHGAYPYDVPDYAS
scFv131    ..GAGLIDAWGHGTEVIVSSTSGQAGQHHHHHHGAYPYDVPDYAS
scFv110    ..NAGWIDAWGHGTEVIVSSTSGQAGQHHHHHHGAYPYDVPDYAS
scFv97     ..GCDNIDAWGHGTEVIVSSTSGQAGQHHHHHHGAYPYDVPDYAS
scFv98     ..GASNIDAWGHGTEVIVSSTSGQAGQHHHHHHGAYPYDVPDYAS
scFv45     ..TGNSIDAWGHGTEIIVSSTSGQAGQHHHHHHGAYPYDVPDYAS
scFv62     ..TGNTIDTWGHGTEVIVSSTSGQAGQHHHHHHGAYPYDVPDYAS
scFv67     ..TGNTIDTWGHGTEVIVSSTSGQAGQHHHHHHGAYPYDVPDYAS
scFv114    ..TGNTIDTWGHGTEVIVSSTSGQAGQHHHHHHGAYPYDVPDYAS
scFv85     ..TGNTIDTWGHGTEVIVSSTSGQAGQHHHHHHGAYPYDVPDYAS
scFv111    ..TGNTIDAWGHGTEVIVSSTSGQAGQHHHHHHGAYPYDVPDYAS
scFv106    ..TGNTIDTWGHGTEVIVSSTSGQAGQHHHHHHGAYPYDVPDYAS
scFv64     ..NGNNIDAWGHGTEVIVSSTSGQAGQHHHHHHGAYPYDVPDYAS
scFv113    ..SGNNIDAWGHGTEVIVSSTSGQAGQHHHHHHGAYPYDVPDYAS
scFv120    ..TGNTIEAWGHRTEVLVSSTSGQAGQHHHHHHGAYPYDVPDYAS
scFv57     ..TGNSIDAWGHGTEVIVSSTSGQAGQHHHHHHGAYPYDVPDYAS
scFv95     ..SGDTIDTWGHGTEVIVSSTSGQAGQHHHHHHGAYPYDVPDYAS
scFv69     ....SNIDAWGHGTEVIVSSTSGQAGQHHHHHHGAYPYDVPDYAS
scFv77     ....SNIDAWGHGTEVIVSSTSGQAGQHHHHHHGAYPYDVPDYAS
scFv93     ....SNIDTWGHGTEVIVSSTSGQAGQHHHHHHGAYPYDVPDYAS
scFv71     .......WGHGTEVIVSSTSGQAGQHHHHHHGAYPYDVPDYAS
scFv61     ..GGENIDTWGHGTEVIVSSTSGQAGQHHHHHHGAYPYDVPDYAS
scFv108    ..GGENIYTCCHGTEVIVSSTSGQDGQHHHHHHGAYPYDVPDYAS
scFv96     ..GGENIDTWGHGTEVIVSSTSGQAGQHHHHHHGAYPYDVPDYAS
scFv117    ..GGENIDTWGHGTEVIVSSTSGQAGQHHHHHHGAYPYDVPDYAS
scFv87     ..SAGIIDAWGHGTEVIVSSTSGQAGQHHHHHHGAYPYDVPDYAS
scFv15     ...............SSSGQAGQHHHHHHGAYPYDVPDYAS
scFv37     ...AGDIDAWGHGTEVIVSSTSGQAGQHHHHHHGAYPYDVPDYAS
scFv44     ...AGDIDAWSHVIDFIVSSTSGQAGQHHHHHHGAYPYDDPDYAS
scFv4      .SDAGDIDAWGHGTEVIVSSTSGQAGQHHHHHHGAYPYDVPDYAS
scFv28     .NYAGTIDAWGHGTEVIVSSTSGQAGQHHHHHHGAYPYDVPDYAS
scFv9      ...APFIDAWGHGTEVIVSSTSGQAGQHHHHHHGAYPYDVPDYAS
scFv10     .DTAGCIDAWGHGTEVIVSSTSGQAGQHHHHHHGAYPYDVPDYAS
scFv29     .SCAGSIDAWGHGTEVIVSSTSGQAGQHHHHHHGAYPYDVPDYAS
scFv31     .GGAGSIDTWGHGTEVIVSSTSGQAGQHHHHHHGAYPYDVPDYAS
scFv11     ...AGEIDAWGHGTEVIVSSTSGQAGQHHHHHHGAYPYDVPDYAS
scFv18     ...AGEIDAWGHGTEVIVSSTSGQAGQHHHHHHGAYPYDVPDYAS
scFv36     .ADAGDIDAWGHGTEVIVSSTSGQAGQHHHHHHGAYPYDVPDYAS
scFv88     ..............................................
scFv63     .....NIDRMGPRDR.................................
scFv91     ..............................................
scFv79     ..............................................
scFv81     ..............................................
scFv89     ..............................................
scFv75     ..............................................
```

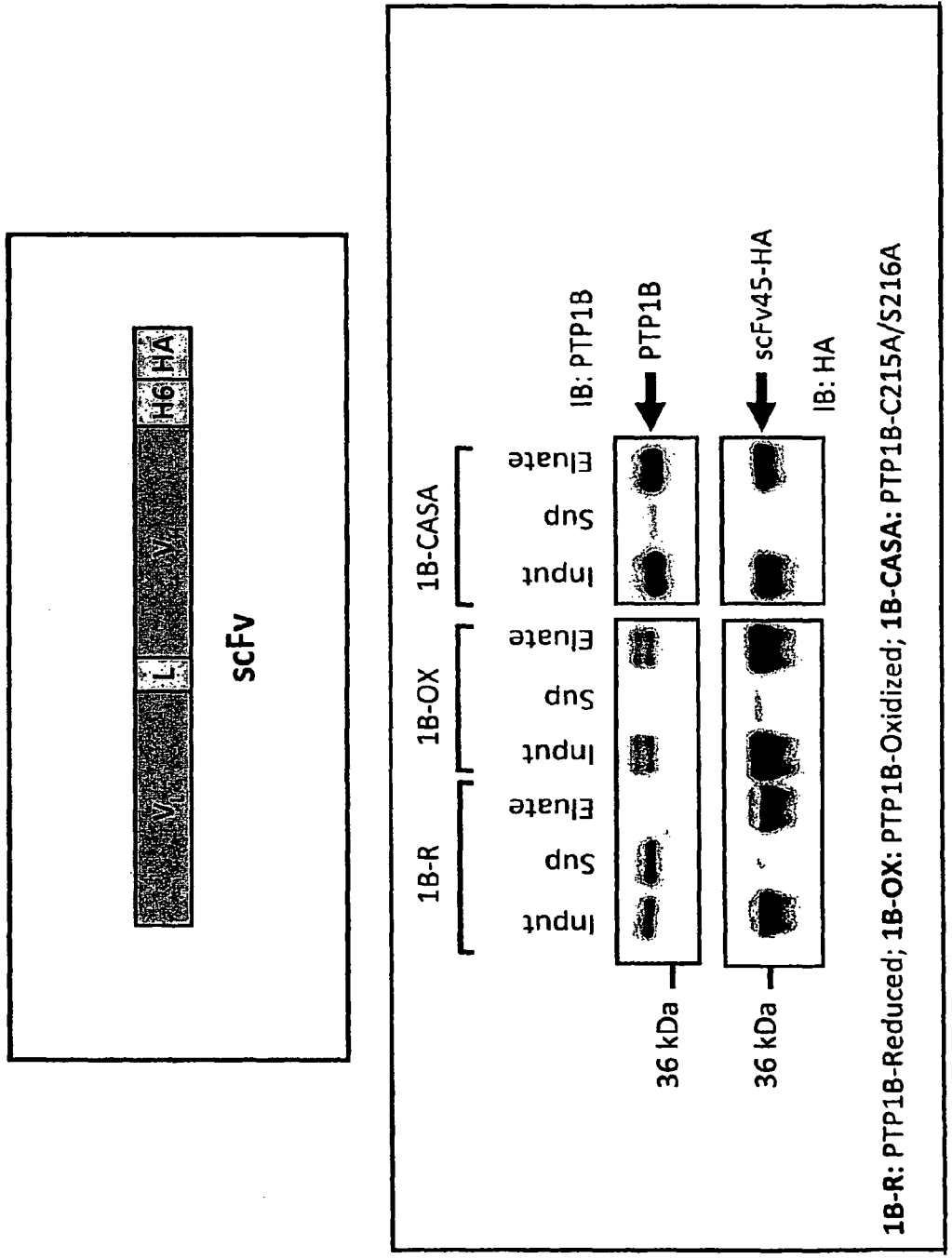
Figure 9a: Conformation-Sensor scFv45 Inhibits PTP1B Reactivation by Selectively Binding to PTP1B-OX in vitro

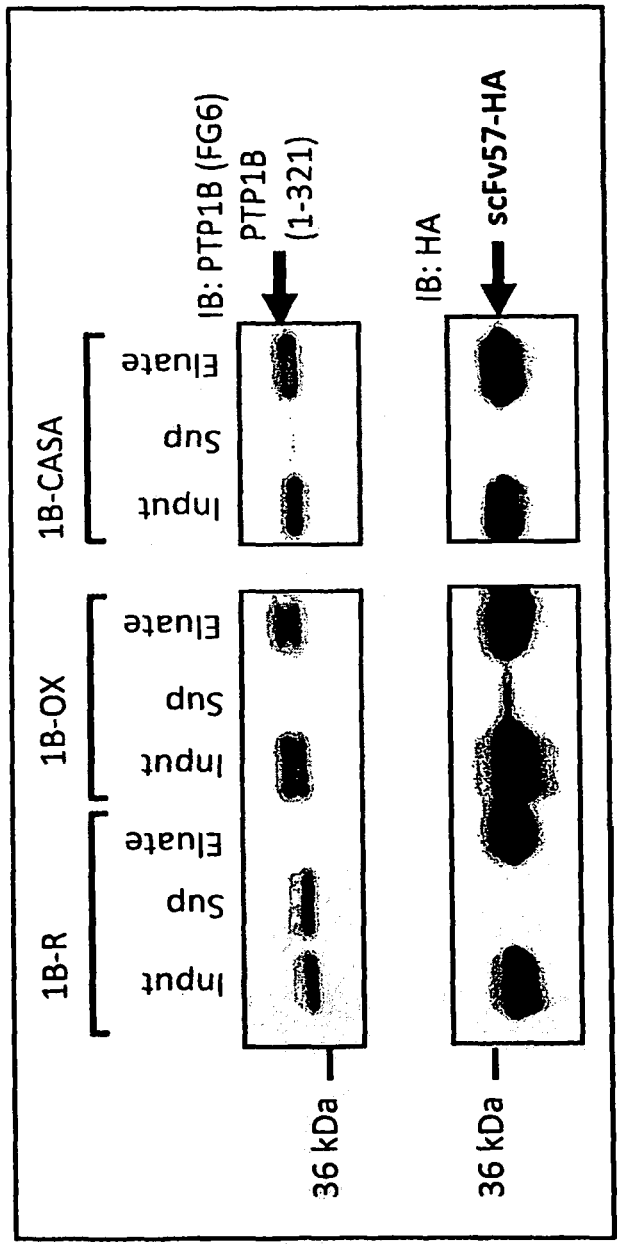
Figure 9b: scFv57 Binds Specifically to PTP1B-OX in vitro

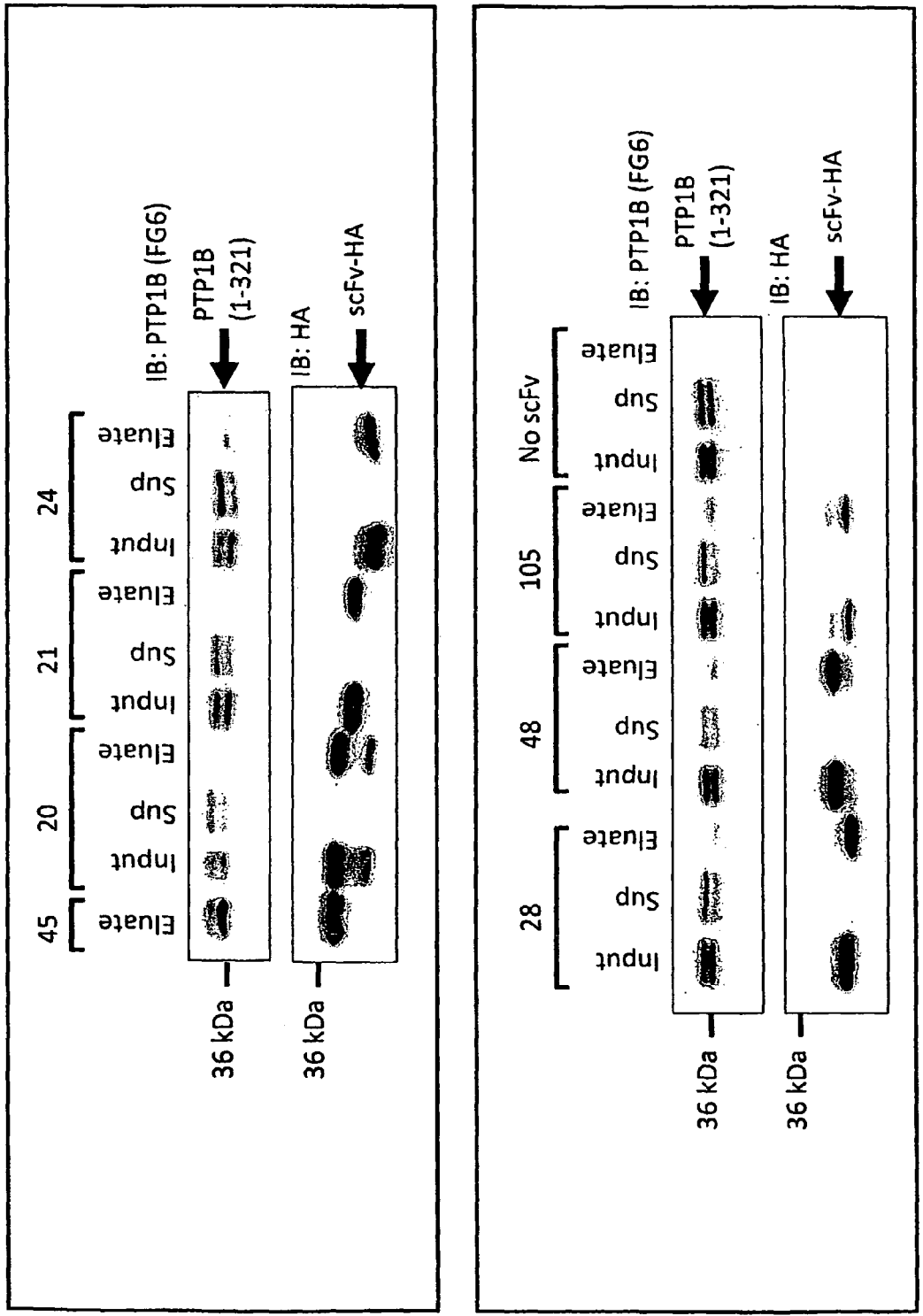
Figure 9c: Specific Interaction between PTP1B-OX and scFvs in vitro

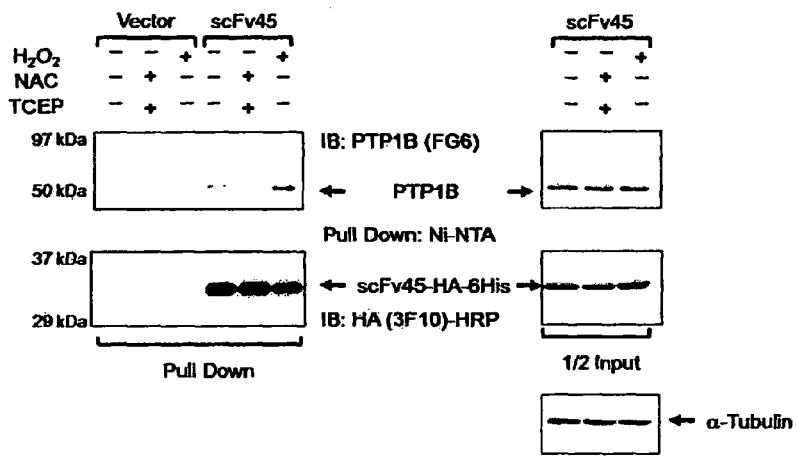
Figure 11a: Interaction between PTP1B$_{OX}$ and Intrabody45 in Mammalian Cell (Pull-down with Ni-NTA Agarose)
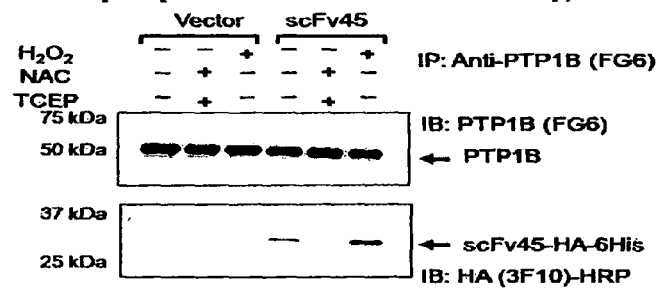
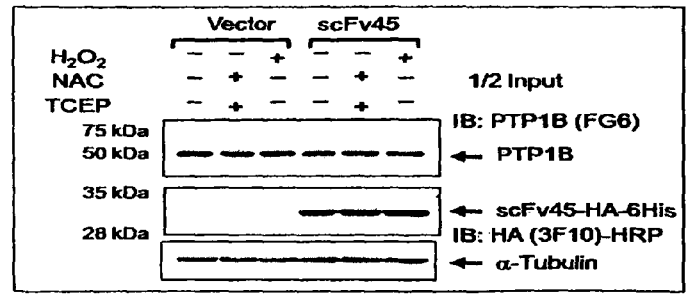
Figure 11b: Interaction between PTP1B$_{OX}$ and Intrabody45 in Mammalian Cell (Immunoprecipitation with anti-PTP1B antibody)

Figure 12a: Screening of PTP1B-OX specific Intrabodies in Mammalian Cell
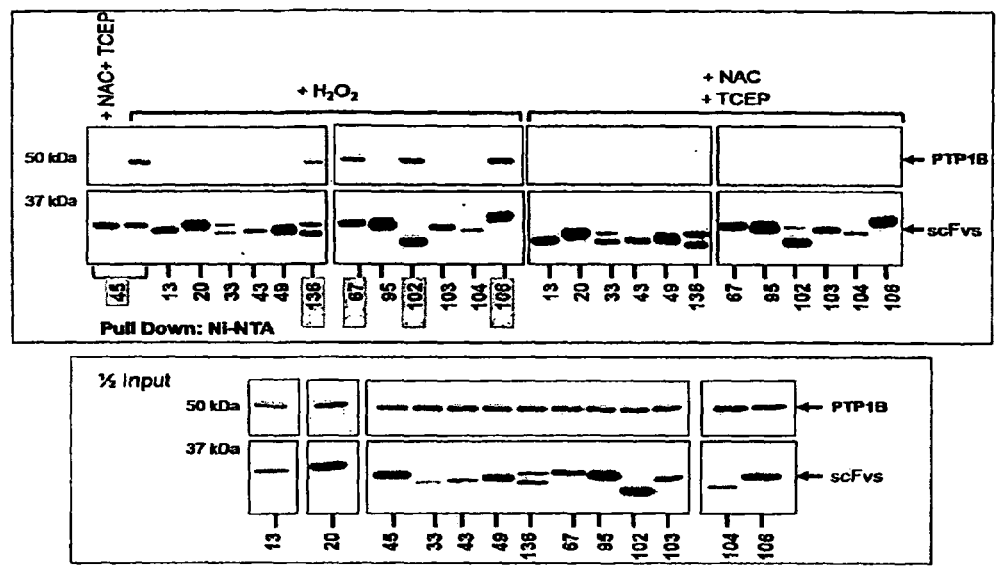
Figure 12b: Screening of PTP1B-OX specific Intrabodies in Mammalian Cell
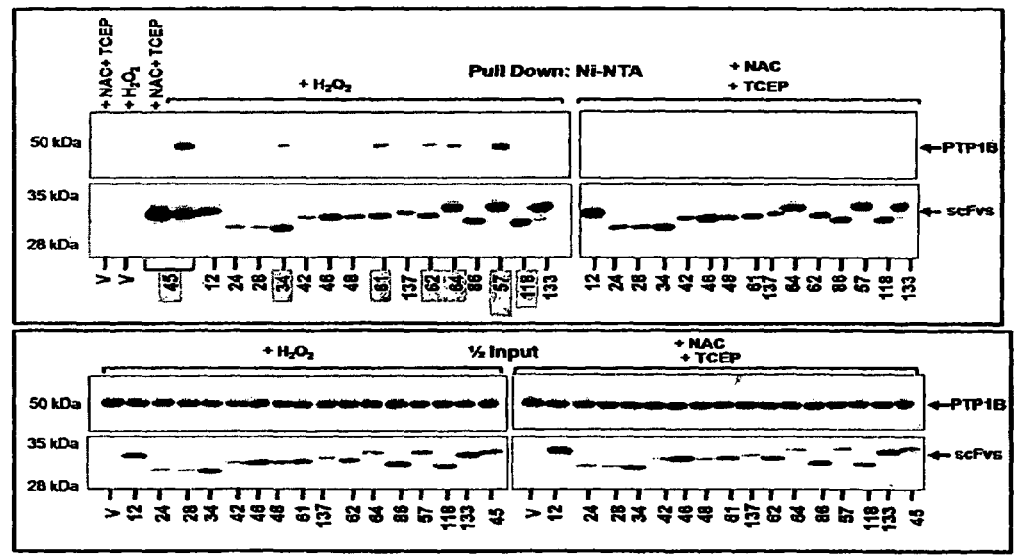

Figure 13: Intrabody 45 Causes Enhanced AKT Activation in Response to Insulin
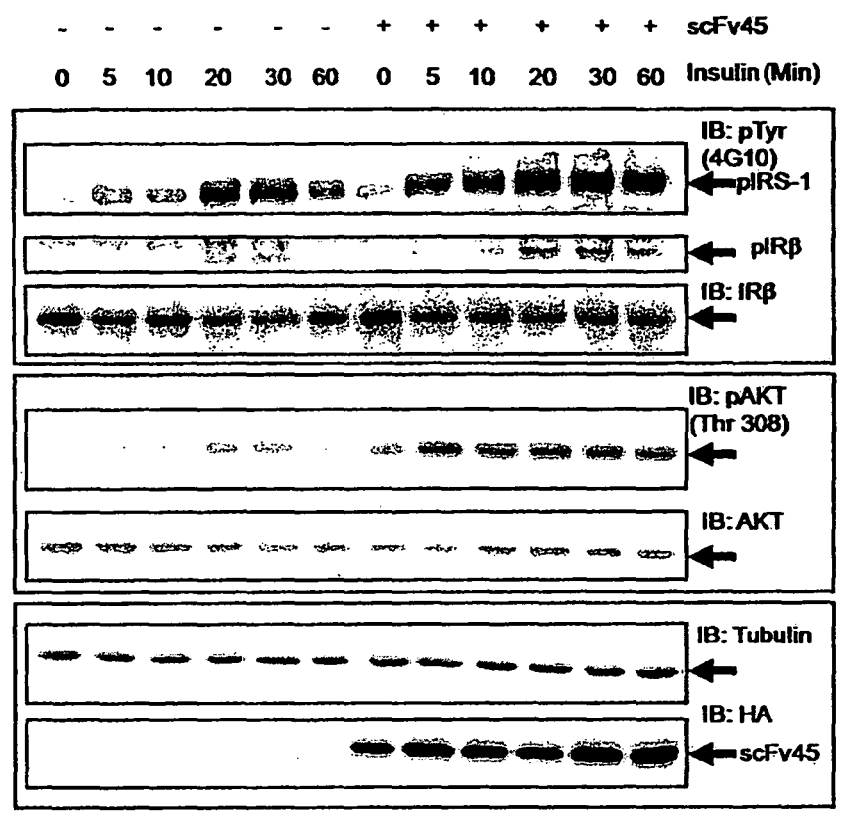

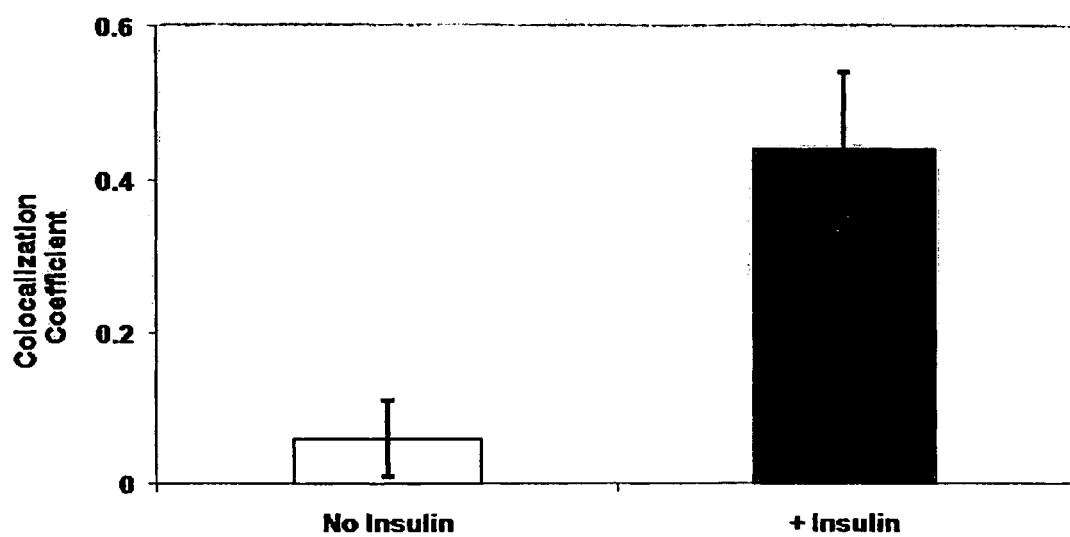
Figure 14b: Intrabody45 Colocalizes with PTP1B-OX in Cos1 Cells in Response to Insulin

US 9,074,002 B2

PTP1B INHIBITORS

FEDERALLY SPONSORED RESEARCH

This invention was made with government support under grant CA53840 and grant GM55989, both awarded by the National Institutes of Health. The government has certain rights in the invention.

CROSS REFERENCE TO RELATED APPLICATIONS

This application is a national stage filing under 35 U.S.C. §371 of International Application PCT/US2010/001251 designating the United States of America, and filed Apr. 27, 2010. This application claims the benefit under 35 U.S.C. §119(e) of U.S. Provisional Application No. 61/173,178, filed Apr. 27, 2009. The entire teachings of the referenced application are incorporated herein by reference.

BACKGROUND OF THE INVENTION

PTP1B Signaling

PTP1B is an intracellular protein tyrosine phosphatase. PTP activity is regulated by modifications of several amino acid residues in the polypeptide, such as phosphorylation of Ser residues (Brautigan and Pinault, 1993; Dadke et al., 2001; Flint et al., 1993) and oxidation of the active Cys residue in its catalytic motif (Lee et al., 1998; Meng et al., 2002), which is evolutionarily conserved among protein tyrosine phosphatases and dual specificity phosphatase family members (Andersen et al., 2001). In its reduced, active state, which is the basal state of the enzyme, PTP1B regulates a number of signaling pathways. For example, PTP1B activity antagonizes insulin signaling. Upon reception of an insulin signal by a target cell, PTP1B is reversibly oxidized, which removes the inhibitory regulation of insulin signaling by PTP1B until the enzyme returns to its reduced, active state. Other signaling pathways, for example EGF and leptin signaling, are also modulated by PTP1B activity. PTP1B is indicated in a number of human diseases, such as obesity and diabetes.

Many small molecule PTP1B inhibitors have been identified. The catalytic pocket of PTP1B tends to be highly charged and, as a result, small molecule inhibitors of PTP1B tend to be highly polar molecules. Such compounds are not passively absorbed by the human body and, thus, cannot be used as drugs via standard enteral or parenteral delivery routes. Because of these characteristics, PTP1B is seen to be an "undruggable" target (See, e.g., Cheng et al., Nat Biotech 2007).

The inability to find drugs that target this well-validated target is illustrated by the lack of clinical trials successfully completed by any of the companies pursuing PTP inhibitors. The identification and development of PTP inhibitors is highly desirable in order to address the major unmet medical need to treat PTP1B-related disorders, such as obesity and diabetes.

SUMMARY OF THE INVENTION

Described herein are agents, including antibodies, antibody fragments, polypeptides and other molecules, such as small organic compounds, that bind and stabilize reversibly oxidized, inactive PTP in such a manner that they inhibit (partially or completely) reactivation of the reversibly oxidized, inactive PTP1B by reduction (by reducing agent) and do not directly inhibit PTP1B activity (have no substantial direct inhibitory effect on phosphatase activity, as assessed, for example, in assays in vitro). Reversibly oxidized, inactive PTP is also referred to herein as PTP in reversibly oxidized, inactive form; PTP1B in cyclic sulphenamide conformation; and reversibly oxidized, inactive conformation of PTP1B. All are designated in the alternative and interchangeably herein as PTP1B-OX or PTP1B-SN. Without wishing to be bound by theory, Applicant describes herein binding to and stabilization of reversibly oxidized, inactive PTP1B. Methods of binding to and stabilizing PTP1B-OX, as well as agents, such as antibodies, antibody fragments, polypeptides and small molecules (such as small organic molecules), that bind to and stabilize PTP1B-OX and inhibit (partially or completely) its reactivation by reduction are encompassed within the scope of the invention described and claimed herein, regardless of the conformation of the inactive form they bind and stabilize.

Also described herein are methods of identifying agents that bind PTP1B-OX and stabilize it in its reversibly oxidized, inactive conformation and methods of screening for molecules that bind, modulate the stability of (e.g., stabilize) PTP1B-OX and do not directly inhibit native PTP enzyme activity (enzyme activity of PTP in its reduced, active form). Such agents may be any type of molecule or belong to any class of molecules. For example, such PTP1B-OX binding molecules may be amino acids, proteins, polypeptides, peptides, antibodies, antibody fragments, carbohydrates, glycans, nucleotides, nucleosides, nucleic acids, saccharides, polysaccharides, glycoproteins, lipids, organic compounds, such as small organic compounds, or any other molecule that binds PTP1B-OX. Further, PTP1B-OX-binding molecules may be in monomeric, dimeric, oligomeric or polymeric form; they may be amino acids, dipeptides, oligopeptides, polypeptides or proteins and analogues and derivatives thereof. Specific embodiments described herein are methods of identifying agents, including small molecules, that specifically bind PTP1B-OX and stabilize it in its reversibly oxidized, inactive conformation and methods of screening for small molecules that specifically bind PTP1B-OX, modulate the stability of (e.g., stabilize) PTP1B-OX and do not directly inhibit native PTP1B enzyme activity (enzyme activity of PTP1B in its reduced, active form). Also described herein are methods of stabilizing reversibly oxidized, inactive PTP1B (PTP1B-OX) and inhibiting its reactivation; methods of modulating PTP1B signaling by modulating (e.g., maintaining or enhancing) the stability of PTP1B-OX (rather than by direct modulation of PTP1B enzyme activity); methods of controlling the size of the pool of active PTP1B in a cell, in which reduction of reversibly oxidized, inactive PTP1B in the cell is hindered or decreased; methods of prolonging inactivation of PTP1B-OX; methods of prolonging the existence of PTP1B in its reversibly oxidized, inactive conformation; and methods of inhibiting reactivation of the reversibly oxidized, inactive form of PTP1B. Also described are methods of controlling (modulating) PTP1B-mediated regulation of signaling in a cell. Methods described herein apply to any pathway in which a stimulus induces transient oxidation and inactivation of a PTP, such as PTP1B (PTP1B-mediated regulation of any signal in a cell that is in response to a stimulus that induces such transient oxidation and inactivation of PTP1B), which, in turn, contributes to enhanced phosphorylation of a member or a target of the signaling pathway. Described herein are methods of controlling (modulating) PTP1B-mediated regulation of insulin, EGF and leptin signaling in cells; methods of controlling or modulating insulin, EGF or leptin signaling-mediated redox regulation of PTP1B activity; and methods of treating a condition (for example insulin resistance, diabetes or obesity) in which PTP1-B-mediated regulation of signaling is involved. Described herein are methods of augmenting a hormone response that is inhibited by PTP1B activity, for example methods of augmenting insulin response by stabilizing reversibly oxidized, inactive PTP1B (PTP1B-OX).

PTP1B-OX-binding polypeptides include all polypeptides that bind and stabilize PTP1B-OX. In certain embodiments, PTP1B-OX-binding polypeptides bind PTP1B-OX specifically (bind PTP1B-OX but do not bind PTP in its reduced state or conformation/active form). In some embodiments, such PTP1B-OX-binding polypeptides mimic the activity of an antibody or antibody fragment provided herein. In some embodiments, PTP1B-OX-binding polypeptides comprise a PTP1B-OX-binding domain or PTP1B-OX targeting domain. In some embodiments, PTP1B-binding polypeptides are fibronectin-like polypeptides comprising a PTP1B-OX-binding domain or PTP1B-OX targeting domain. In specific embodiments, PTP1B-OX binding polypeptides are adnectins or antibodies. These antibodies, antibody fragments and PTP1B-OX-binding polypeptides bind PTP1B-OX and stabilize the reversibly oxidized, inactive form such that reduction and reactivation of PTP1B-OX (and formation of reduced, active PTP1B) is inhibited. Such antibodies, antibody fragments and polypeptides can comprise any amino acid sequence, provided that the antibody, antibody fragment or polypeptide binds reversibly oxidized, inactive PTP1B (PTP1B-OX) and inhibits (partially or completely) its reduction and reactivation (conversion of PTP1B-OX) to reduced, active PTP1B. In certain embodiments, the antibodies, antibody fragments or polypeptides specifically bind PTP1B-OX (bind PTP1B-OX but do not bind PTP1B in its reduced state or conformation/active form). Some embodiments include single chain Fvs (scFvs), for example those provided herein (see scFvs included, as described below, within SEQ ID NO: 26 to SEQ ID NO: 29 and SEQ ID NO: 34 to SEQ ID NO: 149), which bind PTP1B-OX conformation and stabilize the reversibly oxidized, inactive conformation. The sequences provided in SEQ ID NO: 26 to SEQ ID NO: 29 and SEQ ID NO: 34 to SEQ ID NO:149 represent scFv sequences flanked by an N-terminal leader peptide and a C-terminal tag peptide. The N-terminal 22 amino acids MKKTAIAIAVALAGFATVAQAA (SEQ ID NO: 150) and the C-terminal 23 amino acids GQAGQHHHHHHGAYPYDVPDYAS (SEQ ID NO: 151) are coded for by components of the phagemid pComb3XSS (SEQ ID NO: 152) or the mammalian expression vector pcDNA3.2N5/GW/D-TOPO (SEQ ID NO: 23), into which the scFv sequences were cloned. The sequences present between these N- and C-terminal amino acids are the scFv sequences. The sequences are displayed herein with the N-terminal leader peptide, the C-terminal tag and the linker sequences underlined. The linker sequence is used to join a variable light ($V_L$) chain and a variable heavy ($V_H$) chain fragment to produce a scFv.

The scFv sequences provided herein are of the general pattern: NH$_2$—$V_L$-linker-$V_H$—COOH. The N-terminal leader peptide and the C-terminal tag, as well as the linkers, are identified in the provided scFv sequences (provided within SEQ ID NO: 26 to SEQ ID NO: 29 and SEQ ID NO: 34 to SEQ ID NO: 149, as described herein). The sequence between the N-terminal leader peptide and the linker is the $V_L$ fragment of the respective scFv, and the sequence between the linker and the C-terminal tag is the $V_H$ fragment of the respective scFv.

For example:
<u>MKKTAIAIAVALAGFATVAQAA</u>LTQPSSVSANPGGTV-KITCSGSSSAYGYGWYQQKSPGSAPVTVIYNNNKRP-SNIPSRFSGSKSGSTGTLTITGVQAEDEAVYFCGSEDS-STDAIFGAGTTLTVL<u>GQSSRSS</u>TVTLDESGGGLQAPG-GALSLVCKASGFTFSSYDMGWIRQAPGKGLEYVAGI-TDNGRYASYGSAVDGRATISRDNGQSSVRLQLNNLR-AEDTGTYYCARDDGSGWTGNSIDAWGHGTEIIVSST-SGQAGQHHHHHHGAYPYDVPDYAS (SEQ ID NO: 78). In this sequence, the N-terminal tag, the C-terminal tag, and the linker sequence are underlined. The scFv sequence is the sequence starting with "LTQ . . ." and ending with ". . . STS" between the N-terminal leader peptide and the C-terminal tag. Accordingly, the $V_L$ fragment of this scFv is the sequence starting with "LTQ . . ." and ending with ". . . TVL" between the N-terminal leader peptide and the linker, and the $V_H$ fragment of this scFv is the sequence starting with "TVT . . ." and ending with ". . . STS" between the linker and the C-terminal tag. Where possible, the C-terminal tag, the N-terminal leader peptide, the linker and the $V_L$ and $V_H$ fragments are identified in a similar manner in the scFv sequences provided herein.

Fifteen of the listed scFvs (scFv4, scFv28, scFv9, scFv10, scFv29, scFv31, scFv11, scFv18, scFv63, scFv75, scFv79, scFv81, scFv88, scFv89 and scFv91) display truncated amino acid sequences because of incomplete DNA sequences from the sequencing results.

Antigen-binding antibodies, antibody fragments and PTP1B-OX-binding polypeptides can comprise a portion or segment (continuous or not continuous) of a scFv of any one of SEQ ID NO: 26 to SEQ ID NO: 29 or SEQ ID NO: 34 to SEQ ID NO: 149, bind PTP1B-OX and stabilize reversibly oxidized, inactive conformation. For example, some embodiments include antibodies, antibody fragments or PTP1B-OX-binding polypeptides whose amino acid composition is sufficiently similar to all or a portion of a scFv of any one of SEQ ID NO: 26 to SEQ ID NO: 29 or SEQ ID NO: 34 to SEQ ID NO: 149 that they bind reversibly oxidized, inactive PTP1B-OX in such a manner that they inhibit its reduction (reactivation by reducing agent to reduced, active PTP1B). Any of these sequences can be changed by deletion, addition, substitution or replacement of one or more amino acid residues. For example, individual amino acid residues (one or more amino acid residues) of a scFv of any one of SEQ ID NO: 26 to SEQ ID NO: 29 and SEQ ID NO: 34 to SEQ ID NO: 149 may be substituted with or replaced by another amino acid residue, such as by an amino acid residue whose presence results in a silent substitution or a change in sequence that does not substantially alter the ability of the resulting antibody, antibody fragment or polypeptide to bind and stabilize PTP1B-OX. Such silent substitutions are well known to those of skill in the art Amino acid substitutions, additions and replacements can be naturally-occurring and/or non-naturally-occurring amino acid residues, including modified amino acid residues. Antibodies and antibody fragments can be of any length (e.g., shorter or longer than a sequence provided herein) sufficient to bind and stabilize PTP1B-OX. As is well known to the skilled artisan, variable regions can be of varying length (e.g., shorter or longer than the variable region of an antibody described herein). Deletion, substitution, or addition of one or more amino acid residues can result in functional antibodies or antibody fragments. For example, scFvs can comprise linker sequences of varying length and amino acid composition; framework and/or complementarity determining regions (CDR) of varying length and amino acid composition and, optionally, additional N-terminal or C-terminal sequences, for example leader peptides or tags. For example, a scFv can comprise any of the ScFvs whose amino acid sequences are provided herein (e.g., SEQ ID NO: 26-SEQ ID NO: 29, SEQ ID NO: 34-SEQ ID NO: 149) or a variant of any of the scFv sequences represented. Variants can differ from the ScFvs represented in any of SEQ ID NO: 26-29 and SEQ ID NO: 34-149 by one or more (at least one) alteration, which can be a substitution, deletion, addition and/or replacement, as described herein. Variants can be of any length (e.g., shorter or longer than the scFvs whose sequences are provided herein). The one or more alteration can be a naturally-occurring or a non-naturally occurring amino acid residue, including modified amino acid residues. In some embodiments described herein, an antibody, antibody fragment or PTP1B-OX-binding polypeptide can comprise any of the sequences presented herein or a variant thereof. The antibody, antibody fragment or PTP1B-OX-binding polypeptide that binds (specifically binds) PTP1B-OX and stabilizes it in the reversibly oxidized inactive form can comprise any of the sequences presented or a variant thereof. Variants of the amino acid sequences provided herein are referred to, respectively, as variant antibodies, variant antibody fragments or variant PTP1B-OX-binding polypeptides. The phrases antibody that specifically binds PTP1B-OX and stabilizes PTP1B-OX (also referred to as PTP1B-OX conformation or form), antibody fragment that specifically binds PTP1B-OX and stabilizes PTP1B-OX (also referred to as PTP1B-OX conformation or form) or polypeptide that specifically binds PTP1B-OX and stabilizes PTP1B-OX (also referred to as PTP1B-OX conformation or form) or substantially equivalent terms or phrases are intended to encompass antibodies, antibody fragments and PTP1B-OX-binding polypeptides that bind PTP1B-OX and whose sequences are all or a portion of a sequence presented herein or a variant thereof. A variant antibody, a variant antibody fragment and a variant polypeptide are, respectively, an antibody, antibody fragment and polypeptide whose amino acid composition differs from a sequence presented herein and that binds PTP1B-OX and stabilizes it in its reversibly oxidized, inactive conformation, without directly inhibiting PTP1B. Amino acid deletions, additions, replacements or substitutions can occur within the framework and/or complementarity determining regions of the scFvs described herein. Many leader peptides and protein tags are known to the skilled artisan. Leader peptides and/or protein tags may be used for protein purification, detection, solubilization, targeting of a protein or peptide to a subcellular localization or for secretion, and other purposes well known to those of skill in the art. It is well known in the art that scFv linker sequences may vary in length and amino acid sequence.

Typically, the antibody, antibody fragment or PTP1B-OX-binding polypeptide does not bind or directly affect the activity of reduced, active PTP1B. Binding of such antibodies, antibody fragments or polypeptides is referred to herein as specific binding and the antibodies, antibody fragments and polypeptides as antibodies, antibody fragments and polypeptides that specifically bind PTP1B-OX. Antibodies, antibody fragments and polypeptides that specifically bind PTP1B-OX produce their effects on PTP1B-mediated regulation of signaling by stabilizing PTP1B-OX and on their own, do not inhibit (do not directly inhibit) reduced, active PTP1B. Antibodies, antibody fragments and polypeptides that specifically bind PTP1B-OX do not bind the active site of reduced, active PTP1B. They do not bind the active site of the enzyme in its reduced, active state. They may, however, bind residues that are part of the active site, but binding to these residues is restricted to the reversibly oxidized, PTP1B-OX state. In some embodiments, the antibody is an intrabody, such as a scFv expressed inside a cell. In some embodiments, the antibody, antibody fragment or polypeptide is further characterized in that it binds PTP1B-CASA mutant protein.

Also described herein are methods of identifying agents that bind PTP1B-OX and stabilize this inactive form by assessing interference with PTP-antibody binding, PTP-antibody fragment binding, PTP1B-polypeptide binding or PTP1B-small molecule binding. Such agents bind reversibly oxidized, inactive PTP1B (PTP1B-OX) and stabilize it in such a manner that they inhibit reactivation of PTP1B-OX by reduction (by reducing agent) and have no substantial direct inhibitory effect on phosphatase activity/PTP1B activity. In some embodiments, the method is one of identifying or screening for an agent (e.g., an antibody, an antibody fragment, a polypeptide or a small (organic) molecule) that specifically binds PTP1B-OX and stabilizes its conformation. In some embodiments, the ability of a candidate agent to bind to and stabilize PTP1B-OX is assessed by determining whether it is able to interfere with binding to PTP1B-OX by an antibody or antibody-fragment that specifically binds PTP1B-OX and stabilizes its conformation. In some embodiments, the method comprises (a) combining (i) PTP1B-OX; (ii) a molecule that specifically binds PTP1B-OX and stabilizes the conformation (e.g., an antibody that specifically binds PTP1B-OX and stabilizes the conformation; an antibody fragment that specifically binds PTP1B-OX and stabilizes the conformation; a polypeptide that specifically binds PTP1B-OX and stabilizes the conformation; or a small molecule that specifically binds PTP1B-OX and stabilizes the conformation); and (iii) a candidate agent, under conditions appropriate for binding of PTP1B-OX with a molecule that specifically binds PTP1B-OX and stabilizes the conformation;

(b) assessing binding of PTP1B-OX with the molecule a(ii); and (c) comparing binding assessed in (b) with binding of PTP1B-OX with the molecule a(ii) under substantially the same conditions, but in the absence of the candidate agent (also referred to as to an appropriate reference or control), wherein if binding of PTP1B-OX to the molecule a(ii) occurs to a lesser extent in the presence of the candidate agent than in the absence of the candidate agent (or as compared to the reference or control), the candidate agent is an agent that specifically binds PTP1B-OX.

In one embodiment, the method comprises (a) combining (i) PTP1B-OX; (ii) a molecule that is an antibody that specifically binds and stabilizes PTP1B-OX; and (iii) a candidate agent, (e.g., in a cell, in assay media or in a solution). Conditions used are those appropriate for binding of PTP1B-OX with the antibody. In addition, if the candidate agent is an agent that binds PTP1B-OX, binding occurs, forming PTP1B-OX-bound candidate agent. In other embodiments of the method, the molecule of (ii) is an antibody fragment that specifically binds and stabilizes PTP1B-OX, a polypeptide that specifically binds and stabilizes PTP1B-OX, or any molecule that specifically binds and stabilizes PTP1B-OX. In some embodiments, the molecule is a small organic compound.

In certain embodiments, the candidate agent is a small molecule (e.g., a small organic molecule) and the agent identified is a small molecule (e.g., small organic molecule) that specifically binds PTP1B-OX and stabilizes it. The candidate agent can be any of a wide variety of agents, such as but not limited to, an antibody, an antibody fragment (e.g., a scFv intrabody or antigen-binding antibody fragment) or a polypeptide.

In step (c), comparison can be to an appropriate reference or control. An appropriate reference or control, to which binding is compared in the method, is the results of assessing binding under the same conditions as those used for assessing binding of the candidate agent (as described above and elsewhere herein), but in the absence of the candidate agent. Assessment in the absence of the candidate agent can be carried out at the same time the candidate agent is assessed for its ability to bind PTP1B-OX, previously or subsequently, provided that substantially the same conditions (other than presence of the candidate agent) are used. The reference or control can be a pre-established value or set of values; a value or set of values established at the time the assessment is being carried out; or a value or set of values established after assessment of the candidate agent has been completed.

In some embodiments, agents that specifically bind PTP1B-OX are identified by assessing the ability of a candidate agent to disrupt binding of a molecule (for example, an antibody or antibody fragment) to PTP1B-OX. Such an agent can be any molecule that specifically binds to PTP1B-OX. Agents, for example small molecules (e.g., small organic molecules), identified by this method exhibit high affinity for binding the reversibly oxidized, inactive form, as evidenced by their ability to displace a molecule bound to PTP1B-OX. In some embodiments, the method is a method of identifying or screening for an agent that (a) displaces a molecule (e.g., an antibody, antibody fragment, polypeptide or small molecule) that binds to and stabilizes (is bound to and has stabilized) PTP1B-OX and (b) binds to and stabilizes PTP1B-OX. The method comprises:

(a) combining (i) a PTP1B-OX-molecule complex that comprises PTP1B-OX having bound thereto a molecule (e.g., an antibody that specifically binds PTP1B-OX and stabilizes the reversibly oxidized, inactive conformation of PTP1B-OX; an antibody fragment that specifically binds PTP1B-OX and stabilizes the reversibly oxidized, inactive conformation; a polypeptide that specifically binds PTP1B-OX and stabilizes the reversibly oxidized, inactive conformation; a small molecule that specifically binds PTP1B-OX and stabilizes the reversibly oxidized, inactive conformation) and (ii) a candidate agent, under conditions appropriate for detecting displacement of the molecule from PTP1B-OX in the PTP1B-OX molecule complex; and (b) assessing displacement of the molecule from PTP1B-OX in the complex by the candidate agent, wherein if displacement has occurred, the candidate agent is an agent that displaces a molecule (e.g., an antibody, antibody fragment, polypeptide or small molecule) that binds to and stabilizes (is bound to and has stabilized) PTP1B-OX.

Conditions used are those appropriate for detecting displacement of the molecule from the complex.

In one embodiment, the method comprises (a) combining (i) a complex (a PTP1B-OX-antibody complex) that comprises PTP1B-OX having bound thereto a molecule that is an antibody that specifically binds PTP1B-OX and stabilizes the conformation; and (ii) a candidate agent. Conditions used are those appropriate for assessing or detecting displacement of the antibody from the complex. If the candidate agent is an agent that displaces the antibody from the PTP1B-OX-antibody complex, PTP1B-OX-candidate agent complex will form and the antibody will be displaced. In other embodiments of the method, the molecule of (i) (in the complex) is an antibody fragment that specifically binds PTP1B-OX and stabilizes the conformation, a polypeptide that specifically binds PTP1B-OX and stabilizes the conformation, or a small molecule that specifically binds PTP1B-OX and stabilizes the conformation.

In some embodiments, the method further comprises comparing displacement assessed in (b) with displacement of the molecule from PTP1B-OX in the complex under substantially the same conditions, but in the absence of the candidate agent, wherein if displacement occurs to the same or a lesser extent in the presence of the candidate agent than in the absence of the candidate agent, the candidate agent is not an agent that displaces a molecule that binds to and stabilizes (is bound to and has stabilized) PTP1B-OX and binds to and stabilizes PTP1B-OX.

In step (b), comparison can be made to an appropriate reference or control. An appropriate control is described above. Agents can also be identified by insilico screening, such as by using docking methods to design or identify molecules or compounds that bind the reversibly oxidized, inactive form of PTP1B (e.g., with reference to its crystal structure).

Agents identified by methods described herein can be further assessed for their ability to bind and stabilize PTP1B-OX, for example in in vitro assays and in appropriate animal models.

Also described herein are an isolated PTP1B-OX:antibody complex, an isolated PTP1B-OX:antibody fragment complex, and an isolated PTP1B-OX:PTP1B-OX-binding polypeptide complex. In specific embodiments, the antibody component of the isolated PTP1B-OX:antibody complex comprises an amino acid sequence described herein, for example a sequence selected from any of the scFv sequences of SEQ ID NO: 26 to SEQ ID NO: 29 or SEQ ID NO: 34 to SEQ ID NO: 149. In some embodiments, the antibody fragment component of the isolated PTP1B-OX:antibody fragment complex comprises a sufficient portion or segment of the amino acid sequences described herein, for example a sequence selected from any of the scFv sequences of SEQ ID NO: 26 to SEQ ID NO: 29 or SEQ ID NO: 34 to SEQ ID NO: 149. In some embodiments, the PTP1B-OX-binding polypeptide component of the isolated PTP1B-OX: PTP1B-OX-binding polypeptide complex comprises a sufficient portion or segment of the amino acid sequences described herein, for example a sequence selected from a CDR of any of the scFv sequences of SEQ ID NO: 26 to SEQ ID NO: 29 or SEQ ID NO: 34 to SEQ ID NO: 149, to specifically bind reversibly oxidized, inactive PTP1B (PTP1B-OX) and stabilize its conformation such that reduction is inhibited and reactivation of the inactive form is inhibited. Such antibodies, antibody fragments and PTP1B-OX-binding polypeptide can comprise any of the sequences described herein, including variants thereof as described herein.

Further described herein is a method of stabilizing reversibly oxidized, inactive PTP1B (PTP1B-OX) in which reversibly oxidized, inactive PTP is combined with an agent that binds the oxidized conformation and inhibits reactivation of PTP1B-OX by a reducing agent. Here, the agent can be, for example, an antibody that specifically binds reversibly oxidized, inactive PTP1B and stabilizes the inactive conformation; an antibody fragment that specifically binds reversibly oxidized, inactive PTP1B and stabilizes the inactive conformation; a polypeptide that specifically binds reversibly oxidized, inactive PTP1B and stabilizes the inactive conformation; or a small molecule that binds reversibly oxidized, inactive PTP and stabilizes the inactive conformation. Such antibodies, antibody fragments and polypeptides can comprise any amino acid sequence, provided that the antibody, antibody fragment or polypeptide binds reversibly oxidized, inactive PTP1B (PTP1B-OX) and inhibits (partially or completely) its reduction (reactivation by reducing agent to the reduced, active PTP1B). Antibodies, antibody fragments and PTP1B-OX-binding polypeptides used in the method can comprise any of the ScFvs of any one of SEQ ID NO: 26 to SEQ ID NO: 29 or SEQ ID NO: 34 to SEQ ID NO: 149, or any variant thereof, as described herein.

In specific embodiments, the method is a method of stabilizing reversibly oxidized, inactive PTP1B in a cell (e.g., human or other mammalian cell), such as in an individual (e.g. a human or other mammal or vertebrate). In some embodiments, the method is one of stabilizing reversibly oxidized, inactive PTP1B in cells. In some embodiments, the agent is administered by a route and in such a quantity that it enters cells in sufficient amount or concentration to have the desired effect (e.g., inhibiting or preventing reduction of inactive PTP1B-OX and its reactivation). The agent, for example an intrabody (e.g., a scFv), can be administered as a result of/by means of gene expression in cells (e.g., gene therapy).

A further method described herein is a method of decreasing the pool of reduced, active PTP1B in a cell, comprising inhibiting the reduction of reversibly oxidized, inactive PTP1B (PTP1B-OX) in the cell to reduced, active PTP1B. This can be carried out, for example, by contacting reversibly oxidized, inactive PTP1B in the cell with an agent that binds reversibly oxidized, inactive PTP1B and stabilizes the inactive conformation. The agent can be an antibody that specifically binds reversibly oxidized, inactive PTP1B and stabilizes the inactive conformation, an antibody fragment that specifically binds reversibly oxidized, inactive PTP and stabilizes the inactive conformation, a polypeptide that specifically binds reversibly oxidized, inactive PTP1B and stabilizes the inactive conformation or a small molecule that specifically binds reversibly oxidized, inactive PTP1B and stabilizes the inactive conformation. In certain embodiments, the agent is an intrabody, for example a intracellular scFv. The composition of the antibody, antibody fragment or polypeptide can comprise any of the sequences presented herein or a variant thereof, as described herein.

Such antibodies, antibody fragments and polypeptides can comprise any amino acid sequence, provided that the antibody, antibody fragment or polypeptide binds reversibly oxidized, inactive PTP1B (PTP1B-OX) and inhibits (partially or completely) its reduction to reduced, active PTP (reactivation of PTP1B-OX by reduction). Specific embodiments include antibodies that comprise all or a portion (continuous or not continuous) of a sequence selected from the scFv sequences of any one of SEQ ID NO: 26 to SEQ ID NO: 29 on SEQ ID NO. 34 to SEQ ID NO. 149, bind PTP1B-OX conformation and stabilize the reversibly oxidized, inactive conformation. Antibody fragments or PTP1B-OX-binding polypeptides can comprise a portion or segment (continuous or discontinuous) of any of the scFv sequences provided in SEQ ID NO: 26 to SEQ ID NO: 29 or SEQ ID NO: 34 to SEQ ID NO. 145, bind PTP1B-OX and stabilize reversibly oxidized, inactive conformation. For example, embodiments include antibodies, antibody fragments and PTP1B-OX-binding polypeptides whose amino acid composition is sufficiently similar to all or a portion of the scFv sequence of any one of SEQ ID NO: 26 to SEQ ID NO: 29 or SEQ ID NO. 34 to SEQ ID NO. 149 that they bind reversibly oxidized, inactive PTP1B-OX in such a manner that they inhibit (partially or completely) its reduction (reactivation by reducing agent to reduced, active PTP1B). Such antibodies, antibody fragments and PTP1B-OX-binding polypeptides, as well as variant antibodies, variant antibody fragments and variant polypeptides, are described herein.

Additional embodiments of methods are a method of prolonging existence of PTP1B in its oxidized/inactive conformation or prolonging inactivation of PTP1B by stabilizing the inactive form (PTP1B-OX), and a method of inhibiting reactivation of reduced, active PTP1B. In each of these embodiments, an agent (e.g., an antibody, an antibody fragment, a polypeptide, a small organic molecule) that binds to and stabilizes PTP1B-OX and inhibits its reactivation is administered, for example as described above in the context of the method of stabilizing reversibly oxidized, inactive PTP1B in cells.

A method of controlling PTP1B-mediated regulation of signaling in a cell is also described herein. Such a method comprises modulating the pool of reduced, active PTP1B and reversibly oxidized, inactive PTP1B in the cell by controlling the extent to which PTP1B-OX is reduced. In the method, an agent that specifically binds PTP1B-OX and stabilizes the inactive conformation is introduced into or expressed in the cell in sufficient quantity to inhibit or prevent reduction (reactivation) of inactive PTP1B-OX. The agent can be of any type, including but not limited to, proteins, polypeptides, peptides, glycoproteins, glycans, carbohydrates, lipids, antibodies, antibody fragments, or small molecules (e.g., small organic molecules). In a specific embodiment, the agent can be an Adnectin™. In specific embodiments, the agent can be, for example, a small molecule that specifically binds PTP1B-OX and stabilizes the inactive conformation, an antibody that specifically binds PTP1B-OX and stabilizes the inactive conformation, an antibody fragment that specifically binds PTP1B-OX and stabilizes the inactive conformation, or a polypeptide that specifically binds PTP1B-OX and stabilizes the inactive conformation. In specific embodiments, the agent is an intrabody, such as a scFv. Such antibodies, antibody fragments and polypeptides can comprise any amino acid sequence, provided that the antibody, antibody fragment or polypeptide binds reversibly oxidized, inactive PTP1B (PTP1B-OX) and inhibits (partially or completely) its reduction by reducing agent to reduced active PTP1B (reactivation of PTP1B-OX by reduction). Specific embodiments include antibodies that comprise all or a portion of a sequence selected from any of the scFv sequences of any one of SEQ ID NO: 26 to SEQ ID NO: 29 or SEQ ID NO. 34 to SEQ ID NO. 149, bind PTP1B-OX conformation and stabilize the reversibly oxidized, inactive conformation, as well as antibody fragments or PTP1B-OX-binding polypeptides that comprise a portion or segment (contiguous or discontinuous) of any one of SEQ ID NO: 26 to SEQ ID NO: 29 or SEQ ID NO. 34 to SEQ ID NO. 149, bind PTP1B-OX and stabilize the reversibly oxidized, inactive conformation. Further embodiments include antibodies, antibody fragments and polypeptides whose amino acid composition is sufficiently similar to all or a portion of any one of SEQ ID NO: 26 to SEQ ID NO: 29 or SEQ ID NO. 34 to SEQ ID NO. 149 that they bind reversibly oxidized, inactive PTP1B in such a manner that they inhibit its reduction to reduced, active PTP1B (reactivation by reducing agent). Such antibodies, antibody fragments and PTP1B-OX-binding polypeptides, as well as variant antibodies, variant antibody fragments and variant polypeptides, are described herein.

In some embodiments, the method is one of controlling or modulating redox regulation, for example reversible oxidation of PTP1B, such as signaling-mediated redox regulation, of PTP1B. Any PTP1B-mediated regulation of a signaling pathway, for example a signaling pathway involving and/or affected by PTP redox regulation, such as reversible oxidation of PTP1B, may be modulated by methods and agents provided herein. Non-limiting examples of signaling pathways that involve PTP redox regulation are insulin, EGF, and leptin signaling. In some embodiments, the method is a method of controlling PTP1B-mediated regulation of insulin signaling. In some embodiments, the method is a method of controlling PTP1B-mediated regulation of EGF signaling or a method of controlling PTP1B-mediated regulation of leptin signaling.

Also described herein are methods of identifying an agent that binds to and stabilizes PTP1B-OX and does not bind PTP in its reduced, active form (PTP1B). In some embodiments, the method comprises contacting PTP1B with an agent that binds to and stabilizes PTP1B-OX and assessing binding of the agent to PTP1B, wherein if the agent does not bind PTP1B, the agent is identified as an agent that binds and stabilizes PTP1B-OX and does not bind PTP1B.

PTP is a key regulator of insulin and leptin signaling. Consequently, PTP became a highly prized target in the pharmaceutical industry for therapeutic intervention in diabetes and obesity (Andersen et al., FASEB J. 18(1): 8, 2004; Tonks et al, FEBS Lett. 3: 546, 2003). In addition, more recent studies suggest that it may also be a therapeutic target in breast cancer (Tonks, Cancer Cell 11(3): 214, 2007). Although there have been major programs in industry focused on developing small molecule inhibitors of PTP1B, these efforts have been frustrated by technical challenges arising from the chemical properties of the PTP active site. The susceptibility of PTPs to oxidation causes problems in high throughput screens. In addition, the tendency of potent inhibitors to be highly charged, for example non-hydrolyzable pTyr mimetics, presents problems with respect to bioavailability. Consequently new approaches to inhibition of PTP1B are required to reinvigorate drug development efforts.

BRIEF DESCRIPTION OF THE DRAWINGS

FIG. 6: Aligned sequences of scFvs binding PTP1B-OX. The displayed scFv fragments (from the N-terminus to the linker sequence) include the N-terminal tag (MKKTAIAIA-VALAGFATVAQAA, SEQ ID NO: 150), the VL sequence and the linker sequence (GQSSRSS, SEQ ID NO: 20). The complementarity determining regions (CDRs) of the light chain were identified as: CDR1: 29-50, CDR2: 60-83, and CDR3: 100-124. scFv1: SEQ ID NO: 34; scFv16: SEQ ID NO: 49; scFv26: SEQ ID NO: 49; scFv2: SEQ ID NO: 35; scFv8: SEQ ID NO: 41; scFv17: SEQ ID NO: 50; scFv39: SEQ ID NO: 72; scFv14: SEQ ID NO: 47; scFv49: SEQ ID NO: 47; scFv6: SEQ ID NO: 39; scFv12: SEQ ID NO: 45; scFv21: SEQ ID NO: 54; scFv34: SEQ ID NO: 67; scFv13: SEQ ID NO: 46; scFv47: SEQ ID NO: 80; scFv19: SEQ ID NO: 52; scFv22: SEQ ID NO: 55; scFv53: SEQ ID NO: 86; scFv27: SEQ ID NO: 60; scFv40: SEQ ID NO: 73; scFv41: SEQ ID NO: 74; scFv42: SEQ ID NO: 75; scFv48: SEQ ID NO: 81; scFv60: SEQ ID NO: 93; scFv43: SEQ ID NO: 76; scFv58: SEQ ID NO: 91; scFv56: SEQ ID NO: 89; scFv59: SEQ ID NO: 92; scFv50: SEQ ID NO: 83; scFv52: SEQ ID NO: 85; scFv121: SEQ ID NO: 145; scFv123: SEQ ID NO: 146; scFv51: SEQ ID NO: 84; scFv104: SEQ ID NO: 131; scFv20: SEQ ID NO: 53; scFv25: SEQ ID NO: 58; scFv55: SEQ ID NO: 88; scFv32: SEQ ID NO: 65; scFv134: SEQ ID NO: 157; scFv119: SEQ ID NO: 143; scFv46: SEQ ID NO: 79; scFv65: SEQ ID NO: 98; scFv73: SEQ ID NO: 106; scFv90: SEQ ID NO: 121; scFv68: SEQ ID NO: 101; scFv74: SEQ ID NO: 107; scFv70: SEQ ID NO: 103; scFv92: SEQ ID NO: 123; scFv83: SEQ ID NO: 114; scFv72: SEQ ID NO: 105; scFv102: SEQ ID NO: 130; scFv86: SEQ ID NO: 117; scFv84: SEQ ID NO: 115; scFv80: SEQ ID NO: 111; scFv105: SEQ ID NO: 132; scFv112: SEQ ID NO: 137; scFv118: SEQ ID NO: 142; scFv124: SEQ ID NO: 147; scFv115: SEQ ID NO: 140; scFv82: SEQ ID NO: 113; scFv3: SEQ ID NO: 36; scFv30: SEQ ID NO: 63; scFv23: SEQ ID NO: 56; scFv7: SEQ ID NO: 40; scFv35: SEQ ID NO: 68; scFv5: SEQ ID NO: 38; scFv24: SEQ ID NO: 57; scFv33: SEQ ID NO: 66; scFv66: SEQ ID NO: 99; scFv38: SEQ ID NO: 71; scFv54: SEQ ID NO: 87; scFv100: SEQ ID NO: 129; scFv131: SEQ ID NO: 148; scFv110: SEQ ID NO: 135; scFv97: SEQ ID NO: 127; scFv98: SEQ ID NO: 128; scFv45: SEQ ID NO: 78; scFv62: SEQ ID NO: 95; scFv67: SEQ ID NO: 100; scFv114: SEQ ID NO: 139; scFv85: SEQ ID NO: 116; scFv111: SEQ ID NO: 136; scFv106: SEQ ID NO: 133; scFv64: SEQ ID NO: 97; scFv113: SEQ ID NO: 138; scFv120: SEQ ID NO: 144; scFv57: SEQ ID NO: 90; scFv95: SEQ ID NO: 125; scFv69: SEQ ID NO: 102; scFv77: SEQ ID NO: 109; scFv93: SEQ ID NO: 124; scFv71: SEQ ID NO: 104; scFv61: SEQ ID NO: 94; scFv108: SEQ ID NO: 134; scFv96: SEQ ID NO: 126; scFv117: SEQ ID NO: 141; scFv87: SEQ ID NO: 118; scFv15: SEQ ID NO: 48; scFv37: SEQ ID NO: 70; scFv44: SEQ ID NO: 77; scFv4: SEQ ID NO: 37; scFv28: SEQ ID NO: 61; scFv9: SEQ ID NO: 42; scFv10: SEQ ID NO: 43; scFv29: SEQ ID NO: 62; scFv31: SEQ ID NO: 64; scFv11: SEQ ID NO: 44; scFv18: SEQ ID NO: 51; scFv36: SEQ ID NO: 69; scFv88: SEQ ID NO: 119; scFv63: SEQ ID NO: 96; scFv91: SEQ ID NO: 122; scFv79: SEQ ID NO: 110; scFv81: SEQ ID NO: 112; scFv89: SEQ ID NO: 120; scFv75: SEQ ID NO: 108.

FIG. 7: Aligned sequences of scFvs binding PTP1B-OX. The displayed scFv fragments (from the linker sequence to the C-terminus) include the linker sequence (GQSSRSS), SEQ ID NO 20), the VH sequence and the C-terminal tag (GQAGQHHHHHHGAYPYDVPDYAS, SEQ ID NO: 151). The complementarity determining regions (CDRs) of the heavy chain were identified as: CDR1: 157-180, CDR2: 188-204, and CDR3: 240-261. scFv1: SEQ ID NO: 34; scFv16: SEQ ID NO: 49; scFv26: SEQ ID NO: 49; scFv2: SEQ ID NO: 35; scFv8: SEQ ID NO: 41; scFv17: SEQ ID NO: 50; scFv39: SEQ ID NO: 72; scFv14: SEQ ID NO: 47; scFv49: SEQ ID NO: 47; scFv6: SEQ ID NO: 39; scFv12: SEQ ID NO: 45; scFv21: SEQ ID NO: 54; scFv34: SEQ ID NO: 67; scFv13: SEQ ID NO: 46; scFv47: SEQ ID NO: 80; scFv19: SEQ ID NO: 52; scFv22: SEQ ID NO: 55; scFv53: SEQ ID NO: 86; scFv27: SEQ ID NO: 60; scFv40: SEQ ID NO: 73; scFv41: SEQ ID NO: 74; scFv42: SEQ ID NO: 75; scFv48: SEQ ID NO: 81; scFv60: SEQ ID NO: 93; scFv43: SEQ ID NO: 76; scFv58: SEQ ID NO: 91; scFv56: SEQ ID NO: 89; scFv59: SEQ ID NO: 92; scFv50: SEQ ID NO: 83; scFv52: SEQ ID NO: 85; scFv121: SEQ ID NO: 145; scFv123: SEQ ID NO: 146; scFv51: SEQ ID NO: 84; scFv104: SEQ ID NO: 131; scFv20: SEQ ID NO: 53; scFv25: SEQ ID NO: 58; scFv55: SEQ ID NO: 88; scFv32: SEQ ID NO: 65; scFv134:

SEQ ID NO: 157; scFv119: SEQ ID NO: 143; scFv46: SEQ ID NO: 79; scFv65: SEQ ID NO: 98; scFv73: SEQ ID NO: 106; scFv90: SEQ ID NO: 121; scFv68: SEQ ID NO: 101; scFv74: SEQ ID NO: 107; scFv70: SEQ ID NO: 103; scFv92: SEQ ID NO: 123; scFv83: SEQ ID NO: 114; scFv72: SEQ ID NO: 105; scFv102: SEQ ID NO: 130; scFv86: SEQ ID NO: 117; scFv84: SEQ ID NO: 115; scFv80: SEQ ID NO: 111; scFv105: SEQ ID NO: 132; scFv112: SEQ ID NO: 137; scFv118: SEQ ID NO: 142; scFv124: SEQ ID NO: 147; scFv115: SEQ ID NO: 140; scFv82: SEQ ID NO: 113; scFv3: SEQ ID NO: 36; scFv30: SEQ ID NO: 63; scFv23: SEQ ID NO: 56; scFv7: SEQ ID NO: 40; scFv35: SEQ ID NO: 68; scFv5: SEQ ID NO: 38; scFv24: SEQ ID NO: 57; scFv33: SEQ ID NO: 66; scFv66: SEQ ID NO: 99; scFv38: SEQ ID NO: 71; scFv54: SEQ ID NO: 87; scFv100: SEQ ID NO: 129; scFv131: SEQ ID NO: 148; scFv110: SEQ ID NO: 135; scFv97: SEQ ID NO: 127; scFv98: SEQ ID NO: 128; scFv45: SEQ ID NO: 78; scFv62: SEQ ID NO: 95; scFv67: SEQ ID NO: 100; scFv114: SEQ ID NO: 139; scFv85: SEQ ID NO: 116; scFv111: SEQ ID NO: 136; scFv106: SEQ ID NO: 133; scFv64: SEQ ID NO: 97; scFv113: SEQ ID NO: 138; scFv120: SEQ ID NO: 144; scFv57: SEQ ID NO: 90; scFv95: SEQ ID NO: 125; scFv69: SEQ ID NO: 102; scFv77: SEQ ID NO: 109; scFv93: SEQ ID NO: 124; scFv71: SEQ ID NO: 104; scFv61: SEQ ID NO: 94; scFv108: SEQ ID NO: 134; scFv96: SEQ ID NO: 126; scFv117: SEQ ID NO: 141; scFv87: SEQ ID NO: 118; scFv15: SEQ ID NO: 48; scFv37: SEQ ID NO: 70; scFv44: SEQ ID NO: 77; scFv4: SEQ ID NO: 37; scFv28: SEQ ID NO: 61; scFv9: SEQ ID NO: 42; scFv10: SEQ ID NO: 43; scFv29: SEQ ID NO: 62; scFv31: SEQ ID NO: 64; scFv11: SEQ ID NO: 44; scFv18: SEQ ID NO: 51; scFv36: SEQ ID NO: 69; scFv88: SEQ ID NO: 119; scFv63: SEQ ID NO: 96; scFv91: SEQ ID NO: 122; scFv79: SEQ ID NO: 110; scFv81: SEQ ID NO: 112; scFv89: SEQ ID NO: 120; scFv75: SEQ ID NO: 108.

Figure 8:
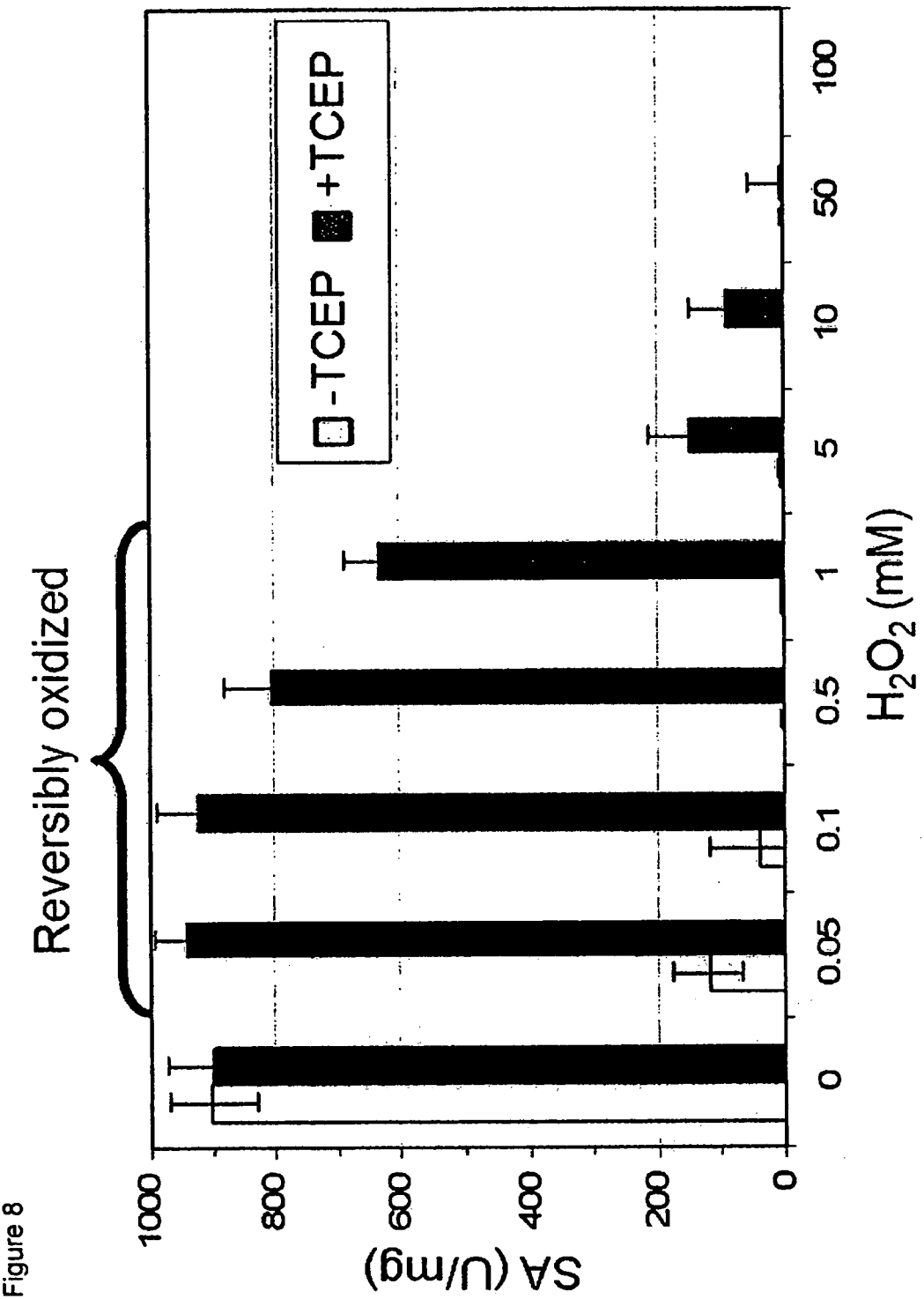

FIG. 8: Reversible oxidation of PTP1B by H2O2.

FIGS. 9a-c: Interaction of scFvs and PTP1B. (a) conformation-sensor scFv45 inhibits PTP1Breactivation by selectively binding to PTP1B-OX in vitro. (b) scFv57 binds specifically to PTP1B-OX in vitro. (c) specific interaction between PTP1B-OX and scFvs in vitro.

Figure 10:
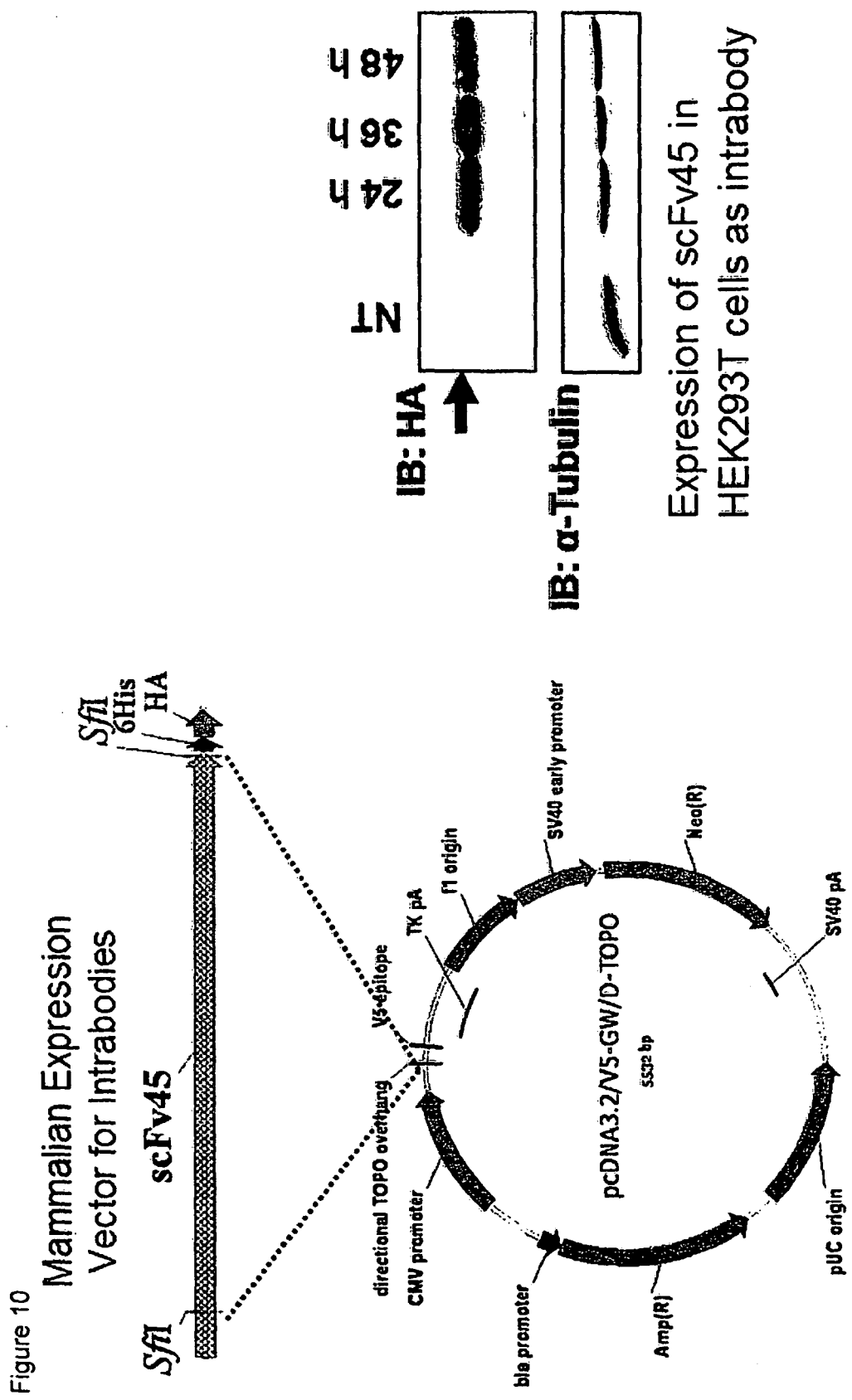

FIG. 10: Intrabody expression in mammalian cells. Left: Exemplary vector map of pcDNA3.2 with scFv45 insert. Right: representative blot showing expression of scFv45 in HEK293T cells as intrabody.

FIGS. 11a-b. Specific interaction of scFv45 and PTP1B-OX. (a) Interaction between PTP1B-OX and intrabody45 in mammalian cells. His-tagged scFv45 was pulled down with Ni-NTA agarose. (b) Interaction between PTP1B-OX and intrabody45 in mammalian cells. PTP was immunoprecipitated with anti-PTP1B antibody.

FIGS. 12a-12b. Screening of PTP1B-OX specific intrabodies in mammalian cells. His-tagged scFvs were pulled down with Ni-NTA agarose. Some scFvs show co-pulldown of PTP1B-OX in the presence of H2O2 (scFv45, 136, 67, 102, and 106), but not in the presence of NAC and TCEP.

FIG. 13: Intrabody 45 causes enhanced AKT activation in response to insulin

Figure 14A:
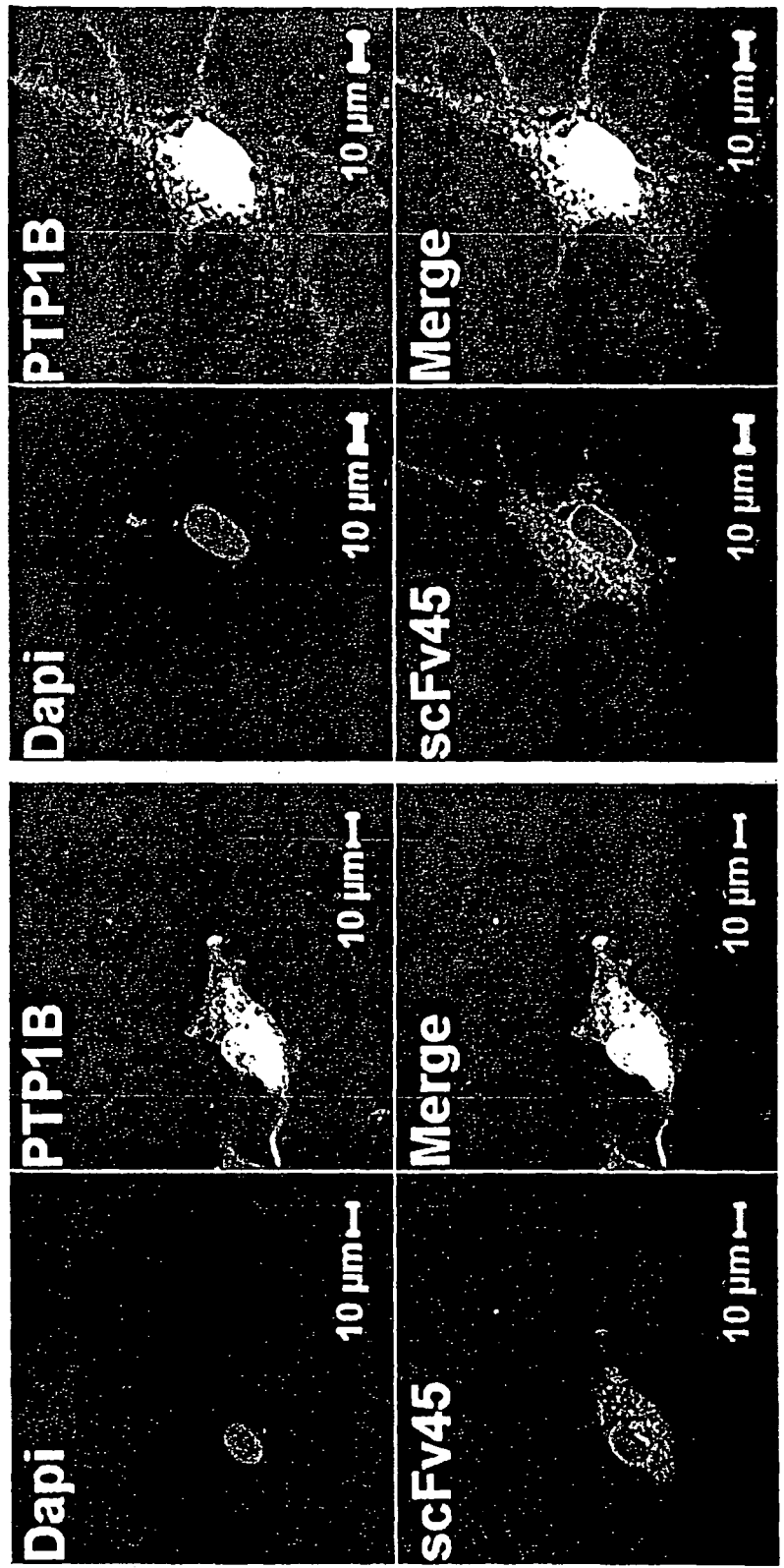

FIGS. 14a-b: (a) Colocalization of PTP1B-OX and intrabody45 in Cos1 cells. (b) Intrabody45 colocalizes with PTP1B-OX in Cos1 cells in response to insulin.

DETAILED DESCRIPTION OF THE INVENTION

PTP1B-Inhibition as a Therapeutic Approach

Inhibition of PTP1B has been suggested as a strategy in the treatment of a number of diseases. For example, inhibition of PTP1B has been demonstrated to augment insulin action. Disruption of the murine PTP1B gene ortholog in a knock-out mouse model results in PTP1B−/−mice exhibiting enhanced insulin sensitivity, decreased levels of circulating insulin and glucose, and resistance to weight gain even on a high-fat diet, relative to control animals having at least one functional PTP1B gene (Elchebly et al., Science 283: 1544 (1999)). Insulin receptor hyperphosphorylation has also been detected in certain tissues of PTP1B deficient mice, consistent with a PTP contribution to the physiologic regulation of insulin and glucose metabolism (id.). This makes PTP1B an attractive target for clinical interventions aimed at ameliorating the state of insulin resistance common in Type II diabetes patients.

Additionally, PTP1B-deficient mice further exhibit decreased adiposity (reduced fat cell mass but not fat cell number), increased basal metabolic rate and energy expenditure, and enhanced insulin-stimulated glucose utilization (Klaman et al., 2000 Mol. Cell. Biol. 20: 5479).

Increased PTP1B activity has been correlated with impaired glucose metabolism in other biological systems (e.g., McGuire et al., Diabetes 40: 939 (1991); Myerovitch et al., J. Clin. Ifzvest. 84: 976 (1989); Sredy et al., Metabolism 44: 1074 (1995)), including PTP1B involvement in biological signal transduction via the insulin receptor (see, e.g., WO 99/46268 and references cited therein).

Further, PTP acts as a negative regulator of signaling that is initiated by several growth factor/hormone receptor PTKs, including p210 Bcr-Abl (LaMontagne et al., Mol. Cell. Biol. 18: 2965-75 (1998); LaMontagne et al., Proc. Am. Acad. Sci. USA 95: 14094-99 (1998)), receptor tyrosine kinases, for example EGF receptor, PDGF receptor, and insulin receptor (IR) (Tonks et al., Curr. Opin. Cell Biol. 13: 182-95 (2001)), and JAK family members, for example Jak2 and others (Myers et al., J. Biol. Chem. 276: 47771-74 (2001)), as well as signaling events induced by cytokines (Tonks and Neel, 2001).

Described herein is production of conformation-specific antibodies that recognize oxidation-specific epitopes in PTP1B-OX that are not found in the active, reduced enzyme. A double point mutation in the PTP-loop of PTP1B, C215A/S216A, induces a stable conformation (referred to as PTP1B-CASA) that is indistinguishable in structure from the PTP1B-OX conformation that is induced by $H_2O_2$. The mutant is useful as an antigen. Phage display technology, which allows rapid and efficient screening of libraries of high complexity (Burton et al, Phage Display: A Laboratory Manual Cold Spring Harbor Laboratory, 3.1-3.18 2001; Hoogenboom et al Immunology Today 21: 371 2000), was adapted and used in the work described herein. Antibody molecules contain discrete protein domains or fragments that can be separated by controlled protease digestion or produced by recombinant techniques. The small Fv (fragment variable), which is composed of the variable light ($V_L$) and variable heavy ($V_H$) regions, were used to generate the library. In a single chain variable fragment (scFv), the two variable regions are artificially joined with a neutral peptide linker. The recombinant antibody scFvs are presented on the surface of bacteriophage and can be selected from combinatorial libraries in vitro. In comparison with classical, animal-based approaches, this has the major advantage of preserving the native conformation of target antigens to allow the generation of conformation specific antibodies. Use of scFvs as intracellular antibodies (intrabodies) to target intracellular proteins has also been reported (Biocca, Trends in Cell Biology, 5: 248 1995). Varying biochemical conditions to include competitive molecules during the selection steps of the phage display technique allows enrichment of highly specific antibodies, for example selecting for antibodies that recognize PTP1B-OX in the presence of excess native PTP1B.

As described further herein, chickens were immunized with purified PTP1B-CASA mutant protein and spleen and bone marrow were harvested from immunized animals in which Applicant detected a robust increase in serum antibody titer to the purified antigen. Total RNA was isolated and first-strand cDNA was synthesized by RT-PCR using an oligo (dT) primer. This first-strand cDNA was used directly for PCR amplification of the $V_L$ and $V_H$ sequences. Two scFv constructs were produced, one with a 7 residue linker and one with a longer, 18 amino acid residue linker sequence between the $V_L$ and $V_H$ domains. The shorter linker (7 residues) proved to be more effective. The scFv antibody construct also encodes two expression tags at the C-terminus of the protein, the 6×His tag for purification of soluble proteins and the HA tag for immunodetection. Two PCR steps were performed to generate scFv constructs. In the first, $V_H$ and $V_L$ segments were amplified separately and in the second overlap PCR, $V_H$ and $V_L$ were combined via the linker sequence to form full-length scFv constructs, which were pooled. A modified version of the pComb3XSS phagemid vector was used to construct the scFv phage display library (Barbas et al, PNAS, 88: 7978 1991; Scott et al., Phage Display: A Laboratory Manual Cold Spring Harbor Laboratory, 2.1-2.19 2001). The library size (expressed as the transformation efficiency of the ligated library construct) was determined to be ~$10^7$. Phage particles displaying scFv on their surface fused to the phage pIII coat protein were harvested from the culture supernatant of phagemid-transformed bacterial cells. A subtractive panning strategy was used to isolate PTP1B-CASA-specific antibodies from the scFv library. PTP1B-CASA was biotinylated at the N-terminus by expression in *E. coli* that overexpressed biotin ligase (Smith et al., Nucleic Acid Res, 26(6): 1414 1998), and purified at homogeneity. This approach was used because chemical biotinylation was observed to be inhibitory to activity of reduced, active PTP1B. This biotinylated PTP1B-CASA mutant was mixed with the library, together with 10-50× molar excess of wild type enzyme, under reducing conditions, to direct selection towards epitopes unique to the oxidized conformation of PTP1B. The PTP1B-CASA-scFv-phage complex from this mixture was isolated on streptavidin beads and phage particles with surface exposed scFvs bound to PTP1B-CASA were then eluted and amplified through four rounds of panning. A total of ~400 individual clones were selected randomly from the enriched scFv pools, sequenced and found to sort into ~100 distinct groups on the basis of differences in their hypervariable regions. Phage expressing these different scFvs were screened for their specificity towards the CASA mutant by ELISA, in which recombinant PTP1B-CASA or wildtype PTP1B was immobilized on the plate surface and bound scFv was detected by recognizing the associated phage with HRP-conjugated anti-phage antibody. Applicant did not find an scFv that distinguished between reduced, active PTP and oxidized, inactive PTP1B-OX using this approach. In this screen, the scFvs are still fused to the surface of the phage particles, which may interfere with recognition of the PTP1B-OX conformation in the assay. In solid-phase ELISA the antigen may be partially denatured due to immobilization on plastic surfaces, which may compromise distinctive conformations. Therefore, Applicant utilized an amber codon in the phagemid vector to express the scFv clones in a non-suppressor bacterial strain to generate scFvs from which the pIII phage protein tag had been removed. These were then subjected to "in-solution" screening, based on a phosphatase enzyme activity assay.

Applicant's hypothesis was that scFvs that are able to bind to and stabilize the oxidized conformation of PTP1B in solution would inhibit reactivation by reducing agent, but have no direct inhibitory effect on phosphatase activity in assays in vitro. Activity was measured using $^{32}$P-labeled pTyr-Reduced Carboxamidomethylated and Maleylated Lysozyme as substrate. Applicant established conditions in which wild type PTP1B could be reversibly oxidized in vitro. PTP1B was inactivated following addition of $H_2O_2$. However, phosphatase activity was completely restored upon the removal of $H_2O_2$ by a quick buffer exchange and addition of the reducing agent TCEP. Purified bacterially-expressed scFvs were incubated with PTP1B after $H_2O_2$ treatment and the ability of an individual scFv to stabilize the reversibly oxidized, inactive conformation of the phosphatase was assessed by the ability of the antibody to inhibit the reactivation of the enzyme by reducing agent. Results showed that scFvs identified as described herein showed significant inhibition of the reactivation of PTP1B-OX by reducing agent, but did not exert any direct inhibitory effect on activity of reduced, active PTP1B. Applicant validated this approach further, by testing the effects of expressing one of the scFvs (scFv45) as a single chain antibody fragment "intrabody" to PTP1B, using 293T cells as the expression system. This intrabody was expressed transiently and then tested for effects on insulin signaling, focusing initially on the tyrosine phosphorylation status of the beta-subunit of the insulin receptor and insulin receptor substrate (IRS-1). Results indicated that for both substrates, expression of the intrabody had no impact on the basal level of tyrosyl phosphorylation, but it enhanced and extended the time course of insulin-induced phosphorylation, consistent with Applicant's proposed mechanism of action.

Applicant developed an alternative strategy that was based on knowledge of the structure of cyclic sulphenamide form PTP1B-OX. In light of Applicant's observation that upon PTP1B oxidation, Tyr 46 adopts a solvent-exposed position, Applicant generated rabbit polyclonal antibodies to a peptide modeled on the sequence that surrounds Tyr 46, using both phosphorylated and unphosphorylated forms of the peptide as antigen. The effects of these affinity-purified antibodies were tested in the assays in vitro described above. Interestingly, the effects of the anti-peptide antibody were similar to those of scFv45 in vitro, whereas the anti-pTyr peptide antibody was without effect. Again, neither antibody exerted a direct inhibitory effect on the activity of PTP1B. Thus, antibodies produced by two distinct approaches resulted in similar data.

Disclosed herein are methods and agents relating to the surprising discovery that the effect of PTP1B on signaling can be inhibited by stabilizing PTP1B in its inactive, reversibly oxidized state (PTP1B-OX), without directly inhibiting activity of PTP1B in its active, reduced state. When PTP1B is oxidized, a sulphenic acid intermediate is produced and is rapidly converted into sulphenyl-amide species, in which the sulfur atom of the catalytic cysteine is covalently linked to the polypeptide backbone nitrogen atom of the amino acid residue situated immediately C-terminal to the cysteine. This creates a cyclic sulphenamide form, referred to herein in the alternative and interchangeably as the OX form or as the SN form (Salmeen et al., Nature 2003, PCT application PCT/US2004/017710). Oxidation of PTP to the cyclic sulphenyl-amide PTP1B-OX form is accompanied by conformational changes in the catalytic site that effectively inhibit substrate binding and, thus, result in inhibition of PTP1B activity (Salmeen et al., Nature 2003). This unusual protein modification protects the active site cysteine residue of PTP1B from irreversible oxidation to sulphinic acid and sulphonic acid and permits redox regulation of the enzyme by promoting its reversible reduction by thiols.

Conventional strategies aimed at PTP1B signaling modulation rely on the identification of agents that directly interfere with the enzymatic activity of the reduced, active PTP1B, for example by inhibitory agents that directly bind the catalytic pocket of the active enzyme. In contrast, methods and compositions described herein relate to modulating the stability of the PTP1B-OX pool in order to modulate PTP1B signaling, for example by stabilizing PTP1B-OX in order to inhibit (partially or completely) PTP1B signaling. In a specific embodiment, the methods and compositions result in stabilization of inactive PTP1B (PTP1B in oxidized form; PTP1B-OX) and reduced (partially or complete) activity of PTP (reduced activity of PTP1B, relative to PTP activity in the absence of the method or composition described herein).

Compositions and methods described herein may find a variety of uses, for instance, in screening for agents that modulate PTP1-mediated regulation of signaling (for example antibody screening, small molecule screening, drug screening) and therapeutic applications in which the PTP1B-OX is stabilized, reduction of reversibly oxidized, inactive PTP1B-OX to reduced, active PTP1B is inhibited, and PTP1B-mediated regulation of signaling is modulated.

Described herein are agents, for example antibodies, antibody fragments, PTP1B-OX-binding polypeptides and small molecules, that selectively bind PTP1B-OX and modulate its stability (stabilize the inactive form), but do not bind to or directly modulate the enzymatic activity of PTP1B in its reduced, active state. Some aspects of this invention relate to methods of identifying agents antibodies, antigen-binding fragments thereof, polypeptides, small molecules) that bind and stabilize PTP1B-OX and do not bind to or directly inhibit enzymatic activity of PTP1B in its reduced, active state.

The term "directly inhibit enzymatic activity of PTP1B," as used herein, refers to a substantial inhibition of enzymatic activity of PTP in its reduced, active state. The terms "enzymatic activity" and "catalytic activity" are used interchangeably herein. The term "PTP1B", as used herein, and if not further qualified, refers to the reduced, active form of PTP1B, which exhibits tyrosine phosphatase activity (Salmeen et al., Nature 2003). It is also referred to herein as "reduced, active PTP1B". For example, an agent that binds the catalytic site of PTP1B in its reduced, active conformation and inhibits enzyme/substrate interaction, resulting in a substantial decrease of enzymatic activity, modulates enzymatic activity of PTP1B in its reduced, active state in the sense this term is used herein. As a further example, an agent, for example an antibody, or antibody fragment thereof, that does not bind the catalytic site of reduced, active PTP1B and/or does not affect the catalytic activity of reduced, active PTP directly, is not encompassed within the term "directly inhibit the enzymatic activity of PTP1B." An agent may, for example, selectively bind and stabilize PTP1B-OX, thus resulting in a decrease of reduced, active PTP1B molecules, which in turn, may result in a decrease in PTP1B signaling, without directly inhibiting the enzymatic activity of PTP1B in its reduced, active state.

One way to determine whether an agent, for example an antibody, or fragment thereof, modulates the enzymatic activity of PTP1B in its reduced, active state, is to measure and compare the enzymatic activity of PTP1B in the presence and in the absence of the agent, for example in an in vitro phosphatase assay under reducing conditions as described herein.

Some methods described herein are assays useful for identifying compounds that modulate (e.g., inhibit, partially or completely) reduction of reversibly oxidized, inactive PTP1B, for example the inactive, reversibly oxidized cyclic sulphenamide form of PTP1B. In some embodiments, agents identified by these assays antagonize indirectly the effect of PTP1B on signaling (e.g., agents that inhibit the reduction of reversibly oxidized, inactive PTP1B-OX to reduced, active PTP1B, or agents that decrease the pool of reduced, active PTP1B, for example by binding and stabilizing PTP1B-OX). A PTP1B modulating agent may be, for example, a physiological substance or a natural or synthetic drug, for example a naturally occurring or recombinantly produced antibody, or antigen-binding fragment thereof, or an organic small molecule as provided herein.

As used herein, the term "PTP" means a protein tyrosine phosphatase enzyme capable of dephosphorylating a phosphorylated tyrosine residue in a protein, polypeptide, or peptide. Such PTPs are identified by their signature catalytic cysteine motif H-C-$(X)_5$-R- (SEQ ID NO: 2), wherein the cysteine residue is the catalytic cysteine and "X" can be any amino acid residue, natural or unnatural.

The term PTP, as used herein, includes "classical" PTPs, which dephosphorylate tyrosine residues and which have the signature motif sequence H-C-S-$(X)_4$-R- (SEQ ID NO: 3), for example, -H-C-S-X-G-X-G-R-X-G- (SEQ ID NO: 4), wherein "X" can be any amino acid residue. Andersen et al. (Mol. Cell. Bio. 21: 7117-7136 (2001); FASEB J. 18: 8-30 (2004), incorporated herein by reference) describe and illustrate this structural relationship among classical protein tyrosine phosphatase domains. Such classical PTPs are described, and GenBank reference numbers provided therefore, in Andersen et al. (2001 Mol. Cell. Biol. 21: 7117) and herein.

For example, the PTP may be PTP1B (protein-coding DNA and amino acid sequences of PTP1B are described, for example, under GenBank accession NM_002827 (SEQ ID NO: 5), NP_002818 (SEQ ID NO: 6), BT006752 (SEQ ID NO: 7), AAP35398 (SEQ ID NO: 8), M31724 (SEQ ID NO: 9), AAA60223 (SEQ ID NO: 10), M33689 (SEQ ID NO: 11), AAA60157 (SEQ ID NO: 12), BC015660 (SEQ ID NO: 13), AAH15660 (SEQ ID NO: 14), BC018164 (SEQ ID NO: 15), AAH18164 (SEQ ID NO: 16), AK316563 (SEQ ID NO: 17), BAG38152 (SEQ ID NO: 18), or sequences relating to Unigene Cluster Hs. 417549 (UGID:223337) *Homo sapiens* (human) PTPN1). The signature motif sequence of PTP1B is generally described as H-C-S-$(X)_4$-R (SEQ ID NO: 3), for example. As a non-limiting example of a mutant PTP1B mimicking the conformation of reversibly oxidized PTP1B, a double mutant PTP1B, in which two mutations have been introduced within the catalytic motif (C215A and S216A), PTP1B-CASA is described herein (SEQ ID NO: 19).

The term "isolated", as used herein, refers to a molecule or agent, for example PTP1B, PTP1B-OX, or PTP1B-CASA, that has been removed from its source, biological environment or milieu (for example by removing a protein from an intact cell source). A "molecule" may be any chemical or biological molecule, whether naturally occurring or non-naturally occurring/synthetic, such as can be made by chemical synthetic methods, recombinant methods or other non-naturally occurring method. A molecule can be, for example, a protein, polypeptide or oligopeptide, a nucleic acid, for example a oligonucleotide or polynucleotide, a molecule in a complex of molecules, a chemical substance, for example a small organic compound, whether naturally occurring or not or synthetic. PTP1B, PTP1B-OX, mutant PTP1B, PTP1B-CASA, a scFv, an antibody, an antigen binding antibody fragment, and a small organic compound are non-limiting examples of molecules. Isolation may be accomplished, for example, by any method suitable for removing or separating a molecule from surrounding molecules or substances, for example those naturally associated with a molecule, such as by using chemical, physical, and/or enzymatic methodology well known in the art of molecule isolation.

Some embodiments involve the use of an agent that binds to PTP1B-OX or a mutant PTP1B, for example PTP1B-CASA. Such agents may be used in methods described herein, including methods to identify molecules that bind PTP1B-OX or bind a mutant PTP (for example, PTP1B-CASA); methods to determine, quantitatively or qualitatively, the binding of a candidate molecule to PTP1B, PTP1B-OX, or to mutant PTP (for example PTP1B-CASA) and methods to modulate PTP1B-mediated regulation of a signaling pathway.

Antibodies, antibody-fragments and PTP1B-OX-binding polypeptides described herein typically comprise L-amino acid residues. They can further comprise D-amino acid residues, naturally-occurring amino acid residues (e.g., L-amino acid residues), non-naturally occurring amino acid residues, modified aminod acid residues, alone or in combination. A variety of peptide bonds can be present, such as at least one psi[CH$_2$NH] reduced amide peptide bond, at least one psi[COCH2] ketomethylene peptide bond, at least one psi[CH(CN)NH] (cyanomethylene)amino peptide bond, at least one psi[CH2CH(OH)] hydroxyethylene peptide bond, at least one psi[CH2O] peptide bond, and/or at least one psi[CH2S] thiomethylene peptide bond.

An antibody, or antigen-binding antibody fragment, for example as described herein, can be prepared by any of a variety of methods well known in the art, including administering an antigen, for example a specific peptide, a specific protein, a fragment of a specific protein, a cell expressing a specific protein or a fragment thereof to an animal to induce production of polyclonal antibodies. The production of monoclonal antibodies is also well known in the art.

Figure 5:
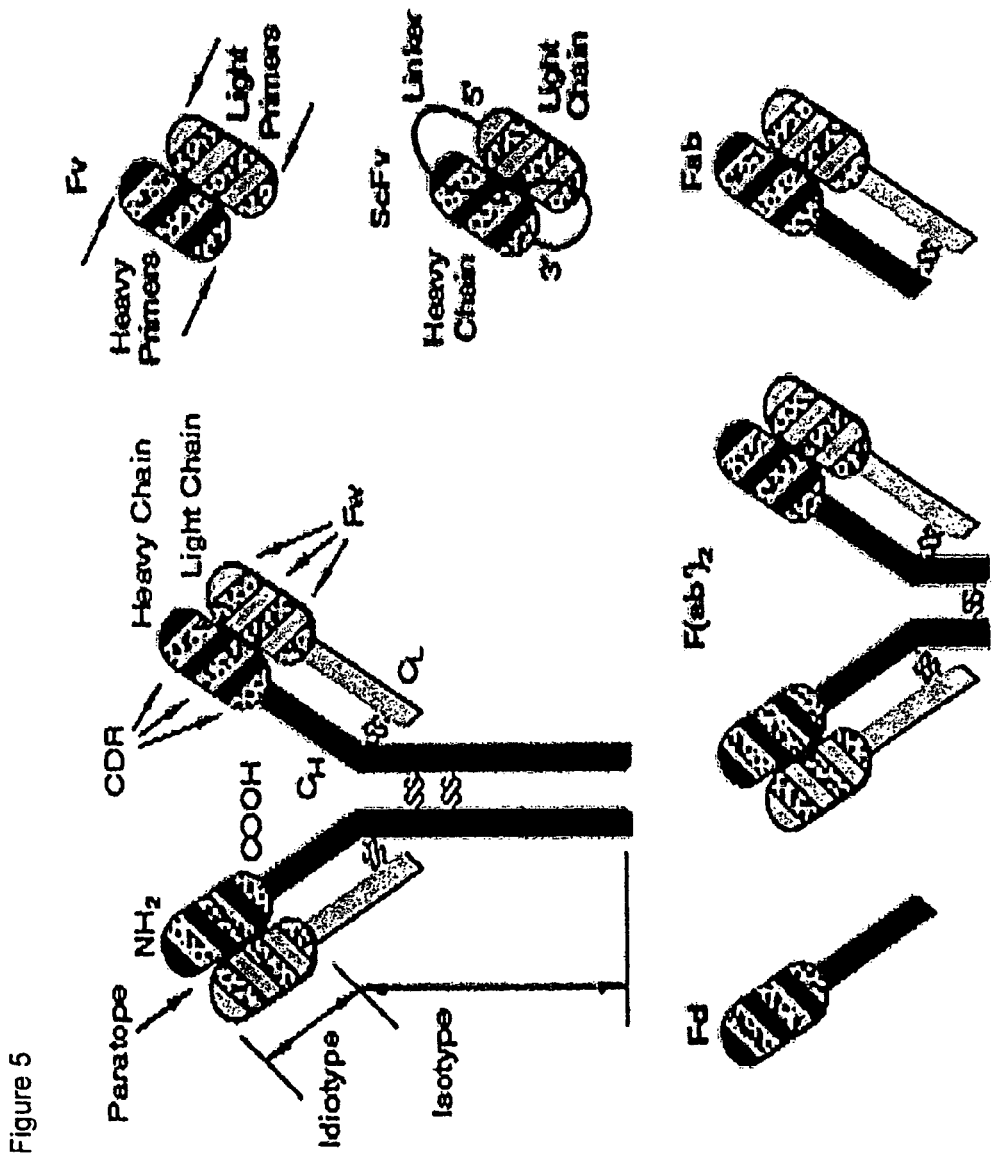
FIG. 5: Basic Antibody Structure and Subunit Composition. The C region of an antibody is relatively conserved while the V region is antigen-specific. The V region consists of alternating framework (FW) and hyper variable complementarity-determining regions (CDR). Antibody molecules contain discrete protein domains or fragments (shown in the shaded area) that can be isolated by protease digestion or produced by recombinant techniques. The smaller Fv (fragment variable) is composed of the VL and VH regions only. In scFvs (single chain Fvs), the two variable regions are artificially joined with a neutral linker and expressed as a single polypeptide chain.

As is well-known in the art, only a small portion of an antibody molecule, the paratope, is involved in the binding of the antibody to its epitope (FIG. 5, see, in general, Clark, W. R. (1986), The Experimental Foundations of Modern Immunology Wiley & Sons, Inc., New York; Roitt, I. (1991) Essential Immunology, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab') fragment (or F(ab')2 fragment), retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

F(ab') fragments derived from serum or cell culture by purification of specific IgG followed by papain digestion show similar binding compared to the complete IgG, while the Fc component does not bind (FIG. 5).

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford). In both the heavy chain Fd fragment and the light chain of IgG immunoglobulins, there are four framework regions (termed Fr or Fw regions) separated respectively by three complementarity determining regions (CDR1 through CDR3). The CDRs, and in particular the CDR3 regions, and more particularly the heavy chain CDR3, are largely responsible for antibody specificity.

It is well-established in the art that the non-CDR regions of a mammalian antibody may be replaced with similar regions of nonspecific or heterospecific antibodies without removing the epitopic specificity of the original antibody. For example, this is the case in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762, and 5,859,205.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention, at least in some aspects, also provides for F(ab'), Fab, Fv, and Fd fragments; chimeric antibodies in which the Fc and/or FR and/or CDR1 and/or CDR2 and/or light chain CDR3 regions have been replaced by homologous human or non-human sequences; chimeric F(ab') fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. In some embodiments, the present invention provides single chain antibodies (for example scFv polypeptides), (single) domain antibodies (FIG. 5). In some embodiments, the single chain antibodies or (single) domain antibodies are intracellular antibodies, termed intrabodies.

Domain antibodies, camelid and camelized antibodies and fragments thereof, are well known in the art (described, for example, in patents and published patent applications of Ablynx NV and Domantis) and can also be used in embodiments described herein.

The term "conformation specific scFvs, as used herein, refers to scFvs that bind PTP1B in a reversibly oxidized, cyclic sulphenyl-amide conformation (PTP1B-OX or PTP1B-SN). They also bind mutant PTP1B resembling PTP1B-OX, for example the double mutant PTP1B-CASA.

Some methods described herein may be used for identifying compounds or agents that bind to the oxidized cyclic sulphenyl-amide form of PTPB1 and inhibit (partially or completely) its reduction to its active cysteine thiol-containing state. Once identified, such agents or compounds are useful for modulating the flux of signal through a pathway that is regulated by PTP1B. In some embodiments, such agents may be used to modulate a pathway that is negatively regulated by PTP1B.

For example, a compound may be identified by crystallizing isolated PTP1B, contacting the crystallized PTP1B with H$_2$O$_2$, generating reversibly oxidized PTP1B-OX and then soaking (or incubating, immersing, exposing, bathing, contacting or otherwise maintaining) the crystal in a solution containing a candidate compound and determining if the compound binds to the PTP1B-OX, for example according to X-ray crystallography methods described herein and known in the art (see, e.g., Salmeen et al. Nature, 2003; Johnson and Blundell, Protein Crystallography (Academic Press 1976); Blundell et al. Nat. Rev. Drug Discov. 1: 45-54 (2002)). Other methods for determining whether a compound binds to a PTP-OX include isothermal titration calorimetry in the solution state (Weber et al., Curr. Opin. Struct. Biol. 13: 115-21 (2003); Ward et al., Prog. Med. Cdaem. 38: 309-76 (2001); Cliff et al., J. Mol. Recognit. 16: 383-91 (2003)) or surface plasmon resonance (e.g., BIAcore, Biosensor, Piscataway, N.J.).

The function and advantage of these and other embodiments of the present invention will be more fully understood from the examples below. The following examples are intended to illustrate the benefits of the present invention, but do not exemplify the full scope of the invention.

EXAMPLES

Example 1

Development of antibodies selectively binding PTP1B-OX from a phage display library 1. Construction of scFv Phage Display Library A phage display library displaying single chain variable fragments (scFvs) fused to its surface protein pIII with a size of ~10$^7$ was constructed from spleen and bone marrow of chickens immunized with PTP1B-CASA (mutant structurally identical to reversibly oxidized PTP1B). Construction of the library is briefly described here.

1.1.

Chicken Immunizations: Chickens were immunized with purified PTP1B-CASA and the blood from each immunized chicken was titrated by ELISA to determine the presence of an antigen-specific immune response. Detection of a strong serum antibody titer was an early indication of the presence of an enriched pool of PTP1B-CASA-binding immunoglobulin genes that make up the building blocks of combinatorial antibody library.

1.2. Total RNA Extraction:

Spleen and bone marrow are the major repository of plasma cells that secrete antibodies against the antigen of interest and contain the highest levels of specific mRNA. Therefore, spleen and bone marrow from immunized animals with elevated immune response against PTP1B-CASA were harvested. Total RNA was isolated from the spleen and bone marrow using TRI-Reagent and isopropanol precipitation.

1.3. First-Strand cDNA Synthesis from the Total RNA:

First-strand cDNA was synthesized from the total RNA extracted from both bone marrow and spleen by reverse transcription-polymerase chain reaction (RT-PCR) using an oligo (dT) primer. This first-strand cDNA was directly used for PCR amplification of the V$_L$ and V$_H$ genes.

1.4. Generation of Recombinant scFvs:

A peptide linker of varying length between the V$_H$ and the V$_L$ domains of immunoglobulin molecule generates recombinant single chain Fvs (scFvs) with improved folding and stability. An equimolar mixture of first-strand cDNA derived from the spleen and bone marrow of the PTP1B-CASA-immunized chickens was used to amplify V$_H$ and V$_L$ genes for the construction of combinatorial scFv antibody libraries. Two scFv constructs were produced, one with a 7 amino acid linker sequence (GQSSRSS) (SEQ ID NO 20) and one with an 18 amino acid linker (GQSSRSSSGGGGSGGGGS) (SEQ ID NO 21). Two PCR steps were performed in order to generate scFv constructs—in the first PCR V$_H$ and V$_L$ gene segments were amplified separately and in the second overlap PCR V$_H$ and V$_L$ were combined via a linker sequence to form a full-length scFv construct. The final scFv PCR products were pooled together, ethanol precipitated and quantified.

1.5. The Phagemid Vector:

A modified version of the pComb3XSS phagemid vector was used for the construction of the scFv antibody libraries. This vector allows for a uniform directional cloning strategy that utilizes a single restriction endonuclease, Sfi I, based on asymmetry of the two sites. This vector contains the amber codon, inserted between the 3' Sfi I restriction site and the 5' end of phage gene III fragment. This allows for expression of soluble antibody fragments in nonsuppressor strains of bacteria without excising the gene III fragment. The pComb3XSS also contains two peptide tags, the histidine (H6) tag for purification of soluble proteins, and the hemagglutinin (HA) tag for immunodetection. This phagemid was modified in such a way that it has a reduced potential for recombination and deletion within the vector. In addition the vector also contains an ampicillin resistant gene for selection purposes.

1.6. Construction of the scFv Library:

Both the scFv PCR products and phagemid were prepared for cloning by restriction endonuclease digestion with Sfi I. The digested products were gel purified and the cloning efficiency of the linearized vectors and scFv inserts was tested using small scale ligations and found to be in the range of 10$^7$ to 10$^8$ cfu/ng of DNA, with minimal background (less than 5%). Library ligation was performed with a 2:1 molar ratio of insert:vector, 1× ligase buffer, 10 µl (1 U/µl) T4 DNA ligase, in a 200-nl reaction. The ligations were incubated overnight at room temperature, ethanol precipitated and resuspended in water. The ligated DNA was transformed into 300 µl of electrocompetent XL-1 Blue cells. This *E. coli* is a male strain that harbors F' pili, through which the filamentous bacteriophage infect the bacteria. The F' factor containing XL-1 Blue cells are maintained by the selection pressure of tetracycline. The library size (expressed as the transformation efficiency of the ligated library construct) was determined by plating the transformed cells on LB/carbenicillin plates. The size of the library was found to be ~10$^7$. The culture was then grown under the selection of carbenicillin to select for transformed bacterial cells. To induce the production of functional phage particles by the infected *E. coli* culture, preparation of a filamentous helper phage VCSM13 (10$^{12}$ PFU/ml) was added and selected with kanamycin (there is a kanamycin resistant gene in the genome of the helper phage). After overnight incubation at 37° C. with shaking, the culture supernatant containing the phage particles was harvested by centrifugation. The bacterial pellet was used to purify phagemid DNA (the library DNA preparation) using the Qiagen Maxiprep kit. The phage particles displaying scFv fused to its pIII coat protein were finally harvested from the supernatants by PEG precipitation.

Example 2

Subtractive Panning for Isolating PTP1B-CASA Specific Antibody Fragments

A subtractive panning protocol was designed which will select for scFvs specific for the PTP1B-CASA mutant while eliminating the pools that recognize and detect the common epitopes on both the oxidized and the reduced form of the enzyme. Addition of molar excess reduced wild type PTP1B in the library in solution will eliminate the scFvs that recognize the common structural epitopes of the two forms of the enzyme. Specific antibodies can be isolated with biotinylated PTP1B-CASA and subsequent capturing of the antigen-antibody complex with streptavidin coated magnetic beads. Different steps of the subtractive panning protocol are briefly described below:

2.1. PTP1B Biotinylation in vivo and Purification of Biotinylated PTP1B:

The biotinylation sequence is a unique peptide, 15 residues long (GLNDIFEAQKIEWHE) (SEQ ID NO 22), which is recognized by biotin ligase. In the presence of ATP, the ligase specifically attaches biotin to the lysine residue in this sequence. This tag was fused to the N-terminal of PTP1B in pET19b vector and the recombinant protein expressed in *E. coli* (BL21), which was already transformed with the recombinant biotin ligase (BirA) in pACYC184 (a ColEI compatible plasmid). Expression of recombinant proteins in bacteria was induced with 1 mM IPTG in presence of 50 µM biotin in the growth medium for 4 hours at 37° C. Biotin-protein ligase activates biotin to form biotinyl 5' adenylate and transfers the biotin to biotin-accepting proteins. Addition of biotin during the time of induction ensures complete biotinylation of the tagged protein. Using an *E. coli* strain that over-expresses biotin ligase, up to 95% biotinylation of substrate proteins is possible. The in vivo biotinylated PTP1B (both CASA and wild type) was purified in a two-step purification scheme. In the first step the biotinylated recombinant protein was separated by monomeric avidin column and in the second step the protein was further purified by an anion exchange column (HiTrap Q FF). The activity of the in vivo biotinylated protein was measured by a pNPP assay and the catalytic activity of PTP1B was found to be conserved by this specific modification. This implies that the N-terminal biotinylation does not cause structural modification at the catalytic site of the enzyme. The in vivo biotinylated protein was used for panning.

2.2. Subtractive Panning:

The scFv library was mixed in solution with 10-50 times molar excess of wild type PTP1B than the biotinylated PTP1B-CASA under reducing conditions for 4 hours at 4° C. to eliminate the pools of antibodies that recognize the common epitopes on both the oxidized and the reduced form of PTP1B. Biotinylated PTP1B-CASA was mixed to this solution and incubated for another 4 hours at 4° C. From this mixture, scFv displaying phage bound to this biotinylated PTP1B-CASA were captured by streptavidin coated magnetic beads. After magnetic separation of the antibody-antigen complex captured on the beads, non-specific binders were removed by repeated washing. Bound phage displaying specific scFvs on their surface were eluted under acidic (glycine-HCl, pH 2.2) condition, neutralized and amplified. Amplified phage from the first round of panning were used for the second round selection and a total of four rounds of panning were performed accordingly under the same condition. The input phage were preincubated with the streptavidin coated beads before each round of panning to eliminate the bead- and streptavidin binding phage. Input and output phage were estimated to determine whether selective enrichment of specific scFv-displaying phage occurred. The detailed protocol for the subtractive panning is described below:

1. The streptavidin (SA) coated magnetic beads were prewashed with 10 volumes of TBS containing 2% BSA and 0.2% NaN3 by mixing and centrifuging at 12,000 rpm for 30 seconds. The washed beads were resuspended in TBS containing 2% BSA, 5 mM DTT and 0.2% NaN3 to make the final SA concentration to 10 mg/ml.

2. The binding capacity of the beads is 5-10 µg (30-60 pmole) of biotinylated antibody (IgG) per mg of SA beads. Therefore, 25 µl of SA beads at 10 mg/ml, should bind 7.5-15.0 pmole of biotinylated protein. Applicant used 400 ng of biotinylated PTP1B-CASA (~10 pmoles). In the first and second panning steps Applicant used 4 µg (10× molar access) and 10 µg (25× molar access) of untagged wild type PTP1B (PTP1B-WT), respectively. In both the 3rd and 4th round of panning we used 20 µg of untagged wild type PTP1B, which is 50× molar access of the biotinylated PTP1B-CASA.

3. The scFv library was preadsorbed by SA beads in 400 µl final volume in 1.5 ml microcentrifuge tube by mixing $2 \times 10^{12}$ phage particles in 400 µl of 2% BSA in TBS plus 1% Tween 20, 10 mM DTT and finally adding 25 µl of prewashed SA beads and incubating for 2 hours at 4° C.

4. Recombinant 37-kDa wild type PTP1B (4 µg) was added in 400 µl 1×TBS, 2% BSA, 0.5% T20 and 5 mM DTT to 200 µl of preadsorbed phage ($10^{12}$ phage particles) and incubated for 4 hours at 4° C. The biotinylated PTP1B-CASA (400 ng) was added in 400 µl 1×TBS, 2% BSA, 0.5% T20 and 5 mM DTT to this mixture and incubated at 4° C. for 4 hours in a humidified box.

5. Pre-washed SA beads (25 µl) were added to the phage/screening molecule reaction in the tubes and incubated for 15 minutes at RT on a rocking platform.

6. To block the additional streptavidin binding sites on the beads 100 µl of 1 mM biotin (~0.1 mM final) was added in TBS containing 2% BSA and 5 mM DTT to the solution and incubated for 5 minutes at RT.

7. The supernatant was aspirated after the incubation and the beads were washed 3× by resuspending the beads in 1 ml of TBS and centrifuging at 12,000 rpm.

8. The phage particles associated with the SA-biotinylated PTP1B-CASA complex were eluted after adding 100 µl of elution buffer (0.2 M glycine-HCl, pH 2.2, 1 mg/ml BSA), pipetting up and down to mix the beads in the elution buffer and incubating for 10 minutes at RT. The beads were held at the bottom of the tube with the magnet, the sup was collected and transferred to a new microfuge tube and neutralized with 20 µl of neutralization buffer (1 M Tris base, pH 9.1).

9. The eluates were added to infect 2-ml overnight culture of XL-1 Blue strain of *E. coli* in SB medium and incubated at room temperature for 15 minutes. To this 6 ml of prewarmed (at 37° C.) SB medium (+1.6 µl of 100 mg/ml carbenicillin+12 µl of 5 mg/ml tetracycline) was added and the culture was transferred to a 50-ml tube and shaken at 250 rpm for 1 hour at 250 rpm. Then 2.4 µl of 100 mg/ml carbenicillin was added to the culture and shaken for an additional hour at 250 rpm and 37° C.

10. Input and Output titering:
   a. Five p. 1 of the infected culture was diluted in 500 µl of SB medium and 10 and 100 µl of this dilution were plated on LB/Amp or LB/Carbenicillin plates for output tittering.
   b. One hundred µl of the prepared *E. coli* culture was infected with 2 µl of a 10-8 dilution of the phage preparation [1 µl in 1000 µl SB (a $10^{-3}$ dilution); mix, 1 µl of the $10^{-3}$ dilution in 1000 µl of SB (a $10^{-6}$ dilution), mix and dilute 10 µl of the $10^{-6}$ dilution in 1000 µl of SB (a 10⁻⁸ dilution)]. The infected culture was incubated for 15 minutes at RT and plated on an LB/Amp plate.

c. The output and input plates were incubated at 37° C. overnight.

11. The helper phage VCSM13 (10¹² pfu) was added to the 8-ml culture and transferred to a 500-ml flask. To this 91 ml of prewarmed (37° C.) of SB medium (with 46 µl of 100 mg/ml carbenicillin and 184 µl of 5 mg/ml tetracycline) was added and finally the culture was shaken at 300 rpm for 2 hours at 37° C. Then 140 µl of 50 mg/ml Kanamycin was added and shaking was continued overnight at 300 rpm and 37° C.

12. The culture was centrifuged at 3000 g for 15 minutes at 4° C. The supernatant was transferred to a clean 500-ml centrifuge bottle and 25 ml 5×PEG/NaCl (20% w/v PEG, 2.5 M NaCL) was added and mixed and incubated on ice for 30 minutes.

13. Phage particles were precipitated by centrifuging at 15,000 g for 15 minutes at 4° C. The supernatant was drained and the phage particles were resuspended in 2 ml of 1% BSA in TBS.

The amplified phage particles form the first round of panning were used for the second round and a total number of four rounds of panning were performed. After each round of panning the output phage titers were determined on LB+ carbenicillin plates and these output titer plates are the source of individual phage particles expressing scFv fused to the surface protein PIII.

2.3. Screening Phage Pools:

The phage pools after each round of panning were screened to assess whether the subtractive panning experiment was successful and to select antibody pools displaying the desired specificity and affinity. Most protocols for evaluating phage display libraries recommend ELISA for isolation of positive clones. However, protocols using antigens coated on plastic lead to partial antigen denaturation, which is not an ideal experiment for screening conformation specific antibodies. It has been reported in some studies that scFvs directed against denatured proteins are less efficient than those against unaltered protein conformations in solution, in immunofluorescence and in vivo expression. So screening against denatured antigen is not adapted to the selection of conformation sensitive scFvs.

Selected pools of antibody-fragment displaying phage after several rounds of panning were analyzed as a pool as well as individually as separate clones. Even if a pool of selected phage shows specificity to the reversibly oxidized form of PTP1B, it still can have some high affinity individual scFvs which are directed to the epitope(s) other than the altered active site and may not be eliminated by the subtractive panning. We systematically analyzed individual scFvs from initial selection after the subtractive panning. Testing clones directly also gives us an immediate idea of the specificity and applicability of the antibody in a cellular context. Analysis of individual clones from a panned pool can be done either with antibody fragment displaying phage prepared from a single clone or with a single antibody fragment prepared from IPTG induced culture as described later.

2.4. Sequence Analysis of Individual scFv Clones:

Individual clones were sequenced from the subtractive panning steps. Analysis of the scFv sequences made it possible to identify at a clonal level different individual antibodies, which are of special interest as the unique sequences of the antibodies might contribute to the specificity to the individual clones. The sequences were aligned with a chicken Ig VL+VH sequence (SEQ ID NO: 1) for selecting functional scFv sequences and sorting them in groups (FIG. 6, FIG. 7). In the displayed alignment the CDRs can be identified. We have identified the CDR residues related to the respective CDRs in the heavy and light chains. For the light chain: CDR1: position 29-50, CDR2: position 60-83, CDR3: position 100-124. For the heavy chain: CDR1: position 157-180, CDR2: position 188-204, CDR3: position 240-261. These CDRs are within alternate framework regions (FR) which are more conserved in amino acid composition.

Sequences were sorted into different groups on the basis of their differences in the hypervariable regions hoping that representative sequences of different groups would recognize PTP1B-CASA mutant with different specificity or affinity. Selection of functional scFv sequences was confirmed by checking whether the sequences are of chicken origin. All the selected sequences in this case aligned significantly with the light and heavy chains of chicken IgG amino acid sequence except for the differences in the hypervariable regions. The selected scFv sequences also contain the 6-His and HA tags at the C-terminal.

Individual clones selected randomly from the enriched scFv pools from the subtractive panning steps were sequenced and aligned for selecting functional scFv sequences. After initial ELISA screening of 576 individual scFv clones 116 candidate PTP1B-binders (SEQ ID NO: 34 to SEQ ID NO: 149) were shortlisted for a final and definitive "in-solution" screening to isolate the conformation sensor scFvs. The amino acid sequences provided in SEQ ID NO: 26 to SEQ ID NO: 29 and SEQ ID NO: 34 to SEQ ID NO:149 represent scFv sequences flanked by leader peptide and tag sequences. The N-terminal 22 amino acids MKKTAIAIAVALAGFATVAQAA (SEQ ID NO: 150), and the C-terminal 23 amino acids GQAGQHHHHHHGAYPYDVPDYAS (SEQ ID NO: 151) are coded for by components of the phagemid pComb3XSS (SEQ ID NO: 152) or the mammalian expression vector pcDNA3.2N5/GW/D-TOPO (SEQ ID NO: 23) into which the scFvs were cloned. The sequences present between these N- and C-terminal amino acids are the scFv sequences. The sequences are displayed herein with the N-terminal leader peptide, the C-terminal tag and the linker sequences underlined. The linker sequence is used to join a variable light ($V_L$) chain and a variable heavy ($V_H$) chain fragment to produce a scFv.

The scFv sequences provided herein are of the general pattern: $NH_2$—$V_L$-linker-$V_H$—COOH. The N-terminal leader peptide and the C-terminal tag as well as the linkers are identified in the provided scFv sequences (SEQ ID NO: 26 to SEQ ID NO: 29 and SEQ ID NO: 34 to SEQ ID NO: 149). The sequence between the N-terminal leader peptide and the linker is the $V_L$ fragment of the respective scFv, and the sequence between the linker and the C-terminal tag is the $V_H$ fragment of the respective scFv.

For example:
MKKTAIAIAVALAGFATVAQAALTQPSSVSANPGGTV-KITCSGSSSAYGYGWYQQKSPGSAPVTVIYNNNKRP-SNIPSRFSGSKSGSTGTLTITGVQAEDEAVYFCGSEDS-STDAIFGAGTTLTVLGQSSRSSTVTLDESGGGLQAPG-GALSLVCKASGFTFSSYDMGWIRQAPGKGLEYVAG I-TDNGRYASYGSAVDGRATISRDNGQSSVRLQLNN LR-AEDTGTYYCARDDGSGWTGNSIDAWGHGTEIIVSST-SGQAGQHHHHHHGAYPYDVPDYAS (SEQ ID NO: 78).

In this sequence, the N-terminal leader peptide, the C-terminal tag, and the linker sequence are underlined. The scFv sequence is the sequence starting with "LTQ . . . " and ending with " . . . STS" between the N-terminal leader peptide and the C-terminal tag. Accordingly, the $V_L$ fragment of this scFv is the sequence starting with "LTQ . . . " and ending with "... TVL" between the N-terminal leader peptide and the linker, and the $V_H$ fragment of this scFv is the sequence starting with "TVT ..." and ending with "... STS" between the linker and the C-terminal tag. Where possible, the C-terminal tag, the N-terminal leader peptide, the linker and the $V_L$ and $V_H$ fragments are identified in a similar manner in the scFv sequences provided herein.

Fifteen of the listed scFvs (scFv4, scFv28, scFv9, scFv10, scFv29, scFv31, scFv11, scFv18, scFv63, scFv75, scFv79, scFv81, scFv88, scFv89 and scFv91) display truncated amino acid sequences because of incomplete DNA sequences from the sequencing results. The alignments provided in FIG. 6 and FIG. 7 allow identification of CDRs even in those sequences.

Antibody fragments or polypeptides can comprise a portion or segment (continuous or discontinuous) of a scFv of any one of SEQ ID NO: 26 to SEQ ID NO: 29 or SEQ ID NO: 34 to SEQ ID NO: 149, bind PTP1B-OX and stabilize reversibly oxidized, inactive conformation. For example, embodiments include antibodies, antibody fragments and polypeptides whose amino acid composition is sufficiently similar to all or a portion of a scFv of any one of SEQ ID NO: 26 to SEQ ID NO: 29 or SEQ ID NO: 34 to SEQ ID NO: 149 that they bind reversibly oxidized, inactive PTP1B-OX in such a manner that they inhibit its reduction (reactivation by reducing agent to reduced, active PTP1B).

As explained above, 15 of the listed scFvs display truncated amino acid sequences because of incomplete DNA sequences from the sequencing results. These clones, however, expressed well as functional scFvs in *E. coli* and bound to PTP1B-CASA in ELISA. Therefore, these scFvs were included in the shortlist of candidates for screening the conformation sensor antibodies against PTP1B-OX. In this screening Applicant included wild type PTP1B, reversibly oxidized by $H_2O_2$, with the individual bacterially expressed scFvs and then added $^{32}P$-labeled reduced carboxamidomethylated and maleylated lysozyme (RCML) as standard PTP1B substrate with or without reducing agent. Conformation-sensor scFvs that are able to bind and stabilize the oxidized conformation in solution would inhibit the enzyme to revert back to its active state when the reducing condition is restored.

Example 3

In Vitro Assessment of PTP1B-OX Stabilization by Selected Scfvs

3. Screening Individual scFvs as Conformation-Sensor Antibodies to PTP-OX:

For purification of individual scFv as functional antibody fragment, single scFv was expressed without pIII fusion in a nonsuppressor strain of *E. coli* (e.g. TOP10F' cells). After several rounds (2 to 4) of subtractive panning and subsequent sequencing, individual clones were chosen for scFv production by IPTG induction. The culture supernatants were then screened directly by ELISA for antigen-specific binding as described earlier.

3.1. Characterization of Selected scFvs:

After panning and initial screening against PTP1B-CASA by ELISA, potential individual scFv clones were selected and their ability to bind specifically to oxidized PTP1B was confirmed by both in vitro and in vivo assays.

3.2. Expression and Purification of Soluble scFvs:

Selected scFv clones were expressed under IPTG induction in TOP10F' *E. coli* and purified from the culture supernatant with Ni-NTA resin exploiting the C-terminal His tag and subsequent elution with imidazole.

TOP10F' *E. coli* cells were grown from single colonies in Super Broth (SB) medium (1% MOPS, pH 7.0, 3% tryptone, 2% yeast extract) at 37° C. with shaking at 250 rpm overnight. This overnight culture was diluted 1:50 in SB medium and incubated at 37° C. at 250 rpm until the $OD_{600\ nm}$=0.8. This culture was then shaken slowly at 100 rpm at 37° C. for 15 minutes to regenerate the sheared F' pili of the TOP10F' strain. This TOP10F' cells were then infected with phage particles expressing individual scFvs by adding $10^{12}$ phage particles/ml of bacterial culture and incubating at room temperature for 15 minutes with occasional gentle shaking. The infected culture was then diluted 1:50 in SB medium+50 µg/ml of Carbenicillin and incubated at 37° C. and 250 rpm until the $OD_{600\ nm}$=0.5. The culture was induced with 1.5 mM IPTG at 30° C. and 250 rpm for 16 hours. The cells were harvested and resuspended in Lysis Buffer (50 mM $NaH_2PO_4$, pH 8.0, 500 mM NaCl, 10 mM imidazole, 1 mM PMSF and EDTA free protease inhibitor cocktail). Resuspended culture was incubated with lysozyme (0.5 mg/ml) for 30 minutes at 4° C. The suspension was sonicated and centrifuged at 50,000 g for 30 minutes at 4° C. The supernatant was used to purify the soluble scFv by using Ni-NTA gravity columns. After adding the supernatant to the column it was washed with 20 column volume of Wash Buffer (50 mM $NaH_2PO_4$, pH 8.0, 500 mM NaCl, 20 mM imidazole). The bound protein was finally eluted with the Elution Buffer (50 mM $NaH_2PO_4$, pH 8.0, 500 mM NaCl, 250 mM imidazole).

3.3. Expression and Purification of Recombinant PTP1B:

The catalytic domain (37 kDa) of wild type PTP1B (PTP1B_WT) or PTP1B-CASA was constructed in a pET19b vector and expressed in BL21 *E. coli*. Single colonies harboring the expression plasmid were grown in LB+Ampicillin (50 µg/ml) overnight. The overnight culture was diluted 1:50 in LB+Ampicillin (50 µg/ml) at 37° C. until $OD_{600\ nm}$=0.6. Expression of recombinant PTP was induced with 0.3 mM IPTG at 37° C., 250 rpm for 4 hours. Cells were harvested and resuspended in Lysis Buffer (25 mM $NaH_2PO_4$, pH 6.5, 10 mM NaCl, 1 mM EDTA, 5 mM DTT, 1 mM PMSF, 2 mM benzamidine and protease inhibitor cocktail). The suspension was incubated with 0.5 mg/ml lysozyme at 4° C. for 30 minutes and sonicated to extract the soluble protein. The sample was then centrifuged at 50,000 g at 4° C. for 30 minutes and supernatant was collected for purification of the recombinant PTP1B. The first purification step was done with a cation exchange column (SP Sepharose HP) using 25 mM $NaH_2PO_4$, pH 6.5, 10 mM NaCl, 1 mM EDTA, 5 mM DTT as the binding buffer and the protein was eluted by a gradient elution with 10-500 mM NaCl. Fractions containing PTP1B were pooled together and used for a final purification step by an anion exchange column (Q Sepharose HP) using 25 mM Tris-Hcl, pH 7.5, 1 mM EDTA, 5 mM DTT as the binding buffer. The purified protein was eluted by a gradient elution with 0-500 mM NaCl.

3.4. Screening for the Conformation-Sensor scFvs:

Reduced carboxamidomethylated and maleylated lysozyme (RCML) was labeled with $^{32}P$ using recombinant GST-FER kinase to stoichiometries up to 0.8 (mol $^{32}P$ incorporated/mol of protein). This $^{32}P$-Labeled phospho-tyrosyl RCML was used as the substrate in the in-solution phosphatase assay for screening the conformation sensor scFvs. Recombinant PTP1B was reversibly oxidized and transiently inactivated with $H_2O_2$ (5× molar excess of the protein). The phosphatase activity was completely restored upon the removal of $H_2O_2$ by a quick buffer exchange and addition of reducing agent (TCEP/DTT). Purified bacterially expressed scFvs (100× molar excess of PTP1B) were incubated with PTP after $H_2O_2$ treatment and its removal and the effect of individual scFv on stabilizing the reversibly oxidized conformation was assessed by the phosphatase assay under reducing condition.

Example 4

Expression of Intrabody in Mammalian Cells

Intracellular antibodies (or intrabodies) have been used successfully for studying biological processes and for blocking proteins inside cells. In the initial screening, four scFv candidates that showed significant inhibition to the reactivation process of transiently inactivated PTP1B (by stabilizing the reversibly oxidized conformation of the enzyme). One of these scFvs (scFv45) was cloned in pcDNA3.2/V5-GW/D-TOPO (SEQ ID NO: 23) expression vector for transient expression of this single chain antibody fragment in mammalian cells as intrabody to PTP1B. The scFv45 sequence from the pCom3×SS phagemid construct was PCR amplified and cloned directionally in the pcDNA3.2/V5-GW/D-TOPO vector in such a way that the 5' and 3' Sfi I restriction sites were retained in the mammalian construct. This particular intrabody was transiently transfected in 293T cells using Fugene 6 transfection reagent. Transfected cells were harvested 24, 36 and 48 hours post transfection and lysed in RIPA buffer (25 mM HEPES, pH 7.5, 150 mM NaCl, 0.25% Deoxychloate, 10% Glycerol, 25 mM NaF, 10 mM $MgCl_2$, 1 mM EDTA, 1% Triton. X-100, 0.5 mM PMSF, 10 mM Benzamidine, protease inhibitor cocktail). Soluble fractions from the samples were used in Western Blot experiment using HRP conjugated anti-HA antibody to detect the expressed scFv. Stable expression of scFv 45 was shown at 24-48 hours post transfection as the PTP1B-OX-specific intrabody.

Figure 1:
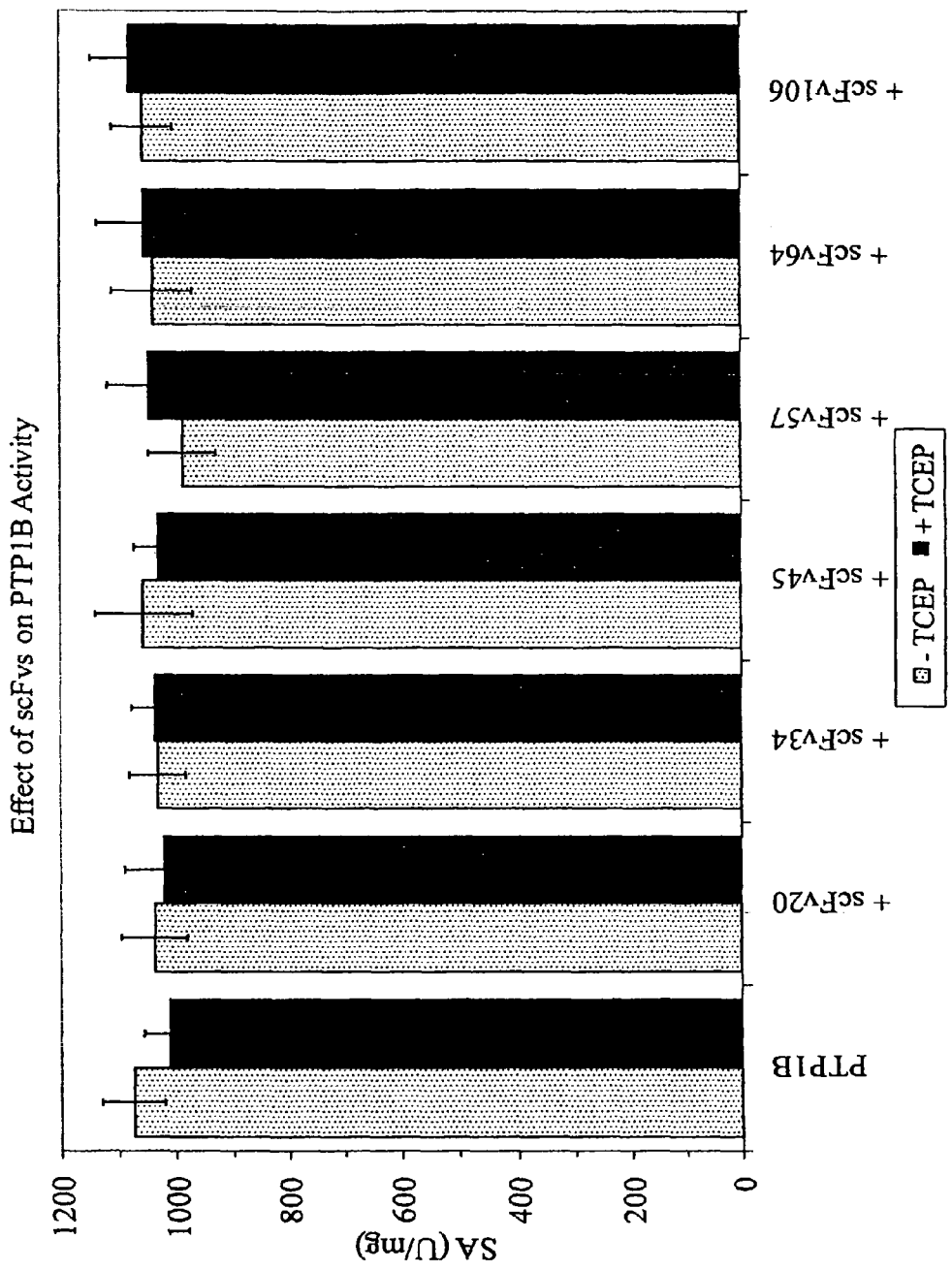
FIG. 1: Effect of individual scFvs on PTP1B activity.
Figure 2:
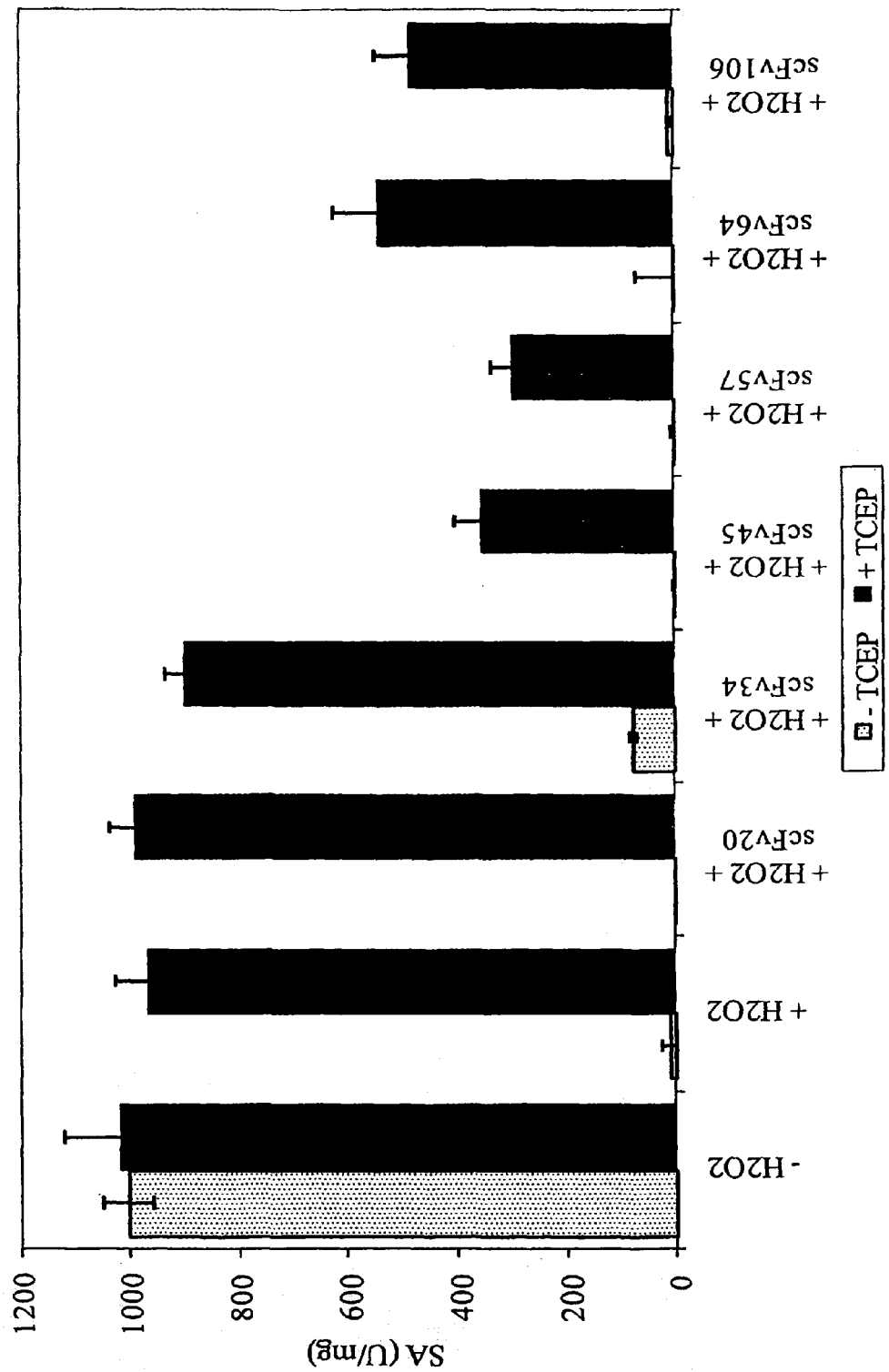
FIG. 2: Screen for scFvs that stabilize the reversibly oxidized form of PTP1B

In order to screen the isolated scFvs for those that inhibit reactivation of PTP1B-OX by reducing agent, but have no direct inhibitory effect on phosphatase activity in assays in vitro, the effect of six scFvs (scFv20, scFv34, scFv45, scFv57, scFv64 and scFv106) on PTP1B activity was determined. PTP1B activity was measured using 32P-labeled pTyr-Reduced Carboxamidomethylated and Maleylated Lysozyme as substrate (FIGS. 1 and 2). Addition of the reducing agent TCEP alone had no substantial effect in PTP1B activity was assessed. None of the above mentioned scFvs had a substantial effect on PTP activity, indicating that no direct inhibition of PTP activity was effected by any of these scFvs (FIG. 1).

In a different experiment, conditions were established in which wild type PTP1B could be reversibly oxidized in vitro. PTP1B was inactivated following addition of $H_2O_2$, however, phosphatase activity was completely restored upon the removal of $H_2O_2$ by a quick buffer exchange and addition of the reducing agent TCEP (FIG. 2, "+$H_2O_2$"). Addition of the reducing agent alone had no substantial effect on PTP1B activity (FIGS. 1 and 2, "PTP1B"). The ability of individual scFvs to stabilize the reversibly oxidized, inactive conformation of the PTP1B was assessed by the ability of the scFv to inhibit the reactivation of the enzyme by reducing agent (FIG. 2). As illustrated in FIG. 2, scFv45, scFv57, scFv64, and scFv106 show a substantial inhibition of the restoration of PTP1B activity after reversible oxidation.

These results reflect the ability of these scFvs to stabilize PTP1B-OX and inhibit the reduction of the OX form back to an active, reduced form, while not directly inhibiting PTP activity. Applicant identified scFvs that showed significant inhibition of the reactivation of PTP1B-OX by reducing agent, but did not exert any direct inhibitory effect on activity (See FIGS. 1 and 2).

In order to validate this approach further, Applicant tested the effects of expressing one of these (scFv45) as a single chain antibody fragment "intrabody" to PTP1B, using 293T cells as a convenient expression system. This intrabody was expressed transiently and then tested for effects on insulin signaling, focusing initially on the tyrosine phosphorylation status of the β-subunit of the insulin receptor and IRS-1 (FIG. 2). Initial indications are that for both substrates expression of the intrabody had no impact on the basal level of tyrosyl phosphorylation, but it enhanced and extended the time course of insulin-induced phosphorylation, consistent with our proposed mechanism of action.

4.1 Role of Reversible PTP1B Oxidation in the Cellular Signaling Response to Insulin:

It was shown in Applicant's lab that stimulation of cells with insulin caused rapid and transient oxidation and inhibition of PTP and that this facilitates increased phosphorylation of receptors. Some scFvs described herein can be used to detect the intracellular reversibly oxidized PTP1B in response to insulin. Since scFvs can also be expressed inside mammalian cells, they may be used to understand the dynamics of PTP redox regulation in vivo in response to insulin.

Once the scFv-PTP1B-OX complex is formed intracellularly, some of the scFvs with high affinity will lock the enzyme in its oxidized form. PTP1B, locked in its reversibly oxidized conformation by the intrabody, should not be able to revert back to its active conformation by thioredoxin or other cellular reducing system. A high affinity intrabody, therefore, can inhibit the pool of active PTP1B simply by keeping the enzyme in its inactive form and hindering its reactivation. This provides a unique opportunity to dissect the status of both upstream and downstream signaling mechanism in response to insulin. For instance, the phosphorylation of the tandem tyrosine residues (pYpY1162/1163) in the activation loop of the β-subunit of insulin receptor and the phosphorylation of PKB/AKT is analyzed using phospho-specific antibodies upon insulin stimulation in cells overexpressing $PTP1B_{ox}$-specific scFv. Insulin signaling events in this system are also analyzed to verify whether locking PTP1B in its oxidized conformation by intracellular scFv can prolong the signals downstream of activated insulin receptor.

Figure 3:
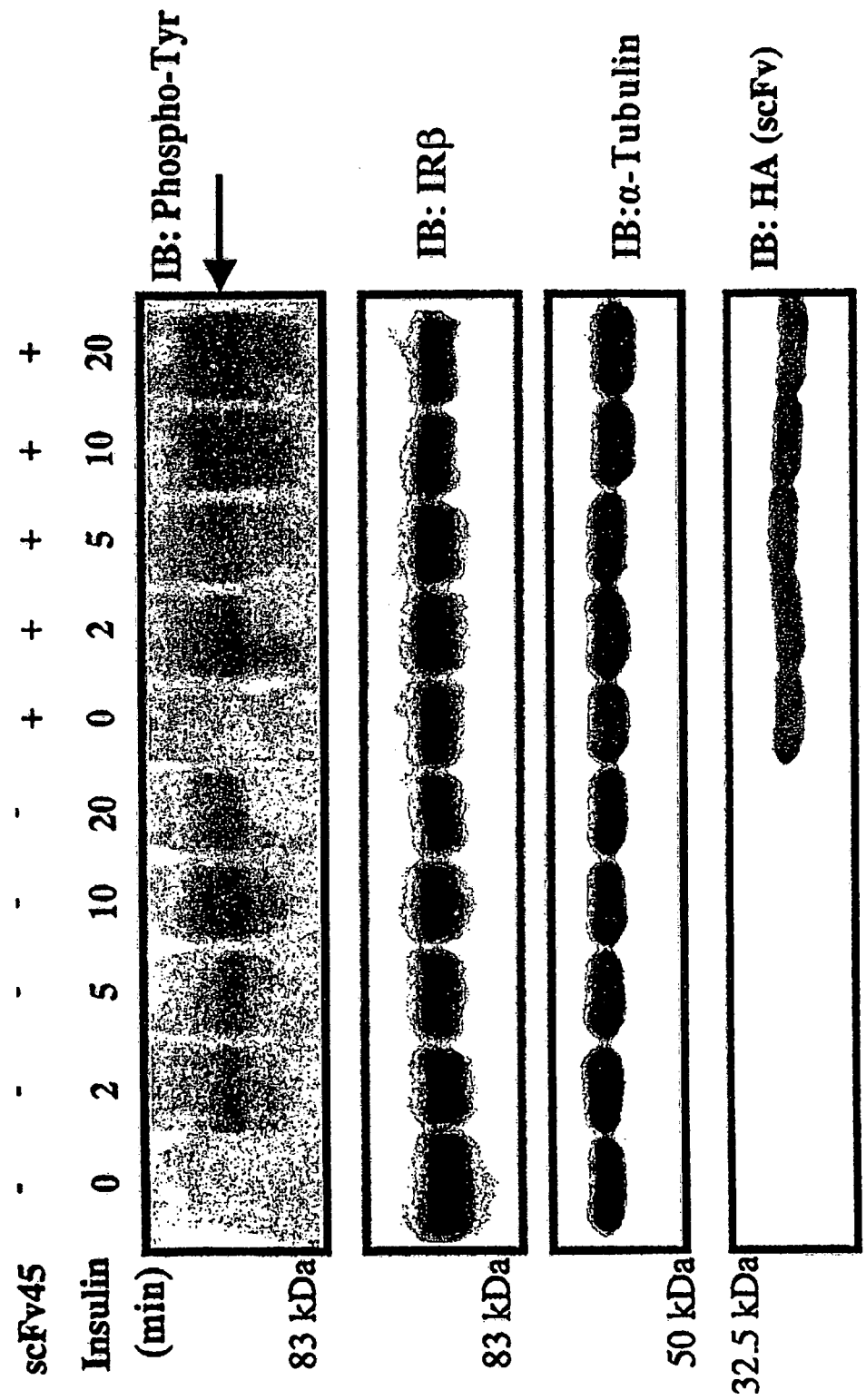
FIG. 3: Effect of scFv45 intrabody on the tyrosine phosphorylation status of the β-subunit of the insulin receptor.
Figure 4:
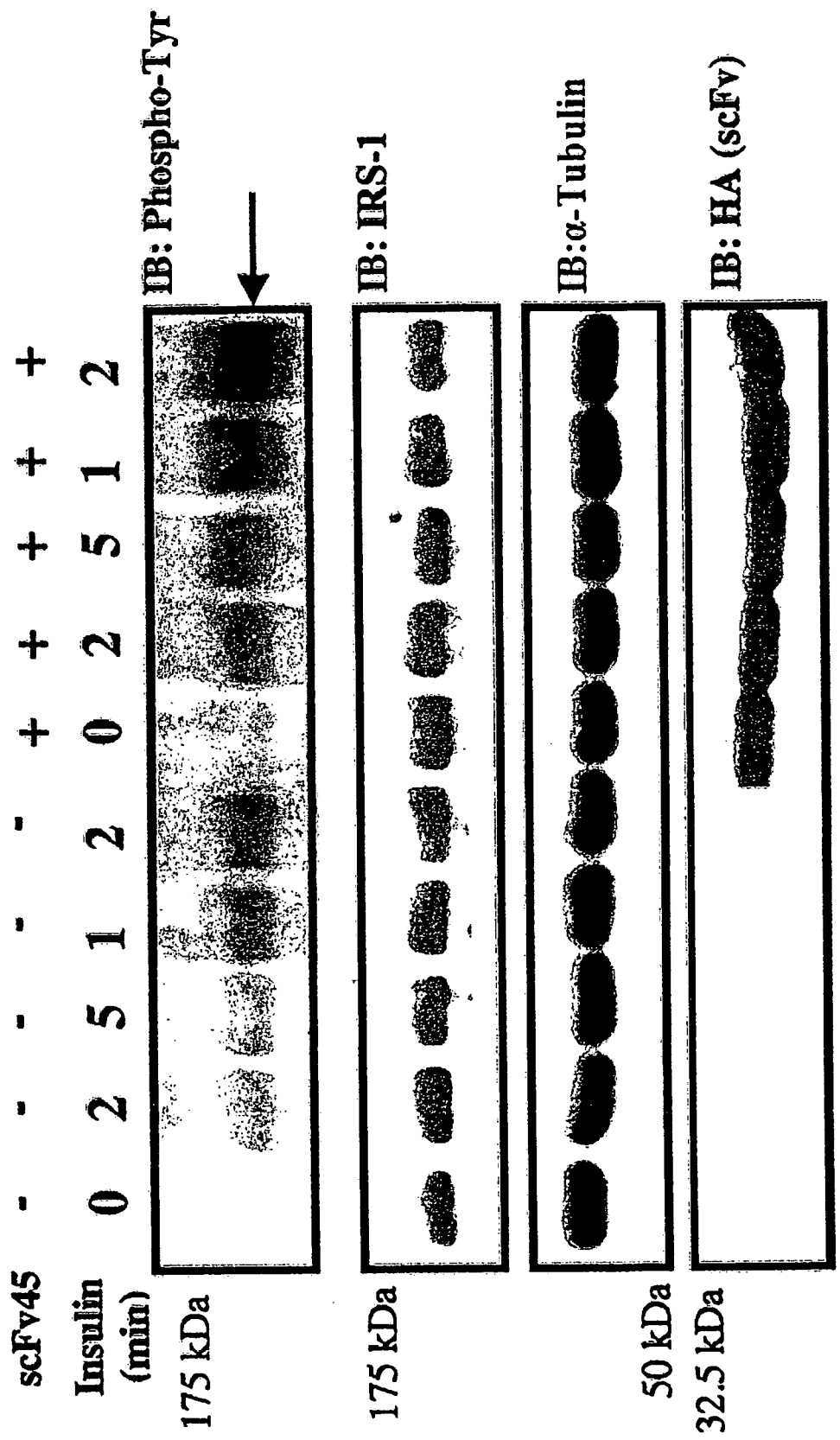
FIG. 4: Effect of scFv45 intrabody expression on the tyrosine phosphorylation status on IRS-1.

Intrabody scFv45 was transfected in 293T cells, serum starved and insulin stimulated to investigate the physiological relevance of this intrabody expression in mammalian cells in the context of PTP1B mediated regulation of insulin signaling (or insulin signaling mediated redox regulation of PTP1B activity). Insulin stimulated 293T cells with or without the intrabody were harvested in RIPA buffer (25 mM HEPES, pH 7.5, 150 mM NaCl, 0.25% Deoxychloate, 10% Glycerol, 25 mM NaF, 10 mM $MgCl_2$, 1 mM EDTA, 1% TritonX-100, 0.5 mM PMSF, 10 mM Benzamidine, protease inhibitor cocktail, 1 mM sodium vanadate) and the cell lysates were examined for total tyrosine phosphosphorylation pattern using phospho-tyrosine specific antibodies (FIGS. 3 and 4). When cells in which scFv45 was overexpressed were stimulated with insulin, insulin receptor β (IRβ) and insulin receptor substrate-1 (IRS-1) showed increased and prolonged tyrosine phosphorylation (FIGS. 3 and 4). This result supports the hypothesis that the intrabody is stabilizing the reversibly oxidized conformation of PTP1B (induced by ROS produced in response to insulin stimulation) in vivo and inhibits its reactivation by cellular reducing machinery.

Example 5

Rabbit Polyclonal Antibody Against PTP1B-OX

In the catalytic cleft of PTP1B, there are two hydrogen bonds that hold the active site together: the first one holds the signature motif at the base of the active site cleft linking the sulfur atom of the cysteine 215 with the serine 222. The second one is between serine 216 and the invariant tyrosine 46 of the pTyr loop that points down to the base of the active site and defines the depth of the cleft. Upon controlled oxidation with stoichiometric quantities of $H_2O_2$, formation of the cyclic sulphenamide intermediate is induced in the PTP1B crystals. One of the critical aspects about this oxidative modification of the active site cysteine is that it induces profound structural rearrangement at the active site cleft. The PTP loop, containing the signature motif, and Tyr46 from the phosphotyrosine binding loop, which are normally buried in the structure, flip out of the active site to adopt solvent exposed positions due to the lack of hydrogen bonding at the catalytic cleft. These conformational changes are readily reversible, consistent with a mechanism for reversible regulation of PTP function.

The crystal structure of the reversibly oxidized, inactive form of PTP1B has been determined previously (Salmeen et al. Nature 2003). The surface representation of the crystal structure indicates that the Tyr46 of the pTyr loop is popped open and becomes solvent exposed as a result of the breaking of hydrogen bonds in the reversibly oxidized conformation. A peptide sequence ($H_2N$-CNRYRDV-OH) (SEQ ID NO: 24) was designed on the basis of the surface structure surrounding the solvent exposed Tyr46 of the reversibly oxidized form of PTPB. This peptide was used as an antigen to generate conformation specific rabbit polyclonal antibodies that would recognize the oxidized form of PTP1B. As a control measure to this approach another peptide ($H_2N$—CNRpYRDV-OH) (SEQ ID NO 25), in which the Tyr46 is phosphorylated was used to generate rabbit polyclonal antibody against the phosphorylated Tyr46. These two polyclonal antibodies were used in the same RCML phosphatase assay as we have described in section 3.4, to detect the ability to recognize the reversibly oxidized conformation of PTP1B. The antibody generated against the solvent exposed peptide sequence surrounding the Tyr46 has similar inhibitory effect to the reactivation of reversibly oxidized PTP1B. Hence, this polyclonal antibody is also able to stabilize the reversibly oxidized conformation of PTP1B and acts as a conformation sensor antibody.

Example 6

Interaction Between PTP1B-Ox and scFvs In Vitro

In their in vitro screening assay, Applicant have found candidate PTP1B-OX specific scFvs (scFv45, scFv57, scFv64 and scFv106) that inhibit reactivation of PTP1B-OX by reducing agent, but have no direct inhibitory effect on phosphatase activity (FIG. 1 and FIG. 2). This result suggests that these candidate scFvs inhibit the reactivation of PTP1B-OX by reducing agent by specifically binding and stabilizing the reversibly oxidized, inactive conformation of the enzyme.

In order to demonstrate direct interaction between PTP1B-OX and candidate scFvs, Applicant performed an in vitro binding assay using purified recombinant PTP1B (37 kDa) and purified scFvs under both oxidizing and reducing conditions. They established conditions in which PTP1B is reversibly oxidized by $H_2O_2$ in solution (FIG. 8). An artificial protein substrate RCML, in which tyrosine was phosphorylated with $^{32}P$ using recombinant GST-FER kinase was used in this assay to measure the phosphatase activity. Recombinant PTP (37 kDa) was incubated with increasing concentration (50 µM to 100 mM) of $H_2O_2$. A quick buffer exchange was done to remove the $H_2O_2$ and reducing agent (TCEP) was added to reactivate the enzyme. Results showed that PTP1B is reversibly oxidized and transiently inactivated when up to 500 µM $H_2O_2$ was used and the activity of the enzyme can be restored fully with the addition of reducing agent under this condition (FIG. 8).

In the in vitro binding assay, purified PTP was reversibly oxidized with µM $H_2O_2$ followed by a quick buffer exchange to remove $H_2O_2$ (FIG. 8). Purified scFv was incubated in molar excess with PTP1B-OX or with PTP under reducing condition (with 2 mM TCEP) in binding buffer (20 mM HEPES, pH 7.4, 300 mM NaCl, 0.05% BSA, 0.05% Tween-20 and 10 mM imidazole) for 2 hours at 4° C. Ni-NTA agarose was added and incubated for one hour at 4° C. Protein complex bound to Ni-NTA agarose beads was pulled down and washed (three times, 5 minutes each, at 4° C.) with binding buffer containing 20 mM imidazole to reduce non-specific binding to the beads. The protein complex was eluted from the Ni-NTA agarose beads with 500 mM imidazole (in binding buffer, pH 7.4) for 15 minutes at 4° C. with gentle shaking. The complex was separated by SDS-PAGE and PTP1B was detected with anti-PTP1B antibody (FG6) and scFv was detected with anti-HA antibody [anti-HA (3F10)-HRP, Roche] by immunoblotting. Eight different scFvs (scFvs 20, 21, 24, 28, 45, 48, 57, and 105), expressed and purified from bacterial cultures were tested by this in vitro binding experiment. Among this group of scFvs, two (scFv45 and scFv 57) showed specific binding to PTP1B-OX, but not to PTP under reducing condition (FIG. 9a and FIG. 9b). Under the conditions used, scFvs 20, 21, 24, 28, 48, and 105 showed no significant binding to PTP1B-OX or to PTP under reducing condition (FIG. 9c).

Example 7

Interaction Between PTP1B-OX and scFvs in Mammalian Cells

One of the positive candidate scFvs (scFv45) was cloned in pcDNA3.2/V5-GW/D-TOPO expression vector and transiently expressed in mammalian cells as stable intracellular antibody (aka intrabody) (FIG. 10). To detect PTP1B-OX and scFv45 interaction in mammalian cells, scFv45 was overexpressed in 293T cells as described herein (See Example 4) and 48 hours post transfection the cells were serum-starved for 16 hours in growth medium (DMEM, low glucose) without serum (FBS), then incubated with 1 mM $H_2O_2$ (in growth medium without serum) for 5 minutes at 37° C. or treated with 20 mM NAC (in growth medium without serum) for 1 hour at 37° C. Cells treated with $H_2O_2$ were washed twice with cold (4° C.) PBS and lysed in lysis buffer (25 mM HEPES, pH 7.4, 150 mM NaCl, 0.25% Deoxycholate, 1% TritonX-100, 25 mM NaF, 10 mM $MgCl_2$, 1 mM EDTA, 10% Glycerol, 0.5 mM PMSF, 10 mM Benzamidine, protease inhibitor cocktail). Cells treated with NAC were lysed with lysis buffer containing 2 mM TCEP to ensure a post-lysis reducing environment. Interaction between PTP1B and intrabody45 were tested by pulling down the protein complex from 1 mg of total cell lysate with Ni-NTA agarose or by immunoprecipitating PTP with anti-PTP1B (FG6). For the pull down experiment, Ni-NTA agarose beads were incubated with the lysates (both oxidized and reduced) at 4° C. Protein complex bound to the Ni-NTA agarose beads was pulled down and washed three times; first with lysis buffer containing 20 mM imidazole followed by two more washes with wash buffer (PBS, pH 7.4, 20 mM imidazole, 0.05% BSA, 0.05% Tween-20 and protease inhibitors). Applicant used 20 mM imidazole in the wash buffer to reduce the non-specific binding of proteins with the Ni-NTA agarose beads. The complex was eluted with wash buffer containing 500 mM imidazole with gentle shaking at 4° C. and the eluate was mixed with SDS sample buffer with DTT. For the immunoprecipitation experiments, 1 mg of total cell lystates (both oxidized and reduced) was incubated with anti-PTP1B antibody (FG6) at 4° C. The interacting protein complex was immunoprecipitated after incubating the lysate-antibody mixture with protein A/G Sepharose at 4° C. After immunoprecipitation, Sepharose beads were washed three times; first with lysis buffer followed by two more washes with wash buffer (PBS, pH 7.4, 0.05% BSA, 0.05% Tween-20 and protease inhibitors). The Sepharose beads were then heated at 90° C. in 2×SDS sample buffer with DTT. Proteins from the pulled down or immunoprecipitated complex were separated by SDS-PAGE. PTP was detected with anti-PTP1B antibody (FG6) and the intrabodies were detected with anti-HA (3F10)-HRP antibody [anti-HA (3F10)-HRP, Roche] by immunoblotting. In both the pull-down and immunoprecipitation experiments, interaction between scFv45 and PTP1B-OX was observed in the $H_2O_2$-treated cells but not in the cells that were under reducing condition (FIG. 11a and FIG. 11b).

In the initial in vitro phosphatase screening assay using reversibly oxidized (with $H_2O_2$) recombinant PTP1B, Applicant found four different PTP1B-OX specific scFvs (scFv45, scFv57, scFv64 and scFv106) from the initial pool of 12 different scFvs. Two of these scFvs (scFv45 and scFv57) were shown to interact with PTP1B-OX, but not with PTP1B under reducing condition in the in vitro interaction assay. Applicant has also shown that scFv45, expressed as an intrabody in mammalian cells, can bind to endogenous PTP1B-OX but not endogenous PTP under reducing conditions. Further assessment was carried out to identify additional PTP1B-OX-specific intrabodies. Additional scFvs have been subcloned in pcDNA3.2/V5-GW/D-TOPO mammalian expression vector (FIG. 10) from their respective phagemid constructs. After transient overexpression of these scFvs as intrabodies in 293T cells, the interaction between endogenous PTP1B and these intrabodies in both $H_2O_2$-treated cells and cells was observed under reducing condition (treated with NAC and lysed with lysis buffer containing TCEP). Using Ni-NTA pull down assay, as described earlier for the mammalian cell lysates, Applicants identified four additional scFvs (scFv57, scFv67, scFv102, scFv106) that bound to endogenous PTP1B-OX strongly; five others (scFv 136, scFv 61, scFv62, scFv64, scFv34 and scFv118) bound weakly to PTP1B-OX (FIG. 12a and FIG. 12b). None of the 28 intrabodies, however, showed any binding to endogenous PTP1B under reducing conditions (FIG. 12a and FIG. 12b). All can be used in the methods and compositions described herein. Additional scFvs, such as some or all of the 137 selected individual scFvs from the library, can be similarly tested by in vitro screening and/or by binding assay in mammalian cells.

Role of Intrabody45 on the Cellular Signaling Response Downstream of Insulin Receptor:

Insulin mediated phosphorylation and activation of IRK causes increased downstream signaling. PTP1B down-regulates this signal by regulating phosphorylation at the level of the receptor and acts as brake in this signaling pathway by maintaining a competitive fine-tuning in this intricate regulatory mechanism. However, stimulation of cells with insulin causes rapid and transient oxidation and inhibition of PTP1B and facilitates increased phosphorylation of receptors. So, generation of ROS by insulin accelerates the signaling by removing the foot off the brake. This transient inactivation of PTP1B is reversible and the brake is restored in the signaling pathway by dephosphorylating and deactivating the insulin receptor by the reactivated PTP1B.

As described herein, Applicant has shown that intrabody45 expression in mammalian cells caused enhanced and prolonged tyrosine phosphorylation of insulin receptor (3 subunit (IRβ) and insulin receptor substrate-1 (IRS-1) (FIGS. 3 and 4). This result supports the hypothesis that the intrabody stabilizes the reversibly oxidized conformation of PTP1B (induced by ROS produced in response to insulin stimulation) in vivo and inhibits its reactivation by cellular reducing machinery.

Insulin induces activation of the insulin-receptor kinase (IRK) through autophosphorylation. Recruitment of insulin-receptor substrate (IRS) proteins induces activation of Phosphoinositide 3-kinase (PI3K). PI3K activation triggers downstream effectors, such as phosphatidylinositol-dependent kinase 1 (PDK1) and protein kinase B or AKT, leading to translocation of glucose transporter 4 (GLUT4) and glucose uptake in muscle, and inactivation of glycogen-synthase kinase 3 (GSK3). PTP1B dephosphorylates membrane-bound or endocytosed insulin receptors, causing their deactivation and plays a negative inhibitory role in the signaling events downstream of insulin receptor.

Applicant assessed the role of PTP1B-OX specific intrabody on the downstream readout of insulin signaling by following the phosphorylation (activation) status of AKT. Cells with or without scFv45 overexpression were stimulated with insulin for different time periods and phosphorylation of AKT activation loop at residue Threonine 308 (T308) was observed with phospho-specific AKT antibody [phospho-Akt (T308), Cell Signaling]. Cells overexpressing scFv45 displayed enhanced and sustained AKT phosphorylation at residue Threonine 308 (T308) (FIG. 13). This result suggests that upon insulin stimulation, intrabody45 binds and stabilizes endogenous PTP1B-OX, causing an enhanced and prolonged phoshorylation of insulin receptor 13 subunit (IRβ) and insulin receptor substrate 1 (IRS-1) and this signal is transmitted downstream to cause an enhanced and prolonged activation of AKT.

Colocalization of Intrabody 45 and PTP1B-OX under Insulin Stimulation:

In order to verify the interaction between PTP1B-OX and scFv45 in mammalian cells, Applicant determined whether PTP and scFv45 colocalized after insulin stimulation, using immunofluorescence. Cos1 cells were grown on cover slips and transfected with scFv45 using Fugene6 as the transfection reagent according to manufacturer's instructions. The cells were serum starved 24 hours post transfection, for 16 hours at 37° C. and then stimulated with 25 nM insulin (in growth medium without serum) or left untreated. Following insulin treatment the cells were washed 2× with PBS and fixed with 5% formalin (in PBS) for 15 minutes at room temperature. The cells were washed with PBS three times at room temperature. The fixed cells were permeabilized with 0.5% Triton-X100 (in PBS) for 5 minutes at room temperature. Cells were rinsed with Wash Buffer [PBS, pH 7.4 with 0.1% BSA, 0.2% TritonX-100, 0.05% Tween-20 and 0.05% sodium azide] at room temperature. The coverslips were blocked with 5% normal goat serum in wash buffer for 1 hour at room temperature to reduce the non-specific binding of the secondary antibodies. To detect endogenous PTP1B, the coverslips were incubated with anti-PTP1B antibody [rabbit polyclonal anti-PTP1B (H-135), Santa Cruz Biotechnology] at RT for 1 hour. The cells were washed with the wash buffer at room temperature to remove excess antibodies. A cocktail of Alexa 594 conjugated anti-HA mouse monoclonal antibody [16B12, Invitrogen, 21288] and goat anti-rabbit alexa 488 (Invitrogen, A-11034) secondary antibody in the blocking buffer (5% normal goat serum) was added to the coverslip and incubated at RT for 1 hour. The coverslips were washed 3× with IF wash buffer and incubated with DAPI (0.3 μg/ml in PBS) for 10 minutes at room temperature to stain the nucleus and washed again with IF wash buffer to remove excess unbound DAPI. The cover slip was mounted on glass slide with Vectasheild Mounting Medium (H-1000, Vector Laboratories) and observed using confocal microscope (LSM 710, Zeiss) with 63× objective lens and immersion oil. Strong colocalization between PTP1B and intrabody45 was observed in cells, following stimulation with insulin; colocalization between PTP1B and intrabody45 was not significant in cells without insulin stimulation (FIG. 14). To quantify colocalization of PTP1B and intrabody45 from the merged images, 15 individual images were analyzed by Zeiss (LSM 710) Colocalization Viewer Software. The degree of colocalization of PTP1B and intrabody45 in each cell was expressed as colocalization coefficients that measure relative number of colocalizing pixels for the respective fluorophores for PTP1B and intrabody45, as compared to the total number of pixels. The numeric range for this colocalization method is set as 0-1, where "0" indicates no colocalization and "1" indicates colocalization of all pixels in a cell.

```
Sequences of scFv45, scFv57, scFv64, and scFv106:
scFv45
                                                  (SEQ ID NO: 26)
M K K T A I A I A V A L A G F A T V A Q A A L T Q P S S V S

A N P G G T V K I T C S G S S S A Y G Y G W Y Q Q K S P G S

A P V T V I Y N N N K R P S N I P S R F S G S K S G S T G T

L T I T G V Q A E D E A V Y F C G S E D S S T D A I F G A G

T T L T V L G Q S S R S S T V T L D E S G G G L Q A P G G A

L S L V C K A S G F T F S S Y D M G W I R Q A P G K G L E Y

V A G I T D N G R Y A S Y G S A V D G R A T I S R D N G Q S

S V R L Q L N N L R A E D T G T Y Y C A R D D G S G W T G N

S I D A W G H G T E V I V S S T S G Q A G Q H H H H H G A

Y P Y D V P D Y A S scFv57
                                                  (SEQ ID NO: 27)
M K K T A I A I A V A L A G F A T V A Q A A L T Q P S S V S

A N P G A F N K I T C S G S S S A Y G Y G W N Q Q K S P G S

A P V T V I Y N N N K R P S N I P S R F S G S K S G S T G T

L T I T G D Q D E D E D F Y F C G S E Y S S T D A I F G A G

T T L T V L G Q S S R S S T V T L D E S G G G L Q A P G G A

L S L V C K A S G F T F S S Y D M G W I P Q A P G K G L E Y

V A G I T D N G I Y A S Y G S A V D G R A T I S R D N R Q S

S V K L Q L N N L K A D D T G T Y Y C A R D D G S G W T G N

S I D A W G H G T E V I V S S T S G Q A G Q H H H H H G A

Y P Y D V P D Y A S scFv64
                                                  (SEQ ID NO: 28)
M K K T A I A I A V A L A G F A T V A Q A A L T Q P S S V S

A N P G D P L K I T C S G D S S G Y G Y G W Y Q Q K S P G S

A P V T V I Y N N N K R P S D I P S R F S G S K S G S T G T

L T I T G V Q A E D E A V Y F C G S E D S N T D A V F G A G

T T L T V L G Q S S R S S T V T L D E S G G G L Q T P G G T

L S L A C K A S G F T F S G Y D M G W V R Q A P G K G L E Y

V A G I T S D G R Y A S Y G S A V D G R A A I W R D N G Q S

T V R L Q L K N L R T E D T A T Y Y C A R N D G S G W N G N
```

-continued

N I D A W G H G T E V I V S S T S <u>G Q A G Q H H H H H H G A</u>
<u>Y P Y D V P D Y A S</u> scFv106
(SEQ ID NO: 29)
<u>M K K T A I A I A V A L A G F A T V A Q A A L</u> T Q P S S V S
A N P G E T V K I T C S G D S S D Y G Y G W Y Q Q K S P G S
A P V T V T Y S N N Q R P P N I P S R F S G S A S G S T A T
L T I T G V Q V E D E A V Y Y C G S E D S T T D A V F G A G
T T L T V L <u>G Q S S R S S</u> A M T L D E S G G G L Q T P G G A
L S L V C K A S G F T F S S Y D M G W V R Q A P G K G L E Y
V A G I T N D G R Y A S Y G S A V D G R A T I S R D N G Q S
T V R L Q L N N L R A E D T G T Y Y C A R D D G S G W T G N
T I D T W G H G T E V I V S S T S <u>G Q A G Q H H H H H H G A</u>
<u>Y P Y D V P D Y A S</u>

Sequences of the PTP1B-OX-Specific scFv Antibodies:
>scFv45
M K K T A I A I A V A L A G F A T V A Q A A L T Q P S S V S
A N P G G T V K I T C S G S S S A Y G Y G W Y Q Q K S P G S
A P V T V I Y N N N K R P S N I P S R F S G S K S G S T G T
L T I T G V Q A E D E A V Y F C G S E D S S T D A I F G A G
T T L T V L G Q S S R S S T V T L D E S G G G L Q A P G G A
L S L V C K A S G F T F S S Y D M G W I R Q A P G K G L E Y
V A G I T N D G R Y A S Y G S A V D G R A T I S R D N G Q S
S V R L Q L N N L R A E D T G T Y Y C A R D D G S G W T G N
S I D A W G H G T E V I V S S T S G Q A G Q H H H H H H G A
Y P Y D V P D Y A S S .

>scFv57
M K K T A I A I A V A L A G F A T V A Q A A L T Q P S S V S
A N P G G T V K I T C S G S S S A Y G Y G W Y Q Q K S P G S
A P V T V I Y N N N K R P S N I P S R F S G S K S G S T G T
L T I T G V Q A E D E A V Y F C G S E D S S T D A I F G A G
T T L T V L G Q S S R S S A V T L D E S G G G L Q T P G G A
L S L V C K A S G F T F S S Y D M G W V R Q A P G K G L E Y
V A G I T N D G R Y A S Y G S A V D G R A T I S R D N G Q S
T V R L Q L N N L R A E D T G T Y Y C A R D D G S G W T G N
T I D T W G H G T E V I V S S T S G Q A G Q H H H H H H G A
Y P Y D V P D Y A S S .

>scFv64
M K K T A I A I A V A L A G F A T V A Q A A L T Q P S S V S
A N P G E T V K I T C S G D S S G Y G Y G W Y Q Q K S P G S
A P V T V I Y N N N K R P S D I P S R F S G S K S G S T G T
L T I T G V Q A E D E A V Y F C G S E D S N T D A V F G A G
T T L T V L G Q S S R S S T V T L D E S G G G L Q T P G G T

```
LSLACKASGFTFSGYDMGWVRQAPGKGLEY

VAGITSDGRYASYGSAVDGRAAIWRDNGQS

TVRLQLKNLRTEDTATYYCARDDGSGWSGN

NIDAWGHGTEVIVSSTSGQAGQHHHHHHGA

YPYDVPDYASS.

>scFv106
MKKTAIAIAVALAGFATVAQAALTQPSSVS

ANPGETVKITCSGDSSDYGYGWYQQKSPGS

APVTVTYSNNQRPPNIPSRFSGSASGSTAT

LTITGVQVEDEAVYYCGSEDSTTDAVFGAG

TTLTVLGQSSRSSAMTLDESGGGLQTPGGA

LSLVCKASGFTFSSYDMGWVRQAPGKGLEY

VAGITNDGRYASYGSAVDGRATISRDNGQS

TVRLQLNNLRAEDTGTYYCARDDGSGWTGN

TIDTWGHGTEVIVSSTSGQAGQHHHHHHGA

YPYDVPDYASS.

>scFv 136
MKKTAIAIAVALAGFATVAQAALTQPSSVS

ANPGETVKITCSGGSYSYGWYQQKSPGSAP

VTVIYSSDKRPSDIPSRFSGSKSGSTSTLT

ITGVQAEDEAVYYCGSRDSNYVGIFGAGTT

LTVLGQSSRSSTVTLDESGGGLQTPGGALS

LVCKASGFTFSSYEMQWVRQAPGKGLEFVA

AISSDGSYTNYGAAVQGRATISRDNGQSTV

RLQLSNLRAEDTATYYCARSPGGYTWWPGA

AGGIDAWGHGTEVIVSSTSGQAGQHHHHHH

GAYPYDVPDYASS.

>scFv 67
MKKTAIAIAVALAGFATVAQAALTQPSSVS

ANPGGTVKITCSGSSSAYGYGWYQQKSPGS

APVTVIYNNNKRPSNIPSRFSGSKSGSTGT

LTITGVQAEDEAVYFCGSEDSSTDAIFGAG

TTLTVLGQSSRSSAVTLDESGGGLQTPGGA

LSLVCKASGFTFSSYDMGWVRQAPGKGLEY

VAGITNDGRYASYGSAVDGRATISRDNGQS

TVRLQLNNLRAEDTGTYYCARDDGSGWTGN

TIDTWGHGTEVIVSSTSGQAGQHHHHHHGA

YPYDVPDYASS.

>scFv 102
MKKTAIAIAVALAGFATVAQAALTQPSSVS

ANPGETVKITCSGGSGSYGWYQQESPGSAP

VTVIYYNDKRPSDIPSRFSGSASGSTATLT

IAGVRAEDEAVYFCGSWDSSTSAGIFGAGT
```

```
ALTVLGQSSRSSAVTLDESGGGLQTPGGGL
SLVCKASGFSSSHGMGWMRQAPGKGLEFVA
GIRSDGSSTAYGAAVDGRATITRDDGQSTV
TLQLNNLRAEDTATYFCAKTNSYNSAGIID
AWGHGTEVIVSSTSGQAGQHHHHHHGAYPY
DVPDYASS.
```

>scFv 34
```
MKKTAIAIAVALAGFATVAQAALTQPSSVS
ANLGGTVEITCSGSSGSYGWYQQKSPGSAP
VTVIYYNDKRPSDIPSRFSGSTSGSTATLT
ITGVQAEDEAVYFCGGYDSNYIGIFGAGTT
LTVLGQSSRSSAVTLDESGGGLQTPRGALS
LVCKASGFTFSSYSMAWVRQAPGKGLEFVA
GIQNDGSITDYGSAVDGRATISRDDGQSTV
RLQLNNLRTEDTATYYCAKTTVADGVIGAY
GIDAWGHGTEVIVSSTSGQAGQHHHHHHGA
YPYDVPDYASS.
```

>scFv 61
```
MKKTAIAIAVALAGFATVAQAALTQPSSVS
ANPGETVKITCSGGGSYAGSYYYGWYQQKA
PGSAPVTLIYDNTNRPSNIPSRFSGSLSGS
TGTLTITGVRAEDEAVYYCGSFDSSTDGGY
AAIFGAGTTLTVLGQSSRSYAVTLDESGGG
LQTPGGGLSLVCKASEFTFSSYAMEWVRQA
PGKGLEWVAYINSDGSSTWYAPAVKGRATI
SRDNGQSTVRLQLNSLRAEDTATYYCTRGS
GGENIDTWGHGTEVIVSSTSGQAGQHHHHH
HGAYPYDVPDYASS.
```

>scFv 62
```
MKKTAIAIAVALAGFATVAQAALTQPSSVS
ANPGETVKITCSGGGSYAGSYYYGWYQQKA
PGSAPVTLIYDNTNRPSNIPSRFSGSLSGS
TGTLTITGVRAEDEAVYYCGSFDSSTDGGY
AAIFGAGTTLTVLGQSSRSSAVTLDESGGG
LQTPGGGLSLVCKASEFTFSSYAMEWVRQA
PGKGLEWVAYINSDGSSTWYAPAVKGRATI
SRDNGQSTVRLQLNSLRAEDTATYYCTRGS
GGENIDTWGHGTEVIVSSTSGQAGQHHHHH
HAAYPYDVPDYASS.
```

>scFv 118
```
MKKTAIAIAVALAGFATVAQAALTQPSSVS
ANLGGTVEITCSGGSGSYGWYQQKSPGGAP
VTVIYYNDKRPSDIPSRFSGSKSGSTATLT
```

-continued

ITGVQVEDEAVYYCGSYDSSYVGIFGVGTT

LTVLGQSSRSSAVTLDESGGGLQTPRGALS

LVCKASGFTFSSYSMAWVRQAPGKGLEFVA

GIQNDGSITDYGSAVDGRATISRDDGQSTV

RLQLNNLRTEDTATYYCAKTTVADGVIGAY

GIDAWGHGTEVIVSSTSGQAGQHHHHHGA

YPYDVPDYASS.

Listing of Sequences in Sequence Listing:
1: Ig VL+VH (Gallus)
2: PTP signature catalytic motif (HCX5R)
3: PTP signature catalytic motif (CSX4R)
4: PTP signature catalytic motif (HCSX4R)
5: NM_002827
6: NP_002818
7: BT006752
8: AAP35398
9: M31724
10: AAA60223
11: M33689
12: AAA60157
13: BC015660
14: AAH15660
15: BC018164
16: AAH18164
17: AK316563
18: BAG38152
19: PTP1B-CASA
20: 7 amino acid residue linker for scFv
21: 18 amino acid residue linker for scFv
22: biotinylation sequence
23: pCDNA3.2/V5-GW/D-TOPO
24: peptide surrounding Tyr46
25: peptide surrounding Tyr46, Tyr46 phosphorylated
26: scFv45, aa
27: scFv57, DNA
28: scFv64, aa
29: scFv106, aa
30: scFv45, DNA
31: scFv57, DNA
32: scFv64, DNA
33: scFv106, DNA
34-149: 116 scFvs (including scFv45, scFv57, scFv64 and scFv106)
150: N-terminal 22 amino acids of scFv sequences
151: C-terminal 23 amino acids of scFv sequences
152: pComb3XSS
153: scFv136
154: scFv139
155: scFv103
156: scFv138
157: scFv134
158: scFv137
159: scFv140
160: scFv136
161: scFv67
162: scFv102
163: scFv34
164: scFv61
165: scFv62
166: scFv118

```
Updated scFv Sequences
>scFv1
MKKTAIAIAVALAGFATVAQAALTQPSSVSANPGETVKITCSGGVGQWYGWYQQKSPGSAPVTLIYESNQR

PSNIPSRFSGSLSGSTATLTITGVQPEDEAVYFCGGYDGNSGIFGAGTTLTVLGQSSRSSAVTLDESGGGL

QTPGRALSLVCKASGFTFSSYDMGWVRQAPGKGLEWVAYINSGSGSSTYYGTAVKGRASISRDNGQSTVRL

QLNNLRVEDTGTYFCAKGASGYYSSSIGAGEIDAWGHGTEVIVSSTSGQAGQHHHHHGAYPYDVPDYAS

>scFv2
MKKTAIAIAVALAGFATVAQAALTQPSSVSANPGGTVKITCSGGGSYYGWYQQKSPGSAPVTVIYDNTNRP

SNIPSRFSGSKSGSTGTLTITGVQADDEAVYYCGSTDSSADGVFGAGTTLTVLGQSSRSSAVTLDESGGGL

QTPGGGLSLVCKGSGFTFSSFDMFWVRQAPGKGLEWVAGIRNDGSDTAYGAAVKGRATISKDNGQSTVRLQ

LNNLRAEDTGTYYCAKAAGYCYVYSCAGSIDAWGHGTEVIVSSTSGQAGQHHHHHGAYPYDVPDYAS

>scFv3
MKKTAIAIAVALAGFATVAQAAVSTNPGDTVKITCSGGNSWYGWFQQKSPGSAPVTVIYGNDERPSDIPSR

FSGSESGSTATLTITGVRAEDEAVYYCGSGDNSGAGIFGAGTTLTVLGQSSRSSAVTLDESGGGLQTPGGA

LSLVCKASGFTFSSNGMAWVRQAPGKGLEWVAGISSSGSYTNYGSAVKGRATISRDNGQSTVRLQLNNLRA

EDTATYYCAKSSYAYYGFGAPFIDAWGHGTEVIVSSTSGQAGQHHHHHGAYPYDVPDYAS
```

-continued

>scFv4
MKKTAIAIAVALAGFATVAQAAVIYDNDKRPSDVPSRFSGSKSGPTATLTITGVQAEDEAVYFCGSRDNSY
VGIFGAGTTLTVLGQSSRSSAVTLDESGGGLQTPGGALSLVCKASGFTFSSYDMFWVRQAPGKGLEFVAQI
NSAGSYTNYGSAVKGRATISRDDGQSTVRLQLNNLRAEDTGIYFCAKSASGYYYSGSDAGDIDAWGHGTEV
IVSSTSGQAGQHHHHHHGAYPYDVPDYAS

>scFv5
MKKTAIAIAVALAGFATVAQAAVSANPGGTVKITCSGSSGRYGWYQQKSPGSAPVTVIYYNDKRPSDIPSR
FSGSASGSTATLTITGVQAEDEAVYFCGSYEVNIHEGIFGAGTSLTVLGQSSRSSTVTLDESGGGLQTPGR
ALSLVCKASGFTFSSNGMYWVRQAPGKGLEWVAGISSSGSYTNYAPAVKGRATISRDNGQSTVRLQLNNLR
AEDTGTYYCAKGASSYSWDGGSIDAWGHGTEVIVSSTSGQAGQHHHHHHGAYPYDVPDYAS

>scFv6
MKKTAIAIAVALAGFATVAQAALTQPSSVSANPGDTVKITCSGSIRYYGWYQQKSPGSAPVTLIYYDDKRP
SDIPSRFSGSASGSTATLTITGVQADDEAIYFCGTADSTSSGAGIFGAGTTLTVLGQSSRSSTVTLDESGG
GLQTPGGALSLVCKGSGFTFSSFNMFWVRQAPGKGLEWVAGIYSSGGGETNYGAAVKGRATISRDNGQSTV
RLQLNNLRAEDTGTYYCAKESADVGCPFTAGCIDTWGHGTEVIVSSTSGQAGQHHHHHHGAYPYDVPDYAS

>scFv7
MKKTAIAIAVALAGFATVAQAAVSASLEGTVEITCSGGSGSYGWFQQKAPGSAPVTLIYDNTNRPSNIPSR
FSGSKSGSTATLTITGVQADDEAIYYCGSWDSSTDAAFGAGTTLTVLGQSSRSSTVTLDESGGGLQTPGGG
LSLVCKASGFTFSDYGMGWVRQAPGKGLEFVAGIGNTGSYTYYGSAVKGRATISRDNGQSTVRLQLNNLRA
EDTGIYFCAKSTDYWTYAGTIDAWGHGTEVIVSSTSGQAGQHHHHHHGAYPYDVPDYAS

>scFv8
MKKTAIAIAVALAGFATVAQAALTQPSSVSANPGETVKITCSGGGSSSYYGWYQQKSPGSAPVTLIYESNE
RPSNIPSRFSGSESGSTGTLTITGVRAEDEAVYYCGSADSSNAGIFGAGTTLTVLGQSSRSSTVTLDESGG
GLQTPGGALSLVCKASGFTFSSFNMGWVRQAPGKGLEFVAGIDNTGSFTHYGAAVKGRATISRDDGQSTVR
LQLDNLRAEDTGTYYCAKASGYYYSGVNAGSIDAWGHGTEVIVSSTSGQAGQHHHHHHGAYPYDVPDYAS

>scFv9
MKKTAIAIAVALAGFATVAQAAVIYGNDERPSDIPSRFSGSESGSTATLTITGVRAEDEAVYYCGSGDNSG
AGIFGAGTTLTVLGQSSRSSAVTLDESGGGLQTPGGALSLVCKASGFTFSSNGMAWVRQAPGKGLEWVAGI
SSSGSYTNYGSAVKGRATISRDNGQSTVRLQLNNLRAEDTATYYCAKSSYAYYGFGAPFIDAWGHGTEVIV
SSTSGQAGQHHHHHHGAYPYDVPDYAS

>scFv10
MKKTAIAIAVALAGFATVAQAAVIYANTDRPSDIPSRFSGSKSGSTATLTITGVRAEDEAVYFCGSGDSST
GIFGAGTTLTVLGQSSRSSAVTLDESGGGLQTPGGTLSLVCKGSGFTFSSVNMFWVRQAPGKGLEWVAGIY
SSGSSTHYGAAVKGRATISRDNGQSTVRLQLNNLRAEDTGIYYCAKDAGCYTSGDTAGCIDAWGHGTEVIV
SSTSGQAGQHHHHHHGAYPYDVPDYAS

>scFv11
MKKTAIAIAVALAGFATVAQAAVIYYNDKRPSNIPSRFSGSGSGSTNTLTIAGVRAEDEAVYYCGNEDSSG
AAFGAGTTLTVLGQSSRSSAVTLDESGGGLQTPGGGLSLVCKASGFTFSDYDMFWVRQAPSKGLEFVAAIT
SSGTGTKYGAAVKGRATISKDNGQRTVRLQLNSLGAEDTGTYYCARSDADSTTWSAGEIDAWGHGTEVIVS
STSGQAGQHHHHHHGAYPYDVPDYAS

>scFv12
MKKTAIAIAVALAGFATVAQAALTQPSSVSANPGEAVKITCSGGGSSSYYGWYQQKSPGSAPVTVIYWDDE
RPSNIPSRFSGSTSGSTGTLTITGVQAEDEAVYFCGGYDSSGDGIFGAGTTLTVLGQSSRSSSGGGSSGGG
GSAVTLDESGGGLQTPGRALSLVCKASGFTFSGYNMGWVRQAPGKGLEWVGGISGSGRYTEYGAAVKGRAT

-continued

ISRDNGQSTVRLQLNNLRAEDTGTYFCAKAAVSDYCGGGCAGDIDAWGHGTEVIVSSTSGQAGQHHHHHHG

AYPYDVPDYAS

>scFv13
MKKTAIAIAVALAGFATVAQAALSRPRCQQTWGGTVKITCSGGDSSYGWYQQKSPGSAPVTLIYDNTNRPS

DIPSRFSGSKSGSTGTLTITGVQAEDEAVYYCGNADSSSTAAFGAGTTLTVLGQSSRSSTVTLDESGGGLQ

TPGGALSLVCKASGFTFSSYAMGWVRQAPGKGLEYVAAISSAGSTTNYGAAVKGRATISRDNGQSTVRLQL

NNLRAEDTATYFCAKAAGSGYYVWSAIAGDIDAWGHGTEVIVSSTSGQAGQHHHHHHGAYPYDVPDYAS

>scFv14
MKKTAIAIAVALAGFATVAQAALTQPSSVSANPGETVKITCSGGYSGYGWFRQKAPGSAPVTLIYANTNRP

SDIPSRFSGSASGSTGTLTITGVQADDEAVYFCGSADSTYGIFGAGTTLTVLGQSSRSSAVTLDESGGGLQ

TPGGALSLVCRASGFTFSDYGMEWVRQAPGKGLEWVAGIDDDGSTTFYAPAVKGRATISRDDGQSTVRLQL

NNLRAEDTATYYCAKSAGRGWNVAGWIDAWGHGTEVIVSSTSGQAGQHHHHHHGAYPYDVPDYAS

>scFv15
MKKTAIAIAVALAGFATVAQAALSRPRCQQTQEHTVKITCSGGVGQWYGWYQQKSPGSAPVTLIYESNQRP

SNIPSRFSGSLSGSTATLTITGVQPEDEAVYFCGGYDGNSGIFGAGTTLTVLGQSSRSSAVTLDESGGGLQ

TPGRALSLVCKASGFTFSSYDMGWVRQAPGKGLEWVAYINSGSGSSTYYGTAVKGRASISRDNGQSTVRLQ

LNNLRVEDTGT

YFCAKGASGYYSSSGQAGQHHHHHHGAYPYDVPDYAS

>scFv16
MKKTAIAIAVALAGFATVAQAALTQPSSVSANLGETVKITCSGGGSYAGSYYYGWYQQKAPGSAPVTLIYD

NTNRPSDIPSRFSGSTSGSTNTLTITGVQADDEAVYFCGSVDSSSGVFGAGTTLTVLGQSSRSSAVTLDES

GGGLQTPGGALSLVCKASGFTFSSFDMFWVRQAPGKGLEYVAEISDTGSSTYYGAAVKGRATISRDNGQST

VRLQLNNLRAEDTGTYFCAKSHSGYGWSTAGDIDAWGHGTEVIVSSTSGQAGQHHHHHHGAYPYDVPDYAS

>scFv17
MKKTAIAIAVALAGFATVAQAALTQPSSVSANPGETVKITCSGGYSYYGWYQQKTPGSAPVTLIYDNTNRP

SDIPSRFSGSKSGSTATLTITGVQVEDEAMYFCGSYEGSTYVGIFGAGTTLTVLGQSSRSSAVTLDESGGG

LQTPGGALSLVCKASGFTFSSYDMAWVRQAPGKGLEFVAGIDIGSYTGYGAAVKGRATISRDNGQSTVRLQ

LNNLRAEDTGTYYCAKAAGSYYYSGAAGSIDAWGHGTEVIVSSTSGQAGQHHHHHHGAYPYDVPDYAS

>scFv18
MKKTAIAIAVALAGFATVAQAAVIYYNDKRPSDIPSRFSGSKSGSTATLTITGVRAEDEAVYYCGSADSTD

AVFGAGTTLTVLGQSSRSSAVTLDESGGGLQTPGGGLSLVCKASGFTFSDYDMFWVRQAPSKGLEFVAAIT

SSGTGTKYGAAVKGRATISKDNGQSTVRLQLNSLRAEDTGTYYCARSDADSTTWSAGEIDAWGHGTEVIVS

STSGQAGQHHHHHHGAYPYDVPDYAS

>scFv19
MKKTAIAIAVALAGFATVAQAALSRPRCQQTWGGTVEITCSGGSNNYGYGWYQQKSPGSAPVTLIYSNDNR

PSNIPSRFSGSTSGSTSTLTITGVQAEDEAVYYCGSYDSSNDSGIFGAGTTLTVLSQSSRSSAVTLDESGG

GLQTPGGGLSLVCKASGFTFSTFNMFWVRQAPGKGLEFVAGISITGGWTGYGAAVKGRATISRDNGQSTVR

LQLNNLRAEDTGTYYCAKPAAWSCYRGCGGEFDAWGHGTEVIVSSTSGQAGQHHHHHHGAYPYDVPDYAS

>scFv20
MKKTAIAIAVALAGFATVAQAALTQPSSVSANLGGIVEITCSGSSGSYGWYQQKSPGSAPVTVIYYNDKRP

SNIPSRFSGSGSGSTNTLTIAGVRAEDEAVYYCGNEDSSGAAFGAGTTLTVLGQSSRSSAVTLDESGGGLQ

TPGGGLSLVCKASGFTFSDYDMFWVRQAPSKGLEFVAAITSSGTGTKYGAAVKGRATISKDNGQRTVRLQL

NSLGAEDTGTYYCARSDADSTTWSAGEIDAWGHGTEVIVSSTSGQAGQHHHHHHGAYPYDVPDYAS

-continued

>scFv21
MKKTAIAIAVALAGFATVAQAALTQPSSVSANPGGTVKITCSGSSGSYYGWYQQKSPGSAPVTVIYDNDKR
PSDVPSRFSGSKSGPTATLTITGVQAEDEAVYFCGSRDNSYVGIFGAGTTLTVLGQSSRSSAVTLDESGGG
LQTPGGALSLVCKASGFTFSSYDMFWVRQAPGKGLEFVAQINSAGSYTNYGSAVKGRATISRDDGQSTVRL
QLNNLRAEDTGIYFCAKSASGYYYSGSDAGDIDAWGHGTEVIVSSTSGQAGQHHHHHGAYPYDVPDYAS

>scFv22
MKKTAIAIAVALAGFATVAQAAVSANPGDTVKITCSGDSNNYGWYQQKSPGSAPVTVIYDNTNRPSNIPSR
FSGSKSGSTATLTITGVQADDEAVYFCGSFDSSTDIFGAGTTLTVLGQSSRSSTVTLDESGGGLQTPGRAL
SLVCKASGFTFSSFNMGWVRQAPGKGLEYVASISSSGSYTAYGSAVKGRATISRDNGQSTVRLQLNNLRAE
DTATYYCAKAAGSAYYYTAVTPAFAGSIDAWGHGTEVIVSSTSGQAGQHHHHHGAYPYDVPDYAS

>scFv23
MKKTAIAIAVALAGFATVAQAAVSANLGGTVEITCSGGGSYYGWYQQKSPGSAPVTVIYANTNGPSDIPSR
FSGSTSGSTATLTITGVQADDEAVYSCGSYDSSYVGIFGAGTTLTVLGQSSRSSTVTLDESGGGLQTPGGA
LSLVCKASGFTFNSYALEWVRQAPGKGLEWVAGISGDGSYRHYGSAVKGRATISRDSGQSTVRLQLNNLRA
EDTGTYYCAKSTGSGAGWGASNIDAWGHGTEVIVSSTSGQAGQHHHHHGAYPYDVPDYAS

>scFv24
KKKTAIAIAVALAGFATVAQAAVSASPGDTVKITCSGGNSSYGYGWYQQKSPGSAPVSVIYYNDERPSDIP
SRFSGSASGSTATLTITGVQADDEAVYYCGNADSSTYAGIFGAGTTLTVLGQSSRSSAVTLDESGGGLQTP
GGGLSLVCKASGFDFSTNAMGWVRQAPGKGLEWVAGISGSGSSTWYATAVKGRATISRDNGQSTVRLQLNN
LRAEDTGTYYCTKYVGDYYWYIDAGSIDAWGHGTEVIVSSTSGQAGQHHHHHGAYPYDVPDYAS

>scFv25
MKKTAIAIAVALAGFATVAQAALTPPSSVSANLGAPVEITCSGSSGNYGWFQQKSPGSAPVTVIYSNDKRP
SDIPSRFSGSLSGSTGTLTITGVRAEDEAVYYCGSIDNTYVGTGAFGAGTTLTVLGQSSRSSTVTLDESGA
GLQTPGRALSLVCKGSGFTFSSFYMFWVRQAPGKGLEFVACISSSGSSTRYGVVVKGRATISRDNGQSTVR
LRLNNLRADDTGTYYCARGTSSGANTIDAWGHGTEVIVSSTSGQAGQHHHHHGAYPYDVPDYAS

>scFv26
MKKTAIAIAVALAGFATVAQAALTQPSSVSANPGETVGITCSGGGSYYGWYQQKSPGSAPVTLIYENDMRP
SNIPSRFSGSTSGSTSTLTITGVQAEDEAVYFCGSYDSSNYVGEFGAGTTLTVLGQSSRSSAVTLDESGGG
LQTPGGALSLVCKASGFTFSSFDMFWVRQAPGKGLEYVAEISDTGSSTYYGAAVKGRATISRDNGQSTVRL
QLNNLRAEDTGTYFCAKSHSGYGWSTAGDIDAWGHGTEVIVSSTSGQAGQHHHHHGAYPYDVPDYAS

>scFv27
MKKTAIAIAVALAGFATVAQAALSRPRCQQTWGGTVKITCSGSNSYYGWYQQKAPGSAPVTLIYDDTNRPS
DIPSRFSGSKSGSTATLTITGVQADDEAVYFCGGFDSSSDSGFGAGTTLTVLGQSSRSSTVTLDESGGGLQ
TPGRALSLVCKASGFTFSSFNMGWVRQAPGKGLEYVASISSSGSYTAYGSAVKGRATISRDNGQSTVRLQL
NNLRAEDTATYYCAKAAGSAYYYTAVTPAFAGSIDAWGHGTEVIVSSTSGQAGQHHHHHGAYPYDVPDYA
S

>scFv28
MKKTAIAIAVALAGFATVAQAAVIYSNDERPSDIPSRFSGSTSGSTSTLTITGVQADDEAVYFCGSADSST
YAGIFGAGTTLTVLGQSSRSSAVTLDESGGGLQTPGGALSLVCKASGFTFSSFNMFWVRQAPGRGLEFVAG
ITSSGGSTYYGTAVKGRATISRDNGQSTVRMQLNNLRAEDTGTYFCARGAYDYYFYWNYAGTIDAWGHGTE
VIVSSTSGQAGQHHHHHGAYPYDVPDYAS

>scFv29
MKKTAIAIAVALAGFATVAQAAVIYDNTNRPSNIPSRFSGSKSGSTGTLTITGVQADDEAVYYCGSTDSSA
DGVFGAGTTLTVLGQSSRSSAVTLDESGGGLQTPGGGLSLVCKGSGFTFSSFDMFWVRQAPGKGLEWVAGI

-continued

RNDGSDTAYGAAVKGRATISKDNGQSTVRLQLNNLRAEDTGTYYCAKAAGYCYVYSCAGSIDAWGHGTEVI

VSSTSGQAGQHHHHHHGAYPYDVPDYAS

>scFv30
MKKTAIAIAVALAGFATVAQAAVSANPGETVKITCSGGGGSYGWYQQKAPGSAPVTVIYDNTNRPSNIPSR

FSGSESGSTATLTITGVRAEDEAAYYCGSADSSDAGIFGAGTTLTVLGQSSRSSAVTLDESGGGLQTPRRA

LSLVCKASGFTFSDYGMAWVRQAPGKGLEWVAGIGSSGSYTDYGSAVKGRATISRDNGQSTVRLQLNNLRA

EDTATYYCAKDIGSVYGCGWWACSAGSIDAWGHGTEVIVSSTSGQAGQHHHHHHGAYPYDVPDYAS

>scFv31
MKKTAIAIAVALAGFATVAQAAVIYDNTNRPSNIPSRFSGSLSGSTNTLTITGVQAEDEAVYFCGGYDSST

DSGMFGAGTTLTVLGQSSRSSAVTLDESGGGLQTPGGGLSLVCKGSGFTFSSYDMAWVRQEPSKGLEFVAS

ISNTGSDTSYAPAVKGRATISRDNGQSTVRLQLNNLRAEDTATYYCAKSAGSYYWNAGGAGSIDTWGHGTE

VIVSSTSGQAGQHHHHHHGAYPYDVPDYAS

>scFv32
MKKTAIAIAVALAGFATVAQAALTQPSSVSANLGGTFKITCSGSSGSYAWYQQKSPGSAPVTVIYWNDKRP

SNIPSRFSGALSGSTATLTITGVQAEDEAVYFCGSADSSGAIFGAGTTLTVLGQSSRSSTVTLDESGGGLQ

TPGGGLSLVCKGSGFAFSNYGMGWMRQAPGKGLEYVAGISTGSYTDYGPAVKGRATISRDNGQSTVRLQLN

NLRAEDAAIYFCAKTAGSGYGCGSGTDLGSIDAWGHGTEVIVSSTSGQAGQHHHHHHGAYPYDVPDYAS

>scFv33
MKKTAIAIAVALAGFATVAQAAVSANPGDTVKITCSGGYSGYGWYQQKSPGSAPVTVIYSNNQRPSNIPSR

FSGSTSGSTNTLTITGVQVEDEAIYFCGGYDCSTGSVKASFGAGTTLTVLGQSSRSSAVTLDESGGGLQTP

GGTLSLVCKGSGFTFSSHGMGWVRQAPGKGLEWVAGIYSGSSTYYGAAVKGRATISRDNGQSTVRLQLNNL

RAEDTATYFCTRGGGAGRIDTWGHGTEVIVSSTSGQAGQHHHHHHGAYPYDVPDYAS

>scFv34
MKKTAIAIAVALAGFATVAQAALTQPSSVSANLGGTVEITCSGSSGSYGWYQQKSPGSAPVTVIYYNDKRP

SDIPSRFSGSTSGSTATLTITGVQAEDEAVYFCGGYDSNYIGIFGAGTTLTVLGQSSRSSAVTLDESGGGL

QTPRGALSLVCKASGFTFSSYSMAWVRQAPGKGLEFVAGIQNDGSITDYGSAVDGRATISRDDGQSTVRLQ

LNNLRTEDTATYYCAKTTVADGVIGAYGIDAWGHGTEVIVSSTSGQAGQHHHHHHGAYPYDVPDYAS

>scFv35
MKKTAIAIAVALAGFATVAQAAVSANPGDTVEITCSGSSGSYGWYQQKSPGSAPVTVIYANTNRPSDIPSR

FSGSKSGSTATLTITGVRAEDEAVYYCGGYDSSTDAGIFGAGTTLTVLGQSSRSSAVTLDESGGGLQTPGG

GLSLVCKASGFTFSDYGMGWMRQAPGKGLEYVAGIDNTGSSTGYGAAVKGRATISRDNRQSTVRLQLNNLR

AEDTGIYFCAKTAGSGGGWWSDWIDAWGHGTEVIVSSTSGQAGQHHHHHHGAYPYDVPDYAS

>scFv36
MKKTAIAIAVALAGFATVAQAALSRPRCQQTLGGTVKITCSGSNGSYDWCHQKTSAGAAAAVIIYDNNKTS

YIPSSLFCASSCSPATLLIIGVVADDDDVDYCGSANDNSSVVIVGATTTMIVRRSSSSSSAMMEDEGGGLL

TTRGGLLILCCAASGFIFSYYEMLWLHPAPGEVQDFVTIISGGGNYTYYGSAVDGGAIISRDDGKRMLMLQ

LNILEDDDTGFYFCADGASGYYYGGADAGDIDAWGHGTEVIVSSTSGQAGQHHHHHHGAYPYDVPDYAS

>scFv37
MKKTAIAIAVALAGFATVAQAALTQPSSVSANLGDTVKITCSGGGGYAGSYYYGWYQHNAAGGAPVTLIYD

NTITPSDIPSRFSGSTSGSTNALTINGVQADYAVYFCGSVNCSSGVFGAGTTLTVLCHSSTSSDVTLDHSR

GGLQTPGGSLSLVCNASGFTFSSFHMFWVRQAPGEGLEYVAEITDTGSSTYYGAAVKGRATISRDNGQSTV

RLQLNNLMADDTGTYFCAKSHSGYGWSTAGDIDAWGHGTEVIVSSTSGQAGQHHHHHHGAYPYDVPDYAS

>scFv38
MKKTAIAIAVALAGFATVAQAALTQPSSVSANPGETVKITCSGGSSGYGWYQQKSPGSAPVTVIYYNDKRP

SDIPSRFSGALSGSTATLTITGVQAEDEAVYFCGSGDSSTVAGIFGAGTTLTVLGQSSRSSAVTLDESGGG

-continued

LQTPGGTLSLVCKASGFDFSSYGMHWVRQEPGKGLEWVAGISRTGSFTYYGAAVKGRAAISRDNGQSTVRL

QLNNLRAEDTGTYYCAKGGSDCSGYRCDYSAGNIDGWGHGTEVIVSSTSGQAGQHHHHHHGAYPYDVPDYA

S

>scFv39
MKKTAIAIAVALAGFATVAQAALTQPSSVSANPGETVKITCSGGGSDYYGWYQQKSPGSAPVTLIYENDKR

PSNIPSRFSGSKSGSTATLTITGVQADDEAVYFCGNADTITGIFGAGTTLTVLGQSSRSSTVTLDESGGGL

QTPGGALSLVCKASGFTFSSYTMAWVRQAPGKGLEWVAGINDGGSYTNYGPAVQGRATISRDNGQSTVRLQ

LNNLRAEDTAIYYCAKSAGGYYYSGAAGTIDAWGHGTEVIVSSTSGQAGQHHHHHHGAYPYDVPDYAS

>scFv40
MKKTAIAIAVALAGFATVAQAALSRPRCQQTWGGIVKLTCSGGSGSCGWYQQKSPGSAPVTLIYDNDKRPS

DIPSRFSGSTSGSTHTLTITGVQAEDEAIYFCGSEDSSTYASGFGAGTTLTVLGQSSRSSAVTLDESGGGL

QTPGRALSLVCKASGFTFSSFNMGWVRQAPGKGLEYVASISSSGSYTAYGSAVKGRATISRDNGQSTVRLQ

LNNLRAEDTATYYCAKAAGSAYYYTAVTPAFAGSIDAWGHGTEVIVPSTSGQAGQHHHHHHGAYPYDVPDY

AS

>scFv41
MKKTAIAIAVALAGFATVAQAALSRPRCQQTWGGTVKITCSGGSSYYGWYQQKSPGSAPVTLIYENNNRPS

DIPSRFSGSASGSTATLTITGVQAEDGAVYFCGSEDSTYVGIFGAGTTLTVLGQSSRSSAVTLDESGGGLQ

TPGRALSLVCKASGFTFSSFNMGWVRQAPGKGLEYVASISSSGSYTAYGSAVKGRATISRDNGQSTVRLQL

NNLGAEDTATYYCAKAAGNAYYYTAVTPAFAGSIDAWGHGTEVIVPSTSGQAGQHHHHHHGAYPYDVPDYA

S

>scFv42
MKKTAIAIAVALAGFATVAQAALTQPSSVSANPGETVEITCSGGGSSSNYGWHQQKSPGSAPVTVIYDNTN

RPPNIPSRFSGSLSGSTGTLTITGVQAEDEAVYYCGGHDSSTYAGIFGAGTTLTVLGQSSRSSAVTLDESG

GGLQTPGRALSLVCKASGFTFSSFNMGWVRQAPGKGLEYVASISSSGSYTAYGSAVKGRATISRDNGQSTV

RLQLNNLRAEDTATYYCAKAAGSAYYYTAVTPAFAGSIDAWGHGTEVIVSSTSGQAGQHHHHHHGAYPYDV

PDYAS

>scFv43
MKKTAIAIAVALAGFATVAQAALTQPSSVSANPGETVKITCSGGGSSYYGWYQQKSPDSAPVTLIYESNK

RPSNIPSRFSGSTSGSTSTLTITGVQADDEAVYFCGSADSSYVGIFGAGTTLTVLGQSSRSSAVTLDESGG

GLQTPGGALSLVCKASGFTFSSFNMGWVRQAPGKGLEYVASISSSGSYTAYGSAVKGRATISRDNGQSTVR

LQLNNLRAEDTATYYCAKAAGSAYYYTAVTPAFAGSIDAWGHGTEVIVSSTSGQAGQHHHHHHGAYPYDVP

DYAS

>scFv44
MKKTAIAIAVALAGFATVAQAALTQPSSVSANLGETVKITCSGGGSYAGCYYYSWYDHTAAGVVPVTLIDS

TIPSSYFRSRFCCSASGSINALTINEDPAYYAVYFCGSVDVFGGVFGASTTLTAPGSSSISSDETLDDSGS

GLRTPGRALNVFCFASGFFFMIFELFGVRQAPGWVLEYIADVSDTGNSTYYRAAVNVRAAISRNNGQMTLR

LLLNDHTADDTCTYFCGYCHSDYCWSTAGDIDAWSHVIDFIVSSTSGQAGQHHHHHHGAYPYDDPDYAS

>scFv45
MKKTAIAIAVALAGFATVAQAALTQPSSVSANPGGTVKITCSGSSSAYGYGWYQQKSPGSAPVTVIYNNNK

RPSNIPSRFSGSKSGSTGTLTITGVQAEDEAVYFCGSEDSSTDAIFGAGTTLTVLGQSSRSSTVTLDESGG

GLQAPGGALSLVCKASGFTFSSYDMGWIRQAPGKGLEYVAGITDNGRYASYGSAVDGRATISRDNGQSSVR

LQLNNLRAEDTGTYYCARDDGSGWTGNSIDAWGHGTEIIVSSTSGQAGQHHHHHHGAYPYDVPDYAS

>scFv46
MKKTAIAIAVALAGFATVAQAALTQPSSVSANLGGTVKITCSGSSGSYGWYQQKSPGSAPVTVIYWNDKRP

SNIPSRFSGALSGSTATLTITGVQAEDEAVYFCGSADSSGAIFGAGTTLTVLGQSSRSSTVTLDESGGGLQ

TPGGGLSLVCKGSGFAFSNYGMGWMRQAPGKGLEYVAGISTGSYTDYGPAVKGRATISRDNGQSTVRLQLN

NLRAEDAAIYFCAKGHGTEIIVSSTSGQAGQHHHHHHGAYPYDVPDYAS

>scFv47
MKKTAIAIAVALAGFATVAQAALSRPRCQQTWGGTVKITCSGGDGSYGWYQQKSPGSAPVTVIYDNTNRPS

DIPSRFSGSKSGSTGTLTITGVQAEDEAVYYCGNADSSGAAAFGAGTTLTVLGQSSRSSAVTLDESGGGLQ

TPGGALSLGCEASGFTFSSYAMGWVRQAPGKGLEYVATISSAGSNTNYGAAVKGRATISRDNGQSTVRLQL

NNLEDDDTATYFCAEAAGNGYYVWSAIAGDIDAWGHGTDVIVSSTSGQAGQHHHHHHGAYPYDVPDYAS

>scFv48
MKKTAIAIAVALAGFATVAQAALTQPSSVSANPGETVKITCSEGGRSSYYGWYQQKAPGSAPVTVIYDSSS

RPSDIPSRFSGSKSGSTGTLTITGVQAEDEAVYYCGSTDSSTSAAIFGAGTTLTVLGQSSRSSTVTLDESG

GGLQTPGRALSLVCKASGFTFSSFNMGWVRQAPGKGLEYVASISSSGSYTAYGSAVKGRATISRDNGQSTV

RLQLNNLRAEDTATYYCAKAAGSAYYYTAVTPAFAGSIDAWGHGTEVIVSSTSGQAGQHHHHHHGAYPYDV

PDYAS

>scFv49
MKKTAIAIAVALAGFATVAQAALTQPSSVSANPGETVEITCSGGGGSYGWFQQKSPGSAPVTLIYNNNNRP

SDIPSRFSGSKSGSTGTLTITGVQAEDEAVYFCGTRDSSYAGIFGAGTTLTVLGQSSRSSAVTLDESGGGL

QTPGGALSLVCKGSGFTFSDYSMMWVRQAPGKGLEWVAGISSNSGTTRYGSAVKGRATISRDNGQSTVRLQ

LNNLRAEDTGTYYCAKTTGVNSYDVPAIDAWGHGTEVIVSSTSGQAGQHHHHHHGAYPYDVPDYAS

>scFv50
MKKTAIAIAVALAGFATVAQAALTQPSSVSANPGDTVEITCSGGYSNYGWYQQKSPGSAPVTVIYGSTSRP

SDIPSRFSGSESGSTGTLTITGVQAEDEAVYFCGNADSSYVGLFGAGTTLTVLGQSSRSSTVTLDESGGGL

QTPGRALSLVCKASGFTFSSFNMGWVRQAPGKGLEYVASISSSGSYTAYGSAVKGRATISRDNGQSTVRLQ

LNNLRAEDTATYYCAKAAGSAYYYTAATPAFAGSIDAWGHGTEVIVSSTSGQAGQHHHHHHGAYPYDVPDY

AS

>scFv51
MKKTAIAIAVALAGFATVAQAALVSANPGETVKITCSGGGSNSAGSYYYGWYQQKPPGSAPVTVIHNNNKR

PSDIPSRFSGSKSGSTGTLTITGVQVDDEAVYYCGSRDSSYIGTFGAGTTLTVLGQSSRSSAVTLDESGGG

LQTPGRALSLACKASGFTFSSFNMGWVRQAPGKGLEYVASISSSGSYTAYGSAVKGRATISRDNGQSTVRL

QLNNLRAEDTATYYCAKAAGSAYYYTAVTPAFAGSIDAWGHGTEVIVSSTSGQAGQHHHHHHGAYPYDVPD

YAS

>scFv52
MKKTAIAIAVALAGFATVAQAALTQPSSVSANPGDPVEITCSGSSGSYGWYQQKAPSSAPVTVIYSNDKRP

SDIPSRFSGSASGSTATLTITGVQAEDEAVYFCGSFDSSAGYGGIFGAGTTLTVLGQSSRSSTVTLDESGG

GLQTPGRALSLVCKASGFTFSSFNMGWVRQAPGKGLEYVASISSSGSYTAYGSAVKGRATISRDNGQSTVR

LQLNNLRAEDTATYYCAKAAGSAYYYTAVTPAFAGSIDAWGHGTEVIVSSTSGQAGQHHHHHHGAYPYDVP

DYAS

>scFv53
MKKTAIAIAVALAGFATVAQAALVSANPGEIVKITCSGNSSYYGWYQQKAPGSAPVTVIYDNNKRPSDIPS

RFSGSKSGSTGTLTITGVQAEDEAVYFCGNGATFGAGTTLTVLGQSSRSSTVTLDESGGGLQTPGRALSLV

CKASGFTFSSFNMGWVRQAPGKGLEYVASISSSGSYTAYGSAVKGRATISRDNGQSTVRLQLNNLRAEDTA

TYYCAKAAGSAYYYTAVTPAFAGSIDAWGHGTEVIVSSTSGQAGQHHHHHHGAYPYDVPDYAS

>scFv54
MKKTAIAIAVALAGFATVAQAALTQPSSVSANPGETVKITCSGGSYSYGWYQQKSPGSAPVTVIYSSDKRP

SDIPSRFSGSKSGSTSTLTITGVQAEDEAVYYCGSRDSSYVGIFGAGTTLTVLGQSSRSSTVTLDESGGGL

QTPGGALSLVCEASGFTFSSYEMQWVRQAPGKGLEFVAAISSDGSYTNYGAAVQGRATISRDNGQSTVRLQ

LSNLRAEDTATYYCARSPGGYTWWPGAAGGIDAWGHGTEVIVSSTSGQAGQHHHHHHGAYPYDVPDYAS

>scFv55
MKKTAIAIAVALAGFATVAQAALVSANLGGTVEITCSGSSGNYGWFQQKSPGSAPVTVIYSNDKRPSDIPS

RFSGSLSGSTGTLTITGVRAEDEAVYYCGSIDNTYVGTGAFGAGTTLTVLGQSSRSSTVTLDESGGGLQTP

GRALSLVCKGSGFTFSSFYMFWVRQAPGKGLEFVASISSSGSSTRYGVVVKGRATISRDNGQSTVRLRLNN

LRAEDTGTYYCARGTSSGANTIDAWGHGTEVIVSSTSGQAGQHHHHHHGAYPYDVPDYAS

>scFv56
MKKTAIAIAVALAGFATVAQAALTQPSSVSANPGETVKITCSGGGSSSYYGWYQQKSPGSAPVTLIYESNK

RPSGIPSRFSGSKSGSTHTLTITGVQAEDEAVYYCGAYDGSSYTGIFGAGTTLTVLGQSSRSSTVTLDESG

GGLQTPGRALSLVCKASGFTFSSFNMGWVRQAPGKGLEYVASISSSGSYTAYGSAVKGRATISRDNGQSTV

RLQLNNLRAEDTATYYCAKAAGSAYYYTAVTPAFAGSIDAWGHGTEVIVSSTSGQAGQHHHHHHGAYPYDV

PDYA

>scFv57
MKKTAIAIAVALAGFATVAQAALTQPSSVSANPGGTVKITCSGSSAYGYGWYQQKSPGSAPVTVIYNNNKRPSNIPSR

FSGSKSGSTGTLTITGVQAEDEAVYFCGSEDSSTDAIFGAGTTLTVLGQSSRSSAVTLDESGGGLQTPGGALSLVCKAS

GFTFSSYDMGWVRQAPGKGLEYVAGITNDGRYASYGSAVDGRATISRDNGQSTVRLQLNNLRAEDTGTYYCARDDGSGW

TGNTIDTWGHGTEVIVSSTSGQAGQHHHHHHGAYPYDVPDYAS

>scFv58
MKKTAIAIAVALAGFATVAQAALTQPSSVSANPGDTVKITCSGGGSSSYYGWYQQRSPGSAPVTLIYSNDK

RPSDIPPRFSGSLSGSTATLTITGVQADDEAVYYCGGYDSSYVGLFGAGTTLTVLGQSSRSSTVTLDESGG

GLQTPGRALSLVCKASGFTFSSFNMGWVRQAPGKGLEYVASISSSGSYTAYGSAVYGRATISRDNGQSTVR

LQLNNLRAEDTATYYCAKAAGSAYYYTAVTPAFAGSIDAWGHGTEVIVSSTSGQAGQHHHHHHGAYPYDVP

DYAS

>scFv59
MKKTAIAIAVALAGFATVAQAALTQPSSVSANPGEIFKITCSGGGSYAGSYYYGWYQQKAPGSAPVTVIYD

NTNRPSNIPSRFSGSKSGSTATLTITGVRADDSAVYYCASTDSSSTGIFGAGTTLTVLGQSSRSSAVTLDE

SGGGLQTPGRALSLVCKASGFTFSSFNMGWVRQAPGKGLEYVASISSSGSYTAYGSAVKGRATISRDNGQS

TVRLQLNNLRAEDTATYYCAKAAGSAYYYTAVTPAFAGSIDAWGHGTEVIVSSTSGQAGQHHHHHHGAYPY

DVPDYAS

>scFv60
MKKTAIAIAVALAGFATVAQAALTQPSSVSANPGAIVKITCSEGGRSSYYGWYQQKAPGSAPVTVIYDSSS

RPSDIPSRFSGSKSGSTGTLTITGVQAEDEAVYYCGSTDSSTSAAIFGAGTTLTVLGQSSRSSTVTLDESG

GGLQTPGRALSLVCKASGFTFSSFNMGWVRQAPGKGLEYVASISSSGSYTAYGSAVKGRATISRDNGQSTV

RLQLNNLRAEDTATYYCAKAAGSAYYYTAVTPAFAGSIDAWGHGTEVIVSSTSGQAGQHHHHHHGAYPYDV

PDYAS

>scFv61
MKKTAIAIAVALAGFATVAQAALTQPSSVSANPGETVKITCSGGGSYAGSYYYGWYQQKAPGSAPVTLIYD

NTNRPSNIPSRFSGSLSGSTGTLTITGVRAEDEAVYYCGSFDSSTDGGYAAIFGAGTTLTVLGQSSRSYAV

TLDESGGGLQTPGGGLSLVCKASEFTFSSYAMEWVRQAPGKGLEWVAYINSDGSSTWYAPAVKGRATISRD

NGQSTVRLQLNSLRAEDTATYYCTRGSGGENIDTWGHGTEVIVSSTSGQAGQHHHHHHGAYPYDVPDYAS

>scFv62
MKKTAIAIAVALAGFATVAQAALTQPSSVSANPGETVKITCSGGGSYAGSYYYGWYQQKAPGSAPVTLIYD

NTNRPSNIPSRFSGSLSGSTGTLTITGVRAEDEAVYYCGSFDSSTDGGYAAIFGAGTTLTVLGQSSRSSAV

TLDESGGGLQTPGGGLSLVCKASEFTFSSYAMEWVRQAPGKGLEWVAYINSDGSSTWYAPAVKGRATISRD

NGQSTVRLQLNSLRAEDTATYYCTRGSGGENIDTWGHGTEVIVSSTSGQAGQHHHHHHAAYPYDVPDYAS

>scFv63 (incomplete sequence information)
SNNYGWHQQKAPGSAPVTVIYDNTNRPSNIPSRFSGSKSSSTHTLTITGVQAEDEAVYYCESADSSSSIFG

AGTTLTVLGQSSRSSAVTLDESGGGLQTPGGTLSLVCKASGFTFSSFNMFWVRQAPGKGLEFVAGIGNTGR

STGYGSAVKGRATISRDNGQSTVRLQLNNLRAEDTGTYYCAQAYGDSNIDRMGPRDR

>scFv64
MKKTAIAIAVALAGFATVAQAALTQPSSVSANPGDPLKITCSGDSSGYGYGWYQQKSPGSAPVTVIYNNNK

RPSDIPSRFSGSKSGSTGTLTITGVQAEDEAVYFCGSEDSNTDAVFGAGTTLTVLGQSSRSSTVTLDESGG

GLQTPGGTLSLACKASGFTFSGYDMGWVRQAPGKGLEYVAGITSDGRYASYGSAVDGRAAIWRDNGQSTVR

LQLKNLRTEDTATYYCARNDGSGWNGNNIDAWGHGTEVIVSSTSGQAGQHHHHHHGAYPYDVPDYAS

>scFv65
MKKTAIAIAVALAGFATVAQAALSRPRCQQTWGGTVKITCSGSSGSYGWYQQKSPGSAPVTLIYESDKRPS

DIPSRFSGSKSGSTGTLTITGVQADDEAVYFCGGYDSSAGIFGAGTTLTVLGQSSRSSAVTLDESGGGLQT

PGGALSLVCKASGFDFSSYGMGWMRQAPGKGLEFVAAIRKDGSYTAYGAAVDGRATISRDDGQSTVRLQLG

NLRAEDTATYFCAKTNSYNSAGIIDAWGHGTEVIVSSTSGQAGQHHHHHHGAYPYDVPDYAS

>scFv66
MKKTAIAIAVALAGFATVAQAALSRPRCQQTWGGTVEITCSGSSGDYGYSWHQQKSPGSAPVTVIYESTKR

PSNIPSRFSGSTSGSTGTLTITGVQVEDEAVYFCGGYDGSTDAIFGAGTTLTVLGQSSRSSAVTLDESGGG

LQMPGGGLSLVCKASGFDFSSSEMQWVRQAPGKGLQWVGIISSSGSTYYGSAVKGRATISRDNGQSAVRLQ

LNNLRAEDTGTYYCTKTTAYAHDIDAWGHGTEVIVSSTSGQAGQHHHHHHGAYPYDVPDYAS

>scFv67
MKKTAIAIAVALAGFATVAQAALTQPSSVSANPGGTVKITCSGSSSAYGYGWYQQKSPGSAPVTVIYNNNK

RPSNIPSRFSGSKSGSTGTLTITGVQAEDEAVYFCGSEDSSTDAIFGAGTTLTVLGQSSRSSAVTLDESGG

GLQTPGGALSLVCKASGFTFSSYDMGWVRQAPGKGLEYVAGITNDGRYASYGSAVDGRATISRDNGQSTVR

LQLNNLRAEDTGTYYCARDDGSGWTGNTIDTWGHGTEVIVSSTSGQAGQHHHHHHGAYPYDVPDYAS

>scFv68
MKKTAIAIAVALAGFATVAQAALTQPSSVSASPGETVKITCSGGGSYGWYRHKSPGSAPVTVIYYNDKRP

SDIPSRFSGSKSGSTSTLTITGVQAEDEADYYCGSYNSNAGYVGIFGAGTTLTVLGQSSRSSTVTLDESGG

GLQTPGGGLSLVCKASGFTFSSYGMGWMRQAPGKGLEFVAGIRKDGRSTAYGAAVDGRATISRDDGQSTLR

LQLGNLRAEDTGTYFCAKTNSYDSAGIIDAWGHGTEVIVSSTSGQAGQHHHHHHGAYPYDVPDYAS

>scFv69
MKKTAIAIAVALAGFATVAQAALTQPSSVSANPGETVKITCSGGGSSNNYGWHQQKAPGSAPVTVIYDNTN

RPSNIPSRFSGSKSSSTHTLTITGVQAEDEAVYYCESADSSSIFGAGTTLTVLGQSSRSSAVTLDESGGG

LQTPGGTLSLVCKASGFTFSSFNMFWVRQAPGKGLEFVAGIGNTGRSTGYGSAVKGRATISRDNGQSTVRL

QLNNLRAEDTGTYYCAKAYGDSNIDAWGHGTEVIVSSTSGQAGQHHHHHHGAYPYDVPDYAS

>scFv70
MKKTAIAIAVALAGFATVAQAALTQPSSVSASLGGIVEITCSGSSGTYGWYQQKSPGSAPVTVIYQNGKRP

SNIPSRFSGSKSGSTATLTITGVQADDEAVYFCGGYDSSTYVGIFGAGTTLTVLGQSSRSSAVTLDESGGG

LQTPGGALSLVCKASGFDFSSYGMGWMRQAPGKGLEFVAAIRKDGSYTAYGAAVDGRATISRDDGQSTVRL

QLGNLRAEDTATYFCAKTNSYNSAGIIDAWGHGTEVIVSSTSGQAGQHHHHHHGAYPYDVPDYAS

>scFv71
MKKTAIAIAVALAGFATVAQAALTQPSSVSANPGETVKITCSGGGSSNNYGWHQQKAPGSAPVTVIYDNTN

RPSNIPSRFSGSKSSSTHTLTITGVQAEDEAVYYCESADSSSIFGAGTTLTVLGQSSRSSAVTLDESGGG

```
-continued
LQTPGGTLSLVCKASGFTFSSFNMFWVRQAPGKGLEFVAGIGNTGRSTGYGSAVKGRATISRDNGQSTVRL

QLNNLRAEDTGTYYCAKALWGHGTEVIVSSTSGQAGQHHHHHHGAYPYDVPDYAS

>scFv72
MKKTAIAIAVALAGFATVAQAALTQPSSVSANPGETVKITCSGSSGSYGWYQQKSPGSAPVSLIYSNDKRP

SDIPSRFSGSKSGSTGTLTITGVQAEDEAVYYCGGWDSYVGIFGAGTTLTVLGQSSRSSAVTLDESGGGLQ

TPGGGLSLVCKASGFSSSHGMGWMRQAPGKGLEFVAGIRSDGSSTAYGAAVDGRATITRDDGQSTVTLQLN

NLRAEDTATYFCAKTNSYNSAGIIDAWGHGTEVIVSSTSGQAGQHHHHHHGAYPYDVPDYAS

>scFv73
MKKTAIAIAVALAGFATVAQAALSRPRCQQTWGGTVKITCSGSSGSYGWYQQKSPGSAPVTLIYESDKRPS

DIPSRFSGSKSGSTGTLTITGVQADDEAVYFCGGYDSSAGIFGAGTTLTVLGQSSRSSAVTLDESGGGLHT

PGGALSLVCKASGFDFSSYGMGWMRQAPGKGLEFVAAIRKDGSYTAYGAAVDGRATISRDDGQSTVRLQLG

NLRAEDTATYFCAKTNSYNSAGIIDAWGHGTEVIVSSTSGQAGQHHHHHHGAYPYDVPDYAS

>scFv74
MKKTAIAIAVALAGFATVAQAALTQPSSVSASPGETVKITCSGGSGSYGWYQQKSPGSAPVTVIYYNDKRP

SDIPSRFSGSKSGSTSTLTITGVQAEDEAVYYCGSYDSSAGYVGIFGAGTTLTVLGQSSRSSTVTLDESGG

GLQTPGGGLSLVCKASGFTFSSYGMGWMRQAPGKGLEFVAGIRKDGSSTAYGAAVDGRATISRDDGQSTLR

LQLGNLRAEDTGTYFCAKTNSYNSAGIIDAWGHGTEVIVSSTSGQAGQHHHHHHGAYPYDVPDYAS

>scFv75 (incomplete sequence information)
RAPVTLIYNNNNRPSDIPPRFSGSKSGSTGTLAITGVQAEDEAVYFCGGYEGSTSTGIFGAGTTLTVLGQS

SRSSAVTLDESGGGLQTPGGALSLVCKASGFDFSSYGMGWMRQAPGKGLEFVAAIKKDGSYTAYGAAVDGR

ATISRDDGQSTVRLQLGNLRAEDTAP

>scFv77
MKKTAIAIAVALAGFATVAQAALTQPSSVSANPGDPFKITCSGGGSSNNYGWHQQKAPGSAPVTVIYDNTN

RPSNIPSRFSGSKSSSTHTLTITGVQAEDEAVYYCESADSSSSIFGAGTTLTVLGQSSRSSAVTLDESGGG

LQTPGGTLSLVCKASGFTFSSFNMFWVRQAPGKGLEFVAGIGNTGRSTGYGSAVKGRATISRDNGQSTVRL

QLNNLRAEDTGTYYCAKAYGDSNIDAWGHGTEVIVSSTSGQAGQHHHHHHGAYPYDVPDYAS

>scFv79 (incomplete sequence information)
LSRPRCQQTWGGTVKITCSGSSGGYGWYRHKSPGTAPVPLIYNNDNRPSDIPSRFSGSKSGSTSTLTITGV

QVQDEDDYFCGGYNKNTYADIFGAGTTLTVLRQSSTSSAVTMDDYGGGLLTTGGALILLCWASGFFTFHGL

DWMRQAPATGLEFVAGIRSDGDSTAYGAAVDGHATVSRDNGQSTMRLQLNILRAEDDATYFCA

>scFv80
MKKTAIAIAVALAGFATVAQAALSRPRCQQTWGGPVKITCSGGSGSYGWYQQKSPGSAPVTVIYYNDQRPS

DIPSRFSGSKSGSTGTLTITGVQAEDEAVYYCGGYDSTYVGIFGAGTTLTVLGQSSRSSAVTLDESGGGLQ

TPRGALSLVCKASGFTFSSYSMAWVRQAPGKGLEFVAGIQNDGSITDYGSAVDGRATISRDDGQSTVRLQL

NNLRTEDTATYYCAKTTVADGVIGAYGIDAWGHGTEVIVSSTSGQAGQHHHHHHGAYPYDVPDYAS

>scFv81 (incomplete sequence information)
ALTQPSSVSANPGGTVKITCSGSSSAYGYGWYQQKSPGSAPVTVIYNNNKRPSNIPSRFSGSKSGSTGTLT

ITGVQAEDEAVYFCGSEDSSTDAIFGAGTTLTVLGQSSRSSTVTLDESGGGLQAPGGALSLVCKASGFTFS

SYDMGWIRQAPGKGLEYVAGITDNGTYASYGS

>scFv82
MKKTAIAIAVALAGFATVAQAALTQPSSVSANLGAFKITCSGGGGSYGWYQQKSPGSAPVTLIYYNDKRPS

DIPSRFSGSKSGSTATLTITGVQANDEAVYFCGSYEGSTYSGIFGAGTTLTVLGQSSRSSTVTLDESGGGL

QTPGGGLSLVCKASGFSSSHGMGWMRQAPGKGLEFVAGIRSDGSSTAYGAAVDGRATITRDDGQSTVTLQL

NNLRAEDTATYFCAKNTTVADGVIGAYGIDAWGHGTEVIVSSTSGQAGQHHHHHHGAYPYDVPDYAS
```

-continued

>scFv83
MKKTAIAIAVALAGFATVAQAALTQPSSVSANLGGPFEITCSGSGSYGWYQQKSPGSAPVTLIYNNNNRP
SDIPPRFSGSKSGSTGTLAITGVQAEDEAVYFCGGYEGSTSTGIFGAGTTLTVLGQSSRSSAVTLDESGGG
LQTPGGALSLVCKASGFDFSSYGMGWMRQAPGKGLEFVAAIRKDGSYTAYGAAVDGRATISRDDGQSTVRL
QLGNLRAEDTATYFCAKTNSYNSAGIIDAWGHGTEVIVSSTSGQAGQHHHHHHGAYPYDVPDYAS

>scFv84
MKKTAIAIAVALAGFATVAQAALKITCSGSSGSYAWYQQKSPGSAPVTLIYESDKRPSDIPSRFSGSKSGS
TGTLTITGVQADDEAVYFCGGYDSSAGIFGAGTTLTVLGQSSRSSAVTLDESGGGLQTPGGALSLVCKASG
FDFSSYGMGWMRQAPGKGLEFVAAIRKDGSYTAYGAAVDGRATISRDDGQSTVRLQLGNLRAEDTATYFCA
KTNSYNSAGIIDAWGHGTEVIVSSTSGQAGQHHHHHHGAYPYDVPDYAS

>scFv85
MKKTAIAIAVALAGFATVAQAALTQPSSVSANPRTLLKITCSGSSSAYGYGWYQQKSPGSAPVTVIYNNNK
RPSNIPSRFSGSKSGSTGTLTITGVQAEDEAVYFCGSEDSSTDAIFGAGTTLTVLGQSSRSSAVTLDESGG
GLQTPGGALSLVCKASGFTFSSYDMGWVRQAPGKGLEYVAGITNDGRYASYGSAVDGRATISRDNGQSTVR
LQLNNLRAEDTGTYYCARNDGSGWTGNTIDTWGHGTEVIVSSTSGQAGQHHHHHHGAYPYDVPDYAS

>scFv86
MKKTAIAIAVALAGFATVAQAALGPDSAVLGVSKPGEALVKTTCSGGGGSYGWYQQKSPGSAPVTVIYYND
KRPSDIPSRFSGSKSGSTGTLTITGVQAEDEAVYFCGSYDSSTDTGIFGAGTTLTVLGQSSRSSTVTLDES
GGGLQTPGGALSLVCKASGFIFSSHGMGWMRQAPGKGLEFVAAISKDGTATYYGPAVKGRATISRDDGQTT
VRLQLNNLRAEDTATYFCAKTKYYNSAGIIDAWGHGTEVIVSSTSGQAGQHHHHHHGAYPYDVPDYAS

>scFv87
MKKTAIAIAVALAGFATVAQAALSRPRVSANPGDPVKITCSGGGSYAGSYYYGWYQQKAPGSAPVTVIYDN
NQRPSNIPSRFSGSLSGSTGTLTITGVRAEDEAVYYCGSFDSSTDSGYAAIFGAGTTLTVLGQSSRSSAVT
LDESGGGLQTPGGGLSLVCKASGFTFSSYAMEWVRQAPGKGLEWVAYINSDGSSTWYATAVXGRATISRDN
GQSTVRLQLNNLRGEDTATYFCAKTKYYNSAGIIDAWGHGTEVIVSSTSGQAGQHHHHHHGAYPYDVPDYA
S

>scFv88 (incomplete sequence information)
GSSGSYGWYQQKSPGSAPVTVIYYNDKRPSDIPSRFSGSTSGSTATLTITGVQAEDEAVYFCGGYDSNYIG
IFGAGTTLTVLGQSSRSSAVTLDESGGGLQTPRGALSLVCKASGFTFSSYSMAWVRQAPGKGLEFVAGIQN
DGSITDYGSAVDGRATISRDDGQSTVRLQLNNLRTEDTATYYCAKTTVADGVI >scFv89 (incomplete sequence information)
ALTQPSSVSANPGDTVKITCSGDSSDYGYGWYQQKSPGSAPVTVTYSNNQRPSDIPSRFSGSASGSTATLT
ITGVQVEDEAVYYCGSEDSTTDAVFGAGTTLTVLGQSSRSSAVTLDESGGGLQTPGGALSLVCKASGFTFS
SYDMGWVRQAPGKGLEYVAGITNDGRYASYGSAVDGRATISRDNGQSTVRLQLNNPQG >scFv90
MKKTAIAIAVALAGFATVAQAALSRPRCQQTWGGTVKITCSGSSGSYGWYQQKSPGSAPVTVIYQNDKRPS
DIPSRFSGSTSGSTATLTITGVQADDEAVYFCGGYDSSAGIFGAGTTLTVLGQSSRSSAVTLDESGGGLQT
PGGALSLVCKASGFSSSHGMGWMRQAPGKGLEFVAGIRSDGSSTAYGAAVDGRATISRDDGQSTVRLQLNN
LRAEDTATYFCAKTNSYNSAGIIDAWGPGTEVIVSSTSGQAGQHHHHHHGAYPYDVPDYAS >scFv91 (incomplete sequence information)
IYDNTNRPSNIPSRFSGSKSSSTHTLTITGVQAEDEAVYYCESADSSSSIFGAGTTLTVLGQSSRSSAVTL
DESGGGLQTPGGTLSLVCKASGFTFSSFNMFWVRQAPGKGLEFVAGIGNTGRSTGYGSAVKGRATISRDNG
QSTVRLQLNNLRAEDTGTYYCAKAYGDS >scFv92
MKKTAIAIAVALAGFATVAQAALTQPSSVSASLGTFLEITCSGSSGTYGWYQQKSPGSAPVTVIYQNGKRP
SNIPSRFSGSKSGSTATLTITGVQADDEAVYFCGGYDSSTYVGIFGAGTTLTVLGQSSRSSAVTLDESGGG -continued

LQTPGGALSLVCKASGFDFSSYGMGWMRQAPGKGLEFVAAIRKDGSYTAYGAAVDGRATISRDDGQSTVRL

QLGNLRAEDTATYFCAKTNSYNSAGIIDAWGHGTEVIVSSTSGQAGQHHHHHHGAYPYDVPDYAS

>scFv93
MKKTAIAIAVALAGFATVAQAALTQPSSVSANPGALFKITCSGGGSSNNYGWHQQKAPGSAPVTVIYDNTN

RPSNIPSRFSGSKSSSTHTLTITGVQAEDEAVYYCESADSSSSIFGAGTTLTVLGQSSRSSTVTLDESGGG

LQTPGGALSLVCKASGFTFSSFNMFWVRQAPGKGLEFVAGIGNTGGSTGYGSAVKGRATISRDNGQSTVRL

QLNNLRAEDTGTYYCAKAYGDSNIDTWGHGTEVIVSSTSGQAGQHHHHHHGAYPYDVPDYAS

>scFv95
MKKTAIAIAVALAGFATVAQAALTQPSSVSANPGETVEITCSGGGGSYGWFQQKSPGSAPVTVIYESTKRP

SNIPSRFSGSGSGSTSTLTITGVRAEDEAVYYCGGYDGSSDAIFGAGTTLTVLGQSSRSSTVTLDESGGGL

QTPGGALSLVCKASGFTFSSHDMGWVRQAPGKGLEYVAGITDDGRYASYGPAVDGRATISRDNGQSTVRLQ

LKNLRAEDTATYYCARDDGSGWSGDTIDTWGHGTEVIVSSTSGQAGQHHHHHHGAYPYDVPDYAS

>scFv96
MKKTAIAIAVALAGFATVAQAALPGVRHRDPGGPDSAVLGVSKPRRNDKITCSGGGSYAGSYYYGWYQQKA

PGSAPVTLIYDNTNRPSNIPSRFSGSLSGSTGTLTITGVRAEDEAVYYCGSFDSSTDGGYAAIFGAGTTLT

VLGQSSRSSAVTLDESGGGLQTPGGGLSLVCKASEFTFSSYAMEWVRQAPGKGLEWVAYINSDGSSTWYAP

AVKGRATISRDNGQSTVRLQLNSLRAEDTATYYCTRGSGGENIDTWGHGTEVIVSSTSGQAGQHHHHHHGA

YPYDVPDYAS

>scFv97
MKKTAIAIAVALAGFATVAQAALTQPSSVSANPGETVKITCSGGSYNAYGWYQQKSPAGAPVTLIYDNTNR

PSNIPSRFSGSKSGSTHTLTITGVQADDEAVYFCGGYDSNADDGIFGAGTTLTVLGQSSRSSTVTLDESGG

GLQTPGGTLSLVCKASGFTFSSYAMNWMRQAPGKGLEWVAGIYSDGRYTNYGAAVKGRATISRDNGQSSVR

LQLNNLRAEDTATYYCTKSADSDYGCDNIDAWGHGTEVIVSSTSGQAGQHHHHHHGAYPYDVPDYAS

>scFv98
MKKTAIAIAVALAGFATVAQAALTQPSSVSANPGETVKITCSGGGSYVGSYYYGWYQQKSPVSAPVTLIYE

STKRPSNIPSRFSGSTSGSMGTLTITGVQAEDEAVYFCGSFDSSSSSVSDTADIFGAGTTLTVLGQSSRSS

TVTLDESGGGLQTPGGALSLVCKASGFTFNSYALEWVRQAPGKGLEWVAGISGDGSFTHYGSAVKGRATIS

RDNGQSTVRLHLNNLRAEDTATYYCAKSTGSGAGWGASNIDAWGHGTEVIVSSTSGQAGQHHHHHHGAYPY

DVPDYAS

>scFv100
MKKTAIAIAVALAGFATVAQAALTQPSSVSANPGETVKITCSGSSDAYGWYQQKSPGSAPVTLIYDNTNRP

PDIPSRFSGALSGSTSTLTITGVRAEDEAVYYCGSADITYIGIFGAGTTLTVLGQSSRSSTVTLDESGGGL

QTPGGGLSLVCKASGFTFSSHTMQWVRQAPGKGLEWVAEISADGSYTTYYGAAVKGRATISRDNGQSTVRL

QLNNLRAEDTATYFCAKSGYGGAGWGAGLIDAWGHGTEVIVSSTSGQAGQHHHHHHGAYPYDVPDYAS

>scFv102
MKKTAIAIAVALAGFATVAQAALTQPSSVSANPGETVKITCSGGGSYGWYQQESPGSAPVTVIYYNDKRP

SDIPSRFSGSASGSTATLTIAGVRAEDEAVYFCGSWDSSTSAGIFGAGTALTVLGQSSRSSAVTLDESGGG

LQTPGGGLSLVCKASGFSSSHGMGWMRQAPGKGLEFVAGIRSDGSSTAYGAAVDGRATITRDDGQSTVTLQ

LNNLRAEDTATYFCAKTNSYNSAGIIDAWGHGTEVIVSSTSGQAGQHHHHHHGAYPYDVPDYAS

>scFv104
MKKTAIAIAVALAGFATVAQAALTQPSSVSANLGGTVEITCSGSGGSYGYYGWYQQKAPGSAPVTVIYDNT

NRPSNIPSRFSGSASGSTGTLTITGVRAEDEAVYFCGGYDSSNTDAFGAGTTLTVLGQSSRSSTVTLDESG

GGLQTPGRALSLVCKASGFTFSSYTMGWVRQAPGKGLEFVAGIGNTGRYTGYGSAVKGRATISRDNGQSTV

RLQLNNLRAEDTGTYYCTKCAYGYYYSWGNIAGSIDAWGHGTEVIVSSTSGQAGQHHHHHHGAYPYDVPDY

AS

-continued

```
>scFv105
MKKTAIAIAVALAGFATVAQAALTQPSSVSANPGEAVKITCSGSSGSYGWYQQKSPGSAPVTVIYYNDKRP
SDIPSRFSGSTSGSTSTLTITGVQAEDEAVYFCGGYDSNYLGIFGAGTTLTVLGQSSRSSAVTLDESGGGL
QTPRGALSLVCKASGFTFSSYSMAWVRQAPGKGLEFVAGIQNDGSITDYGSAVDGRATISRDDGQSTVRLQ
LNNLRTEDTATYYCAKTTVADGVIGAYGIDAWGHGTEVIVSSTSGQAGQHHHHHGAYPYDVPDYAS

>scFv106
MKKTAIAIAVALAGFATVAQAALTQPSSVSANPGETVKITCSGDSSDYGYGWYQQKSPGSAPVTVTYSNNQ
RPPNIPSRFSGSASGSTATLTITGVQVEDEAVYYCGSEDSTTDAVFGAGTTLTVLGQSSRSSAMTLDESGG
GLQTPGGALSLVCKASGFTFSSYDMGWVRQAPGKGLEYVAGITNDGRYASYGSAVDGRATISRDNGQSTVR
LQLNNLRAEDTGTYYCARDDGSGWTGNTIDTWGHGTEVIVSSTSGQAGQHHHHHGAYPYDVPDYAS

>scFv108
MKKTAIAIAVALAGFATVAQAALTQPSSVSANPGETVKITCSGGGSYAGSYYYGWYQQKAPGSAPVTLIYD
NTNRPSNIPSRFSGSLSGSPGTLAITGVRAEDEAVYYCGSFHSSTDGGYAAIFGAGTTLTVLGQTSRSSAV
TLDESGGGLQTPGGGLSLLCKASEFTSISYAMEWVRQAPGKGLEWVAYINSDGSSTWHAPAVKGRATISRD
NGQSTVRLQLNSLRAEDTATYYCTICSGGENIYTCCHGTEVIVSSTSGQDGQHHHHHGAYPYDVPDYAS

>scFv110
MKKTAIAIAVALAGFATVAQAALTQPSSVSANLGGTVKLTCSGGSSYGYSWHQQKSPGSAPVTVIYSNDKR
PSDIPSRFSGSASGSTATLTITGVQVEDEAVYFCGSYDSSSIAGIFGAGTTLTVLGQSSRFSTVTLDESGG
GLQTPGGGLSLVCKASGFTFSSYGMAWVRQAPGKGLEWLAGIYRDDDSTYYAPAVKGRATISRDNGQSTVR
LQLNNLRTEDTATYYCAKESASGGWNAGWIDAWGHGTEVIVSSTSGQAGQHHHHHGAYPYDVPDYAS

>scFv111
MKKTAIAIAVALAGFATVAQAALTQPSSVSANPGETVKLTCSGDSSDYGYGWYQQKSPGSAPVTVIYNNNK
RPSDIPSRFSGSKSGSTGTLTISGVQAEDEAVYFCGSEDSNTDAIFGAGTTLTVLGQSSRSSAVTLDESGG
GLQTPGGALSLVCEASGFTFSSYDMGWIRQAPGKGLEYVAGITSNGRYASYGSAVDGRATISRDNGQSTVR
LQLNNLRAEDTGTYYCARDDGSGWTGNTIDAWGHGTEVIVSSTSGQAGQHHHHHGAYPYDVPDYAS

>scFv112
MKKTAIAIAVALAGFATVAQAALTQPSSVSANLGGTVKITCSGGSGSYGWYQQKSPGSAPVTVIYYNDQRP
SDIPSRFSGSKSGSTGTLTITGVQAEDEAVYYCGGYDSTYVGIFGAGTTLTVLGQSSRSSAVTLDESGGGL
QTPRGALSLVCKASGFTFSSYSMAWVRQAPGKGLEFVAGIQNDGSITDYGSAVDGRATISRDDGQSTVRLQ
LNNLRTEDTATYYCAKTTVADGVIGAYGIDAWGHGTEVIVSSTSGQAGQHHHHHGAYPYDVPDYAS

>scFv113
MKKTAIAIAVALAGFATVAQAALTQPSSVSANPGETVKITCSGDSSGYGYGWYQQKSPGSAPVTVIYNNNK
RPSDIPSRFSGSKSGSTGTLTITGVQAEDEAVYFCGSEDSNTDAVFGAGTTLTVLGQSSRSSTVTLDESGG
GLQTPGGTLSLACKASGFTFSGYDMGWVRQAPGKGLEYVAGITSDGRYASYGSAVDGRAAIWRDNGQSTVR
LQLKNLRTEDTATYYCARDDGSGWSGNNIDAWGHGTEVIVSSTSGQAGQHHHHHGAYPYDVPDYAS

>scFv114
MKKTAIAIAVALAGFATVAQAALTQPSSVSASPGETVKITCSGGSGSYGWYQQKSPGSAPVTVIYYNDKRPSDIPSRFS
GSKSGSTSTLTITGVQAEDEAVYYCGSYDSSAGYVGIFGAGTTLTVLGQSSRSSTVTLDESGGGLQTPGGGLSLVCKAS
GFTFSSYGMGWMRQAPGKGLEFVAGIRKDGSSTAYGAAVDGRATISRDDGQSTLRLQLGNLRAEDTGTYFCAKTNSYNS
AGIIDAWGHGTEVIVSSTSGQAGQHHHHHGAYPYDVPDYAS

>scFv115
MKKTAIAIAVALAGFATVAQAALTQPSSVSANPGETVEITCSGSSGSYGWYQQKPPGSAPVTVIYYNDKRP
SDIPSRFSGSKSGSTGTLTITGVQAEDEAVYYCGGYGSTYLGIFGAGTTLTVLGQSSRSSAVTLDESGGGL
QMPGGGLSLVCKASGFTFSSYAMGWMRQAPGKGLEFVAGILNDGSITDYGSAVKGRATISRDDGQSTVRLQ
LSNLRTEDTATYYCAKTTVGDGVIGAYAIDAWGHGTEVIVSSTSGQAGQHHHHHGAYPYDVPDYAS
```

-continued

>scFv117
MKKTAIAIAVALAGFATVAQAALTQPSSVSANPGETVKITCSGGGSYAGSYYYGWYQQKAPGSAPVTLIYD
NTNRPSNIPSRFSGSLSGSTGTLTITGVRAEDEAVYYCGSFDSSTDSGYAAIFGAGTTLTVLGQSSRSSAV
TLDESGGGLQTPGGALSLVCRASGITFSTYAMEWVRQAPGKGLEFVAVVNAAGSTYYGAAVKGRATISRDN
GQSTVRLQLNNLRAEDTGTYYCTRGSGGENIDAWGHGTEVIVSSTSGQAGQHHHHHGAYPYDVPDYAS

>scFv118
MKKTAIAIAVALAGFATVAQAALTQPSSVSANLGGTVEITCSGGGSGSYGWYQQKSPGGAPVTVIYYNDKRP
SDIPSRFSGSKSGSTATLTITGVQVEDEAVYYCGSYDSSYVGIFGVGTTLTVLGQSSRSSAVTLDESGGGL
QTPRGALSLVCKASGFTFSSYSMAWVRQAPGKGLEFVAGIQNDGSITDYGSAVDGRATISRDDGQSTVRLQ
LNNLRTEDTATYYCAKTTVADGVIGAYGIDAWGHGTEVIVSSTSGQAGQHHHHHGAYPYDVPDYAS

>scFv119
MKKTAIAIAVALAGFATVAQAALTQPSSVSANLGGTVKITCSGGSGSYGWYQQKSPGSAPVTVIYRNDKRP
SNIPSRFSGALSGSTATLTITGVQAEDEAVYFCGSADSSGAIFGAGTTLTALGQSSRSSTVTLEESGGGLH
TPGGGLILLCKGSGVSFCNYGMGWMRRDPGGGLEYVAGISTGSYTYYGPAVKGRGTVSRDNGQSTMRLQLN
HLRAEDETIYFCARTDASSHGCGSGTDLGSIDAWGHGTEVLLSSTSGQAGQHHHHHGAYPYDVPDYAS

>scFv120
MKKTAIAIAVALAGFATVAQAALTQPSSVSANPGETVKLTCSGDSSDYGYGWYQQKSPGSAPVTVIYNNNK
RPSDIPSRFSGSKSGSTGTLTISGVQAEDEAVYFCGSEDSNSDAIFGAGTTLTVLGQSSRSSAVTLDEYGG
GLQTPGGALSLVCEASGFTFSSYDMLRIPHAPGKGLEYVAGLTSNGRYASYGSAVDGRATISRDNGQSTWR
LHLNNLGAEDTGPYYCAGYDGSGWTGNTIEAWGHRTEVLVSSTSGQAGQHHHHHGAYPYDVPDYAS

>scFv121
MKKTAIAIAVALAGFATVAQAALTQPSSVSANLGGTVKITCSGGSSYYGWYQQKSPGSAPVTLIYENNNRP
SDIPSRFSGSASGSTATLTITGVQAEDGAVYFCGSEDSTYVGIFGAGTTLTVLGQSSRSSAVTLDESGGGL
QTPGRALSLVCKASGFTFSSFNMGWVRQAPGKGLEYVASISSSGSYTAYGSAVKGRATISRDNGQSTVRLQ
LNNLRAEDTATYYCAKAAGSAYYYTAVTPAFAGSIDAWGHGTEVIVSSTSGQAGQHHHHHGAYPYDVPDY
AS

>scFv123
MKKTAIAIAVALAGFATVAQAALTQPSSVSANLGGTVKITCSGGSSYYGWYQQKSPGSAPVTLIYENNNRP
SDIPSRFSGSASGSTAPLTITGVQAEDGAVYFCGSEDSTYVGIFGAGTTLTVLGQSSRSSAVTLDESGGGL
QTPGRALSLVCKASGFTFSSFNMGWVRQAPGKGLEYVASISSSGSYTAYGSAVKGRATISRDNGQSTVRLQ
LNNLRAEDTATYYCAKAAGSAYYYTAVTPAFAGSIDACGHGTEVIVSSTSGQAGQHHHHHGAYPYDVPDY
AS

>scFv124
MKKTAIAIAVALAGFATVAQAALTQPSSVSANLGGTVKITCSGGGSGSYGWYQQKSPGSAPVTVIYYNDQRP
SDIPSRFSGSKSGSTGTLTITGVHAEDEAVYYCGGYNSTYVGIFGAGTTLTVLGQSSRSSAVTLDESGGGL
HTPRGALSLICKASGFTFSSYSMAWVQQAPGKGLEFVPGILNDGSITDYGSADDGRATISRDDGQSTVRLH
LINLRTEDTATYYCAKTTVADGVIGAYGIDAWGHGTEVIVSSTSGQAGQHHHHHGAYPYDVPDYAS

>scFv131
MKKTAIAIAVALAGFATVAQAALTQPSSVSANLGGTVEITCSGGSSYYGWYQQKSPGSAPVTVIYWNDKR
PSDIPSRFSGSESGSPATLTITGVRAEDEAVYFCGSGDSSGTGIFGAGTTLTVLGQSSRSSAVTLDESGGG
LQTPGGGLSLVCKASGFSFSDYTMNWVRQAPGKGLEWVGQISSDNGRYTTYGAAVKGRATISRDDGQSTVR
LQLNNLKAEDTATYYCAKESDGDYNGGAGLIDAWGHGTEVIVSSTSGQAGQHHHHHGAYPYDVPDYAS

>scFv134
MKKTAIAIAVALAGFATVAQAALTQPSSVSANLGGTVKITCSGSSGSYGWYQQKSPGSAPVTVIYWNDKRP
SNIPSRFSGALSGSTATLTITGVQAEDEAVYFCGSADSSGAIFGAGTTLTVLGQSSRSSTVTLDESGGGLQ

TPGGGLSLVCKGSGFAFSNYGMGWMRQAPGKGLEYVAGISTGSYTDYGPAVKGRATISRDNGQSTVRLQLN

NLRAEDAAIYFCAKTAGSGYGCGSGTDLGSIDAWGHGTEVIVSSTSGQAGQHHHHHHGAYPYDVPDYAS

Additional scF1, Sequences (6)
>scFv103
MKKTAIAIAVALAGFATVAQAALTQPSSVSANPGETVEITCSGGGGSYGWFQQKSPGSAPVTVIYESTKRP

SNIPSRFSGSGSGSTSTLTITGVRAEDEAVYYCGGYDGSSDAIFGAGTTLTVLGQSSRSSTVTLDESGGGL

QTPGGALSLVCKASGFTFSSHDMGWVRQAPGKGLEYVAGITDDGRYASYGPAVDGRATISRDNGQSTVRLQ

LKNLRAEDTATYYCARDDGSWSGDTIDTWGHGTEVIVSSTSGQAGQHHHHHHGAYPYDVPDYAS

>scFv136
MKKTAIAIAVALAGFATVAQAALTQPSSVSANPGETVKITCSGGGSYSYGWYQQKSPGSAPVTVIYSSDKRP

SDIPSRFSGSKSGSTSTLTITGVQAEDEAVYYCGSRDSNYVGIFGAGTTLTVLGQSSRSSTVTLDESGGGL

QTPGGALSLVCKASGFTFSSYEMQWVRQAPGKGLEFVAAISSDGSYTNYGAAVQGRATISRDNGQSTVRLQ

LSNLRAEDTATYYCARSPGGYTWWPGAAGGIDAWGHGTEVIVSSTSGQAGQHHHHHHGAYPYDVPDYAS

>scFv137
MKKTAIAIAVALAGFATVAQAALTQPSSVSANPGETVKITCSGGGSSNNYGWEQQKAPGSAPVTVIYDNTN

RPSNIPSRFSGSKSSSTHTLTITGVQAEDEAVYYCESADSSSSIFGAGTTLTVLGQSSRSSAVTLDESGGG

LQTPGGTLSLVCKASGFTFSSFNMFWVRQAPGKGLEFVAGIGNTGRSTGYGSAVKGRATISRDNGQSTVRL

QLNNLRAEDTGTYYCAKAYGDSNIDAWGHGTEVIVSSTSGQAGQHHHHHHGAYPYDVPDYAS

>scFv138
MKKTAIAIAVALAGFATVAQAALTQPSSVSANLGGTVEITCSGGGSYYGWYQQKSPGSAPVTVIYANTNGP

SDIPSRFSGSTSGSTATLTITGVQADDEAVYSCGSYDSSYVGIFGAGTTLTVLGQSSRSSTVTLDESGGGL

QTPGGALSLVCKASGFTFNSYALEWVRQAPGKGLEWVAGISGDGSYRHYGSAVKGRATISRDSGQSTVRLQ

LNNLRAEDTGTYYCAKSTGSGAGWGASNIDAWGHGTEVIVSSTSGQAGQHHHHHHGAYPYDVPDYAS

>scFv139
MKKTAIAIAVALAGFATVAQAALTQPSSVSANLGGTVKITCSGGDSSYGWYQQKSPGSAPVTLIYDNTNRP

SDIPSRFSGSKSGSTGTLTITGVQAEDEAVYYCGNADSSSTAAFGAGTTLTVLGQSSRSSTVTLDESGGGL

QTPGGALSLVCKASGFTFSSYAMGWVRQAPGKGLEYVAAISSAGSTTNYGAAVKGRATISSDNGQSTVRLQ

LNNLRAEDTATYFCAKTAGSGYYVWSAIAGDIYAWGHGTEVIVSSTSGQAGQHHHHHHGAYPYDVPDYAS

>scFv140
MKKTAIAIAVALAGFATVAQAALTQPSSVSANPGGTVKITCSGSSGSYYGWYQQKSPGSAPVTVIYDNDKR

PSDVPSRFSGSKSGPTATLTITGVQAEDEAVYFCGSRDNSYVGIFGAGTTLTVLGQSSRSSAVTLDESGGG

LQTPGGALSLVCKASGFTFSSYDMFWVRQAPGKGLEFVAQINSAGSYTNYGSAVKGRATISRDDGQSTVRL

QLNNLRAEDTGIYFCAKSASGYYYSGSDAGDIDAWGTGPKSSSPSTSGPGRPAPSPSPWRIPVRRSGLRFL

ERWARDQLSCTKWLI.
(lacks the C-terminal 6His and HA tag)

scFv45
atgaaaaagacagctatcgcgattgcagtggcactggctggtttcgctaccgtggcccag
 M   K   K   T   A   I   A   I   A   V   A   L   A   G   F   A   T   V   A   Q gcggccctgactcagccgtcctcggtgtcagcgaacccgggaggaaccgtcaagatcacc
 A   A   L   T   Q   P   S   S   V   S   A   N   P   G   G   T   V   K   I   T tgctccgggagtagcagtgcctatggttatggctggtatcagcagaagtccctggcagt
 C   S   G   S   S   S   A   Y   G   Y   G   W   Y   Q   Q   K   S   P   G   S gcccctgtcactgtgacctataacaacactaagagaccctcaaacacccctccacgattc
 A   P   V   T   V   I   Y   N   N   H   K   R   P   S   N   I   P   S   R   F tccggttccaaaccggccccacgggcacattaaccatcaccggggtccaagccgcggac
 S   G   S   K   S   G   S   T   G   T   L   T   I   T   G   V   Q   A   E   D gaggccgtctatttctgtgggagtgaggcagcagcactgatgctacatttggggccggg
 E   A   V   Y   F   C   G   S   E   D   S   S   T   D   A   I   F   G   A   G -continued

```
acaaccctgaccgtcctaggtcagtcctctagatcttccaccgCgacgttggacgagtcc
 T  T  L  T  V  L  G  Q  S  S  R  S  S  T  V  T  L  D  E  S ggggcggcctccaggcgcccggaggagcgctcagcctcgtctgcaaggcctccgggttc
 G  G  G  L  Q  A  P  G  G  A  L  S  L  V  C  K  A  S  G  F accctcagcagttacgacacggggttggatacgacaggcgcccggcaaggggctggaatac
 T  F  S  S  Y  D  M  G  W  I  R  Q  A  P  G  K  C  L  B  Y gttgcgggcattaccgataatggtagatacgcaccatatgggtcggcggtggatggccgt
 V  A  G  I  T  D  N  G  R  Y  A  S  Y  C  S  A  V  D  G  R gccaccatctcgagggaeaacgggcagagctcagtgaggctgcagctgoacaacctcagg
 A  T  I  S  R  D  N  G  Q  S  S  V  R  L  Q  L  N  N  L  R gctgaggacaecggcacctaccactgcgccagagatgacggtagtggttggaccggtaat
 A  E  D  T  G  T  Y  Y  C  A  R  D  D  G  S  G  W  T  G  N agtatcgacgcatggggccacgggaccgaagtcatcgtctcctccactagtggccaggcc
 S  I  D  A  W  G  H  G  T  E  V  I  V  S  S  T  S  G  Q  A ggccagcaccatcaccatcaccatggcgcatacccgcacgacgttccggaccacgcttct
 G  Q  H  H  H  H  H  H  C  A  Y  P  Y  D  V  P  D  Y  A  S tag
- scFv57
atgaaaaagacagatatcgcgattgcagtggcactggccggttccgceaccgtggcccag
 M  K  K  T  A  I  A  I  A  V  A  L  A  G  F  A  T  V  A  Q gcggccctgactcagccgtcctcggtgccagcgaacccggggaggaaccgtcaagatcacc
 A  A  L  T  Q  P  S  S  V  S  A  N  P  G  G  T  V  K  I  T tgctccggggagtagcagtgcctatggttatggctggtatcagcagaagtcacctggcagt
 C  S  G  S  S  S  A  Y  G  Y  G  W  Y  Q  Q  K  S  P  G  S gcccctgtcactgtgatctataacaacaataagagaccccccaaacatccctccacgactc
 A  P  V  T  V  I  Y  N  N  N  K  R  P  S  N  I  P  S  R  F tccggttccaaatccggctccacggggcacatcaaccatcactggggtccaagccgggac
 S  G  S  K  S  G  S  T  G  T  L  T  I  T  G  V  Q  A  E  D goggctgtctattcctgtgggagtgaagacagcagcactgacgctatatctggggccggg
 E  A  V  Y  F  C  G  S  E  D  S  S  T  D  A  I  F  G  A  G acaaccctgaccgtcccggccagtccctagatctcccgccgcgacgtcggacgagtcc
 T  T  L  T  V  L  G  Q  S  S  R  S  S  A  V  T  L  D  E  S ggggcggcctccagacgcccggaggagcgctcagcctcgtctgcaaggcctccgggttc
 G  G  G  L  Q  T  P  G  G  A  L  S  L  V  C  K  A  S  G  F accttcagcagttacgacatggggttgggtgcgacaggcgcccggcaagggactggaatac
 T  F  S  S  Y  D  M  G  W  V  R  Q  A  P  G  K  G  L  E  Y gtcgcgggtattaccaatgatggtagatacgcatcatacgggtcggcggtggatggccgt
 V  A  G  I  T  N  D  G  R  Y  A  S  Y  G  S  A  V  D  G  R gccaccatctcgagggacaacgggcagagcacagtgaggccgcagctgaacaacctcagg
 A  T  I  S  R  D  N  G  Q  S  T  V  R  L  Q  L  N  N  L  R gctgaggacaccggcacccactactgcgccagagatgatggtagtggttggactggtaat
 A  E  D  T  G  T  Y  Y  C  A  R  D  D  G  S  G  W  T  G  N actatcgacacatggggccacgggaccgaagccaccgtctcccccactagtggccaggcc
 T  I  D  T  W  G  H  G  T  E  V  I  V  S  S  T  S  G  Q  A ggccagcaccaccaccatcaccauggcgcatacccgtacgacgctccggactacgcttct
 G  Q  H  H  H  H  H  H  G  A  Y  P  Y  D  V  P  D  Y  A  S tag
- scFv64
acgaaaaagacagctatcgcgattgcagtggcactggctggtttcgctaccgtggcccag
 M  K  K  T  A  I  A  I  A  V  A  L  A  C  F  A  T  V  A  Q gcggccctgacccagccgtcctcggcgtcagcgaacccggggagaaaccgtcaagatcacc
 A  A  L  T  Q  P  S  S  V  S  A  N  P  Q  E  T  V  K  I  T
```

```
cgccccggggatagcagtggctatggctatggctggtatcagcagaagtcacctggcagt
 C  S  G  D  S  S  G  Y  G  Y  G  W  Y  Q  Q  K  S  P  C  S gcccctgccactgtgacccataacaacaataagagaccctcggacatcccttcacgattc
 A  P  V  T  V  I  Y  N  N  N  K  R  P  S  D  I  P  S  R  F tccggctccaaatccggccccacgggcacattaaccatcactggggtccaagccgaggac
 S  G  S  K  S  G  S  T  G  T  L  T  I  T  G  V  Q  A  E  D gaggctgtctatttccgtgggagtgaagacagcaacactgatgctgtattcggggccggg
 E  A  V  Y  F  C  G  S  E  D  S  N  T  D  A  V  F  G  A  G acaaccctgaccgtcccaggtcagtcctctagatcttccaccgcgacgttggacgagtcc
 T  T  L  T  V  L  G  Q  S  S  R  S  S  T  V  T  L  D  E  S ggggcggcctccagacgcccggaggaacgctcagcctcgcctgcaaggcctccgggttc
 G  G  G  L  Q  T  P  G  G  T  L  S  L  A  C  K  A  S  G  F accttcagtggctacgacatgggctgggtgcgacaggcaccggcaaggggctggagtac
 T  F  S  G  Y  D  M  G  W  V  R  Q  A  P  C  K  G  L  E  Y gttgcgggtatcaccagcgatggtagatacgcatcatacgggtcggcggtggatggccgc
 V  A  G  I  T  S  D  G  R  Y  A  S  Y  C  S  A  V  D  G  R gccgccatctggagggacaacgggcagagcacagtgaggctgcagctgaaaaacctcagg
 A  A  I  W  R  D  N  G  Q  S  T  V  R  L  Q  L  K  N  L  R actgaggacaccgccacccactaccgcgccagagatgatggtagtggctggagtggtaat
 T  E  D  T  A  T  Y  Y  C  A  R  D  D  G  S  G  W  S  G  N aatatcgacgcatggggccacgggaccgaagtcatcgtctcctccactagcggccaggcc
 N  I  D  A  W  G  H  G  T  E  V  I  V  S  S  T  S  G  Q  A ggccagcaccatcaccatcaccatggcgcatacccgtacgacgttccggactacgcttct
 G  Q  H  H  H  H  H  H  G  A  Y  P  Y  D  V  P  D  Y  A  S tag
 - scFv106
atgaaaaagacagctatagcgattgcagtggcactggctggtttcgccaccgtggcccag
 M  K  K  T  A  I  A  I  A  V  A  L  A  G  F  A  T  V  A  Q gcggccctgactcagccgtcctcggtgtcagcgaacccaggagaaaccgtcaagatcacc
 A  A  L  T  Q  P  S  S  V  S  A  N  P  G  E  T  V  K  I  T tgctccggggatagcagtgactatggttatggctggtatcagcagaagtcacctggcagt
 C  S  G  D  S  S  D  Y  G  Y  G  W  Y  Q  Q  K  S  P  G  S gcccctgtcactgtgacctatagcaacaaccagagacccccgaacatcccttcacgattc
 A  P  V  T  V  T  Y  S  N  N  Q  R  P  P  N  I  P  S  R  F tccggttccgcatccggctccacagccacattaaccctcactggggtccaagtcgaggac
 S  G  S  A  S  G  S  T  A  T  L  T  I  T  G  V  Q  V  E  D gaggctgtctattcctgtgggagtgaagccagtcccactgatgctgtatttggggccggg
 E  A  V  Y  Y  C  G  S  E  D  S  T  T  D  A  V  F  G  A  C acaaccctgaccgcccaggccagtcctctagatcctcgccatgacgttggacgagtcc
 T  T  L  T  V  L  G  Q  S  S  R  S  S  A  H  T  L  D  E  S ggggcggcctccagacgcccggaggagcgctcagcccgtctgcaaggcctccgggttc
 G  G  G  L  Q  T  P  G  G  A  L  S  L  V  C  K  A  S  G  F accttcagcagttacgacatgggctgggtgcgacaggcgcccggcaaggggctggaatac
 T  F  S  S  Y  D  M  G  W  V  R  Q  A  P  G  K  G  L  E  Y gttgcgggtattaccaatgacggtagatacgcatcatacgggtcggcggtggatggccgt
 V  A  G  I  T  N  D  G  R  Y  A  S  Y  G  S  A  V  D  G  R gccaccatctcgagggacaacgggcagagcacagtgaggctgcagctgaacaacctcagg
 A  T  I  S  R  D  N  G  Q  S  T  V  R  L  Q  L  N  N  L  R gctgaggacaccggcacctactactgcgccagagatgatggtagtggLtggactggtaat
 A  E  D  T  G  T  Y  Y  C  A  R  D  D  G  S  G  K  T  G  N actatcgacacatggggccacgggaccgaagtcatcgtctcctccactagcggccaggcc
 T  I  D  T  W  G  H  G  T  E  V  I  V  S  S  T  S  G  Q  A
```

```
ggccagcaccctccccatcaccatggcgcataccgtacgacgttccggactacgcttct
 G  Q  H  H  H  H  H  H  G  A  Y  P  Y  D  V  P  D  Y  A  S tag
 -
``` scFv136

```
atgaaaaagacagccatcgcgattgcagtggcactggctggttccgctaccgcggcccag
 M  K  K  T  A  I  A  I  A  V  A  L  A  G  F  A  T  V  A  Q gcggccccgactcagccgtccccggcgtcagcaaacccaggagaaaccgtcaagaccacc
 A  A  L  T  Q  P  S  S  V  S  A  N  P  G  E  T  V  K  T  T tgccccgggggcagccacagccatggctggcatcagcagaagcccctggcagcgccccc
 C  S  G  G  S  Y  S  Y  G  W  Y  Q  Q  K  S  P  G  S  A  P gtcaccgtgacctatagcagcgacaagagaccccggacatccttcacgatcctccggt
 V  T  V  I  Y  S  S  D  K  R  P  S  D  I  P  S  R  F  S  C tccaaatccggctcacaagcacantaaccaceactggggtccaagccgaggacgaggct
 S  K  S  G  S  T  S  T  L  T  I  T  G  V  Q  A  E  D  E  A gcccactaccgtgggagcagggacagcaactatgttggtacatccggggccgggacaacc
 V  Y  Y  C  G  S  R  D  S  N  Y  V  G  I  F  G  A  G  T  T ctgaccgtcctaggtcagtcctctagatcttccaccgtgacgttggacgagtccggggc
 L  T  V  L  G  Q  S  S  R  S  S  T  V  T  L  D  E  S  G  G ggcctccagacgcccggaggagcgctcagcctcgcctgcaaggcccccggaccaccttc
 G  L  Q  T  P  G  G  A  L  S  L  V  C  K  A  S  G  F  T  F agcagttatgagacgcagcgggtgcgacaggcgcccggcaaggggccggagctcgtcgca
 S  S  Y  E  M  Q  W  V  R  Q  A  P  G  K  G  L  E  F  V  A gccatcagcagcgacggcagccacacaaactacggggcggcggcgcagggccgcgccacc
 A  I  S  S  D  G  S  Y  T  N  Y  G  A  A  V  Q  G  R  A  T atctcgagggacaacgggcagagcacagtgaggctgcagctgagcaaccctcagggctgag
 I  S  R  D  N  G  G  S  T  V  R  L  Q  L  S  N  L  R  A  B gacccgccacctactactgcgccagaagtcctggtggttacacttggtggcctggagct
 D  T  A  T  Y  Y  C  A  R  S  P  G  G  Y  T  W  P  G  A gctggcggtatcgacgcatggggcacgggaacgaagtcatcgtctcctccactagtggc
 A  G  G  I  D  A  K  C  H  G  T  E  V  I  V  S  S  T  S  G caggccggccagcaccatcaccatcaccatggcgcataccgtacgacgttccggactac
 Q  A  G  Q  H  H  H  H  H  H  C  A  Y  P  Y  D  V  P  D  Y gctccctag
 A  S  -
``` scFv67

```
acgaaaaagacagccatcgcgactgcagtggcaccggccggtcccgctaccgtggcccag
 M  K  K  T  A  I  A  I  A  V  A  I  A  G  F  A  T  V  A  Q gcggccctgactcagccgtccccggtgccagcgaacccgggaggaaccgtcaagatcacc
 A  A  L  T  Q  P  S  S  V  S  A  N  P  G  G  T  V  K  I  T tgccccggggagtagcagcgcccatggccacggctggcatcagcagaagtcacctggcagc
 C  S  G  S  S  S  A  Y  G  Y  G  W  Y  Q  Q  K  S  P  G  S gcccccgtcaccgcgatctataacaacaacaagagaccctcaaacacccctcacgattc
 A  P  V  T  V  I  Y  N  N  N  K  R  P  S  N  I  P  S  P  F tccggttccaaatccggctccacgggcacattaaccatcactggggtccaagccgaggac
 S  G  S  K  S  G  S  T  G  T  L  T  I  T  G  V  Q  A  E  D gaggctgtctatttctgtgggagtgaagacagcagcactgatgctatatttggggccggg
 E  A  V  Y  F  C  G  S  E  D  S  S  T  D  A  I  F  G  A  G acaaccctgaccgtcctaggtcagtcctctagatcttccgccgtgacgttggacgagtcc
 T  T  L  T  V  L  G  Q  S  S  R  S  S  A  V  T  L  D  E  S ggggcggcctccagacgcccggaggagcgctcagccccgcctgcaaggcctccgggttc
 G  G  G  L  Q  T  P  G  G  A  L  S  L  V  C  K  A  S  G  F accttcagcagttacgacacgggtttgggtgcgacaggcgcccggcaagggactggaatac
 T  F  S  S  Y  D  H  C  W  V  R  Q  A  P  G  K  G  L  E  Y
```

-continued

```
gctgcgggtattaccaacgacggcagacacgcaccacacgggccggcggtggatggccgt
 V  A  G  I  T  N  D  G  R  Y  A  S  Y  G  S  A  V  D  G  R gccaccaccccgagggacaacgggcagagcacagcgaggccgcagccgaacaacctcagg
 A  T  I  S  R  D  N  G  Q  S  T  V  R  L  Q  L  N  H  L  R gccgaggacaccggcacccaccaccgcgccagagacaacggcagcggtcggaccggtaat
 A  E  D  T  G  T  Y  Y  C  A  R  D  D  G  S  G  W  T  G  N accatcgacacatggggccacgggaccgaagccaccgtccccccactagcggccaggcc
 T  I  D  T  W  G  H  G  T  E  V  I  V  S  S  T  S  G  Q  A ggccagcaccaccaccaccaccacggcgcacacccgcacgacgccccggaccacgcctct
 G  Q  H  H  H  H  H  H  G  A  Y  P  Y  D  V  P  D  Y  A  S
```

Tag

- scFv102
```
atgaaaaagacagctatcgcgattgcagtggcactggctggtttcgctaccgtggcccag
 M  K  K  T  A  I  A  I  A  V  A  L  A  G  F  A  T  V  A  Q gcggcccccgactcagccgtcctcggcgtcagcgaacccgggagaaaccgtcaagatcacc
 A  A  L  T  Q  P  S  S  V  S  A  M  P  G  E  T  V  K  I  T tgctccgggggtagtggcagctatggctggtatcagcaggagtcacctggcagcgctcct
 C  S  C  C  S  G  S  Y  G  W  Y  Q  Q  E  S  P  G  S  A  P gtcactgtgatctactacaacgacaagagaccctcggacacccccccacgcctctccggc
 V  T  V  I  Y  Y  N  D  K  R  P  S  D  I  P  S  P  F  S  G tccgcatccggctccacagccacattaaccatcgctggggtccgagccgaggacgaggct
 S  A  S  G  S  T  A  T  L  T  I  A  G  V  R  A  E  D  E  A gtctacttctgtgggagccgggatagcagcactagtgctggtatatttggggccgggaca
 V  Y  F  C  G  S  W  D  S  S  T  S  A  G  I  F  G  A  G  T gccctgaccgtcccaggccagtcctctagaccttccgccgcgacgtcggacgagtccggg
 A  L  T  V  L  G  Q  S  S  R  S  S  A  V  T  L  D  E  S  G ggcggcctccagacgcccggaggagggctcagcctcgcctgcaaggcccccggctccagc
 G  G  L  Q  T  P  G  G  G  L  S  L  V  C  K  A  S  G  F  S agcagccatggcatgggctggatgcgccaggcacctggcaagggccctgaattcgtcgcg
 S  S  H  G  M  G  W  M  R  Q  A  P  G  K  G  L  E  F  V  A ggtattagaagtgatggcagtagcacagcatacggggcggcggtggatggccgcgccacc
 G  I  R  S  D  G  S  S  T  A  Y  G  A  A  V  D  G  R  A  T accacaagggacgatgggcagagcacagtgacactgcagctgaacaacctcagggctgag
 I  T  R  D  D  G  Q  S  T  V  T  L  Q  L  N  N  L  R  A  E gacaccgccacctacctctgcgccaaaactaatagttacaatagcgctggcataatcgac
 D  T  A  T  Y  F  C  A  K  T  N  S  Y  N  S  A  G  I  I  D gcatggggccacggggaccgaagtcatcgtctcctccactagtggccaggccggccagcac
 A  W  G  H  G  T  E  V  I  V  S  S  T  S  G  Q  A  G  Q  H catcaccatcaccacggcgcatacccgtacgocgttccggactacgcttcttag
 H  H  H  H  G  A  Y  P  Y  D  V  P  D  Y  A  S  -
```

ScPv34
```
atgaaaaagacagctatcgcgattgcagtggcactggctggtttcgccaccgtggcccag
 M  K  K  T  A  I  A  I  A  V  A  L  A  G  F  A  T  V  A  Q gcggccctgactcagccgtcctcggtgtcagcaaacctgggaggaaccgtcgagaccacc
 A  A  L  T  Q  P  S  S  V  S  A  M  L  G  G  T  V  E  I  T tgctccggggagtagtggcagccatggctggtatcagcagaagtcacctggcagtgcccct
 C  S  C  S  S  G  S  Y  G  W  Y  Q  Q  K  S  P  G  S  A  P gccaccgcgatctattacaacgacaagagaccccggacatcccttcacgattcccggt
 V  T  V  I  Y  Y  N  D  K  R  P  S  D  I  P  S  R  F  S  G tccacatccggctccacagccacattaaccaccaccggggtccaagccgaggacgaggct
 S  T  S  G  S  T  A  T  L  T  I  T  G  V  Q  A  E  D  E  A gcccatttccgtggtggccacgacagcaactatatcggtatatttggggccgggacaacc
 V  Y  F  C  G  G  Y  D  S  N  Y  I  G  I  F  G  A  G  T  T
```

-continued

```
ccgaccgtcctaggtcagccctccagatcttccgccgcgacgttggacgagtccgggggc
 L  T  V  L  G  Q  S  S  R  S  S  A  V  T  L  D  E  S  G  G ggcctccagacgcccgaggagcgctcagcctcgtccgcaaggcctccgggttcaccttc
 G  L  Q  T  P  R  G  A  L  S  L  V  C  K  A  S  G  F  T  F agcagttacagcatggcctgggtgcgacaggcgcccggcaaggggctggagttcgtcgcg
 S  S  Y  S  M  A  W  V  R  Q  A  P  G  K  G  L  E  F  V  A ggtattcagaatgatggtagtatcacagattacgggtcggcggtggatggccgtgccacc
 G  I  Q  N  D  G  S  I  T  D  Y  G  S  A  V  D  G  R  A  T acctcgagggacgacgggcagagcacagtgaggctgcagctgaacaacctcaggactgag
 I  S  R  D  D  G  Q  S  T  V  R  L  Q  L  N  N  L  P  T  E gacaccgcccctactactgcgccaaaactactgttgctgatggtgtcatcggtgcttat
 D  T  A  T  Y  Y  C  A  K  T  T  V  A  D  G  V  I  G  A  Y ggcatcgacgcatggggccacgggaccgaagtcatcgcccccctccaccagtggccaggcc
 G  I  D  A  W  G  H  G  T  E  V  I  V  S  S  T  S  G  Q  A ggccagcaccatcaccatcaccatggcgcacaccgtacgacgttccggaccacgcttct
 G  Q  H  H  H  H  H  H  G  A  Y  P  Y  D  V  P  D  Y  A  S tag
 - scFv61
acgaaaaagacagccaccgcgattgcagtggcaccggctggtttcgccaccgtggcccag
 M  K  K  T  A  I  A  I  A  V  A  L  A  C  F  A  T  V  A  Q gcggccctgactcagccgccctcggtgccagcaaacccaggagaaaccgccaagatcacc
 A  A  L  T  Q  P  S  S  V  S  A  H  P  C  E  T  V  K  I  T cgctccggggtggcagctacgctggaagttactatcatggctggtaccagcagaaggca
 C  S  C  G  G  S  Y  A  G  S  Y  Y  Y  G  W  Y  Q  Q  K  A cctggcagcgccctgccactctgatctatgacaacaccaacgaccctcgaacacccct
 P  G  S  A  P  V  T  L  I  Y  D  N  T  N  R  P  S  N  I  P tcacgactccccggttccctatccggctccacgggcacattaaccatcactggggtccga
 S  R  F  S  C  S  L  S  C  S  T  G  T  L  T  I  T  G  V  R gccgaggacgaggctgcctattactgtgggagctccgacagcagcaccgacggcggatac
 A  E  D  E  A  V  Y  Y  C  G  S  F  D  S  S  T  D  G  G  Y gccgccatacttggggccgggacaaccccgaccgtcctaggtcagccctccagaccccac
 A  A  I  F  G  A  G  T  T  L  T  V  L  G  Q  S  S  R  S  Y gccgtgacgttggacgagtccggggcggcccccagacgcccggaggagggctcagcctc
 A  V  T  L  D  E  S  G  G  G  L  Q  T  P  G  G  G  L  S  L gtctgcaaggcctccgagttcaccctcagcagttatgccatggagcgggtgcgcaggca
 V  C  K  A  S  E  F  T  F  S  S  Y  A  M  E  W  V  P  Q  A cccggcaaggggctggagcgggtcgcctatattaacagcgatggtagtcgcacatggtac
 P  G  K  G  L  E  W  V  A  Y  I  N  S  D  C  S  S  T  W  Y gcacctgcggtgaaggccgcgccaccacctcgagggacaacgggcagagcacagtgagg
 A  P  A  V  K  G  P  A  T  I  S  P  D  N  C  Q  S  T  V  R ctgcagctgaacagcctcagggctgaagacaccgccacctaccacgcaccagaggttct
 L  Q  L  N  S  L  P  A  E  D  T  A  T  Y  Y  C  T  P  G  S ggtggtgaaaatatagacacatggggccacgggaccgaagtcatcgtctcctctactagt
 G  G  E  N  I  D  T  W  G  H  G  T  E  V  I  V  S  S  T  S ggccaggccggccagcaccatcaccatcaccatggcgcatacccgcacgacgttcccgac
 G  Q  A  G  Q  H  H  H  H  H  H  C  A  Y  P  Y  D  V  P  D cacgctccttag
 Y  A  S  - scFv62
atgaaaaagacagctaccgcgactgcagtggcaccggctggcttcgccaccgtggcccag
 M  K  K  T  A  T  A  T  A  V  A  L  A  G  F  A  T  V  A  Q gcggccctgactcagccgcccccggtgtcagcaaacccaggagaaaccgccaagaccacc
 A  A  L  T  Q  P  S  S  V  S  A  N  P  Q  E  T  V  K  I  T
```

```
tgctccgggggtggcagctatgctggaagccactatcacggctggtaccagcagaaggca
 C   S   G   G   G   S   Y   A   G   S   Y   Y   Y   C   W   Y   Q   Q   K   A cctggcagtgccctgtcaccccgatctacgacaacaccaacagaccctcgaacatccct
 P   G   S   A   P   V   T   L   I   Y   D   N   T   H   R   P   S   N   I   P ccacgactctccggtccccatccggctccacgggcacattaaccatcactggggtccga
 S   R   F   S   G   S   L   S   G   S   T   G   T   L   T   I   T   G   V   R gccgaggacgaggccgtctattactgtgggagctccgacagcagcactgacggtggatat
 A   E   D   E   A   V   Y   Y   C   G   S   F   D   S   S   T   D   G   G   Y gctgccatattcggggccgggacaaccctgaccgtcctaggtcagtcctctaaatcttcc
 A   A   I   F   G   A   G   T   T   L   T   V   L   G   Q   S   S   R   S   S gccgcgacgctggacgagcccgggggcggccccagacgcccggaggagggctcagcccc
 A   V   T   L   D   E   S   G   C   C   L   Q   T   P   G   G   G   L   S   L gtctgcaaggcctccgagttccacttcagcagttatgccatggagtgggtgcgccaggca
 V   C   K   A   S   E   F   T   F   S   S   Y   A   H   E   W   V   R   Q   A cccggcaaggggctggagtgggtcgcctatattaacagcgatggtagtagcacatggtac
 P   G   K   G   L   E   W   V   A   Y   I   N   S   D   G   S   S   T   W   Y gcacctgcggtgaagggccgcgccaccatctcgagggacaacgggcagagcacagtgagg
 A   P   A   V   K   G   R   A   T   X   S   R   D   N   G   Q   S   T   V   R ctgcagccgaacagcctcagggccgaggacaccgccacccaccaccgcaccagaggctcc
 L   Q   L   N   S   L   R   A   E   D   T   A   T   Y   Y   C   T   R   G   S ggcggcgaaaatatagacacatggggccacgggaccgaagtcatcgcccctccactagt
 G   G   E   N   I   D   T   W   C   H   C   T   E   V   I   V   S   S   T   S ggccaggccggccagcaccatcaccatcaccatgccgcatacccgtacgacgttccagac
 G   Q   A   G   Q   H   H   H   H   H   H   A   A   Y   P   Y   D   V   P   D tacgcttcttag
 Y   A   S   - scFv118
atgaaaaagacagctatcgcgatcgcagtggcaccggctggtttcgctaccgtggcccag
 M   K   K   T   A   I   A   I   A   V   A   L   A   C   F   A   T   V   A   Q gcggccccgactcagccgccctcggtgtcagcaaacctgggaggaaccgtcgagatcacc
 A   A   L   T   Q   P   S   S   V   S   A   N   L   G   G   T   V   E   I   T tgctccggggggtagcggcagctatggctggtatcagcagaagtcaccggcggcgcccct
 C   S   G   G   S   G   S   Y   G   W   Y   Q   Q   K   S   P   G   G   A   P gtcactgtgacctattacaacgacaagagaccctcggacacccccccacgattctccggt
 V   T   V   I   Y   Y   N   D   K   R   P   S   D   I   P   S   R   F   S   G tccaaatccggctccacagccacaccaaccatcactggggtccaagtcgaggacgaggct
 S   K   S   G   S   T   A   T   L   T   I   T   G   V   Q   V   E   D   E   A gtctactactgtgggagctacgacagcagctatgctggtatatctggggtcgggacaacc
 V   Y   Y   C   G   S   Y   D   S   S   Y   V   G   I   F   G   V   G   T   T ctgaccgccccaggccagccctctagaccccgccgtgacgtcggacgagtccggggc
 L   T   V   L   G   Q   S   S   R   S   S   A   V   T   L   D   E   S   C   G ggccccagacgccccgaggagcgctcagcccgtctgcaoggcctccgggtccaccttc
 G   L   Q   T   P   P   G   A   L   S   L   V   C   K   A   S   G   F   T   F agcagtcacagcatggcccgggtgcgacaggcgcccggcaaggggctggagttcgtcgcg
 S   S   Y   S   M   A   W   V   R   Q   A   P   G   K   C   L   E   F   V   A ggcactcagaatgatggcagtatcacagattacgggtcggcggtggacggccgtgccacc
 G   I   Q   N   D   G   S   I   T   D   Y   G   S   A   V   D   G   R   A   T atctcgagggacgacgggcagagcacagtgaggccgcagctgaacaaccccaggactgag
 I   S   R   D   D   G   Q   S   T   V   R   L   Q   L   N   N   L   R   T   E gacaccgccacctaccaccgcgccaaaaccactgttgctgatggtgttatcggtgcttat
 D   T   A   T   Y   Y   C   A   K   T   T   V   A   D   G   V   I   G   A   Y ggcatcgacgcatggggccacgggaccgaagccaccgtctcctccactagtggccaggcc
 G   I   D   A   W   G   H   G   T   E   V   I   V   S   S   T   S   G   Q   A
```

-continued

```
ggccagcaccatcaccatcaccatggcgcataccccgcacgacgttccggactacgcttct
 G  Q  H  H  H  H  H  H  G  A  Y  P  Y  D  V  P  D  Y  A  S
``` tag

-

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

The indefinite articles "a" and "an", as used herein in the specification and in the claims, unless clearly indicated to the contrary, should be understood to mean "at least one."

The phrase "and/or," as used herein in the specification and in the claims, should be understood to mean "either or both" of the elements so conjoined (elements that are conjunctively present in some cases and disjunctively present in other cases). Other elements may optionally be present other than the elements specifically identified by the "and/or" clause, whether related or unrelated to those elements specifically identified unless clearly indicated to the contrary. Thus, as a non-limiting example, a reference to "A and/or B", when used in conjunction with open-ended language such as "comprising" can refer, in some embodiments, to A without B (optionally including elements other than B); in some embodiments, to B without A (optionally including elements other than A); and in some embodiments, to both A and B (optionally including other elements); etc.

```
scFv8    MKKTAIAIAVALAGFATVAQAALTQ........PSSV...SANPGETVKITCSG.GG...SSSYYGWYQQKSPGSAPVTLIYESNERPSNIPSR
scFv104  MKKTAIAIAVALAGFATVAQAALTQ........PSSV...SANLGGTVEITCSGSGG...SYGYYGWYQQKAPGSAPVTVIYDNTNRPSNIPSR
scFv12   MKKTAIAIAVALAGFATVAQAALTQ........PSSV...SANPGEAVKITCSG.GG...SSSYYGWYQQKSPGSAPVTVIYWDDERPSNIPSR
scFv17   MKKTAIAIAVALAGFATVAQAALTQ........PSSV...SANPGETVKITCSG..G...YS.YYGWYQQKTPGSAPVTLIYDNTNRPSDIPSR
scFv21   MKKTAIAIAVALAGFATVAQAALTQ........PSSV...SANPGGTVKITCSG..S...SGSYYGWYQQKSPGSAPVTVIYDNDKRPSDVPSR
scFv39   MKKTAIAIAVALAGFATVAQAALTQ........PSSV...SANPGETVKITCSG..G...GSDYYGWYQQKSPGSAPVTLIYENDKRPSNIPSR
scFv54   MKKTAIAIAVALAGFATVAQAALTQ........PSSV...SANPGETVKITCSG..G...SYSY.GWYQQKSPGSAPVTVIYSSDKRPSDIPSR
scFv136  MKKTAIAIAVALAGFATVAQAALTQ........PSSV...SANPGETVKITCSG..G...SYSY.GWYQQKSPGSAPVTVIYSSDKRPSDIPSR
scFv13   MKKTAIAIAVALAGFATVAQAALSR........PRC....QQTWGGTVKITCSGG.....DSSYYGWYQQKSPGSAPVTLIYDNTNRPSDIPSR
scFv47   MKKTAIAIAVALAGFATVAQAALSR........PRC....QQTWGGTVKITCSGG.....DGSYYGWYQQKSPGSAPVTVIYDNTNRPSDIPSR
scFv139  MKKTAIAIAVALAGFATVAQAALTQ........PSSV...SANLGGTVKITCSGG.....DSSYYGWYQQKSPGSAPVTLIYDNTNRPSDIPSR
scFv22   MKKTAIAIAVALAGFATVAQAA..........V...SANPGDTVKITCSGD.....SNNYGWYQQKSPGSAPVTVIYDNTNRPSNIPSR
scFv53   MKKTAIAIAVALAGFATVAQAAL..........V...SANPGEIVKITCSGN.....SSYYGWYQQKAPGSAPVTVIYDNNKRPSDIPSR
scFv27   MKKTAIAIAVALAGFATVAQAALSR........PR.C...QQTWGGTVKITCSGS.....NSYYGWYQQKAPGSAPVTLIYDDTNRPSDIPSR
scFv40   MKKTAIAIAVALAGFATVAQAALSR........PR.C...QQTWGGIVKLTCSGG.....SGSCGWYQQKSPGSAPVTLIYDNDKRPSDIPSR scFv41   MKKTAIAIAVALAGFATVAQAALSR........PR.C...QQTWGGTVKITCSGG.....SSYYGWYQQKSPGSAPVTLIYENNNRPSDIPSR
scFv42   MKKTAIAIAVALAGFATVAQAALTQ........PSSV...SANPGETVEITCSGGGS....SSNYGWHQQKSPGSAPVTVIYDNTNRPPNIPSR
scFv48   MKKTAIAIAVALAGFATVAQAALTQ........PSSV...SANPGETVKITCSEGGR....SSYYGWYQQKAPGSAPVTVIYDSSSRPSDIPSR
scFv60   MKKTAIAIAVALAGFATVAQAALTQ........PSSV...SANPGAIVKITCSEGGR....SSYYGWYQQKAPGSAPVTVIYDSSSRPSDIPSR
scFv43   MKKTAIAIAVALAGFATVAQAALTQ........PSSV...SANPGETVKITCSGGGS....SSYYGWYQQKSPGSAPVTLIYESNKRPSNIPSR
scFv58   MKKTAIAIAVALAGFATVAQAALTQ........PSSV...SANPGDTVKITCSGGGS....SSYYGWYQQRSPGSAPVTLIYSNDKRPSDIPSR
scFv56   MKKTAIAIAVALAGFATVAQAALTQ........PSSV...SANPGETVKITCSGGGS....SSYYGWYQQKSPGSAPVTLIYESNKRPSDIPSR
scFv59   MKKTAIAIAVALAGFATVAQAALTQ........PSSV...SANPGEIFKITCSGGGSY.AGSYYYGWYQQKAPGSAPVTVIYDNTNRPSNIPSR
scFv50   MKKTAIAIAVALAGFATVAQAALTQ........PSSV...SANPGDTVEITCSGG.....YSNYGWYQQKSPGSAPVTVIYGSTSRPSDIPSR
scFv52   MKKTAIAIAVALAGFATVAQAALTQ........PSSV...SANPGDPVEITCSGS.....SGSYGWYQQKAPGSAPVTVIYSNDKRPSDIPSR
scFv121  MKKTAIAIAVALAGFATVAQAALTQ........PSSV...SANLGGTVKITCSGG.....SSYYGWYQQKSPGSAPVTLIYENNNRPSDIPSR
scFv123  MKKTAIAIAVALAGFATVAQAALTQ........PSSV...SANLGGTVKITCSGG.....SSYYGWYQQKSPGSAPVTLIYENNNRPSDIPSR
scFv51   MKKTAIAIAVALAGFATVAQAAL..........V...SANPGETVKITCSGGGSNSAGSYYYGWYQQKPPGSAPVTVIHNNNKRPSDIPSR
scFv45   MKKTAIAIAVALAGFATVAQAALTQ........PSSV...SANPGGTVKITCSGSSS....AYGYGWYQQKSPGSAPVTVIYNNNKRPSNIPSR
scFv57   MKKTAIAIAVALAGFATVAQAALTQ........PSSV...SANPGGTVKITCSGSSS....AYGYGWYQQKSPGSAPVTVIYNNNKRPSNIPSR scFv67   MKKTAIAIAVALAGFATVAQAALTQ........PSSV...SANPGGTVKITCSGSSS....AYGYGWYQQKSPGSAPVTVIYNNNKRPSNIPSR
scFv85   MKKTAIAIAVALAGFATVAQAALTQ........PSSV...SANPRTLLKITCSGSSS....AYGYGWYQQKSPGSAPVTVIYNNNKRPSNIPSR
scFv111  MKKTAIAIAVALAGFATVAQAALTQ........PSSV...SANPGETVKLTCSGDSS....DYGYGWYQQKSPGSAPVTVIYNNNKRPSNIPSR
scFv106  MKKTAIAIAVALAGFATVAQAALTQ........PSSV...SANPGETVKITCSGDSS....DYGYGWYQQKSPGSAPVTVTYSNNQRPPNIPSR
scFv64   MKKTAIAIAVALAGFATVAQAALTQ........PSSV...SANPGDPLKITCSGDSS....GYGYGWYQQKSPGSAPVTVIYNNNKRPSDIPSR
scFv113  MKKTAIAIAVALAGFATVAQAALTQ........PSSV...SANPGETVKITCSGDSS....GYGYGWYQQKSPGSAPVTVIYNNNKRPSDIPSR
scFv120  MKKTAIAIAVALAGFATVAQAALTQ........PSSV...SANPGETVKLTCSGDSS....DYGYGWYQQKSPGSAPVTVIYNNNKRPSDIPSR
scFv95   MKKTAIAIAVALAGFATVAQAALTQ........PSSV...SANPGETVEITCSGGGG....SYG..WFQQKSPGSAPVTVIYESTKRPSNIPSR
scFv103  MKKTAIAIAVALAGFATVAQAALTQ........PSSV...SANPGETVEITCSGGGG....SYG..WFQQKSPGSAPVTVIYESTKRPSNIPSR
scFv97   MKKTAIAIAVALAGFATVAQAALTQ........PSSV...SANPGETVKITCSGGSY....N.AYGWYQQKPAGAPVTLIYDNTNRPSNIPSR
scFv3    MKKTAIAIAVALAGFATVAQAA..........V...STNPGDTVKITCSG..G....NSWYGWFQQKSPGSAPVTVIYGNDERPSDIPSR
scFv30   MKKTAIAIAVALAGFATVAQAA..........V...SANPGETVKITCSG..G....GGSYGWYQQKAPGSAPVTVIYDNTNRPSNIPSR
scFv35   MKKTAIAIAVALAGFATVAQAA..........V...SANPGDTVEITCSG..S....SGSYGWYQQKSPGSAPVTVIYANTNRPSDIPSR
scFv23   MKKTAIAIAVALAGFATVAQAA..........V...SANLGGTVEITCSG..G....GSYYGWYQQKSPGSAPVTVIYANTNGPSDIPSR
scFv138  MKKTAIAIAVALAGFATVAQAALTQ........PSSV...SANLGGTVEITCSG..G....GSYYGWYQQKSPGSAPVTVIYANTNGPSDIPSR
```

```
scFv5    MKKTAIAIAVALAGFATVAQAA...|........|...V...|SANPG|GTVKITCSG|...S.....|SGRYGWYQQKSPGSAPVTVIYYNDK|RPSDIPSR
scFv24   MKKTAIAIAVALAGFATVAQAA...|........|...V...|SASPG|DTVKITCSG|GNS....|SYGYGWYQQKSPGSAPVSVIYYNDE|RPSDIPSR
scFv25   MKKTAIAIAVALAGFATVAQAALTP|........|PSSV...|SANLG|APVEITCSG|S......|SGNYGWYQQKSPGSAPVTVIYSNDK|RPSDIPSR
scFv55   MKKTAIAIAVALAGFATVAQAAL..|........|...V...|SANLG|GTVEITCSG|S......|SGNYGWFQQKSPGSAPVTVIYSNDK|RPSDIPSR
scFv19   MKKTAIAIAVALAGFATVAQAALSR|........|PR.C...|QQTWG|GTVEITCSG|GSN....|NYGYGWYQQKSPGSAPVTLIYSNDN|RPSNIPSR
scFv66   MKKTAIAIAVALAGFATVAQAALSR|........|PR.C...|QQTWG|GTVEITCSG|SSG....|DYGYSWHQQKSPGSAPVTVIYESTK|RPSNIPSR
scFv20   MKKTAIAIAVALAGFATVAQAALTQ|........|PSSV...|SANLG|GIVEITCSG|SSG....|..SYGWYQQKSPGSAPVTVIYYNDK|RPSNIPSR
scFv32   MKKTAIAIAVALAGFATVAQAALTQ|........|PSSV...|SANLG|GTFKITCSG|SSG....|..SYAWYQQKSPGSAPVTVIYWNDK|RPSNIPSR
scFv134  MKKTAIAIAVALAGFATVAQAALTQ|........|PSSV...|SANLG|GTVKITCSG|SSG....|..SYGWYQQKSPGSAPVTVIYWNDK|RPSNIPSR
scFv119  MKKTAIAIAVALAGFATVAQAALTQ|........|PSSV...|SANLG|GTVKITCSG|SSG....|..SYGWYQQKSPGSAPVTVIYRNDK|RPSNIPSR
scFv46   MKKTAIAIAVALAGFATVAQAALTQ|........|PSSV...|SANLG|GTVKITCSG|SSG....|..SYGWYQQKSPGSAPVTVIYWNDK|RPSNIPSR
scFv34   MKKTAIAIAVALAGFATVAQAALTQ|........|PSSV...|SANLG|GTVEITCSG|SSG....|..SYGWYQQKSPGSAPVTVIYYNDK|RPSNIPSR
scFv105  MKKTAIAIAVALAGFATVAQAALTQ|........|PSSV...|SANPG|EAVKITCSG|SSG....|..SYGWYQQKSPGSAPVTVIYYNDK|RPSNIPSR
scFv112  MKKTAIAIAVALAGFATVAQAALTQ|........|PSSV...|SANLG|GTVKITCSG|GSG....|..SYGWYQQKSPGSAPVTVIYYNDQ|RPSDIPSR
scFv118  MKKTAIAIAVALAGFATVAQAALTQ|........|PSSV...|SANLG|GTVEITCSG|GSG....|..SYGWYQQKSPGGAPVTVIYYNDK|RPSDIPSR scFv124  MKKTAIAIAVALAGFATVAQAALTQ|........|PSSV...|SANLG|GTVKITCSG|GSG....|..SYGWYQQKSPGSAPVTVIYYNDQ|RPSDIPSR
scFv80   MKKTAIAIAVALAGFATVAQAALSR|........|PRC....|QQTWG|GPVKITCSG|GSG....|..SYGWYQQKSPGSAPVTVIYYNDQ|RPSDIPSR
scFv115  MKKTAIAIAVALAGFATVAQAALTQ|........|PSSV...|SANPG|ETVEITCSG|GSG....|..SYGWYQQKPPGSAPVTVIYYNDK|RPSDIPSR
scFv82   MKKTAIAIAVALAGFATVAQAALTQ|........|PSSV...|SANLG|.APKITCSG|GGG....|..SYGWYQQKSPGSAPVTLIYYNDK|RPSDIPSR
scFv65   MKKTAIAIAVALAGFATVAQAALSR|........|PRC....|QQTWG|GTVKITCSG|SSG....|..SYGWYQQKSPGSAPVTLIYESDK|RPSNIPSR
scFv73   MKKTAIAIAVALAGFATVAQAALSR|........|PRC....|QQTWG|GTVKITCSG|SSG....|..SYGWYQQKSPGSAPVTLIYESDK|RPSNIPSR
scFv90   MKKTAIAIAVALAGFATVAQAALSR|........|PRC....|QQTWG|GTVKITCSG|SSG....|..SYGWYQQKSPGSAPVTVIYQNDK|RPSNIPSR
scFv68   MKKTAIAIAVALAGFATVAQAALTQ|........|PSSV...|SASPG|ETVKITCSG|GSG....|..SYGWYRHKSPGSAPVTVIYYNDK|RPSNIPSR
scFv74   MKKTAIAIAVALAGFATVAQAALTQ|........|PSSV...|SASPG|ETVKITCSG|GSG....|..SYGWYQQKSPGSAPVTVIYYNDK|RPSNIPSR
scFv114  MKKTAIAIAVALAGFATVAQAALTQ|........|PSSV...|SASPG|ETVKITCSG|GSG....|..SYGWYQQKSPGSAPVTVIYYNDK|RPSNIPSR
scFv70   MKKTAIAIAVALAGFATVAQAALTQ|........|PSSV...|SASLG|GIVEITCSG|SSG....|..TYGWYQQKSPGSAPVTVIYQNGK|RPSNIPSR
scFv92   MKKTAIAIAVALAGFATVAQAALTQ|........|PSSV...|SASLG|TFLEITCSG|SSG....|..TYGWYQQKSPGSAPVTVIYQNGK|RPSNIPSR
scFv83   MKKTAIAIAVALAGFATVAQAALTQ|........|PSSV...|SANLG|GPFEITCSG|SSG....|..SYGWYQQKSPGSAPVTLIYNNNN|RPSDIPPR
scFv72   MKKTAIAIAVALAGFATVAQAALTQ|........|PSSV...|SANPG|GTVKITCSG|SSG....|..SYGWYQQKSPGSAPVSLIYSNDK|RPSDIPSR
scFv102  MKKTAIAIAVALAGFATVAQAALTQ|........|PSSV...|SANPG|ETVKITCSG|GSG....|..SYGWYQQESPGSAPVTVIYYNDK|RPSDIPSR scFv86   MKKTAIAIAVALAGFATVAQAALGP|........|DSAVLGV|SKPGE|ALVKTTCSG|GGG....|..SYGWYQQKSPGSAPVTVIYYNDK|RPSDIPSR
scFv84   MKKTAIAIAVALAGFATVAQAAL..|........|.......|.....|.KITCSG|SSG....|..SYAWYQQKSPGSAPVTLIYESDK|RPSDIPSR
scFv110  MKKTAIAIAVALAGFATVAQAALTQ|........|PSSV...|SANLG|GTVKLTCSG|GSSY...|..GYSWHQQKSPGSAPVTVIYSNDK|RPSDIPSR
scFv6    MKKTAIAIAVALAGFATVAQAALTQ|........|PSSV...|SANPG|DTVKITCSG|.SIR...|..YYGWYQQKSPGSAPVTLIYYDDK|RPSDIPSR
scFv38   MKKTAIAIAVALAGFATVAQAALTQ|........|PSSV...|SANPG|ETVKITCSG|.GSS...|..GYGWYQQKSPGSAPVTVIYYNDK|RPSDIPSR
scFv49   MKKTAIAIAVALAGFATVAQAALTQ|........|PSSV...|SANPG|ETVEITCSG|.GGG...|..SYGWFQQKSPGSAPVTLIYNNNN|RPSNIPSR
scFv100  MKKTAIAIAVALAGFATVAQAALTQ|........|PSSV...|SANPG|ETVKITCSG|.SSD...|..AYGWYQQKSPGSAPVTLIYDNTN|RPPDIPSR
scFv131  MKKTAIAIAVALAGFATVAQAALTQ|........|PSSV...|SANLG|GTVKITCSG|GSSG...|..YYGWYQQKSPGSAPVTVIYWNDK|RPSNIPSR
scFv14   MKKTAIAIAVALAGFATVAQAALTQ|........|PSSV...|SANPG|ETVKITCSG|GYSG...|..YYGWFRQKAPGSAPVTLIYANTN|RPSNIPSR
scFv16   MKKTAIAIAVALAGFATVAQAALTQ|........|PSSV...|SANLG|ETVKITCSG|GGSYAG.|SYYYGWYQQKAPGSAPVTLIYDNTN|RPSNIPSR
scFv26   MKKTAIAIAVALAGFATVAQAALTQ|........|PSSV...|SANPG|ETVGITCSG|GGSY...|..YYGWYQQKSPGSAPVTLIYENDM|RPSNIPSR
scFv37   MKKTAIAIAVALAGFATVAQAALTQ|........|PSSV...|SANLG|ETVKITCSG|GGSYAG.|SYYYGWYQHNAAGGAPVTLIYDNDI|TPSDIPSR
scFv7    MKKTAIAIAVALAGFATVAQAAV..|........|.......|SASLE|GTVEITCSG|GSG....|..SYGWFQQKAPGSAPVTLIYDNDN|RPSNIPSR
scFv33   MKKTAIAIAVALAGFATVAQAAV..|........|.......|SANPG|DTVKITCSG|GYS....|..GYGWYQQKSPGSAPVTVIYSNNQ|RPSNIPSR
scFv61   MKKTAIAIAVALAGFATVAQAALTQ|........|PSSVS..|.ANPG|ETVKITCSG|GGSY.AGSYY|YGWYQQKAPGSAPVTLIYDNTN|RPSNIPSR scFv62   MKKTAIAIAVALAGFATVAQAALTQ|........|PSSVS..|.ANPG|ETVKITCSG|GGSY.AGSYY|YGWYQQKAPGSAPVTLIYDNTN|RPSNIPSR
scFv108  MKKTAIAIAVALAGFATVAQAALTQ|........|PSSVS..|.ANPG|ETVKITCSG|GGSY.AGSYY|YGWYQQKAPGSAPVTLIYDNTN|RPSNIPSR
scFv96   MKKTAIAIAVALAGFATVAQAALPG|VRHRDPGG|PDSAVLGV|SKPRR|NDKITCSG|GGSY.AGSYY|YGWYQQKAPGSAPVTLIYDNTN|RPSNIPSR
scFv117  MKKTAIAIAVALAGFATVAQAALY.|........|PSSV...|.ANPG|ETVKITCSG|GGSY...|..YGWYQQKAPGSAPVTLIYDNTN|RPSNIPSR
scFv87   MKKTAIAIAVALAGFATVAQAALSR|........|.PRVS..|.ANPG|DPVKITCSG|GGSY.AGSYY|YGWYQQKAPGSAPVTVIYDNNQ|RPSNIPSR
scFv98   MKKTAIAIAVALAGFATVAQAALTQ|........|PSSVS..|.ANPG|ETVKITCSG|GGSY.VGSYY|YGWYQQKSPVSAPVTLIYESTK|RPSNIPSR
scFv69   MKKTAIAIAVALAGFATVAQAALTQ|........|PSSVS..|.ANPG|ETVKITCSG|GGS....|..SNNYGWHQQKAPGSAPVTLIYDNTN|RPSNIPSR
scFv137  MKKTAIAIAVALAGFATVAQAALTQ|........|PSSVS..|.ANPG|ETVKITCSG|GGS....|..SNNYGWHQQKAPGSAPVTLIYDNTN|RPSNIPSR
scFv77   MKKTAIAIAVALAGFATVAQAALTQ|........|PSSVS..|.ANPG|DPFKITCSG|GGS....|..SNNYGWHQQKAPGSAPVTLIYDNTN|RPSNIPSR
scFv93   MKKTAIAIAVALAGFATVAQAALTQ|........|PSSVS..|.ANPG|ALFKITCSG|GGS....|..SNNYGWHQQKAPGSAPVTLIYDNTN|RPSNIPSR
scFv15   MKKTAIAIAVALAGFATVAQAALSR|........|PRC....|QQTQE|HTVKITCSG|GVG....|..QWYGWYQQKSPGSAPVTLIYESNQ|RPSNIPSR
scFv4    MKKTAIAIAVALAGFATVAQAA...|........|.......|.....|..........|.......|.........................VIYDNDK|RPSDVPSR
scFv28   MKKTAIAIAVALAGFATVAQAA...|........|.......|.....|..........|.......|.........................VIYSNDE|RPSDIPSR
scFv9    MKKTAIAIAVALAGFATVAQAA...|........|.......|.....|..........|.......|.........................VIYGNDE|RPSDIPSR
scFv10   MKKTAIAIAVALAGFATVAQAA...|........|.......|.....|..........|.......|.........................VIYANTD|RPSDIPSR scFv29   MKKTAIAIAVALAGFATVAQAA...|........|.......|.....|..........|.......|.........................VIYDNTN|RPSNIPSR
scFv31   MKKTAIAIAVALAGFATVAQAA...|........|.......|.....|..........|.......|.........................VIYDNTN|RPSNIPSR
scFv11   MKKTAIAIAVALAGFATVAQAA...|........|.......|.....|..........|.......|.........................VIYYNDK|RPSNIPSR
scFv18   MKKTAIAIAVALAGFATVAQAA...|........|.......|.....|..........|.......|.........................VIYYNDK|RPSNIPSR
scFv36   MKKTAIAIAVALAGFATVAQAALSR|........|PRC....|QQTLG|GTVKITCSG|SNG....|..SYDWCHQKTSAGAAAAVIIYDNNK|TSYIPSS
scFv44   MKKTAIAIAVALAGFATVAQAALTQ|........|PSSV...|SANLG|ETVKITCSG|GGSY.AGCYY|YSWYDHTAAGVVPVTLI.DSTI|PSSYFRSR
scFv89   .............ALTQ|........|PSSV...|SANPG|DTVKITCSG|DSS....|..DYGYGWYQQKSPGSAPVTVTYSNNQ|RPSDIPSR
scFv88   ................|........|.......|.....|..........|GSSGS..|..YGWYQQKSPGSAPVTVIYYNDK|RPSDIPSR
scFv63   ................|........|.......|.....|..........|.......|..SNNYGWHQQKAPGSAPVTLIYDNTN|RPSNIPSR
scFv91   ................|........|.......|.....|..........|.......|........................IYDNTN|RPSNIPSR
scFv79   ................|........|LSRPRC.|QQTWG|GTVKITCSG|SSG....|..GYGWYRHKSPGTAPVPLIYNNDN|RPSDIPSR
scFv81   .............ALTQ|........|PSSV...|SANPG|GTVKITCSG|SSS....|..AYGYGWYQQKSPGSAPVTVIYNNNK|RPSNIPSR
scFv75   ................|........|.......|.....|..........|.......|.........RAPVTLIYNNNN|RPSDIPPR
```

```
scFv8   FSGSESGSTGTLTITGVRAEDEAVYYCGSAD.SS....NA.GIFGAGTTLTVLGQSSRSS..........TVTLDESGGGLQTPGGALSLVCK
scFv104 FSGSASGSTGTLTITGVRAEDEAVYFCGGYD.SS....NT.DAFGAGTTLTVLGQSSRSS..........TVTLDESGGGLQTPGRALSLVCK
scFv12  FSGSTSGSTGTLTITGVQAEDEAVYFCGGYD.SS....GD.GIFGAGTTLTVLGQSSRSSSGGGSSGGGGSAVTLDESGGGLQTPGGALSLVCK
scFv17  FSGSKSGTATLTITGVQVEDEAMYFCGSYEGS....YV.GIFGAGTTLTVLGQSSRSS..........AVTLDESGGGLQTPGGALSLVCK
scFv21  FSGSKSGPTATLTITGVQAEDEAVYFCGSRD.NS....YV.GIFGAGTTLTVLGQSSRSS..........AVTLDESGGGLQTPGGALSLVCK
scFv39  FSGSKSGTATLTITGVQADDEAVYFCGNAD..T....IT.GIFGAGTTLTVLGQSSRSS..........TVTLDESGGGLQTPGGALSLVCK
scFv54  FSGSKSGSTSTLTITGVQAEDEAVYYCGSRD.SS....YV.GIFGAGTTLTVLGQSSRSS..........TVTLDESGGGLQTPGGALSLVCE
scFv136 FSGSKSGSTSTLTITGVQAEDEAVYYCGSRD.SN....YV.GIFGAGTTLTVLGQSSRSS..........TVTLDESGGGLQTPGGALSLVCE
scFv13  FSGSKSGSTGTLTITGVQAEDEAVYYCGNADSSS....T..AAFGAGTTLTVLGQSSRSS..........TVTLDESGGGLQTPGGALSLVCK
scFv47  FSGSKSGSTATLTITGVQAEDEAVYYCGNADSSG....A..AAFGAGTTLTVLGQSSRSS..........AVTLDESGGGLQTPGGALSLGCE
scFv139 FSGSKSGSTATLTITGVQAEDEAVYYCGNADSSS....T..AAFGAGTTLTVLGQSSRSS..........AVTLDESGGGLQTPGGALSLVCK
scFv22  FSGSKSGTATLTITGVQADDEAVYFCGSFDSST......DIFGAGTTLTVLGQSSRSS..........TVTLDESGGGLQTPGRALSLVCK
scFv53  FSGSKSGSTGTLTITGVQADDEAVYFCGNGAT..........FGAGTTLTVLGQSSRSS..........TVTLDESGGGLQTPGRALSLVCK
scFv27  FSGSKSGSTATLTITGVQADDEAVYFCGGFDSSS...D.SGFGAGTTLTVLGQSSRSS..........TVTLDESGGGLQTPGRALSLVCK
scFv40  FSGSTSGSTHTLTITGVQAEDEAIYFCGSEDSST....YA.SGFGAGTTLTVLGQSSRSS..........AVTLDESGGGLQTPGRALSLVCK scFv41  FSGSASGSTATLTITGVQAEDGAVYFCGSEDS.T....YV.GIFGAGTTLTVLGQSSRSS..........AVTLDESGGGLQTPGRALSLVCK
scFv42  FSGSLSGSTGTLTITGVQAEDEAVYYCGGHDSST....YA.AIFGAGTTLTVLGQSSRSS..........AVTLDESGGGLQTPGRALSLVCK
scFv48  FSGSKSGSTGTLTITGVQAEDEAVYYCGSTDSST....SA.AIFGAGTTLTVLGQSSRSS..........AVTLDESGGGLQTPGGALSLVCK
scFv60  FSGSKSGSTGTLTITGVQAEDEAVYYCGSTDSST....SA.AIFGAGTTLTVLGQSSRSS..........AVTLDESGGGLQTPGGALSLVCK
scFv43  FSGSTSGSTSTLTITGVQADDEAVYFCGSAD.SS....YV.GIFGAGTTLTVLGQSSRSS..........AVTLDESGGGLQTPGGALSLVCK
scFv58  FSGSLSGSTGTLTITGVQAEDEAVYYCGGYD.SS....YV.GLFGAGTTLTVLGQSSRSS..........TVTLDESGGGLQTPGGALSLVCK
scFv56  FSGSKSGSTHTLTITGVQAEDEAVYYCGAYDGS....YT.GIFGAGTTLTVLGQSSRSS..........TVTLDESGGGLQTPGRALSLVCK
scFv59  FSGSKSGSTATLTITGVRADDSAVYYCASTDSSS....T..GIFGAGTTLTVLGQSSRSS..........AVTLDESGGGLQTPGRALSLVCK
scFv50  FSGSESGSTGTLTITGVQAEDEAVYFCGNADSS....YV.GLFGAGTTLTVLGQSSRSS..........TVTLDESGGGLQTPGGALSLVCK
scFv52  FSGSASGSTGTLTITGVQAEDEAVYFCGSFDSSA..GYG.GIFGAGTTLTVLGQSSRSS..........TVTLDESGGGLQTPGGALSLVCK
scFv121 FSGSASGSTATLTITGVQAEDGAVYFCGSEDST.....YV.GIFGAGTTLTVLGQSSRSS..........AVTLDESGGGLQTPGRALSLVCK
scFv123 FSGSASGSTAPLTITGVQAEDGAVYFCGSEDST......YV.GIFGAGTTLTVLGQSSRSS..........AVTLDESGGGLQTPGRALSLVCK
scFv51  FSGSKSGSTGTLTITGVQVDDEAVYYCGSRDSS....YI.GTFGAGTTLTVLGQSSRSS..........AVTLDESGGGLQTPGRALSLACK
scFv45  FSGSKSGSTGTLTITGVQAEDEAVYFCGSEDSS....D..AIFGAGTTLTVLGQSSRSS..........TVTLDESGGGLQAPGGALSLVCK
scFv57  FSGSKSGSTGTLTITGVQAEDEAVYFCGSEDSST....D..AIFGAGTTLTVLGQSSRSS..........AVTLDESGGGLQTPGGALSLVCK scFv67  FSGSKSGSTGTLTITGVQAEDEAVYFCGSEDSST....D..AIFGAGTTLTVLGQSSRSS..........AVTLDESGGGLQTPGGALSLVCK
scFv85  FSGSKSGSTGTLTITGVQAEDEAVYFCGSEDSST....D..AIFGAGTTLTVLGQSSRSS..........AVTLDESGGGLQTPGGALSLVCK
scFv111 FSGSKSGSTGTLTISGVQAEDEAVYFCGSEDSNT....D..AIFGAGTTLTVLGQSSRSS..........AVTLDESGGGLQTPGGALSLVCE
scFv106 FSGSASGSTGTLTITGVQVEDEAVYYCGSEDSTT....D..AVFGAGTTLTVLGQSSRSS..........AMTLDESGGGLQTPGGALSLVCK
scFv64  FSGSKSGSTGTLTITGVQAEDEAVYFCGSEDSNT....D..AVFGAGTTLTVLGQSSRSS..........TVTLDESGGGLQTPGGTLSLACK
scFv113 FSGSKSGSTGTLTITGVQAEDEAVYFCGSEDSNT....D..AVFGAGTTLTVLGQSSRSS..........TVTLDESGGGLQTPGGTLSLACK
scFv120 FSGSKSGSTGTLTISGVQAEDEAVYFCGSEDSNS....D..AIFGAGTTLTVLGQSSRSS..........AVTLDEYGGGLQTPGGALSLVCE
scFv95  FSGSGSGSTGTLTITGVQAEDEAVYYCGGYDSS....D..AIFGAGTTLTVLGQSSRSS..........TVTLDESGGGLQTPGGALSLVCK
scFv103 FSGSGSGSTGTLTITGVRAEDEAVYYCGGYDGSS....D..GIFGAGTTLTVLGQSSRSS..........TVTLDESGGGLQTPGGALSLVCK
scFv97  FSGSKSGSTHTLTITGVQADDEAVYFCGGYDSNA....DD.GIFGAGTTLTVLGQSSRSS..........TVTLDESGGGLQTPGGTLSLVCK
scFv3   FSGSESGSTATLTITGVRAEDEAVYYCGSGDNS.....GA.GIFGAGTTLTVLGQSSRSS..........AVTLDESGGGLQTPGGALSLVCK
scFv30  FSGSESGSTGTLTITGVRAEDEAAYYCGSADSS....DA.GIFGAGTTLTVLGQSSRSS..........AVTLDESGGGLQTPRRALSLVCK
scFv35  FSGSKSGSTATLTITGVQAEDEAVYYCGGYDSST....DA.GIFGAGTTLTVLGQSSRSS..........AVTLDESGGGLQTPGGGLSLVCK
scFv23  FSGSTSGSTATLTITGVQADDEAVYSCGSYDSS....YV.GIFGAGTTLTVLGQSSRSS..........TVTLDESGGGLQTPGGALSLVCK
scFv138 FSGSTSGSTATLTITGVQADDEAVYSCGSYDSS....YV.GIFGAGTTLTVLGQSSRSS..........TVTLDESGGGLQTPGGALSLVCK scFv5   FSGSASGSTATLTITGVQAEDEAVYFCGSYEVNI....HE.GIFGAGTSLTVLGQSSRSS..........TVTLDESGGGLQTPGRALSLVCK
scFv24  FSGSASGSTATLTITGVQADDEAVYYCGNADSST....YA.AVTLDESGGGLQTPGGGLSLVCK
scFv25  FSGSLSGSTGTLTITGVRAEDEAVYYCGSIDNTY...VGT.GAFGAGTTLTVLGQSSRSS..........TVTLDESGAGLQTPGRALSLVCK
scFv55  FSGSLSGSTGTLTITGVRAEDEAVYYCGSIDNTY...VGT.GAFGAGTTLTVLGQSSRSS..........TVTLDESGGGLQTPGRALSLVCK
scFv19  FSGSTSGSTSTLTITGVQAEDEAVYYCGSYDSSN....DS.GIFGAGTTLTVLSQSSRSS..........AVTLDESGGGLQTPGGGLSLVCK
scFv66  FSGSTSGSTGTLTITGVQVEDEAVYFCGGYDGST....DA.IFGAGTTLTVLGQSSRSS..........AVTLDESGGGLQMPGGGLSLVCK
scFv20  FSGSGSGSTNTLTITGVQAEDEAVYYCGNEDGG......AAFGAGTTLTVLGQSSRSS..........TVTLDESGGGLQTPGGGLSLVCK
scFv32  FSGALSGSTATLTITGVQAEDEAVYFCGSADSSG......AIFGAGTTLTVLGQSSRSS..........TVTLDESGGGLQTPGGGLSLVCK
scFv134 FSGALSGSTATLTITGVQAEDEAVYFCGSADSSG......AIFGAGTTLTVLGQSSRSS..........TVTLDESGGGLQTPGGGLSLVCK
scFv119 FSGALSGSTATLTITGVQAEDEAVYFCGSADSSG......AIFGAGTTLTALGQSSRSS..........TVTLEESGGLHTPGGILVCK
scFv46  FSGALSGSTATLTITGVQAEDEAVYFCGSADSSG......AIFGAGTTLTVLGQSSRSS..........TVTLDESGGGLQTPGGGLSLVCK
scFv34  FSGSTSGSTATLTITGVQAEDEAVYFCGGYD.SN....YI.GIFGAGTTLTVLGQSSRSS..........AVTLDESGGGLQTPRGALSLVCK
scFv105 FSGSTSGSTSTLTITGVQAEDEAVYFCGGYD.SN....YL.GIFGAGTTLTVLGQSSRSS..........AVTLDESGGGLQTPRGALSLVCK
scFv112 FSGSKSGSTGTLTITGVQAEDEAVYFCGGYD.ST....YV.GIFGAGTTLTVLGQSSRSS..........AVTLDESGGGLQTPRGALSLVCK
scFv118 FSGSKSGSTATLTITGVQVEDEAVYYCGSYD.SS....YV.GIFGVGTTLTVLGQSSRSS..........AVTLDESGGGLQTPRGALSLVCK scFv124 FSGSKSGSTGTLTITGVHAEDEAVYYCGGYN.ST....YV.GIFGAGTTLTVLGQSSRSS..........AVTLDESGGGLHTPRGALSLICK
scFv80  FSGSKSGSTGTLTITGVQAEDEAVYYCGGYD.ST....YV.GIFGAGTTLTVLGQSSRSS..........AVTLDESGGGLQTPRGALSLVCK
scFv115 FSGSKSGSTGTLTITGVQAEDEAVYYCGGYG.ST....YL.GIFGAGTTLTVLGQSSRSS..........AVTLDESGGGLQMPGGGLSLVCK
scFv82  FSGSKSGSTATLTITGVQANDEAVYFCGSYEGST....YS.GIFGAGTTLTVLGQSSRSS..........TVTLDESGGGLQTPGGALSLVCK
scFv65  FSGSKSGSTGTLTITGVQADDEAVYFCGGYDSSA......GIFGAGTTLTVLGQSSRSS..........TVTLDESGGGLQTPGGALSLVCK
scFv73  FSGSKSGSTGTLTITGVQADDEAVYFCGGYDSSA......GIFGAGTTLTVLGQSSRSS..........TVTLDESGGGLHTPGGALSLVCK
scFv90  FSGSTSGSTATLTITGVQADDEAVYFCGGYDSSA......GIFGAGTTLTVLGQSSRSS..........TVTLDESGGGLQTPGGALSLVCK
scFv68  FSGSKSGSTSTLTITGVQAEDEADYYCGSYNSNA..GYV.GIFGAGTTLTVLGQSSRSS..........TVTLDESGGGLQTPGGGLSLVCK
scFv74  FSGSKSGSTSTLTITGVQAEDEAVYYCGSYDSSA..GYV.GIFGAGTTLTVLGQSSRSS..........TVTLDESGGGLQTPGGGLSLVCK
scFv114 FSGSKSGSTGTLTITGVQAEDEAVYYCGSYDSSA..GYV.GIFGAGTTLTVLGQSSRSS..........TVTLDESGGGLQTPGGGLSLVCK
scFv70  FSGSKSGSTGTLTITGVQADDEAVYFCGGYDSST....YV.GIFGAGTTLTVLGQSSRSS..........AVTLDESGGGLQTPGGGLSLVCK
scFv92  FSGSKSGSTGTLTITGVQADDEAVYFCGGYDSST....YV.GIFGAGTTLTVLGQSSRSS..........AVTLDESGGGLQTPGGGLSLVCK
scFv83  FSGSKSGSTGTLAITGVQAEDEAVYFCGGYEGST....ST.GIFGAGTTLTVLGQSSRSS..........AVTLDESGGGLQTPGGGLSLVCK
scFv72  FSGSASGSTGTLTITGVQAEDEAVYYCGGWDSYV......GIFGAGTTLTVLGQSSRSS..........AVTLDESGGGLQTPGGGLSLVCK
scFv102 FSGSASGSTATLTITAGVRAEDEAVYFCGSWDSST....SA.GIFGAGTALTVLGQSSRSS..........AVTLDESGGGLQTPGGGLSLVCK
```

-continued

```
scFv86   FSGSKSGSTGTLTITGVQAEDEAVYFCGSYDSST....DT.GIPGAGTTLTVLGQSSRSS..........TVTLDESGGGLQTPGGALSLVCK
scFv84   FSGSKSGSTGTLTITGVQADDEAVYFCGGYDSSA......GIPGAGTTLTVLGQSSRSS..........AVTLDESGGGLQTPGGALSLVCK
scFv110  FSGSASGSTATLTITGVQVEDEAVYFCGSYDSSS....IA.GIPGAGTTLTVLGQSSRPS..........TVTLDESGGGLQTPGGGLSLVCK
scFv6    FSGSASGSTATLTITGVQADDEAIYFCGTADSTS...SGA.GIPGAGTTLTVLGQSSRSS..........TVTLDESGGGLQTPGGALSLVCK
scFv38   FSGALSGSTATLTITGVQAEDEAIYFCGSGDS.S...TVA.GIPGAGTTLTVLGQSSRSS..........AVTLDESGGGLQTPGGTLSLVCK
scFv49   FSGSKSGSTGTLTITGVQAEDEAVYFCGTRDS....SYA.GIPGAGTTLTVLGQSSRSS..........AVTLDESGGGLQTPGGGLSLVCK
scFv100  FSGALSGSTSTLTITGVRAEDEAVYYCGSADI.....TYI.GIPGAGTTLTVLGQSSRSS..........TVTLDESGGGLQTPGGGLSLVCK
scFv131  FSGSESGSPATLTITGVRAEDEAVYFCGSGDS.....SGT.GIPGAGTTLTVLGQSSRSS..........AVTLDESGGGLQTPGGGLSLVCK
scFv14   FSGSASGSTGTLTITGVQADDEAVYFCGSADS.T...Y...GIPGAGTTLTVLGQSSRSS..........AVTLDESGGGLQTPGGALSLVCR
scFv16   FSGSTSGSTNTLTITGVQAEDEAVYFCGSVDS...S....GVPGAGTTLTVLGQSSRSS..........AVTLDESGGGLQTPGGALSLVCK
scFv26   FSGSTSGSTSTLTITGVQAEDEAVYFCGSYDS.S...NYV.GEPGAGTTLTVLGQSSRSS..........AVTLDESGGGLQTPGGALSLVCK
scFv37   FSGSTSGSTNALTINGVQA.DYAVYFCGSVNC.S...S..GVPGAGTTLTVLCHSSTSS..........DVTLDHSRGGLQTPGGSLSLVCN
scFv7    FSGSKSGSTATLTITGVQADDEAIYYCGSWDSST...D...AAPGAGTTLTVLGQSSRSS..........TVTLDESGGGLQTPGGGLSLVCK
scFv33   FSGSTSGSTNTLTITGVQAEDEAVYFCGGYDCST...GSVKASPGAGTTLTVLGQSSRSS..........AVTLDESGGGLQTPGGTLSLVCK
scFv61   FSGSLSGSTGTLTITGVRAEDEAVYYCGSPDSSTDG..GYAAIPGAGTTLTVLGQSSRSY..........AVTLDESGGGLQTPGGGLSLVCK scFv62   FSGSLSGSTGTLTITGVRAEDEAVYYCGSPDSSTDG..GYAAIPGAGTTLTVLGQSSRSS..........AVTLDESGGGLQTPGGGLSLVCK
scFv108  FSGSLSGSPGTLAITGVRAEDEAVYYCGSPHSSTDG..GYAAIPGAGTTLTVLGQTSRSS..........AVTLDESGGGLQTPGGGLSLLCK
scFv96   FSGSLSGSTGTLTITGVRAEDEAVYYCGSPDSSTDG..GYAAIPGAGTTLTVLGQSSRSS..........AVTLDESGGGLQTPGGGLSLVCK
scFv117  FSGSLSGSTGTLTITGVRAEDEAVYYCGSPDSSTDS..GYAAIPGAGTTLTVLGQSSRSS..........AVTLDESGGGLQTPGGALSLVCR
scFv87   FSGSLSGSTGTLTITGVRAEDEAVYYCGSPDSSTDS..GYAAIPGAGTTLTVLGQSSRSS..........AVTLDESGGGLQTPGGGLSLVCK
scFv98   FSGSTSGSMGTLTITGVQAEDEAVYYCGSPDSSSSVSDTADIPGAGTTLTVLGQSSRSS..........TVTLDESGGGLQTPGGTLSLVCK
scFv69   FSGSKSSSTHTLTITGVQAEDEAVYYCESADSSS.....SIPGAGTTLTVLGQSSRSS..........AVTLDESGGGLQTPGGTLSLVCK
scFv137  FSGSKSSSTHTLTITGVQAEDEAVYYCESADSSS......SIPGAGTTLTVLGQSSRSS..........AVTLDESGGGLQTPGGTLSLVCK
scFv77   FSGSKSSSTHTLTITGVQAEDEAVYYCESADSSS......SIPGAGTTLTVLGQSSRSS..........AVTLDESGGGLQTPGGTLSLVCK
scFv93   FSGSKSSSTHTLTITGVQAEDEAVYYCESADSSS......SIPGAGTTLTVLGQSSRSS..........TVTLDESGGGLQTPGGALSLVCK
scFv15   FSGSLSGSTATLTITGVPEDEAVYFCGSYDGNS.......GIPGAGTTLTVLGQSSRSS..........AVTLDESGGGLQTPGRALSLVCK
scFv4    FSGSKSGPTATLTITGVQAEDEAVYFCGSRDNS......YVGIPGAGTTLTVLGQSSRSS..........AVTLDESGGGLQTPGGALSLVCK
scFv28   FSGSTSGSTSTLTITGVQAEDEAVYYCGSADSST......YAGIPGAGTTLTVLGQSSRSS..........AVTLDESGGGLQTPGGALSLVCK
scFv9    FSGSESGSTATLTITGVRAEDEAVYYCGSGDNS......GAGIPGAGTTLTVLGQSSRSS..........AVTLDESGGGLQTPGGALSLVCK
scFv10   FSGSKSGSTATLTITGVRAEDEAVYFCGSGDSS.......TGIPGAGTTLTVLGQSSRSS..........AVTLDESGGGLQTPGGTLSLVCK scFv29   FSGSKSGSTGTLTITGVQADDEAVYYCGSTDSSA.....D.GVPGAGTTLTVLGQSSRSS..........AVTLDESGGGLQTPGGGLSLVCK
scFv31   FSGSLSGSTNTLTITGVQAEDEAVYFCGGYDSST.....DSGMPGAGTTLTVLGQSSRSS..........AVTLDESGGGLQTPGGGLSLVCK
scFv11   FSGSGSGSTNTLTIAGVRAEDEAVYYCGNEDSS.......AAPGAGTTLTVLGQSSRSS..........AVTLDESGGGLQTPGGGLSLVCK
scFv18   FSGSKSGSTATLTITGVRAEDEAVYFCGSADST.......DAVPGAGTTLTVLGQSSRSS..........AVTLDESGGGLQTPGGGLSLVCK
scFv36   LFCASSSPATLTITGVVADDDDVDYCGSANDNS.......SVVIVGATTTMIVRRSSSSSS..........AMMEDEGGGLLTTRGGLLILCCA
scFv44   FCCSASGSINALTINEDPAY.YAVYFCGSVDVPG......GVPGASTTLTAPGSSSISS..........DETLDDSGSGLRTPGRALNVFCF
scFv89   FSGSASGSTATLTITGVQVEDEAVYYCGSEDSTT......DAVPGAGTTLTVLGQSSRSS..........AVTLDESGGGLQTPGGALSLVCK
scFv88   FSGSTSGSTATLTITGVQAEDEAVYFCGGYDSNY......IGIPGAGTTLTVLGQSSRSS..........AVTLDESGGGLQTPGRGLSLVCK
scFv63   FSGSKSSSTHTLTITGVQAEDEAVYYCESADSSS......SIPGAGTTLTVLGQSSRSS..........AVTLDESGGGLQTPGGTLSLVCK
scFv91   FSGSKSSSTHTLTITGVQAEDEAVYYCESADSSS......SIPGAGTTLTVLGQSSRSS..........AVTLDESGGGLQTPGGTLSLVCK
scFv79   FSGSKSGSTSTLTITGVQVQDEDDYFCGGYNKNT.....YADIPGAGTTLTVLRQSSTSS..........AVTMDDYGGGLLTTGGALILLCW
scFv81   FSGSKSGSTGTLTITGVQAEDEAVYFCGSEDSST......DAIPGAGTTLTVLGQSSRSS..........TVTLDESGGGLQAPGGALSLVCK
scFv75   FSGSKSGSTGTLAITGVQAEDEAVYFCGGYEGST......STGIPGAGTTLTVLGQSSRSS..........AVTLDESGGGLQTPGGALSLVCK scFv8    ASGFTFSSFNMGWVRQAPGKGLEFVAGIDN.TGSFTHYGAAVKGRATISRDDGQSTVRLQLDNLRAEDTGTYYCAKAS.GYYY...SGVN.AGS
scFv104  ASGFTFSSYTMGWVRQAPGKGLEFVAGIDN.TGRYTEYGSAVKGRATISRDNGQSTVRLQLNNLRAEDTGTYYCTKCAYGYYY...SWGNIAGS
scFv12   ASGFTFSGYNMGWVRQAPGKGLEWVGGISG.SGRYTEYGAAVKGRATISRDNGQSTVRLQLNNLRAEDTGTYFCAKAAVSDYC...GGGC.AGD
scFv17   ASGFTFSSYDMAWVRQAPGKGLEFVAGI.D.IGSYTGYGAAVKGRATISRDNGQSTVRLQLNNLRAEDTGTYYCAKAAGSYYY...SGA..AGS
scFv21   ASGFTFSSYDMFWVRQAPGKGLEFVAQINS.AGSYTNYGSAVKGRATISRDDGQSTVRLQLNNLRAEDTGIYFCAKSASGYYY...SGSD.AGD
scFv39   ASGFTFSSYTMAWVRQAPGKGLEWVAGIND.GGSYTNYGAAVKGRATAIYYGSAVKGRATISRDNGQSTVRLQLNNLRAEDTAIYYCAKSAGGYYY...SGA..AGT
scFv54   ASGFTFSSYEMQWVRQAPGKGLEFVAAIS.DGSYTNYGAVQGRATISRDNGQSTVRLQLSNLRAEDTATYYCARSPGGYTW...WPGA.AGG
scFv136  ASGFTFSSYEMQWVRQAPGKGLEFVAAIS.SDGSYTNYGAVQGRATISRDNGQSTVRLQLSNLRAEDTATYYCARSPGGYTW...WPGA.AGG
scFv13   ASGFTFSSYAMGWVRQAPGKGLEYVAAIS.SAGSTINYGAAVKGRATISRDNGQSTVRLQLNNLRAEDTATYFCAKAAGSGYY...VWSAIAGD
scFv47   ASGFTFSSYAMGWVRQAPGKGLEYVATISS.AGSNINYGAAVKGRATISRDNGQSTVRLQLNNLEDDDTATYFCAEAAGNGYY...VWSAIAGD
scFv139  ASGFTFSSYAMGWVRQAPGKGLEYVAAIS.AGSTINYGAAVKGRATISRDNGQSTVRLQLNNLRAEDTATYYCAKTAGSGYY...VWSAIAGD
scFv22   ASGFTFSSFNMGWVRQAPGKGLEYVASISS.SGSYIAYGSAVKGRATISRDNGQSTVRLQLNNLRAEDTATYYCAKAAGSAYYYTAVTPAHAGS
scFv53   ASGFTFSSFNMGWVRQAPGKGLEYVASISS.SGSYIAYGSAVKGRATISRDNGQSTVRLQLNNLRAEDTATYYCAKAAGSAYYYTAVTPAHAGS
scFv27   ASGFTFSSFNMGWVRQAPGKGLEYVASISS.SGSYIAYGSAVKGRATISRDNGQSTVRLQLNNLRAEDTATYYCAKAAGSAYYYTAVTPAHAGS
scFv40   ASGFTFSSFNMGWVRQAPGKGLEYVASISS.SGSYIAYGSAVKGRATISRDNGQSTVRLQLNNLRAEDTATYYCAKAAGSAYYYTAVTPAHAGS scFv41   ASGFTFSSFNMGWVRQAPGKGLEYVASIS.SGSYIAYGSAVKGRATISRDNGQSTVRLQLNNLGAEDTATYYCAKAAGNAYYYTAVTPAHAGS
scFv42   ASGFTFSSFNMGWVRQAPGKGLEYVASISS.SGSYIAYGSAVKGRATISRDNGQSTVRLQLNNLRAEDTATYYCAKAAGSAYYYTAVTPAHAGS
scFv48   ASGFTFSSFNMGWVRQAPGKGLEYVASISS.SGSYIAYGSAVKGRATISRDNGQSTVRLQLNNLRAEDTATYYCAKAAGSAYYYTAVTPAHAGS
scFv60   ASGFTFSSFNMGWVRQAPGKGLEYVASISS.SGSYIAYGSAVKGRATISRDNGQSTVRLQLNNLRAEDTATYYCAKAAGSAYYYTAVTPAHAGS
scFv43   ASGFTFSSFNMGWVRQAPGKGLEYVASISS.SGSYIAYGSAVKGRATISRDNGQSTVRLQLNNLRAEDTATYYCAKAAGSAYYYTAVTPAHAGS
scFv58   ASGFTFSSFNMGWVRQAPGKGLEYVASISS.SGSYIAYGSAVKGRATISRDNGQSTVRLQLNNLRAEDTATYYCAKAAGSAYYYTAVTPAHAGS
scFv56   ASGFTFSSFNMGWVRQAPGKGLEYVASISS.SGSYIAYGSAVKGRATISRDNGQSTVRLQLNNLRAEDTATYYCAKAAGSAYYYTAVTPAHAGS
scFv59   ASGFTFSSFNMGWVRQAPGKGLEYVASISS.SGSYIAYGSAVKGRATISRDNGQSTVRLQLNNLRAEDTATYYCAKAAGSAYYYTAVTPAHAGS
scFv50   ASGFTFSSFNMGWVRQAPGKGLEYVASISS.SGSYIAYGSAVKGRATISRDNGQSTVRLQLNNLRAEDTATYYCAKAAGSAYYYTAATPAHAGS
scFv52   ASGFTFSSFNMGWVRQAPGKGLEYVASISS.SGSYIAYGSAVKGRATISRDNGQSTVRLQLNNLRAEDTATYYCAKAAGSAYYYTAVTPAHAGS
scFv121  ASGFTFSSFNMGWVRQAPGKGLEYVASISS.SGSYIAYGSAVKGRATISRDNGQSTVRLQLNNLRAEDTATYYCAKAAGSAYYYTAVTPAHAGS
scFv123  ASGFTFSSFNMGWVRQAPGKGLEYVASISS.SGSYIAYGSAVKGRATISRDNGQSTVRLQLNNLRAEDTATYYCAKAAGSAYYYTAVTPAHAGS
scFv51   ASGFTFSSFNMGWVRQAPGKGLEYVASISS.SGSYIAYGSAVKGRATISRDNGQSTVRLQLNNLRAEDTATYYCAKAAGSAYYYTAVTPAHAGS
scFv45   ASGFTFSSYDMGWIRQAPGKGLEYVAGITD.NGRYASYGSAVDGRATISRDNGQSVRLQLNNLRAEDTGTYYCARDDGSGWT.......GNS
scFv57   ASGFTFSSYDMGWVRQAPGKGLEYVAGITN.DGRYASYGSAVDGRATISRDNGQSVRLQLNNLRAEDTGTYYCARDDGSGWT.......GNT
```

```
scFv67   ASGFTFSSYDMGWVRQAPGKGLEYVAGIIN.DGRYASYGSAVDGRATISRDNGQSTVRLQLNNLRAEDTGTYYCARDDGSGWT........GNT
scFv85   ASGFTFSSYDMGWVRQAPGKGLEYVAGIIN.DGRYASYGSAVDGRATISRDNGQSTVRLQLNNLRAEDTGTYYCARNDGSGWT........GNT
scFv111  ASGFTFSSYDMGWIRQAPGKGLEYVAGIIN.NGRYASYGSAVDGRATISRDNGQSTVRLQLNNLRAEDTGTYYCARDDGSGWT........GNT
scFv106  ASGFTFSSYDMGWVRQAPGKGLEYVAGIIN.DGRYASYGSAVDGRATISRDNGQSTVRLQLNNLRAEDTGTYYCARDDGSGWT........GNT
scFv64   ASGFTFSGYDMGWVRQAPGKGLEYVAGITS.DGRYASYGSAVDGRAAIWRDNGQSTVRLQLKNLRTEDTATYYCARNDGSGWN........GNN
scFv113  ASGFTFSGYDMGWVRQAPGKGLEYVAGITS.DGRYASYGSAVDGRAAIWRDNGQSTVRLQLKNLRTEDTATYYCARDDGSGWS........GNN
scFv120  ASGFTFSSYDMLRIPHAPGKGLEYVAGLTS.NGRYASYGSAVDGRATISRDNGQSTWRLHLNNLGAEDTGPYYCAGYDDGSGWT........GNT
scFv95   ASGFTFSSHDMGWVRQAPGKGLEYVAGITD.DGRYASYGPAVDGRATISRDNGQSTVRLQLKNLRAEDTATYYCARDDGSGWS........GDT
scFv103  ASGFTFSSHDMGWVRQAPGKGLEYVAGITD.DGRYASYGPAVDGRATISRDNGQSTVRLQLKNLRAEDTATYYCARDDGSGWS........GDT
scFv97   ASGFTFSSYAMNWMRQAPGKGLEYVAGIAA.NDGRATISRDNGQSSVRLQLNNLRAEDTATYYCTKSADSDYG........CDN
scFv3    ASGFTFSSNGMAWVRQAPGKGLEWVAGISS.SGSYTNYGSAVKGRATISRDNGQSTVRLQLNNLRAEDTATYYCAKSSYAYYGF.G.....APF
scFv30   ASGFTFSDYGMAWVRQAPGKGLEYVAGIGS.SGSYTDYGSAVKGRATISRDNGQSTVRLQLNNLRAEDTATYYCAKDIGSVYGC.GWWACSAGS
scFv35   ASGFTFSDYGMGWVRQAPGKGLEYVAGIDN.TGSSTGYGAAVKGRATISRDNRQSTVRLQLNNLRAEDTGIYFCAKTAGS...GG.GWW...SDW
scFv23   ASGFTFNSYALEWVRQAPGKGLEWVAGISG.DGSYRHYGSAVKGRATISRDSGQSTVRLQLNNLRAEDTGTYYCAKSTGSGAGW.G.....ASN
scFv138  ASGFTFNSYALEWVRQAPGKGLEWVAGISG.DGSYRHYGSAVKGRATISRDSGQSTVRLQLNNLRAEDTGTYYCAKSTGSGAGW.G.....ASN scFv5    ASGFTFSSNGMYWVRQAPGKGLEWVAGISS.SGSYTNYAPAVKGRATISRDNGQSTVRLQLNNLRAEDTGTYYCAKGASSYS......W..DGGS
scFv24   ASGFDFSTNAMGWVRQAPGKGLEWVAGISS.SGSSTWYATAVDGRATISRDNGQSTVRLQLNNLRAEDTGTYYCARGTSSG.....WYIDAGS
scFv25   GSGFTFSSFYMFWVRQAPGKGLEFVACISS.SGSSTRYGVVVKGRATISRDNGQSTVRLRLNNLRADDTGTYYCARGTSSG........ANT
scFv55   GSGFTFSSFYMFWVRQAPGKGLEFVASISS.SGSSTRYGVVVKGRATISRDNGQSTVRLRLNNLRADDTGTYYCARGTSSG..........ANT
scFv19   ASGFTFSTFNMFWVRQAPGKGLEFVAGISI.TGGWTGYGAAVKGRATISRDNGQSTVRLQLNNLRAEDTGTYYCAKPAAWSCY.....RGCGGE
scFv66   ASGFDFSSSEMQWVRQAPGKGLQWV.GIIS.SGSSTWYGAAVDGRATISRDNGQSAVRLQLNNLRAEDTGTYYCTKTTAYA..........HD
scFv20   ASGFTFSDYDMFWVRQAPSKGLEVAAIIS.SGTGTKYGAAVKGRATISKDNGQRTVRLQLNSLGAEDTGTYYCARS..DADS....TTWSAGE
scFv32   GSGFAFSNYGMGWMRQAPGKGLEYVAGI.S.TGSYTDYGPAVKGRATISRDNGQSTVRLQLNNLRAEDAAIYFCAKT.AGSGYGCGSGTDLGS
scFv134  GSGFAFSNYGMGWMRQAPGKGLEYVAGI.S.TGSYTDYGPAVKGRATISRDNGQSTVRLQLNNLRAEDAAIYFCAKT.AGSGYGCGSGTDLGS
scFv119  GSGVSFCNYGMGWMRRDPGGGLEYVAGI.S.TGSYTDYGPAVKGRGTVSRDNGQSTMRLQLNHLRAEDETIYFCART.DASSHGCGSGTDLGS
scFv46   GSGFAFSNYGMGWMRQAPGKGLEFVAGI.S.TGSYTDYGPAVKGRATISRDNGQSTVRLQLNNLRAEDAAIYFCAK..............
scFv34   ASGFTFSSYSMAWVRQAPGKGLEFVAGIQN.DGSITDYGSAVDGRATISRDDGQSTVRLQLNNLRTEDTATYYCAK...TTVA...DGVIGAYG
scFv105  ASGFTFSSYSMAWVRQAPGKGLEFVAGIQN.DGSITDYGSAVDGRATISRDDGQSTVRLQLNNLRTEDTATYYCAK...TTVA...DGVIGAYG
scFv112  ASGFTFSSYSMAWVRQAPGKGLEFVAGIQN.DGSITDYGSAVDGRATISRDDGQSTVRLQLNNLRTEDTATYYCAK...TTVA...DGVIGAYG
scFv118  ASGFTFSSYSMAWVRQAPGKGLEFVAGIQN.DGSITDYGSAVDGRATISRDDGQSTVRLQLNNLRTEDTATYYCAK...TTVA...DGVIGAYG scFv124  ASGFTFSSYSMAWVQQAPGKGLEFVPGILN.DGSITDYGSADDGRATISRDDGQSTVRLHLINLRTEDTATYYCAK...TTVA...DGVIGAYG
scFv80   ASGFTFSSYSMAWVRQAPGKGLEFVAGIQN.DGSITDYGSAVDGRATISRDDGQSTVRLQLNNLRTEDTATYYCAK...TTVA...DGVIGAYG
scFv115  ASGFTFSSYAMGWVRQAPGKGLEFVAGILN.DGSITDYGSAVDGRATISRDDGQSTVRLQLSNLRTEDTATYYCAK...TTVG...DGVIGAYA
scFv82   ASGFS.SSHGMGWMRQAPGKGLEFVAGIRS.DGSSTAYGAAVDGRATITRDDGQSTVTLQLNNLRAEDTATYFCAKN..TTVA...DGVIGAYG
scFv65   ASGFDFSSYGMGWMRQAPGKGLEFVAAIRK.DGSYTAYGAAVDGRATISRDDGQSTVRLQLGNLRAEDTATYFCAKT.NSYN...SAGI...
scFv73   ASGFDFSSYGMGWMRQAPGKGLEFVAGIRK.DGSYTAYGAAVDGRATISRDDGQSTVRLQLGNLRAEDTATYFCAKT.NSYN...SAGI...
scFv90   ASGFS.SSHGMGWMRQAPGKGLEFVAGIRS.DGSSTAYGAAVDGRATISRDDGQSTVRLQLGNLRAEDTATYFCAKT.NSYN...SAGI...
scFv68   ASGFTFSSYGMGWMRQAPGKGLEFVAGIRK.DGRSTAYGAAVDGRATISRDDGQSTLRLQLGNLRAEDTGTYFCAKT.NSYD...SAGI...
scFv74   ASGFTFSSYGMGWMRQAPGKGLEFVAGIRK.DGSSTAYGAAVDGRATISRDDGQSTLRLQLGNLRAEDTGTYFCAKT.NSYN...SAGI...
scFv114  ASGFTFSSYGMGWMRQAPGKGLEFVAGIRK.DGSSTAYGAAVDGRATISRDDGQSTVRLQLGNLRAEDTATYFCAKT.NSYN...SAGI...
scFv70   ASGFDFSSYGMGWMRQAPGKGLEFVAAIRK.DGSYTAYGAAVDGRATISRDDGQSTVRLQLGNLRAEDTATYFCAKT.NSYN...SAGI...
scFv92   ASGFDFSSYGMGWMRQAPGKGLEFVAAIRK.DGSYTAYGAAVDGRATISRDDGQSTVRLQLGNLRAEDTATYFCAKT.NSYN...SAGI...
scFv83   ASGFDFSSYGMGWMRQAPGKGLEFVAAIRK.DGSYTAYGAAVDGRATISRDDGQSTVRLQLGNLRAEDTATYFCAKT.NSYN...SAGI...
scFv72   ASGFS.SSHGMGWMRQAPGKGLEFVAGIRS.DGSSTAYGAAVDGRATITRDDGQSTVTLQLNNLRAEDTATYFCAKT.NSYN...SAGI...
scFv102  ASGFS.SSHGMGWMRQAPGKGLEFVAGIRS.DGSSTAYGAAVDGRATITRDDGQSTVTLQLNNLRAEDTATYFCAKT.NSYN...SAGI...

scFv86   ASGFIFSSHGMGWMRQAPGKGLEFVAAISK.DGTATYYGPAVKGRATISRDDGQTTVRLQLNNLRAEDTATYFCAKT..KYYN...SAGI...
scFv84   ASGFDFSSYGMGWMRQAPGKGLEFVAAIRK.DGSYTAYGAAVDGRATISRDDGQSTVRLQLGNLRAEDTATYFCAKT..NSYN...SAGI...
scFv110  ASGFTFSSYGMAWVRQAPGKGLEWLAGIYR.DDDSTYYAPAVKGRATISRDNGQSTVRLQLNNLRTEDTATYYCAKE..SA.....SGGWNAGW
scFv6    GSGFTFSSFNMFWVRQAPGKGLEWVAGIYS.SGGETNYGAAVKGRATISRDNGQSTVRLQLNNLRAEDTGTYYCAKESADVG...CPFT..AGN
scFv38   ASGFDFSSYGMHWVRQEPGKGLEWVAGI.SRTGSFTYGAAVKGRAAISRDNGQSTVRLQLNNLRAEDTGTYYCAKGGSDCSGYRCDYS..AGN
scFv49   GSGFTFSDYSMMWVRQAPGKGLEWVAGI.SSNSGTTRYGSAVKGRATISRDNGQSTVRLQLNNLRAEDTGTYYCAKTTGVNS......YD..VPA
scFv100  ASGFTFSSHTMQWVRQAPGKGLEWAEISADGSYTTYYGAAVKGRATISRDNGQSTVRLQLNNLRAEDTATYFCAKSGYGGA.....GWG..AGL
scFv131  ASGFSFSDYTMNWVRQAPGKGLEWVGQISSSDGNGRYTDYGAAVKGRATISRDNGQSTVRLQLNNLKAEDTGTYYCAKESDGDY..NGG..AGL
scFv14   ASGFTFSDYGMEWVRQAPGKGLEWVAGI.DDDGSTIFYAPAVKGRATISRDNGQSTVRLQLNNLRAEDTATYYCAKS.AGRG...WNV..AGW
scFv16   ASGFTFSSFDMFWVRQAPGKGLEYVAEI.SDTGSSTYYGAAVKGRATISRDNGQSTVRLQLNNLRAEDTGTYFCAKSHSGYG....WST..AGD
scFv26   ASGFTFSSFDMFWVRQAPGKGLEYVAEI.SDTGSSTYYGAAVKGRATISRDNGQSTVRLQLNNLRAEDTGTYFCAKSHSGYG....WST..AGD
scFv37   ASGFTFSSFHMFWVRQAPGEGLEYVAEI.TDTGSSTYYGAAVKGRATISRDNGQSTVRLQLNNLMADDTGTYFCAKSHSGYG....WST..AGD
scFv7    ASGFTFSDYGMGWVRQAPGKGLEWVAGIGN.TGSYTYYGSAVKGRATISRDNGQSTVRLQLNNLRAEDTGIYFCAKSTDYWTY........AGT
scFv33   GSGFTFSSHGMGWVRQAPGKGLEWVAGI.Y.SGSSTYYGAAVKGRATISRDNGQSTVRLQLNNLRAEDTATYFCTRGGG............AGR
scFv61   ASEFTFSSYAMEWVRQAPGKGLEWVAYINS.DGSSTWYAPAVKGRATISRDNGQSTVRLQLNSLRAEDTATYYCTRG....S.........GGEN scFv62   ASGFTFSSYAMEWVRQAPGKGLEWVAYINS.DGSSTWYAPAVKGRATISRDNGQSTVRLQLNSLRAEDTATYYCTRG....S.........GGEN
scFv108  ASEFTSISYAMEWVRQAPGKGLEWVAYINS.DGSSTWHAPAVKGRATISRDNGQSTVRLQLNSLRAEDTATYYCTIC....S.........GGEN
scFv96   ASEFTFSSYAMEWVRQAPGKGLEWVAYINS.DGSSTWYATAVKGRATISRDNGQSTVRLQLNSLRAEDTATYYCTRG....S.........GGEN
scFv117  ASGITFSTYAMEWVRQAPGKGLEFVAVVNA.AGS.TYYGAAVKGRATISRDNGQSTVRLQLNNLRAEDTGTYYCTRG....S.........GGEN
scFv87   ASGFTFSSYAMEWVRQAPGKGLEWVAYINS.DGSSTWYATAVKGRATISRDNGQSTVRLQLNNLRGEDTATYFCAKTKYYN..........SAGI
scFv98   ASGFTFNSYALEWVRQAPGKGLEWVAGISG.DGSFTHYGSAVKGRATISRDNGQSTVRLHLNNLRAEDTATYYCAKSTGSGAGW......GASN
scFv69   ASGFTFSSFNMEWVRQAPGKGLEFVAGIGN.TGRSTGYGSAVKGRATISRDNGQSTVRLQLNNLRAEDTGTYYCAKAY............GDSN
scFv137  ASGFTFSSFNMEWVRQAPGKGLEFVAGIGN.TGRSTGYGSAVKGRATISRDNGQSTVRLQLNNLRAEDTGTYYCAKAY............GDSN
scFv77   ASGFTFSSFNMEWVRQAPGKGLEFVAGIGN.TGSSTGYGSAVKGRATISRDNGQSTVRLQLNNLRAEDTGTYYCAKAY............GDSN
scFv93   ASGFTFSSFNMEWVRQAPGKGLEFVAGIGN.TGGSTGYGSAVKGRATISRDNGQSTVRLQLNNLRAEDTGTYYCAKAY............GDSN
scFv15   ASGFTFSSYDMGWVRQAPGKGLEWVAYINSGSGSSTYYGIAVKGRASISRDNGQSTVRLQLNNLRVEDTGTYFCAKGASGYY............
scFv4    ASGFTFSSYDMFWVRQAPGKGLEWVAQINS.AGSYTNYGSAVKGRASISRDNGQSTVRLQLNNLRAEDTGIYFCAKSASGYYY....SGSDAGD
scFv28   ASGFTFSSFNMFWVRQAPGRGLEFVAGITS.SGGTYYGTAVKGRATISRDNGQSTVRMQLNNLRAEDTGTYFCARGAYDYYF....YWNYAGT
scFv9    ASGFTFSSNGMAWVRQAPGKGLEWVAGISS.SGSYTNYGSAVKGRATISRDNGQSTVRLQLNNLRAEDTATYYCAKSSYAYYG....FG..APF
scFv10   GSGFTFSSVNMFWVRQAPGKGLEWVAGIYS.SGSSTHYGAAVKGRATISRDNGQSTVRLQLNNLRAEDTGIYYCAKDA.GCYT....SGDTAGC
```

```
scFv29   GSGFTFSSFDMWVRQAPGKGLEWVAYINSGSGSSTYYGTAVKGRASISRDNGQSTVRLQLNNLRVEDTGTYFCAKGASGYY..........|.GS
scFv31   GSGFTFSSYDMAWVRQEPSKGLEFVAQINS.AGSYTNYGSAVKGRATISRDDGQSTVRLQLNNLRAEDTGIYFCAKSASGYYY....SGSDAGS
scFv11   ASGFTFSDYDMFWVRQAPGKGLEFVAGITS.SGGSTYYGTAVKGRATISRDNGQSTVRMQLNNLRAEDTGTYFCARGAYDYYF....YWNYAGE
scFv18   ASGFTFSDYDMFWVRQASKGLEFVAGISS.SGSYTNYGSAVKGRATISRDNGQSTVRLQLNNLRAEDTATYYCAKSSYAYYG....FG..AGE
scFv36   ASGPIFSYYEMLWLHPAPGEVQEWVAGIYS.SGSSTHYGAAVKGRATISRDNGQSTVRLQLNNLRAEDTGIYYCAKDA.GCYT....SGDTAGD
scFv44   ASGFFFMIFELFGVRQAPGWVLEWVAGIRN.DGSDTAYGAAVKGRATISKDNGQSTVRLQLNNLRAEDTGTYYCAKAAG.YCY....VYSCAGD
scFv89   ASGFTFSSYDMGWVRQAPGKGLEFVASISN.TGSDTSYAHAVKGRATISRDNGQSTVRLQLNNLRAEDTATYYCAKSAGSYYW....NAGGA..
scFv88   ASGFTFSSYSMAWVRQAPGKGLEFVAAITS.SGTGTKYGAAVKGRATISKDNGQRTVRLQLNSLGAEDTGTYYCARSDADSTT....WS..A..
scFv63   ASGFTFSSFNMFWVRQAPGKGLEFVAAITS.SGTGTKYGAAVKGRATISKDNGQSTVRLQLNSLRAEDTGTYYCARSDADSTT....WS..A.N
scFv91   ASGFTFSSFNMFWVRQAPGKGLDFVTIISG.GGNYTYYGSAVDGGAIISRDDGKRMLMLQLNILEDDDTGFYFCADGASGYYY....GGADA.
scFv79   ASGF.FTFHGLDWMRQAPATGLEYIADVSD.TGNSTYYRAAVNVRAAISRNNGQMTLRLLLNDHTADDTCTYFCGYCHSDYCW......STA..
scFv81   ASGFTFSSYDMGWIRQAPGKGLEYVAGITIN.DGRYASYGSAVDGRATISRDNGQSTVRLQLNNPQG..................|........
scFv75   ASGFDFSSYGMGWMRQAPGKGLEFVAGIQN.DGSITDYGSAVDGRATISRDDGQSTVRLQLNNLRTEDTATYYCAKTTVADGVI......|...

scFv8    IDAWGHGTEVIVSSTSGQAGQHHHHHGAYPYDVPDYAS..............................................
scFv104  IDAWGHGTEVIVSSTSGQAGQHHHHHGAYPYDVPDYAS..............................................
scFv12   IDAWGHGTEVIVSSTSGQAGQHHHHHGAYPYDVPDYAS..............................................
scFv17   IDAWGHGTEVIVSSTSGQAGQHHHHHGAYPYDVPDYAS..............................................
scFv21   IDAWGHGTEVIVSSTSGQAGQHHHHHGAYPYDVPDYAS..............................................
scFv39   IDAWGHGTEVIVSSTSGQAGQHHHHHGAYPYDVPDYAS..............................................
scFv54   IDAWGHGTEVIVSSTSGQAGQHHHHHGAYPYDVPDYAS..............................................
scFv136  IDAWGHGTEVIVSSTSGQAGQHHHHHGAYPYDVPDYAS..............................................
scFv13   IDAWGHGTEVIVSSTSGQAGQHHHHHGAYPYDVPDYAS..............................................
scFv47   IDAWGHGTDVIVSSTSGQAGQHHHHHGAYPYDVPDYAS..............................................
scFv139  IYAWGHGTEVIVSSTSGQAGQHHHHHGAYPYDVPDYAS..............................................
scFv22   IDAWGHGTEVIVSSTSGQAGQHHHHHGAYPYDVPDYAS..............................................
scFv53   IDAWGHGTEVIVSSTSGQAGQHHHHHGAYPYDVPDYAS..............................................
scFv27   IDAWGHGTEVIVSSTSGQAGQHHHHHGAYPYDVPDYAS..............................................
scFv40   IDAWGHGTEVIVPSTSGQAGQHHHHHGAYPYDVPDYAS..............................................

scFv41   IDAWGHGTEVIVPSTSGQAGQHHHHHGAYPYDVPDYAS..............................................
scFv42   IDAWGHGTEVIVSSTSGQAGQHHHHHGAYPYDVPDYAS..............................................
scFv48   IDAWGHGTEVIVSSTSGQAGQHHHHHGAYPYDVPDYAS..............................................
scFv60   IDAWGHGTEVIVSSTSGQAGQHHHHHGAYPYDVPDYAS..............................................
scFv43   IDAWGHGTEVIVSSTSGQAGQHHHHHGAYPYDVPDYAS..............................................
scFv58   IDAWGHGTEVIVSSTSGQAGQHHHHHGAYPYDVPDYAS..............................................
scFv56   IDAWGHGTEVIVSSTSGQAGQHHHHHGAYPYDVPDYA...............................................
scFv59   IDAWGHGTEVIVSSTSGQAGQHHHHHGAYPYDVPDYAS..............................................
scFv50   IDAWGHGTEVIVSSTSGQAGQHHHHHGAYPYDVPDYAS..............................................
scFv52   IDAWGHGTEVIVSSTSGQAGQHHHHHGAYPYDVPDYAS..............................................
scFv121  IDAWGHGTEVIVSSTSGQAGQHHHHHGAYPYDVPDYAS..............................................
scFv123  IDACGHGTEVIVSSTSGQAGQHHHHHGAYPYDVPDYAS..............................................
scFv51   IDAWGHGTEVIVSSTSGQAGQHHHHHGAYPYDVPDYAS..............................................
scFv45   IDAWGHGTEIIVSSTSGQAGQHHHHHGAYPYDVPDYAS..............................................
scFv57   IDTWGHGTEVIVSSTSGQAGQHHHHHGAYPYDVPDYAS..............................................

scFv67   IDTWGHGTEVIVSSTSGQAGQHHHHHGAYPYDVPDYAS..............................................
scFv85   IDTWGHGTEVIVSSTSGQAGQHHHHHGAYPYDVPDYAS..............................................
scFv111  IDAWGHGTEVIVSSTSGQAGQHHHHHGAYPYDVPDYAS..............................................
scFv106  IDTWGHGTEVIVSSTSGQAGQHHHHHGAYPYDVPDYAS..............................................
scFv64   IDAWGHGTEVIVSSTSGQAGQHHHHHGAYPYDVPDYAS..............................................
scFv113  IDAWGHGTEVIVSSTSGQAGQHHHHHGAYPYDVPDYAS..............................................
scFv120  IEAWGHRTEVLVSSTSGQAGQHHHHHGAYPYDVPDYAS..............................................
scFv95   IDTWGHGTEVIVSSTSGQAGQHHHHHGAYPYDVPDYAS..............................................
scFv103  IDTWGHGTEVIVSSTSGQAGQHHHHHGAYPYDVPDYAS..............................................
scFv97   IDAWGHGTEVIVSSTSGQAGQHHHHHGAYPYDVPDYAS..............................................
scFv3    IDAWGHGTEVIVSSTSGQAGQHHHHHGAYPYDVPDYAS..............................................
scFv30   IDAWGHGTEVIVSSTSGQAGQHHHHHGAYPYDVPDYAS..............................................
scFv35   IDAWGHGTEVIVSSTSGQAGQHHHHHGAYPYDVPDYAS..............................................
scFv23   IDAWGHGTEVIVSSTSGQAGQHHHHHGAYPYDVPDYAS..............................................
scFv138  IDAWGHGTEVIVSSTSGQAGQHHHHHGAYPYDVPDYAS..............................................

scFv5    IDAWGHGTEVIVSSTSGQAGQHHHHHGAYPYDVPDYAS..............................................
scFv24   IDAWGHGTEVIVSSTSGQAGQHHHHHGAYPYDVPDYAS..............................................
scFv25   IDAWGHGTEVIVSSTSGQAGQHHHHHGAYPYDVPDYAS..............................................
scFv55   IDAWGHGTEVIVSSTSGQAGQHHHHHGAYPYDVPDYAS..............................................
scFv19   FDAWGHGTEVIVSSTSGQAGQHHHHHGAYPYDVPDYAS..............................................
scFv66   IDAWGHGTEVIVSSTSGQAGQHHHHHGAYPYDVPDYAS..............................................
scFv20   IDAWGHGTEVIVSSTSGQAGQHHHHHGAYPYDVPDYAS..............................................
scFv32   IDAWGHGTEVIVSSTSGQAGQHHHHHGAYPYDVPDYAS..............................................
scFv134  IDAWGHGTEVIVSSTSGQAGQHHHHHGAYPYDVPDYAS..............................................
scFv119  IDAWGHGTEVLLSSTSGQAGQHHHHHGAYPYDVPDYAS..............................................
scFv46   ....GHGTEIIVSSTSGQAGQHHHHHGAYPYDVPDYAS..............................................
scFv34   IDAWGHGTEVIVSSTSGQAGQHHHHHGAYPYDVPDYAS..............................................
scFv105  IDAWGHGTEVIVSSTSGQAGQHHHHHGAYPYDVPDYAS..............................................
scFv112  IDAWGHGTEVIVSSTSGQAGQHHHHHGAYPYDVPDYAS..............................................
scFv118  IDAWGHGTEVIVSSTSGQAGQHHHHHGAYPYDVPDYAS..............................................
```

```
scFv124   IDAWGHGTEVIVSSTSGQAGQHHHHHHGAYPYDVPDYAS............................
scFv80    IDAWGHGTEVIVSSTSGQAGQHHHHHHGAYPYDVPDYAS............................
scFv115   IDAWGHGTEVIVSSTSGQAGQHHHHHHGAYPYDVPDYAS............................
scFv82    IDAWGHGTEVIVSSTSGQAGQHHHHHHGAYPYDVPDYAS............................
scFv65    IDAWGHGTEVIVSSTSGQAGQHHHHHHGAYPYDVPDYAS............................
scFv73    IDAWGHGTEVIVSSTSGQAGQHHHHHHGAYPYDVPDYAS............................
scFv90    IDAWGPGTEVIVSSTSGQAGQHHHHHHGAYPYDVPDYAS............................
scFv68    IDAWGHGTEVIVSSTSGQAGQHHHHHHGAYPYDVPDYAS............................
scFv74    IDAWGHGTEVIVSSTSGQAGQHHHHHHGAYPYDVPDYAS............................
scFv114   IDAWGHGTEVIVSSTSGQAGQHHHHHHGAYPYDVPDYAS............................
scFv70    IDAWGHGTEVIVSSTSGQAGQHHHHHHGAYPYDVPDYAS............................
scFv92    IDAWGHGTEVIVSSTSGQAGQHHHHHHGAYPYDVPDYAS............................
scFv83    IDAWGHGTEVIVSSTSGQAGQHHHHHHGAYPYDVPDYAS............................
scFv72    IDAWGHGTEVIVSSTSGQAGQHHHHHHGAYPYDVPDYAS............................
scFv102   IDAWGHGTEVIVSSTSGQAGQHHHHHHGAYPYDVPDYAS............................

scFv86    IDAWGHGTEVIVSSTSGQAGQHHHHHHGAYPYDVPDYAS............................
scFv84    IDAWGHGTEVIVSSTSGQAGQHHHHHHGAYPYDVPDYAS............................
scFv110   IDAWGHGTEVIVSSTSGQAGQHHHHHHGAYPYDVPDYAS............................
scFv6     IDTWGHGTEVIVSSTSGQAGQHHHHHHGAYPYDVPDYAS............................
scFv38    IDGWGHGTEVIVSSTSGQAGQHHHHHHGAYPYDVPDYAS............................
scFv49    IDAWGHGTEVIVSSTSGQAGQHHHHHHGAYPYDVPDYAS............................
scFv100   IDAWGHGTEVIVSSTSGQAGQHHHHHHGAYPYDVPDYAS............................
scFv131   IDAWGHGTEVIVSSTSGQAGQHHHHHHGAYPYDVPDYAS............................
scFv14    IDAWGHGTEVIVSSTSGQAGQHHHHHHGAYPYDVPDYAS............................
scFv16    IDAWGHGTEVIVSSTSGQAGQHHHHHHGAYPYDVPDYAS............................
scFv26    IDAWGHGTEVIVSSTSGQAGQHHHHHHGAYPYDVPDYAS............................
scFv37    IDAWGHGTEVIVSSTSGQAGQHHHHHHGAYPYDVPDYAS............................
scFv7     IDAWGHGTEVIVSSTSGQAGQHHHHHHGAYPYDVPDYAS............................
scFv33    IDTWGHGTEVIVSSTSGQAGQHHHHHHGAYPYDVPDYAS............................
scFv61    IDTWGHGTEVIVSSTSGQAGQHHHHHHGAYPYDVPDYAS............................

scFv62    IDTWGHGTEVIVSSTSGQAGQHHHHHHAAYPYDVPDYAS............................
scFv108   IYTCCHGTEVIVSSTSGQDGQHHHHHHGAYPYDVPDYAS............................
scFv96    IDTWGHGTEVIVSSTSGQAGQHHHHHHGAYPYDVPDYAS............................
scFv117   IDAWGHGTEVIVSSTSGQAGQHHHHHHGAYPYDVPDYAS............................
scFv87    IDAWGHGTEVIVSSTSGQAGQHHHHHHGAYPYDVPDYAS............................
scFv98    IDAWGHGTEVIVSSTSGQAGQHHHHHHGAYPYDVPDYAS............................
scFv69    IDAWGHGTEVIVSSTSGQAGQHHHHHHGAYPYDVPDYAS............................
scFv137   IDAWGHGTEVIVSSTSGQAGQHHHHHHGAYPYDVPDYAS............................
scFv77    IDAWGHGTEVIVSSTSGQAGQHHHHHHGAYPYDVPDYAS............................
scFv93    IDTWGHGTEVIVSSTSGQAGQHHHHHHGAYPYDVPDYAS............................
scFv15    ..............SSSGQAGQHHHHHHGAYPYDVPDYAS............................
scFv4     IDAWGHGTEVIVSSTSGQAGQHHHHHHGAYPYDVPDYAS............................
scFv28    IDAWGHGTEVIVSSTSGQAGQHHHHHHGAYPYDVPDYAS............................
scFv9     IDAWGHGTEVIVSSTSGQAGQHHHHHHGAYPYDVPDYAS............................
scFv10    IDAWGHGTEVIVSSTSGQAGQHHHHHHGAYPYDVPDYAS............................

scFv29    IDAWGHGTEVIVSSTSGQAGQHHHHHHGAYPYDVPDYAS............................
scFv31    IDTWGHGTEVIVSSTSGQAGQHHHHHHGAYPYDVPDYAS............................
scFv11    IDAWGHGTEVIVSSTSGQAGQHHHHHHGAYPYDVPDYAS............................
scFv18    IDAWGHGTEVIVSSTSGQAGQHHHHHHGAYPYDVPDYAS............................
scFv36    IDAWGHGTEVIVSSTSGQAGQHHHHHHGAYPYDVPDYAS............................
scFv44    IDAWSHVIDFIVSSTSGQAGQHHHHHHGAYPYDDPDYAS............................
scFv89    ...................................................................
scFv88    .......................................................................
scFv63    IDRMGPRDR..............................................................
scFv91    .......................................................................
scFv79    .......................................................................
scFv81    .......................................................................
scFv75    .......................................................................
```

```
  scFv2   MKKTAIAIAVALAGFATVAQAALTQ--------PSSV---SANPGGTVKITCSG-GG---S--YYGWYQQKSPGSAPVTVIYDNTNRPSNIP
  scFv8   MKKTAIAIAVALAGFATVAQAALTQ--------PSSV---SANPGETVKITCSG-GG---SSSYYGWYQQKSPGSAPVTLIYESNERPSNIP
scFv104   MKKTAIAIAVALAGFATVAQAALTQ--------PSSV---SANLGGTVEITCSGSGG---SYGYYGWYQQKAPGSAPVTVIYDNTNRPSNIP
 scFv12   MKKTAIAIAVALAGFATVAQAALTQ--------PSSV---SANPGEAVKITCSG-GG---SSSYYGWYQQKSPGSAPVTVIYWDDERPSNIP
 scFv17   MKKTAIAIAVALAGFATVAQAALTQ--------PSSV---SANPGETVKITCSG--G---YS-YYGWYQQKTPGSAPVTLIYENDKRPSDIP
 scFv21   MKKTAIAIAVALAGFATVAQAALTQ--------PSSV---SANPGGTVKITCSG--S---SCSYYGWYQQKSPGSAPVTVIYDNDKRPSDVP
 scFv39   MKKTAIAIAVALAGFATVAQAALTQ--------PSSV---SANPGETVKITCSG--G---GSDYYGWYQQKSPGSAPVTLIYENDKRPSNIP
 scFv54   MKKTAIAIAVALAGFATVAQAALTQ--------PSSV---SANPGETVKITCSG--G---SYSY-GWYQQKSPGSAPVTVIYSSDKRPSDIP
scFv136   MKKTAIAIAVALAGFATVAQAALTQ--------PSSV---SANPGETVKITCSG--G---SYSY-GWYQQKSPGSAPVTVIYSSDKRPSDIP
 scFv13   MKKTAIAIAVALAGFATVAQAALSR--------PRC----QQTWGGTVKITCSGG------DSSYGWYQQKSPGSAPVTLIYDNTNRPSDIP
 scFv47   MKKTAIAIAVALAGFATVAQAALSR--------PRC----QQTWGGTVKITCSGG------DGSYGWYQQKSPGSAPVTVIYDNTNRPSDIP
scFv139   MKKTAIAIAVALAGFATVAQAALTQ--------PSSV---SANLGGTVKITCSGG------DSSYGWYQQKSPGSAPVTLIYDNTNRPSDIP
 scFv22   MKKTAIAIAVALAGFATVAQAA----------V---SANPGDTVKITCSGD------SNNYGWYQQKSPGSAPVTVIYDNTNRPSNIP
 scFv53   MKKTAIAIAVALAGFATVAQAAL------------V---SANPGEIVKITCSGN------SSYYGWYQQKAPGSAPVTVIYDNNKRPSDIP
```

```
  scFv27  MKKTAIAIAVALAGFATVAQAALSR--------PR-C---QQTWGGTVKITCSGS------NSYYGWYQQKAPGSAPVTLIYDDTNRPSDIP
  scFv40  MKKTAIAIAVALAGFATVAQAALSR--------PR-C---QQTWGGIVKLTCSGG------SGSCGWYQQKSPGSAPVTLIYDNDKRPSDIP
  scFv41  MKKTAIAIAVALAGFATVAQAALSR--------PR-C---QQTWGGTVKITCSGG------SSYYGWYQQKSPGSAPVTLIYENNNRPSDIP
  scFv42  MKKTAIAIAVALAGFATVAQAALTQ--------PSSV---SANPGETVEITCSGGGS----SSNYGWHQQSPGSAPVTVIYDNTNRPPNIP
  scFv48  MKKTAIAIAVALAGFATVAQAALTQ--------PSSV---SANPGETVKITCSEGGR----SSYYGWYQQKAPGSAPVTVIYDSSSRPSDIP
  scFv60  MKKTAIAIAVALAGFATVAQAALTQ--------PSSV---SANPGAIVKITCSEGGR----SSYYGWYQQKAPGSAPVTVIYDSSSRPSDIP
  scFv43  MKKTAIAIAVALAGFATVAQAALTQ--------PSSV---SANPGETVKITCSGGGS----SSYYGWYQQKSPDSAPVTLIYESNKRPSNIP
  scFv58  MKKTAIAIAVALAGFATVAQAALTQ--------PSSV---SANPGDTVKITCSGGGS----SSYYGWYQQKRSPGSAPVTLIYSNDKRPSDIP
  scFv56  MKKTAIAIAVALAGFATVAQAALTQ--------PSSV---SANPGETVKITCSGGGS----SSYYGWYQQKSPGSAPVTLIYESNKRPSGIP
  scFv59  MKKTAIAIAVALAGFATVAQAALTQ--------PSSV---SANPGEIFKITCSGGGSY-AGSYYYGWYQQKAPGSAPVTVIYDNTNRPSNIP
  scFv50  MKKTAIAIAVALAGFATVAQAALTQ--------PSSV---SANPGDTVEITCSGG------YSNYGWYQQKSPGSAPVTVIYGSTSRPSDIP
  scFv52  MKKTAIAIAVALAGFATVAQAALTQ--------PSSV---SANPGDPVEITCSGS------SGSYGWYQQKAPSSAPVTVIYSNDKRPSDIP
 scFv121  MKKTAIAIAVALAGFATVAQAALTQ--------PSSV---SANLGGTVKITCSGG------SSYYGWYQQKSPGSAPVTLIYENNNRPSDIP
 scFv123  MKKTAIAIAVALAGFATVAQAALTQ--------PSSV---SANLGGTVKITCSGG------SSYYGWYQQKSPGSAPVTLIYENNNRPSDIP
  scFv51  MKKTAIAIAVALAGFATVAQAAL-------------V---SANPGETVKITCSGGGSNSAGSYYYGWYQQKPPGSAPVTVIHNNNKRPSDIP scFv45  MKKTAIAIAVALAGFATVAQAALTQ--------PSSV---SANPGGTVKITCSGSSS----AYGYGWYQQKSPGSAPVTVIYNNNKRPSNIP
  scFv57  MKKTAIAIAVALAGFATVAQAALTQ--------PSSV---SANPGETVKITCSGSSS----AYGYGWYQQKSPGSAPVTVIYNNNKRPSNIP
  scFv67  MKKTAIAIAVALAGFATVAQAALTQ--------PSSV---SANPGETVKITCSGSSS----AYGYGWYQQKSPGSAPVTVIYNNNKRPSNIP
  scFv85  MKKTAIAIAVALAGFATVAQAALTQ--------PSSV---SANPRTLLKITCSGSSS----AYGYGWYQQKSPGSAPVTVIYNNNKRPSNIP
 scFv111  MKKTAIAIAVALAGFATVAQAALTQ--------PSSV---SANPGETVKLTCSGDSS----DYGYGWYQQKSPGSAPVTVIYNNNKRPSDIP
 scFv106  MKKTAIAIAVALAGFATVAQAALTQ--------PSSV---SANPGETVKITCSGDSS----DYGYGWYQQKSPGSAPVTVTYSNNQRPPNIP
  scFv64  MKKTAIAIAVALAGFATVAQAALTQ--------PSSV---SANPGDPLKITCSGDSS----GYGYGWYQQKSPGSAPVTVIYNNNKRPSDIP
 scFv113  MKKTAIAIAVALAGFATVAQAALTQ--------PSSV---SANPGETVKITCSGDSS----GYGYGWYQQKSPGSAPVTVIYNNNKRPSDIP
 scFv120  MKKTAIAIAVALAGFATVAQAALTQ--------PSSV---SANPGETVKLTCSGDSS----DYGYGWYQQKSPGSAPVTVIYNNNKRPSDIP
  scFv95  MKKTAIAIAVALAGFATVAQAALTQ--------PSSV---SANPGETVEITCSGGGG----SYG--WFQQKSPGSAPVTVIYESTKRPSNIP
 scFv103  MKKTAIAIAVALAGFATVAQAALTQ--------PSSV---SANPGETVEITCSGGGG----SYG--WFQQKSPGSAPVTVIYESTKRPSNIP
  scFv97  MKKTAIAIAVALAGFATVAQAALTQ--------PSSV---SANPGETVKITCSGGSY----N-AYGWYQQKSPAGAPVTLIYDNTNRPSNIP
   scFv3  MKKTAIAIAVALAGFATVAQAA--------------V---STNPGDTVKITCSG--G----NSWYGWFQQKSPGSAPVTVIYGNDERPSDIP
  scFv30  MKKTAIAIAVALAGFATVAQAA--------------V---SANPGETVKITCSG--G----GGSYGWYQQKRPGSAPVTVIYDNTNRPSNIP
  scFv35  MKKTAIAIAVALAGFATVAQAA--------------V---SANPGDTVEITCSG--S----SGSYGWYQQKSPGSAPVTVIYANTNRPSDIP scFv23  MKKTAIAIAVALAGFATVAQAA--------------V---SANLGGTVEITCSG--G----GSYYGWYQQKSPGSAPVTVIYANTNGPSDIP
 scFv138  MKKTAIAIAVALAGFATVAQAALTQ--------PSSV---SANLGGTVEITCSG--G----GSYYGWYQQKSPGSAPVTVIYANTNGPSDIP
   scFv5  MKKTAIAIAVALAGFATVAQAA--------------V---SANPGDTVKITCSG--S----SGRYGWYQQKSPGSAPVTVIYYNDKRPSDIP
  scFv24  MKKTAIAIAVALAGFATVAQAA--------------V---SASPGDTVKITCSGGNS----SYGYGWYQQKSPGSAPVSVIYYNDERPSDIP
  scFv25  MKKTAIAIAVALAGFATVAQAALTP--------PSSV---SANLGAPVEITCSGS------SGNYGWFQQKSPGSAPVTVIYSNDKRPSDIP
  scFv55  MKKTAIAIAVALAGFATVAQAAL-------------V---SANLGGTVEITCSGS------SGNYGWYQQKSPGSAPVTVIYSNDKRPSDIP
  scFv19  MKKTAIAIAVALAGFATVAQAALSR--------PR-C---QQTWGGTVEITCSGGSN----NYGYGWYQQKSPGSAPVTLIYSNDNRPSNIP
  scFv66  MKKTAIAIAVALAGFATVAQAALSR--------PR-C---QQTWGGTVKITCSGSSG----DYGYSWHQQKSPGSAPVTVIYESTKRPSNIP
  scFv20  MKKTAIAIAVALAGFATVAQAALTQ--------PSSV---SANLGGIVEITCSGSSG------SYGWYQQKSPGSAPVTVIYYNDKRPSNIP
  scFv32  MKKTAIAIAVALAGFATVAQAALTQ--------PSSV---SANLGGTFKITCSGSSG------SYAWYQQKSPGSAPVTVIYWNDKRPSNIP
 scFv134  MKKTAIAIAVALAGFATVAQAALTQ--------PSSV---SANLGGTVKITCSGSSG------SYGWYQQKSPGSAPVTVIYWNDKRPSNIP
 scFv119  MKKTAIAIAVALAGFATVAQAALTQ--------PSSV---SANLGGTVKITCSGSSG------SYGWYQQKSPGSAPVTVIYRNDKRPSNIP
  scFv46  MKKTAIAIAVALAGFATVAQAALTQ--------PSSV---SANLGGTVKITCSGSSG------SYGWYQQKSPGSAPVTVIYWNDKRPSNIP
  scFv34  MKKTAIAIAVALAGFATVAQAALTQ--------PSSV---SANLGGTVEITCSGSSG------SYGWYQQKSPGSAPVTVIYYNDKRPSDIP
 scFv105  MKKTAIAIAVALAGFATVAQAALTQ--------PSSV---SANPGEAVKITCSGSSG------SYGWYQQKSPGSAPVTVIYYNDKRPSDIP scFv112  MKKTAIAIAVALAGFATVAQAALTQ--------PSSV---SANLGGTVKITCSGGSG------SYGWYQQKSPGSAPVTVIYYNDQRPSDIP
 scFv118  MKKTAIAIAVALAGFATVAQAALTQ--------PSSV---SANLGGTVEITCSGGSG------SYGWYQQKSPGGAPVTVIYYNDKRPSDIP
 scFv115  MKKTAIAIAVALAGFATVAQAALTQ--------PSSV---SANLGGTVEITCSGGSG------SYGWYQQKSPGGAPVTVIYYNDKRPSDIP
  scFv82  MKKTAIAIAVALAGFATVAQAALTQ--------PSSV---SANLG-AFKITCSGGGG------SYGWYQQKSPGSAPVTLIYYNDKRPSDIP
  scFv65  MKKTAIAIAVALAGFATVAQAALSR--------PRC----QQTWGGTVKITCSGSSG------SYGWYQQKSPGSAPVTLIYESDKRPSDIP
  scFv73  MKKTAIAIAVALAGFATVAQAALSR--------PRC----QQTWGGTVKITCSGSSG------SYGWYQQKSPGSAPVTLIYESDKRPSDIP
  scFv90  MKKTAIAIAVALAGFATVAQAALSR--------PRC----QQTWGGTVKITCSGSSG------SYGWYQQKSPGSAPVTVIYQNDKRPSDIP
  scFv68  MKKTAIAIAVALAGFATVAQAALTQ--------PSSV---SASPGETVKITCSGGSG------SYGWYRHKSPGSAPVTVIYYNDKRPSDIP
  scFv74  MKKTAIAIAVALAGFATVAQAALTQ--------PSSV---SASPGETVKITCSGGSG------SYGWYQQKSPGSAPVTVIYYNDKRPSDIP
 scFv114  MKKTAIAIAVALAGFATVAQAALTQ--------PSSV---SASPGETVKITCSGGSG------SYGWYQQKSPGSAPVTVIYYNDKRPSDIP
  scFv70  MKKTAIAIAVALAGFATVAQAALTQ--------PSSV---SASLGGIVKITCSGGSG------TYGWYQQKSPGSAPVTVIYQNGKRPSNIP
  scFv92  MKKTAIAIAVALAGFATVAQAALTQ--------PSSV---SASLGTFLEITCSGGSG------TYGWYQQKSPGSAPVTVIYQNGKRPSNIP
  scFv83  MKKTAIAIAVALAGFATVAQAALTQ--------PSSV---SANLGGPFEITCSGGSG------SYGWYQQKSPGSAPVTLIYNNNNRPSDIP
  scFv72  MKKTAIAIAVALAGFATVAQAALTQ--------PSSV---SANPGETVKITCSGSSG------SYGWYQQKSPGSAPVSLIYSNDKRPSDIP
 scFv102  MKKTAIAIAVALAGFATVAQAALTQ--------PSSV---SANPGETVKITCSGGSG------SYGWYQQESPGSAPVTVIYYNDKRPSDIP scFv86  MKKTAIAIAVALAGFATVAQAALGP--------DSAVLGVSKPGEALVKTTCSGGGG------SYGWYQQKSPGSAPVTVIYYNDKRPSDIP
  scFv84  MKKTAIAIAVALAGFATVAQAAL-----------------KITCSGSG--------------SYAWYQQKSPGSAPVTLIYESDKRPSDIP
 scFv110  MKKTAIAIAVALAGFATVAQAALTQ--------PSSV---SANLGGTVKLTCSGGSSY-----GYSWHQQKSPGSAPVTVIYSNDKRPSDIP
   scFv6  MKKTAIAIAVALAGFATVAQAALTQ--------PSSV---SANPGDTVKITCSG-SIR-----YYGWYQQKSPGSAPVTLIYYDDKRPSDIP
  scFv38  MKKTAIAIAVALAGFATVAQAALTQ--------PSSV---SANPGETVKITCSG-GSS-----GYGWYQQKSPGSAPVTVIYYNDKRPSDIP
  scFv49  MKKTAIAIAVALAGFATVAQAALTQ--------PSSV---SANPGETVKITCSG-GGG-----SYGWFQQKSPGSAPVTLIYNNNNRPSDIP
 scFv100  MKKTAIAIAVALAGFATVAQAALTQ--------PSSV---SANPGETVKITCSG-SSD-----AYGYGWYQQKSPGSAPVTLIYDNTNRPPDIP
 scFv131  MKKTAIAIAVALAGFATVAQAALTQ--------PSSV---SANLGGTVEITCSGGSSS-----YYGWYQQKSPGSAPVTVIYWNDKRPSDIP
  scFv14  MKKTAIAIAVALAGFATVAQAALTQ--------PSSV---SANPGETVKITCSGGYSG-----YGWFRQKAPGSAPVTLIYANTNRPSDIP
  scFv16  MKKTAIAIAVALAGFATVAQAALTQ--------PSSV---SANLGETVKITCSGGSYAG-SYYYGWYQQKSPGSAPVTLIYDNTNRPSDIP
  scFv26  MKKTAIAIAVALAGFATVAQAALTQ--------PSSV---SANPGETVGITCSGGGSY-----YGWYQQKSPGSAPVTLIYENDMRPSNIP
  scFv37  MKKTAIAIAVALAGFATVAQAALTQ--------PSSV---SANLGDTVKITCSGGGYAG-SYYYGWYQHNAAGGAPVTLIYDNTITPSDIP
   scFv7  MKKTAIAIAVALAGFATVAQAAV--------------SASLEGTVEITCSGGSG------SYGWFQQKAPGSAPVTVIYDNTNRPSDIP
  scFv33  MKKTAIAIAVALAGFATVAQAAV----------------SANPGDTVKITCSGGYS------GYGWYQQKSPGSAPVTVIYSNNQRPSNIP
  scFv61  MKKTAIAIAVALAGFATVAQAALTQ--------PSSVS---ANPGETVKITCSGGGSY-AGSYYYGWYQQKAPGSAPVTLIYDNTNRPSNIP
```

```
     scFv62 MKKTAIAIAVALAGFATVAQAALTQ--------PSSVS---ANPGETVKITCSGGGSY-AGSYYYGWYQQKAPGSAPVTLIYDNTNRPSNIP
    scFv108 MKKTAIAIAVALAGFATVAQAALTQ--------PSSVS---ANPGETVKITCSGGGSY-AGSYYYGWYQQKAPGSAPVTLIYDNTNRPSNIP
     scFv96 MKKTAIAIAVALAGFATVAQAALPGVRHRDPGGPDSAVLGVSKPRRNDKITCSGGGSY-AGSYYYGWYQQKAPGSAPVTLIYDNTNRPSNIP
    scFv117 MKKTAIAIAVALAGFATVAQAALTQ--------PSSVS---ANPGETVKITCSGGGSY-AGSYYYGWYQQKAPGSAPVTLIYDNTNRPSNIP
     scFv87 MKKTAIAIAVALAGFATVAQAALSR--------PRVS---ANPGDPVKITCSGGGSY-AGSYYYGWYQQKAPGSAPVTVIYDNNQRPSNIP
     scFv98 MKKTAIAIAVALAGFATVAQAALTQ--------PSSVS---ANPGETVKITCSGGGSY-VGSYYYGWYQQKSPVSAPVTLIYESTKRPSNIP
     scFv69 MKKTAIAIAVALAGFATVAQAALTQ--------PSSVS---ANPGETVKITCSGGGS----SNNYGWHQQKAPGSAPVTVIYDNTNRPSNIP
    scFv137 MKKTAIAIAVALAGFATVAQAALTQ--------PSSVS---ANPGETVKITCSGGGS----SNNYGWHQQKAPGSAPVTVIYDNTNRPSNIP
     scFv77 MKKTAIAIAVALAGFATVAQAALTQ--------PSSVS---ANPGDPFKITCSGGGS----SNNYGWHQQKAPGSAPVTVIYDNTNRPSNIP
     scFv93 MKKTAIAIAVALAGFATVAQAALTQ--------PSSVS---ANPGALFKITCSGGGS----SNNYGWHQQKAPGSAPVTVIYDNTNRPSNIP
     scFv71 MKKTAIAIAVALAGFATVAQAALTQ--------PSSVS---ANPGETVKITCSGGGS----SNNYGWHQQKAPGSAPVTVIYDNTNRPSNIP
    scFv140 MKKTAIAIAVALAGFATVAQAALTQ--------PSSV---SANPGGTVKITCSGSSG-----SYYGWYQQKSPGSAPVTVIYDNDKRPSDVP
     scFv15 MKKTAIAIAVALAGFATVAQAALSR--------PRC----QQTQEHTVKITCSGGVG-----QWYGWYQQKSPGSAPVTLIYESNQRPSNIP
      scFv4 MKKTAIAIAVALAGFATVAQAA--------------------------------------------------------VIYDNDKRPSDVP
     scFv28 MKKTAIAIAVALAGFATVAQAA--------------------------------------------------------VIYSNDERPSDIP scFv9 MKKTAIAIAVALAGFATVAQAA--------------------------------------------------------VIYGNDERPSDIP
     scFv10 MKKTAIAIAVALAGFATVAQAA--------------------------------------------------------VIYANTDRPSDIP
     scFv29 MKKTAIAIAVALAGFATVAQAA--------------------------------------------------------VIYDNTNRPSNIP
     scFv31 MKKTAIAIAVALAGFATVAQAA--------------------------------------------------------VIYDNTNRPSNIP
     scFv11 MKKTAIAIAVALAGFATVAQAA--------------------------------------------------------VIYYNDKRPSNIP
     scFv18 MKKTAIAIAVALAGFATVAQAA--------------------------------------------------------VIYYNDKRPSDIP
     scFv36 MKKTAIAIAVALAGFATVAQAALSR--------PRC----QQTLGGTVKITCSGSNG------SYDWCHQKTSAGAAAAVIIYDNNKTSYIP
     scFv44 MKKTAIAIAVALAGFATVAQAALTQ--------PSSV---SANLGETVKITCSGGGSY-AGCYYYSWYDHTAAGVVPVTLI-DSTIPSSYFR
     scFv89                   ALTQ--------PSSV---SANPGDTVKITCSGDSS----DYGYGWYQQKSPGSAPVTVTYSNNQRPSDIP
     scFv88                                                            GSSGSYGWYQQKSPGSAPVTVIYYNDKRPSDIP
     scFv63                                                            SNNYGWHQQKAPGSAPVTVIYDNTNRPSNIP
     scFv91                                                                           IYDNTNRPSNIP
     scFv79                                           LSRPRCQQTWGGTVKITCSGSSG------GYGWYRHKSPGTAPVPLIYNNDNRPSNIP
     scFv81                   ALTQ--------PSSV---SANPGGTVKITCSGSSS----AYGYGWYQQKSPGSAPVTVIYNNNKRPSNIP
     scFv75                                                                   RAPVTLIYNNNNRPSDIP
  consensus mkktaiaiavalagfatvaqaAltq        pssv. san.g.tvkitcsg.... .....ygwyqqkspgsspvtvIY.n..RPS#IP scFv2 SRFSGSKSGSTGTLTITGVQADDEAVYYCGSTD-SS----AD-GVFGAGTTLTVLGQSSRSS----------AVTLDESGGGLQTPGGLS
      scFv8 SRFSGSESGSTGTLTITGVRAEDEAVYYCGSAD-SS----NA-GIFGAGTTLTVLGQSSRSS----------TVTLDESGGGLQTPGGALS
    scFv104 SRFSGSASGSTGTLTITGVRAEDEAVYFCGYD-SS----NT-DRFGAGTTLTVLGQSSRSS----------TVTLDESGGGLQTPGRALS
     scFv12 SRFSGSTSGSTGTLTITGVQAEDEAVYYCGSRD-GD--GIFGAGTTLTVLGQSSRSSSGGGSSGGGGSAVTLDESGGGLQTPGRALS
     scFv17 SRFSGSKSGSTATLTITGVQVEDEAMYFCGSYECST----YV-GIFGAGTTLTVLGQSSRSS----------AVTLDESGGGLQTPGGALS
     scFv21 SRFSGSKSGPTATLTITGVQAEDEAMYFCGSRD-NS----YV-GIFGAGTTLTVLGQSSRSS----------AVTLDESGGGLQTPGGALS
     scFv39 SRFSGSKSGSTATLTITGVQADDEAVYFCGNAD--T----IT-GIFGAGTTLTVLGQSSRSS----------TVTLDESGGGLQTPGGALS
     scFv54 SRFSGSKSGSTSTLTITGVQAEDEAVYYCGSRD-SS----YV-GIFGAGTTLTVLGQSSRSS----------TVTLDESGGGLQTPGGALS
    scFv136 SRFSGSKSGSTGTLTITGVQAEDEAVYYCGSRD-SN----YV-GIFGAGTTLTVLGQSSRSS----------TVTLDESGGGLQTPGGALS
     scFv13 SRFSGSKSGSTGTLTITGVQAEDEAVYYCGNADSS-----T-AAFGAGTTLTVLGQSSRSS----------TVTLDESGGGLQTPGGALS
     scFv47 SRFSGSKSGSTGTLTITGVQAEDEAVYYCGNADSSG-----A-AAFGAGTTLTVLGQSSRSS----------AVTLDESGGGLQTPGGALS
    scFv139 SRFSGSKSGSTGTLTITGVQAEDEAVYYCGNADSS-----T-AAFGAGTTLTVLGQSSRSS----------TVTLDESGGGLQTPGGALS
     scFv22 SRFSGSKSGSTATLTITGVQADDEAVYFCGSFDSST-------DIFGAGTTLTVLGQSSRSS----------TVTLDESGGGLQTPGRALS
     scFv53 SRFSGSKSGSTGTLTITGVQAEDEAVYFCGNGAT----------FGAGTTLTVLGQSSRSS----------TVTLDESGGGLQTPGRALS scFv27 SRFSGSKSGSTATLTITGVQADDEAVYYCGGFDSSS-----D-SGFGAGTTLTVLGQSSRSS----------TVTLDESGGGLQTPGRALS
     scFv40 SRFSGSTSGSTHTLTITGVQAEDEAIYFCGSFDSST----YA-SGFGAGTTLTVLGQSSRSS----------AVTLDESGGGLQTPGRALS
     scFv41 SRFSGSASGSTATLTITGVQAEDGAVYFCGSEDS-T----YV-GIFGAGTTLTVLGQSSRSS----------AVTLDESGGGLQTPGRALS
     scFv42 SRFSGSLSGSTGTLTITGVQAEDEAVYYCGGHDSST----YA-GIFGAGTTLTVLGQSSRSS----------AVTLDESGGGLQTPGGALS
     scFv48 SRFSGSKSGSTGTLTITGVQAEDEAVYYCGSTDSST----SA-AIFGAGTTLTVLGQSSRSS----------TVTLDESGGGLQTPGGALS
     scFv60 SRFSGSKSGSTGTLTITGVQAEDEAVYYCGSTDSST----SA-AIFGAGTTLTVLGQSSRSS----------TVTLDESGGGLQTPGGALS
     scFv43 SRFSGSTSGSTSTLTITGVQADDEAVYFCGSAD-SS----YV-GIFGAGTTLTVLGQSSRSS----------AVTLDESGGGLQTPGGALS
     scFv58 PRFSGSLSGSTATLTITGVQAEDEAVYYCGGYD-SS----YV-GLFGAGTTLTVLGQSSRSS----------TVTLDESGGGLQTPGGALS
     scFv56 SRFSGSKSGSTHTLTITGVQAEDEAVYYCGAYDGSS----YT-GIFGAGTTLTVLGQSSRSS----------TVTLDESGGGLQTPGGALS
     scFv59 SRFSGSKSGSTATLTITGVRADDSAVYYCASTDSSS-----T-GIFGAGTTLTVLGQSSRSS----------AVTLDESGGGLQTPGGALS
     scFv50 SRFSGSESGSTGTLTITGVQAEDEAVYYCGNADSS-----YV-GLFGAGTTLTVLGQSSRSS----------TVTLDESGGGLQTPGGALS
     scFv52 SRFSGSASGSTATLTITGVQAEDEAVYYCGSFDSSA----GYG-GIFGAGTTLTVLGQSSRSS----------TVTLDESGGGLQTPGGALS
    scFv121 SRFSGSASGSTATLTITGVQAEDGAVYFCGSEDST-----YV-GIFGAGTTLTVLGQSSRSS----------AVTLDESGGGLQTPGRALS
    scFv123 SRFSGSASGSTAPLTITGVQAEDGAVYFCGSEDST-----YV-GIFGAGTTLTVLGQSSRSS----------AVTLDESGGGLQTPGRALS
     scFv51 SRFSGSKSGSTGTLTITGVQVDDEAVYYCGSRDSS-----YI-GTFGAGTTLTVLGQSSRSS----------AVTLDESGGGLQTPGRALS scFv45 SRFSGSKSGSTGTLTITGVQAEDEAVYFCGSEDSST----D--AIFGAGTTLTVLGQSSRSS----------TVTLDESGGGLQAPGGALS
     scFv57 SRFSGSKSGSTGTLTITGVQAEDEAVYFCGSEDSST----D--AIFGAGTTLTVLGQSSRSS----------AVTLDESGGGLQTPGGALS
     scFv67 SRFSGSKSGSTGTLTITGVQAEDEAVYFCGSEDSST----D--AIFGAGTTLTVLGQSSRSS----------AVTLDESGGGLQTPGGALS
     scFv85 SRFSGSKSGSTGTLTITGVQAEDEAVYFCGSEDSST----D--AIFGAGTTLTVLGQSSRSS----------AVTLDESGGGLQTPGGALS
    scFv111 SRFSGSKSGSTGTLTISGVQAEDEAVYFCGSEDSNT----D--AIFGAGTTLTVLGQSSRSS----------AVTLDESGGGLQTPGGALS
    scFv106 SRFSGSASGSTATLTITGVQVEDEAVYYCGSEDSTT----D--AVFGAGTTLTVLGQSSRSS----------AMTLDESGGGLQTPGGALS
     scFv64 SRFSGSKSGSTGTLTITGVQAEDEAVYFCGSEDSST----D--AVFGAGTTLTVLGQSSRSS----------TVTLDESGGGLQTPGGTLS
    scFv113 SRFSGSKSGSTGTLTITGVQAEDEAVYFCGSEDSNT----D--AVFGAGTTLTVLGQSSRSS----------TVTLDESGGGLQTPGGTLS
    scFv120 SRFSGSKSGSTGTLTISGVQAEDEAVYFCGSEDSNS----D--AIFGAGTTLTVLGQSSRSS----------AVTLDEYGGGLQTPGGALS
     scFv95 SRFSGSGSGSTSTLTITGVQAEDEAVYYCGGYDGSS----D--AIFGAGTTLTVLGQSSRSS----------TVTLDESGGGLQTPGGALS
    scFv103 SRFSGSKSGSTGTLTITGVRAEDEAVYYCGGYDSS-----D--AIFGAGTTLTVLGQSSRSS----------TVTLDESGGGLQTPGGALS
     scFv97 SRFSGSKSGSTHTLTITGVQADDEAVYFCGGYDSNA----DD-GIFGAGTTLTVLGQSSRSS----------TVTLDESGGGLQTPGGTLS
      scFv3 SRFSGSESGSTATLTITGVRAEDEAVYYCGSGDNS-----GA-GIFGAGTTLTVLGQSSRSS----------AVTLDESGGGLQTPGGTLS
     scFv30 SRFSGSESGSTATLTITGVRAEDEAAYYCGSADSS-----DA-GIFGAGTTLTVLGQSSRSS----------AVTLDESGGGLQTPRRTLS
     scFv35 SRFSGSKSGSTATLTITGVRAEDEAVYYCGGYDSST----DA-GIFGAGTTLTVLGQSSRSS----------AVTLDESGGGLQTPGGGLS
```

```
  scFv23  SRFSGSTSGSTATLTITGVQADDEAVYSCGSYDSS-----YV-GIFGAGTTLTVLGQSSRSS----------TVTLDESGGGLQTPGGALS
 scFv138  SRFSGSTSGSTATLTITGVQADDEAVYSCGSYDSS-----YV-GIFGAGTTLTVLGQSSRSS----------TVTLDESGGGLQTPGGALS
   scFv5  SRFSGSASGSTATLTITGVQADDEAVYFCGSYEVNI----HE-GIFGAGTTLTVLGQSSRSS----------TVTLDESGGGLQTPGRALS
  scFv24  SRFSGSASGSTATLTITGVQADDEAVYYCGNADSST----YA-GIFGAGTTLTVLGQSSRSS----------AVTLDESGGGLQTPGGGLS
  scFv25  SRFSGSSSGSTGTLTITGVRAEDEAVYYCGSIDNTY---VGT-GAFGAGTTLTVLGQSSRSS----------TVTLDESGAGLQTPGRALS
  scFv55  SRFSGSSSGSTGTLTITGVRAEDEAVYYCGSIDNTY---VGT-GAFGAGTTLTVLGQSSRSS----------TVTLDESGGGLQTPGRALS
  scFv19  SRFSGSTSGSTSTLTITGVQAEDEAVYYCGSYDSSN----DS-GIFGAGTTLTVLSQSSRSS----------AVTLDESGGGLQTPGGGLS
  scFv66  SRFSGSTSGSTGTLTITGVQVEDEAVYFCGGYDGST----DA--IFGAGTTLTVLGQSSRSS----------AVTLDESGGGLQMPGGGLS
  scFv20  SRFSGSGSGSTNTLTIAGVRAEDEAVYYCGNEDSSG-------AAFGAGTTLTVLGQSSRSS----------AVTLDESGGGLQTPGGGLS
  scFv32  SRFSGASSGSTATLTITGVQADDEAVYFCGSADSSG-------AIFGAGTTLTVLGQSSRSS----------TVTLDESGGGLQTPGGGLS
 scFv134  SRFSGASSGSTATLTITGVQADDEAVYFCGSADSSG-------AIFGAGTTLTVLGQSSRSS----------TVTLDESGGGLQTPGGGLS
 scFv119  SRFSGASSGSTATLTITGVQADDEAVYFCGSADSSG-------AIFGAGTTLTALGQSSRSS----------TVTLEESGGGLHTPGGGLI
  scFv46  SRFSGASSGSTATLTITGVQADDEAVYFCGSADSSG-------AIFGAGTTLTVLGQSSRSS----------TVTLDESGGGLQTPGGGLS
  scFv34  SRFSGSTSGSTSTLTITGVQADDEAVYFCGGYD-SN----YI-GIFGAGTTLTVLGQSSRSS----------AVTLDESGGGLQTPRGALS
 scFv105  SRFSGSTSGSTSTLTITGVQADDEAVYFCGGYD-SN----YL-GIFGAGTTLTVLGQSSRSS----------AVTLDESGGGLQTPRGALS scFv112  SRFSGSKSGSTGTLTITGVQAEDEAVYYCGGYD-ST----YV-GIFGAGTTLTVLGQSSRSS----------AVTLDESGGGLQTPRGALS
 scFv118  SRFSGSKSGSTATLTITGVQVEDEAVYFCGGYD-SS----YV-GIFGVGTTLTVLGQSSRSS----------AVTLDESGGGLQTPRGALS
 scFv115  SRFSGSKSGSTATLTITGVQVEDEAVYYCGGYD-SS----YV-GIFGVGTTLTVLGQSSRSS----------AVTLDESGGGLQTPRGALS
  scFv82  SRFSGSKSGSTATLTITGVQANDEAVYFCGSYEGST----YS-GIFGAGTTLTVLGQSSRSS----------TVTLDESGGGLQTPGGGLS
  scFv65  SRFSGSKSGSTGTLTITGVQADDEAVYFCGGYDSSA-------GIFGAGTTLTVLGQSSRSS----------AVTLDESGGGLQTPGGALS
  scFv73  SRFSGSKSGSTGTLTITGVQADDEAVYFCGGYDSSA-------GIFGAGTTLTVLGQSSRSS----------AVTLDESGGGLHTPGGALS
  scFv90  SRFSGSTSGSTATLTITGVQADDEAVYFCGGYDSSA-------GIFGAGTTLTVLGQSSRSS----------AVTLDESGGGLQTPGGALS
  scFv68  SRFSGSKSGSTSTLTITGVQAEDEADYYCGSYNSNA---GYV-GIFGAGTTLTVLGQSSRSS----------TVTLDESGGGLQTPGGGLS
  scFv74  SRFSGSKSGSTSTLTITGVQADDEAVYYCGSYDSSA---GYV-GIFGAGTTLTVLGQSSRSS----------TVTLDESGGGLQTPGGGLS
 scFv114  SRFSGSKSGSTSTLTITGVQADDEAVYYCGSYDSSA---GYV-GIFGAGTTLTVLGQSSRSS----------TVTLDESGGGLQTPGGGLS
  scFv70  SRFSGSKSGSTATLTITGVQADDEAVYFCGGYDSST----YV-GIFGAGTTLTVLGQSSRSS----------AVTLDESGGGLQTPGGALS
  scFv92  SRFSGSKSGSTATLTITGVQADDEAVYFCGGYDSST----YV-GIFGAGTTLTVLGQSSRSS----------AVTLDESGGGLQTPGGALS
  scFv83  PRFSGSKSGSTGTLAITGVQADDEAVYFCGGYEGST----ST-GIFGAGTTLTVLGQSSRSS----------AVTLDESGGGLQTPGGALS
  scFv72  SRFSGSKSGSTGTLTITGVQAEDEAVYYCGGWDSYV-------GIFGAGTTLTVLGQSSRSS----------AVTLDESGGGLQTPGGGLS
 scFv102  SRFSGSASGSTATLTIAGVRAEDEAVYFCGSWDSST----SA-GIFGAGTALTVLGQSSRSS----------AVTLDESGGGLQTPGGGLS scFv86  SRFSGSKSGSTGTLTITGVQAEDEAVYFCGSYDSST----DT-GIFGAGTTLTVLGQSSRSS----------TVTLDESGGGLQTPGGALS
  scFv84  SRFSGSKSGSTGTLTITGVQADDEAVYFCGGYDSSA-------GIFGAGTTLTVLGQSSRSS----------AVTLDESGGGLQTPGGALS
 scFv110  SRFSGSASGSTATLTITGVQVEDEAVYFCGSYDSSS----IA-GIFGAGTTLTVLGQSSRFS----------TVTLDESGGGLQTPGGGLS
   scFv6  SRFSGSASGSTATLTITGVQADDEAIYFCGTADSTS-------SGA-GIFGAGTTLTVLGQSSRSS------TVTLDESGGGLQTPGGALS
  scFv38  SRFSGALSGSTATLTITGVQADDEAVYFCGSGDS-S---TVA-GIFGAGTTLTVLGQSSRSS----------AVTLDESGGGLQTPGGTLS
  scFv49  SRFSGSKSGSTGTLTITGVQADDEAVYFCGTRDS-----SVA-GIFGAGTTLTVLGQSSRSS----------AVTLDESGGGLQTPGGALS
 scFv100  SRFSGALSGSTSTLTITGVRAEDEAVYYCGSADI-----TYI-GIFGAGTTLTVLGQSSRSS----------TVTLDESGGGLQTPGGGLS
 scFv131  SRFSGSESGSPATLTITGVQADDEAVYFCGSGDS-----SGT-GIFGAGTTLTVLGQSSRSS----------AVTLDESGGGLQTPGGGLS
  scFv14  SRFSGSASGSTGTLTITGVQADDEAVYFCGSADS-T---Y---GIFGAGTTLTVLGQSSRSS----------AVTLDESGGGLQTPGGALS
  scFv16  SRFSGSTSGSTNTLTITGVQADDEAVYFCGSVDS-S---S---GVFGAGTTLTVLGQSSRSS----------AVTLDESGGGLQTPGGALS
  scFv26  SRFSGSTSGSTSTLTITGVQAEDEAVYFCGSYDS-S---NYV-GEFGAGTTLTVLGQSSRSS----------AVTLDESGGGLQTPGGALS
  scFv37  SRFSGSTSGSTNALTINGVQA-DYAVYFCGSVNC-S---S---GVFGAGTTLTVLGHSSTSS----------DVTLDHSRGGLQTPGGSLS
   scFv7  SRFSGSKSGSTSTLTITGVQADDEAIYYCGSWDSST---D---AAFGAGTTLTVLGQSSRSS----------TVTLDESGGGLQTPGGGLS
  scFv33  SRFSGSTSGSTNTLTITGVQVEDEAIYFCGGYDCST---GSVKASFGAGTTLTVLGQSSRSS----------AVTLDESGGGLQTPGGTLS
  scFv61  SRFSGSLSGSTGTLTITGVRAEDEAVYYCGSFDSSTDG--GYAAIFGAGTTLTVLGQSSRSY----------AVTLDESGGGLQTPGGGLS scFv62  SRFSGSLSGSTGTLTITGVRAEDEAVYYCGSFDSSTDG--GYAAIFGAGTTLTVLGQSSRSS----------AVTLDESGGGLQTPGGGLS
 scFv108  SRFSGSLSGSPGTLAITGVRAEDEAVYYCGSFHSSTDG--GYAAIFGAGTTLTVLGQTSRSS----------AVTLDESGGGLQTPGGGLS
  scFv96  SRFSGSLSGSTGTLTITGVRAEDEAVYYCGSFDSSTDG--GYAAIFGAGTTLTVLGQSSRSS----------AVTLDESGGGLQTPGGGLS
 scFv117  SRFSGSLSGSTGTLTITGVRAEDEAVYYCGSFDSSTDS--GYAAIFGAGTTLTVLGQSSRSS----------AVTLDESGGGLQTPGGALS
  scFv87  SRFSGSLSGSTGTLTITGVRAEDEAVYYCGSFDSSTDS--GYAAIFGAGTTLTVLGQSSRSS----------AVTLDESGGGLQTPGGGLS
  scFv98  SRFSGSTSGSMGTLTITGVQAEDEAVYFCGSFDSSSSSVSDTADIFGAGTTLTVLGQSSRSS----------TVTLDESGGGLQTPGGALS
  scFv69  SRFSGSKSSSTHTLTITGVQAEDEAVYYCESADSSS-------SIFGAGTTLTVLGQSSRSS----------AVTLDESGGGLQTPGGTLS
 scFv137  SRFSGSKSSSTHTLTITGVQADDEAVYYCESADSSS-------SIFGAGTTLTVLGQSSRSS----------AVTLDESGGGLQTPGGTLS
  scFv77  SRFSGSKSSSTHTLTITGVQAEDEAVYYCESADSSS-------SIFGAGTTLTVLGQSSRSS----------AVTLDESGGGLQTPGGTLS
  scFv93  SRFSGSKSSSTHTLTITGVQAEDEAVYYCESADSSS-------SIFGAGTTLTVLGQSSRSS----------TVTLDESGGGLQTPGGALS
  scFv71  SRFSGSKSSSTHTLTITGVQAEDEAVYYCESADST--------SIFGAGTTLTVLGQSSRSS----------AVTLDESGGGLQTPGGTLS
 scFv140  SRFSGSKSGPTATLTITGVQAEDEAVYFCGSRDNSY------VGIFGAGTTLTVLGQSSRSS----------AVTLDESGGGLQTPGGALS
  scFv15  SRFSGSLSGSTATLTITGVQPEDEAVYFCGGYDGNS-------GIFGAGTTLTVLGQSSRSS----------AVTLDESGGGLQTPGRALS
   scFv4  SRFSGSKSGPTATLTITGVQAEDEAVYFCGSRDNS-------YVGIFGAGTTLTVLGQSSRSS----------AVTLDESGGGLQTPGGALS
  scFv28  SRFSGSTSGSTSTLTITGVQADDEAVYFCGSADSST-----YAGIFGAGTTLTVLGQSSRSS----------AVTLDESGGGLQTPGGALS scFv9  SRFSGSESGSTATLTITGVRAEDEAVYYCGSGDNS------GAGIFGAGTTLTVLGQSSRSS----------AVTLDESGGGLQTPGGALS
  scFv10  SRFSGSKSGSTATLTITGVRAEDEAVYYCGSGDSS-------TGIFGAGTTLTVLGQSSRSS----------AVTLDESGGGLQTPGGTLS
  scFv29  SRFSGSKSGSTGTLTITGVQADDEAVYYCGSTDSSA-----D-GVFGAGTTLTVLGQSSRSS----------AVTLDESGGGLQTPGGGLS
  scFv31  SRFSGSLSGSTNTLTITGVQAEDEAVYFCGGYDSST-----DSGMFGAGTTLTVLGQSSRSS----------AVTLDESGGGLQTPGGALS
  scFv11  SRFSGSGSGSTNTLTIAGVRAEDEAVYYCGNEDSS-------GAAFGAGTTLTVLGQSSRSS----------AVTLDESGGGLQTPGGGLS
  scFv18  SRFSGSKSGSTATLTITGVQAEDEAVYFCGSADST-------DAVFGAGTTLTVLGQSSRSS----------AVTLDESGGGLQTPGGALS
  scFv36  SSLFCASSCSPATLLIIGVVADDDDVDYCGSANDNS-----SVVEVGATTTMIVRRSSSSSS----------AMMEDEGGGLLTTPGGLLI
  scFv44  SRFCCSASCSINALTINEDPAY-YAVYFCGSVDVFG-------GVFGASTTLTAPGSSSISS----------DETLDDSGSGLRTPGRALN
  scFv89  SRFSGSASCSTATLTITGVQVEDEAVYYCGSEDSTT------DAVFGAGTTLTVLGQSSRSS----------AVTLDESGGGLQTPGGALS
  scFv88  SRFSGSTSCSTATLTITGVQAEDEAVYFCGGYDSNY------IGIFGAGTTLTVLGQSSRSS----------AVTLDESGGGLQTPGRALS
  scFv63  SRFSGSKSSSTHTLTITGVQAEDEAVYYCESADSSS-------SIFGAGTTLTVLGQSSRSS----------AVTLDESGGGLQTPGGTLS
  scFv91  SRFSGSKSSSTHTLTITGVQAEDEAVYYCESADSSS-------SIFGAGTTLTVLGQSSRSS----------AVTLDESGGGLQTPGGTLS
  scFv79  SRFSGSKSGSTSTLTITGVQVQDEDDYFCGGYNKNT-----YADIFGAGTTLTVLRQSSTSS----------AVTMDDYGGGLLTTPGGALI
  scFv81  SRFSGSKSGSTATLTITGVQAEDEAVYFCGSEDSST------DAIFGAGTTLTVLGQSSRSS----------TVTLDESGGGLQAPGGALS
  scFv75  PRFSGSKSGSTGTLAITGVQAEDEAVYFCGGYEGST------STGIFGAGTTLTVLGQSSRSS----------AVTLDESGGGLQTPGGALS
consensus  SRFSGS.SGST.TLTITGVqa#DEAVY%CGs.#ss.    ....giFGAGTTLTVLGQSSRSS                    aVTLDESGGGLQTPGgaLS
```

```
scFv2   LVCKGSGFTFSSFDMFWVRQAPGKGLEWVAGIRN-DGSDTAYGAAVKGRATISKDNGQSTVRLQLNNLRAEDTGTYYCAKAA-GYCY---VY
scFv8   LVCKASGFTFSSFNMGWVRQAPGKGLEFVAGIDN-TGSFTHYGAAVKGRATISRDDGQSTVRLQLDNLRAEDTGTYYCAKAS-GYYY---SG
scFv104 LVCKASGFTFSSYTMGWVRQAPGKGLEFVAGIGN-TGRYTGYGSAVKGRATISRDNGQSTVRLQLNNLRAEDTGTYYCTKCAYGYYY---SW
scFv12  LVCKASGFTFSGYNMGWVRQAPGKGLEWVGGISG-SGRYTEYGAAVKGRATISRDNGQSTVRLQLNNLRAEDTGTYFCAKAAVSDYC---GG
scFv17  LVCKASGFTFSSYDMAWVRQAPGKGLEFVAGI-D-IGSYTGYGAAVKGRATISRDNGQSTVRLQLNNLRAEDTGTYYCAKAAGSYYY---SG
scFv21  LVCKASGFTFSSYDMFWVRQAPGKGLEFVAQINS-AGSYTNYGSAVKGRATISRDDGQSTVRLQLNNLRAEDTGIYFCAKSASGYYY---SG
scFv39  LVCKASGFTFSSYTMAWVRQAPGKGLEWVAGIND-GGSYTNYGAAVKGRATISRDNGQSTVRLQLNNLRAEDTAIYYCAKSAGGYYY---SG
scFv54  LVCEASGFTFSSYEMQWVRQAPGKGLEFVAAISS-DGSYTNYGAAVQGRATISRDNGQSTVRLQLSNLRAEDTATYYCARSPGGYTW---WP
scFv136 LVCKASGFTFSSYEMQWVRQAPGKGLEFVAAISS-DGSYTNYGAAVQGRATISRDNGQSTVRLQLSNLRAEDTATYYCARSPGGYTW---WP
scFv13  LVCKASGFTFSSYAMGWVRQAPGKGLEYVAAISS-AGSTTNYGAAVKGRATISRDNGQSTVRLQLNNLRAEDTATYFCAKAAGSGYY---VW
scFv47  LGCEASGFTFSSYAMGWVRQAPGKGLEYVATISS-AGSNTNYGAAVKGRATISRDNGQSTVRLQLNNLEDDDTATYFCAEAAGNGYY---VW
scFv139 LVCKASGFTFSSYAMGWVRQAPGKGLEYVAAISS-AGSTTNYGAAVKGRATISSDNGQSTVRLQLNNLRAEDTATYYCAKTAGSGYY---VW
scFv22  LVCKASGFTFSSFNMGWVRQAPGKGLEYVASISS-SGSYTAYGSAVKGRATISRDNGQSTVRLQLNNLRAEDTATYYCAKAAGSAYYYTAVT
scFv53  LVCKASGFTFSSFNMGWVRQAPGKGLEYVASISS-SGSYTAYGSAVKGRATISRDNGQSTVRLQLNNLRAEDTATYYCAKAAGSAYYYTAVT scFv27  LVCKASGFTFSSFNMGWVRQAPGKGLEYVASISS-SGSYTAYGSAVKGRATISRDNGQSTVRLQLNNLRAEDTATYYCAKAAGSAYYYTAVT
scFv40  LVCKASGFTFSSFNMGWVRQAPGKGLEYVASISS-SGSYTAYGSAVKGRATISRDNGQSTVRLQLNNLRAEDTATYYCAKAAGSAYYYTAVT
scFv41  LVCKASGFTFSSFNMGWVRQAPGKGLEYVASISS-SGSYTAYGSAVKGRATISRDNGQSTVRLQLNNLGAEDTATYYCAKAAGNAYYYTAVT
scFv42  LVCKASGFTFSSFNMGWVRQAPGKGLEYVASISS-SGSYTAYGSAVKGRATISRDNGQSTVRLQLNNLRAEDTATYYCAKAAGSAYYYTAVT
scFv48  LVCKASGFTFSSFNMGWVRQAPGKGLEYVASISS-SGSYTAYGSAVKGRATISRDNGQSTVRLQLNNLRAEDTATYYCAKAAGSAYYYTAVT
scFv60  LVCKASGFTFSSFNMGWVRQAPGKGLEYVASISS-SGSYTAYGSAVKGRATISRDNGQSTVRLQLNNLRAEDTATYYCAKAAGSAYYYTAVT
scFv43  LVCKASGFTFSSFNMGWVRQAPGKGLEYVASISS-SGSYTAYGSAVKGRATISRDNGQSTVRLQLNNLRAEDTATYYCAKAAGSAYYYTAVT
scFv58  LVCKASGFTFSSFNMGWVRQAPGKGLEYVASISS-SGSYTAYGSAVKGRATISRDNGQSTVRLQLNNLRAEDTATYYCAKAAGSAYYYTAVT
scFv56  LVCKASGFTFSSFNMGWVRQAPGKGLEYVASISS-SGSYTAYGSAVKGRATISRDNGQSTVRLQLNNLRAEDTATYYCAKAAGSAYYYTAVT
scFv59  LVCKASGFTFSSFNMGWVRQAPGKGLEYVASISS-SGSYTAYGSAVKGRATISRDNGQSTVRLQLNNLRAEDTATYYCAKAAGSAYYYTAVT
scFv50  LVCKASGFTFSSFNMGWVRQAPGKGLEYVASISS-SGSYTAYGSAVKGRATISRDNGQSTVRLQLNNLRAEDTATYYCAKAAGSAYYYTAAT
scFv52  LVCKASGFTFSSFNMGWVRQAPGKGLEYVASISS-SGSYTAYGSAVKGRATISRDNGQSTVRLQLNNLRAEDTATYYCAKAAGSAYYYTAVT
scFv121 LVCKASGFTFSSFNMGWVRQAPGKGLEYVASISS-SGSYTAYGSAVKGRATISRDNGQSTVRLQLNNLRAEDTATYYCAKAAGSAYYYTAVT
scFv123 LVCKASGFTFSSFNMGWVRQAPGKGLEYVASISS-SGSYTAYGSAVKGRATISRDNGQSTVRLQLNNLRAEDTATYYCAKAAGSAYYYTAVT
scFv51  LACKASGFTFSSFNMGWVRQAPGKGLEYVASISS-SGSYTAYGSAVKGRATISRDNGQSTVRLQLNNLRAEDTATYYCAKAAGSAYYYTAVT scFv45  LVCKASGFTFSSYDMGWIRQAPGKGLEYVAGITD-NGRYASYGSAVDGRATISRDNGQSSVRLQLNNLRAEDTGTYYCARDDGSGWT-----
scFv57  LVCKASGFTFSSYDMGWVRQAPGKGLEYVAGITN-DGRYASYGSAVDGRATISRDNGQSTVRLQLNNLRAEDTGTYYCARDDGSGWT-----
scFv67  LVCKASGFTFSSYDMGWVRQAPGKGLEYVAGITN-DGRYASYGSAVDGRATISRDNGQSTVRLQLNNLRAEDTGTYYCARDDGSGWT-----
scFv85  LVCKASGFTFSSYDMGWVRQAPGKGLEYVAGITN-DGRYASYGSAVDGRATISRDNGQSTVRLQLNNLRAEDTGTYYCARNDGSGWT-----
scFv111 LVCEASGFTFSSYDMGWIRQAPGKGLEYVAGITN-NGRYASYGSAVDGRATISRDNGQSTVRLQLNNLRAEDTGTYYCARDDGSGWT-----
scFv106 LVCKASGFTFSSYDMGWVRQAPGKGLEYVAGITN-DGRYASYGSAVDGRATISRDNGQSTVRLQLNNLRAEDTGTYYCARDDGSGWT-----
scFv64  LACKASGFTFSGYDMGWVRQAPGKGLEYVAGITS-DGRYASYGSAVDGRAAIWRDNGQSTVRLQLKNLRTEDTATYYCARNDGSGWN-----
scFv113 LACKASGFTFSGYDMGWVRQAPGKGLEYVAGITS-DGRYASYGSAVDGRAAIWRDNGQSTVRLQLKNLRTEDTATYYCARDDGSGWS-----
scFv120 LVCEASGFTFSSYDMLRIPHAPGKGLEYVAGLTS-NGRYASYGSAVDGRATISRDNGQSTWRLHLNNLGAEDTGPYYCAGYDGSGWT-----
scFv95  LVCKASGFTFSSHDMGWVRQAPGKGLEYVAGITD-DGRYASYGPAVDGRATISRDNGQSTVRLQLKNLRAEDTATYYCARDDGSGWS-----
scFv103 LVCKASGFTFSSHDMGWVRQAPGKGLEYVAGITD-DGRYASYGPAVDGRATISRDNGQSTVRLQLKNLRAEDTATYYCARDDGSGWS-----
scFv97  LVCKASGFTFSSYAMNWVRQAPGKGLEWVAGIYS-DGRYTNYGAAVKGRATISRDNGQSSVRLQLNNLRAEDTATYYCTKSADSDYG-----
scFv3   LVCKASGFTFSSNGMAWVRQAPGKGLEWVAGISS-SGSYTNYSAVKGRATISRDNGQSTVRLQLNNLRAEDTATYYCAKSSYAYYGF-G--
scFv30  LVCKASGFTFSDYGMAWVRQAPGKGLEWVAGIGS-SGSYTDYSAVKGRATISRDNGQSTVRLQLNNLRAEDTATYYCAKDIGSVYGC-GWW
scFv35  LVCKASGFTFSDYGMGWVRQAPGKGLEYVAGIDN-TGSSTGYGAAVKGRATISRDNRQSTVRLQLNNLRAEDTGIYFCAKTAGS--GG-GWW scFv23  LVCKASGFTFNSYALEWVRQAPGKGLEWVAGISG-DGSYRHYGSAVKGRATISRDSGQSTVRLQLNNLRAEDTGTYYCAKSTGSGAGW-G--
scFv138 LVCKASGFTFNSYALEWVRQAPGKGLEWVAGISG-DGSYRHYGSAVKGRATISRDSGQSTVRLQLNNLRAEDTGTYYCAKSTGSGAGW-G--
scFv5   LVCKASGFTFSSNGMYWVRQAPGKGLEWVAGISS-SGSYTNYAPAVKGRATISRDNGQSTVRLQLNNLRAEDTGTYYCAKGASSYS-----W
scFv24  LVCKASGFDFSTNAMGWVRQAPGKGLEWVAGI-SG-SGSSTNYATAVKGRATISRDNGQSTVRLQLNNLRAEDTGTYYCTKYVGDYY-----W
scFv25  LVCKGSGFTFSSFYMFWVRQAPGKGLEFVACISS-SGSSTRYGVVVKGRATISRDNGQSTVRLRLNNLRADDTGTYYCARGTSSG-------
scFv55  LVCKGSGFTFSSFYMFWVRQAPGKGLEFVASISS-SGSSTRYGVVVKGRATISRDNGQSTVRLRLNNLRAEDTGTYYCARGTSSG-------
scFv19  LVCKASGFTFSTFNMFWVRQAPGKGLEFVAGISI-TGGWTGYGAAVKGRATISRDNGQSTVRLQLNNLRAEDTGTYYCAKPAAWSCY-----
scFv66  LVCKASGFDFSSSEMQWVRQAPGKGLQWV-GIIS-SSGSTYYGSAVKGRATISRDNGQSAVRLQLNNLRAEDTGTYYCTKTTAYA-------
scFv20  LVCKASGFTFSDYDMFWVRQAPSKGLEFVAAITS-SGTGTKYGAAVKGRATISKDNGQRTVRLQLNSLGAEDTGTYYCARS--DADS----T
scFv32  LVCKGSGFAFSNYGMGWMRQAPGKGLEYVAGI-S-TGSYTDYGPAVKGRATISRDNGQSTVRLQLNNLRAEDAAIYFCAKT--AGSGYGCGS
scFv134 LVCKGSGFAFSNYGMGWMRQAPGKGLEYVAGI-S-TGSYTDYGPAVKGRATISRDNGQSTVRLQLNNLRAEDAAIYFCAKT--AGSGYGCGS
scFv119 LLCKGSGVSFCNYGMGWMRRDPGGGLEYVAGI-S-TGSYTYYGPAVKGRGTVSRDNGQSTMRLQLNNLRAEDETIYFCART--DASSHGCGS
scFv46  LVCKGSGFAFSNYGMGWMRQAPGKGLEYVAGI-S-TGSYTDYGPAVKGRATISRDNGQSTVRLQLNNLRAEDAAIYFCAK------------
scFv46  LVCKASGFTFSSYSMAWMRQAPGKGLEFVAGIQN-DGSITDYGSAVDGRATISRDDGQSTVRLQLNNLRTEDTATYYCAK---TTVA---DG
scFv105 LVCKASGFTFSSYSMAWMRQAPGKGLEFVAGIQN-DGSITDYGSAVDGRATISRDDGQSTVRLQLNNLRTEDTATYYCAK---TTVA---DG scFv112 LVCKASGFTFSSYSMAWMRQAPGKGLEFVAGIQN-DGSITDYGSAVDGRATISRDDGQSTVRLQLNNLRTEDTATYYCAK---TTVA---DG
scFv118 LVCKASGFTFSSYSMAWMRQAPGKGLEFVAGIQN-DGSITDYGSAVDGRATISRDDGQSTVRLQLNNLRTEDTATYYCAK---TTVA---DG
scFv115 LVCKASGFTFSSYSMAWMRQAPGKGLEFVPGILN-DGSITDYGSADDGRATISRDDGQSTVRLHLINLRTEDTATYYCAK---TTVG---DG
scFv82  LVCKASGFS-SSHGMGWMRQAPGKGLEFVAGIRS-DGSTAYGAAVDGRATITRDDGQSTVTLQLNNLRAEDTATYFCAKN--TTVA---DG
scFv65  LVCKASGFDFSSYGMGWMRQAPGKGLEFVAAIRK-DGSYTAYGSAVDGRATISRDDGQSTVRLQLGNLRAEDTATYFCAKT--NSYN---SA
scFv73  LVCKASGFDFSSYGMGWMRQAPGKGLEFVAAIRK-DGSYTAYGSAVDGRATISRDDGQSTVRLQLGNLRAEDTATYFCAKT--NSYN---SA
scFv90  LVCKASGFS-SSHGMGWMRQAPGKGLEFVAGIRS-DGSTAYGAAVDGRATISRDDGQSTVRLQLNNLRAEDTATYFCAKT--NSYN---SA
scFv68  LVCKASGFTFSSYGMGWMRQAPGKGLEFVAGIRK-DGRSTAYGAAVDGRATISRDDGQSTLRLQLGNLRAEDTGTYFCAKT--NSYD---SA
scFv74  LVCKASGFTFSSYGMGWMRQAPGKGLEFVAGIRK-DGSSTAYGAAVDGRATISRDDGQSTLRLQLGNLRAEDTGTYFCAKT--NSYN---SA
scFv114 LVCKASGFTFSSYGMGWMRQAPGKGLEFVAGIRK-DGSSTAYGAAVDGRATISRDDGQSTLRLQLGNLRAEDTGTYFCAKT--NSYN---SA
scFv70  LVCKASGFDFSSYGMGWMRQAPGKGLEFVAAIRK-DGSYTAYGSAVDGRATISRDDGQSTVRLQLGNLRAEDTATYFCAKT--NSYN---SA
scFv92  LVCKASGFDFSSYGMGWMRQAPGKGLEFVAAIRK-DGSYTAYGSAVDGRATISRDDGQSTVRLQLGNLRAEDTATYFCAKT--NSYN---SA
scFv83  LVCKASGFDFSSYGMGWMRQAPGKGLEFVAAIRK-DGSYTAYGSAVDGRATISRDDGQSTVRLQLGNLRAEDTATYFCAKT--NSYN---SA
scFv72  LVCKASGFS-SSHGMGWMRQAPGKGLEFVAGIRS-DGSTAYGAAVDGRATITRDDGQSTVTLQLNNLRAEDTATYFCAKT--NSYN---SA
scFv102 LVCKASGFS-SSHGMGWMRQAPGKGLEFVAGIRS-DGSTAYGAAVDGRATITRDDGQSTVTLQLNNLRAEDTATYFCAKT--NSYN---SA
```

```
  scFv86  LVCKASGFIFSSHGMGWMRQAPGKGLEFVAAISK-DGTATYYGPAVKGRATISRDDGQTTVRLQLNNLRAEDTATYFCAKT--KYYN---SA
  scFv84  LVCKASGFDFSSYGMWMRQAPGKGLEFVAAIRK-DGSYTAYGAAVDGRATISRDDGQSTVRLQLGNLRAEDTATYFCAKT--NSYN---SA
 scFv110  LVCKASGFTFSSYGMAWMRQAPGKGLEWLAGIYR-DDDSTYYAPAVKGRATISRDNGQSTVRLQLNNLRTEDTATYYCAKE--SA-----SG
   scFv6  LVCKGSGFTFSSFNMFWVRQAPGKGLEWVAGIYSSGGGETNYGAAVKGRATISRDNGQSTVRLQLNNLRAEDTGTYYCAKESADVG---CPF
  scFv38  LVCKASGFDFSSYGMHWVRQEPGKGLEWVAGI-SRTGSFTYYGAAVKGRAAISRDNGQSTVRLQLNNLRAEDTGTYYCAKGGSDCSGYRCDY
  scFv49  LVCKGSGFTFSDYSMMWVRQAPGKGLEWVAGI-SSNSGTTYYGSAVKGRATISRDNGQSTVRLQLNNLRAEDTATYFCAKTTGVNS-----Y
 scFv100  LVCKASGFTFSSHTMQWVRQAPGKGLEWVAEISADGSYTTYYGAAVKGRATISRDNGQSTVRLQLNNLRAEDTATYFCAKSGYGGA----GW
 scFv131  LVCKASGFSPSDYTMNWVRQAPGKGLEWVGQISSDNGRYTTYGAAVKGRATISRDDGQSTVRLQLNNLKAEDTATYYCAKESDGDY----NG
  scFv14  LVCRASGFTFSDYGMEWVRQAPGKGLEWVAGI-DDDGSTTFYRPAVKGRATISRDDGQSTVRLQLNNLRAEDTATYYCAKS-AGRG----WN
  scFv16  LVCKASGFTFSSFDMFWVRQAPGKGLEYVAEI-SDTGSSTYYGAAVKGRATISRDNGQSTVRLQLNNLRAEDTGTYFCAKSHSGYG----WS
  scFv26  LVCKASGFTFSSFDMFWVRQAPGKGLEYVAEI-SDTGSSTYYGAAVKGRATISRDNGQSTVRLQLNNLRAEDTGTYFCAKSHSGYG----WS
  scFv37  LVCNASGFTFSSFHMFWVRQAPGEGLEYVAEI-TDTGSSTYYGAAVKGRATISRDNGQSTVRLQLNNLMADDTGTYFCAKSHSGYG----WS
   scFv7  LVCKASGFTFSDYGMGWVRQAPGKGLEFVAGIGN-TGSYTYYGSAVKGRATISRDNGQSTVRLQLNNLRAEDTGIYFCAKSTDYWTY-----
  scFv33  LVCKGSGFTFSSHGMGWVRQAPGKGLEWVAGI-Y-SGSSTYYGAAVKGRATISRDNGQSTVRLQLNNLRAEDTATYYFCTRGGG--------
  scFv61  LVCKASEFTFSSYAMEWVRQAPGKGLEWVAYINS-DGSSTWYAPAVKGRATISRDNGQSTVRLQLNSLRAEDTATYYCTRG---S------- scFv62  LVCKASEFTFSSYAMEWVRQAPGKGLEWVAYINS-DGSSTWYAPAVKGRATISRDNGQSTVRLQLNSLRAEDTATYYCTRG---S-------
 scFv108  LLCKASEFTSISYAMEWVRQAPGKGLEWVAYINS-DGSSTWHAPAVKGRATISRDNGQSTVRLQLNSLRAEDTATYYCTIC---S-------
  scFv96  LVCKASEFTFSSYAMEWVRQAPGKGLEWVAYINS-DGSSTWYAPAVKGRATISRDNGQSTVRLQLNSLRAEDTATYYCTRG---S-------
 scFv117  LVCRASGITFSTYAMEWVRQAPGKGLEFVAVVNA-AGS-TYYGAAVKGRATISRDNGQSTVRLQLNNLRAEDTGTYYCTRG---S-------
  scFv87  LVCKASGFTFSSYAMEWVRQAPGKGLEWVAYINS-DGSSTWYATAVKGRATISRDNGQSTVRLQLNRGEDTATYFCAKTKYYN-------
  scFv98  LVCKASGFTFNSYALEWVRQAPGKGLEWVAGISG-GSFTHYGSAVKGRATISRDNGQSTVRLHLNNLRAEDTGTYYCAKSTGSSGAGW----
  scFv69  LVCKASGFTFSSFNMFWVRQAPGKGLEFVAGIGN-TGRSTGYGSAVKGRATISRDNGQSTVRLQLNNLRAEDTGTYYCAKAY---------
 scFv137  LVCKASGFTFSSFNMFWVRQAPGKGLEFVAGIGN-TGRSTGYGSAVKGRATISRDNGQSTVRLQLNNLRAEDTGTYYCAKAY---------
  scFv77  LVCKASGFTFSSFNMFWVRQAPGKGLEFVAGIGN-TGRSTGYGSAVKGRATISRDNGQSTVRLQLNNLRAEDTGTYYCAKAY---------
  scFv93  LVCKASGFTFSSFNMFWVRQAPGKGLEFVAGIGN-TGGSTGYGSAVKGRATISRDNGQSTVRLQLNNLRAEDTGTYYCAKAY---------
  scFv71  LVCKASGFTFSSFNMFWVRQAPGKGLEFVAGIGN-TGRSTGYGSAVKGRATISRDNGQSTVRLQLNNLRAEDTGTYYCAKAL---------
 scFv140  LVCKASGFTFSSYDMFWVRQAPGKGLEFVAQINS-AGSYTNYGSAVKGRATISRDDGQSTVRLQLNNLRAEDTGIYFCAKSASGYYY----S
  scFv15  LVCKASGFTFSSYDMGWVRQAPGKGLEWVAYINSGSSYTTYGTAVKGRASISRDNGQSTVRLQLNNLRVEDTGIYFCAKGASGYY------
   scFv4  LVCKASGFTFSSYDMFWVRQAPGKGLEFVAQINS-AGSYTNYGSAVKGRATISRDNGQSTVRLQLNNLRAEDTGIYFCAKSASGYYY----S
  scFv28  LVCKASGFTFSSFNMFWVRQAPGRGLEFVAGITS-SGGSTYYGTAVKGRATISRDNGQSTVRMQLNNLRAEDTGTYFCARGAYDYYF----Y scFv9  LVCKASGFTFSSNGMAWVRQAPGKGLEWVAGISS-SGSYTNYGSAVKGRATISRDNGQSTVRLQLNNLRAEDTATYYCAKSSYAYYG----F
  scFv10  LVCKGSGFTFSSVNMFWVRQAPGKGLEWVAGIYS-SGSSTHYGAAVKGRATISRDNGQSTVRLQLNNLRAEDTGIYYCAKDA-GCYT----S
  scFv29  LVCKGSGFTFSSFDMFWVRQAPGKGLEWVAGIRN-DGSDTAYGAAVKGRATISRDKDNGQSTVRLQLNNLRAEDTGTYYCAKAAG-YCY----V
  scFv31  LVCKGSGFTFSSYDMAWVRQEPSKGLEFVASISN-SGSDTSYAPAVKGRATISRDNGQSTVRLQLNNLRAEDTATYYCAKSAGSYYW----N
  scFv11  LVCKASGFTFSDYDMFWVRQAPSKGLEFVAAITS-SGTGTKYGAAVKGRATISRDNGQRTVRLQLNSLGAEDTGTYYCARSDADSTT----W
  scFv18  LVCKASGFTFSDYDMFWVRQAPSKGLEFVAAITS-SGTGTKYGAAVKGRATISRDNGQSTVRLQLNSLRAEDTGTYYCARSDADSTT----W
  scFv36  LCCAASGFIFSYYEMLWLHPAPGEVQDFVTIISC-GGNYTYYGSAVDGGAIISRDDGKRMLMLQLNILEDDDTGFYFCADGASGYYY----G
  scFv44  VFCFASGFFFMIFELFGVRQAPGWVLEYIADVSD-TGNSTYYRAAVNVRAAISRNNGQMTLRLLLNDHTADDTCTYFCGYCHSDYCW-----
  scFv89  LVCKASGFTFSSYDMGWVRQAPGKGLEYVAGITN-DGRYASYGSAVDGRATISRDNGQSTVRLQLNNPQG
  scFv88  LVCKASGFTFSSYSMAWVRQAPGKGLEFVAGIQN-DGSITDYGSAVDGRATISRDDGQSTVRLQLNNLRTEDTATYYCAKTTVADGVI
  scFv63  LVCKASGFTFSSFNMFWVRQAPGKGLEFVAGIGN-TGTSTGYGSAVKGRATISRDNGQSTVRLQLNNLRAEDTGTYYCAQAYGDS-------
  scFv91  LVCKASGFTFSSFNMFWVRQAPGKGLEFVAGIGN-TGTSTGYGSAVKGRATISRDNGQSTVRLQLNNLRAEDTATYYCAKAYGDS
  scFv79  LLCWASGF-FTFHGLDWMRQAPATGLEFVAGIGS-DGDSTAYGAAVDGHATVSRDNGQSTMRLQLNILRAEDDATYFCA
  scFv81  LVCKASGFTFSSYDMGWIRQAPGKGLEYVAGITD-NGTYASYGS
  scFv75  LVCKASGFDFSSYGMGWMRQAPGKGLEFVAAIKK-DGSYTAYGAAVDGRATISRDDGQSTVRLQLGNLRAEDTAP
consensus  LVCKaSGFtFSsy.M.WvRQRPGKGLE.VAgI.. .Gs.t.YG.AVkGRATISRD#GQSTvRLQLnnLraEDT.tY%Cak............

scFv1  IG-AGEIDAWGHGTEVIVSSTSGQAGQHHHHHHGAYPYDVPDYAS
   scFv2  SC-AGSIDAWGHGTEVIVSSTSGQAGQHHHHHHGAYPYDVPDYAS
   scFv8  VN-AGSIDAWGHGTEVIVSSTSGQAGQHHHHHHGAYPYDVPDYAS
 scFv104  GNIAGSIDAWGHGTEVIVSSTSGQAGQHHHHHHGAYPYDVPDYAS
  scFv12  GC-AGDIDAWGHGTEVIVSSTSGQAGQHHHHHHGAYPYDVPDYAS
  scFv17  A--AGSIDAWGHGTEVIVSSTSGQAGQHHHHHHGAYPYDVPDYAS
  scFv21  SD-AGDIDAWGHGTEVIVSSTSGQAGQHHHHHHGAYPYDVPDYAS
  scFv39  A--AGTIDAWGHGTEVIVSSTSGQAGQHHHHHHGAYPYDVPDYAS
  scFv54  GA-AGGIDAWGHGTEVIVSSTSGQAGQHHHHHHGAYPYDVPDYAS
 scFv136  GA-AGGIDAWGHGTEVIVSSTSGQAGQHHHHHHGAYPYDVPDYAS
  scFv13  SAIAGDIDAWGHGTEVIVSSTSGQAGQHHHHHHGAYPYDVPDYAS
  scFv47  SAIAGDIDAWGHGTDVIVSSTSGQAGQHHHHHHGAYPYDVPDYAS
 scFv139  SAIAGDIYAWGHGTEVIVSSTSGQAGQHHHHHHGAYPYDVPDYAS
  scFv22  PAFAGSIDAWGHGTEVIVSSTSGQAGQHHHHHHGAYPYDVPDYAS
  scFv53  PAFAGSIDAWGHGTEVIVSSTSGQAGQHHHHHHGAYPYDVPDYAS scFv27  PAFAGSIDAWGHGTEVIVSSTSGQAGQHHHHHHGAYPYDVPDYAS
  scFv40  PAFAGSIDAWGHGTEVIVSSTSGQAGQHHHHHHGAYPYDVPDYAS
  scFv41  PAFAGSIDAWGHGTEVIVPSTSGQAGQHHHHHHGAYPYDVPDYAS
  scFv42  PAFAGSIDAWGHGTEVIVSSTSGQAGQHHHHHHGAYPYDVPDYAS
  scFv48  PAFAGSIDAWGHGTEVIVSSTSGQAGQHHHHHHGAYPYDVPDYAS
  scFv60  PAFAGSIDAWGHGTEVIVSSTSGQAGQHHHHHHGAYPYDVPDYAS
  scFv43  PAFAGSIDAWGHGTEVIVSSTSGQAGQHHHHHHGAYPYDVPDYAS
  scFv58  PAFAGSIDAWGHGTEVIVSSTSGQAGQHHHHHHGAYPYDVPDYAS
  scFv56  PAFAGSIDAWGHGTEVIVSSTSGQAGQHHHHHHGAYPYDVPDYA
  scFv59  PAFAGSIDAWGHGTEVIVSSTSGQAGQHHHHHHGAYPYDVPDYAS
  scFv50  PAFAGSIDAWGHGTEVIVSSTSGQAGQHHHHHHGAYPYDVPDYAS
  scFv52  PAFAGSIDAWGHGTEVIVSSTSGQAGQHHHHHHGAYPYDVPDYAS
 scFv121  PAFAGSIDAWGHGTEVIVSSTSGQAGQHHHHHHGAYPYDVPDYAS
 scFv123  PAFAGSIDACGHGTEVIVSSTSGQAGQHHHHHHGAYPYDVPDYAS
  scFv51  PAFAGSIDAWGHGTEVIVSSTSGQAGQHHHHHHGAYPYDVPDYAS
```

```
scFv45    ---GNSIDAWGHGTEIIVSSTSGQAGQHHHHHGAYPYDVPDYAS
scFv57    ---GNTIDTWGHGTEVIVSSTSGQAGQHHHHHGAYPYDVPDYAS
scFv67    ---GNTIDTWGHGTEVIVSSTSGQAGQHHHHHGAYPYDVPDYAS
scFv85    ---GNTIDTWGHGTEVIVSSTSGQAGQHHHHHGAYPYDVPDYAS
scFv111   ---GNTIDAWGHGTEVIVSSTSGQAGQHHHHHGAYPYDVPDYAS
scFv106   ---GNTIDTWGHGTEVIVSSTSGQAGQHHHHHGAYPYDVPDYAS
scFv64    ---GNNIDAWGHGTEVIVSSTSGQAGQHHHHHGAYPYDVPDYAS
scFv113   ---GNNIDAWGHGTEVIVSSTSGQAGQHHHHHGAYPYDVPDYAS
scFv120   ---GNTIEAWGHRTEVLVSSTSGQAGQHHHHHGAYPYDVPDYAS
scFv95    ---GDTIDTWGHGTEVIVSSTSGQAGQHHHHHGAYPYDVPDYAS
scFv103   ---GDTIDTWGHGTEVIVSSTSGQAGQHHHHHGAYPYDVPDYAS
scFv97    ---GDNIDAWGHGTEVIVSSTSGQAGQHHHHHGAYPYDVPDYAS
scFv3     ---APFIDAWGHGTEVIVSSTSGQAGQHHHHHGAYPYDVPDYAS
scFv30    ACSAGSIDAWGHGTEVIVSSTSGQAGQHHHHHGAYPYDVPDYAS
scFv35    ---SDWIDAWGHGTEVIVSSTSGQAGQHHHHHGAYPYDVPDYAS scFv23    ---ASNIDAWGHGTEVIVSSTSGQAGQHHHHHGAYPYDVPDYAS
scFv138   ---ASNIDAWGHGTEVIVSSTSGQAGQHHHHHGAYPYDVPDYAS
scFv5     --DGGSIDAWGHGTEVIVSSTSGQAGQHHHHHGAYPYDVPDYAS
scFv24    YIDAGSIDAWGHGTEVIVSSTSGQAGQHHHHHGAYPYDVPDYAS
scFv25    ---ANTIDAWGHGTEVIVSSTSGQAGQHHHHHGAYPYDVPDYAS
scFv55    ---ANTIDAWGHGTEVIVSSTSGQAGQHHHHHGAYPYDVPDYAS
scFv19    RGCGGEFDAWGHGTEVIVSSTSGQAGQHHHHHGAYPYDVPDYAS
scFv66    ----HDIDAWGHGTEVIVSSTSGQAGQHHHHHGAYPYDVPDYAS
scFv20    TWSAGEIDAWGHGTEVIVSSTSGQAGQHHHHHGAYPYDVPDYAS
scFv32    GTDLGSIDAWGHGTEVIVSSTSGQAGQHHHHHGAYPYDVPDYAS
scFv134   GTDLGSIDAWGHGTEVIVSSTSGQAGQHHHHHGAYPYDVPDYAS
scFv119   GTDLGSIDAWGHGTEVLLSSTSGQAGQHHHHHGAYPYDVPDYAS
scFv46    ----------GHGTEIIVSSTSGQAGQHHHHHGAYPYDVPDYAS
scFv34    VIGAYGIDAWGHGTEVIVSSTSGQAGQHHHHHGAYPYDVPDYAS
scFv105   VIGAYGIDAWGHGTEVIVSSTSGQAGQHHHHHGAYPYDVPDYAS scFv112   VIGAYGIDAWGHGTEVIVSSTSGQAGQHHHHHGAYPYDVPDYAS
scFv118   VIGAYGIDAWGHGTEVIVSSTSGQAGQHHHHHGAYPYDVPDYAS
scFv115   VIGAYAIDAWGHGTEVIVSSTSGQAGQHHHHHGAYPYDVPDYAS
scFv82    VIGAYGIDAWGHGTEVIVSSTSGQAGQHHHHHGAYPYDVPDYAS
scFv65    GI----IDAWGHGTEVIVSSTSGQAGQHHHHHGAYPYDVPDYAS
scFv73    GI----IDAWGHGTEVIVSSTSGQAGQHHHHHGAYPYDVPDYAS
scFv90    GI----IDAWGPGTEVIVSSTSGQAGQHHHHHGAYPYDVPDYAS
scFv68    GI----IDAWGHGTEVIVSSTSGQAGQHHHHHGAYPYDVPDYAS
scFv74    GI----IDAWGHGTEVIVSSTSGQAGQHHHHHGAYPYDVPDYAS
scFv114   GI----IDAWGHGTEVIVSSTSGQAGQHHHHHGAYPYDVPDYAS
scFv70    GI----IDAWGHGTEVIVSSTSGQAGQHHHHHGAYPYDVPDYAS
scFv92    GI----IDAWGHGTEVIVSSTSGQAGQHHHHHGAYPYDVPDYAS
scFv83    GI----IDAWGHGTEVIVSSTSGQAGQHHHHHGAYPYDVPDYAS
scFv72    GI----IDAWGHGTEVIVSSTSGQAGQHHHHHGAYPYDVPDYAS
scFv102   GI----IDAWGHGTEVIVSSTSGQAGQHHHHHGAYPYDVPDYAS scFv86    GI----IDAWGHGTEVIVSSTSGQAGQHHHHHGAYPYDVPDYAS
scFv84    GI----IDAWGHGTEVIVSSTSGQAGQHHHHHGAYPYDVPDYAS
scFv110   GWNAGWIDAWGHGTEVIVSSTSGQAGQHHHHHGAYPYDVPDYAS
scFv6     T--AGCIDTWGHGTEVIVSSTSGQAGQHHHHHGAYPYDVPDYAS
scFv38    S--AGNIDGWGHGTEVIVSSTSGQAGQHHHHHGAYPYDVPDYAS
scFv49    D--VPAIDAWGHGTEVIVSSTSGQAGQHHHHHGAYPYDVPDYAS
scFv100   G--AGLIDAWGHGTEVIVSSTSGQAGQHHHHHGAYPYDVPDYAS
scFv131   G--AGLIDAWGHGTEVIVSSTSGQAGQHHHHHGAYPYDVPDYAS
scFv14    V--AGWIDAWGHGTEVIVSSTSGQAGQHHHHHGAYPYDVPDYAS
scFv16    T--AGDIDAWGHGTEVIVSSTSGQAGQHHHHHGAYPYDVPDYAS
scFv26    T--AGDIDAWGHGTEVIVSSTSGQAGQHHHHHGAYPYDVPDYAS
scFv37    T--AGDIDAWGHGTEVIVSSTSGQAGQHHHHHGAYPYDVPDYAS
scFv7     ---AGTIDAWGHGTEVIVSSTSGQAGQHHHHHGAYPYDVPDYAS
scFv33    ---AGRIDTWGHGTEVIVSSTSGQAGQHHHHHGAYPYDVPDYAS
scFv61    --GGENIDTWGHGTEVIVSSTSGQAGQHHHHHGAYPYDVPDYAS scFv62    --GGENIDTWGHGTEVIVSSTSGQAGQHHHHHAAYPYDVPDYAS
scFv108   --GGENIYTCCHGTEVIVSSTSGQDGQHHHHHGAYPYDVPDYAS
scFv96    --GGENIDTWGHGTEVIVSSTSGQAGQHHHHHGAYPYDVPDYAS
scFv117   --GGENIDAWGHGTEVIVSSTSGQAGQHHHHHGAYPYDVPDYAS
scFv87    --SAGIIDAWGHGTEVIVSSTSGQAGQHHHHHGAYPYDVPDYAS
scFv98    --GASNIDAWGHGTEVIVSSTSGQAGQHHHHHGAYPYDVPDYAS
scFv69    --GDSNIDAWGHGTEVIVSSTSGQAGQHHHHHGAYPYDVPDYAS
scFv137   --GDSNIDAWGHGTEVIVSSTSGQAGQHHHHHGAYPYDVPDYAS
scFv77    --GDSNIDAWGHGTEVIVSSTSGQAGQHHHHHGAYPYDVPDYAS
scFv93    --GDSNIDTWGHGTEVIVSSTSGQAGQHHHHHGAYPYDVPDYAS
scFv71    --------WGHGTEVIVSSTSGQAGQHHHHHGAYPYDVPDYAS
scFv140   GSDAGDIDAWGTGPKSSSPSTSGPGRPAPSPSPWRIPVRRSGLRFLERWARDQLSCTKWLILACKSTHECTERMINALHISANDHATAG
scFv15    ------------------SSSGQAGQHHHHHGAYPYDVPDYAS
scFv4     GSDAGDIDAWGHGTEVIVSSTSGQAGQHHHHHGAYPYDVPDYAS
scFv28    WNYAGTIDAWGHGTEVIVSSTSGQAGQHHHHHGAYPYDVPDYAS
```

```
     scFv9   G--APFIDAWGHGTEVIVSSTSGQAGQHHHHHGAYPYDVPDYAS
     scFv10  GDTAGCIDAWGHGTEVIVSSTSGQAGQHHHHHGAYPYDVPDYAS
     scFv29  YSCAGSIDAWGHGTEVIVSSTSGQAGQHHHHHGAYPYDVPDYAS
     scFv31  AGGAGSIDTWGHGTEVIVSSTSGQAGQHHHHHGAYPYDVPDYAS
     scFv11  S--AGEIDAWGHGTEVIVSSTSGQAGQHHHHHGAYPYDVPDYAS
     scFv18  S--AGEIDAWGHGTEVIVSSTSGQAGQHHHHHGAYPYDVPDYAS
     scFv36  GADAGDIDAWGHGTEVIVSSTSGQAGQHHHHHGAYPYDVPDYAS
     scFv44  -STAGDIDAWSHVIDFIVSSTSGQAGQHHHHHGAYPYDVPDYAS
     scFv89
     scFv88
     scFv63  -----NIDRMGPRDR
     scFv91
     scFv79
     scFv81
     scFv75
     consensus ...a..idawghgtevivsstsgqagqhhhhhgaypydvpdyas
```

REFERENCES

All publications, patents and sequence database entries mentioned herein, including those items listed below, are hereby incorporated by reference in their entirety as if each individual publication or patent was specifically and individually indicated to be incorporated by reference. In case of conflict, the present application, including any definitions herein, will control.

What is claimed is:

1. An isolated antibody that specifically binds and stabilizes oxidized Protein Tyrosine Phosphatase 1B (PTP1B-OX) or an antibody fragment that specifically binds and stabilizes PTP1B-OX, but does not bind to or directly inhibit the activity of reduced, active Protein Tyrosine Phosphatase 1B (PTP1B).

2. The isolated antibody, or the antibody fragment of claim 1, wherein the antibody or antibody fragment comprises an amino acid sequence selected from the amino acid sequence of any one of SEQ ID NO: 26 to SEQ ID NO: 29; SEQ ID NO: 100; SEQ ID NO: 130; SEQ ID NO: 67; SEQ ID NO: 94; SEQ ID NO: 95; SEQ ID NO: 97; SEQ ID NO: 142; SEQ ID NO: 81; and SEQ ID NO: 132.

3. The isolated antibody, or the antibody fragment of claim 1, wherein the antibody or antibody fragment comprises a $V_H$ fragment, a $V_L$ fragment, or a $V_H$ fragment and a $V_L$ fragment selected from the amino acid sequence of any one of SEQ ID NO: 26 to SEQ ID NO: 29; SEQ ID NO: 100; SEQ ID NO: 130; SEQ ID NO: 67; SEQ ID NO: 94; SEQ ID NO: 95; SEQ ID NO: 97; SEQ ID NO: 142; SEQ ID NO: 81; and SEQ ID NO: 132.

4. The isolated antibody, or the antibody fragment, of claim 1, wherein the antibody or antigen binding fragment thereof is a scFv.

5. An isolated PTP1B-OX binding polypeptide, comprising the heavy chain CDR1, CDR2, and CDR3 amino acid sequences and the light chain CDR1, CDR2, and CDR3 amino acid sequences selected from the amino acid sequence of any one of SEQ ID NO: 26 to SEQ ID NO: 29; SEQ ID NO: 100; SEQ ID NO: 130; SEQ ID NO: 67; SEQ ID NO: 94; SEQ ID NO: 95; SEQ ID NO: 97; SEQ ID NO: 142; SEQ ID NO: 81; and SEQ ID NO: 132.

6. A method of identifying an agent that (a) specifically binds PTP1B-OX, a stable comformation (PTP1B-CASA), or both PTP1B-OX and PTP1B-CASA and (b) stabilizes PTP1B-OX, comprising:
   (a) combining (i) PTP1B-OX PTP1B-CASA or both PTP1B-OX and PTP1B-CASA; (ii) an antibody that specifically binds and stabilizes PTP1B-OX or an antigen-binding antibody fragment that specifically binds and stabilizes PTP1B-OX; and (iii) a candidate agent, under conditions appropriate for binding of PTP1B-OX with the antibody or antigen-binding antibody fragment;
   (b) assessing binding of PTP1B-OX or PTP1B-CASA with the antibody or antigen-binding antibody fragment;
   (c) comparing binding assessed in (b) to (i) binding of PTP1B-OX or PTP1B-CASA with the antibody or the antigen-binding fragment in the absence of the candidate agent or (ii) a reference or control,
   wherein if binding occurs to a lesser extent in the presence of the candidate agent than in the absence of the candidate agent or to a lesser extent as compared to the reference or control, the candidate agent is an agent that specifically binds and stabilizes PTP1B-OX or PTP1B-CASA.

7. The method of claim 6, wherein the antibody comprises an amino acid sequence selected from the amino acid sequence of any one of SEQ ID NO: 26 to SEQ ID NO: 29; SEQ ID NO: 100; SEQ ID NO: 130; SEQ ID NO: 67; SEQ ID NO: 94; SEQ ID NO: 95; SEQ ID NO: 97; SEQ ID NO: 142; SEQ ID NO: 81; and SEQ ID NO: 132.

8. A method of identifying an agent that displaces an antibody or antibody fragment that binds to and stabilizes PTP1B-OX and binds to and stabilizes PTP1B-OX, comprising:
   (a) combining (i) PTP1B-OX or a mutant PTP1B that mimics PTP1B-OX conformation with (ii) an antibody or antibody fragment that specifically binds and stabilizes PTP1B-OX thereby producing a (PTP1B-OX or mutant PTP1B):(antibody or antibody fragment) complex;
   (b) combining the complex produced in (a) with a candidate agent, under conditions appropriate for detection of displacement of the antibody or antibody fragment from the complex;
   (c) assessing displacement of the antibody or antibody fragment from PTP1B-OX or mutant PTP1B in the complex by the candidate agent,
   wherein displacement has occurred, the candidate agent is an agent that displaces an antibody or antibody fragment that binds to and stabilizes PTP1B-OX and binds to and stabilizes PTP1B-OX.

* * * * *

```
                        SEQUENCE LISTING

<160> NUMBER OF SEQ ID NOS: 166

<210> SEQ ID NO 1
<211> LENGTH: 288
<212> TYPE: PRT
<213> ORGANISM: Artificial Sequence
<220> FEATURE:
<223> OTHER INFORMATION: recombinant protein
<220> FEATURE:
<221> NAME/KEY: misc_feature
<222> LOCATION: (18)..(18)
<223> OTHER INFORMATION: Xaa can be any naturally occurring amino acid

<400> SEQUENCE: 1

Leu Leu Ala Val Leu Ala His Thr Ser Gly Ser Leu Val Gln Ala Ala
1               5                   10                  15

Leu Xaa Gln Pro Ser Ser Val Ser Ala Asn Pro Gly Glu Thr Val Glu
            20                  25                  30

Ile Thr Cys Ser Gly Gly Tyr Ser Ser Asn Tyr Gly Trp Tyr Gln Gln
        35                  40                  45

Lys Ser Pro Gly Ser Ala Pro Val Thr Val Ile Tyr Glu Ser Thr Lys
    50                  55                  60

Arg Pro Ser Asn Ile Pro Ser Arg Phe Ser Gly Ser Lys Ser Gly Ser
65                  70                  75                  80

Thr Ala Thr Leu Thr Ile Thr Gly Val Gln Ala Glu Asp Glu Ala Val
                85                  90                  95

Tyr Phe Cys Ser Ser Ser Thr Ala Gly Ile Phe Gly Ala Gly Thr Thr
            100                 105                 110

Leu Thr Val Leu Gly Ser Ser Ser Thr Ala Gly Ile Phe Gly Ala Gly
        115                 120                 125

Thr Thr Leu Thr Val Leu Gly Gln Pro Lys Val Ala Pro Thr Val Thr
    130                 135                 140

Leu Asp Glu Ser Gly Gly Gly Leu Gln Thr Pro Gly Gly Thr Leu Ser
145                 150                 155                 160

Leu Val Cys Lys Ala Ser Gly Phe Thr Phe Ser Ser Val Asn Met Ala
                165                 170                 175

Trp Val Arg Gln Ala Pro Gly Lys Gly Leu Glu Phe Val Ala Gly Ile
            180                 185                 190
```

```
Tyr Thr Asp Asn Arg Tyr Thr Gly Tyr Gly Ser Ala Val Lys Gly Arg
            195                 200                 205

Ala Thr Ile Ser Arg Asp Asn Gly Gln Ser Thr Val Arg Leu Gln Leu
    210                 215                 220

Asn Asn Leu Arg Ala Glu Asp Thr Gly Ile Tyr Phe Cys Ala Lys Ala
225                 230                 235                 240

Ala Asp Ala Tyr Cys Thr Trp Ser Asp Gly Ser Cys His Gly Val Ile
                245                 250                 255

Asp Thr Ala Gly Gly Ile Asp Ala Trp Gly His Gly Thr Glu Val Ile
            260                 265                 270

Val Ser Ser Ala Ser Pro Thr Ser Pro Pro Arg Leu Tyr Pro Leu Ser
        275                 280                 285

<210> SEQ ID NO 2
<211> LENGTH: 8
<212> TYPE: PRT
<213> ORGANISM: Artificial Sequence
<220> FEATURE:
<223> OTHER INFORMATION: recombinant protein
<220> FEATURE:
<221> NAME/KEY: misc_feature
<222> LOCATION: (3)..(7)
<223> OTHER INFORMATION: Xaa can be any naturally occurring amino acid

<400> SEQUENCE: 2

His Cys Xaa Xaa Xaa Xaa Xaa Arg
1               5

<210> SEQ ID NO 3
<211> LENGTH: 7
<212> TYPE: PRT
<213> ORGANISM: Artificial Sequence
<220> FEATURE:
<223> OTHER INFORMATION: recombinant protein
<220> FEATURE:
<221> NAME/KEY: misc_feature
<222> LOCATION: (3)..(6)
<223> OTHER INFORMATION: Xaa can be any naturally occurring amino acid

<400> SEQUENCE: 3

Cys Ser Xaa Xaa Xaa Xaa Arg
1               5

<210> SEQ ID NO 4
<211> LENGTH: 10
<212> TYPE: PRT
<213> ORGANISM: Artificial Sequence
<220> FEATURE:
<223> OTHER INFORMATION: recombinant protein
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 4

His Cys Ser Xaa Gly Xaa Gly Arg Xaa Gly
1               5                   10
```

<210> SEQ ID NO 5
<211> LENGTH: 3318
<212> TYPE: DNA
<213> ORGANISM: Homo sapiens

<400> SEQUENCE: 5

```
gtgatgcgta gttccggctg ccggttgaca tgaagaagca gcagcggcta gggcggcggt      60
agctgcaggg gtcgggatt gcagcgggcc tcggggctaa gagcgcgacg cggcctagag      120
cggcagacgc cgcagtgggc cgagaaggag gcgcagcagc cgccctggcc cgtcatggag     180
atggaaaagg agttcgagca gatcgacaag tccgggagct gggcggccat ttaccaggat     240
atccgacatg aagccagtga cttcccatgt agagtggcca agcttcctaa gaacaaaaac     300
cgaaataggt acagagacgt cagtcccttt gaccatagtc ggattaaact acatcaagaa     360
gataatgact atatcaacgc tagtttgata aaaatggaag aagcccaaag gagttacatt     420
cttacccagg gcccttttgcc taacacatgc ggtcactttt gggagatggt gtgggagcag     480
aaaagcaggg gtgtcgtcat gctcaacaga gtgatggaga aaggttcgtt aaaatgcgca     540
caatactggc cacaaaaaga gaaaaagag atgatctttg aagacacaaa tttgaaatta     600
acattgatct ctgaagatat caagtcatat tatacagtgc gacagctaga attggaaaac     660
cttacaaccc aagaaactcg agagatctta catttccact ataccacatg gcctgacttt     720
ggagtccctg aatcaccagc ctcattcttg aactttcttt tcaaagtccg agagtcaggg     780
tcactcagcc cggagcacgg gcccgttgtg gtgcactgca gtgcaggcat cggcaggtct     840
ggaaccttct gtctggctga tacctgcctc ttgctgatgg acaagaggaa agaccccttct     900 tccgttgata tcaagaaagt gctgttagaa atgaggaagt ttcggatggg gctgatccag     960
acagccgacc agctgcgctt ctcctacctg gctgtgatcg aaggtgccaa attcatcatg     1020
ggggactctt ccgtgcagga tcagtggaag gagctttccc acgaggacct ggagccccca     1080
cccgagcata tccccccacc tcccggcca cccaaacgaa tcctggagcc acacaatggg     1140
aaatgcaggg agttcttccc aaatcaccag tgggtgaagg aagagaccca ggaggataaa     1200
gactgcccca tcaaggaaga aaaaggaagc cccttaaatg ccgcacccta cggcatcgaa     1260
agcatgagtc aagacactga agttagaagt cgggtcgtgg ggggaagtct tcgaggtgcc     1320
caggctgcct ccccagccaa aggggagccg tcactgcccg agaaggacga ggaccatgca     1380
ctgagttact ggaagccctt cctggtcaac atgtgcgtgg ctacggtcct cacggccggc     1440
gcttacctct gctacaggtt cctgttcaac agcaacacat agcctgaccc tcctccactc     1500
cacctccacc cactgtccgc ctctgcccgc agagcccacg cccgactagc aggcatgccg     1560
cggtaggtaa gggccgccgg accgcgtaga gagccgggcc ccggacggac gttggttctg     1620
cactaaaacc catcttcccc ggatgtgtgt ctcacccctc atccttttac tttttgcccc     1680
ttccactttg agtaccaaat ccacaagcca tttttgagg agagtgaaag agagtaccat     1740
gctggcggcg cagagggaag gggcctacac ccgtcttggg gctcgcccca cccagggctc     1800
cctcctggag catcccaggc gggcggcacg ccaacagccc cccccttgaa tctgcaggga     1860
gcaactctcc actccatatt tatttaaaca attttttccc caaaggcatc catagtgcac     1920
tagcattttc ttgaaccaat aatgtattaa aatttttga tgtcagcctt gcatcaaggg     1980
ctttatcaaa aagtacaata ataaatcctc aggtagtact gggaatggaa ggctttgcca     2040
tgggcctgct gcgtcagacc agtactggga aggaggacgg ttgtaagcag ttgttatta      2100 gtgatattgt gggtaacgtg agaagataga acaatgctat aatatataat gaacacgtgg      2160
```

-continued

```
gtatttaata agaaacatga tgtgagatta ctttgtcccg cttattctcc tccctgttat    2220
ctgctagatc tagttctcaa tcactgctcc cccgtgtgta ttagaatgca tgtaaggtct    2280
tcttgtgtcc tgatgaaaaa tatgtgcttg aaatgagaaa ctttgatctc tgcttactaa    2340
tgtgccccat gtccaagtcc aacctgcctg tgcatgacct gatcattaca tggctgtggt    2400
tcctaagcct gttgctgaag tcattgtcgc tcagcaatag ggtgcagttt tccaggaata    2460
ggcatttgcc taattcctgg catgacactc tagtgacttc ctggtgaggc ccagcctgtc    2520
ctggtacagc agggtcttgc tgtaactcag acattccaag ggtatgggaa gccatattca    2580
cacctcacgc tctggacatg atttagggaa gcagggacac cccccgcccc ccacctttgg    2640
gatcagcctc cgccattcca agtcaacact cttcttgagc agaccgtgat ttggaagaga    2700
ggcacctgct ggaaaccaca cttcttgaaa cagcctgggt gacggtcctt taggcagcct    2760
gccgccgtct ctgtcccggt tcaccttgcc gagagaggcg cgtctgcccc accctcaaac    2820 cctgtgggc ctgatggtgc tcacgactct tcctgcaaag ggaactgaag acctccacat    2880
taagtggctt tttaacatga aaaacacggc agctgtagcc cccgagctac tctcttgcca    2940
gcattttcac attttgcctt tctcgtggta gaagccagta cagagaaatt ctgtggtggg    3000
aacattcgag gtgtcaccct gcagagctat ggtgaggtgt ggataaggct taggtgccag    3060
gctgtaagca ttctgagctg ggcttgttgt ttttaagtcc tgtatatgta tgtagtagtt    3120
tgggtgtgta tatatagtag catttcaaaa tggacgtact ggtttaacct cctatccttg    3180
gagagcagct ggctctccac cttgttacac attatgttag agaggtagcg agctgctctg    3240
ctatatgcct taagccaata tttactcatc aggtcattat tttttacaat ggccatggaa    3300
taaaccattt ttacaaaa                                                 3318
```

<210> SEQ ID NO 6
<211> LENGTH: 435
<212> TYPE: PRT
<213> ORGANISM: Homo sapiens

<400> SEQUENCE: 6

Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr

```
            165                 170                 175
Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
            195                 200                 205

Gly Pro Val Val His Cys Ser Ala Gly Ile Gly Arg Ser Gly Thr
210                 215                 220

Phe Cys Leu Ala Asp Thr Cys Leu Leu Met Asp Lys Arg Lys Asp
225                 230                 235                 240

Pro Ser Ser Val Asp Ile Lys Lys Val Leu Leu Glu Met Arg Lys Phe
                245                 250                 255

Arg Met Gly Leu Ile Gln Thr Ala Asp Gln Leu Arg Phe Ser Tyr Leu
            260                 265                 270

Ala Val Ile Glu Gly Ala Lys Phe Ile Met Gly Asp Ser Ser Val Gln
            275                 280                 285

Asp Gln Trp Lys Glu Leu Ser His Glu Asp Leu Glu Pro Pro Glu
290                 295                 300

His Ile Pro Pro Pro Arg Pro Lys Arg Ile Leu Glu Pro His
305                 310                 315                 320

Asn Gly Lys Cys Arg Glu Phe Phe Pro Asn His Gln Trp Val Lys Glu
                325                 330                 335

Glu Thr Gln Glu Asp Lys Asp Cys Pro Ile Lys Glu Lys Gly Ser
            340                 345                 350

Pro Leu Asn Ala Ala Pro Tyr Gly Ile Glu Ser Met Ser Gln Asp Thr
            355                 360                 365

Glu Val Arg Ser Arg Val Val Gly Gly Ser Leu Arg Gly Ala Gln Ala
            370                 375                 380

Ala Ser Pro Ala Lys Gly Glu Pro Ser Leu Pro Glu Lys Asp Glu Asp
385                 390                 395                 400

His Ala Leu Ser Tyr Trp Lys Pro Phe Leu Val Asn Met Cys Val Ala
                405                 410                 415

Thr Val Leu Thr Ala Gly Ala Tyr Leu Cys Tyr Arg Phe Leu Phe Asn
            420                 425                 430

Ser Asn Thr
        435

<210> SEQ ID NO 7
<211> LENGTH: 1308
<212> TYPE: DNA
<213> ORGANISM: Homo sapiens

<400> SEQUENCE: 7
atggagatgg aaaaggagtt cgagcagatc gacaagtccg ggagctgggc ggccatttac        60
caggatatcc gacatgaagc cagtgacttc ccatgtagag tggccaagct tcctaagaac       120
aaaaaccgaa ataggtacag agacgtcagt cccttttgacc atagtcggat taaactacat       180
caagaagata tgactatat caacgctagt ttgataaaaa tggaagaagc ccaaaggagt       240
tacattctta cccagggccc tttgcctaac acatgcggtc acttttggga gatggtgtgg       300
gagcagaaaa gcagggtgt cgtcatgctc aacagagtga tggagaaagg ttcgttaaaa       360
tgcgcacaat actggccaca aaagaagaa aaagagatga tctttgaaga cacaaatttg       420
aaattaacat tgatctctga agatatcaag tcatatttta cagtgcgaca gctagaattg       480
gaaaacctta caacccaaga aactcgagag atcttacatt ccactatac cacatggcct       540
```

```
gactttggag tccctgaatc accagcctca ttcttgaact ttcttttcaa agtccgagag    600
tcagggtcac tcagcccgga gcacgggccc gttgtggtgc actgcagtgc aggcatcggc    660
aggtctggaa ccttctgtct ggctgatacc tgcctcttgc tgatggacaa gaggaaagac    720
ccttcttccg ttgatatcaa gaaagtgctg ttagaaatga ggaagtttcg gatggggctg    780
atccagacag ccgaccagct gcgcttctcc tacctggctg tgatcgaagg tgccaaattc    840
atcatggggg actcttccgt gcaggatcag tggaaggagc tttcccacga ggacctggag    900
cccccacccg agcatatccc cccacctccc cggccaccca acgaatcct ggagccacac     960 aatgggaaat gcagggagtt cttcccaaat caccagtggg tgaaggaaga ccccaggag    1020 gataaagact gccccatcaa ggaagaaaaa ggaagcccct aaatgccgc accctacggc    1080 atcgaaagca tgagtcaaga cactgaagtt agaagtcggg tcgtgggggg aagtcttcga    1140
ggtgcccagg ctgcctcccc agccaaaggg gagccgtcac tgcccgagaa ggacgaggac    1200
catgcactga gttactggaa gcccttcctg gtcaacatgt gcgtggctac ggtcctcacg    1260
gccggcgctt acctctgcta caggttcctg ttcaacagca acacatag                 1308
```

<210> SEQ ID NO 8
<211> LENGTH: 435
<212> TYPE: PRT
<213> ORGANISM: Homo sapiens

<400> SEQUENCE: 8

```
Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
        195                 200                 205

Gly Pro Val Val Val His Cys Ser Ala Gly Ile Gly Arg Ser Gly Thr
    210                 215                 220

Phe Cys Leu Ala Asp Thr Cys Leu Leu Leu Met Asp Lys Arg Lys Asp
225                 230                 235                 240
```

```
Pro Ser Ser Val Asp Ile Lys Lys Val Leu Glu Met Arg Lys Phe
                245                 250                 255

Arg Met Gly Leu Ile Gln Thr Ala Asp Gln Leu Arg Phe Ser Tyr Leu
        260                 265                 270

Ala Val Ile Glu Gly Ala Lys Phe Ile Met Gly Asp Ser Ser Val Gln
            275                 280                 285

Asp Gln Trp Lys Glu Leu Ser His Glu Asp Leu Glu Pro Pro Glu
        290                 295                 300

His Ile Pro Pro Pro Arg Pro Pro Lys Arg Ile Leu Glu Pro His
305                 310                 315                 320

Asn Gly Lys Cys Arg Glu Phe Phe Pro Asn His Gln Trp Val Lys Glu
                325                 330                 335

Glu Thr Gln Glu Asp Lys Asp Cys Pro Ile Lys Glu Glu Lys Gly Ser
            340                 345                 350

Pro Leu Asn Ala Ala Pro Tyr Gly Ile Glu Ser Met Ser Gln Asp Thr
        355                 360                 365

Glu Val Arg Ser Arg Val Val Gly Gly Ser Leu Arg Gly Ala Gln Ala
        370                 375                 380

Ala Ser Pro Ala Lys Gly Glu Pro Ser Leu Pro Glu Lys Asp Glu Asp
385                 390                 395                 400

His Ala Leu Ser Tyr Trp Lys Pro Phe Leu Val Asn Met Cys Val Ala
                405                 410                 415

Thr Val Leu Thr Ala Gly Ala Tyr Leu Cys Tyr Arg Phe Leu Phe Asn
            420                 425                 430

Ser Asn Thr
        435

<210> SEQ ID NO 9
<211> LENGTH: 3247
<212> TYPE: DNA
<213> ORGANISM: Homo sapiens

<400> SEQUENCE: 9
gggcgggcct cggggctaag agcgcgacgc ctagagcggc agacggcgca gtgggccgag    60
aaggaggcgc agcagccgcc ctggcccgtc atggagatgg aaaaggagtt cgagcagatc   120
gacaagtccg ggagctgggc ggccatttac caggatatcc acatgaagc cagtgacttc   180 ccatgtagag tggccaagct tcctaagaac aaaaaccgaa ataggtacag agacgtcagt   240 cccttttgacc atagtcggat taaactacat caagaagata atgactatat caacgctagt   300
ttgataaaaa tggaagaagc ccaaaggagt tacattctta cccagggccc tttgcctaac   360
acatgcggtc acttttggga gatggtgtgg gagcagaaaa gcaggggtgt cgtcatgctc   420
aacagagtga tggagaaagg ttcgttaaaa tgcgcacaat actggccaca aaaagaagaa   480
aaagagatga tctttgaaga cacaaatttg aaattaacat tgatctctga agatatcaag   540
tcatattata cagtgcgaca gctagaattg gaaaacctta caaccaaga aactcgagag   600 atcttacatt tccactatac cacatggcct gactttggag tccctgaatc accagcctca   660
ttcttgaact ttctttttcaa agtccgagag tcagggtcac tcagcccgga gcacgggccc   720
gttgtggtgc actgcagtgc aggcatcggc aggtctggaa ccttctgtct ggctgatacc   780
tgcctcctgc tgatggacaa gaggaaagac ccttcttccg ttgatatcaa gaaagtgctg   840
ttagaaatga ggaagtttcg gatggggttg atccagacag ccgaccagct gcgcttctcc   900
tacctggctg tgatcgaagg tgccaaattc atcatggggg actcttccgt gcaggatcag   960
```

```
tggaaggagc tttcccacga ggacctggag cccccacccg agcatatccc cccacctccc   1020
cggccaccca aacgaatcct ggagccacac aatgggaaat gcagggagtt cttcccaaat   1080
caccagtggg tgaaggaaga gacccaggag gataaagact gccccatcaa ggaagaaaaa   1140
ggaagcccct taaatgccgc accctacggg atcgaaagca tgagtcaaga cactgaagtt   1200
agaagtcggg tcgtgggggg aagtcttcga ggtgcccagg ctgcctcccc agccaaaggg   1260
gagccgtcac tgcccgagaa ggacgaggac catgcactga gttactggaa gcccttcctg   1320
gtcaacatgt gcgtggctac ggtcctcacg gccggcgctt acctctgcta caggttcctg   1380
ttcaacagca acacatagcc tgaccctcct ccactccacc tccacccact gtccgcctct   1440
gcccgcagag cccacgcccg actagcaggc atgccgcggt aggtaagggc cgccggaccg   1500
cgtagagagc cgggcccggg acggacgttg gttctgcact aaaacccatc ttccccggat   1560
gtgtgtctca cccctcatcc ttttactttt tgccccttcc actttgagta ccaaatccac   1620
aagccatttt ttgaggagag tgaaagagag taccatgctg gcggcgcaga gggaaggggc   1680
ctacacccgt cttgggggctc gccccaccca gggctccctc ctggagcatc ccaggcggcg   1740
cacgccaaca gcccccccct tgaatctgca gggagcaact ctccactcca tatttattta   1800
aacaattttt tccccaaagg catccatagt gcactagcat tttcttgaac caataatgta   1860
ttaaaatttt ttgatgtcag ccttgcatca agggctttat caaaaagtac aataataaat   1920
cctcaggtag tactgggaat ggaaggcttt gccatgggcc tgctgcgtca gaccagtact   1980
gggaaggagg acggttgtaa gcagttgtta tttagtgata ttgtgggtaa cgtgagaaga   2040
tagaacaatg ctataatata taatgaacac gtgggtattt aataagaaac atgatgtgag   2100
attactttgt cccgcttatt ctcctccctg ttatctgcta gatctagttc tcaatcactg   2160
ctcccccgtg tgtattagaa tgcatgtaag gtcttcttgt gtcctgatga aaatatgtg    2220 cttgaaatga gaaactttga tctctgctta ctaatgtgcc ccatgtccaa gtccaacctg   2280
cctgtgcatg acctgatcat tacatggctg tggttcctaa gctgttgct gaagtcattg    2340 tcgctcagca atagggtgca gttttccagg aataggcatt tgctaattcc tggcatgaca   2400
ctctagtgac ttcctggtga ggcccagcct gtcctggtac agcagggtct tgctgtaact   2460
cagacattcc aagggtatgg gaagccatat tcacacctca cgctctggac atgatttagg   2520
gaagcaggga caccccccgc cccccacctt tgggatcagc ctccgccatt ccaagtcaac   2580
actcttcttg agcagaccgt gatttggaag agaggcacct gctggaaacc acacttcttg   2640
aaacagcctg ggtgacggtc ctttaggcag cctgccgccg tctctgtccc ggttcacctt   2700
gccgagagag gcgcgtctgc cccaccctca aaccctgtgg ggcctgatgg tgctcacgac   2760
tcttcctgca aagggaactg aagacctcca cattaagtgg cttttttaaca tgaaaaacac   2820 ggcagctgta gctcccgagc tactctcttg ccagcatttt cacattttgc ctttctcgtg   2880
gtagaagcca gtacagagaa attctgtggt gggaacattc gaggtgtcac cctgcagagc   2940
tatggtgagg tgtggataag gcttaggtgc caggctgtaa gcattctgag ctggcttgtt   3000
gtttttaagt cctgtatatg tatgtagtag tttgggtgtg tatatatagt agcatttcaa   3060
aatggacgta ctggtttaac ctcctatcct tggagagcag ctggctctcc accttgttac   3120
acattatgtt agagaggtag cgagctgctc tgctatatgc cttaagccaa tatttactca   3180
tcaggtcatt attttttaca atggccatgg aataaaccat ttttacaaaa ataaaaacaa   3240
aaaaagc                                                              3247
```

```
<210> SEQ ID NO 10
<211> LENGTH: 435
<212> TYPE: PRT
<213> ORGANISM: Homo sapiens

<400> SEQUENCE: 10

Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
        195                 200                 205

Gly Pro Val Val His Cys Ser Ala Gly Ile Gly Arg Ser Gly Thr
    210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Lys Phe
                245                 250                 255

Arg Met Gly Leu Ile Gln Thr Ala Asp Gln Leu Arg Phe Ser Tyr Leu
            260                 265                 270

Ala Val Ile Glu Gly Ala Lys Phe Ile Met Gly Asp Ser Ser Val Gln
        275                 280                 285

Asp Gln Trp Lys Glu Leu Ser His Glu Asp Leu Glu Pro Pro Pro Glu
    290                 295                 300

His Ile Pro Pro Pro Arg Pro Pro Lys Arg Ile Leu Glu Pro His
305                 310                 315                 320

Asn Gly Lys Cys Arg Glu Phe Phe Pro Asn His Gln Trp Val Lys Glu
                325                 330                 335

Glu Thr Gln Glu Asp Lys Asp Cys Pro Ile Lys Glu Glu Lys Gly Ser
            340                 345                 350

Pro Leu Asn Ala Ala Pro Tyr Gly Ile Glu Ser Met Ser Gln Asp Thr
        355                 360                 365

Glu Val Arg Ser Arg Val Val Gly Gly Ser Leu Arg Gly Ala Gln Ala
    370                 375                 380
```

```
Ala Ser Pro Ala Lys Gly Glu Pro Ser Leu Pro Glu Lys Asp Glu Asp
385                 390                 395                 400

His Ala Leu Ser Tyr Trp Lys Pro Phe Leu Val Asn Met Cys Val Ala
            405                 410                 415

Thr Val Leu Thr Ala Gly Ala Tyr Leu Cys Tyr Arg Phe Leu Phe Asn
                420                 425                 430

Ser Asn Thr
        435

<210> SEQ ID NO 11
<211> LENGTH: 3215
<212> TYPE: DNA
<213> ORGANISM: Homo sapiens

<400> SEQUENCE: 11
```

| | | | | | |
|---|---|---|---|---|---|
| gcgcgacgcg | gcctagagcg | gcagacggcg | cagtgggccg | agaaggaggc | gcagcagccg | 60 |
| ccctggcccg | tcatggagat | ggaaaaggag | ttcgagcaga | tcgacaagtc | cgggagctgg | 120 |
| gcggccattt | accaggatat | ccgacatgaa | gccagtgact | tcccatgtag | agtggccaag | 180 |
| cttcctaaga | acaaaaaccg | aaataggtac | agagacgtca | gtccctttga | ccatagtcgg | 240 |
| attaaactac | atcaagaaga | taatgactat | atcaacgcta | gtttgataaa | aatggaagaa | 300 |
| gcccaaagga | gttacattct | tacccagggc | cctttgccta | acacatgcgg | tcacttttgg | 360 |
| gagatggtgt | gggagcagaa | aagcaggggt | gtcgtcatgc | tcaacagagt | gatggagaaa | 420 |
| ggttcgttaa | atgcgcaca | atactggcca | caaaagaag | aaaagagat | gatctttgaa | 480 |
| gacacaaatt | tgaaattaac | attgatctct | gaagatatca | agtcatatta | tacagtgcga | 540 |
| cagctagaat | ggaaaaacct | tacaacccaa | gaaactcgag | agatcttaca | tttccactat | 600 |
| accacatggc | ctgactttgg | agtccctgaa | tcaccagcct | cattcttgaa | ctttcttttc | 660 |
| aaagtccgag | agtcagggtc | actcagcccg | gagcacgggc | ccgttgtggt | gcactgcagt | 720 |
| gcaggcatcg | gcaggtctgg | aaccttctgt | ctggctgata | cctgcctctt | gctgatggac | 780 |
| aagaggaaag | acccttcttc | cgttgatatc | aagaaagtgc | tgttagaaat | gaggaagttt | 840 |
| cggatggggc | tgatccagac | agccgaccag | ctgcgcttct | cctacctggc | tgtgatcgaa | 900 |
| ggtgccaaat | tcatcatggg | ggactcttcc | gtgcaggatc | agtggaagga | gctttcccac | 960 |
| gaggacctgg | agcccccacc | cgagcatatc | cccccacctc | cccggccacc | caaacgaatc | 1020 |
| ctggagccac | acaatgggaa | atgcagggag | ttcttcccaa | atcaccagtg | ggtgaaggaa | 1080 |
| gagacccagg | aggataaaga | ctgccccatc | aaggaagaaa | aaggaagccc | cttaaatgcc | 1140 |
| gcaccctacg | gcatcgaaag | catgagtcaa | gacactgaag | ttagaagtcg | ggtcgtgggg | 1200 |
| ggaagtcttc | gaggtgccca | ggctgcctcc | ccagccaaag | gggagccgtc | actgcccgag | 1260 |
| aaggacgagg | accatgcact | gagttactgg | aagcccttcc | tggtcaacat | gtgcgtggct | 1320 |
| acggtcctca | cggccggcgc | ttacctctgc | tacaggttcc | tgttcaacag | caacacatag | 1380 |
| cctgaccctc | ctccactcca | cctccaccca | ctgtccgcct | ctgcccgcag | agcccacgcc | 1440 |
| cgactagcag | gcatgccgcg | gtaggtaagg | gccgccggac | cgcgtagaga | gccgggcccc | 1500 |
| ggacggacgt | tggttctgca | ctaaaaccca | tcttccccgg | atgtgtgtct | caccccctcat | 1560 |
| ccttttactt | tttgcccctt | ccactttgag | taccaaatcc | acaagccatt | ttttgaggag | 1620 |
| agtgaaagag | agtaccatgc | tggcggcgca | gagggaaggg | gcctacaccc | gtcttggggc | 1680 |
| tcgccccacc | cagggctccc | tcctggagca | tcccaggcgg | gcggcacgcc | agacagcccc | 1740 |
| cccttgaat | ctgcagggag | caactctcca | ctccatattt | atttaaacaa | ttttttcccc | 1800 |

```
aaaggcatcc atagtgcact agcattttct tgaaccaata atgtattaaa attttttgat    1860
gtcagccttg catcaagggc tttatcaaaa agtacaataa taaatcctca ggtagtactg    1920
ggaatggaag ctttgccat gggcctgctg cgtcagacca gtactgggaa ggaggacggt     1980
tgtaagcagt tgttatttag tgatattgtg ggtaacgtga aagatagaa caatgctata     2040
atatataatg aacacgtggg tatttaataa gaaacatgat gtgagattac tttgtcccgc    2100
ttattctgct ccctgttatc tgctagatct agttctcaat cactgctccc cgtgtgtat    2160
tagaatgcat gtaaggtctt cttgtgtcct gatgaaaaat atgtgcttga aatgagaaac    2220
tttgatctct gcttactaat gtgccccatg tccaagtcca acctgcctgt gcatgacctg    2280
atcattacat ggctgtggtt cctaagcctg ttgctgaagt cattgtcgct cagcaatagg    2340
gtgcagtttt ccaggaatag catttgcct aattcctggc atgacactct agtgacttcc     2400
tggtgaggcc cagcctgtcc tggtacagca gggtcttgct gtaactcaga cattccaagg    2460
gtatgggaag ccatattcac acctcacgct ctggacatga tttagggaag cagggacacc    2520
ccccgccccc cacctttggg atcagcctcc gccattccaa gtcgacactc ttcttgagca    2580
gaccgtgatt tggaagagag gcacctgctg gaaaccacac ttcttgaaac agcctgggtg    2640
acggtccttt aggcagcctg ccgccgtctc tgtcccggtt caccttgccg agagaggcgc    2700
gtctgcccca ccctcaaacc ctgtggggcc tgatggtgct cacgactctt cctgcaaagg    2760
gaactgaaga cctccacatt aagtggcttt ttaacatgaa aaacacggca gctgtagctc    2820
ccgagctact ctcttgccag catttttcaca ttttgccttt ctcgtggtag aagccagtac   2880
agagaaattc tgtggtggga acattcgagg tgtcaccctg cagagctatg gtgaggtgtg    2940
gataaggctt aggtgccagg ctgtaagcat tctgagctgg cttgttgttt ttaagtcctg    3000
tatatgtatg tagtagtttg ggtgtgtata tatagtagca tttcaaaatg gacgtactgg    3060
tttaacctcc tatccttgga gagcagctgg ctctccacct tgttacacat tatgttagag    3120
aggtagcgag ctgctctgct atgtccttaa gccaatattt actcatcagg tcattatttt    3180
ttacaatggc catggaataa accattttta caaaa                               3215
```

<210> SEQ ID NO 12
<211> LENGTH: 435
<212> TYPE: PRT
<213> ORGANISM: Homo sapiens

<400> SEQUENCE: 12

```
Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
```

```
                    115                 120                 125
Glu Glu Lys Glu Met Ile Phe Glu Asp Thr Asn Leu Lys Leu Thr Leu
            130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
        195                 200                 205

Gly Pro Val Val His Cys Ser Ala Gly Ile Gly Arg Ser Gly Thr
210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Lys Phe
                245                 250                 255

Arg Met Gly Leu Ile Gln Thr Ala Asp Gln Leu Arg Phe Ser Tyr Leu
            260                 265                 270

Ala Val Ile Glu Gly Ala Lys Phe Ile Met Gly Asp Ser Ser Val Gln
        275                 280                 285

Asp Gln Trp Lys Glu Leu Ser His Glu Asp Leu Glu Pro Pro Pro Glu
290                 295                 300

His Ile Pro Pro Pro Arg Pro Pro Lys Arg Ile Leu Glu Pro His
305                 310                 315                 320

Asn Gly Lys Cys Arg Glu Phe Phe Pro Asn His Gln Trp Val Lys Glu
                325                 330                 335

Glu Thr Gln Glu Asp Lys Asp Cys Pro Ile Lys Glu Glu Lys Gly Ser
            340                 345                 350

Pro Leu Asn Ala Ala Pro Tyr Gly Ile Glu Ser Met Ser Gln Asp Thr
        355                 360                 365

Glu Val Arg Ser Arg Val Val Gly Gly Ser Leu Arg Gly Ala Gln Ala
370                 375                 380

Ala Ser Pro Ala Lys Gly Glu Pro Ser Leu Pro Glu Lys Asp Glu Asp
385                 390                 395                 400

His Ala Leu Ser Tyr Trp Lys Pro Phe Leu Val Asn Met Cys Val Ala
                405                 410                 415

Thr Val Leu Thr Ala Gly Ala Tyr Leu Cys Tyr Arg Phe Leu Phe Asn
            420                 425                 430

Ser Asn Thr
        435

<210> SEQ ID NO 13
<211> LENGTH: 3295
<212> TYPE: DNA
<213> ORGANISM: Homo sapiens

<400> SEQUENCE: 13
cagcagcggc tagggcggcg gtagctgcag gggtcgggga ttgcagcggg cctcggggct      60
aagagcgcga cgcggcctag agcggcagac ggcgcagtgg gccgagaagg aggcgcagca     120
gccgccctgg cccgtcatgg agatggaaaa ggagttcgag cagatcgaca agtccgggag     180
ctgggcggcc atttaccagg atatccgaca tgaagccagt gacttcccat gtagagtggc     240
caagcttcct aagaacaaaa accgaaatag gtacagagac gtcagtccct ttgaccatag     300
```

```
tcggattaaa ctacatcaag aagataatga ctatatcaac gctagtttga taaaaatgga    360
agaagcccaa aggagttaca ttcttaccca gggccctttg cctaacacat gcggtcactt    420
ttgggagatg gtgtgggagc agaaaagcag gggtgtcgtc atgctcaaca gagtgatgga    480
gaaaggttcg ttaaaatgcg cacaatactg gccacaaaaa aagagaaaaag agatgatctt    540 tgaagacaca aatttgaaat taacattgat ctctgaagat atcaagtcat attatacagt    600
gcgacagcta gaattggaaa acctacaac ccaagaaact cgagagatct tacatttcca    660
ctataccaca tggcctgact ttggagtccc tgaatcacca gcctcattct tgaactttct    720
tttcaaagtc cgagagtcag ggtcactcag cccggagcac gggcccgttg tggtgcactg    780
cagtgcaggc atcggcaggt ctggaacctt ctgtctggct gatacctgcc tcttgctgat    840
ggacaagagg aaagacccctt cttccgttga tatcaagaaa gtgctgttag aaatgaggaa    900
gtttcggatg gggctgatcc agacagccga ccagctgcgc ttctcctacc tggctgtgat    960
cgaaggtgcc aaattcatca tgggggactc ttccgtgcag gatcagtgga aggagctttc   1020
ccacgaggac ctggagcccc acccgagca tatcccccca cctcccggc cacccaaacg    1080 aatcctggag ccacacaatg ggaaatgcag ggagttcttc ccaaatcacc agtgggtgaa   1140
ggaagagacc caggaggata agactgccc catcaaggaa gaaaaaggaa gccccttaaa    1200
tgccgcaccc tacggcatcg aaagcatgag tcaagacact gaagttagaa gtcgggtcgt   1260
ggggggaagt cttcgaggtg cccaggctgc ctccccagcc aaaggggagc cgtcactgcc   1320
cgagaaggac gaggaccatg cactgagtta ctggaagccc ttcctggtca acatgtgcgt   1380
ggctacggtc ctcacggccg gcgcttacct ctgctacagg ttcctgttca acagcaacac   1440
atagcctgac cctcctccac tccacctcca cccactgtcc gcctctgccc gcagagccca   1500
cgcccgacta gcaggcatgc cgcggtaggt aagggccgcc ggaccgcgta gagagccggg   1560
ccccggacgg acgttggttc tgcactaaaa cccatcttcc ccggatgtgt gtctcacccc   1620
tcatcctttt acttttttgcc ccttccactt tgagtaccaa atccacaagc catttttga    1680 ggagagtgaa agagagtacc atgctggcgg cgcagaggga aggggcctac acccgtcttg   1740
gggctcgccc cacccagggc tccctcctgg agcatcccag gcgggcggca cgccaacagc   1800
cccccccttg aatctgcagg gagcaactct ccactccata tttattttaaa caatttttc    1860 cccaaaggca tccatagtgc actagcattt tcttgaacca ataatgtatt aaaattttt    1920 gatgtcagcc ttgcatcaag ggctttatca aaaagtacaa taataaatcc tcaggtagta    1980
ctgggaatgg aaggctttgc catgggcctg ctgcgtcaga ccagtactgg gaaggaggac    2040
ggttgtaagc agttgttatt tagtgatatt gtgggtaacg tgagaagata aacaatgct    2100 ataatatata atgaacacgt gggtatttaa taagaaacat gatgtgagat tacttttgtcc   2160 cgcttattct cctccctgtt atctgctaga tctagttctc aatcactgct cccccgtgtg    2220
tattagaatg catgtaaggt cttccttgtgt cctgatgaaa aatatgtgct tgaaatgaga    2280
aactttgatc tctgcttact aatgtgcccc atgtccaagt ccaacctgcc tgtgcatgac    2340
ctgatcatta catggctgtg gttcctaagc ctgttgctga agtcattgtc gctcagcaat    2400
agggtgcagt tttccaggaa taggcatttg cctaattcct ggcatgacac tctagtgact    2460
tcctggtgag gcccagcctg tcctggtaca gcagggtctt gctgtaactc agacattcca    2520
agggtatggg aagccatatt cacacctcac gctctggaca tgatttaggg aagcagggac    2580 acccccgcc ccccacctt gggatcagcc tccgccattc caagtcaaca ctcttcttga    2640
```

```
gcagaccgtg atttggaaga gaggcacctg ctggaaacca cacttcttga aacagcctgg    2700
gtgacggtcc tttaggcagc ctgccgccgt ctctgtcccg gttcaccttg ccgagagagg    2760
cgcgtctgcc ccaccctcaa accctgtggg gcctgatggt gctcacgact cttcctgcaa    2820
agggaactga agacctccac attaagtggc tttttaacat gaaaaacacg gcagctgtag    2880
ctcccgagct actctcttgc cagcattttc acattttgcc tttctcgtgg tagaagccag    2940
tacagagaaa ttctgtggtg ggaacattcg aggtgtcacc ctgcagagct atggtgaggt    3000
gtggataagg cttaggtgcc aggctgtaag cattctgagc tgggcttgtt gtttttaagt    3060
cctgtatatg tatgtagtag tttgggtgtg tatatatagt agcatttcaa aatggacgta    3120
ctggtttaac ctcctatcct tggagagcag ctggctctcc accttgttac acattatgtt    3180
agagaggtag cgagctgctc tgctatatgc cttaagccaa tatttactca tcaggtcatt    3240 atttttttaca atggccatgg aataaaccat ttttacaaaa aaaaaaaaaa aaaaa        3295
```

<210> SEQ ID NO 14
<211> LENGTH: 435
<212> TYPE: PRT
<213> ORGANISM: Homo sapiens

<400> SEQUENCE: 14

```
Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
        195                 200                 205

Gly Pro Val Val His Cys Ser Ala Gly Ile Gly Arg Ser Gly Thr
    210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Lys Phe
                245                 250                 255

Arg Met Gly Leu Ile Gln Thr Ala Asp Gln Leu Arg Phe Ser Tyr Leu
```

```
                260                 265                 270
Ala Val Ile Glu Gly Ala Lys Phe Ile Met Gly Asp Ser Ser Val Gln
            275                 280                 285

Asp Gln Trp Lys Glu Leu Ser His Glu Asp Leu Glu Pro Pro Pro Glu
            290                 295                 300

His Ile Pro Pro Pro Arg Pro Lys Arg Ile Leu Glu Pro His
305                 310                 315                 320

Asn Gly Lys Cys Arg Glu Phe Phe Pro Asn His Gln Trp Val Lys Glu
                325                 330                 335

Glu Thr Gln Glu Asp Lys Asp Cys Pro Ile Lys Glu Lys Gly Ser
            340                 345                 350

Pro Leu Asn Ala Ala Pro Tyr Gly Ile Glu Ser Met Ser Gln Asp Thr
            355                 360                 365

Glu Val Arg Ser Arg Val Val Gly Gly Ser Leu Arg Gly Ala Gln Ala
            370                 375                 380

Ala Ser Pro Ala Lys Gly Glu Pro Ser Leu Pro Glu Lys Asp Glu Asp
385                 390                 395                 400

His Ala Leu Ser Tyr Trp Lys Pro Phe Leu Val Asn Met Cys Val Ala
                405                 410                 415

Thr Val Leu Thr Ala Gly Ala Tyr Leu Cys Tyr Arg Phe Leu Phe Asn
            420                 425                 430

Ser Asn Thr
        435

<210> SEQ ID NO 15
<211> LENGTH: 3275
<212> TYPE: DNA
<213> ORGANISM: Homo sapiens

<400> SEQUENCE: 15
ggtagctgca ggggtcgggg attgcagcgg gcctcggggc taagagcgcg acgcggccta    60
gagcggcaga cggcgcagtg ggccgagaag gaggcgcagc agccgccctg gcccgtcatg   120
gagatggaaa aggagttcga gcagatcgac aagtccggga gctgggcggc catttaccag   180
gatatccgac atgaagccag tgacttccca tgtagagtgg ccaagcttcc taagaacaaa   240
aaccgaaata ggtacagaga cgtcagtccc tttgaccata gtcggattaa actacatcaa   300
gaagataatg actatatcaa cgctagtttg ataaaaatgg aagaagccca aaggagttac   360
attcttaccc agggccttt gcctaacaca tgcggtcact tttgggagat ggtgtgggag   420
cagaaaagca ggggtgtcgt catgctcaac agagtgatgg agaaaggttc gttaaaatgc   480
gcacaatact ggccacaaaa agaagaaaaa gagatgatct ttgaagacac aaatttgaaa   540
ttaacattga tctctgaaga tatcaagtca tattatacag tgcgacagct agaattggaa   600
aaccttacaa cccaagaaac tcgagagatc ttacatttcc actataccac atggcctgac   660
tttggagtcc ctgaatcacc agcctcattc ttgaactttc ttttcaaagt ccgagagtca   720
gggtcactca gcccggagca cgggcccgtt gtggtgcact gcagtgcagg catcggcagg   780
tctggaacct tctgtctggc tgataccctgc ctcttgctga tggacaagag gaaagaccct   840
tcttccgttg atatcaagaa agtgctgtta gaaatgagga gtttcggat ggggctgatc   900 cagacagccg accagctgcg cttctcctac ctggctgtga tcgaaggtgc caaattcatc   960 atggggact cttccgtgca ggatcagtgg aaggagcttt cccacgagga cctggagccc  1020
ccacccgagc atatcccccc acctcccgg ccacccaaac gaatcctgga gccacacaat  1080
```

| | |
|---|---|
| gggaaatgca gggagttctt cccaaatcac cagtgggtga aggaagagac ccaggaggat | 1140 |
| aaagactgcc ccatcaagga agaaaaagga agccccttaa atgccgcacc ctacggcatc | 1200 |
| gaaagcatga gtcaagacac tgaagttaga agtcgggtcg tgggggggaag tcttcgaggt | 1260 |
| gcccaggctg cctccccagc caaggggag ccgtcactgc ccgagaagga cgaggaccat | 1320 |
| gcactgagtt actggaagcc cttcctggtc aacatgtgcg tggctacggt cctcacggcc | 1380 |
| ggcgcttacc tctgctacag gttcctgttc aacagcaaca catagcctga ccctcctcca | 1440 |
| ctccacctcc acccactgtc cgcctctgcc cgcagagccc acgcccgact agcaggcatg | 1500 |
| ccgcggtagg taagggccgc cggaccgcgt agagagtcgg gccccggacg gacgttggtt | 1560 |
| ctgcactaaa acccatcttc cccggatgtg tgtctcaccc ctcatccttt tacttttttgc | 1620 |
| cccttccact ttgagtacca aatccacaag ccattttttg aggagagtga aagagagtac | 1680 |
| catgctggcg gcgcagaggg aaggggccta cacccgtctt ggggctcgcc ccacccaggg | 1740 |
| ctccctcctg gagcatccca ggcgggcggc acgccaacag ccccccccctt gaatctgcag | 1800 |
| ggagcaactc tccactccat atttatttaa acaatttttt ccccaaaggc atccatagtg | 1860 |
| cacttgcatt ttcttgaacc aataatgtat taaaattttt tgatgtcagc cttgcatcaa | 1920 |
| gggctttatc aaaaagtaca ataataaatc ctcaggtagt actgggaatg gaaggctttg | 1980 |
| ccatgggcct gctgcgtcag accagtactg ggaaggagga cggttgtaag cagttgttat | 2040 |
| ttagtgatat tgtgggtaac gtgagaagat agaacaatgc tataatatat aatgaacacg | 2100 |
| tgggtattta ataagaaaca tgatgtgaga ttactttgtc ccgcttattc tcctccctgt | 2160 |
| tatctgctag atctagttct caatcactgc tcccccgtgt gtattagaat gcatgtaagg | 2220 |
| tcttcttgtg tcctgatgaa aaatatgtgc ttgaaatgag aaactttgat ctctgcttac | 2280 |
| taatgtgccc catgtccaag tccaacctgc ctgtgcatga cctgatcatt acatggctgt | 2340 |
| ggttcctaag cctgttgctg aagtcattgt cgctcagcaa tagggtgcag ttttccagga | 2400 |
| ataggcatt gcctaattcc tggcatgaca ctctagtgac ttcctggtga ggcccagcct | 2460 |
| gtcctggtac agcagggtct tgctgtaact cagacattcc aagggtatgg gaagccatat | 2520 |
| tcacacctca cgctctggac atgatttagg gaagcaggga cacccccgc ccccacctt | 2580 |
| tgggatcagc ctccgccatt ccaagtcaac actcttcttg agcagaccgt gatttggaag | 2640 |
| agaggcacct gctggaaacc acacttcttg aaacagcctg ggtgacggtc ctttaggcag | 2700 |
| cctgccgccg tctctgtccc ggttcacctt gccgagagag gcgcgtctgc cccaccctca | 2760 |
| aaccctgtgg ggcctgatgg tgctcacgac tcttcctgca aagggaactg aagacctcca | 2820 |
| cattaagtgg ctttttaaca tgaaaaacac ggcagctgta gctcccgagc tactctcttg | 2880 |
| ccagcatttt cacattttgc ctttctcgtg gtagaagcca gtacagagaa attctgtggt | 2940 |
| gggaacattc gaggtgtcac cctgcagagc tatggtgagg tgtggataag gcttaggtgc | 3000 |
| caggctgtaa gcattctgag ctgggcttgt tgttttttaag tcctgtatat gtatgtagta | 3060 |
| gtttgggtgt gtatatatag tagcatttca aaatggacgt actggtttaa cctcctatcc | 3120 |
| ttggagagca gctggctctc cacttgtta cacattatgt tagagaggta gcgagctgct | 3180 |
| ctgctatatg cctaagcca atatttactc atcaggtcat tatttttac aatggccatg | 3240 |
| gaataaacca ttttacaaa aaaaaaaaaa aaaaa | 3275 |

<210> SEQ ID NO 16
<211> LENGTH: 435
<212> TYPE: PRT
<213> ORGANISM: Homo sapiens

```
<400> SEQUENCE: 16

Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
        195                 200                 205

Gly Pro Val Val His Cys Ser Ala Gly Ile Gly Arg Ser Gly Thr
    210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Lys Phe
            245                 250                 255

Arg Met Gly Leu Ile Gln Thr Ala Asp Gln Leu Arg Phe Ser Tyr Leu
        260                 265                 270

Ala Val Ile Glu Gly Ala Lys Phe Ile Met Gly Asp Ser Ser Val Gln
    275                 280                 285

Asp Gln Trp Lys Glu Leu Ser His Glu Asp Leu Glu Pro Pro Pro Glu
290                 295                 300

His Ile Pro Pro Pro Arg Pro Pro Lys Arg Ile Leu Glu Pro His
305                 310                 315                 320

Asn Gly Lys Cys Arg Glu Phe Phe Pro Asn His Gln Trp Val Lys Glu
            325                 330                 335

Glu Thr Gln Glu Asp Lys Asp Cys Pro Ile Lys Glu Glu Lys Gly Ser
        340                 345                 350

Pro Leu Asn Ala Ala Pro Tyr Gly Ile Glu Ser Met Ser Gln Asp Thr
    355                 360                 365

Glu Val Arg Ser Arg Val Val Gly Gly Ser Leu Arg Gly Ala Gln Ala
370                 375                 380

Ala Ser Pro Ala Lys Gly Glu Pro Ser Leu Pro Glu Lys Asp Glu Asp
385                 390                 395                 400

His Ala Leu Ser Tyr Trp Lys Pro Phe Leu Val Asn Met Cys Val Ala
```

```
                    405                 410                 415
Thr Val Leu Thr Ala Gly Ala Tyr Leu Cys Tyr Arg Phe Leu Phe Asn
                420                 425                 430

Ser Asn Thr
        435

<210> SEQ ID NO 17
<211> LENGTH: 1457
<212> TYPE: DNA
<213> ORGANISM: Homo sapiens

<400> SEQUENCE: 17
gacatgaaga agcagcagcg gctagggcgg cggtagctgc aggggtcggg gattgcagcg      60
ggcctcgggg ctaagagcgc gacgctggcc tagagcggca gacggcgcag tgggccgaga     120
aggaggcgca gcagccgccc tggcccgtca tggagatgga aaaggagttt gagcagatcg     180
acaagtccgg gagctgggcg gccatttacc aggatatccg acatgaagcc agtgacttcc     240
catgtagagt ggccaagctt cctaagaaca aaaaccgaaa taggtacaga gacgtcagtc     300
cctttgacca tagtcggatt aaactacatc aagaagataa tgactatatc aacgctagtt     360
tgataaaaat ggaagaagcc caaggagtt acattcttac ccagggccct ttgcctaaca      420
catgcggtca cttttgggag atggtgtggg agcagaaaag caggggtgtc gtcatgctca     480
acagagtgat ggagaaggt tcgttaaaat gcgcacaata ctggccacaa aaagaagaaa      540 agagatgat ctttgaagac acaaatttga aattaacatt gatctctgaa gatatcaagt      600
catattatac agtcgacag ctagaattgg aaaaccttac aacccaagaa actcgagaga      660
tcttacattt ccactatacc acatggcctg actttggagt ccctgaatca ccagcctcat     720
tcttgaactt tcttttcaaa gtccgagagt cagggtcact cagcccggag cacgggcccg     780
ttgtggtgca ctgcagtgca ggcatcggca ggtctggaac cttctgtctg ctgatacct      840 gcctcttgct gatggacaag aggaaagacc cttcttccgt tgatatcaag aaagtgctgt     900
tagaaatgag gaagtttcgg atggggctga tccagacagc cgaccagctg cgcttctcct     960
acctggctgt gatcgaaggt gccaaattca tcatggggga ctcttccgtg caggatcagt    1020
ggaaggagct ttcccacgag gacctggagc ccccacctga gcatatcccc ccacctcccc    1080
ggccacccaa acgaatcctg gagccacaca atgggaaatg cagggagttc ttcccaaatc    1140
accagtgggt gaaggaagag acccaggagg ataaagactg ccccatcaag gaagaaaaag    1200
gaagcccctt aaatgccgca ccctacggca tcgaaagcat gagtcaagac actgaagtta    1260
gaagtcgggt cgtgggggga agtcttcgag gtgcccaggc tgcctcccca gccaaagggg    1320
agccgtcact gcccgagaag gacgaggacc atgcactgag ttactggaag ccctccctgg    1380
tcaacatgtg cgtggctacg gtcctcacgg ccggcgctta cctctgctac aggttcctgt    1440
tcaacagcaa cacatag                                                   1457

<210> SEQ ID NO 18
<211> LENGTH: 435
<212> TYPE: PRT
<213> ORGANISM: Homo sapiens

<400> SEQUENCE: 18

Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
            20                  25                  30
```

```
Arg Val Ala Lys Leu Pro Lys Asn Lys Asn Arg Asn Arg Tyr Arg Asp
            35                  40                  45

Val Ser Pro Phe Asp His Ser Arg Ile Lys Leu His Gln Glu Asp Asn
 50                  55                  60

Asp Tyr Ile Asn Ala Ser Leu Ile Lys Met Glu Glu Ala Gln Arg Ser
 65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
                    100                 105                 110

Val Met Glu Lys Gly Ser Leu Lys Cys Ala Gln Tyr Trp Pro Gln Lys
                115                 120                 125

Glu Glu Lys Glu Met Ile Phe Glu Asp Thr Asn Leu Lys Leu Thr Leu
                130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                    165                 170                 175

Thr Thr Trp Pro Asp Phe Gly Val Pro Glu Ser Pro Ala Ser Phe Leu
                180                 185                 190

Asn Phe Leu Phe Lys Val Arg Glu Ser Gly Ser Leu Ser Pro Glu His
                195                 200                 205

Gly Pro Val Val His Cys Ser Ala Gly Ile Gly Arg Ser Gly Thr
    210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Lys Phe
                    245                 250                 255

Arg Met Gly Leu Ile Gln Thr Ala Asp Gln Leu Arg Phe Ser Tyr Leu
                260                 265                 270

Ala Val Ile Glu Gly Ala Lys Phe Ile Met Gly Asp Ser Ser Val Gln
                275                 280                 285

Asp Gln Trp Lys Glu Leu Ser His Glu Asp Leu Glu Pro Pro Glu
                290                 295                 300

His Ile Pro Pro Pro Arg Pro Pro Lys Arg Ile Leu Glu Pro His
305                 310                 315                 320

Asn Gly Lys Cys Arg Glu Phe Phe Pro Asn His Gln Trp Val Lys Glu
                    325                 330                 335

Glu Thr Gln Glu Asp Lys Asp Cys Pro Ile Lys Glu Glu Lys Gly Ser
                340                 345                 350

Pro Leu Asn Ala Ala Pro Tyr Gly Ile Glu Ser Met Ser Gln Asp Thr
                355                 360                 365

Glu Val Arg Ser Arg Val Val Gly Gly Ser Leu Arg Gly Ala Gln Ala
                370                 375                 380

Ala Ser Pro Ala Lys Gly Glu Pro Ser Leu Pro Glu Lys Asp Glu Asp
385                 390                 395                 400

His Ala Leu Ser Tyr Trp Lys Pro Phe Leu Val Asn Met Cys Val Ala
                    405                 410                 415

Thr Val Leu Thr Ala Gly Ala Tyr Leu Cys Tyr Arg Phe Leu Phe Asn
                420                 425                 430

Ser Asn Thr
        435
```

<210> SEQ ID NO 19
<211> LENGTH: 435
<212> TYPE: PRT
<213> ORGANISM: Homo sapiens

<400> SEQUENCE: 19

```
Met Glu Met Glu Lys Glu Phe Glu Gln Ile Asp Lys Ser Gly Ser Trp
1               5                   10                  15
Ala Ala Ile Tyr Gln Asp Ile Arg His Glu Ala Ser Asp Phe Pro Cys
            20                  25                  30
Arg Val Ala Lys Leu Pro Lys Asn Lys Asn Arg Asn Arg Tyr Arg Asp
        35                  40                  45
Val Ser Pro Phe Asp His Ser Arg Ile Lys Leu His Gln Glu Asp Asn
    50                  55                  60
Asp Tyr Ile Asn Ala Ser Leu Ile Lys Met Glu Glu Ala Gln Arg Ser
65                  70                  75                  80
Tyr Ile Leu Thr Gln Gly Pro Leu Pro Asn Thr Cys Gly His Phe Trp
                85                  90                  95
Glu Met Val Trp Glu Gln Lys Ser Arg Gly Val Val Met Leu Asn Arg
            100                 105                 110
Val Met Glu Lys Gly Ser Leu Lys Cys Ala Gln Tyr Trp Pro Gln Lys
        115                 120                 125
Glu Glu Lys Glu Met Ile Phe Glu Asp Thr Asn Leu Lys Leu Thr Leu
    130                 135                 140
Ile Ser Glu Asp Ile Lys Ser Tyr Tyr Thr Val Arg Gln Leu Glu Leu
145                 150                 155                 160
Glu Asn Leu Thr Thr Gln Glu Thr Arg Glu Ile Leu His Phe His Tyr
                165                 170                 175
Thr Thr Trp Pro Asp Phe Gly Val Pro Glu Ser Pro Ala Ser Phe Leu
            180                 185                 190
Asn Phe Leu Phe Lys Val Arg Glu Ser Gly Ser Leu Ser Pro Glu His
        195                 200                 205
Gly Pro Val Val Val His Ala Ala Gly Ile Gly Arg Ser Gly Thr
    210                 215                 220
Phe Cys Leu Ala Asp Thr Cys Leu Leu Leu Met Asp Lys Arg Lys Asp
225                 230                 235                 240
Pro Ser Ser Val Asp Ile Lys Lys Val Leu Leu Glu Met Arg Lys Phe
                245                 250                 255
Arg Met Gly Leu Ile Gln Thr Ala Asp Gln Leu Arg Phe Ser Tyr Leu
            260                 265                 270
Ala Val Ile Glu Gly Ala Lys Phe Ile Met Gly Asp Ser Ser Val Gln
        275                 280                 285
Asp Gln Trp Lys Glu Leu Ser His Glu Asp Leu Glu Pro Pro Pro Glu
    290                 295                 300
His Ile Pro Pro Pro Arg Pro Pro Lys Arg Ile Leu Glu Pro His
305                 310                 315                 320
Asn Gly Lys Cys Arg Glu Phe Phe Pro Asn His Gln Trp Val Lys Glu
                325                 330                 335
Glu Thr Gln Glu Asp Lys Asp Cys Pro Ile Lys Glu Glu Lys Gly Ser
            340                 345                 350
Pro Leu Asn Ala Ala Pro Tyr Gly Ile Glu Ser Met Ser Gln Asp Thr
        355                 360                 365
Glu Val Arg Ser Arg Val Val Gly Gly Ser Leu Arg Gly Ala Gln Ala
    370                 375                 380
```

```
Ala Ser Pro Ala Lys Gly Glu Pro Ser Leu Pro Glu Lys Asp Glu Asp
385                 390                 395                 400

His Ala Leu Ser Tyr Trp Lys Pro Phe Leu Val Asn Met Cys Val Ala
                405                 410                 415

Thr Val Leu Thr Ala Gly Ala Tyr Leu Cys Tyr Arg Phe Leu Phe Asn
            420                 425                 430

Ser Asn Thr
        435

<210> SEQ ID NO 20
<211> LENGTH: 7
<212> TYPE: PRT
<213> ORGANISM: Artificial Sequence
<220> FEATURE:
<223> OTHER INFORMATION: recombinant protein

<400> SEQUENCE: 20

Gly Gln Ser Ser Arg Ser Ser
1               5

<210> SEQ ID NO 21
<211> LENGTH: 18
<212> TYPE: PRT
<213> ORGANISM: Artificial Sequence
<220> FEATURE:
<223> OTHER INFORMATION: recombinant protein

<400> SEQUENCE: 21

Gly Gln Ser Ser Arg Ser Ser Gly Gly Gly Gly Ser Gly Gly Gly
1               5                   10                  15

Gly Ser

<210> SEQ ID NO 22
<211> LENGTH: 15
<212> TYPE: PRT
<213> ORGANISM: Artificial Sequence
<220> FEATURE:
<223> OTHER INFORMATION: recombinant protein

<400> SEQUENCE: 22

Gly Leu Asn Asp Ile Phe Glu Ala Gln Lys Ile Glu Trp His Glu
1               5                   10                  15

<210> SEQ ID NO 23
<211> LENGTH: 5532
<212> TYPE: DNA
<213> ORGANISM: Artificial Sequence
<220> FEATURE:
<223> OTHER INFORMATION: recombinant plasmid

<400> SEQUENCE: 23
gacggatcgg gagatctccc gatccctat  ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacgggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
```

```
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagt    900
taagctatca caagtttgt acaaaaaagc aggctccgcg gccgcccct tcaccaaggg    960 tgggcgcgcc gacccagctt tcttgtacaa agtggttgat ctagagggcc gcggttcga    1020 aggtaagcct atccctaacc ctctcctcgg tctcgattct acgcgtaccg gttagtaatg    1080
agtttaaacg ggggaggcta actgaaacac ggaaggagac aataccggaa ggaacccgcg    1140
ctatgacggc aataaaaaga cagaataaaa cgcacgggtg ttgggtcgtt tgttcataaa    1200
cgcggggttc ggtcccaggg ctggcactct gtcgataccc caccgagacc ccattggggc    1260
caatacgccc gcgtttcttc cttttcccca ccccaccccc caagttcggg tgaaggccca    1320
gggctcgcag ccaacgtcgg ggcggcaggc cctgccatag cagatctgcg cagctggggc    1380 tctaggggt atcccacgc gccctgtagc ggcgcattaa gcgcggcggg tgtggtggtt    1440
acgcgcagcg tgaccgctac acttgccagc gccctagcgc ccgctccttt cgctttcttc    1500
ccttcctttc tcgccacgtt cgccggcttt cccgtcaag ctctaaatcg ggggctccct    1560
ttagggttcc gatttagtgc tttacggcac ctcgacccca aaaaacttga ttagggtgat    1620
ggttcacgta gtgggccatc gccctgatag acggtttttc gccctttgac gttggagtcc    1680
acgttcttta atagtggact cttgttccaa actggaacaa cactcaaccc tatctcggtc    1740
tattcttttg atttataagg gattttgccg atttcggcct attggttaaa aaatgagctg    1800
atttaacaaa aatttaacgc gaattaattc tgtggaatgt gtgtcagtta gggtgtggaa    1860
agtccccagg ctccccagca ggcagaagta tgcaaagcat gcatctcaat tagtcagcaa    1920
ccaggtgtgg aaagtcccca ggctccccag caggcagaag tatgcaaagc atgcatctca    1980
attagtcagc aaccatagtc ccgcccctaa ctccgcccat cccgcccta actccgccca    2040 gttccgccca ttctccgccc catggctgac taattttttt tatttatgca gaggccgagg    2100
ccgcctctgc ctctgagcta ttccagaagt agtgaggagg ctttttttgga ggcctaggct    2160 tttgcaaaaa gctcccggga gcttgtatat ccatttttcgg atctgatcaa gagacaggat    2220
gaggatcgtt tcgcatgatt gaacaagatg gattgcacgc aggttctccg gccgcttggg    2280
tggagaggct attcggctat gactgggcac aacagacaat cggctgctct gatgccgccg    2340
tgttccggct gtcagcgcag gggcgcccgg ttcttttttgt caagaccgac ctgtccggtg    2400
ccctgaatga actgcaggac gaggcagcgc ggctatcgtg gctggccacg acgggcgttc    2460
cttgcgcagc tgtgctcgac gttgtcactg aagcgggaag ggactggctg ctattgggcg    2520
aagtgccggg gcaggatctc ctgtcatctc accttgctcc tgccgagaaa gtatccatca    2580
tggctgatgc aatgcggcgg ctgcatacgc ttgatccggc tacctgccca ttcgaccacc    2640
aagcgaaaca tcgcatcgag cgagcacgta ctcggatgga agccggtctt gtcgatcagg    2700
atgatctgga cgaagagcat caggggctcg cgccagccga actgttcgcc aggctcaagg    2760
cgcgcatgcc cgacggcgag gatctcgtcg tgacccatgg cgatgcctgc ttgccgaata    2820
```

```
tcatggtgga aaatggccgc ttttctggat tcatcgactg tggccggctg ggtgtggcgg    2880
accgctatca ggacatagcg ttggctaccc gtgatattgc tgaagagctt ggcggcgaat    2940
gggctgaccg cttcctcgtg ctttacggta tcgccgctcc cgattcgcag cgcatcgcct    3000
tctatcgcct tcttgacgag ttcttctgag cgggactctg gggttcgcga aatgaccgac    3060
caagcgacgc ccaacctgcc atcacgagat ttcgattcca ccgccgcctt ctatgaaagg    3120
ttgggcttcg gaatcgtttt ccgggacgcc ggctggatga tcctccagcg cggggatctc    3180
atgctggagt tcttcgccca ccccaacttg tttattgcag cttataatgg ttacaaataa    3240
agcaatagca tcacaaattt cacaaataaa gcatttttt cactgcattc tagttgtggt    3300
ttgtccaaac tcatcaatgt atcttatcat gtctgtatac cgtcgacctc tagctagagc    3360
ttggcgtaat catggtcata gctgtttcct gtgtgaaatt gttatccgct cacaattcca    3420
cacaacatac gagccggaag cataaagtgt aaagcctggg gtgcctaatg agtgagctaa    3480
ctcacattaa ttgcgttgcg ctcactgccc gctttccagt cgggaaacct gtcgtgccag    3540
ctgcattaat gaatcggcca acgcgcgggg agaggcggtt tgcgtattgg gcgctcttcc    3600
gcttcctcgc tcactgactc gctgcgctcg tcgttcggc tgcggcgagc ggtatcagct    3660
cactcaaagg cggtaatacg gttatccaca gaatcagggg ataacgcagg aaagaacatg    3720
tgagcaaaag gccagcaaaa ggccaggaac cgtaaaaagg ccgcgttgct ggcgtttttc    3780
cataggctcc gcccccctga cgagcatcac aaaaatcgac gctcaagtca gaggtggcga    3840
aacccgacag gactataaag ataccaggcg tttccccctg gaagctccct cgtgcgctct    3900
cctgttccga ccctgccgct taccggatac ctgtccgcct ttctcccttc gggaagcgtg    3960
gcgctttctc atagctcacg ctgtaggtat ctcagttcgg tgtaggtcgt tcgctccaag    4020
ctgggctgtg tgcacgaacc ccccgttcag cccgaccgct gcgccttatc cggtaactat    4080
cgtcttgagt ccaacccggt aagacacgac ttatcgccac tggcagcagc cactggtaac    4140
aggattagca gagcgaggta tgtaggcggt gctacagagt tcttgaagtg gtggcctaac    4200
tacggctaca ctagaagaac agtatttggt atctgcgctc tgctgaagcc agttaccttc    4260
ggaaaaagag ttggtagctc ttgatccggc aaacaaacca ccgctggtag cggtggtttt    4320
tttgtttgca agcagcagat tacgcgcaga aaaaaggat ctcaagaaga tcctttgatc    4380
ttttctacgg ggtctgacgc tcagtggaac gaaaactcac gttaagggat tttggtcatg    4440
agattatcaa aaaggatctt cacctagatc cttttaaatt aaaaatgaag ttttaaatca    4500
atctaaagta tatatgagta aacttggtct gacagttacc aatgcttaat cagtgaggca    4560
cctatctcag cgatctgtct atttcgttca tccatagttg cctgactccc cgtcgtgtag    4620
ataactacga tacgggaggg cttaccatct ggccccagtg ctgcaatgat accgcgagac    4680
ccacgctcac cggctccaga tttatcagca ataaccagc cagccggaag ggccgagcgc    4740
agaagtggtc ctgcaacttt atccgcctcc atccagtcta ttaattgttg ccgggaagct    4800
agagtaagta gttcgccagt taatagtttg cgcaacgttg ttgccattgc tacaggcatc    4860
gtggtgtcac gctcgtcgtt tggtatggct tcattcagct ccggttccca acgatcaagg    4920
cgagttacat gatcccccat gttgtgcaaa aaagcggtta gctccttcgg tcctccgatc    4980
gttgtcagaa gtaagttggc cgcagtgtta tcactcatgg ttatggcagc actgcataat    5040
tctcttactg tcatgccatc cgtaagatgc ttttctgtga ctggtgagta ctcaaccaag    5100
tcattctgag aatagtgtat gcggcgaccg agttgctctt gcccggcgtc aatacgggat    5160
aataccgcgc cacatagcag aactttaaaa gtgctcatca ttggaaaacg ttcttcgggg    5220
```

-continued

```
cgaaaactct caaggatctt accgctgttg agatccagtt cgatgtaacc cactcgtgca    5280
cccaactgat cttcagcatc ttttactttc accagcgttt ctgggtgagc aaaaacagga    5340
aggcaaaatg ccgcaaaaaa gggaataagg gcgacacgga aatgttgaat actcatactc    5400 ttccttttc aatattattg aagcatttat cagggttatt gtctcatgag cggatacata     5460
tttgaatgta tttagaaaaa taaacaaata ggggttccgc gcacatttcc ccgaaaagtg    5520
ccacctgacg tc                                                        5532
```

```
<210> SEQ ID NO 24
<211> LENGTH: 7
<212> TYPE: PRT
<213> ORGANISM: Artificial Sequence
<220> FEATURE:
<223> OTHER INFORMATION: recombinant protein

<400> SEQUENCE: 24

Cys Asn Arg Tyr Arg Asp Val
1               5

<210> SEQ ID NO 25
<211> LENGTH: 7
<212> TYPE: PRT
<213> ORGANISM: Artificial Sequence
<220> FEATURE:
<223> OTHER INFORMATION: recombinant protein
<220> FEATURE:
<221> NAME/KEY: MOD_RES
<222> LOCATION: (4)..(4)
<223> OTHER INFORMATION: PHOSPHORYLATION

<400> SEQUENCE: 25

Cys Asn Arg Tyr Arg Asp Val
1               5

<210> SEQ ID NO 26
<211> LENGTH: 280
<212> TYPE: PRT
<213> ORGANISM: Artificial Sequence
<220> FEATURE:
<223> OTHER INFORMATION: recombinant protein

<400> SEQUENCE: 26

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Gly Thr Val Lys Ile Thr Cys Ser Gly Ser Ser Ser Ala Tyr
        35                  40                  45

Gly Tyr Gly Trp Tyr Gln Gln Lys Ser Pro Gly Ser Ala Pro Val Thr
    50                  55                  60

Val Ile Tyr Asn Asn Asn Lys Arg Pro Ser Asn Ile Pro Ser Arg Phe
65                  70                  75                  80

Ser Gly Ser Lys Ser Gly Ser Thr Gly Thr Leu Thr Ile Thr Gly Val
                85                  90                  95

Gln Ala Glu Asp Glu Ala Val Tyr Phe Cys Ser Glu Asp Ser Ser
            100                 105                 110

Thr Asp Ala Ile Phe Gly Ala Gly Thr Thr Leu Thr Val Leu Gly Gln
        115                 120                 125

Ser Ser Arg Ser Ser Thr Val Thr Leu Asp Glu Ser Gly Gly Gly Leu
    130                 135                 140
```

```
Gln Ala Pro Gly Gly Ala Leu Ser Leu Val Cys Lys Ala Ser Gly Phe
145                 150                 155                 160

Thr Phe Ser Ser Tyr Asp Met Gly Trp Ile Arg Gln Ala Pro Gly Lys
            165                 170                 175

Gly Leu Glu Tyr Val Ala Gly Ile Thr Asp Asn Gly Arg Tyr Ala Ser
        180                 185                 190

Tyr Gly Ser Ala Val Asp Gly Arg Ala Thr Ile Ser Arg Asp Asn Gly
    195                 200                 205

Gln Ser Ser Val Arg Leu Gln Leu Asn Asn Leu Arg Ala Glu Asp Thr
210                 215                 220

Gly Thr Tyr Tyr Cys Ala Arg Asp Asp Gly Ser Gly Trp Thr Gly Asn
225                 230                 235                 240

Ser Ile Asp Ala Trp Gly His Gly Thr Glu Val Ile Val Ser Ser Thr
            245                 250                 255

Ser Gly Gln Ala Gly Gln His His His His His Gly Ala Tyr Pro
        260                 265                 270

Tyr Asp Val Pro Asp Tyr Ala Ser
    275                 280

<210> SEQ ID NO 27
<211> LENGTH: 280
<212> TYPE: PRT
<213> ORGANISM: Artificial Sequence
<220> FEATURE:
<223> OTHER INFORMATION: recombinant protein

<400> SEQUENCE: 27

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Ala Phe Asn Lys Ile Thr Cys Ser Gly Ser Ser Ser Ala Tyr
        35                  40                  45

Gly Tyr Gly Trp Asn Gln Gln Lys Ser Pro Gly Ser Ala Pro Val Thr
    50                  55                  60

Val Ile Tyr Asn Asn Asn Lys Arg Pro Ser Asn Ile Pro Ser Arg Phe
65                  70                  75                  80

Ser Gly Ser Lys Ser Gly Ser Thr Gly Thr Leu Thr Ile Thr Gly Asp
            85                  90                  95

Gln Asp Glu Asp Glu Asp Phe Tyr Phe Cys Gly Ser Glu Tyr Ser Ser
        100                 105                 110

Thr Asp Ala Ile Phe Gly Ala Gly Thr Thr Leu Thr Val Leu Gly Gln
    115                 120                 125

Ser Ser Arg Ser Ser Thr Val Thr Leu Asp Glu Ser Gly Gly Gly Leu
130                 135                 140

Gln Ala Pro Gly Gly Ala Leu Ser Leu Val Cys Lys Ala Ser Gly Phe
145                 150                 155                 160

Thr Phe Ser Ser Tyr Asp Met Gly Trp Ile Pro Gln Ala Pro Gly Lys
            165                 170                 175

Gly Leu Glu Tyr Val Ala Gly Ile Thr Asp Asn Gly Ile Tyr Ala Ser
        180                 185                 190

Tyr Gly Ser Ala Val Asp Gly Arg Ala Thr Ile Ser Arg Asp Asn Arg
    195                 200                 205

Gln Ser Ser Val Lys Leu Gln Leu Asn Asn Leu Lys Ala Asp Asp Thr
210                 215                 220
```

```
Gly Thr Tyr Tyr Cys Ala Arg Asp Asp Gly Ser Gly Trp Thr Gly Asn
225                 230                 235                 240

Ser Ile Asp Ala Trp Gly His Gly Thr Glu Val Ile Val Ser Ser Thr
                245                 250                 255

Ser Gly Gln Ala Gly Gln His His His His His Gly Ala Tyr Pro
            260                 265                 270

Tyr Asp Val Pro Asp Tyr Ala Ser
        275                 280

<210> SEQ ID NO 28
<211> LENGTH: 280
<212> TYPE: PRT
<213> ORGANISM: Artificial Sequence
<220> FEATURE:
<223> OTHER INFORMATION: recombinant protein

<400> SEQUENCE: 28

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Asp Pro Leu Lys Ile Thr Cys Ser Gly Asp Ser Ser Gly Tyr
        35                  40                  45

Gly Tyr Gly Trp Tyr Gln Gln Lys Ser Pro Gly Ser Ala Pro Val Thr
    50                  55                  60

Val Ile Tyr Asn Asn Asn Lys Arg Pro Ser Asp Ile Pro Ser Arg Phe
65                  70                  75                  80

Ser Gly Ser Lys Ser Gly Ser Thr Gly Thr Leu Thr Ile Thr Gly Val
                85                  90                  95

Gln Ala Glu Asp Glu Ala Val Tyr Phe Cys Gly Ser Glu Asp Ser Asn
            100                 105                 110

Thr Asp Ala Val Phe Gly Ala Gly Thr Thr Leu Thr Val Leu Gly Gln
        115                 120                 125

Ser Ser Arg Ser Ser Thr Val Thr Leu Asp Glu Ser Gly Gly Gly Leu
    130                 135                 140

Gln Thr Pro Gly Gly Thr Leu Ser Leu Ala Cys Lys Ala Ser Gly Phe
145                 150                 155                 160

Thr Phe Ser Gly Tyr Asp Met Gly Trp Val Arg Gln Ala Pro Gly Lys
                165                 170                 175

Gly Leu Glu Tyr Val Ala Gly Ile Thr Ser Asp Gly Arg Tyr Ala Ser
            180                 185                 190

Tyr Gly Ser Ala Val Asp Gly Arg Ala Ala Ile Trp Arg Asp Asn Gly
        195                 200                 205

Gln Ser Thr Val Arg Leu Gln Leu Lys Asn Leu Arg Thr Glu Asp Thr
    210                 215                 220

Ala Thr Tyr Tyr Cys Ala Arg Asn Asp Gly Ser Gly Trp Asn Gly Asn
225                 230                 235                 240

Asn Ile Asp Ala Trp Gly His Gly Thr Glu Val Ile Val Ser Ser Thr
                245                 250                 255

Ser Gly Gln Ala Gly Gln His His His His His Gly Ala Tyr Pro
            260                 265                 270

Tyr Asp Val Pro Asp Tyr Ala Ser
        275                 280

<210> SEQ ID NO 29
```

<211> LENGTH: 280
<212> TYPE: PRT
<213> ORGANISM: Artificial Sequence
<220> FEATURE:
<223> OTHER INFORMATION: recombinant protein

<400> SEQUENCE: 29

```
Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Lys Ile Thr Cys Ser Gly Asp Ser Ser Asp Tyr
        35                  40                  45

Gly Tyr Gly Trp Tyr Gln Gln Lys Ser Pro Gly Ser Ala Pro Val Thr
    50                  55                  60

Val Thr Tyr Ser Asn Asn Gln Arg Pro Pro Asn Ile Pro Ser Arg Phe
65                  70                  75                  80

Ser Gly Ser Ala Ser Gly Ser Thr Ala Thr Leu Thr Ile Thr Gly Val
                85                  90                  95

Gln Val Glu Asp Glu Ala Val Tyr Tyr Cys Gly Ser Glu Asp Ser Thr
            100                 105                 110

Thr Asp Ala Val Phe Gly Ala Gly Thr Thr Leu Thr Val Leu Gly Gln
        115                 120                 125

Ser Ser Arg Ser Ser Ala Met Thr Leu Asp Glu Ser Gly Gly Gly Leu
    130                 135                 140

Gln Thr Pro Gly Gly Ala Leu Ser Leu Val Cys Lys Ala Ser Gly Phe
145                 150                 155                 160

Thr Phe Ser Ser Tyr Asp Met Gly Trp Val Arg Gln Ala Pro Gly Lys
                165                 170                 175

Gly Leu Glu Tyr Val Ala Gly Ile Thr Asn Asp Gly Arg Tyr Ala Ser
            180                 185                 190

Tyr Gly Ser Ala Val Asp Gly Arg Ala Thr Ile Ser Arg Asp Asn Gly
        195                 200                 205

Gln Ser Thr Val Arg Leu Gln Leu Asn Asn Leu Arg Ala Glu Asp Thr
    210                 215                 220

Gly Thr Tyr Tyr Cys Ala Arg Asp Asp Gly Ser Gly Trp Thr Gly Asn
225                 230                 235                 240

Thr Ile Asp Thr Trp Gly His Gly Thr Glu Val Ile Val Ser Ser Thr
                245                 250                 255

Ser Gly Gln Ala Gly Gln His His His His His Gly Ala Tyr Pro
            260                 265                 270

Tyr Asp Val Pro Asp Tyr Ala Ser
        275                 280
```

<210> SEQ ID NO 30
<211> LENGTH: 843
<212> TYPE: DNA
<213> ORGANISM: Artificial sequence
<220> FEATURE:
<223> OTHER INFORMATION: recombinant DNA

<400> SEQUENCE: 30

```
atgaaaaaga cagctatcgc gattgcagtg gcactggctg gtttcgctac cgtggcccag      60
gcggccctga ctcagccgtc ctcggtgtca gcgaacccgg gaggaaccgt caagatcacc     120
tgctccggga gtagcagtgc ctatggttat ggctggtatc agcagaagtc acctggcagt     180
gcccctgtca ctgtgatcta taacaacaat aagagaccct caaacatccc ttcacgattc     240
```

```
tccggttcca atccggctc cacgggcaca ttaaccatca ctggggtcca agccgaggac      300
gaggccgtct atttctgtgg gagtgaagac agcagcactg atgctatatt tggggccggg      360
acaaccctga ccgtcctagg tcagtcctct agatcttcca ccgtgacgtt ggacgagtcc      420
gggggcggcc tccaggcgcc cggaggagcg ctcagcctcg tctgcaaggc ctccgggttc      480
accttcagca gttacgacat gggttggata cgacaggcgc ccggcaaggg gctggaatac      540
gttgcgggta ttaccgataa tggtagatac gcatcatatg ggtcggcggt ggatggccgt      600
gccaccatct cgagggacaa cgggcagagc tcagtgaggc tgcagctgaa caacctcagg      660
gctgaggaca ccggcaccta ctactgtgcc agagatgacg gtagtggttg gactggtaat      720
agtatcgacg catggggcca cgggaccgaa gtcatcgtct cctccactag tggccaggcc      780
ggccagcacc atcaccatca ccatggcgca tacccgtacg acgttccgga ctacgcttct      840
tag                                                                   843

<210> SEQ ID NO 31
<211> LENGTH: 843
<212> TYPE: DNA
<213> ORGANISM: Artificial Sequence
<220> FEATURE:
<223> OTHER INFORMATION: recombinant DNA

<400> SEQUENCE: 31
atgaaaaaga cagctatcgc gattgcagtg gcactggctg gtttcgctac cgtggcccag       60
gcggccctga ctcagccgtc ctcggtgtca gcgaacccgg gagcatttaa caagatcacc      120
tgctccggga gtagcagtgc ctatggttat ggctggaatc agcagaagtc acctggcagt      180
gcccctgtca ctgtgatcta taacaacaat aagagaccct caaacatccc ttcacgattc      240
tccggttcca atccggctc cacgggcaca ttaaccatca ctggggacca agacgaggac      300
gaggacttct atttctgtgg gagtgaatac agtagtactg atgctatatt tggggccggg      360
acaaccctga ccgtcctatg tcagtcctct acatcttcca ccgtgacgtt ggacgagtcc      420
gggggcggcc tccaggcacc cggaggagcg ctcagcctcg tctgcaaggc ctccgggttc      480
accttcagca gttacgacat gggttggata ccacaggcgc ccggcaaggg gctggaatac      540
gttgcgggta ttaccgataa tggtatatac gcatcatatg ggtcggcggt ggatggccgt      600
gccaccatct cgagggacaa caggcagagc tcagtgaagc tgcagctgaa caacctcaag      660
gctgacgaca ccggcaccta ctactgtgcc agagatgacg gtagtggttg gactggtaat      720
agtatcgacg catggggcca cgggaccgaa gtcatcgtct cctccactag tggccaggcc      780
ggccagcacc atcaccatca ccatggcgca tacccgtacg acgttccgga ctacgcttct      840
tag                                                                   843

<210> SEQ ID NO 32
<211> LENGTH: 843
<212> TYPE: DNA
<213> ORGANISM: Artificial Sequence
<220> FEATURE:
<223> OTHER INFORMATION: recombinant DNA

<400> SEQUENCE: 32
atgaaaaaga cagctatcgc gattgcagtg gcactggctg gtttcgctac cgtggcccag       60
gcggccctga ctcagccgtc ttcggtgtca gcgaacccgg gagacccttt aaagatcacc      120
tgctccgggg atagcagtgg ctatggttat ggctggtatc agcagaagtc acctggcagt      180
```

-continued

```
gccctgtca ctgtgatcta aacaacaat aagagaccct cggacatccc ttcacgattc    240
tccggttcca atccggctc cacgggcaca ttaaccatca ctggggtcca agccgaggac    300
gaggctgtct atttctgtgg gagtgaagac agcaacactg atgctgtatt tggggccggg    360
acaaccctga ccgtcctagg tcagtcctct agatcttcca ccgtgacgtt ggacgagtcc    420
gggggcggcc tccagacgcc cggaggaacg ctcagcctcg cctgcaaggc ctccgggttc    480
accttcagtg gttacgacat gggctgggtg cgacaggcac ccggcaaggg gctggagtac    540
gttgcgggta ttaccagtga tggtagatac gcatcatacg ggtcggcggt ggatggccgt    600
gccgccatct ggagggacaa cgggcagagc acagtgaggc tgcagctgaa aaacctcagg    660
actgaggaca ccgccaccta ctactgcgcc agaaatgatg gtagtggttg aatggtaat    720 aatatcgacg catggggcca cgggaccgaa gtcatcgtct cctccactag tggccaggcc    780
ggccagcacc atcaccatca ccatggcgca tacccgtacg acgttccgga ctacgcttct    840
tag    843
```

<210> SEQ ID NO 33
<211> LENGTH: 843
<212> TYPE: DNA
<213> ORGANISM: Artificial Sequence
<220> FEATURE:
<223> OTHER INFORMATION: recombinant DNA

<400> SEQUENCE: 33

```
atgaaaaaga cagctatcgc gattgcagtg gcactggctg gtttcgctac cgtggcccag    60
gcggccctga ctcagccgtc ctcggtgtca gcgaacccag agaaaccgt caagatcacc    120 tgctccgggg atagcagtga ctatggttat ggctggtatc agcagaagtc acctggcagt    180
gcccctgtca ctgtgaccta tagcaacaac cagagacccc cgaacatccc ttcacgattc    240
tccggttccg catccggctc cacagccaca ttaaccatca ctggggtcca agtcgaggac    300
gaggctgtct attactgtgg gagtgaagac agtaccactg atgctgtatt tggggccggg    360
acaaccctga ccgtcctagg tcagtcctct agatcttccg ccatgacgtt ggacgagtcc    420
gggggcggcc tccagacgcc cggaggagcg ctcagcctcg tctgcaaggc ctccgggttc    480
accttcagca gttacgacat gggttgggtg cgacaggcgc ccggcaaggg gctggaatac    540
gttgcgggta ttaccaatga tggtagatac gcatcatacg ggtcggcggt ggatggccgt    600
gccaccatct cgagggacaa cgggcagagc acagtgaggc tgcagctgaa caacctcagg    660
gctgaggaca ccgcaccta ctactgcgcc agagatgatg gtagtggttg gactggtaat    720
actatcgaca catggggcca cgggaccgaa gtcatcgtct cctccactag tggccaggcc    780
ggccagcacc atcaccatca ccatggcgca tacccgtacg acgttccgga ctacgcttct    840
tag    843
```

<210> SEQ ID NO 34
<211> LENGTH: 283
<212> TYPE: PRT
<213> ORGANISM: Artificial Sequence
<220> FEATURE:
<223> OTHER INFORMATION: recombinant protein

<400> SEQUENCE: 34

```
Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30
```

-continued

```
Pro Gly Glu Thr Val Lys Ile Thr Cys Ser Gly Gly Val Gly Gln Trp
         35                  40                  45
Tyr Gly Trp Tyr Gln Gln Lys Ser Pro Gly Ser Ala Pro Val Thr Leu
 50                  55                  60
Ile Tyr Glu Ser Asn Gln Arg Pro Ser Asn Ile Pro Ser Arg Phe Ser
 65                  70                  75                  80
Gly Ser Leu Ser Gly Ser Thr Ala Thr Leu Thr Ile Thr Gly Val Gln
                 85                  90                  95
Pro Glu Asp Glu Ala Val Tyr Phe Cys Gly Gly Tyr Asp Gly Asn Ser
            100                 105                 110
Gly Ile Phe Gly Ala Gly Thr Thr Leu Thr Val Leu Gly Gln Ser Ser
        115                 120                 125
Arg Ser Ser Ala Val Thr Leu Asp Glu Ser Gly Gly Gly Leu Gln Thr
130                 135                 140
Pro Gly Arg Ala Leu Ser Leu Val Cys Lys Ala Ser Gly Phe Thr Phe
145                 150                 155                 160
Ser Ser Tyr Asp Met Gly Trp Val Arg Gln Ala Pro Gly Lys Gly Leu
                165                 170                 175
Glu Trp Val Ala Tyr Ile Asn Ser Gly Ser Gly Ser Thr Tyr Tyr
            180                 185                 190
Gly Thr Ala Val Lys Gly Arg Ala Ser Ile Ser Arg Asp Asn Gly Gln
        195                 200                 205
Ser Thr Val Arg Leu Gln Leu Asn Asn Leu Arg Val Glu Asp Thr Gly
210                 215                 220
Thr Tyr Phe Cys Ala Lys Gly Ala Ser Gly Tyr Tyr Ser Ser Ser Ile
225                 230                 235                 240
Gly Ala Gly Glu Ile Asp Ala Trp Gly His Gly Thr Glu Val Ile Val
                245                 250                 255
Ser Ser Thr Ser Gly Gln Ala Gly Gln His His His His His His Gly
            260                 265                 270
Ala Tyr Pro Tyr Asp Val Pro Asp Tyr Ala Ser
        275                 280

<210> SEQ ID NO 35
<211> LENGTH: 281
<212> TYPE: PRT
<213> ORGANISM: Artificial Sequence
<220> FEATURE:
<223> OTHER INFORMATION: recombinant protein

<400> SEQUENCE: 35

Met Lys Lys Thr Ala Ile Ala Ile Ala Val Ala Leu Ala Gly Phe Ala
 1               5                  10                  15
Thr Val Ala Gln Ala Ala Leu Thr Gln Pro Ser Ser Val Ser Ala Asn
            20                  25                  30
Pro Gly Gly Thr Val Lys Ile Thr Cys Ser Gly Gly Gly Ser Tyr Tyr
        35                  40                  45
Gly Trp Tyr Gln Gln Lys Ser Pro Gly Ser Ala Pro Val Thr Val Ile
 50                  55                  60
Tyr Asp Asn Thr Asn Arg Pro Ser Asn Ile Pro Ser Arg Phe Ser Gly
 65                  70                  75                  80
Ser Lys Ser Gly Ser Thr Gly Thr Leu Thr Ile Thr Gly Val Gln Ala
                 85                  90                  95
Asp Asp Glu Ala Val Tyr Tyr Cys Gly Ser Thr Asp Ser Ser Ala Asp
            100                 105                 110
```

Gly Val Phe Gly Ala Gly Thr Thr Leu Thr Val Leu Gly Gln Ser Ser
            115                 120                 125

Arg Ser Ser Ala Val Thr Leu Asp Glu Ser Gly Gly Gly Leu Gln Thr
130                 135                 140

Pro Gly Gly Gly Leu Ser Leu Val Cys Lys Gly Ser Gly Phe Thr Phe
145                 150                 155                 160

Ser Ser Phe Asp Met Phe Trp Val Arg Gln Ala Pro Gly Lys Gly Leu
                165                 170                 175

Glu Trp Val Ala Gly Ile Arg Asn Asp Gly Ser Asp Thr Ala Tyr Gly
            180                 185                 190

Ala Ala Val Lys Gly Arg Ala Thr Ile Ser Lys Asp Asn Gly Gln Ser
            195                 200                 205

Thr Val Arg Leu Gln Leu Asn Asn Leu Arg Ala Glu Asp Thr Gly Thr
        210                 215                 220

Tyr Tyr Cys Ala Lys Ala Ala Gly Tyr Cys Tyr Val Tyr Ser Cys Ala
225                 230                 235                 240

Gly Ser Ile Asp Ala Trp Gly His Gly Thr Glu Val Ile Val Ser Ser
                245                 250                 255

Thr Ser Gly Gln Ala Gly Gln His His His His His Gly Ala Tyr
            260                 265                 270

Pro Tyr Asp Val Pro Asp Tyr Ala Ser
            275                 280

<210> SEQ ID NO 36
<211> LENGTH: 274
<212> TYPE: PRT
<213> ORGANISM: Artificial Sequence
<220> FEATURE:
<223> OTHER INFORMATION: recombinant protein

<400> SEQUENCE: 36

Met Lys Lys Thr Ala Ile Ala Ile Ala Val Ala Leu Ala Gly Phe Ala
1               5                   10                  15

Thr Val Ala Gln Ala Ala Val Ser Thr Asn Pro Gly Asp Thr Val Lys
            20                  25                  30

Ile Thr Cys Ser Gly Gly Asn Ser Trp Tyr Gly Trp Phe Gln Gln Lys
        35                  40                  45

Ser Pro Gly Ser Ala Pro Val Thr Val Ile Tyr Gly Asn Asp Glu Arg
    50                  55                  60

Pro Ser Asp Ile Pro Ser Arg Phe Ser Gly Ser Glu Ser Gly Ser Thr
65                  70                  75                  80

Ala Thr Leu Thr Ile Thr Gly Val Arg Ala Glu Asp Glu Ala Val Tyr
                85                  90                  95

Tyr Cys Gly Ser Gly Asp Asn Ser Gly Ala Gly Ile Phe Gly Ala Gly
            100                 105                 110

Thr Thr Leu Thr Val Leu Gly Gln Ser Ser Arg Ser Ser Ala Val Thr
        115                 120                 125

Leu Asp Glu Ser Gly Gly Gly Leu Gln Thr Pro Gly Gly Ala Leu Ser
    130                 135                 140

Leu Val Cys Lys Ala Ser Gly Phe Thr Phe Ser Ser Asn Gly Met Ala
145                 150                 155                 160

Trp Val Arg Gln Ala Pro Gly Lys Gly Leu Glu Trp Val Ala Gly Ile
                165                 170                 175

Ser Ser Ser Gly Ser Tyr Thr Asn Tyr Gly Ser Ala Val Lys Gly Arg
            180                 185                 190

```
Ala Thr Ile Ser Arg Asp Asn Gly Gln Ser Thr Val Arg Leu Gln Leu
            195                 200                 205

Asn Asn Leu Arg Ala Glu Asp Thr Ala Thr Tyr Tyr Cys Ala Lys Ser
210                 215                 220

Ser Tyr Ala Tyr Tyr Gly Phe Gly Ala Pro Phe Ile Asp Ala Trp Gly
225                 230                 235                 240

His Gly Thr Glu Val Ile Val Ser Ser Thr Ser Gly Gln Ala Gly Gln
            245                 250                 255

His His His His His His Gly Ala Tyr Pro Tyr Asp Val Pro Asp Tyr
            260                 265                 270

Ala Ser

<210> SEQ ID NO 37
<211> LENGTH: 242
<212> TYPE: PRT
<213> ORGANISM: Artificial Sequence
<220> FEATURE:
<223> OTHER INFORMATION: recombinant protein

<400> SEQUENCE: 37

Met Lys Lys Thr Ala Ile Ala Ile Ala Val Ala Leu Ala Gly Phe Ala
1               5                   10                  15

Thr Val Ala Gln Ala Ala Val Ile Tyr Asp Asn Asp Lys Arg Pro Ser
            20                  25                  30

Asp Val Pro Ser Arg Phe Ser Gly Ser Lys Ser Gly Pro Thr Ala Thr
        35                  40                  45

Leu Thr Ile Thr Gly Val Gln Ala Glu Asp Glu Ala Val Tyr Phe Cys
50                  55                  60

Gly Ser Arg Asp Asn Ser Tyr Val Gly Ile Phe Gly Ala Gly Thr Thr
65                  70                  75                  80

Leu Thr Val Leu Gly Gln Ser Ser Arg Ser Ser Ala Val Thr Leu Asp
            85                  90                  95

Glu Ser Gly Gly Gly Leu Gln Thr Pro Gly Gly Ala Leu Ser Leu Val
            100                 105                 110

Cys Lys Ala Ser Gly Phe Thr Phe Ser Ser Tyr Asp Met Phe Trp Val
        115                 120                 125

Arg Gln Ala Pro Gly Lys Gly Leu Glu Phe Val Ala Gln Ile Asn Ser
130                 135                 140

Ala Gly Ser Tyr Thr Asn Tyr Gly Ser Ala Val Lys Gly Arg Ala Thr
145                 150                 155                 160

Ile Ser Arg Asp Asp Gly Gln Ser Thr Val Arg Leu Gln Leu Asn Asn
            165                 170                 175

Leu Arg Ala Glu Asp Thr Gly Ile Tyr Phe Cys Ala Lys Ser Ala Ser
            180                 185                 190

Gly Tyr Tyr Tyr Ser Gly Ser Asp Ala Gly Asp Ile Asp Ala Trp Gly
        195                 200                 205

His Gly Thr Glu Val Ile Val Ser Ser Thr Ser Gly Gln Ala Gly Gln
            210                 215                 220

His His His His His His Gly Ala Tyr Pro Tyr Asp Val Pro Asp Tyr
225                 230                 235                 240

Ala Ser

<210> SEQ ID NO 38
<211> LENGTH: 274
<212> TYPE: PRT
```

<213> ORGANISM: Artificial Sequence
<220> FEATURE:
<223> OTHER INFORMATION: recombinant protein

<400> SEQUENCE: 38

Met Lys Lys Thr Ala Ile Ala Ile Ala Val Ala Leu Ala Gly Phe Ala
1               5                   10                  15

Thr Val Ala Gln Ala Ala Val Ser Ala Asn Pro Gly Gly Thr Val Lys
            20                  25                  30

Ile Thr Cys Ser Gly Ser Ser Gly Arg Tyr Gly Trp Tyr Gln Gln Lys
        35                  40                  45

Ser Pro Gly Ser Ala Pro Val Thr Val Ile Tyr Tyr Asn Asp Lys Arg
50                  55                  60

Pro Ser Asp Ile Pro Ser Arg Phe Ser Gly Ser Ala Ser Gly Ser Thr
65                  70                  75                  80

Ala Thr Leu Thr Ile Thr Gly Val Gln Ala Glu Asp Glu Ala Val Tyr
                85                  90                  95

Phe Cys Gly Ser Tyr Glu Val Asn Ile His Glu Gly Ile Phe Gly Ala
            100                 105                 110

Gly Thr Ser Leu Thr Val Leu Gly Gln Ser Ser Arg Ser Ser Thr Val
        115                 120                 125

Thr Leu Asp Glu Ser Gly Gly Gly Leu Gln Thr Pro Gly Arg Ala Leu
130                 135                 140

Ser Leu Val Cys Lys Ala Ser Gly Phe Thr Phe Ser Ser Asn Gly Met
145                 150                 155                 160

Tyr Trp Val Arg Gln Ala Pro Gly Lys Gly Leu Glu Trp Val Ala Gly
                165                 170                 175

Ile Ser Ser Ser Gly Ser Tyr Thr Asn Tyr Ala Pro Ala Val Lys Gly
            180                 185                 190

Arg Ala Thr Ile Ser Arg Asp Asn Gly Gln Ser Thr Val Arg Leu Gln
        195                 200                 205

Leu Asn Asn Leu Arg Ala Glu Asp Thr Gly Thr Tyr Tyr Cys Ala Lys
210                 215                 220

Gly Ala Ser Ser Tyr Ser Trp Asp Gly Gly Ser Ile Asp Ala Trp Gly
225                 230                 235                 240

His Gly Thr Glu Val Ile Val Ser Ser Thr Ser Gly Gln Ala Gly Gln
                245                 250                 255

His His His His His His Gly Ala Tyr Pro Tyr Asp Val Pro Asp Tyr
            260                 265                 270

Ala Ser

<210> SEQ ID NO 39
<211> LENGTH: 284
<212> TYPE: PRT
<213> ORGANISM: Artificial Sequence
<220> FEATURE:
<223> OTHER INFORMATION: recombinant protein

<400> SEQUENCE: 39

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Asp Thr Val Lys Ile Thr Cys Ser Gly Ser Ile Arg Tyr Tyr
        35                  40                  45

Gly Trp Tyr Gln Gln Lys Ser Pro Gly Ser Ala Pro Val Thr Leu Ile

```
                    50                  55                  60

Tyr Tyr Asp Asp Lys Arg Pro Ser Asp Ile Pro Ser Arg Phe Ser Gly
 65                  70                  75                  80

Ser Ala Ser Gly Ser Thr Ala Thr Leu Thr Ile Thr Gly Val Gln Ala
                    85                  90                  95

Asp Asp Glu Ala Ile Tyr Phe Cys Gly Thr Ala Asp Ser Thr Ser Ser
                100                 105                 110

Gly Ala Gly Ile Phe Gly Ala Gly Thr Thr Leu Thr Val Leu Gly Gln
            115                 120                 125

Ser Ser Arg Ser Ser Thr Val Thr Leu Asp Glu Ser Gly Gly Gly Leu
        130                 135                 140

Gln Thr Pro Gly Gly Ala Leu Ser Leu Val Cys Lys Gly Ser Gly Phe
145                 150                 155                 160

Thr Phe Ser Ser Phe Asn Met Phe Trp Val Arg Gln Ala Pro Gly Lys
                165                 170                 175

Gly Leu Glu Trp Val Ala Gly Ile Tyr Ser Gly Gly Gly Glu Thr
                180                 185                 190

Asn Tyr Gly Ala Ala Val Lys Gly Arg Ala Thr Ile Ser Arg Asp Asn
            195                 200                 205

Gly Gln Ser Thr Val Arg Leu Gln Leu Asn Asn Leu Arg Ala Glu Asp
        210                 215                 220

Thr Gly Thr Tyr Tyr Cys Ala Lys Glu Ser Ala Asp Val Gly Cys Pro
225                 230                 235                 240

Phe Thr Ala Gly Cys Ile Asp Thr Trp Gly His Gly Thr Glu Val Ile
                245                 250                 255

Val Ser Ser Thr Ser Gly Gln Ala Gly Gln His His His His His His
            260                 265                 270

Gly Ala Tyr Pro Tyr Asp Val Pro Asp Tyr Ala Ser
        275                 280

<210> SEQ ID NO 40
<211> LENGTH: 272
<212> TYPE: PRT
<213> ORGANISM: Artificial Sequence
<220> FEATURE:
<223> OTHER INFORMATION: recombinant protein

<400> SEQUENCE: 40

Met Lys Lys Thr Ala Ile Ala Ile Ala Val Ala Leu Ala Gly Phe Ala
 1               5                  10                  15

Thr Val Ala Gln Ala Ala Val Ser Ala Ser Leu Glu Gly Thr Val Glu
                20                  25                  30

Ile Thr Cys Ser Gly Gly Ser Gly Ser Tyr Gly Trp Phe Gln Gln Lys
            35                  40                  45

Ala Pro Gly Ser Ala Pro Val Thr Leu Ile Tyr Asp Asn Thr Asn Arg
        50                  55                  60

Pro Ser Asn Ile Pro Ser Arg Phe Ser Gly Ser Lys Ser Gly Ser Thr
 65                  70                  75                  80

Ala Thr Leu Thr Ile Thr Gly Val Gln Ala Asp Asp Glu Ala Ile Tyr
                85                  90                  95

Tyr Cys Gly Ser Trp Asp Ser Ser Asp Ala Ala Phe Gly Ala Gly
            100                 105                 110

Thr Thr Leu Thr Val Leu Gly Gln Ser Ser Arg Ser Ser Thr Val Thr
        115                 120                 125

Leu Asp Glu Ser Gly Gly Gly Leu Gln Thr Pro Gly Gly Gly Leu Ser
```

```
          130                 135                 140
Leu Val Cys Lys Ala Ser Gly Phe Thr Phe Ser Asp Tyr Gly Met Gly
145                 150                 155                 160

Trp Val Arg Gln Ala Pro Gly Lys Gly Leu Glu Phe Val Ala Gly Ile
                165                 170                 175

Gly Asn Thr Gly Ser Tyr Thr Tyr Tyr Gly Ser Ala Val Lys Gly Arg
                180                 185                 190

Ala Thr Ile Ser Arg Asp Asn Gly Gln Ser Thr Val Arg Leu Gln Leu
            195                 200                 205

Asn Asn Leu Arg Ala Glu Asp Thr Gly Ile Tyr Phe Cys Ala Lys Ser
        210                 215                 220

Thr Asp Tyr Trp Thr Tyr Ala Gly Thr Ile Asp Ala Trp Gly His Gly
225                 230                 235                 240

Thr Glu Val Ile Val Ser Ser Thr Ser Gly Gln Ala Gly Gln His His
                245                 250                 255

His His His His Gly Ala Tyr Pro Tyr Asp Val Pro Asp Tyr Ala Ser
            260                 265                 270
```

<210> SEQ ID NO 41
<211> LENGTH: 283
<212> TYPE: PRT
<213> ORGANISM: Artificial Sequence
<220> FEATURE:
<223> OTHER INFORMATION: recombinant protein

<400> SEQUENCE: 41

```
Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
                20                  25                  30

Pro Gly Glu Thr Val Lys Ile Thr Cys Ser Gly Gly Gly Ser Ser Ser
            35                  40                  45

Tyr Tyr Gly Trp Tyr Gln Gln Lys Ser Pro Gly Ser Ala Pro Val Thr
50                  55                  60

Leu Ile Tyr Glu Ser Asn Glu Arg Pro Ser Asn Ile Pro Ser Arg Phe
65                  70                  75                  80

Ser Gly Ser Glu Ser Gly Ser Thr Gly Thr Leu Thr Ile Thr Gly Val
                85                  90                  95

Arg Ala Glu Asp Glu Ala Val Tyr Tyr Cys Gly Ser Ala Asp Ser Ser
                100                 105                 110

Asn Ala Gly Ile Phe Gly Ala Gly Thr Thr Leu Thr Val Leu Gly Gln
            115                 120                 125

Ser Ser Arg Ser Ser Thr Val Thr Leu Asp Glu Ser Gly Gly Gly Leu
        130                 135                 140

Gln Thr Pro Gly Gly Ala Leu Ser Leu Val Cys Lys Ala Ser Gly Phe
145                 150                 155                 160

Thr Phe Ser Ser Phe Asn Met Gly Trp Val Arg Gln Ala Pro Gly Lys
                165                 170                 175

Gly Leu Glu Phe Val Ala Gly Ile Asp Asn Thr Gly Ser Phe Thr His
                180                 185                 190

Tyr Gly Ala Ala Val Lys Gly Arg Ala Thr Ile Ser Arg Asp Asp Gly
            195                 200                 205

Gln Ser Thr Val Arg Leu Gln Leu Asp Asn Leu Arg Ala Glu Asp Thr
        210                 215                 220

Gly Thr Tyr Tyr Cys Ala Lys Ala Ser Gly Tyr Tyr Tyr Ser Gly Val
```

```
                 225                 230                 235                 240
Asn Ala Gly Ser Ile Asp Ala Trp Gly His Gly Thr Glu Val Ile Val
                245                 250                 255

Ser Ser Thr Ser Gly Gln Ala Gly Gln His His His His His His Gly
            260                 265                 270

Ala Tyr Pro Tyr Asp Val Pro Asp Tyr Ala Ser
        275                 280

<210> SEQ ID NO 42
<211> LENGTH: 240
<212> TYPE: PRT
<213> ORGANISM: Artificial Sequence
<220> FEATURE:
<223> OTHER INFORMATION: recombinant protein

<400> SEQUENCE: 42

Met Lys Lys Thr Ala Ile Ala Ile Ala Val Ala Leu Ala Gly Phe Ala
1               5                   10                  15

Thr Val Ala Gln Ala Ala Val Ile Tyr Gly Asn Asp Glu Arg Pro Ser
            20                  25                  30

Asp Ile Pro Ser Arg Phe Ser Gly Ser Glu Ser Gly Ser Thr Ala Thr
        35                  40                  45

Leu Thr Ile Thr Gly Val Arg Ala Glu Asp Glu Ala Val Tyr Tyr Cys
    50                  55                  60

Gly Ser Gly Asp Asn Ser Gly Ala Gly Ile Phe Gly Ala Gly Thr Thr
65                  70                  75                  80

Leu Thr Val Leu Gly Gln Ser Ser Arg Ser Ser Ala Val Thr Leu Asp
                85                  90                  95

Glu Ser Gly Gly Gly Leu Gln Thr Pro Gly Gly Ala Leu Ser Leu Val
            100                 105                 110

Cys Lys Ala Ser Gly Phe Thr Phe Ser Ser Asn Gly Met Ala Trp Val
        115                 120                 125

Arg Gln Ala Pro Gly Lys Gly Leu Glu Trp Val Ala Gly Ile Ser Ser
    130                 135                 140

Ser Gly Ser Tyr Thr Asn Tyr Gly Ser Ala Val Lys Gly Arg Ala Thr
145                 150                 155                 160

Ile Ser Arg Asp Asn Gly Gln Ser Thr Val Arg Leu Gln Leu Asn Asn
                165                 170                 175

Leu Arg Ala Glu Asp Thr Ala Thr Tyr Tyr Cys Ala Lys Ser Ser Tyr
            180                 185                 190

Ala Tyr Tyr Gly Phe Gly Ala Pro Phe Ile Asp Ala Trp Gly His Gly
        195                 200                 205

Thr Glu Val Ile Val Ser Ser Thr Ser Gly Gln Ala Gly Gln His His
    210                 215                 220

His His His His Gly Ala Tyr Pro Tyr Asp Val Pro Asp Tyr Ala Ser
225                 230                 235                 240

<210> SEQ ID NO 43
<211> LENGTH: 240
<212> TYPE: PRT
<213> ORGANISM: Artificial Sequence
<220> FEATURE:
<223> OTHER INFORMATION: recombinant protein

<400> SEQUENCE: 43

Met Lys Lys Thr Ala Ile Ala Ile Ala Val Ala Leu Ala Gly Phe Ala
1               5                   10                  15
```

Thr Val Ala Gln Ala Ala Val Ile Tyr Ala Asn Thr Asp Arg Pro Ser
            20                  25                  30

Asp Ile Pro Ser Arg Phe Ser Gly Ser Lys Ser Gly Thr Ala Thr
        35                  40                  45

Leu Thr Ile Thr Gly Val Arg Ala Glu Asp Glu Ala Val Tyr Phe Cys
50                  55                  60

Gly Ser Gly Asp Ser Ser Thr Gly Ile Phe Gly Ala Gly Thr Thr Leu
65                  70                  75                  80

Thr Val Leu Gly Gln Ser Ser Arg Ser Ser Ala Val Thr Leu Asp Glu
                85                  90                  95

Ser Gly Gly Gly Leu Gln Thr Pro Gly Gly Thr Leu Ser Leu Val Cys
            100                 105                 110

Lys Gly Ser Gly Phe Thr Phe Ser Ser Val Asn Met Phe Trp Val Arg
            115                 120                 125

Gln Ala Pro Gly Lys Gly Leu Glu Trp Val Ala Gly Ile Tyr Ser Ser
        130                 135                 140

Gly Ser Ser Thr His Tyr Gly Ala Ala Val Lys Gly Arg Ala Thr Ile
145                 150                 155                 160

Ser Arg Asp Asn Gly Gln Ser Thr Val Arg Leu Gln Leu Asn Asn Leu
                165                 170                 175

Arg Ala Glu Asp Thr Gly Ile Tyr Tyr Cys Ala Lys Asp Ala Gly Cys
            180                 185                 190

Tyr Thr Ser Gly Asp Thr Ala Gly Cys Ile Asp Ala Trp Gly His Gly
        195                 200                 205

Thr Glu Val Ile Val Ser Ser Thr Ser Gly Ala Gly Gln His His
    210                 215                 220

His His His His Gly Ala Tyr Pro Tyr Asp Val Pro Asp Tyr Ala Ser
225                 230                 235                 240

<210> SEQ ID NO 44
<211> LENGTH: 239
<212> TYPE: PRT
<213> ORGANISM: Artificial Sequence
<220> FEATURE:
<223> OTHER INFORMATION: recombinant protein

<400> SEQUENCE: 44

Met Lys Lys Thr Ala Ile Ala Ile Ala Val Ala Leu Ala Gly Phe Ala
1               5                   10                  15

Thr Val Ala Gln Ala Ala Val Ile Tyr Tyr Asn Asp Lys Arg Pro Ser
            20                  25                  30

Asn Ile Pro Ser Arg Phe Ser Gly Ser Gly Ser Gly Ser Thr Asn Thr
        35                  40                  45

Leu Thr Ile Ala Gly Val Arg Ala Glu Asp Glu Ala Val Tyr Tyr Cys
50                  55                  60

Gly Asn Glu Asp Ser Ser Gly Ala Ala Phe Gly Ala Gly Thr Thr Leu
65                  70                  75                  80

Thr Val Leu Gly Gln Ser Ser Arg Ser Ser Ala Val Thr Leu Asp Glu
                85                  90                  95

Ser Gly Gly Gly Leu Gln Thr Pro Gly Gly Gly Leu Ser Leu Val Cys
            100                 105                 110

Lys Ala Ser Gly Phe Thr Phe Ser Asp Tyr Asp Met Phe Trp Val Arg
            115                 120                 125

Gln Ala Pro Ser Lys Gly Leu Glu Phe Val Ala Ala Ile Thr Ser Ser
        130                 135                 140

```
Gly Thr Gly Thr Lys Tyr Gly Ala Ala Val Lys Gly Arg Ala Thr Ile
145                 150                 155                 160

Ser Lys Asp Asn Gly Gln Arg Thr Val Arg Leu Gln Leu Asn Ser Leu
                165                 170                 175

Gly Ala Glu Asp Thr Gly Thr Tyr Tyr Cys Ala Arg Ser Asp Ala Asp
            180                 185                 190

Ser Thr Thr Trp Ser Ala Gly Glu Ile Asp Ala Trp Gly His Gly Thr
        195                 200                 205

Glu Val Ile Val Ser Ser Thr Ser Gly Gln Ala Gly Gln His His His
    210                 215                 220

His His His Gly Ala Tyr Pro Tyr Asp Val Pro Asp Tyr Ala Ser
225                 230                 235
```

<210> SEQ ID NO 45
<211> LENGTH: 295
<212> TYPE: PRT
<213> ORGANISM: Artificial Sequence
<220> FEATURE:
<223> OTHER INFORMATION: recombinant protein

<400> SEQUENCE: 45

```
Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Ala Val Lys Ile Thr Cys Ser Gly Gly Ser Ser Ser
        35                  40                  45

Tyr Tyr Gly Trp Tyr Gln Gln Lys Ser Pro Gly Ser Ala Pro Val Thr
    50                  55                  60

Val Ile Tyr Trp Asp Asp Glu Arg Pro Ser Asn Ile Pro Ser Arg Phe
65                  70                  75                  80

Ser Gly Ser Thr Ser Gly Ser Thr Gly Thr Leu Thr Ile Thr Gly Val
                85                  90                  95

Gln Ala Glu Asp Glu Ala Val Tyr Phe Cys Gly Gly Tyr Asp Ser Ser
            100                 105                 110

Gly Asp Gly Ile Phe Gly Ala Gly Thr Thr Leu Thr Val Leu Gly Gln
        115                 120                 125

Ser Ser Arg Ser Ser Ser Gly Gly Ser Ser Gly Gly Gly Gly Ser
130                 135                 140

Ala Val Thr Leu Asp Glu Ser Gly Gly Leu Gln Thr Pro Gly Arg
145                 150                 155                 160

Ala Leu Ser Leu Val Cys Lys Ala Ser Gly Phe Thr Phe Ser Gly Tyr
                165                 170                 175

Asn Met Gly Trp Val Arg Gln Ala Pro Gly Lys Gly Leu Glu Trp Val
            180                 185                 190

Gly Gly Ile Ser Gly Ser Gly Arg Tyr Thr Glu Tyr Gly Ala Ala Val
        195                 200                 205

Lys Gly Arg Ala Thr Ile Ser Arg Asp Asn Gly Gln Ser Thr Val Arg
    210                 215                 220

Leu Gln Leu Asn Asn Leu Arg Ala Glu Asp Thr Gly Thr Tyr Phe Cys
225                 230                 235                 240

Ala Lys Ala Ala Val Ser Asp Tyr Cys Gly Gly Cys Ala Gly Asp
                245                 250                 255

Ile Asp Ala Trp Gly His Gly Thr Glu Val Ile Val Ser Ser Thr Ser
            260                 265                 270
```

```
Gly Gln Ala Gly Gln His His His His His Gly Ala Tyr Pro Tyr
            275                 280                 285

Asp Val Pro Asp Tyr Ala Ser
    290                 295

<210> SEQ ID NO 46
<211> LENGTH: 282
<212> TYPE: PRT
<213> ORGANISM: Artificial Sequence
<220> FEATURE:
<223> OTHER INFORMATION: recombinant protein

<400> SEQUENCE: 46

Met Lys Lys Thr Ala Ile Ala Ile Ala Val Ala Leu Ala Gly Phe Ala
1               5                   10                  15

Thr Val Ala Gln Ala Ala Leu Ser Arg Pro Arg Cys Gln Gln Thr Trp
                20                  25                  30

Gly Gly Thr Val Lys Ile Thr Cys Ser Gly Gly Asp Ser Ser Tyr Gly
            35                  40                  45

Trp Tyr Gln Gln Lys Ser Pro Gly Ser Ala Pro Val Thr Leu Ile Tyr
    50                  55                  60

Asp Asn Thr Asn Arg Pro Ser Asp Ile Pro Ser Arg Phe Ser Gly Ser
65                  70                  75                  80

Lys Ser Gly Ser Thr Gly Thr Leu Thr Ile Thr Gly Val Gln Ala Glu
                85                  90                  95

Asp Glu Ala Val Tyr Tyr Cys Gly Asn Ala Asp Ser Ser Thr Ala
            100                 105                 110

Ala Phe Gly Ala Gly Thr Thr Leu Thr Val Leu Gly Gln Ser Ser Arg
            115                 120                 125

Ser Ser Thr Val Thr Leu Asp Glu Ser Gly Gly Gly Leu Gln Thr Pro
    130                 135                 140

Gly Gly Ala Leu Ser Leu Val Cys Lys Ala Ser Gly Phe Thr Phe Ser
145                 150                 155                 160

Ser Tyr Ala Met Gly Trp Val Arg Gln Ala Pro Gly Lys Gly Leu Glu
                165                 170                 175

Tyr Val Ala Ala Ile Ser Ser Ala Gly Ser Thr Thr Asn Tyr Gly Ala
            180                 185                 190

Ala Val Lys Gly Arg Ala Thr Ile Ser Arg Asp Asn Gly Gln Ser Thr
        195                 200                 205

Val Arg Leu Gln Leu Asn Asn Leu Arg Ala Glu Asp Thr Ala Thr Tyr
    210                 215                 220

Phe Cys Ala Lys Ala Ala Gly Ser Gly Tyr Tyr Val Trp Ser Ala Ile
225                 230                 235                 240

Ala Gly Asp Ile Asp Ala Trp Gly His Gly Thr Glu Val Ile Val Ser
                245                 250                 255

Ser Thr Ser Gly Gln Ala Gly Gln His His His His His Gly Ala
            260                 265                 270

Tyr Pro Tyr Asp Val Pro Asp Tyr Ala Ser
    275                 280

<210> SEQ ID NO 47
<211> LENGTH: 278
<212> TYPE: PRT
<213> ORGANISM: Artificial Sequence
<220> FEATURE:
<223> OTHER INFORMATION: recombinant protein

<400> SEQUENCE: 47
```

```
Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Lys Ile Thr Cys Ser Gly Gly Tyr Ser Gly Tyr
            35                  40                  45

Gly Trp Phe Arg Gln Lys Ala Pro Gly Ser Ala Pro Val Thr Leu Ile
        50                  55                  60

Tyr Ala Asn Thr Asn Arg Pro Ser Asp Ile Pro Ser Arg Phe Ser Gly
65                  70                  75                  80

Ser Ala Ser Gly Ser Thr Gly Thr Leu Thr Ile Thr Gly Val Gln Ala
                85                  90                  95

Asp Asp Glu Ala Val Tyr Phe Cys Gly Ser Ala Asp Ser Thr Tyr Gly
            100                 105                 110

Ile Phe Gly Ala Gly Thr Thr Leu Thr Val Leu Gly Gln Ser Ser Arg
            115                 120                 125

Ser Ser Ala Val Thr Leu Asp Glu Ser Gly Gly Leu Gln Thr Pro
            130                 135                 140

Gly Gly Ala Leu Ser Leu Val Cys Arg Ala Ser Gly Phe Thr Phe Ser
145                 150                 155                 160

Asp Tyr Gly Met Glu Trp Val Arg Gln Ala Pro Gly Lys Gly Leu Glu
            165                 170                 175

Trp Val Ala Gly Ile Asp Asp Asp Gly Ser Thr Thr Phe Tyr Ala Pro
            180                 185                 190

Ala Val Lys Gly Arg Ala Thr Ile Ser Arg Asp Asp Gly Gln Ser Thr
            195                 200                 205

Val Arg Leu Gln Leu Asn Asn Leu Arg Ala Glu Asp Thr Ala Thr Tyr
            210                 215                 220

Tyr Cys Ala Lys Ser Ala Gly Arg Gly Trp Asn Val Ala Gly Trp Ile
225                 230                 235                 240

Asp Ala Trp Gly His Gly Thr Glu Val Ile Val Ser Ser Thr Ser Gly
            245                 250                 255

Gln Ala Gly Gln His His His His His Gly Ala Tyr Pro Tyr Asp
            260                 265                 270

Val Pro Asp Tyr Ala Ser
            275

<210> SEQ ID NO 48
<211> LENGTH: 261
<212> TYPE: PRT
<213> ORGANISM: Artificial Sequence
<220> FEATURE:
<223> OTHER INFORMATION: recombinant protein

<400> SEQUENCE: 48

Met Lys Lys Thr Ala Ile Ala Ile Ala Val Ala Leu Ala Gly Phe Ala
1               5                   10                  15

Thr Val Ala Gln Ala Ala Leu Ser Arg Pro Arg Cys Gln Gln Thr Gln
            20                  25                  30

Glu His Thr Val Lys Ile Thr Cys Ser Gly Gly Val Gly Gln Trp Tyr
            35                  40                  45

Gly Trp Tyr Gln Gln Lys Ser Pro Gly Ser Ala Pro Val Thr Leu Ile
        50                  55                  60

Tyr Glu Ser Asn Gln Arg Pro Ser Asn Ile Pro Ser Arg Phe Ser Gly
65                  70                  75                  80
```

```
Ser Leu Ser Gly Ser Thr Ala Thr Leu Thr Ile Thr Gly Val Gln Pro
                85                  90                  95

Glu Asp Glu Ala Val Tyr Phe Cys Gly Gly Tyr Asp Gly Asn Ser Gly
            100                 105                 110

Ile Phe Gly Ala Gly Thr Thr Leu Thr Val Leu Gly Gln Ser Ser Arg
        115                 120                 125

Ser Ser Ala Val Thr Leu Asp Glu Ser Gly Gly Gly Leu Gln Thr Pro
130                 135                 140

Gly Arg Ala Leu Ser Leu Val Cys Lys Ala Ser Gly Phe Thr Phe Ser
145                 150                 155                 160

Ser Tyr Asp Met Gly Trp Val Arg Gln Ala Pro Gly Lys Gly Leu Glu
                165                 170                 175

Trp Val Ala Tyr Ile Asn Ser Gly Ser Gly Ser Ser Thr Tyr Tyr Gly
            180                 185                 190

Thr Ala Val Lys Gly Arg Ala Ser Ile Ser Arg Asp Asn Gly Gln Ser
        195                 200                 205

Thr Val Arg Leu Gln Leu Asn Asn Leu Arg Val Glu Asp Thr Gly Thr
210                 215                 220

Tyr Phe Cys Ala Lys Gly Ala Ser Gly Tyr Tyr Ser Ser Ser Gly Gln
225                 230                 235                 240

Ala Gly Gln His His His His His His Gly Ala Tyr Pro Tyr Asp Val
                245                 250                 255

Pro Asp Tyr Ala Ser
            260

<210> SEQ ID NO 49
<211> LENGTH: 284
<212> TYPE: PRT
<213> ORGANISM: Artificial Sequence
<220> FEATURE:
<223> OTHER INFORMATION: recombinant protein

<400> SEQUENCE: 49

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Leu Gly Glu Thr Val Lys Ile Thr Cys Ser Gly Gly Gly Ser Tyr Ala
        35                  40                  45

Gly Ser Tyr Tyr Gly Trp Tyr Gln Gln Lys Ala Pro Gly Ser Ala
    50                  55                  60

Pro Val Thr Leu Ile Tyr Asp Asn Thr Asn Arg Pro Ser Asp Ile Pro
65                  70                  75                  80

Ser Arg Phe Ser Gly Ser Thr Ser Gly Ser Thr Asn Thr Leu Thr Ile
                85                  90                  95

Thr Gly Val Gln Ala Asp Asp Glu Ala Val Tyr Phe Cys Gly Ser Val
            100                 105                 110

Asp Ser Ser Ser Gly Val Phe Gly Ala Gly Thr Thr Leu Thr Val Leu
        115                 120                 125

Gly Gln Ser Ser Arg Ser Ser Ala Val Thr Leu Asp Glu Ser Gly Gly
130                 135                 140

Gly Leu Gln Thr Pro Gly Gly Ala Leu Ser Leu Val Cys Lys Ala Ser
145                 150                 155                 160

Gly Phe Thr Phe Ser Ser Phe Asp Met Phe Trp Val Arg Gln Ala Pro
                165                 170                 175
```

Gly Lys Gly Leu Glu Tyr Val Ala Glu Ile Ser Asp Thr Gly Ser Ser
            180                 185                 190

Thr Tyr Tyr Gly Ala Ala Val Lys Gly Arg Ala Thr Ile Ser Arg Asp
        195                 200                 205

Asn Gly Gln Ser Thr Val Arg Leu Gln Leu Asn Asn Leu Arg Ala Glu
210                 215                 220

Asp Thr Gly Thr Tyr Phe Cys Ala Lys Ser His Ser Gly Tyr Gly Trp
225                 230                 235                 240

Ser Thr Ala Gly Asp Ile Asp Ala Trp Gly His Gly Thr Glu Val Ile
                245                 250                 255

Val Ser Ser Thr Ser Gly Gln Ala Gly Gln His His His His His His
            260                 265                 270

Gly Ala Tyr Pro Tyr Asp Val Pro Asp Tyr Ala Ser
            275                 280

<210> SEQ ID NO 50
<211> LENGTH: 281
<212> TYPE: PRT
<213> ORGANISM: Artificial Sequence
<220> FEATURE:
<223> OTHER INFORMATION: recombinant protein

<400> SEQUENCE: 50

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Lys Ile Thr Cys Ser Gly Gly Tyr Ser Tyr Tyr
        35                  40                  45

Gly Trp Tyr Gln Gln Lys Thr Pro Gly Ser Ala Pro Val Thr Leu Ile
    50                  55                  60

Tyr Asp Asn Thr Asn Arg Pro Ser Asp Ile Pro Ser Arg Phe Ser Gly
65                  70                  75                  80

Ser Lys Ser Gly Ser Thr Ala Thr Leu Thr Ile Thr Gly Val Gln Val
                85                  90                  95

Glu Asp Glu Ala Met Tyr Phe Cys Gly Ser Tyr Glu Gly Ser Thr Tyr
            100                 105                 110

Val Gly Ile Phe Gly Ala Gly Thr Thr Leu Thr Val Leu Gly Gln Ser
        115                 120                 125

Ser Arg Ser Ser Ala Val Thr Leu Asp Glu Ser Gly Gly Gly Leu Gln
    130                 135                 140

Thr Pro Gly Gly Ala Leu Ser Leu Val Cys Lys Ala Ser Gly Phe Thr
145                 150                 155                 160

Phe Ser Ser Tyr Asp Met Ala Trp Val Arg Gln Ala Pro Gly Lys Gly
                165                 170                 175

Leu Glu Phe Val Ala Gly Ile Asp Ile Gly Ser Tyr Thr Gly Tyr Gly
            180                 185                 190

Ala Ala Val Lys Gly Arg Ala Thr Ile Ser Arg Asp Asn Gly Gln Ser
        195                 200                 205

Thr Val Arg Leu Gln Leu Asn Asn Leu Arg Ala Glu Asp Thr Gly Thr
    210                 215                 220

Tyr Tyr Cys Ala Lys Ala Gly Ser Tyr Tyr Ser Gly Ala Ala
225                 230                 235                 240

Gly Ser Ile Asp Ala Trp Gly His Gly Thr Glu Val Ile Val Ser Ser
                245                 250                 255

```
Thr Ser Gly Gln Ala Gly Gln His His His His His Gly Ala Tyr
            260                 265                 270

Pro Tyr Asp Val Pro Asp Tyr Ala Ser
        275                 280

<210> SEQ ID NO 51
<211> LENGTH: 239
<212> TYPE: PRT
<213> ORGANISM: Artificial Sequence
<220> FEATURE:
<223> OTHER INFORMATION: recombinant protein

<400> SEQUENCE: 51

Met Lys Lys Thr Ala Ile Ala Ile Ala Val Ala Leu Ala Gly Phe Ala
1               5                   10                  15

Thr Val Ala Gln Ala Ala Val Ile Tyr Tyr Asn Asp Lys Arg Pro Ser
            20                  25                  30

Asp Ile Pro Ser Arg Phe Ser Gly Ser Lys Ser Gly Ser Thr Ala Thr
        35                  40                  45

Leu Thr Ile Thr Gly Val Arg Ala Glu Asp Glu Ala Val Tyr Tyr Cys
    50                  55                  60

Gly Ser Ala Asp Ser Thr Asp Ala Val Phe Gly Ala Gly Thr Thr Leu
65                  70                  75                  80

Thr Val Leu Gly Gln Ser Ser Arg Ser Ser Ala Val Thr Leu Asp Glu
                85                  90                  95

Ser Gly Gly Gly Leu Gln Thr Pro Gly Gly Gly Leu Ser Leu Val Cys
            100                 105                 110

Lys Ala Ser Gly Phe Thr Phe Ser Asp Tyr Asp Met Phe Trp Val Arg
        115                 120                 125

Gln Ala Pro Ser Lys Gly Leu Glu Phe Val Ala Ala Ile Thr Ser Ser
    130                 135                 140

Gly Thr Gly Thr Lys Tyr Gly Ala Ala Val Lys Gly Arg Ala Thr Ile
145                 150                 155                 160

Ser Lys Asp Asn Gly Gln Ser Thr Val Arg Leu Gln Leu Asn Ser Leu
                165                 170                 175

Arg Ala Glu Asp Thr Gly Thr Tyr Tyr Cys Ala Arg Ser Asp Ala Asp
            180                 185                 190

Ser Thr Thr Trp Ser Ala Gly Glu Ile Asp Ala Trp Gly His Gly Thr
        195                 200                 205

Glu Val Ile Val Ser Ser Thr Ser Gly Gln Ala Gly Gln His His His
    210                 215                 220

His His His Gly Ala Tyr Pro Tyr Asp Val Pro Asp Tyr Ala Ser
225                 230                 235

<210> SEQ ID NO 52
<211> LENGTH: 283
<212> TYPE: PRT
<213> ORGANISM: Artificial Sequence
<220> FEATURE:
<223> OTHER INFORMATION: recombinant protein

<400> SEQUENCE: 52

Met Lys Lys Thr Ala Ile Ala Ile Ala Val Ala Leu Ala Gly Phe Ala
1               5                   10                  15

Thr Val Ala Gln Ala Ala Leu Ser Arg Pro Arg Cys Gln Gln Thr Trp
            20                  25                  30

Gly Gly Thr Val Glu Ile Thr Cys Ser Gly Gly Ser Asn Asn Tyr Gly
```

```
                35                  40                  45
Tyr Gly Trp Tyr Gln Gln Lys Ser Pro Gly Ser Ala Pro Val Thr Leu
 50                  55                  60

Ile Tyr Ser Asn Asp Asn Arg Pro Ser Asn Ile Pro Ser Arg Phe Ser
 65                  70                  75                  80

Gly Ser Thr Ser Gly Ser Thr Ser Thr Leu Thr Ile Thr Gly Val Gln
                 85                  90                  95

Ala Glu Asp Glu Ala Val Tyr Tyr Cys Gly Ser Tyr Asp Ser Ser Asn
                100                 105                 110

Asp Ser Gly Ile Phe Gly Ala Gly Thr Thr Leu Thr Val Leu Ser Gln
            115                 120                 125

Ser Ser Arg Ser Ser Ala Val Thr Leu Asp Glu Ser Gly Gly Gly Leu
        130                 135                 140

Gln Thr Pro Gly Gly Gly Leu Ser Leu Val Cys Lys Ala Ser Gly Phe
145                 150                 155                 160

Thr Phe Ser Thr Phe Asn Met Phe Trp Val Arg Gln Ala Pro Gly Lys
                165                 170                 175

Gly Leu Glu Phe Val Ala Gly Ile Ser Ile Thr Gly Gly Trp Thr Gly
            180                 185                 190

Tyr Gly Ala Ala Val Lys Gly Arg Ala Thr Ile Ser Arg Asp Asn Gly
        195                 200                 205

Gln Ser Thr Val Arg Leu Gln Leu Asn Asn Leu Arg Ala Glu Asp Thr
210                 215                 220

Gly Thr Tyr Tyr Cys Ala Lys Pro Ala Ala Trp Ser Cys Tyr Arg Gly
225                 230                 235                 240

Cys Gly Gly Glu Phe Asp Ala Trp Gly His Gly Thr Glu Val Ile Val
                245                 250                 255

Ser Ser Thr Ser Gly Gln Ala Gly Gln His His His His His His Gly
            260                 265                 270

Ala Tyr Pro Tyr Asp Val Pro Asp Tyr Ala Ser
        275                 280

<210> SEQ ID NO 53
<211> LENGTH: 279
<212> TYPE: PRT
<213> ORGANISM: Artificial Sequence
<220> FEATURE:
<223> OTHER INFORMATION: recombinant protein

<400> SEQUENCE: 53

Met Lys Lys Thr Ala Ile Ala Ile Ala Val Ala Leu Ala Gly Phe Ala
 1               5                  10                  15

Thr Val Ala Gln Ala Ala Leu Thr Gln Pro Ser Ser Val Ser Ala Asn
                20                  25                  30

Leu Gly Gly Ile Val Glu Ile Thr Cys Ser Gly Ser Ser Gly Ser Tyr
            35                  40                  45

Gly Trp Tyr Gln Gln Lys Ser Pro Gly Ser Ala Pro Val Thr Val Ile
        50                  55                  60

Tyr Tyr Asn Asp Lys Arg Pro Ser Asn Ile Pro Ser Arg Phe Ser Gly
 65                  70                  75                  80

Ser Gly Ser Gly Ser Thr Asn Thr Leu Thr Ile Ala Gly Val Arg Ala
                 85                  90                  95

Glu Asp Glu Ala Val Tyr Tyr Cys Gly Asn Glu Asp Ser Ser Gly Ala
                100                 105                 110

Ala Phe Gly Ala Gly Thr Thr Leu Thr Val Leu Gly Gln Ser Ser Arg
```

```
            115                 120                 125
Ser Ser Ala Val Thr Leu Asp Glu Ser Gly Gly Gly Leu Gln Thr Pro
    130                 135                 140

Gly Gly Gly Leu Ser Leu Val Cys Lys Ala Ser Gly Phe Thr Phe Ser
145                 150                 155                 160

Asp Tyr Asp Met Phe Trp Val Arg Gln Ala Pro Ser Lys Gly Leu Glu
                165                 170                 175

Phe Val Ala Ala Ile Thr Ser Ser Gly Thr Gly Thr Lys Tyr Gly Ala
            180                 185                 190

Ala Val Lys Gly Arg Ala Thr Ile Ser Lys Asp Asn Gly Gln Arg Thr
        195                 200                 205

Val Arg Leu Gln Leu Asn Ser Leu Gly Ala Glu Asp Thr Gly Thr Tyr
    210                 215                 220

Tyr Cys Ala Arg Ser Asp Ala Asp Ser Thr Thr Trp Ser Ala Gly Glu
225                 230                 235                 240

Ile Asp Ala Trp Gly His Gly Thr Glu Val Ile Val Ser Ser Thr Ser
                245                 250                 255

Gly Gln Ala Gly Gln His His His His His His Gly Ala Tyr Pro Tyr
            260                 265                 270

Asp Val Pro Asp Tyr Ala Ser
        275

<210> SEQ ID NO 54
<211> LENGTH: 283
<212> TYPE: PRT
<213> ORGANISM: Artificial Sequence
<220> FEATURE:
<223> OTHER INFORMATION: recombinant protein

<400> SEQUENCE: 54

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Gly Thr Val Lys Ile Thr Cys Ser Gly Ser Ser Gly Ser Tyr
        35                  40                  45

Tyr Gly Trp Tyr Gln Gln Lys Ser Pro Gly Ser Ala Pro Val Thr Val
    50                  55                  60

Ile Tyr Asp Asn Asp Lys Arg Pro Ser Asp Val Pro Ser Arg Phe Ser
65                  70                  75                  80

Gly Ser Lys Ser Gly Pro Thr Ala Thr Leu Thr Ile Thr Gly Val Gln
                85                  90                  95

Ala Glu Asp Glu Ala Val Tyr Phe Cys Gly Ser Arg Asp Asn Ser Tyr
            100                 105                 110

Val Gly Ile Phe Gly Ala Gly Thr Thr Leu Thr Val Leu Gly Gln Ser
        115                 120                 125

Ser Arg Ser Ser Ala Val Thr Leu Asp Glu Ser Gly Gly Gly Leu Gln
    130                 135                 140

Thr Pro Gly Gly Ala Leu Ser Leu Val Cys Lys Ala Ser Gly Phe Thr
145                 150                 155                 160

Phe Ser Ser Tyr Asp Met Phe Trp Val Arg Gln Ala Pro Gly Lys Gly
                165                 170                 175

Leu Glu Phe Val Ala Gln Ile Asn Ser Ala Gly Ser Tyr Thr Asn Tyr
            180                 185                 190

Gly Ser Ala Val Lys Gly Arg Ala Thr Ile Ser Arg Asp Asp Gly Gln
```

```
                195                 200                 205
Ser Thr Val Arg Leu Gln Leu Asn Asn Leu Arg Ala Glu Asp Thr Gly
    210                 215                 220

Ile Tyr Phe Cys Ala Lys Ser Ala Ser Gly Tyr Tyr Ser Gly Ser
225                 230                 235                 240

Asp Ala Gly Asp Ile Asp Ala Trp Gly His Gly Thr Glu Val Ile Val
                245                 250                 255

Ser Ser Thr Ser Gly Gln Ala Gly Gln His His His His His Gly
        260                 265                 270

Ala Tyr Pro Tyr Asp Val Pro Asp Tyr Ala Ser
            275                 280

<210> SEQ ID NO 55
<211> LENGTH: 279
<212> TYPE: PRT
<213> ORGANISM: Artificial Sequence
<220> FEATURE:
<223> OTHER INFORMATION: recombinant protein

<400> SEQUENCE: 55

Met Lys Lys Thr Ala Ile Ala Ile Ala Val Ala Leu Ala Gly Phe Ala
1               5                   10                  15

Thr Val Ala Gln Ala Ala Val Ser Ala Asn Pro Gly Asp Thr Val Lys
            20                  25                  30

Ile Thr Cys Ser Gly Asp Ser Asn Asn Tyr Gly Trp Tyr Gln Gln Lys
        35                  40                  45

Ser Pro Gly Ser Ala Pro Val Thr Val Ile Tyr Asp Asn Thr Asn Arg
50                  55                  60

Pro Ser Asn Ile Pro Ser Arg Phe Ser Gly Ser Lys Ser Gly Ser Thr
65                  70                  75                  80

Ala Thr Leu Thr Ile Thr Gly Val Gln Ala Asp Asp Glu Ala Val Tyr
                85                  90                  95

Phe Cys Gly Ser Phe Asp Ser Ser Thr Asp Ile Phe Gly Ala Gly Thr
            100                 105                 110

Thr Leu Thr Val Leu Gly Gln Ser Ser Arg Ser Ser Thr Val Thr Leu
        115                 120                 125

Asp Glu Ser Gly Gly Gly Leu Gln Thr Pro Gly Arg Ala Leu Ser Leu
130                 135                 140

Val Cys Lys Ala Ser Gly Phe Thr Phe Ser Ser Phe Asn Met Gly Trp
145                 150                 155                 160

Val Arg Gln Ala Pro Gly Lys Gly Leu Glu Tyr Val Ala Ser Ile Ser
                165                 170                 175

Ser Ser Gly Ser Tyr Thr Ala Tyr Gly Ser Ala Val Lys Gly Arg Ala
            180                 185                 190

Thr Ile Ser Arg Asp Asn Gly Gln Ser Thr Val Arg Leu Gln Leu Asn
        195                 200                 205

Asn Leu Arg Ala Glu Asp Thr Ala Thr Tyr Tyr Cys Ala Lys Ala Ala
210                 215                 220

Gly Ser Ala Tyr Tyr Thr Ala Val Thr Pro Ala Phe Ala Gly Ser
225                 230                 235                 240

Ile Asp Ala Trp Gly His Gly Thr Glu Val Ile Val Ser Ser Thr Ser
                245                 250                 255

Gly Gln Ala Gly Gln His His His His His Gly Ala Tyr Pro Tyr
            260                 265                 270

Asp Val Pro Asp Tyr Ala Ser
```

-continued

275

<210> SEQ ID NO 56
<211> LENGTH: 274
<212> TYPE: PRT
<213> ORGANISM: Artificial Sequence
<220> FEATURE:
<223> OTHER INFORMATION: recombinant protein

<400> SEQUENCE: 56

Met Lys Lys Thr Ala Ile Ala Ile Ala Val Ala Leu Ala Gly Phe Ala
1               5                   10                  15

Thr Val Ala Gln Ala Ala Val Ser Ala Asn Leu Gly Gly Thr Val Glu
            20                  25                  30

Ile Thr Cys Ser Gly Gly Gly Ser Tyr Tyr Gly Trp Tyr Gln Gln Lys
        35                  40                  45

Ser Pro Gly Ser Ala Pro Val Thr Val Ile Tyr Ala Asn Thr Asn Gly
    50                  55                  60

Pro Ser Asp Ile Pro Ser Arg Phe Ser Gly Ser Thr Gly Ser Thr
65                  70                  75                  80

Ala Thr Leu Thr Ile Thr Gly Val Gln Ala Asp Asp Glu Ala Val Tyr
                85                  90                  95

Ser Cys Gly Ser Tyr Asp Ser Ser Tyr Val Gly Ile Phe Gly Ala Gly
            100                 105                 110

Thr Thr Leu Thr Val Leu Gly Gln Ser Ser Arg Ser Ser Thr Val Thr
        115                 120                 125

Leu Asp Glu Ser Gly Gly Gly Leu Gln Thr Pro Gly Gly Ala Leu Ser
    130                 135                 140

Leu Val Cys Lys Ala Ser Gly Phe Thr Phe Asn Ser Tyr Ala Leu Glu
145                 150                 155                 160

Trp Val Arg Gln Ala Pro Gly Lys Gly Leu Glu Trp Val Ala Gly Ile
                165                 170                 175

Ser Gly Asp Gly Ser Tyr Arg His Tyr Gly Ser Ala Val Lys Gly Arg
            180                 185                 190

Ala Thr Ile Ser Arg Asp Ser Gly Gln Ser Thr Val Arg Leu Gln Leu
        195                 200                 205

Asn Asn Leu Arg Ala Glu Asp Thr Gly Thr Tyr Tyr Cys Ala Lys Ser
    210                 215                 220

Thr Gly Ser Gly Ala Gly Trp Gly Ala Ser Asn Ile Asp Ala Trp Gly
225                 230                 235                 240

His Gly Thr Glu Val Ile Val Ser Ser Thr Ser Gly Gln Ala Gly Gln
                245                 250                 255

His His His His His His Gly Ala Tyr Pro Tyr Asp Val Pro Asp Tyr
            260                 265                 270

Ala Ser

<210> SEQ ID NO 57
<211> LENGTH: 278
<212> TYPE: PRT
<213> ORGANISM: Artificial Sequence
<220> FEATURE:
<223> OTHER INFORMATION: recombinant protein

<400> SEQUENCE: 57

Met Lys Lys Thr Ala Ile Ala Ile Ala Val Ala Leu Ala Gly Phe Ala
1               5                   10                  15

Thr Val Ala Gln Ala Ala Val Ser Ala Ser Pro Gly Asp Thr Val Lys

```
            20              25                  30
Ile Thr Cys Ser Gly Gly Asn Ser Ser Tyr Gly Tyr Gly Trp Tyr Gln
            35                  40                  45

Gln Lys Ser Pro Gly Ser Ala Pro Val Ser Val Ile Tyr Tyr Asn Asp
        50                  55                  60

Glu Arg Pro Ser Asp Ile Pro Ser Arg Phe Ser Gly Ser Ala Ser Gly
65                  70                  75                  80

Ser Thr Ala Thr Leu Thr Ile Thr Gly Val Gln Ala Asp Asp Glu Ala
                85                  90                  95

Val Tyr Tyr Cys Gly Asn Ala Asp Ser Ser Thr Tyr Ala Gly Ile Phe
            100                 105                 110

Gly Ala Gly Thr Thr Leu Thr Val Leu Gly Gln Ser Ser Arg Ser Ser
            115                 120                 125

Ala Val Thr Leu Asp Glu Ser Gly Gly Gly Leu Gln Thr Pro Gly Gly
        130                 135                 140

Gly Leu Ser Leu Val Cys Lys Ala Ser Gly Phe Asp Phe Ser Thr Asn
145                 150                 155                 160

Ala Met Gly Trp Val Arg Gln Ala Pro Gly Lys Gly Leu Glu Trp Val
                165                 170                 175

Ala Gly Ile Ser Gly Ser Gly Ser Ser Thr Trp Tyr Ala Thr Ala Val
            180                 185                 190

Lys Gly Arg Ala Thr Ile Ser Arg Asp Asn Gly Gln Ser Thr Val Arg
        195                 200                 205

Leu Gln Leu Asn Asn Leu Arg Ala Glu Asp Thr Gly Thr Tyr Tyr Cys
    210                 215                 220

Thr Lys Tyr Val Gly Asp Tyr Tyr Trp Tyr Ile Asp Ala Gly Ser Ile
225                 230                 235                 240

Asp Ala Trp Gly His Gly Thr Glu Val Ile Val Ser Thr Ser Ser Gly
                245                 250                 255

Gln Ala Gly Gln His His His His His Gly Ala Tyr Pro Tyr Asp
            260                 265                 270

Val Pro Asp Tyr Ala Ser
            275

<210> SEQ ID NO 58
<211> LENGTH: 278
<212> TYPE: PRT
<213> ORGANISM: Artificial Sequence
<220> FEATURE:
<223> OTHER INFORMATION: recombinant protein

<400> SEQUENCE: 58

Met Lys Lys Thr Ala Ile Ala Ile Ala Val Ala Leu Ala Gly Phe Ala
1               5                   10                  15

Thr Val Ala Gln Ala Ala Leu Thr Pro Pro Ser Ser Val Ser Ala Asn
            20                  25                  30

Leu Gly Ala Pro Val Glu Ile Thr Cys Ser Gly Ser Ser Gly Asn Tyr
            35                  40                  45

Gly Trp Phe Gln Gln Lys Ser Pro Gly Ser Ala Pro Val Thr Val Ile
        50                  55                  60

Tyr Ser Asn Asp Lys Arg Pro Ser Asp Ile Pro Ser Arg Phe Ser Gly
65                  70                  75                  80

Ser Leu Ser Gly Ser Thr Gly Thr Leu Thr Ile Thr Gly Val Arg Ala
                85                  90                  95

Glu Asp Glu Ala Val Tyr Tyr Cys Gly Ser Ile Asp Asn Thr Tyr Val
```

```
                    100                 105                 110
Gly Thr Gly Ala Phe Gly Ala Gly Thr Thr Leu Thr Val Leu Gly Gln
            115                 120                 125

Ser Ser Arg Ser Ser Thr Val Thr Leu Asp Glu Ser Gly Ala Gly Leu
    130                 135                 140

Gln Thr Pro Gly Arg Ala Leu Ser Leu Val Cys Lys Gly Ser Gly Phe
145                 150                 155                 160

Thr Phe Ser Ser Phe Tyr Met Phe Trp Val Arg Gln Ala Pro Gly Lys
                165                 170                 175

Gly Leu Glu Phe Val Ala Cys Ile Ser Ser Gly Ser Ser Thr Arg
            180                 185                 190

Tyr Gly Val Val Lys Gly Arg Ala Thr Ile Ser Arg Asp Asn Gly
        195                 200                 205

Gln Ser Thr Val Arg Leu Arg Leu Asn Asn Leu Arg Ala Asp Asp Thr
    210                 215                 220

Gly Thr Tyr Tyr Cys Ala Arg Gly Thr Ser Ser Gly Ala Asn Thr Ile
225                 230                 235                 240

Asp Ala Trp Gly His Gly Thr Glu Val Ile Val Ser Ser Thr Ser Gly
                245                 250                 255

Gln Ala Gly Gln His His His His His Gly Ala Tyr Pro Tyr Asp
            260                 265                 270

Val Pro Asp Tyr Ala Ser
        275

<210> SEQ ID NO 59
<211> LENGTH: 281
<212> TYPE: PRT
<213> ORGANISM: Artificial Sequence
<220> FEATURE:
<223> OTHER INFORMATION: recombinant protein

<400> SEQUENCE: 59

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Gly Ile Thr Cys Ser Gly Gly Ser Tyr Tyr
        35                  40                  45

Gly Trp Tyr Gln Gln Lys Ser Pro Gly Ser Ala Pro Val Thr Leu Ile
    50                  55                  60

Tyr Glu Asn Asp Met Arg Pro Ser Asn Ile Pro Ser Arg Phe Ser Gly
65                  70                  75                  80

Ser Thr Ser Gly Ser Thr Ser Thr Leu Thr Ile Thr Gly Val Gln Ala
                85                  90                  95

Glu Asp Glu Ala Val Tyr Phe Cys Gly Ser Tyr Asp Ser Ser Asn Tyr
            100                 105                 110

Val Gly Glu Phe Gly Ala Gly Thr Thr Leu Thr Val Leu Gly Gln Ser
        115                 120                 125

Ser Arg Ser Ser Ala Val Thr Leu Asp Glu Ser Gly Gly Gly Leu Gln
    130                 135                 140

Thr Pro Gly Gly Ala Leu Ser Leu Val Cys Lys Ala Ser Gly Phe Thr
145                 150                 155                 160

Phe Ser Ser Phe Asp Met Phe Trp Val Arg Gln Ala Pro Gly Lys Gly
                165                 170                 175

Leu Glu Tyr Val Ala Glu Ile Ser Asp Thr Gly Ser Ser Thr Tyr Tyr
```

```
            180                 185                 190
Gly Ala Val Lys Gly Arg Ala Thr Ile Ser Arg Asp Asn Gly Gln
            195                 200                 205

Ser Thr Val Arg Leu Gln Leu Asn Asn Leu Arg Ala Glu Asp Thr Gly
    210                 215                 220

Thr Tyr Phe Cys Ala Lys Ser His Ser Gly Tyr Gly Trp Ser Thr Ala
225                 230                 235                 240

Gly Asp Ile Asp Ala Trp Gly His Gly Thr Glu Val Ile Val Ser Ser
                245                 250                 255

Thr Ser Gly Gln Ala Gly Gln His His His His His Gly Ala Tyr
            260                 265                 270

Pro Tyr Asp Val Pro Asp Tyr Ala Ser
            275                 280

<210> SEQ ID NO 60
<211> LENGTH: 285
<212> TYPE: PRT
<213> ORGANISM: Artificial Sequence
<220> FEATURE:
<223> OTHER INFORMATION: recombinant protein

<400> SEQUENCE: 60

Met Lys Lys Thr Ala Ile Ala Ile Ala Val Ala Leu Ala Gly Phe Ala
1               5                   10                  15

Thr Val Ala Gln Ala Ala Leu Ser Arg Pro Arg Cys Gln Gln Thr Trp
            20                  25                  30

Gly Gly Thr Val Lys Ile Thr Cys Ser Gly Ser Asn Ser Tyr Tyr Gly
        35                  40                  45

Trp Tyr Gln Gln Lys Ala Pro Gly Ser Ala Pro Val Thr Leu Ile Tyr
    50                  55                  60

Asp Asp Thr Asn Arg Pro Ser Asp Ile Pro Ser Arg Phe Ser Gly Ser
65              70                  75                  80

Lys Ser Gly Ser Thr Ala Thr Leu Thr Ile Thr Gly Val Gln Ala Asp
                85                  90                  95

Asp Glu Ala Val Tyr Phe Cys Gly Gly Phe Asp Ser Ser Ser Asp Ser
            100                 105                 110

Gly Phe Gly Ala Gly Thr Thr Leu Thr Val Leu Gly Gln Ser Ser Arg
        115                 120                 125

Ser Ser Thr Val Thr Leu Asp Glu Ser Gly Gly Leu Gln Thr Pro
    130                 135                 140

Gly Arg Ala Leu Ser Leu Val Cys Lys Ala Ser Gly Phe Thr Phe Ser
145                 150                 155                 160

Ser Phe Asn Met Gly Trp Val Arg Gln Ala Pro Gly Lys Gly Leu Glu
                165                 170                 175

Tyr Val Ala Ser Ile Ser Ser Gly Ser Tyr Thr Ala Tyr Gly Ser
            180                 185                 190

Ala Val Lys Gly Arg Ala Thr Ile Ser Arg Asp Asn Gly Gln Ser Thr
            195                 200                 205

Val Arg Leu Gln Leu Asn Asn Leu Arg Ala Glu Asp Thr Ala Thr Tyr
    210                 215                 220

Tyr Cys Ala Lys Ala Ala Gly Ser Ala Tyr Tyr Tyr Thr Ala Val Thr
225                 230                 235                 240

Pro Ala Phe Ala Gly Ser Ile Asp Ala Trp Gly His Gly Thr Glu Val
                245                 250                 255

Ile Val Ser Ser Thr Ser Gly Gln Ala Gly Gln His His His His His
```

<210> SEQ ID NO 61
<211> LENGTH: 243
<212> TYPE: PRT
<213> ORGANISM: Artificial Sequence
<220> FEATURE:
<223> OTHER INFORMATION: recombinant protein

<400> SEQUENCE: 61

```
His Gly Ala Tyr Pro Tyr Asp Val Pro Asp Tyr Ala Ser
            275                 280                 285

Met Lys Lys Thr Ala Ile Ala Ile Ala Val Ala Leu Ala Gly Phe Ala
1               5                   10                  15

Thr Val Ala Gln Ala Ala Val Ile Tyr Ser Asn Asp Glu Arg Pro Ser
            20                  25                  30

Asp Ile Pro Ser Arg Phe Ser Gly Ser Thr Ser Gly Ser Thr Ser Thr
        35                  40                  45

Leu Thr Ile Thr Gly Val Gln Ala Asp Asp Glu Ala Val Tyr Phe Cys
    50                  55                  60

Gly Ser Ala Asp Ser Ser Thr Tyr Ala Gly Ile Phe Gly Ala Gly Thr
65                  70                  75                  80

Thr Leu Thr Val Leu Gly Gln Ser Ser Arg Ser Ser Ala Val Thr Leu
                85                  90                  95

Asp Glu Ser Gly Gly Gly Leu Gln Thr Pro Gly Gly Ala Leu Ser Leu
            100                 105                 110

Val Cys Lys Ala Ser Gly Phe Thr Phe Ser Ser Phe Asn Met Phe Trp
        115                 120                 125

Val Arg Gln Ala Pro Gly Arg Gly Leu Glu Phe Val Ala Gly Ile Thr
    130                 135                 140

Ser Ser Gly Gly Ser Thr Tyr Tyr Gly Thr Ala Val Lys Gly Arg Ala
145                 150                 155                 160

Thr Ile Ser Arg Asp Asn Gly Gln Ser Thr Val Arg Met Gln Leu Asn
                165                 170                 175

Asn Leu Arg Ala Glu Asp Thr Gly Thr Tyr Phe Cys Ala Arg Gly Ala
            180                 185                 190

Tyr Asp Tyr Tyr Phe Tyr Trp Asn Tyr Ala Gly Thr Ile Asp Ala Trp
        195                 200                 205

Gly His Gly Thr Glu Val Ile Val Ser Ser Thr Ser Gly Gln Ala Gly
    210                 215                 220

Gln His His His His His Gly Ala Tyr Pro Tyr Asp Val Pro Asp
225                 230                 235                 240

Tyr Ala Ser
```

<210> SEQ ID NO 62
<211> LENGTH: 241
<212> TYPE: PRT
<213> ORGANISM: Artificial Sequence
<220> FEATURE:
<223> OTHER INFORMATION: recombinant protein

<400> SEQUENCE: 62

```
Met Lys Lys Thr Ala Ile Ala Ile Ala Val Ala Leu Ala Gly Phe Ala
1               5                   10                  15

Thr Val Ala Gln Ala Ala Val Ile Tyr Asp Asn Thr Asn Arg Pro Ser
            20                  25                  30

Asn Ile Pro Ser Arg Phe Ser Gly Ser Lys Ser Gly Ser Thr Gly Thr
```

```
            35                  40                  45
Leu Thr Ile Thr Gly Val Gln Ala Asp Glu Ala Val Tyr Tyr Cys
 50                  55                  60
Gly Ser Thr Asp Ser Ser Ala Asp Gly Val Phe Gly Ala Gly Thr Thr
 65                  70                  75                  80
Leu Thr Val Leu Gly Gln Ser Ser Arg Ser Ala Val Thr Leu Asp
                 85                  90                  95
Glu Ser Gly Gly Gly Leu Gln Thr Pro Gly Gly Gly Leu Ser Leu Val
                100                 105                 110
Cys Lys Gly Ser Gly Phe Thr Phe Ser Ser Phe Asp Met Phe Trp Val
                115                 120                 125
Arg Gln Ala Pro Gly Lys Gly Leu Glu Trp Val Ala Gly Ile Arg Asn
                130                 135                 140
Asp Gly Ser Asp Thr Ala Tyr Gly Ala Ala Val Lys Gly Arg Ala Thr
145                 150                 155                 160
Ile Ser Lys Asp Asn Gly Gln Ser Thr Val Arg Leu Gln Leu Asn Asn
                165                 170                 175
Leu Arg Ala Glu Asp Thr Gly Thr Tyr Tyr Cys Ala Lys Ala Ala Gly
                180                 185                 190
Tyr Cys Tyr Val Tyr Ser Cys Ala Gly Ser Ile Asp Ala Trp Gly His
                195                 200                 205
Gly Thr Glu Val Ile Val Ser Ser Thr Ser Gly Gln Ala Gly Gln His
210                 215                 220
His His His His Gly Ala Tyr Pro Tyr Asp Val Pro Asp Tyr Ala
225                 230                 235                 240
Ser

<210> SEQ ID NO 63
<211> LENGTH: 279
<212> TYPE: PRT
<213> ORGANISM: Artificial Sequence
<220> FEATURE:
<223> OTHER INFORMATION: recombinant protein

<400> SEQUENCE: 63

Met Lys Lys Thr Ala Ile Ala Ile Ala Val Ala Leu Ala Gly Phe Ala
 1                   5                  10                  15
Thr Val Ala Gln Ala Ala Val Ser Ala Asn Pro Gly Glu Thr Val Lys
                 20                  25                  30
Ile Thr Cys Ser Gly Gly Gly Ser Tyr Gly Trp Tyr Gln Gln Lys
                 35                  40                  45
Ala Pro Gly Ser Ala Pro Val Thr Val Ile Tyr Asp Asn Thr Asn Arg
 50                  55                  60
Pro Ser Asn Ile Pro Ser Arg Phe Ser Gly Glu Ser Gly Ser Thr
 65                  70                  75                  80
Ala Thr Leu Thr Ile Thr Gly Val Arg Ala Glu Asp Glu Ala Ala Tyr
                 85                  90                  95
Tyr Cys Gly Ser Ala Asp Ser Ser Asp Ala Gly Ile Phe Gly Ala Gly
                100                 105                 110
Thr Thr Leu Thr Val Leu Gly Gln Ser Ser Arg Ser Ser Ala Val Thr
                115                 120                 125
Leu Asp Glu Ser Gly Gly Gly Leu Gln Thr Pro Arg Arg Ala Leu Ser
                130                 135                 140
Leu Val Cys Lys Ala Ser Gly Phe Thr Phe Ser Asp Tyr Gly Met Ala
145                 150                 155                 160
```

```
Trp Val Arg Gln Ala Pro Gly Lys Gly Leu Glu Trp Val Ala Gly Ile
            165                 170                 175

Gly Ser Ser Gly Ser Tyr Thr Asp Tyr Gly Ser Ala Val Lys Gly Arg
        180                 185                 190

Ala Thr Ile Ser Arg Asp Asn Gly Gln Ser Thr Val Arg Leu Gln Leu
            195                 200                 205

Asn Asn Leu Arg Ala Glu Asp Thr Ala Thr Tyr Tyr Cys Ala Lys Asp
210                 215                 220

Ile Gly Ser Val Tyr Gly Cys Gly Trp Trp Ala Cys Ser Ala Gly Ser
225                 230                 235                 240

Ile Asp Ala Trp Gly His Gly Thr Glu Val Ile Val Ser Ser Thr Ser
            245                 250                 255

Gly Gln Ala Gly Gln His His His His His Gly Ala Tyr Pro Tyr
        260                 265                 270

Asp Val Pro Asp Tyr Ala Ser
        275

<210> SEQ ID NO 64
<211> LENGTH: 243
<212> TYPE: PRT
<213> ORGANISM: Artificial Sequence
<220> FEATURE:
<223> OTHER INFORMATION: recombinant protein

<400> SEQUENCE: 64

Met Lys Lys Thr Ala Ile Ala Ile Ala Val Ala Leu Ala Gly Phe Ala
1               5                   10                  15

Thr Val Ala Gln Ala Ala Val Ile Tyr Asp Asn Thr Asn Arg Pro Ser
            20                  25                  30

Asn Ile Pro Ser Arg Phe Ser Gly Ser Leu Ser Gly Ser Thr Asn Thr
        35                  40                  45

Leu Thr Ile Thr Gly Val Gln Ala Glu Asp Glu Ala Val Tyr Phe Cys
    50                  55                  60

Gly Gly Tyr Asp Ser Ser Thr Asp Ser Gly Met Phe Gly Ala Gly Thr
65                  70                  75                  80

Thr Leu Thr Val Leu Gly Gln Ser Ser Arg Ser Ser Ala Val Thr Leu
            85                  90                  95

Asp Glu Ser Gly Gly Gly Leu Gln Thr Pro Gly Gly Gly Leu Ser Leu
            100                 105                 110

Val Cys Lys Gly Ser Gly Phe Thr Phe Ser Ser Tyr Asp Met Ala Trp
        115                 120                 125

Val Arg Gln Glu Pro Ser Lys Gly Leu Glu Phe Val Ala Ser Ile Ser
    130                 135                 140

Asn Thr Gly Ser Asp Thr Ser Tyr Ala Pro Ala Val Lys Gly Arg Ala
145                 150                 155                 160

Thr Ile Ser Arg Asp Asn Gly Gln Ser Thr Val Arg Leu Gln Leu Asn
            165                 170                 175

Asn Leu Arg Ala Glu Asp Thr Ala Thr Tyr Tyr Cys Ala Lys Ser Ala
        180                 185                 190

Gly Ser Tyr Tyr Trp Asn Ala Gly Gly Ala Gly Ser Ile Asp Thr Trp
    195                 200                 205

Gly His Gly Thr Glu Val Ile Val Ser Ser Ser Gly Gln Ala Gly
            210                 215                 220

Gln His His His His His His Gly Ala Tyr Pro Tyr Asp Val Pro Asp
225                 230                 235                 240
```

Tyr Ala Ser

<210> SEQ ID NO 65
<211> LENGTH: 282
<212> TYPE: PRT
<213> ORGANISM: Artificial Sequence
<220> FEATURE:
<223> OTHER INFORMATION: recombinant protein

<400> SEQUENCE: 65

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Leu Gly Gly Thr Phe Lys Ile Thr Cys Ser Gly Ser Ser Gly Ser Tyr
        35                  40                  45

Ala Trp Tyr Gln Gln Lys Ser Pro Gly Ser Ala Pro Val Thr Val Ile
    50                  55                  60

Tyr Trp Asn Asp Lys Arg Pro Ser Asn Ile Pro Ser Arg Phe Ser Gly
65                  70                  75                  80

Ala Leu Ser Gly Ser Thr Ala Thr Leu Thr Ile Thr Gly Val Gln Ala
                85                  90                  95

Glu Asp Glu Ala Val Tyr Phe Cys Gly Ser Ala Asp Ser Ser Gly Ala
            100                 105                 110

Ile Phe Gly Ala Gly Thr Thr Leu Thr Val Leu Gly Gln Ser Ser Arg
        115                 120                 125

Ser Ser Thr Val Thr Leu Asp Glu Ser Gly Gly Leu Gln Thr Pro
    130                 135                 140

Gly Gly Gly Leu Ser Leu Val Cys Lys Gly Ser Gly Phe Ala Phe Ser
145                 150                 155                 160

Asn Tyr Gly Met Gly Trp Met Arg Gln Ala Pro Gly Lys Gly Leu Glu
                165                 170                 175

Tyr Val Ala Gly Ile Ser Thr Gly Ser Tyr Thr Asp Tyr Gly Pro Ala
            180                 185                 190

Val Lys Gly Arg Ala Thr Ile Ser Arg Asp Asn Gly Gln Ser Thr Val
        195                 200                 205

Arg Leu Gln Leu Asn Asn Leu Arg Ala Glu Asp Ala Ala Ile Tyr Phe
    210                 215                 220

Cys Ala Lys Thr Ala Gly Ser Gly Tyr Gly Cys Gly Ser Gly Thr Asp
225                 230                 235                 240

Leu Gly Ser Ile Asp Ala Trp Gly His Gly Thr Glu Val Ile Val Ser
                245                 250                 255

Ser Thr Ser Gly Gln Ala Gly Gln His His His His His His Gly Ala
            260                 265                 270

Tyr Pro Tyr Asp Val Pro Asp Tyr Ala Ser
        275                 280

<210> SEQ ID NO 66
<211> LENGTH: 270
<212> TYPE: PRT
<213> ORGANISM: Artificial Sequence
<220> FEATURE:
<223> OTHER INFORMATION: recombinant protein

<400> SEQUENCE: 66

Met Lys Lys Thr Ala Ile Ala Ile Ala Val Ala Leu Ala Gly Phe Ala
1               5                   10                  15

```
Thr Val Ala Gln Ala Ala Val Ser Ala Asn Pro Gly Asp Thr Val Lys
             20                  25                  30
Ile Thr Cys Ser Gly Gly Tyr Ser Gly Tyr Gly Trp Tyr Gln Gln Lys
         35                  40                  45
Ser Pro Gly Ser Ala Pro Val Thr Val Ile Tyr Ser Asn Asn Gln Arg
 50                  55                  60
Pro Ser Asn Ile Pro Ser Arg Phe Ser Gly Ser Thr Ser Gly Ser Thr
 65                  70                  75                  80
Asn Thr Leu Thr Ile Thr Gly Val Gln Val Glu Asp Glu Ala Ile Tyr
                 85                  90                  95
Phe Cys Gly Gly Tyr Asp Cys Ser Thr Gly Ser Val Lys Ala Ser Phe
            100                 105                 110
Gly Ala Gly Thr Thr Leu Thr Val Leu Gly Gln Ser Ser Arg Ser Ser
            115                 120                 125
Ala Val Thr Leu Asp Glu Ser Gly Gly Gly Leu Gln Thr Pro Gly Gly
130                 135                 140
Thr Leu Ser Leu Val Cys Lys Gly Ser Gly Phe Thr Phe Ser Ser His
145                 150                 155                 160
Gly Met Gly Trp Val Arg Gln Ala Pro Gly Lys Gly Leu Glu Trp Val
                165                 170                 175
Ala Gly Ile Tyr Ser Gly Ser Ser Thr Tyr Tyr Gly Ala Ala Val Lys
            180                 185                 190
Gly Arg Ala Thr Ile Ser Arg Asp Asn Gly Gln Ser Thr Val Arg Leu
            195                 200                 205
Gln Leu Asn Asn Leu Arg Ala Glu Asp Thr Ala Thr Tyr Phe Cys Thr
210                 215                 220
Arg Gly Gly Gly Ala Gly Arg Ile Asp Thr Trp Gly His Gly Thr Glu
225                 230                 235                 240
Val Ile Val Ser Ser Thr Ser Gly Gln Ala Gly Gln His His His His
                245                 250                 255
His His Gly Ala Tyr Pro Tyr Asp Val Pro Asp Tyr Ala Ser
            260                 265                 270
```

<210> SEQ ID NO 67
<211> LENGTH: 286
<212> TYPE: PRT
<213> ORGANISM: Artificial Sequence
<220> FEATURE:
<223> OTHER INFORMATION: recombinant protein

<400> SEQUENCE: 67

```
Met Lys Lys Thr Ala Ile Ala Ile Ala Val Ala Leu Ala Gly Phe Ala
 1               5                  10                  15
Thr Val Ala Gln Ala Ala Leu Thr Gln Pro Ser Ser Val Ser Ala Asn
             20                  25                  30
Pro Gly Gly Thr Val Glu Ile Thr Cys Ser Gly Ser Ser Gly Ser His
         35                  40                  45
Gly Trp Tyr Gln Gln Lys Ser Pro Gly Ser Ala Pro Val Thr Val Ile
 50                  55                  60
Tyr Asp Asn Thr Asn Arg Pro Ser Asp Ile Pro Ser Arg Phe Ser Gly
 65                  70                  75                  80
Ser Leu Ser Gly Ser Thr Ala Thr Leu Thr Ile Thr Gly Val Gln Ala
                 85                  90                  95
Glu Asp Glu Ala Val Tyr Tyr Cys Gly Ser Phe Asp Thr Asn Ser Asp
            100                 105                 110
```

Ser Gly Tyr Val Gly Ile Phe Gly Ala Arg Thr Thr Leu Thr Val Leu
            115                 120                 125

Gly Gln Ser Ser Arg Ser Ser Thr Glu Thr Leu Asp Asp Ser Gly Gly
        130                 135                 140

Gly Leu Gln Thr Pro Gly Gly Ala Leu Ser Leu Val Cys Asn Ala Ser
145                 150                 155                 160

Gly Phe Thr Phe Ile Ser Tyr Asp Met Phe Trp Val Arg Gln Ala Pro
                165                 170                 175

Gly Lys Gly Leu Glu Phe Val Thr Gln Ile Asn Ser Ala Gly Ser Tyr
                180                 185                 190

Thr Asn Tyr Gly Ser Ala Val Asn Gly Arg Ala Thr Ile Ser Arg Asn
            195                 200                 205

Asp Gly Gln Ile Thr Val Arg Leu Gln Leu Asn Asp Leu Thr Ala Asp
        210                 215                 220

Asp Thr Gly Ile Tyr Phe Cys Ala Glu Ser Ala Ser Gly Tyr Asp Tyr
225                 230                 235                 240

Ser Gly Ser Asp Ala Gly Asp Ile Asn Ala Trp Gly His Gly Thr Glu
                245                 250                 255

Val Val Val Ser Ser Thr Ser Gly Gln Ala Gly Gln His His His His
            260                 265                 270

His His Gly Ala Tyr Pro Tyr Asp Val Pro Asp Tyr Ala Ser
        275                 280                 285

<210> SEQ ID NO 68
<211> LENGTH: 275
<212> TYPE: PRT
<213> ORGANISM: Artificial Sequence
<220> FEATURE:
<223> OTHER INFORMATION: recombinant protein

<400> SEQUENCE: 68

Met Lys Lys Thr Ala Ile Ala Ile Ala Val Ala Leu Ala Gly Phe Ala
1               5                   10                  15

Thr Val Ala Gln Ala Ala Val Ser Ala Asn Pro Gly Asp Thr Val Glu
            20                  25                  30

Ile Thr Cys Ser Gly Ser Ser Gly Ser Tyr Gly Trp Tyr Gln Gln Lys
        35                  40                  45

Ser Pro Gly Ser Ala Pro Val Thr Val Ile Tyr Ala Asn Thr Asn Arg
    50                  55                  60

Pro Ser Asp Ile Pro Ser Arg Phe Ser Gly Ser Lys Ser Gly Ser Thr
65                  70                  75                  80

Ala Thr Leu Thr Ile Thr Gly Val Arg Ala Glu Asp Glu Ala Val Tyr
                85                  90                  95

Tyr Cys Gly Gly Tyr Asp Ser Ser Thr Asp Ala Gly Ile Phe Gly Ala
            100                 105                 110

Gly Thr Thr Leu Thr Val Leu Gly Gln Ser Ser Arg Ser Ser Ala Val
        115                 120                 125

Thr Leu Asp Glu Ser Gly Gly Gly Leu Gln Thr Pro Gly Gly Gly Leu
    130                 135                 140

Ser Leu Val Cys Lys Ala Ser Gly Phe Thr Phe Ser Tyr Gly Met Gly
145                 150                 155                 160

Gly Trp Met Arg Gln Ala Pro Gly Lys Gly Leu Glu Tyr Val Ala Gly
                165                 170                 175

Ile Asp Asn Thr Gly Ser Ser Thr Gly Tyr Gly Ala Ala Val Lys Gly
            180                 185                 190

-continued

Arg Ala Thr Ile Ser Arg Asp Asn Arg Gln Ser Thr Val Arg Leu Gln
        195                 200                 205

Leu Asn Asn Leu Arg Ala Glu Asp Thr Gly Ile Tyr Phe Cys Ala Lys
210                 215                 220

Thr Ala Gly Ser Gly Gly Gly Trp Trp Ser Asp Trp Ile Asp Ala Trp
225                 230                 235                 240

Gly His Gly Thr Glu Val Ile Val Ser Thr Ser Gly Gln Ala Gly
            245                 250                 255

Gln His His His His His His Gly Ala Tyr Pro Tyr Asp Val Pro Asp
        260                 265                 270

Tyr Ala Ser
        275

<210> SEQ ID NO 69
<211> LENGTH: 282
<212> TYPE: PRT
<213> ORGANISM: Artificial Sequence
<220> FEATURE:
<223> OTHER INFORMATION: recombinant protein

<400> SEQUENCE: 69

Met Lys Lys Thr Ala Ile Ala Ile Ala Val Ala Leu Ala Gly Phe Ala
1               5                   10                  15

Thr Val Ala Gln Ala Ala Leu Ser Arg Pro Arg Cys Gln Gln Thr Leu
            20                  25                  30

Gly Gly Thr Val Lys Ile Thr Cys Ser Gly Ser Asn Gly Ser Tyr Asp
        35                  40                  45

Trp Cys His Gln Lys Thr Ser Ala Gly Ala Ala Ala Val Ile Ile
    50                  55                  60

Tyr Asp Asn Asn Lys Thr Ser Tyr Ile Pro Ser Ser Leu Phe Cys Ala
65                  70                  75                  80

Ser Ser Cys Ser Pro Ala Thr Leu Leu Ile Ile Gly Val Val Ala Asp
                85                  90                  95

Asp Asp Asp Val Asp Tyr Cys Gly Ser Ala Asn Asp Asn Ser Ser Val
                100                 105                 110

Val Ile Val Gly Ala Thr Thr Thr Met Ile Val Arg Arg Ser Ser Ser
            115                 120                 125

Ser Ser Ser Ala Met Met Glu Asp Glu Gly Gly Gly Leu Leu Thr Thr
        130                 135                 140

Arg Gly Gly Leu Leu Ile Leu Cys Cys Ala Ala Ser Gly Phe Ile Phe
145                 150                 155                 160

Ser Tyr Tyr Glu Met Leu Trp Leu His Pro Ala Pro Gly Glu Val Gln
                165                 170                 175

Asp Phe Val Thr Ile Ile Ser Gly Gly Gly Asn Tyr Thr Tyr Tyr Gly
            180                 185                 190

Ser Ala Val Asp Gly Gly Ala Ile Ile Ser Arg Asp Asp Gly Lys Arg
        195                 200                 205

Met Leu Met Leu Gln Leu Asn Ile Leu Glu Asp Asp Asp Thr Gly Phe
210                 215                 220

Tyr Phe Cys Ala Asp Gly Ala Ser Gly Tyr Tyr Tyr Gly Gly Ala Asp
225                 230                 235                 240

Ala Gly Asp Ile Asp Ala Trp Gly His Gly Thr Glu Val Ile Val Ser
                245                 250                 255

Ser Thr Ser Gly Gln Ala Gly Gln His His His His His Gly Ala
        260                 265                 270

```
Tyr Pro Tyr Asp Val Pro Asp Tyr Ala Ser
        275                 280

<210> SEQ ID NO 70
<211> LENGTH: 283
<212> TYPE: PRT
<213> ORGANISM: Artificial Sequence
<220> FEATURE:
<223> OTHER INFORMATION: recombinant protein

<400> SEQUENCE: 70

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Leu Gly Asp Thr Val Lys Ile Thr Cys Ser Gly Gly Gly Tyr Ala
        35                  40                  45

Gly Ser Tyr Tyr Tyr Gly Trp Tyr Gln His Asn Ala Ala Gly Gly Ala
    50                  55                  60

Pro Val Thr Leu Ile Tyr Asp Asn Thr Ile Thr Pro Ser Asp Ile Pro
65                  70                  75                  80

Ser Arg Phe Ser Gly Ser Thr Ser Gly Ser Thr Asn Ala Leu Thr Ile
                85                  90                  95

Asn Gly Val Gln Ala Asp Tyr Val Tyr Phe Cys Gly Ser Val Asn
            100                 105                 110

Cys Ser Ser Gly Val Phe Gly Ala Gly Thr Thr Leu Thr Val Leu Cys
        115                 120                 125

His Ser Ser Thr Ser Ser Asp Val Thr Leu Asp His Ser Arg Gly Gly
    130                 135                 140

Leu Gln Thr Pro Gly Gly Ser Leu Ser Leu Val Cys Asn Ala Ser Gly
145                 150                 155                 160

Phe Thr Phe Ser Ser Phe His Met Phe Trp Val Arg Gln Ala Pro Gly
                165                 170                 175

Glu Gly Leu Glu Tyr Val Ala Glu Ile Thr Asp Thr Gly Ser Ser Thr
            180                 185                 190

Tyr Tyr Gly Ala Ala Val Lys Gly Arg Ala Thr Ile Ser Arg Asp Asn
        195                 200                 205

Gly Gln Ser Thr Val Arg Leu Gln Leu Asn Asn Leu Met Ala Asp Asp
    210                 215                 220

Thr Gly Thr Tyr Phe Cys Ala Lys Ser His Ser Gly Tyr Gly Trp Ser
225                 230                 235                 240

Thr Ala Gly Asp Ile Asp Ala Trp Gly His Gly Thr Glu Val Ile Val
                245                 250                 255

Ser Ser Thr Ser Gly Gln Ala Gly Gln His His His His His Gly
            260                 265                 270

Ala Tyr Pro Tyr Asp Val Pro Asp Tyr Ala Ser
        275                 280

<210> SEQ ID NO 71
<211> LENGTH: 285
<212> TYPE: PRT
<213> ORGANISM: Artificial Sequence
<220> FEATURE:
<223> OTHER INFORMATION: recombinant protein

<400> SEQUENCE: 71

Met Lys Lys Thr Ala Ile Ala Ile Ala Val Ala Leu Ala Gly Phe Ala
```

```
            1               5                  10                 15
        Thr Val Ala Gln Ala Ala Leu Thr Gln Pro Ser Ser Val Ser Ala Asn
                        20                 25                 30
        Pro Gly Glu Thr Val Lys Ile Thr Cys Ser Gly Gly Ser Gly Tyr
                    35                 40                 45
        Gly Trp Tyr Gln Gln Lys Ser Pro Gly Ser Ala Pro Val Thr Val Ile
                50                 55                 60
        Tyr Tyr Asn Asp Lys Arg Pro Ser Asp Ile Pro Ser Arg Phe Ser Gly
         65                 70                 75                 80
        Ala Leu Ser Gly Ser Thr Ala Thr Leu Thr Ile Thr Gly Val Gln Ala
                            85                 90                 95
        Glu Asp Glu Ala Val Tyr Phe Cys Gly Ser Gly Asp Ser Ser Thr Val
                        100                105                110
        Ala Gly Ile Phe Gly Ala Gly Thr Thr Leu Thr Val Leu Gly Gln Ser
                    115                120                125
        Ser Arg Ser Ser Ala Val Thr Leu Asp Glu Ser Gly Gly Gly Leu Gln
            130                135                140
        Thr Pro Gly Gly Thr Leu Ser Leu Val Cys Lys Ala Ser Gly Phe Asp
        145                150                155                160
        Phe Ser Ser Tyr Gly Met His Trp Val Arg Gln Glu Pro Gly Lys Gly
                        165                170                175
        Leu Glu Trp Val Ala Gly Ile Ser Arg Thr Gly Ser Phe Thr Tyr Tyr
                    180                185                190
        Gly Ala Ala Val Lys Gly Arg Ala Ala Ile Ser Arg Asp Asn Gly Gln
                195                200                205
        Ser Thr Val Arg Leu Gln Leu Asn Asn Leu Arg Ala Glu Asp Thr Gly
            210                215                220
        Thr Tyr Tyr Cys Ala Lys Gly Gly Ser Asp Cys Ser Gly Tyr Arg Cys
        225                230                235                240
        Asp Tyr Ser Ala Gly Asn Ile Asp Gly Trp Gly His Gly Thr Glu Val
                        245                250                255
        Ile Val Ser Ser Thr Ser Gly Gln Ala Gly Gln His His His His His
                    260                265                270
        His Gly Ala Tyr Pro Tyr Asp Val Pro Asp Tyr Ala Ser
                275                280                285

<210> SEQ ID NO 72
<211> LENGTH: 281
<212> TYPE: PRT
<213> ORGANISM: Artificial Sequence
<220> FEATURE:
<223> OTHER INFORMATION: recombinant protein

<400> SEQUENCE: 72

Met Lys Lys Thr Ala Ile Ala Ile Ala Val Ala Leu Ala Gly Phe Ala
 1               5                  10                 15
Thr Val Ala Gln Ala Ala Leu Thr Gln Pro Ser Ser Val Ser Ala Asn
                20                 25                 30
Pro Gly Glu Thr Val Lys Ile Thr Cys Ser Gly Gly Gly Ser Asp Tyr
            35                 40                 45
Tyr Gly Trp Tyr Gln Gln Lys Ser Pro Gly Ser Ala Pro Val Thr Leu
        50                 55                 60
Ile Tyr Glu Asn Asp Lys Arg Pro Ser Asn Ile Pro Ser Arg Phe Ser
 65                 70                 75                 80
Gly Ser Lys Ser Gly Ser Thr Ala Thr Leu Thr Ile Thr Gly Val Gln
```

Ala Asp Asp Glu Ala Val Tyr Phe Cys Gly Asn Ala Asp Thr Ile Thr
                85                  90                  95

Gly Ile Phe Gly Ala Gly Thr Thr Leu Thr Val Leu Gly Gln Ser Ser
            100                 105                 110

Arg Ser Ser Thr Val Thr Leu Asp Glu Ser Gly Gly Gly Leu Gln Thr
        115                 120                 125

Pro Gly Gly Ala Leu Ser Leu Val Cys Lys Ala Ser Gly Phe Thr Phe
130                 135                 140

Ser Ser Tyr Thr Met Ala Trp Val Arg Gln Ala Pro Gly Lys Gly Leu
145                 150                 155                 160

Glu Trp Val Ala Gly Ile Asn Asp Gly Ser Tyr Thr Asn Tyr Gly
                165                 170                 175

Pro Ala Val Gln Gly Arg Ala Thr Ile Ser Arg Asp Asn Gly Gln Ser
            180                 185                 190

Thr Val Arg Leu Gln Leu Asn Asn Leu Arg Ala Glu Asp Thr Ala Ile
        195                 200                 205

Tyr Tyr Cys Ala Lys Ser Ala Gly Tyr Tyr Tyr Ser Gly Ala Ala
225                 210                 215                 220

Gly Thr Ile Asp Ala Trp Gly His Gly Thr Glu Val Ile Val Ser Ser
                245                 250                 255

Thr Ser Gly Gln Ala Gly Gln His His His His His Gly Ala Tyr
            260                 265                 270

Pro Tyr Asp Val Pro Asp Tyr Ala Ser
        275                 280

<210> SEQ ID NO 73
<211> LENGTH: 286
<212> TYPE: PRT
<213> ORGANISM: Artificial Sequence
<220> FEATURE:
<223> OTHER INFORMATION: recombinant protein

<400> SEQUENCE: 73

Met Lys Lys Thr Ala Ile Ala Ile Ala Val Ala Leu Ala Gly Phe Ala
1               5                   10                  15

Thr Val Ala Gln Ala Ala Leu Ser Arg Pro Arg Cys Gln Gln Thr Trp
            20                  25                  30

Gly Gly Ile Val Lys Leu Thr Cys Ser Gly Ser Gly Ser Cys Gly
        35                  40                  45

Trp Tyr Gln Gln Lys Ser Pro Gly Ser Ala Pro Val Thr Leu Ile Tyr
    50                  55                  60

Asp Asn Asp Lys Arg Pro Ser Asp Ile Pro Ser Arg Phe Ser Gly Ser
65                  70                  75                  80

Thr Ser Gly Ser Thr His Thr Leu Thr Ile Thr Gly Val Gln Ala Glu
                85                  90                  95

Asp Glu Ala Ile Tyr Phe Cys Gly Ser Glu Asp Ser Ser Thr Tyr Ala
            100                 105                 110

Ser Gly Phe Gly Ala Gly Thr Thr Leu Thr Val Leu Gly Gln Ser Ser
        115                 120                 125

Arg Ser Ser Ala Val Thr Leu Asp Glu Ser Gly Gly Gly Leu Gln Thr
    130                 135                 140

Pro Gly Arg Ala Leu Ser Leu Val Cys Lys Ala Ser Gly Phe Thr Phe
145                 150                 155                 160

Ser Ser Phe Asn Met Gly Trp Val Arg Gln Ala Pro Gly Lys Gly Leu

```
                    165                 170                 175
Glu Tyr Val Ala Ser Ile Ser Ser Gly Ser Tyr Thr Ala Tyr Gly
                180                 185                 190

Ser Ala Val Lys Gly Arg Ala Thr Ile Ser Arg Asp Asn Gly Gln Ser
            195                 200                 205

Thr Val Arg Leu Gln Leu Asn Asn Leu Arg Ala Glu Asp Thr Ala Thr
        210                 215                 220

Tyr Tyr Cys Ala Lys Ala Ala Gly Ser Ala Tyr Tyr Thr Ala Val
225                 230                 235                 240

Thr Pro Ala Phe Ala Gly Ser Ile Asp Ala Trp Gly His Gly Thr Glu
                245                 250                 255

Val Ile Val Pro Ser Thr Ser Gly Gln Ala Gly Gln His His His
            260                 265                 270

His His Gly Ala Tyr Pro Tyr Asp Val Pro Asp Tyr Ala Ser
        275                 280                 285

<210> SEQ ID NO 74
<211> LENGTH: 285
<212> TYPE: PRT
<213> ORGANISM: Artificial Sequence
<220> FEATURE:
<223> OTHER INFORMATION: recombinant protein

<400> SEQUENCE: 74

Met Lys Lys Thr Ala Ile Ala Ile Ala Val Ala Leu Ala Gly Phe Ala
1               5                   10                  15

Thr Val Ala Gln Ala Ala Leu Ser Arg Pro Arg Cys Gln Gln Thr Trp
            20                  25                  30

Gly Gly Thr Val Lys Ile Thr Cys Ser Gly Gly Ser Ser Tyr Tyr Gly
        35                  40                  45

Trp Tyr Gln Gln Lys Ser Pro Gly Ser Ala Pro Val Thr Leu Ile Tyr
    50                  55                  60

Glu Asn Asn Asn Arg Pro Ser Asp Ile Pro Ser Arg Phe Ser Gly Ser
65                  70                  75                  80

Ala Ser Gly Ser Thr Ala Thr Leu Thr Ile Thr Gly Val Gln Ala Glu
                85                  90                  95

Asp Gly Ala Val Tyr Phe Cys Gly Ser Glu Asp Ser Thr Tyr Val Gly
            100                 105                 110

Ile Phe Gly Ala Gly Thr Thr Leu Thr Val Leu Gly Gln Ser Ser Arg
        115                 120                 125

Ser Ser Ala Val Thr Leu Asp Glu Ser Gly Gly Gly Leu Gln Thr Pro
    130                 135                 140

Gly Arg Ala Leu Ser Leu Val Cys Lys Ala Ser Gly Phe Thr Phe Ser
145                 150                 155                 160

Ser Phe Asn Met Gly Trp Val Arg Gln Ala Pro Gly Lys Gly Leu Glu
                165                 170                 175

Tyr Val Ala Ser Ile Ser Ser Ser Gly Ser Tyr Thr Ala Tyr Gly Ser
            180                 185                 190

Ala Val Lys Gly Arg Ala Thr Ile Ser Arg Asp Asn Gly Gln Ser Thr
        195                 200                 205

Val Arg Leu Gln Leu Asn Asn Leu Gly Ala Glu Asp Thr Ala Thr Tyr
    210                 215                 220

Tyr Cys Ala Lys Ala Ala Gly Asn Ala Tyr Tyr Thr Ala Val Thr
225                 230                 235                 240

Pro Ala Phe Ala Gly Ser Ile Asp Ala Trp Gly His Gly Thr Glu Val
```

```
                    245                 250                 255
Ile Val Pro Ser Thr Ser Gly Gln Ala Gly Gln His His His His
                260                 265                 270

His Gly Ala Tyr Pro Tyr Asp Val Pro Asp Tyr Ala Ser
        275                 280                 285

<210> SEQ ID NO 75
<211> LENGTH: 289
<212> TYPE: PRT
<213> ORGANISM: Artificial Sequence
<220> FEATURE:
<223> OTHER INFORMATION: recombinant protein

<400> SEQUENCE: 75

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Glu Ile Thr Cys Ser Gly Gly Ser Ser Ser
        35                  40                  45

Asn Tyr Gly Trp His Gln Gln Lys Ser Pro Gly Ser Ala Pro Val Thr
    50                  55                  60

Val Ile Tyr Asp Asn Thr Asn Arg Pro Pro Asn Ile Pro Ser Arg Phe
65                  70                  75                  80

Ser Gly Ser Leu Ser Gly Ser Thr Gly Thr Leu Thr Ile Thr Gly Val
                85                  90                  95

Gln Ala Glu Asp Glu Ala Val Tyr Tyr Cys Gly Gly His Asp Ser Ser
            100                 105                 110

Thr Tyr Ala Gly Ile Phe Gly Ala Gly Thr Thr Leu Thr Val Leu Gly
        115                 120                 125

Gln Ser Ser Arg Ser Ser Ala Val Thr Leu Asp Glu Ser Gly Gly Gly
    130                 135                 140

Leu Gln Thr Pro Gly Arg Ala Leu Ser Leu Val Cys Lys Ala Ser Gly
145                 150                 155                 160

Phe Thr Phe Ser Ser Phe Asn Met Gly Trp Val Arg Gln Ala Pro Gly
                165                 170                 175

Lys Gly Leu Glu Tyr Val Ala Ser Ile Ser Ser Ser Gly Ser Tyr Thr
            180                 185                 190

Ala Tyr Gly Ser Ala Val Lys Gly Arg Ala Thr Ile Ser Arg Asp Asn
        195                 200                 205

Gly Gln Ser Thr Val Arg Leu Gln Leu Asn Asn Leu Arg Ala Glu Asp
    210                 215                 220

Thr Ala Thr Tyr Tyr Cys Ala Lys Ala Ala Gly Ser Ala Tyr Tyr
225                 230                 235                 240

Thr Ala Val Thr Pro Ala Phe Ala Gly Ser Ile Asp Ala Trp Gly His
                245                 250                 255

Gly Thr Glu Val Ile Val Ser Thr Ser Gly Gln Ala Gly Gln His
            260                 265                 270

His His His His Gly Ala Tyr Pro Tyr Asp Val Pro Asp Tyr Ala
        275                 280                 285

Ser

<210> SEQ ID NO 76
<211> LENGTH: 288
<212> TYPE: PRT
<213> ORGANISM: Artificial Sequence
```

<220> FEATURE:
<223> OTHER INFORMATION: recombinant protein

<400> SEQUENCE: 76

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Lys Ile Thr Cys Ser Gly Gly Ser Ser Ser
            35                  40                  45

Tyr Tyr Gly Trp Tyr Gln Gln Lys Ser Pro Asp Ser Ala Pro Val Thr
        50                  55                  60

Leu Ile Tyr Glu Ser Asn Lys Arg Pro Ser Asn Ile Pro Ser Arg Phe
65                  70                  75                  80

Ser Gly Ser Thr Ser Gly Ser Thr Ser Thr Leu Thr Ile Thr Gly Val
                85                  90                  95

Gln Ala Asp Asp Glu Ala Val Tyr Phe Cys Gly Ser Ala Asp Ser Ser
            100                 105                 110

Tyr Val Gly Ile Phe Gly Ala Gly Thr Thr Leu Thr Val Leu Gly Gln
        115                 120                 125

Ser Ser Arg Ser Ser Ala Val Thr Leu Asp Glu Ser Gly Gly Gly Leu
    130                 135                 140

Gln Thr Pro Gly Gly Ala Leu Ser Leu Val Cys Lys Ala Ser Gly Phe
145                 150                 155                 160

Thr Phe Ser Ser Phe Asn Met Gly Trp Val Arg Gln Ala Pro Gly Lys
                165                 170                 175

Gly Leu Glu Tyr Val Ala Ser Ile Ser Ser Gly Ser Tyr Thr Ala
            180                 185                 190

Tyr Gly Ser Ala Val Lys Gly Arg Ala Thr Ile Ser Arg Asp Asn Gly
        195                 200                 205

Gln Ser Thr Val Arg Leu Gln Leu Asn Asn Leu Arg Ala Glu Asp Thr
    210                 215                 220

Ala Thr Tyr Tyr Cys Ala Lys Ala Ala Gly Ser Ala Tyr Tyr Thr
225                 230                 235                 240

Ala Val Thr Pro Ala Phe Ala Gly Ser Ile Asp Ala Trp Gly His Gly
                245                 250                 255

Thr Glu Val Ile Val Ser Ser Thr Ser Gly Gln Ala Gly Gln His His
            260                 265                 270

His His His His Gly Ala Tyr Pro Tyr Asp Val Pro Asp Tyr Ala Ser
        275                 280                 285

<210> SEQ ID NO 77
<211> LENGTH: 282
<212> TYPE: PRT
<213> ORGANISM: Artificial Sequence
<220> FEATURE:
<223> OTHER INFORMATION: recombinant protein

<400> SEQUENCE: 77

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Leu Gly Glu Thr Val Lys Ile Thr Cys Ser Gly Gly Ser Tyr Ala
            35                  40                  45

Gly Cys Tyr Tyr Tyr Ser Trp Tyr Asp His Thr Ala Ala Gly Val Val

```
                50                  55                  60
Pro Val Thr Leu Ile Asp Ser Thr Ile Pro Ser Ser Tyr Phe Arg Ser
 65                  70                  75                  80

Arg Phe Cys Cys Ser Ala Ser Gly Ser Ile Asn Ala Leu Thr Ile Asn
                 85                  90                  95

Glu Asp Pro Ala Tyr Tyr Ala Val Tyr Phe Cys Gly Ser Val Asp Val
                100                 105                 110

Phe Gly Gly Val Phe Gly Ala Ser Thr Thr Leu Thr Ala Pro Gly Ser
                115                 120                 125

Ser Ser Ile Ser Ser Asp Glu Thr Leu Asp Asp Ser Gly Ser Gly Leu
                130                 135                 140

Arg Thr Pro Gly Arg Ala Leu Asn Val Phe Cys Phe Ala Ser Gly Phe
145                 150                 155                 160

Phe Phe Met Ile Phe Glu Leu Phe Gly Val Arg Gln Ala Pro Gly Trp
                165                 170                 175

Val Leu Glu Tyr Ile Ala Asp Val Ser Asp Thr Gly Asn Ser Thr Tyr
                180                 185                 190

Tyr Arg Ala Ala Val Asn Val Arg Ala Ala Ile Ser Arg Asn Asn Gly
                195                 200                 205

Gln Met Thr Leu Arg Leu Leu Leu Asn Asp His Thr Ala Asp Asp Thr
                210                 215                 220

Cys Thr Tyr Phe Cys Gly Tyr Cys His Ser Asp Tyr Cys Trp Ser Thr
225                 230                 235                 240

Ala Gly Asp Ile Asp Ala Trp Ser His Val Ile Asp Phe Ile Val Ser
                245                 250                 255

Ser Thr Ser Gly Gln Ala Gly Gln His His His His His Gly Ala
                260                 265                 270

Tyr Pro Tyr Asp Asp Pro Asp Tyr Ala Ser
                275                 280

<210> SEQ ID NO 78
<211> LENGTH: 280
<212> TYPE: PRT
<213> ORGANISM: Artificial Sequence
<220> FEATURE:
<223> OTHER INFORMATION: recombinant protein

<400> SEQUENCE: 78

Met Lys Lys Thr Ala Ile Ala Ile Ala Val Ala Leu Ala Gly Phe Ala
 1               5                  10                  15

Thr Val Ala Gln Ala Ala Leu Thr Gln Pro Ser Ser Val Ser Ala Asn
                 20                  25                  30

Pro Gly Gly Thr Val Lys Ile Thr Cys Ser Gly Ser Ser Ser Ala Tyr
                 35                  40                  45

Gly Tyr Gly Trp Tyr Gln Gln Lys Ser Pro Gly Ser Ala Pro Val Thr
 50                  55                  60

Val Ile Tyr Asn Asn Lys Arg Pro Ser Asn Ile Pro Ser Arg Phe
 65                  70                  75                  80

Ser Gly Ser Lys Ser Gly Ser Thr Gly Thr Leu Thr Ile Thr Gly Val
                 85                  90                  95

Gln Ala Glu Asp Glu Ala Val Tyr Phe Cys Gly Ser Glu Asp Ser Ser
                100                 105                 110

Thr Asp Ala Ile Phe Gly Ala Gly Thr Thr Leu Thr Val Leu Gly Gln
                115                 120                 125

Ser Ser Arg Ser Ser Thr Val Thr Leu Asp Glu Ser Gly Gly Gly Leu
```

```
            130                 135                 140
Gln Ala Pro Gly Gly Ala Leu Ser Leu Val Cys Lys Ala Ser Gly Phe
145                 150                 155                 160

Thr Phe Ser Ser Tyr Asp Met Gly Trp Ile Arg Gln Ala Pro Gly Lys
                165                 170                 175

Gly Leu Glu Tyr Val Ala Gly Ile Thr Asp Asn Gly Arg Tyr Ala Ser
            180                 185                 190

Tyr Gly Ser Ala Val Asp Gly Arg Ala Thr Ile Ser Arg Asp Asn Gly
        195                 200                 205

Gln Ser Ser Val Arg Leu Gln Leu Asn Asn Leu Arg Ala Glu Asp Thr
    210                 215                 220

Gly Thr Tyr Tyr Cys Ala Arg Asp Asp Gly Ser Gly Trp Thr Gly Asn
225                 230                 235                 240

Ser Ile Asp Ala Trp Gly His Gly Thr Glu Ile Val Ser Ser Thr
                245                 250                 255

Ser Gly Gln Ala Gly Gln His His His His His Gly Ala Tyr Pro
            260                 265                 270

Tyr Asp Val Pro Asp Tyr Ala Ser
    275                 280

<210> SEQ ID NO 79
<211> LENGTH: 262
<212> TYPE: PRT
<213> ORGANISM: Artificial Sequence
<220> FEATURE:
<223> OTHER INFORMATION: recombinant protein

<400> SEQUENCE: 79

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Leu Gly Gly Thr Val Lys Ile Thr Cys Ser Gly Ser Ser Gly Ser Tyr
        35                  40                  45

Gly Trp Tyr Gln Gln Lys Ser Pro Gly Ser Ala Pro Val Thr Val Ile
    50                  55                  60

Tyr Trp Asn Asp Lys Arg Pro Ser Asn Ile Pro Ser Arg Phe Ser Gly
65                  70                  75                  80

Ala Leu Ser Gly Ser Thr Ala Thr Leu Thr Ile Thr Gly Val Gln Ala
                85                  90                  95

Glu Asp Glu Ala Val Tyr Phe Cys Gly Ser Ala Asp Ser Ser Gly Ala
            100                 105                 110

Ile Phe Gly Ala Gly Thr Thr Leu Thr Val Leu Gly Gln Ser Ser Arg
        115                 120                 125

Ser Ser Thr Val Thr Leu Asp Glu Ser Gly Gly Gly Leu Gln Thr Pro
    130                 135                 140

Gly Gly Gly Leu Ser Leu Val Cys Lys Gly Ser Gly Phe Ala Phe Ser
145                 150                 155                 160

Asn Tyr Gly Met Gly Trp Met Arg Gln Ala Pro Gly Lys Gly Leu Glu
                165                 170                 175

Tyr Val Ala Gly Ile Ser Thr Gly Ser Tyr Thr Asp Tyr Gly Pro Ala
            180                 185                 190

Val Lys Gly Arg Ala Thr Ile Ser Arg Asp Asn Gly Gln Ser Thr Val
        195                 200                 205

Arg Leu Gln Leu Asn Asn Leu Arg Ala Glu Asp Ala Ala Ile Tyr Phe
```

```
            210                 215                 220

Cys Ala Lys Gly His Gly Thr Glu Ile Ile Val Ser Ser Thr Ser Gly
225                 230                 235                 240

Gln Ala Gly Gln His His His His His Gly Ala Tyr Pro Tyr Asp
                245                 250                 255

Val Pro Asp Tyr Ala Ser
            260

<210> SEQ ID NO 80
<211> LENGTH: 282
<212> TYPE: PRT
<213> ORGANISM: Artificial Sequence
<220> FEATURE:
<223> OTHER INFORMATION: recombinant protein

<400> SEQUENCE: 80

Met Lys Lys Thr Ala Ile Ala Ile Ala Val Ala Leu Ala Gly Phe Ala
1               5                   10                  15

Thr Val Ala Gln Ala Ala Leu Ser Arg Pro Arg Cys Gln Gln Thr Trp
            20                  25                  30

Gly Gly Thr Val Lys Ile Thr Cys Ser Gly Gly Asp Gly Ser Tyr Gly
        35                  40                  45

Trp Tyr Gln Gln Lys Ser Pro Gly Ser Ala Pro Val Thr Val Ile Tyr
    50                  55                  60

Asp Asn Thr Asn Arg Pro Ser Asp Ile Pro Ser Arg Phe Ser Gly Ser
65                  70                  75                  80

Lys Ser Gly Ser Thr Gly Thr Leu Thr Ile Thr Gly Val Gln Ala Glu
                85                  90                  95

Asp Glu Ala Val Tyr Tyr Cys Gly Asn Ala Asp Ser Ser Gly Ala Ala
            100                 105                 110

Ala Phe Gly Ala Gly Thr Thr Leu Thr Val Leu Gly Gln Ser Ser Arg
        115                 120                 125

Ser Ser Ala Val Thr Leu Asp Glu Ser Gly Gly Gly Leu Gln Thr Pro
    130                 135                 140

Gly Gly Ala Leu Ser Leu Gly Cys Glu Ala Ser Gly Phe Thr Phe Ser
145                 150                 155                 160

Ser Tyr Ala Met Gly Trp Val Arg Gln Ala Pro Gly Lys Gly Leu Glu
                165                 170                 175

Tyr Val Ala Thr Ile Ser Ser Ala Gly Ser Asn Thr Asn Tyr Gly Ala
            180                 185                 190

Ala Val Lys Gly Arg Ala Thr Ile Ser Arg Asp Asn Gly Gln Ser Thr
        195                 200                 205

Val Arg Leu Gln Leu Asn Asn Leu Glu Asp Asp Thr Ala Thr Tyr
    210                 215                 220

Phe Cys Ala Glu Ala Ala Gly Asn Gly Tyr Tyr Val Trp Ser Ala Ile
225                 230                 235                 240

Ala Gly Asp Ile Asp Ala Trp Gly His Gly Thr Asp Val Ile Val Ser
                245                 250                 255

Ser Thr Ser Gly Gln Ala Gly Gln His His His His His Gly Ala
            260                 265                 270

Tyr Pro Tyr Asp Val Pro Asp Tyr Ala Ser
        275                 280

<210> SEQ ID NO 81
<211> LENGTH: 289
<212> TYPE: PRT
```

<213> ORGANISM: Artificial Sequence
<220> FEATURE:
<223> OTHER INFORMATION: recombinant protein

<400> SEQUENCE: 81

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Lys Ile Thr Cys Ser Glu Gly Arg Ser Ser
        35                  40                  45

Tyr Tyr Gly Trp Tyr Gln Gln Lys Ala Pro Gly Ser Ala Pro Val Thr
    50                  55                  60

Val Ile Tyr Asp Ser Ser Arg Pro Ser Asp Ile Pro Ser Arg Phe
65              70                  75                  80

Ser Gly Ser Lys Ser Gly Ser Thr Gly Thr Leu Thr Ile Thr Gly Val
                85                  90                  95

Gln Ala Glu Asp Glu Ala Val Tyr Tyr Cys Gly Ser Thr Asp Ser Ser
            100                 105                 110

Thr Ser Ala Ala Ile Phe Gly Ala Gly Thr Thr Leu Thr Val Leu Gly
        115                 120                 125

Gln Ser Ser Arg Ser Ser Thr Val Thr Leu Asp Glu Ser Gly Gly Gly
130                 135                 140

Leu Gln Thr Pro Gly Arg Ala Leu Ser Leu Val Cys Lys Ala Ser Gly
145                 150                 155                 160

Phe Thr Phe Ser Ser Phe Asn Met Gly Trp Val Arg Gln Ala Pro Gly
                165                 170                 175

Lys Gly Leu Glu Tyr Val Ala Ser Ile Ser Ser Gly Ser Tyr Thr
            180                 185                 190

Ala Tyr Gly Ser Ala Val Lys Gly Arg Ala Thr Ile Ser Arg Asp Asn
        195                 200                 205

Gly Gln Ser Thr Val Arg Leu Gln Leu Asn Asn Leu Arg Ala Glu Asp
210                 215                 220

Thr Ala Thr Tyr Tyr Cys Ala Lys Ala Ala Gly Ser Ala Tyr Tyr
225                 230                 235                 240

Thr Ala Val Thr Pro Ala Phe Ala Gly Ser Ile Asp Ala Trp Gly His
                245                 250                 255

Gly Thr Glu Val Ile Val Ser Ser Thr Ser Gly Gln Ala Gly Gln His
            260                 265                 270

His His His His Gly Ala Tyr Pro Tyr Asp Val Pro Asp Tyr Ala
        275                 280                 285

Ser

<210> SEQ ID NO 82
<211> LENGTH: 279
<212> TYPE: PRT
<213> ORGANISM: Artificial Sequence
<220> FEATURE:
<223> OTHER INFORMATION: recombinant protein

<400> SEQUENCE: 82

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Glu Ile Thr Cys Ser Gly Gly Gly Gly Ser Tyr

```
            35                  40                  45
Gly Trp Phe Gln Gln Lys Ser Pro Gly Ser Ala Pro Val Thr Leu Ile
 50                  55                  60

Tyr Asn Asn Asn Arg Pro Ser Asp Ile Pro Ser Arg Phe Ser Gly
 65                  70                  75                  80

Ser Lys Ser Gly Ser Thr Gly Thr Leu Thr Ile Thr Gly Val Gln Ala
                 85                  90                  95

Glu Asp Glu Ala Val Tyr Phe Cys Gly Thr Arg Asp Ser Ser Tyr Ala
                100                 105                 110

Gly Ile Phe Gly Ala Gly Thr Thr Leu Thr Val Leu Gly Gln Ser Ser
                115                 120                 125

Arg Ser Ser Ala Val Thr Leu Asp Glu Ser Gly Gly Gly Leu Gln Thr
        130                 135                 140

Pro Gly Gly Ala Leu Ser Leu Val Cys Lys Gly Ser Gly Phe Thr Phe
145                 150                 155                 160

Ser Asp Tyr Ser Met Met Trp Val Arg Gln Ala Pro Gly Lys Gly Leu
                165                 170                 175

Glu Trp Val Ala Gly Ile Ser Ser Asn Ser Gly Thr Thr Arg Tyr Gly
                180                 185                 190

Ser Ala Val Lys Gly Arg Ala Thr Ile Ser Arg Asp Asn Gly Gln Ser
        195                 200                 205

Thr Val Arg Leu Gln Leu Asn Asn Leu Arg Ala Glu Asp Thr Gly Thr
210                 215                 220

Tyr Tyr Cys Ala Lys Thr Thr Gly Val Asn Ser Tyr Asp Val Pro Ala
225                 230                 235                 240

Ile Asp Ala Trp Gly His Gly Thr Glu Val Ile Val Ser Ser Thr Ser
                245                 250                 255

Gly Gln Ala Gly Gln His His His His His Gly Ala Tyr Pro Tyr
        260                 265                 270

Asp Val Pro Asp Tyr Ala Ser
        275

<210> SEQ ID NO 83
<211> LENGTH: 286
<212> TYPE: PRT
<213> ORGANISM: Artificial Sequence
<220> FEATURE:
<223> OTHER INFORMATION: recombinant protein

<400> SEQUENCE: 83

Met Lys Lys Thr Ala Ile Ala Ile Ala Val Ala Leu Ala Gly Phe Ala
 1               5                  10                  15

Thr Val Ala Gln Ala Ala Leu Thr Gln Pro Ser Ser Val Ser Ala Asn
                20                  25                  30

Pro Gly Asp Thr Val Glu Ile Thr Cys Ser Gly Gly Tyr Ser Asn Tyr
        35                  40                  45

Gly Trp Tyr Gln Gln Lys Ser Pro Gly Ser Ala Pro Val Thr Val Ile
 50                  55                  60

Tyr Gly Ser Thr Ser Arg Pro Ser Asp Ile Pro Ser Arg Phe Ser Gly
 65                  70                  75                  80

Ser Glu Ser Gly Ser Thr Gly Thr Leu Thr Ile Thr Gly Val Gln Ala
                 85                  90                  95

Glu Asp Glu Ala Val Tyr Phe Cys Gly Asn Ala Asp Ser Ser Tyr Val
                100                 105                 110

Gly Leu Phe Gly Ala Gly Thr Thr Leu Thr Val Leu Gly Gln Ser Ser
```

```
                115                 120                 125
Arg Ser Ser Thr Val Thr Leu Asp Glu Ser Gly Gly Gly Leu Gln Thr
130                 135                 140

Pro Gly Arg Ala Leu Ser Leu Val Cys Lys Ala Ser Gly Phe Thr Phe
145                 150                 155                 160

Ser Ser Phe Asn Met Gly Trp Val Arg Gln Ala Pro Gly Lys Gly Leu
                165                 170                 175

Glu Tyr Val Ala Ser Ile Ser Ser Gly Ser Tyr Thr Ala Tyr Gly
            180                 185                 190

Ser Ala Val Lys Gly Arg Ala Thr Ile Ser Arg Asp Asn Gly Gln Ser
        195                 200                 205

Thr Val Arg Leu Gln Leu Asn Asn Leu Arg Ala Glu Asp Thr Ala Thr
210                 215                 220

Tyr Tyr Cys Ala Lys Ala Ala Gly Ser Ala Tyr Tyr Thr Ala Ala
225                 230                 235                 240

Thr Pro Ala Phe Ala Gly Ser Ile Asp Ala Trp Gly His Gly Thr Glu
                245                 250                 255

Val Ile Val Ser Ser Thr Ser Gly Gln Ala Gly Gln His His His His
            260                 265                 270

His His Gly Ala Tyr Pro Tyr Asp Val Pro Asp Tyr Ala Ser
        275                 280                 285
```

<210> SEQ ID NO 84
<211> LENGTH: 287
<212> TYPE: PRT
<213> ORGANISM: Artificial Sequence
<220> FEATURE:
<223> OTHER INFORMATION: recombinant protein

<400> SEQUENCE: 84

```
Met Lys Lys Thr Ala Ile Ala Ile Ala Val Ala Leu Ala Gly Phe Ala
1               5                   10                  15

Thr Val Ala Gln Ala Ala Leu Val Ser Ala Asn Pro Gly Glu Thr Val
            20                  25                  30

Lys Ile Thr Cys Ser Gly Gly Gly Ser Asn Ser Ala Gly Ser Tyr Tyr
        35                  40                  45

Tyr Gly Trp Tyr Gln Gln Lys Pro Gly Ser Ala Pro Val Thr Val
50                  55                  60

Ile His Asn Asn Asn Lys Arg Pro Ser Asp Ile Pro Ser Arg Phe Ser
65                  70                  75                  80

Gly Ser Lys Ser Gly Ser Thr Gly Thr Leu Thr Ile Thr Gly Val Gln
                85                  90                  95

Val Asp Asp Glu Ala Val Tyr Tyr Cys Gly Ser Arg Asp Ser Ser Tyr
            100                 105                 110

Ile Gly Thr Phe Gly Ala Gly Thr Thr Leu Thr Val Leu Gly Gln Ser
        115                 120                 125

Ser Arg Ser Ser Ala Val Thr Leu Asp Glu Ser Gly Gly Gly Leu Gln
    130                 135                 140

Thr Pro Gly Arg Ala Leu Ser Leu Ala Cys Lys Ala Ser Gly Phe Thr
145                 150                 155                 160

Phe Ser Ser Phe Asn Met Gly Trp Val Arg Gln Ala Pro Gly Lys Gly
                165                 170                 175

Leu Glu Tyr Val Ala Ser Ile Ser Ser Gly Ser Tyr Thr Ala Tyr
            180                 185                 190

Gly Ser Ala Val Lys Gly Arg Ala Thr Ile Ser Arg Asp Asn Gly Gln
        195                 200                 205
```

```
                195                 200                 205
Ser Thr Val Arg Leu Gln Leu Asn Asn Leu Arg Ala Glu Asp Thr Ala
    210                 215                 220

Thr Tyr Tyr Cys Ala Lys Ala Ala Gly Ser Ala Tyr Tyr Tyr Thr Ala
225                 230                 235                 240

Val Thr Pro Ala Phe Ala Gly Ser Ile Asp Ala Trp Gly His Gly Thr
                245                 250                 255

Glu Val Ile Val Ser Ser Thr Ser Gly Gln Ala Gly Gln His His His
            260                 265                 270

His His His Gly Ala Tyr Pro Tyr Asp Val Pro Asp Tyr Ala Ser
        275                 280                 285

<210> SEQ ID NO 85
<211> LENGTH: 288
<212> TYPE: PRT
<213> ORGANISM: Artificial Sequence
<220> FEATURE:
<223> OTHER INFORMATION: recombinant protein

<400> SEQUENCE: 85

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Asp Pro Val Glu Ile Thr Cys Ser Gly Ser Ser Gly Ser Tyr
        35                  40                  45

Gly Trp Tyr Gln Gln Lys Ala Pro Ser Ser Ala Pro Val Thr Val Ile
    50                  55                  60

Tyr Ser Asn Asp Lys Arg Pro Ser Asp Ile Pro Ser Arg Phe Ser Gly
65                  70                  75                  80

Ser Ala Ser Gly Ser Thr Ala Thr Leu Thr Ile Thr Gly Val Gln Ala
                85                  90                  95

Glu Asp Glu Ala Val Tyr Phe Cys Gly Ser Phe Asp Ser Ser Ala Gly
            100                 105                 110

Tyr Gly Gly Ile Phe Gly Ala Gly Thr Thr Leu Thr Val Leu Gly Gln
        115                 120                 125

Ser Ser Arg Ser Ser Thr Val Thr Leu Asp Glu Ser Gly Gly Gly Leu
    130                 135                 140

Gln Thr Pro Gly Arg Ala Leu Ser Leu Val Cys Lys Ala Ser Gly Phe
145                 150                 155                 160

Thr Phe Ser Ser Phe Asn Met Gly Trp Val Arg Gln Ala Pro Gly Lys
                165                 170                 175

Gly Leu Glu Tyr Val Ala Ser Ile Ser Ser Ser Gly Ser Tyr Thr Ala
            180                 185                 190

Tyr Gly Ser Ala Val Lys Gly Arg Ala Thr Ile Ser Arg Asp Asn Gly
        195                 200                 205

Gln Ser Thr Val Arg Leu Gln Leu Asn Asn Leu Arg Ala Glu Asp Thr
    210                 215                 220

Ala Thr Tyr Tyr Cys Ala Lys Ala Ala Gly Ser Ala Tyr Tyr Tyr Thr
225                 230                 235                 240

Ala Val Thr Pro Ala Phe Ala Gly Ser Ile Asp Ala Trp Gly His Gly
                245                 250                 255

Thr Glu Val Ile Val Ser Ser Thr Ser Gly Gln Ala Gly Gln His His
            260                 265                 270

His His His His Gly Ala Tyr Pro Tyr Asp Val Pro Asp Tyr Ala Ser
```

275             280             285

<210> SEQ ID NO 86
<211> LENGTH: 276
<212> TYPE: PRT
<213> ORGANISM: Artificial Sequence
<220> FEATURE:
<223> OTHER INFORMATION: recombinant protein

<400> SEQUENCE: 86

Met Lys Lys Thr Ala Ile Ala Ile Ala Val Ala Leu Ala Gly Phe Ala
1               5                   10                  15

Thr Val Ala Gln Ala Ala Leu Val Ser Ala Asn Pro Gly Glu Ile Val
            20                  25                  30

Lys Ile Thr Cys Ser Gly Asn Ser Ser Tyr Tyr Gly Trp Tyr Gln Gln
        35                  40                  45

Lys Ala Pro Gly Ser Ala Pro Val Thr Val Ile Tyr Asp Asn Asn Lys
    50                  55                  60

Arg Pro Ser Asp Ile Pro Ser Arg Phe Ser Gly Ser Lys Ser Gly Ser
65                  70                  75                  80

Thr Gly Thr Leu Thr Ile Thr Gly Val Gln Ala Glu Asp Glu Ala Val
                85                  90                  95

Tyr Phe Cys Gly Asn Gly Ala Thr Phe Gly Ala Gly Thr Thr Leu Thr
            100                 105                 110

Val Leu Gly Gln Ser Ser Arg Ser Ser Thr Val Thr Leu Asp Glu Ser
        115                 120                 125

Gly Gly Gly Leu Gln Thr Pro Gly Arg Ala Leu Ser Leu Val Cys Lys
    130                 135                 140

Ala Ser Gly Phe Thr Phe Ser Ser Phe Asn Met Gly Trp Val Arg Gln
145                 150                 155                 160

Ala Pro Gly Lys Gly Leu Glu Tyr Val Ala Ser Ile Ser Ser Ser Gly
                165                 170                 175

Ser Tyr Thr Ala Tyr Gly Ser Ala Val Lys Gly Arg Ala Thr Ile Ser
            180                 185                 190

Arg Asp Asn Gly Gln Ser Thr Val Arg Leu Gln Leu Asn Asn Leu Arg
        195                 200                 205

Ala Glu Asp Thr Ala Thr Tyr Tyr Cys Ala Lys Ala Ala Gly Ser Ala
    210                 215                 220

Tyr Tyr Tyr Thr Ala Val Thr Pro Ala Phe Ala Gly Ser Ile Asp Ala
225                 230                 235                 240

Trp Gly His Gly Thr Glu Val Ile Val Ser Ser Thr Ser Gly Gln Ala
                245                 250                 255

Gly Gln His His His His His His Gly Ala Tyr Pro Tyr Asp Val Pro
            260                 265                 270

Asp Tyr Ala Ser
    275

<210> SEQ ID NO 87
<211> LENGTH: 282
<212> TYPE: PRT
<213> ORGANISM: Artificial Sequence
<220> FEATURE:
<223> OTHER INFORMATION: recombinant protein

<400> SEQUENCE: 87

Met Lys Lys Thr Ala Ile Ala Ile Ala Val Ala Leu Ala Gly Phe Ala
1               5                   10                  15

```
Thr Val Ala Gln Ala Ala Leu Thr Gln Pro Ser Ser Val Ser Ala Asn
            20                  25                  30

Pro Gly Glu Thr Val Lys Ile Thr Cys Ser Gly Gly Ser Tyr Ser Tyr
        35                  40                  45

Gly Trp Tyr Gln Gln Lys Ser Pro Gly Ser Ala Pro Val Thr Val Ile
    50                  55                  60

Tyr Ser Ser Asp Lys Arg Pro Ser Asp Ile Pro Ser Arg Phe Ser Gly
65                  70                  75                  80

Ser Lys Ser Gly Ser Thr Ser Thr Leu Thr Ile Thr Gly Val Gln Ala
                85                  90                  95

Glu Asp Glu Ala Val Tyr Tyr Cys Gly Ser Arg Asp Ser Ser Tyr Val
            100                 105                 110

Gly Ile Phe Gly Ala Gly Thr Thr Leu Thr Val Leu Gly Gln Ser Ser
        115                 120                 125

Arg Ser Ser Thr Val Thr Leu Asp Glu Ser Gly Gly Gly Leu Gln Thr
    130                 135                 140

Pro Gly Gly Ala Leu Ser Leu Val Cys Glu Ala Ser Gly Phe Thr Phe
145                 150                 155                 160

Ser Ser Tyr Glu Met Gln Trp Val Arg Gln Ala Pro Gly Lys Gly Leu
                165                 170                 175

Glu Phe Val Ala Ala Ile Ser Ser Asp Gly Ser Tyr Thr Asn Tyr Gly
            180                 185                 190

Ala Ala Val Gln Gly Arg Ala Thr Ile Ser Arg Asp Asn Gly Gln Ser
        195                 200                 205

Thr Val Arg Leu Gln Leu Ser Asn Leu Arg Ala Glu Asp Thr Ala Thr
    210                 215                 220

Tyr Tyr Cys Ala Arg Ser Pro Gly Gly Tyr Thr Trp Trp Pro Gly Ala
225                 230                 235                 240

Ala Gly Gly Ile Asp Ala Trp Gly His Gly Thr Glu Val Ile Val Ser
                245                 250                 255

Ser Thr Ser Gly Gln Ala Gly Gln His His His His His Gly Ala
            260                 265                 270

Tyr Pro Tyr Asp Val Pro Asp Tyr Ala Ser
            275                 280

<210> SEQ ID NO 88
<211> LENGTH: 273
<212> TYPE: PRT
<213> ORGANISM: Artificial Sequence
<220> FEATURE:
<223> OTHER INFORMATION: recombinant protein

<400> SEQUENCE: 88

Met Lys Lys Thr Ala Ile Ala Ile Ala Val Ala Leu Ala Gly Phe Ala
1               5                   10                  15

Thr Val Ala Gln Ala Ala Leu Val Ser Ala Asn Leu Gly Gly Thr Val
            20                  25                  30

Glu Ile Thr Cys Ser Gly Ser Ser Gly Asn Tyr Gly Trp Phe Gln Gln
        35                  40                  45

Lys Ser Pro Gly Ser Ala Pro Val Thr Val Ile Tyr Ser Asn Asp Lys
    50                  55                  60

Arg Pro Ser Asp Ile Pro Ser Arg Phe Ser Gly Ser Leu Ser Gly Ser
65                  70                  75                  80

Thr Gly Thr Leu Thr Ile Thr Gly Val Arg Ala Glu Asp Glu Ala Val
                85                  90                  95
```

Tyr Tyr Cys Gly Ser Ile Asp Asn Thr Tyr Val Gly Thr Gly Ala Phe
            100                 105                 110

Gly Ala Gly Thr Thr Leu Thr Val Leu Gly Gln Ser Ser Arg Ser Ser
        115                 120                 125

Thr Val Thr Leu Asp Glu Ser Gly Gly Gly Leu Gln Thr Pro Gly Arg
    130                 135                 140

Ala Leu Ser Leu Val Cys Lys Gly Ser Gly Phe Thr Phe Ser Ser Phe
145                 150                 155                 160

Tyr Met Phe Trp Val Arg Gln Ala Pro Gly Lys Gly Leu Glu Phe Val
                165                 170                 175

Ala Ser Ile Ser Ser Ser Gly Ser Ser Thr Arg Tyr Gly Val Val Val
            180                 185                 190

Lys Gly Arg Ala Thr Ile Ser Arg Asp Asn Gly Gln Ser Thr Val Arg
        195                 200                 205

Leu Arg Leu Asn Asn Leu Arg Ala Glu Asp Thr Gly Thr Tyr Tyr Cys
    210                 215                 220

Ala Arg Gly Thr Ser Ser Gly Ala Asn Thr Ile Asp Ala Trp Gly His
225                 230                 235                 240

Gly Thr Glu Val Ile Val Ser Ser Thr Ser Gly Gln Ala Gly Gln His
                245                 250                 255

His His His His Gly Ala Tyr Pro Tyr Asp Val Pro Asp Tyr Ala
            260                 265                 270

Ser

<210> SEQ ID NO 89
<211> LENGTH: 288
<212> TYPE: PRT
<213> ORGANISM: Artificial Sequence
<220> FEATURE:
<223> OTHER INFORMATION: recombinant protein

<400> SEQUENCE: 89

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Lys Ile Thr Cys Ser Gly Gly Gly Ser Ser Ser
        35                  40                  45

Tyr Tyr Gly Trp Tyr Gln Gln Lys Ser Pro Gly Ser Ala Pro Val Thr
    50                  55                  60

Leu Ile Tyr Glu Ser Asn Lys Arg Pro Ser Gly Ile Pro Ser Arg Phe
65                  70                  75                  80

Ser Gly Ser Lys Ser Gly Ser Thr His Thr Leu Thr Ile Thr Gly Val
                85                  90                  95

Gln Ala Glu Asp Glu Ala Val Tyr Tyr Cys Gly Ala Tyr Asp Gly Ser
            100                 105                 110

Ser Tyr Thr Gly Ile Phe Gly Ala Gly Thr Thr Leu Thr Val Leu Gly
        115                 120                 125

Gln Ser Ser Arg Ser Ser Thr Val Thr Leu Asp Glu Ser Gly Gly Gly
    130                 135                 140

Leu Gln Thr Pro Gly Arg Ala Leu Ser Leu Val Cys Lys Ala Ser Gly
145                 150                 155                 160

Phe Thr Phe Ser Ser Phe Asn Met Gly Trp Val Arg Gln Ala Pro Gly
                165                 170                 175

Lys Gly Leu Glu Tyr Val Ala Ser Ile Ser Ser Ser Gly Ser Tyr Thr

```
                180                 185                 190
Ala Tyr Gly Ser Ala Val Lys Gly Arg Ala Thr Ile Ser Arg Asp Asn
                195                 200                 205

Gly Gln Ser Thr Val Arg Leu Gln Leu Asn Asn Leu Arg Ala Glu Asp
            210                 215                 220

Thr Ala Thr Tyr Tyr Cys Ala Lys Ala Ala Gly Ser Ala Tyr Tyr Tyr
225                 230                 235                 240

Thr Ala Val Thr Pro Ala Phe Ala Gly Ser Ile Asp Ala Trp Gly His
                245                 250                 255

Gly Thr Glu Val Ile Val Ser Ser Thr Ser Gly Gln Ala Gly Gln His
            260                 265                 270

His His His His His Gly Ala Tyr Pro Tyr Asp Val Pro Asp Tyr Ala
        275                 280                 285

<210> SEQ ID NO 90
<211> LENGTH: 280
<212> TYPE: PRT
<213> ORGANISM: Artificial Sequence
<220> FEATURE:
<223> OTHER INFORMATION: recombinant protein

<400> SEQUENCE: 90

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Ala Phe Asn Lys Ile Thr Cys Ser Gly Ser Ser Ser Ala Tyr
        35                  40                  45

Gly Tyr Gly Trp Asn Gln Gln Lys Ser Pro Gly Ser Ala Pro Val Thr
    50                  55                  60

Val Ile Tyr Asn Asn Asn Lys Arg Pro Ser Asn Ile Pro Ser Arg Phe
65                  70                  75                  80

Ser Gly Ser Lys Ser Gly Ser Thr Gly Thr Leu Thr Ile Thr Gly Asp
                85                  90                  95

Gln Asp Glu Asp Glu Asp Phe Tyr Phe Cys Gly Ser Glu Tyr Ser Ser
            100                 105                 110

Thr Asp Ala Ile Phe Gly Ala Gly Thr Thr Leu Thr Val Leu Cys Gln
        115                 120                 125

Ser Ser Thr Ser Ser Thr Val Thr Leu Asp Glu Ser Gly Gly Gly Leu
    130                 135                 140

Gln Ala Pro Gly Gly Ala Leu Ser Leu Val Cys Lys Ala Ser Gly Phe
145                 150                 155                 160

Thr Phe Ser Ser Tyr Asp Met Gly Trp Ile Pro Gln Ala Pro Gly Lys
                165                 170                 175

Gly Leu Glu Tyr Val Ala Gly Ile Thr Asp Asn Gly Ile Tyr Ala Ser
            180                 185                 190

Tyr Gly Ser Ala Val Asp Gly Arg Ala Thr Ile Ser Arg Asp Asn Arg
        195                 200                 205

Gln Ser Ser Val Lys Leu Gln Leu Asn Asn Leu Lys Ala Asp Asp Thr
    210                 215                 220

Gly Thr Tyr Tyr Cys Ala Arg Asp Asp Gly Ser Gly Trp Thr Gly Asn
225                 230                 235                 240

Ser Ile Asp Ala Trp Gly His Gly Thr Glu Val Ile Val Ser Ser Thr
                245                 250                 255

Ser Gly Gln Ala Gly Gln His His His His His His Gly Ala Tyr Pro
```

260                 265                 270
Tyr Asp Val Pro Asp Tyr Ala Ser
            275                 280

<210> SEQ ID NO 91
<211> LENGTH: 288
<212> TYPE: PRT
<213> ORGANISM: Artificial Sequence
<220> FEATURE:
<223> OTHER INFORMATION: recombinant protein

<400> SEQUENCE: 91

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Asp Thr Val Lys Ile Thr Cys Ser Gly Gly Gly Ser Ser Ser
        35                  40                  45

Tyr Tyr Gly Trp Tyr Gln Gln Arg Ser Pro Gly Ser Ala Pro Val Thr
    50                  55                  60

Leu Ile Tyr Ser Asn Asp Lys Arg Pro Ser Asp Ile Pro Pro Arg Phe
65                  70                  75                  80

Ser Gly Ser Leu Ser Gly Ser Thr Ala Thr Leu Thr Ile Thr Gly Val
                85                  90                  95

Gln Ala Asp Asp Glu Ala Val Tyr Tyr Cys Gly Gly Tyr Asp Ser Ser
            100                 105                 110

Tyr Val Gly Leu Phe Gly Ala Gly Thr Thr Leu Thr Val Leu Gly Gln
        115                 120                 125

Ser Ser Arg Ser Ser Thr Val Thr Leu Asp Glu Ser Gly Gly Gly Leu
    130                 135                 140

Gln Thr Pro Gly Arg Ala Leu Ser Leu Val Cys Lys Ala Ser Gly Phe
145                 150                 155                 160

Thr Phe Ser Ser Phe Asn Met Gly Trp Val Arg Gln Ala Pro Gly Lys
                165                 170                 175

Gly Leu Glu Tyr Val Ala Ser Ile Ser Ser Ser Gly Ser Tyr Thr Ala
            180                 185                 190

Tyr Gly Ser Ala Val Lys Gly Arg Ala Thr Ile Ser Arg Asp Asn Gly
        195                 200                 205

Gln Ser Thr Val Arg Leu Gln Leu Asn Asn Leu Arg Ala Glu Asp Thr
    210                 215                 220

Ala Thr Tyr Tyr Cys Ala Lys Ala Ala Gly Ser Ala Tyr Tyr Tyr Thr
225                 230                 235                 240

Ala Val Thr Pro Ala Phe Ala Gly Ser Ile Asp Ala Trp Gly His Gly
                245                 250                 255

Thr Glu Val Ile Val Ser Ser Thr Ser Gly Gln Ala Gly Gln His His
            260                 265                 270

His His His His Gly Ala Tyr Pro Tyr Asp Val Pro Asp Tyr Ala Ser
        275                 280                 285

<210> SEQ ID NO 92
<211> LENGTH: 291
<212> TYPE: PRT
<213> ORGANISM: Artificial Sequence
<220> FEATURE:
<223> OTHER INFORMATION: recombinant protein

<400> SEQUENCE: 92

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Ile Phe Lys Ile Thr Cys Ser Gly Gly Gly Ser Tyr Ala
            35                  40                  45

Gly Ser Tyr Tyr Tyr Gly Trp Tyr Gln Gln Lys Ala Pro Gly Ser Ala
        50                  55                  60

Pro Val Thr Val Ile Tyr Asp Asn Thr Asn Arg Pro Ser Asn Ile Pro
65                  70                  75                  80

Ser Arg Phe Ser Gly Ser Lys Ser Gly Ser Thr Ala Thr Leu Thr Ile
                85                  90                  95

Thr Gly Val Arg Ala Asp Asp Ser Ala Val Tyr Tyr Cys Ala Ser Thr
            100                 105                 110

Asp Ser Ser Ser Thr Gly Ile Phe Gly Ala Gly Thr Thr Leu Thr Val
            115                 120                 125

Leu Gly Gln Ser Ser Arg Ser Ser Ala Val Thr Leu Asp Glu Ser Gly
        130                 135                 140

Gly Gly Leu Gln Thr Pro Gly Arg Ala Leu Ser Leu Val Cys Lys Ala
145                 150                 155                 160

Ser Gly Phe Thr Phe Ser Ser Phe Asn Met Gly Trp Val Arg Gln Ala
                165                 170                 175

Pro Gly Lys Gly Leu Glu Tyr Val Ala Ser Ile Ser Ser Ser Gly Ser
            180                 185                 190

Tyr Thr Ala Tyr Gly Ser Ala Val Lys Gly Arg Ala Thr Ile Ser Arg
        195                 200                 205

Asp Asn Gly Gln Ser Thr Val Arg Leu Gln Leu Asn Asn Leu Arg Ala
210                 215                 220

Glu Asp Thr Ala Thr Tyr Tyr Cys Ala Lys Ala Ala Gly Ser Ala Tyr
225                 230                 235                 240

Tyr Tyr Thr Ala Val Thr Pro Ala Phe Ala Gly Ser Ile Asp Ala Trp
            245                 250                 255

Gly His Gly Thr Glu Val Ile Val Ser Ser Thr Ser Gly Gln Ala Gly
            260                 265                 270

Gln His His His His His His Gly Ala Tyr Pro Tyr Asp Val Pro Asp
        275                 280                 285

Tyr Ala Ser
    290

<210> SEQ ID NO 93
<211> LENGTH: 289
<212> TYPE: PRT
<213> ORGANISM: Artificial Sequence
<220> FEATURE:
<223> OTHER INFORMATION: recombinant protein

<400> SEQUENCE: 93

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Ala Ile Val Lys Ile Thr Cys Ser Glu Gly Gly Arg Ser Ser
            35                  40                  45

Tyr Tyr Gly Trp Tyr Gln Gln Lys Ala Pro Gly Ser Ala Pro Val Thr
        50                  55                  60

```
Val Ile Tyr Asp Ser Ser Arg Pro Ser Asp Ile Pro Ser Arg Phe
 65                  70                  75                  80

Ser Gly Ser Lys Ser Gly Ser Thr Gly Thr Leu Thr Ile Thr Gly Val
                 85                  90                  95

Gln Ala Glu Asp Glu Ala Val Tyr Tyr Cys Gly Ser Thr Asp Ser Ser
            100                 105                 110

Thr Ser Ala Ala Ile Phe Gly Ala Gly Thr Thr Leu Thr Val Leu Gly
        115                 120                 125

Gln Ser Ser Arg Ser Ser Thr Val Thr Leu Asp Glu Ser Gly Gly Gly
    130                 135                 140

Leu Gln Thr Pro Gly Arg Ala Leu Ser Leu Val Cys Lys Ala Ser Gly
145                 150                 155                 160

Phe Thr Phe Ser Ser Phe Asn Met Gly Trp Val Arg Gln Ala Pro Gly
                165                 170                 175

Lys Gly Leu Glu Tyr Val Ala Ser Ile Ser Ser Ser Gly Ser Tyr Thr
            180                 185                 190

Ala Tyr Gly Ser Ala Val Lys Gly Arg Ala Thr Ile Ser Arg Asp Asn
        195                 200                 205

Gly Gln Ser Thr Val Arg Leu Gln Leu Asn Asn Leu Arg Ala Glu Asp
    210                 215                 220

Thr Ala Thr Tyr Tyr Cys Ala Lys Ala Ala Gly Ser Ala Tyr Tyr Tyr
225                 230                 235                 240

Thr Ala Val Thr Pro Ala Phe Ala Gly Ser Ile Asp Ala Trp Gly His
                245                 250                 255

Gly Thr Glu Val Ile Val Ser Ser Thr Ser Gly Gln Ala Gly Gln His
            260                 265                 270

His His His His His Gly Ala Tyr Pro Tyr Asp Val Pro Asp Tyr Ala
        275                 280                 285

Ser

<210> SEQ ID NO 94
<211> LENGTH: 283
<212> TYPE: PRT
<213> ORGANISM: Artificial Sequence
<220> FEATURE:
<223> OTHER INFORMATION: recombinant protein

<400> SEQUENCE: 94

Met Lys Lys Thr Ala Ile Ala Ile Ala Val Ala Leu Ala Gly Phe Ala
  1               5                  10                  15

Thr Val Ala Gln Ala Ala Leu Thr Gln Pro Ser Ser Val Ser Ala Asn
             20                  25                  30

Pro Gly Glu Thr Val Lys Ile Thr Cys Ser Gly Gly Gly Ser Tyr Ala
         35                  40                  45

Gly Ser Tyr Tyr Tyr Gly Trp Tyr Gln Gln Lys Ala Pro Gly Ser Ala
     50                  55                  60

Pro Val Thr Leu Ile Tyr Asp Asn Thr Asn Arg Pro Ser Asn Ile Pro
 65                  70                  75                  80

Ser Arg Phe Ser Gly Ser Leu Ser Gly Ser Thr Gly Thr Leu Thr Ile
                 85                  90                  95

Thr Gly Val Arg Ala Glu Asp Glu Ala Val Tyr Tyr Cys Gly Ser Phe
            100                 105                 110

Asp Ser Ser Thr Asp Gly Gly Tyr Ala Ala Ile Phe Gly Ala Gly Thr
        115                 120                 125

Thr Leu Thr Val Leu Gly Gln Ser Ser Arg Ser Ser Ala Val Thr Leu
```

```
                130                 135                 140
Asp Glu Ser Gly Gly Gly Leu Gln Thr Pro Gly Gly Leu Ser Leu
145                 150                 155                 160

Val Cys Lys Ala Ser Glu Phe Thr Phe Ser Ser Tyr Ala Met Glu Trp
                165                 170                 175

Val Arg Gln Ala Pro Gly Lys Gly Leu Glu Trp Val Ala Tyr Ile Asn
                180                 185                 190

Ser Asp Gly Ser Ser Thr Trp Tyr Ala Pro Ala Val Lys Gly Arg Ala
                195                 200                 205

Thr Ile Ser Arg Asp Asn Gly Gln Ser Thr Val Arg Leu Gln Leu Asn
210                 215                 220

Ser Leu Arg Ala Glu Asp Thr Ala Thr Tyr Tyr Cys Thr Arg Gly Ser
225                 230                 235                 240

Gly Gly Glu Asn Ile Asp Thr Trp Gly His Gly Thr Glu Val Ile Val
                245                 250                 255

Ser Ser Thr Ser Gly Gln Ala Gly Gln His His His His His His Gly
                260                 265                 270

Ala Tyr Pro Tyr Asp Val Pro Asp Tyr Ala Ser
                275                 280

<210> SEQ ID NO 95
<211> LENGTH: 280
<212> TYPE: PRT
<213> ORGANISM: Artificial Sequence
<220> FEATURE:
<223> OTHER INFORMATION: recombinant protein

<400> SEQUENCE: 95

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
                20                  25                  30

Pro Gly Gly Thr Val Lys Ile Thr Cys Ser Gly Ser Ser Ser Ala Tyr
                35                  40                  45

Gly Tyr Gly Trp Tyr Gln Gln Lys Ser Pro Gly Ser Ala Pro Val Thr
50                  55                  60

Val Ile Tyr Asn Asn Asn Lys Arg Pro Ser Asn Ile Pro Ser Arg Phe
65                  70                  75                  80

Ser Gly Ser Lys Ser Gly Ser Thr Gly Thr Leu Thr Ile Thr Gly Val
                85                  90                  95

Gln Ala Glu Asp Glu Ala Val Tyr Phe Cys Gly Ser Glu Asp Ser Ser
                100                 105                 110

Thr Asp Ala Ile Phe Gly Ala Gly Thr Thr Leu Thr Val Leu Gly Gln
                115                 120                 125

Ser Ser Arg Ser Ser Ala Val Thr Leu Asp Glu Ser Gly Gly Gly Leu
                130                 135                 140

Gln Thr Pro Gly Gly Ala Leu Ser Leu Val Cys Lys Ala Ser Gly Phe
145                 150                 155                 160

Thr Phe Ser Ser Tyr Asp Met Gly Trp Val Arg Gln Ala Pro Gly Lys
                165                 170                 175

Gly Leu Glu Tyr Val Ala Gly Ile Thr Asn Asp Gly Arg Tyr Ala Ser
                180                 185                 190

Tyr Gly Ser Ala Val Asp Gly Arg Ala Thr Ile Ser Arg Asp Asn Gly
                195                 200                 205

Gln Ser Thr Val Arg Leu Gln Leu Asn Asn Leu Arg Ala Glu Asp Thr
```

```
            210                 215                 220
Gly Thr Tyr Tyr Cys Ala Arg Asp Asp Gly Ser Gly Trp Thr Gly Asn
225                 230                 235                 240

Thr Ile Asp Thr Trp Gly His Gly Thr Glu Val Ile Val Ser Ser Thr
                245                 250                 255

Ser Gly Gln Ala Gly Gln His His His His His His Gly Ala Tyr Pro
            260                 265                 270

Tyr Asp Val Pro Asp Tyr Ala Ser
        275                 280

<210> SEQ ID NO 96
<211> LENGTH: 199
<212> TYPE: PRT
<213> ORGANISM: Artificial Sequence
<220> FEATURE:
<223> OTHER INFORMATION: recombinant protein

<400> SEQUENCE: 96

Ser Asn Asn Tyr Gly Trp His Gln Gln Lys Ala Pro Gly Ser Ala Pro
1               5                   10                  15

Val Thr Val Ile Tyr Asp Asn Thr Asn Arg Pro Ser Asn Ile Pro Ser
            20                  25                  30

Arg Phe Ser Gly Ser Lys Ser Ser Thr His Thr Leu Thr Ile Thr
        35                  40                  45

Gly Val Gln Ala Glu Asp Glu Ala Val Tyr Tyr Cys Glu Ser Ala Asp
    50                  55                  60

Ser Ser Ser Ser Ile Phe Gly Ala Gly Thr Thr Leu Thr Val Leu Gly
65                  70                  75                  80

Gln Ser Ser Arg Ser Ser Ala Val Thr Leu Asp Glu Ser Gly Gly Gly
            85                  90                  95

Leu Gln Thr Pro Gly Gly Thr Leu Ser Leu Val Cys Lys Ala Ser Gly
        100                 105                 110

Phe Thr Phe Ser Ser Phe Asn Met Phe Trp Val Arg Gln Ala Pro Gly
    115                 120                 125

Lys Gly Leu Glu Phe Val Ala Gly Ile Gly Asn Thr Gly Arg Ser Thr
130                 135                 140

Gly Tyr Gly Ser Ala Val Lys Gly Arg Ala Thr Ile Ser Arg Asp Asn
145                 150                 155                 160

Gly Gln Ser Thr Val Arg Leu Gln Leu Asn Asn Leu Arg Ala Glu Asp
            165                 170                 175

Thr Gly Thr Tyr Tyr Cys Ala Gln Ala Tyr Gly Asp Ser Asn Ile Asp
        180                 185                 190

Arg Met Gly Pro Arg Asp Arg
        195

<210> SEQ ID NO 97
<211> LENGTH: 280
<212> TYPE: PRT
<213> ORGANISM: Artificial Sequence
<220> FEATURE:
<223> OTHER INFORMATION: recombinant protein

<400> SEQUENCE: 97

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30
```

Pro Gly Asp Pro Leu Lys Ile Thr Cys Ser Gly Asp Ser Ser Gly Tyr
            35                  40                  45

Gly Tyr Gly Trp Tyr Gln Gln Lys Ser Pro Gly Ser Ala Pro Val Thr
 50                  55                  60

Val Ile Tyr Asn Asn Asn Lys Arg Pro Ser Asp Ile Pro Ser Arg Phe
65                  70                  75                  80

Ser Gly Ser Lys Ser Gly Ser Thr Gly Thr Leu Thr Ile Thr Gly Val
                85                  90                  95

Gln Ala Glu Asp Glu Ala Val Tyr Phe Cys Gly Ser Glu Asp Ser Asn
            100                 105                 110

Thr Asp Ala Val Phe Gly Ala Gly Thr Thr Leu Thr Val Leu Gly Gln
            115                 120                 125

Ser Ser Arg Ser Ser Thr Val Thr Leu Asp Glu Ser Gly Gly Gly Leu
130                 135                 140

Gln Thr Pro Gly Gly Thr Leu Ser Leu Ala Cys Lys Ala Ser Gly Phe
145                 150                 155                 160

Thr Phe Ser Gly Tyr Asp Met Gly Trp Val Arg Gln Ala Pro Gly Lys
                165                 170                 175

Gly Leu Glu Tyr Val Ala Gly Ile Thr Ser Asp Gly Arg Tyr Ala Ser
            180                 185                 190

Tyr Gly Ser Ala Val Asp Gly Arg Ala Ala Ile Trp Arg Asp Asn Gly
195                 200                 205

Gln Ser Thr Val Arg Leu Gln Leu Lys Asn Leu Arg Thr Glu Asp Thr
            210                 215                 220

Ala Thr Tyr Tyr Cys Ala Arg Asn Asp Gly Ser Gly Trp Asn Gly Asn
225                 230                 235                 240

Asn Ile Asp Ala Trp Gly His Gly Thr Glu Val Ile Val Ser Ser Thr
                245                 250                 255

Ser Gly Gln Ala Gly Gln His His His His His Gly Ala Tyr Pro
            260                 265                 270

Tyr Asp Val Pro Asp Tyr Ala Ser
            275                 280

<210> SEQ ID NO 98
<211> LENGTH: 275
<212> TYPE: PRT
<213> ORGANISM: Artificial Sequence
<220> FEATURE:
<223> OTHER INFORMATION: recombinant protein

<400> SEQUENCE: 98

Met Lys Lys Thr Ala Ile Ala Ile Ala Val Ala Leu Ala Gly Phe Ala
1               5                   10                  15

Thr Val Ala Gln Ala Ala Leu Ser Arg Pro Arg Cys Gln Gln Thr Trp
            20                  25                  30

Gly Gly Thr Val Lys Ile Thr Cys Ser Gly Ser Ser Gly Ser Tyr Gly
            35                  40                  45

Trp Tyr Gln Gln Lys Ser Pro Gly Ser Ala Pro Val Thr Leu Ile Tyr
 50                  55                  60

Glu Ser Asp Lys Arg Pro Ser Asp Ile Pro Ser Arg Phe Ser Gly Ser
65                  70                  75                  80

Lys Ser Gly Ser Thr Gly Thr Leu Thr Ile Thr Gly Val Gln Ala Asp
                85                  90                  95

Asp Glu Ala Val Tyr Phe Cys Gly Gly Tyr Asp Ser Ser Ala Gly Ile
            100                 105                 110

Phe Gly Ala Gly Thr Thr Leu Thr Val Leu Gly Gln Ser Ser Arg Ser
            115                 120                 125

Ser Ala Val Thr Leu Asp Glu Ser Gly Gly Leu Gln Thr Pro Gly
    130                 135                 140

Gly Ala Leu Ser Leu Val Cys Lys Ala Ser Gly Phe Asp Phe Ser Ser
145                 150                 155                 160

Tyr Gly Met Gly Trp Met Arg Gln Ala Pro Gly Lys Gly Leu Glu Phe
                165                 170                 175

Val Ala Ala Ile Arg Lys Asp Gly Ser Tyr Thr Ala Tyr Gly Ala Ala
                180                 185                 190

Val Asp Gly Arg Ala Thr Ile Ser Arg Asp Asp Gly Gln Ser Thr Val
                195                 200                 205

Arg Leu Gln Leu Gly Asn Leu Arg Ala Glu Asp Thr Ala Thr Tyr Phe
            210                 215                 220

Cys Ala Lys Thr Asn Ser Tyr Asn Ser Ala Gly Ile Ile Asp Ala Trp
225                 230                 235                 240

Gly His Gly Thr Glu Val Ile Val Ser Thr Ser Gly Gln Ala Gly
                245                 250                 255

Gln His His His His His Gly Ala Tyr Pro Tyr Asp Val Pro Asp
            260                 265                 270

Tyr Ala Ser
        275

<210> SEQ ID NO 99
<211> LENGTH: 275
<212> TYPE: PRT
<213> ORGANISM: Artificial Sequence
<220> FEATURE:
<223> OTHER INFORMATION: recombinant protein

<400> SEQUENCE: 99

Met Lys Lys Thr Ala Ile Ala Ile Ala Val Ala Leu Ala Gly Phe Ala
1               5                   10                  15

Thr Val Ala Gln Ala Ala Leu Ser Arg Pro Arg Cys Gln Gln Thr Trp
            20                  25                  30

Gly Gly Thr Val Glu Ile Thr Cys Ser Gly Ser Ser Gly Asp Tyr Gly
            35                  40                  45

Tyr Ser Trp His Gln Gln Lys Ser Pro Gly Ser Ala Pro Val Thr Val
    50                  55                  60

Ile Tyr Glu Ser Thr Lys Arg Pro Ser Asn Ile Pro Ser Arg Phe Ser
65                  70                  75                  80

Gly Ser Thr Ser Gly Ser Thr Gly Thr Leu Thr Ile Thr Gly Val Gln
                85                  90                  95

Val Glu Asp Glu Ala Val Tyr Phe Cys Gly Gly Tyr Asp Gly Ser Thr
            100                 105                 110

Asp Ala Ile Phe Gly Ala Gly Thr Thr Leu Thr Val Leu Gly Gln Ser
            115                 120                 125

Ser Arg Ser Ser Ala Val Thr Leu Asp Glu Ser Gly Gly Gly Leu Gln
    130                 135                 140

Met Pro Gly Gly Gly Leu Ser Leu Val Cys Lys Ala Ser Gly Phe Asp
145                 150                 155                 160

Phe Ser Ser Ser Glu Met Gln Trp Val Arg Gln Ala Pro Gly Lys Gly
                165                 170                 175

Leu Gln Trp Val Gly Ile Ile Ser Ser Ser Gly Ser Thr Tyr Tyr Gly
            180                 185                 190

```
Ser Ala Val Lys Gly Arg Ala Thr Ile Ser Arg Asp Asn Gly Gln Ser
            195                 200                 205

Ala Val Arg Leu Gln Leu Asn Asn Leu Arg Ala Glu Asp Thr Gly Thr
            210                 215                 220

Tyr Tyr Cys Thr Lys Thr Thr Ala Tyr Ala His Asp Ile Asp Ala Trp
225                 230                 235                 240

Gly His Gly Thr Glu Val Ile Val Ser Ser Thr Ser Gly Gln Ala Gly
            245                 250                 255

Gln His His His His His Gly Ala Tyr Pro Tyr Asp Val Pro Asp
            260                 265                 270

Tyr Ala Ser
        275

<210> SEQ ID NO 100
<211> LENGTH: 280
<212> TYPE: PRT
<213> ORGANISM: Artificial Sequence
<220> FEATURE:
<223> OTHER INFORMATION: recombinant protein

<400> SEQUENCE: 100

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Gly Thr Val Lys Ile Thr Cys Ser Gly Ser Ser Ser Ala Tyr
        35                  40                  45

Gly Tyr Gly Trp Tyr Gln Gln Lys Ser Pro Gly Ser Ala Pro Val Thr
    50                  55                  60

Val Ile Tyr Asn Asn Asn Lys Arg Pro Ser Asn Ile Pro Ser Arg Phe
65                  70                  75                  80

Ser Gly Ser Lys Ser Gly Ser Thr Gly Thr Leu Thr Ile Thr Gly Val
            85                  90                  95

Gln Ala Glu Asp Glu Ala Val Tyr Phe Cys Gly Ser Glu Asp Ser Ser
            100                 105                 110

Thr Asp Ala Ile Phe Gly Ala Gly Thr Thr Leu Thr Val Leu Gly Gln
            115                 120                 125

Ser Ser Arg Ser Ser Ala Val Thr Leu Asp Glu Ser Gly Gly Gly Leu
            130                 135                 140

Gln Thr Pro Gly Gly Ala Leu Ser Leu Val Cys Lys Ala Ser Gly Phe
145                 150                 155                 160

Thr Phe Ser Ser Tyr Asp Met Gly Trp Val Arg Gln Ala Pro Gly Lys
            165                 170                 175

Gly Leu Glu Tyr Val Ala Gly Ile Thr Asn Asp Gly Arg Tyr Ala Ser
            180                 185                 190

Tyr Gly Ser Ala Val Asp Gly Arg Ala Thr Ile Ser Arg Asp Asn Gly
            195                 200                 205

Gln Ser Thr Val Arg Leu Gln Leu Asn Asn Leu Arg Ala Glu Asp Thr
            210                 215                 220

Gly Thr Tyr Tyr Cys Ala Arg Asp Asp Gly Ser Gly Trp Thr Gly Asn
225                 230                 235                 240

Thr Ile Asp Thr Trp Gly His Gly Thr Glu Val Ile Val Ser Ser Thr
            245                 250                 255

Ser Gly Gln Ala Gly Gln His His His His His Gly Ala Tyr Pro
            260                 265                 270
```

Tyr Asp Val Pro Asp Tyr Ala Ser
            275                 280

<210> SEQ ID NO 101
<211> LENGTH: 279
<212> TYPE: PRT
<213> ORGANISM: Artificial Sequence
<220> FEATURE:
<223> OTHER INFORMATION: recombinant protein

<400> SEQUENCE: 101

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Ser
            20                  25                  30

Pro Gly Glu Thr Val Lys Ile Thr Cys Ser Gly Gly Ser Gly Ser Tyr
        35                  40                  45

Gly Trp Tyr Arg His Lys Ser Pro Gly Ser Ala Pro Val Thr Val Ile
    50                  55                  60

Tyr Tyr Asn Asp Lys Arg Pro Ser Asp Ile Pro Ser Arg Phe Ser Gly
65                  70                  75                  80

Ser Lys Ser Gly Ser Thr Ser Thr Leu Thr Ile Thr Gly Val Gln Ala
                85                  90                  95

Glu Asp Glu Ala Asp Tyr Tyr Cys Gly Ser Tyr Asn Ser Asn Ala Gly
            100                 105                 110

Tyr Val Gly Ile Phe Gly Ala Gly Thr Thr Leu Thr Val Leu Gly Gln
        115                 120                 125

Ser Ser Arg Ser Ser Thr Val Thr Leu Asp Glu Ser Gly Gly Gly Leu
    130                 135                 140

Gln Thr Pro Gly Gly Gly Leu Ser Leu Val Cys Lys Ala Ser Gly Phe
145                 150                 155                 160

Thr Phe Ser Ser Tyr Gly Met Gly Trp Met Arg Gln Ala Pro Gly Lys
                165                 170                 175

Gly Leu Glu Phe Val Ala Gly Ile Arg Lys Asp Gly Arg Ser Thr Ala
            180                 185                 190

Tyr Gly Ala Ala Val Asp Gly Arg Ala Thr Ile Ser Arg Asp Asp Gly
        195                 200                 205

Gln Ser Thr Leu Arg Leu Gln Leu Gly Asn Leu Arg Ala Glu Asp Thr
    210                 215                 220

Gly Thr Tyr Phe Cys Ala Lys Thr Asn Ser Tyr Asp Ser Ala Gly Ile
225                 230                 235                 240

Ile Asp Ala Trp Gly His Gly Thr Glu Val Ile Val Ser Ser Thr Ser
                245                 250                 255

Gly Gln Ala Gly Gln His His His His His Gly Ala Tyr Pro Tyr
            260                 265                 270

Asp Val Pro Asp Tyr Ala Ser
        275

<210> SEQ ID NO 102
<211> LENGTH: 275
<212> TYPE: PRT
<213> ORGANISM: Artificial Sequence
<220> FEATURE:
<223> OTHER INFORMATION: recombinant protein

<400> SEQUENCE: 102

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Lys Ile Thr Cys Ser Gly Gly Ser Ser Asn
        35                  40                  45

Asn Tyr Gly Trp His Gln Gln Lys Ala Pro Gly Ser Ala Pro Val Thr
 50                  55                  60

Val Ile Tyr Asp Asn Thr Asn Arg Pro Ser Asn Ile Pro Ser Arg Phe
65                  70                  75                  80

Ser Gly Ser Lys Ser Ser Ser Thr His Thr Leu Thr Ile Thr Gly Val
                85                  90                  95

Gln Ala Glu Asp Glu Ala Val Tyr Tyr Cys Ser Ala Asp Ser Ser
            100                 105                 110

Ser Ser Ile Phe Gly Ala Gly Thr Thr Leu Thr Val Leu Gly Gln Ser
            115                 120                 125

Ser Arg Ser Ser Ala Val Thr Leu Asp Glu Ser Gly Gly Gly Leu Gln
    130                 135                 140

Thr Pro Gly Gly Thr Leu Ser Leu Val Cys Lys Ala Ser Gly Phe Thr
145                 150                 155                 160

Phe Ser Ser Phe Asn Met Phe Trp Val Arg Gln Ala Pro Gly Lys Gly
                165                 170                 175

Leu Glu Phe Val Ala Gly Ile Gly Asn Thr Gly Arg Ser Thr Gly Tyr
            180                 185                 190

Gly Ser Ala Val Lys Gly Arg Ala Thr Ile Ser Arg Asp Asn Gly Gln
        195                 200                 205

Ser Thr Val Arg Leu Gln Leu Asn Asn Leu Arg Ala Glu Asp Thr Gly
    210                 215                 220

Thr Tyr Tyr Cys Ala Lys Ala Tyr Gly Asp Ser Asn Ile Asp Ala Trp
225                 230                 235                 240

Gly His Gly Thr Glu Val Ile Val Ser Ser Thr Ser Gly Gln Ala Gly
            245                 250                 255

Gln His His His His His His Gly Ala Tyr Pro Tyr Asp Val Pro Asp
        260                 265                 270

Tyr Ala Ser
        275

<210> SEQ ID NO 103
<211> LENGTH: 278
<212> TYPE: PRT
<213> ORGANISM: Artificial Sequence
<220> FEATURE:
<223> OTHER INFORMATION: recombinant protein

<400> SEQUENCE: 103

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Ser
            20                  25                  30

Leu Gly Gly Ile Val Glu Ile Thr Cys Ser Gly Ser Ser Gly Thr Tyr
        35                  40                  45

Gly Trp Tyr Gln Gln Lys Ser Pro Gly Ser Ala Pro Val Thr Val Ile
    50                  55                  60

Tyr Gln Asn Gly Lys Arg Pro Ser Asn Ile Pro Ser Arg Phe Ser Gly
65                  70                  75                  80

Ser Lys Ser Gly Ser Thr Ala Thr Leu Thr Ile Thr Gly Val Gln Ala
                85                  90                  95

```
Asp Asp Glu Ala Val Tyr Phe Cys Gly Gly Tyr Asp Ser Ser Thr Tyr
                100                 105                 110

Val Gly Ile Phe Gly Ala Gly Thr Thr Leu Thr Val Leu Gly Gln Ser
            115                 120                 125

Ser Arg Ser Ser Ala Val Thr Leu Asp Glu Ser Gly Gly Gly Leu Gln
130                 135                 140

Thr Pro Gly Gly Ala Leu Ser Leu Val Cys Lys Ala Ser Gly Phe Asp
145                 150                 155                 160

Phe Ser Ser Tyr Gly Met Gly Trp Met Arg Gln Ala Pro Gly Lys Gly
                165                 170                 175

Leu Glu Phe Val Ala Ala Ile Arg Lys Asp Gly Ser Tyr Thr Ala Tyr
            180                 185                 190

Gly Ala Ala Val Asp Gly Arg Ala Thr Ile Ser Arg Asp Asp Gly Gln
        195                 200                 205

Ser Thr Val Arg Leu Gln Leu Gly Asn Leu Arg Ala Glu Asp Thr Ala
    210                 215                 220

Thr Tyr Phe Cys Ala Lys Thr Asn Ser Tyr Asn Ser Ala Gly Ile Ile
225                 230                 235                 240

Asp Ala Trp Gly His Gly Thr Glu Val Ile Val Ser Thr Ser Gly
                245                 250                 255

Gln Ala Gly Gln His His His His His Gly Ala Tyr Pro Tyr Asp
                260                 265                 270

Val Pro Asp Tyr Ala Ser
            275

<210> SEQ ID NO 104
<211> LENGTH: 268
<212> TYPE: PRT
<213> ORGANISM: Artificial Sequence
<220> FEATURE:
<223> OTHER INFORMATION: recombinant protein

<400> SEQUENCE: 104

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Lys Ile Thr Cys Ser Gly Gly Ser Ser Asn
        35                  40                  45

Asn Tyr Gly Trp His Gln Gln Lys Ala Pro Gly Ser Ala Pro Val Thr
    50                  55                  60

Val Ile Tyr Asp Asn Thr Asn Arg Pro Ser Asn Ile Pro Ser Arg Phe
65                  70                  75                  80

Ser Gly Ser Lys Ser Ser Ser Thr His Thr Leu Thr Ile Thr Gly Val
                85                  90                  95

Gln Ala Glu Asp Glu Ala Val Tyr Tyr Cys Glu Ser Ala Asp Ser Ser
            100                 105                 110

Ser Ser Ile Phe Gly Ala Gly Thr Thr Leu Thr Val Leu Gly Gln Ser
        115                 120                 125

Ser Arg Ser Ser Ala Val Thr Leu Asp Glu Ser Gly Gly Gly Leu Gln
    130                 135                 140

Thr Pro Gly Gly Thr Leu Ser Leu Val Cys Lys Ala Ser Gly Phe Thr
145                 150                 155                 160

Phe Ser Ser Phe Asn Met Phe Trp Val Arg Gln Ala Pro Gly Lys Gly
                165                 170                 175
```

Leu Glu Phe Val Ala Gly Ile Gly Asn Thr Gly Arg Ser Thr Gly Tyr
            180                 185                 190

Gly Ser Ala Val Lys Gly Arg Ala Thr Ile Ser Arg Asp Asn Gly Gln
            195                 200                 205

Ser Thr Val Arg Leu Gln Leu Asn Asn Leu Arg Ala Glu Asp Thr Gly
            210                 215                 220

Thr Tyr Tyr Cys Ala Lys Ala Leu Trp Gly His Gly Thr Glu Val Ile
225                 230                 235                 240

Val Ser Ser Thr Ser Gly Gln Ala Gly Gln His His His His His His
            245                 250                 255

Gly Ala Tyr Pro Tyr Asp Val Pro Asp Tyr Ala Ser
            260                 265

<210> SEQ ID NO 105
<211> LENGTH: 275
<212> TYPE: PRT
<213> ORGANISM: Artificial Sequence
<220> FEATURE:
<223> OTHER INFORMATION: recombinant protein

<400> SEQUENCE: 105

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Lys Ile Thr Cys Ser Gly Ser Ser Gly Ser Tyr
            35                  40                  45

Gly Trp Tyr Gln Gln Lys Ser Pro Gly Ser Ala Pro Val Ser Leu Ile
50                  55                  60

Tyr Ser Asn Asp Lys Arg Pro Ser Asp Ile Pro Ser Arg Phe Ser Gly
65                  70                  75                  80

Ser Lys Ser Gly Ser Thr Gly Thr Leu Thr Ile Thr Gly Val Gln Ala
            85                  90                  95

Glu Asp Glu Ala Val Tyr Tyr Cys Gly Gly Trp Asp Ser Tyr Val Gly
            100                 105                 110

Ile Phe Gly Ala Gly Thr Thr Leu Thr Val Leu Gly Gln Ser Ser Arg
            115                 120                 125

Ser Ser Ala Val Thr Leu Asp Glu Ser Gly Gly Gly Leu Gln Thr Pro
            130                 135                 140

Gly Gly Gly Leu Ser Leu Val Cys Lys Ala Ser Gly Phe Ser Ser Ser
145                 150                 155                 160

His Gly Met Gly Trp Met Arg Gln Ala Pro Gly Lys Gly Leu Glu Phe
            165                 170                 175

Val Ala Gly Ile Arg Ser Asp Gly Ser Ser Thr Ala Tyr Gly Ala Ala
            180                 185                 190

Val Asp Gly Arg Ala Thr Ile Thr Arg Asp Asp Gly Gln Ser Thr Val
            195                 200                 205

Thr Leu Gln Leu Asn Asn Leu Arg Ala Glu Asp Thr Ala Thr Tyr Phe
            210                 215                 220

Cys Ala Lys Thr Asn Ser Tyr Asn Ser Ala Gly Ile Ile Asp Ala Trp
225                 230                 235                 240

Gly His Gly Thr Glu Val Ile Val Ser Ser Thr Ser Gly Gln Ala Gly
            245                 250                 255

Gln His His His His His His Gly Ala Tyr Pro Tyr Asp Val Pro Asp
            260                 265                 270

-continued

Tyr Ala Ser
        275

<210> SEQ ID NO 106
<211> LENGTH: 275
<212> TYPE: PRT
<213> ORGANISM: Artificial Sequence
<220> FEATURE:
<223> OTHER INFORMATION: recombinant protein

<400> SEQUENCE: 106

Met Lys Lys Thr Ala Ile Ala Ile Ala Val Ala Leu Ala Gly Phe Ala
1               5                   10                  15

Thr Val Ala Gln Ala Ala Leu Ser Arg Pro Arg Cys Gln Gln Thr Trp
            20                  25                  30

Gly Gly Thr Val Lys Ile Thr Cys Ser Gly Ser Ser Ser Tyr Gly
        35                  40                  45

Trp Tyr Gln Gln Lys Ser Pro Gly Ser Ala Pro Val Thr Leu Ile Tyr
    50                  55                  60

Glu Ser Asp Lys Arg Pro Ser Asp Ile Pro Ser Arg Phe Ser Gly Ser
65              70                  75                  80

Lys Ser Gly Ser Thr Gly Thr Leu Thr Ile Thr Gly Val Gln Ala Asp
                85                  90                  95

Asp Glu Ala Val Tyr Phe Cys Gly Gly Tyr Asp Ser Ser Ala Gly Ile
            100                 105                 110

Phe Gly Ala Gly Thr Thr Leu Thr Val Leu Gly Gln Ser Ser Arg Ser
        115                 120                 125

Ser Ala Val Thr Leu Asp Glu Ser Gly Gly Gly Leu His Thr Pro Gly
    130                 135                 140

Gly Ala Leu Ser Leu Val Cys Lys Ala Ser Gly Phe Asp Phe Ser Ser
145                 150                 155                 160

Tyr Gly Met Gly Trp Met Arg Gln Ala Pro Gly Lys Gly Leu Glu Phe
                165                 170                 175

Val Ala Ala Ile Arg Lys Asp Gly Ser Tyr Thr Ala Tyr Gly Ala Ala
            180                 185                 190

Val Asp Gly Arg Ala Thr Ile Ser Arg Asp Asp Gly Gln Ser Thr Val
        195                 200                 205

Arg Leu Gln Leu Gly Asn Leu Arg Ala Glu Asp Thr Ala Thr Tyr Phe
    210                 215                 220

Cys Ala Lys Thr Asn Ser Tyr Asn Ser Ala Gly Ile Ile Asp Ala Trp
225                 230                 235                 240

Gly His Gly Thr Glu Val Ile Val Ser Ser Thr Ser Gly Gln Ala Gly
                245                 250                 255

Gln His His His His His His Gly Ala Tyr Pro Tyr Asp Val Pro Asp
            260                 265                 270

Tyr Ala Ser
        275

<210> SEQ ID NO 107
<211> LENGTH: 279
<212> TYPE: PRT
<213> ORGANISM: Artificial Sequence
<220> FEATURE:
<223> OTHER INFORMATION: recombinant protein

<400> SEQUENCE: 107

Met Lys Lys Thr Ala Ile Ala Ile Ala Val Ala Leu Ala Gly Phe Ala

```
            1               5                   10                  15
         Thr Val Gln Ala Ala Leu Thr Gln Pro Ser Ser Val Ser Ala Ser
                    20                  25                  30
         Pro Gly Glu Thr Val Lys Ile Thr Cys Ser Gly Gly Ser Gly Ser Tyr
                    35                  40                  45
         Gly Trp Tyr Gln Gln Lys Ser Pro Gly Ser Ala Pro Val Thr Val Ile
                    50                  55                  60
         Tyr Tyr Asn Asp Lys Arg Pro Ser Asp Ile Pro Ser Arg Phe Ser Gly
         65                  70                  75                  80
         Ser Lys Ser Gly Ser Thr Ser Thr Leu Thr Ile Thr Gly Val Gln Ala
                    85                  90                  95
         Glu Asp Glu Ala Val Tyr Tyr Cys Gly Ser Tyr Asp Ser Ser Ala Gly
                    100                 105                 110
         Tyr Val Gly Ile Phe Gly Ala Gly Thr Thr Leu Thr Val Leu Gly Gln
                    115                 120                 125
         Ser Ser Arg Ser Ser Thr Val Thr Leu Asp Glu Ser Gly Gly Gly Leu
                    130                 135                 140
         Gln Thr Pro Gly Gly Gly Leu Ser Leu Val Cys Lys Ala Ser Gly Phe
         145                 150                 155                 160
         Thr Phe Ser Ser Tyr Gly Met Gly Trp Met Arg Gln Ala Pro Gly Lys
                    165                 170                 175
         Gly Leu Glu Phe Val Ala Gly Ile Arg Lys Asp Gly Ser Ser Thr Ala
                    180                 185                 190
         Tyr Gly Ala Ala Val Asp Gly Arg Ala Thr Ile Ser Arg Asp Asp Gly
                    195                 200                 205
         Gln Ser Thr Leu Arg Leu Gln Leu Gly Asn Leu Arg Ala Glu Asp Thr
                    210                 215                 220
         Gly Thr Tyr Phe Cys Ala Lys Thr Asn Ser Tyr Asn Ser Ala Gly Ile
         225                 230                 235                 240
         Ile Asp Ala Trp Gly His Gly Thr Glu Val Ile Val Ser Ser Thr Ser
                    245                 250                 255
         Gly Gln Ala Gly Gln His His His His His His Gly Ala Tyr Pro Tyr
                    260                 265                 270
         Asp Val Pro Asp Tyr Ala Ser
                    275

<210> SEQ ID NO 108
<211> LENGTH: 168
<212> TYPE: PRT
<213> ORGANISM: Artificial Sequence
<220> FEATURE:
<223> OTHER INFORMATION: recombinant protein

<400> SEQUENCE: 108

Arg Ala Pro Val Thr Leu Ile Tyr Asn Asn Asn Arg Pro Ser Asp
         1               5                   10                  15
         Ile Pro Pro Arg Phe Ser Gly Ser Lys Ser Gly Ser Thr Gly Thr Leu
                    20                  25                  30
         Ala Ile Thr Gly Val Gln Ala Glu Asp Glu Ala Val Tyr Phe Cys Gly
                    35                  40                  45
         Gly Tyr Glu Gly Ser Thr Ser Thr Gly Ile Phe Gly Ala Gly Thr Thr
                    50                  55                  60
         Leu Thr Val Leu Gly Gln Ser Ser Arg Ser Ser Ala Val Thr Leu Asp
         65                  70                  75                  80
         Glu Ser Gly Gly Gly Leu Gln Thr Pro Gly Gly Ala Leu Ser Leu Val
```

```
                     85                  90                  95
Cys Lys Ala Ser Gly Phe Asp Phe Ser Ser Tyr Gly Met Gly Trp Met
            100                 105                 110

Arg Gln Ala Pro Gly Lys Gly Leu Glu Phe Val Ala Ala Ile Lys Lys
            115                 120                 125

Asp Gly Ser Tyr Thr Ala Tyr Gly Ala Ala Val Asp Gly Arg Ala Thr
            130                 135                 140

Ile Ser Arg Asp Asp Gly Gln Ser Thr Val Arg Leu Gln Leu Gly Asn
145                 150                 155                 160

Leu Arg Ala Glu Asp Thr Ala Pro
                165

<210> SEQ ID NO 109
<211> LENGTH: 275
<212> TYPE: PRT
<213> ORGANISM: Artificial Sequence
<220> FEATURE:
<223> OTHER INFORMATION: recombinant protein

<400> SEQUENCE: 109

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Asp Pro Phe Lys Ile Thr Cys Ser Gly Gly Ser Ser Asn
            35                  40                  45

Asn Tyr Gly Trp His Gln Gln Lys Ala Pro Gly Ser Ala Pro Val Thr
    50                  55                  60

Val Ile Tyr Asp Asn Thr Asn Arg Pro Ser Asn Ile Pro Ser Arg Phe
65                  70                  75                  80

Ser Gly Ser Lys Ser Ser Ser Thr His Thr Leu Thr Ile Thr Gly Val
                85                  90                  95

Gln Ala Glu Asp Glu Ala Val Tyr Tyr Cys Gly Ser Ala Asp Ser Ser
            100                 105                 110

Ser Ser Ile Phe Gly Ala Gly Thr Thr Leu Thr Val Leu Gly Gln Ser
            115                 120                 125

Ser Arg Ser Ser Ala Val Thr Leu Asp Glu Ser Gly Gly Gly Leu Gln
            130                 135                 140

Thr Pro Gly Gly Thr Leu Ser Leu Val Cys Lys Ala Ser Gly Phe Thr
145                 150                 155                 160

Phe Ser Ser Phe Asn Met Phe Trp Val Arg Gln Ala Pro Gly Lys Gly
                165                 170                 175

Leu Glu Phe Val Ala Gly Ile Gly Asn Thr Gly Arg Ser Thr Gly Tyr
            180                 185                 190

Gly Ser Ala Val Lys Gly Arg Ala Thr Ile Ser Arg Asp Asn Gly Gln
            195                 200                 205

Ser Thr Val Arg Leu Gln Leu Asn Asn Leu Arg Ala Glu Asp Thr Gly
            210                 215                 220

Thr Tyr Tyr Cys Ala Lys Ala Tyr Gly Asp Ser Asn Ile Asp Ala Trp
225                 230                 235                 240

Gly His Gly Thr Glu Val Ile Val Ser Ser Thr Ser Gly Gln Ala Gly
                245                 250                 255

Gln His His His His His Gly Ala Tyr Pro Tyr Asp Val Pro Asp
            260                 265                 270

Tyr Ala Ser
```

```
                275

<210> SEQ ID NO 110
<211> LENGTH: 205
<212> TYPE: PRT
<213> ORGANISM: Artificial Sequence
<220> FEATURE:
<223> OTHER INFORMATION: recombinant protein

<400> SEQUENCE: 110

Leu Ser Arg Pro Arg Cys Gln Gln Thr Trp Gly Gly Thr Val Lys Ile
1               5                   10                  15

Thr Cys Ser Gly Ser Ser Gly Gly Tyr Gly Trp Tyr Arg His Lys Ser
            20                  25                  30

Pro Gly Thr Ala Pro Val Pro Leu Ile Tyr Asn Asn Asp Asn Arg Pro
        35                  40                  45

Ser Asp Ile Pro Ser Arg Phe Ser Gly Ser Lys Ser Gly Ser Thr Ser
    50                  55                  60

Thr Leu Thr Ile Thr Gly Val Gln Val Gln Asp Glu Asp Asp Tyr Phe
65                  70                  75                  80

Cys Gly Gly Tyr Asn Lys Asn Thr Tyr Ala Asp Ile Phe Gly Ala Gly
                85                  90                  95

Thr Thr Leu Thr Val Leu Arg Gln Ser Ser Thr Ser Ser Ala Val Thr
            100                 105                 110

Met Asp Asp Tyr Gly Gly Gly Leu Leu Thr Thr Gly Gly Ala Leu Ile
            115                 120                 125

Leu Leu Cys Trp Ala Ser Gly Phe Phe Thr Phe His Gly Leu Asp Trp
        130                 135                 140

Met Arg Gln Ala Pro Ala Thr Gly Leu Glu Phe Val Ala Gly Ile Arg
145                 150                 155                 160

Ser Asp Gly Asp Ser Thr Ala Tyr Gly Ala Ala Val Asp Gly His Ala
                165                 170                 175

Thr Val Ser Arg Asp Asn Gly Ser Thr Met Arg Leu Gln Leu Asn
            180                 185                 190

Ile Leu Arg Ala Glu Asp Asp Ala Thr Tyr Phe Cys Ala
        195                 200                 205

<210> SEQ ID NO 111
<211> LENGTH: 279
<212> TYPE: PRT
<213> ORGANISM: Artificial Sequence
<220> FEATURE:
<223> OTHER INFORMATION: recombinant protein

<400> SEQUENCE: 111

Met Lys Lys Thr Ala Ile Ala Ile Ala Val Ala Leu Ala Gly Phe Ala
1               5                   10                  15

Thr Val Ala Gln Ala Ala Leu Ser Arg Pro Arg Cys Gln Gln Thr Trp
            20                  25                  30

Gly Gly Pro Val Lys Ile Thr Cys Ser Gly Gly Ser Gly Ser Tyr Gly
        35                  40                  45

Trp Tyr Gln Gln Lys Ser Pro Gly Ser Ala Pro Val Thr Val Ile Tyr
    50                  55                  60

Tyr Asn Asp Gln Arg Pro Ser Asp Ile Pro Ser Arg Phe Ser Gly Ser
65                  70                  75                  80

Lys Ser Gly Ser Thr Gly Thr Leu Thr Ile Thr Gly Val Gln Ala Glu
                85                  90                  95
```

```
Asp Glu Ala Val Tyr Tyr Cys Gly Gly Tyr Asp Ser Thr Tyr Val Gly
                100                 105                 110

Ile Phe Gly Ala Gly Thr Thr Leu Thr Val Leu Gly Gln Ser Ser Arg
            115                 120                 125

Ser Ser Ala Val Thr Leu Asp Glu Ser Gly Gly Gly Leu Gln Thr Pro
        130                 135                 140

Arg Gly Ala Leu Ser Leu Val Cys Lys Ala Ser Gly Phe Thr Phe Ser
145                 150                 155                 160

Ser Tyr Ser Met Ala Trp Val Arg Gln Ala Pro Gly Lys Gly Leu Glu
                165                 170                 175

Phe Val Ala Gly Ile Gln Asn Asp Gly Ser Ile Thr Asp Tyr Gly Ser
            180                 185                 190

Ala Val Asp Gly Arg Ala Thr Ile Ser Arg Asp Asp Gly Gln Ser Thr
        195                 200                 205

Val Arg Leu Gln Leu Asn Asn Leu Arg Thr Glu Asp Thr Ala Thr Tyr
    210                 215                 220

Tyr Cys Ala Lys Thr Thr Val Ala Asp Gly Val Ile Gly Ala Tyr Gly
225                 230                 235                 240

Ile Asp Ala Trp Gly His Gly Thr Glu Val Ile Val Ser Ser Thr Ser
                245                 250                 255

Gly Gln Ala Gly Gln His His His His His His Gly Ala Tyr Pro Tyr
                260                 265                 270

Asp Val Pro Asp Tyr Ala Ser
                275

<210> SEQ ID NO 112
<211> LENGTH: 174
<212> TYPE: PRT
<213> ORGANISM: Artificial Sequence
<220> FEATURE:
<223> OTHER INFORMATION: recombinant protein

<400> SEQUENCE: 112

Ala Leu Thr Gln Pro Ser Ser Val Ser Ala Asn Pro Gly Gly Thr Val
1               5                   10                  15

Lys Ile Thr Cys Ser Gly Ser Ser Ala Tyr Gly Tyr Gly Trp Tyr
            20                  25                  30

Gln Gln Lys Ser Pro Gly Ser Ala Pro Val Thr Val Ile Tyr Asn Asn
        35                  40                  45

Asn Lys Arg Pro Ser Asn Ile Pro Ser Arg Phe Ser Gly Ser Lys Ser
    50                  55                  60

Gly Ser Thr Gly Thr Leu Thr Ile Thr Gly Val Gln Ala Glu Asp Glu
65                  70                  75                  80

Ala Val Tyr Phe Cys Gly Ser Glu Asp Ser Ser Thr Asp Ala Ile Phe
                85                  90                  95

Gly Ala Gly Thr Thr Leu Thr Val Leu Gly Gln Ser Ser Arg Ser Ser
            100                 105                 110

Thr Val Thr Leu Asp Glu Ser Gly Gly Gly Leu Gln Ala Pro Gly Gly
        115                 120                 125

Ala Leu Ser Leu Val Cys Lys Ala Ser Gly Phe Thr Phe Ser Ser Tyr
    130                 135                 140

Asp Met Gly Trp Ile Arg Gln Ala Pro Gly Lys Gly Leu Glu Tyr Val
145                 150                 155                 160

Ala Gly Ile Thr Asp Asn Gly Thr Tyr Ala Ser Tyr Gly Ser
                165                 170
```

```
<210> SEQ ID NO 113
<211> LENGTH: 280
<212> TYPE: PRT
<213> ORGANISM: Artificial Sequence
<220> FEATURE:
<223> OTHER INFORMATION: recombinant protein

<400> SEQUENCE: 113

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Leu Gly Ala Phe Lys Ile Thr Cys Ser Gly Gly Gly Ser Tyr Gly
        35                  40                  45

Trp Tyr Gln Gln Lys Ser Pro Gly Ser Ala Pro Val Thr Leu Ile Tyr
    50                  55                  60

Tyr Asn Asp Lys Arg Pro Ser Asp Ile Pro Ser Arg Phe Ser Gly Ser
65                  70                  75                  80

Lys Ser Gly Ser Thr Ala Thr Leu Thr Ile Thr Gly Val Gln Ala Asn
                85                  90                  95

Asp Glu Ala Val Tyr Phe Cys Gly Ser Tyr Glu Gly Ser Thr Tyr Ser
            100                 105                 110

Gly Ile Phe Gly Ala Gly Thr Thr Leu Thr Val Leu Gly Gln Ser Ser
        115                 120                 125

Arg Ser Ser Thr Val Thr Leu Asp Glu Ser Gly Gly Gly Leu Gln Thr
    130                 135                 140

Pro Gly Gly Gly Leu Ser Leu Val Cys Lys Ala Ser Gly Phe Ser Ser
145                 150                 155                 160

Ser His Gly Met Gly Trp Met Arg Gln Ala Pro Gly Lys Gly Leu Glu
                165                 170                 175

Phe Val Ala Gly Ile Arg Ser Asp Gly Ser Ser Thr Ala Tyr Gly Ala
            180                 185                 190

Ala Val Asp Gly Arg Ala Thr Ile Thr Arg Asp Asp Gly Gln Ser Thr
        195                 200                 205

Val Thr Leu Gln Leu Asn Asn Leu Arg Ala Glu Asp Thr Ala Thr Tyr
    210                 215                 220

Phe Cys Ala Lys Asn Thr Thr Val Ala Asp Gly Val Ile Gly Ala Tyr
225                 230                 235                 240

Gly Ile Asp Ala Trp Gly His Gly Thr Glu Val Ile Val Ser Ser Thr
                245                 250                 255

Ser Gly Gln Ala Gly Gln His His His His His Gly Ala Tyr Pro
            260                 265                 270

Tyr Asp Val Pro Asp Tyr Ala Ser
        275                 280

<210> SEQ ID NO 114
<211> LENGTH: 278
<212> TYPE: PRT
<213> ORGANISM: Artificial Sequence
<220> FEATURE:
<223> OTHER INFORMATION: recombinant protein

<400> SEQUENCE: 114

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30
```

Leu Gly Gly Pro Phe Glu Ile Thr Cys Ser Gly Ser Ser Gly Ser Tyr
            35                  40                  45

Gly Trp Tyr Gln Gln Lys Ser Pro Gly Ser Ala Pro Val Thr Leu Ile
    50                  55                  60

Tyr Asn Asn Asn Arg Pro Ser Asp Ile Pro Pro Arg Phe Ser Gly
65                  70                  75                  80

Ser Lys Ser Gly Ser Thr Gly Thr Leu Ala Ile Thr Gly Val Gln Ala
                85                  90                  95

Glu Asp Glu Ala Val Tyr Phe Cys Gly Gly Tyr Glu Gly Ser Thr Ser
            100                 105                 110

Thr Gly Ile Phe Gly Ala Gly Thr Thr Leu Thr Val Leu Gly Gln Ser
        115                 120                 125

Ser Arg Ser Ser Ala Val Thr Leu Asp Glu Ser Gly Gly Gly Leu Gln
    130                 135                 140

Thr Pro Gly Gly Ala Leu Ser Leu Val Cys Lys Ala Ser Gly Phe Asp
145                 150                 155                 160

Phe Ser Ser Tyr Gly Met Gly Trp Met Arg Gln Ala Pro Gly Lys Gly
                165                 170                 175

Leu Glu Phe Val Ala Ala Ile Arg Lys Asp Gly Ser Tyr Thr Ala Tyr
            180                 185                 190

Gly Ala Ala Val Asp Gly Arg Ala Thr Ile Ser Arg Asp Asp Gly Gln
        195                 200                 205

Ser Thr Val Arg Leu Gln Leu Gly Asn Leu Arg Ala Glu Asp Thr Ala
    210                 215                 220

Thr Tyr Phe Cys Ala Lys Thr Asn Ser Tyr Asn Ser Ala Gly Ile Ile
225                 230                 235                 240

Asp Ala Trp Gly His Gly Thr Glu Val Ile Val Ser Ser Thr Ser Gly
                245                 250                 255

Gln Ala Gly Gln His His His His His Gly Ala Tyr Pro Tyr Asp
            260                 265                 270

Val Pro Asp Tyr Ala Ser
            275

<210> SEQ ID NO 115
<211> LENGTH: 262
<212> TYPE: PRT
<213> ORGANISM: Artificial Sequence
<220> FEATURE:
<223> OTHER INFORMATION: recombinant protein

<400> SEQUENCE: 115

Met Lys Lys Thr Ala Ile Ala Ile Ala Val Ala Leu Ala Gly Phe Ala
1               5                   10                  15

Thr Val Ala Gln Ala Ala Leu Lys Ile Thr Cys Ser Gly Ser Ser Gly
            20                  25                  30

Ser Tyr Ala Trp Tyr Gln Gln Lys Ser Pro Gly Ser Ala Pro Val Thr
        35                  40                  45

Leu Ile Tyr Glu Ser Asp Lys Arg Pro Ser Asp Ile Pro Ser Arg Phe
    50                  55                  60

Ser Gly Ser Lys Ser Gly Ser Thr Gly Thr Leu Thr Ile Thr Gly Val
65                  70                  75                  80

Gln Ala Asp Asp Glu Ala Val Tyr Phe Cys Gly Gly Tyr Asp Ser Ser
                85                  90                  95

Ala Gly Ile Phe Gly Ala Gly Thr Thr Leu Thr Val Leu Gly Gln Ser
            100                 105                 110

Ser Arg Ser Ser Ala Val Thr Leu Asp Glu Ser Gly Gly Gly Leu Gln
            115                 120                 125

Thr Pro Gly Gly Ala Leu Ser Leu Val Cys Lys Ala Ser Gly Phe Asp
        130                 135                 140

Phe Ser Ser Tyr Gly Met Gly Trp Met Arg Gln Ala Pro Gly Lys Gly
145                 150                 155                 160

Leu Glu Phe Val Ala Ala Ile Arg Lys Asp Gly Ser Tyr Thr Ala Tyr
                165                 170                 175

Gly Ala Ala Val Asp Gly Arg Ala Thr Ile Ser Arg Asp Asp Gly Gln
            180                 185                 190

Ser Thr Val Arg Leu Gln Leu Gly Asn Leu Arg Ala Glu Asp Thr Ala
        195                 200                 205

Thr Tyr Phe Cys Ala Lys Thr Asn Ser Tyr Asn Ser Ala Gly Ile Ile
210                 215                 220

Asp Ala Trp Gly His Gly Thr Glu Val Ile Val Ser Thr Ser Gly
225                 230                 235                 240

Gln Ala Gly Gln His His His His His Gly Ala Tyr Pro Tyr Asp
            245                 250                 255

Val Pro Asp Tyr Ala Ser
            260

<210> SEQ ID NO 116
<211> LENGTH: 280
<212> TYPE: PRT
<213> ORGANISM: Artificial Sequence
<220> FEATURE:
<223> OTHER INFORMATION: recombinant protein

<400> SEQUENCE: 116

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Arg Thr Leu Leu Lys Ile Thr Cys Ser Gly Ser Ser Ser Ala Tyr
        35                  40                  45

Gly Tyr Gly Trp Tyr Gln Gln Lys Ser Pro Gly Ser Ala Pro Val Thr
    50                  55                  60

Val Ile Tyr Asn Asn Lys Arg Pro Ser Asn Ile Pro Ser Arg Phe
65                  70                  75                  80

Ser Gly Ser Lys Ser Gly Ser Thr Gly Thr Leu Thr Ile Thr Gly Val
                85                  90                  95

Gln Ala Glu Asp Glu Ala Val Tyr Phe Cys Gly Ser Glu Asp Ser Ser
            100                 105                 110

Thr Asp Ala Ile Phe Gly Ala Gly Thr Thr Leu Thr Val Leu Gly Gln
        115                 120                 125

Ser Ser Arg Ser Ser Ala Val Thr Leu Asp Glu Ser Gly Gly Gly Leu
    130                 135                 140

Gln Thr Pro Gly Gly Ala Leu Ser Leu Val Cys Lys Ala Ser Gly Phe
145                 150                 155                 160

Thr Phe Ser Ser Tyr Asp Met Gly Trp Val Arg Gln Ala Pro Gly Lys
                165                 170                 175

Gly Leu Glu Tyr Val Ala Gly Ile Thr Asn Asp Gly Arg Tyr Ala Ser
            180                 185                 190

Tyr Gly Ser Ala Val Asp Gly Arg Ala Thr Ile Ser Arg Asp Asn Gly
        195                 200                 205

```
Gln Ser Thr Val Arg Leu Gln Leu Asn Asn Leu Arg Ala Glu Asp Thr
    210                 215                 220

Gly Thr Tyr Tyr Cys Ala Arg Asn Asp Gly Ser Gly Trp Thr Gly Asn
225                 230                 235                 240

Thr Ile Asp Thr Trp Gly His Gly Thr Glu Val Ile Val Ser Ser Thr
                245                 250                 255

Ser Gly Gln Ala Gly Gln His His His His His Gly Ala Tyr Pro
            260                 265                 270

Tyr Asp Val Pro Asp Tyr Ala Ser
        275                 280

<210> SEQ ID NO 117
<211> LENGTH: 281
<212> TYPE: PRT
<213> ORGANISM: Artificial Sequence
<220> FEATURE:
<223> OTHER INFORMATION: recombinant protein

<400> SEQUENCE: 117

Met Lys Lys Thr Ala Ile Ala Ile Ala Val Ala Leu Ala Gly Phe Ala
1               5                   10                  15

Thr Val Ala Gln Ala Ala Leu Gly Pro Asp Ser Ala Val Leu Gly Val
            20                  25                  30

Ser Lys Pro Gly Glu Ala Leu Val Lys Thr Thr Cys Ser Gly Gly Gly
        35                  40                  45

Gly Ser Tyr Gly Trp Tyr Gln Gln Lys Ser Pro Gly Ser Ala Pro Val
    50                  55                  60

Thr Val Ile Tyr Tyr Asn Asp Lys Arg Pro Ser Asp Ile Pro Ser Arg
65                  70                  75                  80

Phe Ser Gly Ser Lys Ser Gly Ser Thr Gly Thr Leu Thr Ile Thr Gly
                85                  90                  95

Val Gln Ala Glu Asp Glu Ala Val Tyr Phe Cys Gly Ser Tyr Asp Ser
            100                 105                 110

Ser Thr Asp Thr Gly Ile Phe Gly Ala Gly Thr Thr Leu Thr Val Leu
        115                 120                 125

Gly Gln Ser Ser Arg Ser Ser Thr Val Thr Leu Asp Glu Ser Gly Gly
    130                 135                 140

Gly Leu Gln Thr Pro Gly Gly Ala Leu Ser Leu Val Cys Lys Ala Ser
145                 150                 155                 160

Gly Phe Ile Phe Ser Ser His Gly Met Gly Trp Met Arg Gln Ala Pro
                165                 170                 175

Gly Lys Gly Leu Glu Phe Val Ala Ala Ile Ser Lys Asp Gly Thr Ala
            180                 185                 190

Thr Tyr Tyr Gly Pro Ala Val Lys Gly Arg Ala Thr Ile Ser Arg Asp
        195                 200                 205

Asp Gly Gln Thr Thr Val Arg Leu Gln Leu Asn Asn Leu Arg Ala Glu
    210                 215                 220

Asp Thr Ala Thr Tyr Phe Cys Ala Lys Thr Lys Tyr Tyr Asn Ser Ala
225                 230                 235                 240

Gly Ile Ile Asp Ala Trp Gly His Gly Thr Glu Val Ile Val Ser Ser
                245                 250                 255

Thr Ser Gly Gln Ala Gly Gln His His His His His Gly Ala Tyr
            260                 265                 270

Pro Tyr Asp Val Pro Asp Tyr Ala Ser
        275                 280
```

<210> SEQ ID NO 118
<211> LENGTH: 285
<212> TYPE: PRT
<213> ORGANISM: Artificial Sequence
<220> FEATURE:
<223> OTHER INFORMATION: recombinant protein

<400> SEQUENCE: 118

Met Lys Lys Thr Ala Ile Ala Ile Ala Val Ala Leu Ala Gly Phe Ala
1               5                   10                  15

Thr Val Ala Gln Ala Ala Leu Ser Arg Pro Arg Val Ser Ala Asn Pro
            20                  25                  30

Gly Asp Pro Val Lys Ile Thr Cys Ser Gly Gly Ser Tyr Ala Gly
        35                  40                  45

Ser Tyr Tyr Tyr Gly Trp Tyr Gln Gln Lys Ala Pro Gly Ser Ala Pro
    50                  55                  60

Val Thr Val Ile Tyr Asp Asn Asn Gln Arg Pro Ser Asn Ile Pro Ser
65                  70                  75                  80

Arg Phe Ser Gly Ser Leu Ser Gly Ser Thr Gly Thr Leu Thr Ile Thr
                85                  90                  95

Gly Val Arg Ala Glu Asp Glu Ala Val Tyr Tyr Cys Gly Ser Phe Asp
            100                 105                 110

Ser Ser Thr Asp Ser Gly Tyr Ala Ala Ile Phe Gly Ala Gly Thr Thr
        115                 120                 125

Leu Thr Val Leu Gly Gln Ser Ser Arg Ser Ser Ala Val Thr Leu Asp
    130                 135                 140

Glu Ser Gly Gly Gly Leu Gln Thr Pro Gly Gly Gly Leu Ser Leu Val
145                 150                 155                 160

Cys Lys Ala Ser Gly Phe Thr Phe Ser Ser Tyr Ala Met Glu Trp Val
                165                 170                 175

Arg Gln Ala Pro Gly Lys Gly Leu Glu Trp Val Ala Tyr Ile Asn Ser
            180                 185                 190

Asp Gly Ser Ser Thr Trp Tyr Ala Thr Ala Val Lys Gly Arg Ala Thr
        195                 200                 205

Ile Ser Arg Asp Asn Gly Gln Ser Thr Val Arg Leu Gln Leu Asn Asn
    210                 215                 220

Leu Arg Gly Glu Asp Thr Ala Thr Tyr Phe Cys Ala Lys Thr Lys Tyr
225                 230                 235                 240

Tyr Asn Ser Ala Gly Ile Ile Asp Ala Trp Gly His Gly Thr Glu Val
                245                 250                 255

Ile Val Ser Ser Thr Ser Gly Gln Ala Gly Gln His His His His
            260                 265                 270

His Gly Ala Tyr Pro Tyr Asp Val Pro Asp Tyr Ala Ser
        275                 280                 285

<210> SEQ ID NO 119
<211> LENGTH: 195
<212> TYPE: PRT
<213> ORGANISM: Artificial Sequence
<220> FEATURE:
<223> OTHER INFORMATION: recombinant protein

<400> SEQUENCE: 119

Gly Ser Ser Gly Ser Tyr Gly Trp Tyr Gln Gln Lys Ser Pro Gly Ser
1               5                   10                  15

Ala Pro Val Thr Val Ile Tyr Tyr Asn Asp Lys Arg Pro Ser Asp Ile

```
                    20                  25                  30

Pro Ser Arg Phe Ser Gly Ser Thr Ser Gly Ser Thr Ala Thr Leu Thr
            35                  40                  45

Ile Thr Gly Val Gln Ala Glu Asp Glu Ala Val Tyr Phe Cys Gly Gly
 50                  55                  60

Tyr Asp Ser Asn Tyr Ile Gly Ile Phe Gly Ala Gly Thr Thr Leu Thr
 65                  70                  75                  80

Val Leu Gly Gln Ser Ser Arg Ser Ser Ala Val Thr Leu Asp Glu Ser
                85                  90                  95

Gly Gly Gly Leu Gln Thr Pro Arg Gly Ala Leu Ser Leu Val Cys Lys
            100                 105                 110

Ala Ser Gly Phe Thr Phe Ser Ser Tyr Ser Met Ala Trp Val Arg Gln
        115                 120                 125

Ala Pro Gly Lys Gly Leu Glu Phe Val Ala Gly Ile Gln Asn Asp Gly
    130                 135                 140

Ser Ile Thr Asp Tyr Gly Ser Ala Val Asp Gly Arg Ala Thr Ile Ser
145                 150                 155                 160

Arg Asp Asp Gly Gln Ser Thr Val Arg Leu Gln Leu Asn Asn Leu Arg
                165                 170                 175

Thr Glu Asp Thr Ala Thr Tyr Tyr Cys Ala Lys Thr Thr Val Ala Asp
            180                 185                 190

Gly Val Ile
        195

<210> SEQ ID NO 120
<211> LENGTH: 200
<212> TYPE: PRT
<213> ORGANISM: Artificial Sequence
<220> FEATURE:
<223> OTHER INFORMATION: recombinant protein

<400> SEQUENCE: 120

Ala Leu Thr Gln Pro Ser Ser Val Ser Ala Asn Pro Gly Asp Thr Val
 1               5                  10                  15

Lys Ile Thr Cys Ser Gly Asp Ser Ser Asp Tyr Gly Tyr Gly Trp Tyr
                20                  25                  30

Gln Gln Lys Ser Pro Gly Ser Ala Pro Val Thr Val Thr Tyr Ser Asn
            35                  40                  45

Asn Gln Arg Pro Ser Asp Ile Pro Ser Arg Phe Ser Gly Ser Ala Ser
        50                  55                  60

Gly Ser Thr Ala Thr Leu Thr Ile Thr Gly Val Gln Val Glu Asp Glu
 65                  70                  75                  80

Ala Val Tyr Tyr Cys Gly Ser Glu Asp Ser Thr Thr Asp Ala Val Phe
                85                  90                  95

Gly Ala Gly Thr Thr Leu Thr Val Leu Gly Gln Ser Ser Arg Ser Ser
            100                 105                 110

Ala Val Thr Leu Asp Glu Ser Gly Gly Gly Leu Gln Thr Pro Gly Gly
        115                 120                 125

Ala Leu Ser Leu Val Cys Lys Ala Ser Gly Phe Thr Phe Ser Ser Tyr
    130                 135                 140

Asp Met Gly Trp Val Arg Gln Ala Pro Gly Lys Gly Leu Glu Tyr Val
145                 150                 155                 160

Ala Gly Ile Thr Asn Asp Gly Arg Tyr Ala Ser Tyr Gly Ser Ala Val
                165                 170                 175

Asp Gly Arg Ala Thr Ile Ser Arg Asp Asn Gly Gln Ser Thr Val Arg
```

```
                180                 185                 190
Leu Gln Leu Asn Asn Pro Gln Gly
            195                 200
```

<210> SEQ ID NO 121
<211> LENGTH: 274
<212> TYPE: PRT
<213> ORGANISM: Artificial Sequence
<220> FEATURE:
<223> OTHER INFORMATION: recombinant protein

<400> SEQUENCE: 121

```
Met Lys Lys Thr Ala Ile Ala Ile Ala Val Ala Leu Ala Gly Phe Ala
1               5                   10                  15

Thr Val Ala Gln Ala Ala Leu Ser Arg Pro Arg Cys Gln Gln Thr Trp
            20                  25                  30

Gly Gly Thr Val Lys Ile Thr Cys Ser Gly Ser Ser Gly Ser Tyr Gly
        35                  40                  45

Trp Tyr Gln Gln Lys Ser Pro Gly Ser Ala Pro Val Thr Val Ile Tyr
    50                  55                  60

Gln Asn Asp Lys Arg Pro Ser Asp Ile Pro Ser Arg Phe Ser Gly Ser
65                  70                  75                  80

Thr Ser Gly Ser Thr Ala Thr Leu Thr Ile Thr Gly Val Gln Ala Asp
                85                  90                  95

Asp Glu Ala Val Tyr Phe Cys Gly Gly Tyr Asp Ser Ser Ala Gly Ile
            100                 105                 110

Phe Gly Ala Gly Thr Thr Leu Thr Val Leu Gly Gln Ser Ser Arg Ser
        115                 120                 125

Ser Ala Val Thr Leu Asp Glu Ser Gly Gly Gly Leu Gln Thr Pro Gly
    130                 135                 140

Gly Ala Leu Ser Leu Val Cys Lys Ala Ser Gly Phe Ser Ser Ser His
145                 150                 155                 160

Gly Met Gly Trp Met Arg Gln Ala Pro Gly Lys Gly Leu Glu Phe Val
                165                 170                 175

Ala Gly Ile Arg Ser Asp Gly Ser Ser Thr Ala Tyr Gly Ala Ala Val
            180                 185                 190

Asp Gly Arg Ala Thr Ile Ser Arg Asp Gly Gln Ser Thr Val Arg
        195                 200                 205

Leu Gln Leu Asn Asn Leu Arg Ala Glu Asp Thr Ala Thr Tyr Phe Cys
    210                 215                 220

Ala Lys Thr Asn Ser Tyr Asn Ser Ala Gly Ile Ile Asp Ala Trp Gly
225                 230                 235                 240

Pro Gly Thr Glu Val Ile Val Ser Ser Thr Ser Gly Gln Ala Gly Gln
                245                 250                 255

His His His His His His Gly Ala Tyr Pro Tyr Asp Val Pro Asp Tyr
            260                 265                 270

Ala Ser
```

<210> SEQ ID NO 122
<211> LENGTH: 170
<212> TYPE: PRT
<213> ORGANISM: Artificial Sequence
<220> FEATURE:
<223> OTHER INFORMATION: recombinant protein

<400> SEQUENCE: 122

```
Ile Tyr Asp Asn Thr Asn Arg Pro Ser Asn Ile Pro Ser Arg Phe Ser
```

```
            1               5                  10                 15
         Gly Ser Lys Ser Ser Thr His Thr Leu Thr Ile Thr Gly Val Gln
                        20                 25                 30
         Ala Glu Asp Glu Ala Val Tyr Tyr Cys Glu Ser Ala Asp Ser Ser
                        35                 40                 45
         Ser Ile Phe Gly Ala Gly Thr Thr Leu Thr Val Leu Gly Gln Ser Ser
             50                 55                 60
         Arg Ser Ser Ala Val Thr Leu Asp Glu Ser Gly Gly Gly Leu Gln Thr
         65                 70                 75                 80
         Pro Gly Gly Thr Leu Ser Leu Val Cys Lys Ala Ser Gly Phe Thr Phe
                        85                 90                 95
         Ser Ser Phe Asn Met Phe Trp Val Arg Gln Ala Pro Gly Lys Gly Leu
                        100                105                110
         Glu Phe Val Ala Gly Ile Gly Asn Thr Gly Arg Ser Thr Gly Tyr Gly
                        115                120                125
         Ser Ala Val Lys Gly Arg Ala Thr Ile Ser Arg Asp Asn Gly Gln Ser
                        130                135                140
         Thr Val Arg Leu Gln Leu Asn Asn Leu Arg Ala Glu Asp Thr Gly Thr
         145                150                155                160
         Tyr Tyr Cys Ala Lys Ala Tyr Gly Asp Ser
                        165                170

<210> SEQ ID NO 123
<211> LENGTH: 278
<212> TYPE: PRT
<213> ORGANISM: Artificial Sequence
<220> FEATURE:
<223> OTHER INFORMATION: recombinant protein

<400> SEQUENCE: 123

Met Lys Lys Thr Ala Ile Ala Ile Ala Val Ala Leu Ala Gly Phe Ala
1               5                  10                 15

Thr Val Ala Gln Ala Ala Leu Thr Gln Pro Ser Ser Val Ser Ala Ser
                20                 25                 30

Leu Gly Thr Phe Leu Glu Ile Thr Cys Ser Gly Ser Ser Gly Thr Tyr
            35                 40                 45

Gly Trp Tyr Gln Gln Lys Ser Pro Gly Ser Ala Pro Val Thr Val Ile
        50                 55                 60

Tyr Gln Asn Gly Lys Arg Pro Ser Asn Ile Pro Ser Arg Phe Ser Gly
65              70                 75                 80

Ser Lys Ser Gly Ser Thr Ala Thr Leu Thr Ile Thr Gly Val Gln Ala
                85                 90                 95

Asp Asp Glu Ala Val Tyr Phe Cys Gly Gly Tyr Asp Ser Ser Thr Tyr
                100                105                110

Val Gly Ile Phe Gly Ala Gly Thr Thr Leu Thr Val Leu Gly Gln Ser
            115                120                125

Ser Arg Ser Ser Ala Val Thr Leu Asp Glu Ser Gly Gly Gly Leu Gln
            130                135                140

Thr Pro Gly Gly Ala Leu Ser Leu Val Cys Lys Ala Ser Gly Phe Asp
145                150                155                160

Phe Ser Ser Tyr Gly Met Gly Trp Met Arg Gln Ala Pro Gly Lys Gly
                165                170                175

Leu Glu Phe Val Ala Ala Ile Arg Lys Asp Gly Ser Tyr Thr Ala Tyr
                180                185                190

Gly Ala Ala Val Asp Gly Arg Ala Thr Ile Ser Arg Asp Asp Gly Gln
```

```
                195                 200                 205
Ser Thr Val Arg Leu Gln Leu Gly Asn Leu Arg Ala Glu Asp Thr Ala
    210                 215                 220

Thr Tyr Phe Cys Ala Lys Thr Asn Ser Tyr Asn Ser Ala Gly Ile Ile
225                 230                 235                 240

Asp Ala Trp Gly His Gly Thr Glu Val Ile Val Ser Ser Thr Ser Gly
                245                 250                 255

Gln Ala Gly Gln His His His His His Gly Ala Tyr Pro Tyr Asp
            260                 265                 270

Val Pro Asp Tyr Ala Ser
        275

<210> SEQ ID NO 124
<211> LENGTH: 275
<212> TYPE: PRT
<213> ORGANISM: Artificial Sequence
<220> FEATURE:
<223> OTHER INFORMATION: recombinant protein

<400> SEQUENCE: 124

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Ala Leu Phe Lys Ile Thr Cys Ser Gly Gly Ser Ser Asn
        35                  40                  45

Asn Tyr Gly Trp His Gln Gln Lys Ala Pro Gly Ser Ala Pro Val Thr
    50                  55                  60

Val Ile Tyr Asp Asn Thr Asn Arg Pro Ser Asn Ile Pro Ser Arg Phe
65                  70                  75                  80

Ser Gly Ser Lys Ser Ser Ser Thr His Thr Leu Thr Ile Thr Gly Val
                85                  90                  95

Gln Ala Glu Asp Glu Ala Val Tyr Tyr Cys Ser Ala Asp Ser Ser
            100                 105                 110

Ser Ser Ile Phe Gly Ala Gly Thr Thr Leu Thr Val Leu Gly Gln Ser
        115                 120                 125

Ser Arg Ser Ser Thr Val Thr Leu Asp Glu Ser Gly Gly Gly Leu Gln
    130                 135                 140

Thr Pro Gly Gly Ala Leu Ser Leu Val Cys Lys Ala Ser Gly Phe Thr
145                 150                 155                 160

Phe Ser Ser Phe Asn Met Phe Trp Val Arg Gln Ala Pro Gly Lys Gly
                165                 170                 175

Leu Glu Phe Val Ala Gly Ile Gly Asn Thr Gly Gly Ser Thr Gly Tyr
            180                 185                 190

Gly Ser Ala Val Lys Gly Arg Ala Thr Ile Ser Arg Asp Asn Gly Gln
        195                 200                 205

Ser Thr Val Arg Leu Gln Leu Asn Asn Leu Arg Ala Glu Asp Thr Gly
    210                 215                 220

Thr Tyr Tyr Cys Ala Lys Ala Tyr Gly Asp Ser Asn Ile Asp Thr Trp
225                 230                 235                 240

Gly His Gly Thr Glu Val Ile Val Ser Ser Thr Ser Gly Gln Ala Gly
                245                 250                 255

Gln His His His His His Gly Ala Tyr Pro Tyr Asp Val Pro Asp
            260                 265                 270

Tyr Ala Ser
```

-continued

```
                275

<210> SEQ ID NO 125
<211> LENGTH: 278
<212> TYPE: PRT
<213> ORGANISM: Artificial Sequence
<220> FEATURE:
<223> OTHER INFORMATION: recombinant protein

<400> SEQUENCE: 125

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Glu Ile Thr Cys Ser Gly Gly Gly Ser Tyr
        35                  40                  45

Gly Trp Phe Gln Gln Lys Ser Pro Gly Ser Ala Pro Val Thr Val Ile
    50                  55                  60

Tyr Glu Ser Thr Lys Arg Pro Ser Asn Ile Pro Ser Arg Phe Ser Gly
65                  70                  75                  80

Ser Gly Ser Gly Ser Thr Ser Thr Leu Thr Ile Thr Gly Val Arg Ala
                85                  90                  95

Glu Asp Glu Ala Val Tyr Tyr Cys Gly Gly Tyr Asp Gly Ser Ser Asp
            100                 105                 110

Ala Ile Phe Gly Ala Gly Thr Thr Leu Thr Val Leu Gly Gln Ser Ser
        115                 120                 125

Arg Ser Ser Thr Val Thr Leu Asp Glu Ser Gly Gly Gly Leu Gln Thr
130                 135                 140

Pro Gly Gly Ala Leu Ser Leu Val Cys Lys Ala Ser Gly Phe Thr Phe
145                 150                 155                 160

Ser Ser His Asp Met Gly Trp Val Arg Gln Ala Pro Gly Lys Gly Leu
                165                 170                 175

Glu Tyr Val Ala Gly Ile Thr Asp Asp Gly Arg Tyr Ala Ser Tyr Gly
            180                 185                 190

Pro Ala Val Asp Gly Arg Ala Thr Ile Ser Arg Asp Asn Gly Gln Ser
        195                 200                 205

Thr Val Arg Leu Gln Leu Lys Asn Leu Arg Ala Glu Asp Thr Ala Thr
    210                 215                 220

Tyr Tyr Cys Ala Arg Asp Asp Gly Ser Gly Trp Ser Gly Asp Thr Ile
225                 230                 235                 240

Asp Thr Trp Gly His Gly Thr Glu Val Ile Val Ser Ser Thr Ser Gly
                245                 250                 255

Gln Ala Gly Gln His His His His His Gly Ala Tyr Pro Tyr Asp
            260                 265                 270

Val Pro Asp Tyr Ala Ser
        275

<210> SEQ ID NO 126
<211> LENGTH: 294
<212> TYPE: PRT
<213> ORGANISM: Artificial Sequence
<220> FEATURE:
<223> OTHER INFORMATION: recombinant protein

<400> SEQUENCE: 126

Met Lys Lys Thr Ala Ile Ala Ile Ala Val Ala Leu Ala Gly Phe Ala
1               5                   10                  15
```

```
Thr Val Ala Gln Ala Ala Leu Pro Gly Val Arg His Arg Asp Pro Gly
             20                  25                  30

Gly Pro Asp Ser Ala Val Leu Gly Val Ser Lys Pro Arg Arg Asn Asp
         35                  40                  45

Lys Ile Thr Cys Ser Gly Gly Ser Tyr Ala Gly Ser Tyr Tyr Tyr
 50                  55                  60

Gly Trp Tyr Gln Gln Lys Ala Pro Gly Ser Ala Pro Val Thr Leu Ile
 65                  70                  75                  80

Tyr Asp Asn Thr Asn Arg Pro Ser Asn Ile Pro Ser Arg Phe Ser Gly
                 85                  90                  95

Ser Leu Ser Gly Ser Thr Gly Thr Leu Thr Ile Thr Gly Val Arg Ala
            100                 105                 110

Glu Asp Glu Ala Val Tyr Tyr Cys Gly Ser Phe Asp Ser Ser Thr Asp
            115                 120                 125

Gly Gly Tyr Ala Ala Ile Phe Gly Ala Gly Thr Thr Leu Thr Val Leu
        130                 135                 140

Gly Gln Ser Ser Arg Ser Ser Ala Val Thr Leu Asp Glu Ser Gly Gly
145                 150                 155                 160

Gly Leu Gln Thr Pro Gly Gly Gly Leu Ser Leu Val Cys Lys Ala Ser
                165                 170                 175

Glu Phe Thr Phe Ser Ser Tyr Ala Met Glu Trp Val Arg Gln Ala Pro
            180                 185                 190

Gly Lys Gly Leu Glu Trp Val Ala Tyr Ile Asn Ser Asp Gly Ser Ser
                195                 200                 205

Thr Trp Tyr Ala Pro Ala Val Lys Gly Arg Ala Thr Ile Ser Arg Asp
210                 215                 220

Asn Gly Gln Ser Thr Val Arg Leu Gln Leu Asn Ser Leu Arg Ala Glu
225                 230                 235                 240

Asp Thr Ala Thr Tyr Tyr Cys Thr Arg Gly Ser Gly Gly Glu Asn Ile
                245                 250                 255

Asp Thr Trp Gly His Gly Thr Glu Val Ile Val Ser Ser Thr Ser Gly
            260                 265                 270

Gln Ala Gly Gln His His His His His Gly Ala Tyr Pro Tyr Asp
        275                 280                 285

Val Pro Asp Tyr Ala Ser
        290

<210> SEQ ID NO 127
<211> LENGTH: 280
<212> TYPE: PRT
<213> ORGANISM: Artificial Sequence
<220> FEATURE:
<223> OTHER INFORMATION: recombinant protein

<400> SEQUENCE: 127

Met Lys Lys Thr Ala Ile Ala Ile Ala Val Ala Leu Ala Gly Phe Ala
 1               5                  10                  15

Thr Val Ala Gln Ala Ala Leu Thr Gln Pro Ser Ser Val Ser Ala Asn
             20                  25                  30

Pro Gly Glu Thr Val Lys Ile Thr Cys Ser Gly Gly Ser Tyr Asn Ala
         35                  40                  45

Tyr Gly Trp Tyr Gln Gln Lys Ser Pro Ala Gly Ala Pro Val Thr Leu
     50                  55                  60

Ile Tyr Asp Asn Thr Asn Arg Pro Ser Asn Ile Pro Ser Arg Phe Ser
 65                  70                  75                  80
```

Gly Ser Lys Ser Gly Ser Thr His Thr Leu Thr Ile Thr Gly Val Gln
                85                  90                  95

Ala Asp Asp Glu Ala Val Tyr Phe Cys Gly Gly Tyr Asp Ser Asn Ala
            100                 105                 110

Asp Asp Gly Ile Phe Gly Ala Gly Thr Thr Leu Thr Val Leu Gly Gln
            115                 120                 125

Ser Ser Arg Ser Ser Thr Val Thr Leu Asp Glu Ser Gly Gly Gly Leu
            130                 135                 140

Gln Thr Pro Gly Gly Thr Leu Ser Leu Val Cys Lys Ala Ser Gly Phe
145                 150                 155                 160

Thr Phe Ser Ser Tyr Ala Met Asn Trp Met Arg Gln Ala Pro Gly Lys
                165                 170                 175

Gly Leu Glu Trp Val Ala Gly Ile Tyr Ser Asp Gly Arg Tyr Thr Asn
            180                 185                 190

Tyr Gly Ala Ala Val Lys Gly Arg Ala Thr Ile Ser Arg Asp Asn Gly
            195                 200                 205

Gln Ser Ser Val Arg Leu Gln Leu Asn Asn Leu Arg Ala Glu Asp Thr
            210                 215                 220

Ala Thr Tyr Tyr Cys Thr Lys Ser Ala Asp Ser Asp Tyr Gly Cys Asp
225                 230                 235                 240

Asn Ile Asp Ala Trp Gly His Gly Thr Glu Val Ile Val Ser Ser Thr
                245                 250                 255

Ser Gly Gln Ala Gly Gln His His His His His Gly Ala Tyr Pro
            260                 265                 270

Tyr Asp Val Pro Asp Tyr Ala Ser
            275                 280

<210> SEQ ID NO 128
<211> LENGTH: 291
<212> TYPE: PRT
<213> ORGANISM: Artificial Sequence
<220> FEATURE:
<223> OTHER INFORMATION: recombinant protein

<400> SEQUENCE: 128

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Lys Ile Thr Cys Ser Gly Gly Gly Ser Tyr Val
            35                  40                  45

Gly Ser Tyr Tyr Tyr Gly Trp Tyr Gln Gln Lys Ser Pro Val Ser Ala
            50                  55                  60

Pro Val Thr Leu Ile Tyr Glu Ser Thr Lys Arg Pro Ser Asn Ile Pro
65                  70                  75                  80

Ser Arg Phe Ser Gly Ser Thr Ser Gly Ser Met Gly Thr Leu Thr Ile
                85                  90                  95

Thr Gly Val Gln Ala Glu Asp Glu Ala Val Tyr Phe Cys Gly Ser Phe
            100                 105                 110

Asp Ser Ser Ser Ser Val Ser Asp Thr Ala Asp Ile Phe Gly Ala
            115                 120                 125

Gly Thr Thr Leu Thr Val Leu Gly Gln Ser Ser Arg Ser Ser Thr Val
            130                 135                 140

Thr Leu Asp Glu Ser Gly Gly Gly Leu Gln Thr Pro Gly Gly Ala Leu
145                 150                 155                 160

```
Ser Leu Val Cys Lys Ala Ser Gly Phe Thr Phe Asn Ser Tyr Ala Leu
            165                 170                 175

Glu Trp Val Arg Gln Ala Pro Gly Lys Gly Leu Glu Trp Val Ala Gly
        180                 185                 190

Ile Ser Gly Asp Gly Ser Phe Thr His Tyr Gly Ser Ala Val Lys Gly
        195                 200                 205

Arg Ala Thr Ile Ser Arg Asp Asn Gly Gln Ser Thr Val Arg Leu His
210                 215                 220

Leu Asn Asn Leu Arg Ala Glu Asp Thr Ala Thr Tyr Tyr Cys Ala Lys
225                 230                 235                 240

Ser Thr Gly Ser Gly Ala Gly Trp Gly Ala Ser Asn Ile Asp Ala Trp
            245                 250                 255

Gly His Gly Thr Glu Val Ile Val Ser Ser Thr Ser Gly Gln Ala Gly
            260                 265                 270

Gln His His His His His Gly Ala Tyr Pro Tyr Asp Val Pro Asp
            275                 280                 285

Tyr Ala Ser
    290

<210> SEQ ID NO 129
<211> LENGTH: 281
<212> TYPE: PRT
<213> ORGANISM: Artificial Sequence
<220> FEATURE:
<223> OTHER INFORMATION: recombinant protein

<400> SEQUENCE: 129

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Lys Ile Thr Cys Ser Gly Ser Ser Asp Ala Tyr
        35                  40                  45

Gly Trp Tyr Gln Gln Lys Ser Pro Gly Ser Ala Pro Val Thr Leu Ile
    50                  55                  60

Tyr Asp Asn Thr Asn Arg Pro Pro Asp Ile Pro Ser Arg Phe Ser Gly
65                  70                  75                  80

Ala Leu Ser Gly Ser Thr Ser Thr Leu Thr Ile Thr Gly Val Arg Ala
                85                  90                  95

Glu Asp Glu Ala Val Tyr Tyr Cys Gly Ser Ala Asp Ile Thr Tyr Ile
            100                 105                 110

Gly Ile Phe Gly Ala Gly Thr Thr Leu Thr Val Leu Gly Gln Ser Ser
        115                 120                 125

Arg Ser Ser Thr Val Thr Leu Asp Glu Ser Gly Gly Gly Leu Gln Thr
130                 135                 140

Pro Gly Gly Gly Leu Ser Leu Val Cys Lys Ala Ser Gly Phe Thr Phe
145                 150                 155                 160

Ser Ser His Thr Met Gln Trp Val Arg Gln Ala Pro Gly Lys Gly Leu
                165                 170                 175

Glu Trp Val Ala Glu Ile Ser Ala Asp Gly Ser Tyr Thr Thr Tyr Tyr
            180                 185                 190

Gly Ala Ala Val Lys Gly Arg Ala Thr Ile Ser Arg Asp Asn Gly Gln
        195                 200                 205

Ser Thr Val Arg Leu Gln Leu Asn Asn Leu Arg Ala Glu Asp Thr Ala
    210                 215                 220
```

Thr Tyr Phe Cys Ala Lys Ser Gly Tyr Gly Ala Gly Trp Gly Ala
225                 230                 235                 240

Gly Leu Ile Asp Ala Trp Gly His Gly Thr Glu Val Ile Val Ser Ser
            245                 250                 255

Thr Ser Gly Gln Ala Gly Gln His His His His His Gly Ala Tyr
        260                 265                 270

Pro Tyr Asp Val Pro Asp Tyr Ala Ser
    275                 280

<210> SEQ ID NO 130
<211> LENGTH: 277
<212> TYPE: PRT
<213> ORGANISM: Artificial Sequence
<220> FEATURE:
<223> OTHER INFORMATION: recombinant protein

<400> SEQUENCE: 130

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Lys Ile Thr Cys Ser Gly Gly Ser Gly Ser Tyr
        35                  40                  45

Gly Trp Tyr Gln Gln Glu Ser Pro Gly Ser Ala Pro Val Thr Val Ile
    50                  55                  60

Tyr Tyr Asn Asp Lys Arg Pro Ser Asp Ile Pro Ser Arg Phe Ser Gly
65                  70                  75                  80

Ser Ala Ser Gly Ser Thr Ala Thr Leu Thr Ile Ala Gly Val Arg Ala
                85                  90                  95

Glu Asp Glu Ala Val Tyr Phe Cys Gly Ser Trp Asp Ser Ser Thr Ser
            100                 105                 110

Ala Gly Ile Phe Gly Ala Gly Thr Ala Leu Thr Val Leu Gly Gln Ser
        115                 120                 125

Ser Arg Ser Ser Ala Val Thr Leu Asp Glu Ser Gly Gly Gly Leu Gln
    130                 135                 140

Thr Pro Gly Gly Gly Leu Ser Leu Val Cys Lys Ala Ser Gly Phe Ser
145                 150                 155                 160

Ser Ser His Gly Met Gly Trp Met Arg Gln Ala Pro Gly Lys Gly Leu
                165                 170                 175

Glu Phe Val Ala Gly Ile Arg Ser Asp Gly Ser Ser Thr Ala Tyr Gly
            180                 185                 190

Ala Ala Val Asp Gly Arg Ala Thr Ile Thr Arg Asp Asp Gly Gln Ser
        195                 200                 205

Thr Val Thr Leu Gln Leu Asn Asn Leu Arg Ala Glu Asp Thr Ala Thr
    210                 215                 220

Tyr Phe Cys Ala Lys Thr Asn Ser Tyr Asn Ser Ala Gly Ile Ile Asp
225                 230                 235                 240

Ala Trp Gly His Gly Thr Glu Val Ile Val Ser Ser Thr Ser Gly Gln
                245                 250                 255

Ala Gly Gln His His His His His Gly Ala Tyr Pro Tyr Asp Val
            260                 265                 270

Pro Asp Tyr Ala Ser
    275

<210> SEQ ID NO 131
<211> LENGTH: 286

<212> TYPE: PRT
<213> ORGANISM: Artificial Sequence
<220> FEATURE:
<223> OTHER INFORMATION: recombinant protein

<400> SEQUENCE: 131

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Leu Gly Gly Thr Val Glu Ile Thr Cys Ser Gly Ser Gly Gly Ser Tyr
        35                  40                  45

Gly Tyr Tyr Gly Trp Tyr Gln Gln Lys Ala Pro Gly Ser Ala Pro Val
    50                  55                  60

Thr Val Ile Tyr Asp Asn Thr Asn Arg Pro Ser Asn Ile Pro Ser Arg
65                  70                  75                  80

Phe Ser Gly Ser Ala Ser Gly Ser Thr Gly Thr Leu Thr Ile Thr Gly
                85                  90                  95

Val Arg Ala Glu Asp Glu Ala Val Tyr Phe Cys Gly Tyr Tyr Asp Ser
            100                 105                 110

Ser Asn Thr Asp Ala Phe Gly Ala Gly Thr Thr Leu Thr Val Leu Gly
        115                 120                 125

Gln Ser Ser Arg Ser Ser Thr Val Thr Leu Asp Glu Ser Gly Gly Gly
    130                 135                 140

Leu Gln Thr Pro Gly Arg Ala Leu Ser Leu Val Cys Lys Ala Ser Gly
145                 150                 155                 160

Phe Thr Phe Ser Ser Tyr Thr Met Gly Trp Val Arg Gln Ala Pro Gly
                165                 170                 175

Lys Gly Leu Glu Phe Val Ala Gly Ile Gly Asn Thr Gly Arg Tyr Thr
            180                 185                 190

Gly Tyr Gly Ser Ala Val Lys Gly Arg Ala Thr Ile Ser Arg Asp Asn
        195                 200                 205

Gly Gln Ser Thr Val Arg Leu Gln Leu Asn Asn Leu Arg Ala Glu Asp
    210                 215                 220

Thr Gly Thr Tyr Tyr Cys Thr Lys Cys Ala Tyr Gly Tyr Tyr Tyr Ser
225                 230                 235                 240

Trp Gly Asn Ile Ala Gly Ser Ile Asp Ala Trp Gly His Gly Thr Glu
                245                 250                 255

Val Ile Val Ser Ser Thr Ser Gly Gln Ala Gly Gln His His His His
            260                 265                 270

His His Gly Ala Tyr Pro Tyr Asp Val Pro Asp Tyr Ala Ser
        275                 280                 285

<210> SEQ ID NO 132
<211> LENGTH: 280
<212> TYPE: PRT
<213> ORGANISM: Artificial Sequence
<220> FEATURE:
<223> OTHER INFORMATION: recombinant protein

<400> SEQUENCE: 132

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Ala Val Lys Ile Thr Cys Ser Gly Ser Ser Gly Ser Tyr
        35                  40                  45

Gly Trp Tyr Gln Gln Lys Ser Pro Gly Ser Ala Pro Val Thr Val Ile
                50                  55                  60

Tyr Tyr Asn Asp Lys Arg Pro Ser Asp Ile Pro Ser Arg Phe Ser Gly
 65                  70                  75                  80

Ser Thr Ser Gly Ser Thr Ser Thr Leu Thr Ile Thr Gly Val Gln Ala
                    85                  90                  95

Glu Asp Glu Ala Val Tyr Phe Cys Gly Gly Tyr Asp Ser Asn Tyr Leu
                100                 105                 110

Gly Ile Phe Gly Ala Gly Thr Thr Leu Thr Val Leu Gly Gln Ser Ser
            115                 120                 125

Arg Ser Ser Ala Val Thr Leu Asp Glu Ser Gly Gly Gly Leu Gln Thr
130                 135                 140

Pro Arg Gly Ala Leu Ser Leu Val Cys Lys Ala Ser Gly Phe Thr Phe
145                 150                 155                 160

Ser Ser Tyr Ser Met Ala Trp Val Arg Gln Ala Pro Gly Lys Gly Leu
                165                 170                 175

Glu Phe Val Ala Gly Ile Gln Asn Asp Gly Ser Ile Thr Asp Tyr Gly
                180                 185                 190

Ser Ala Val Asp Gly Arg Ala Thr Ile Ser Arg Asp Asp Gly Gln Ser
            195                 200                 205

Thr Val Arg Leu Gln Leu Asn Asn Leu Arg Thr Glu Asp Thr Ala Thr
210                 215                 220

Tyr Tyr Cys Ala Lys Thr Thr Val Ala Asp Gly Val Ile Gly Ala Tyr
225                 230                 235                 240

Gly Ile Asp Ala Trp Gly His Gly Thr Glu Val Ile Val Ser Ser Thr
                245                 250                 255

Ser Gly Gln Ala Gly Gln His His His His His Gly Ala Tyr Pro
            260                 265                 270

Tyr Asp Val Pro Asp Tyr Ala Ser
            275                 280

<210> SEQ ID NO 133
<211> LENGTH: 280
<212> TYPE: PRT
<213> ORGANISM: Artificial Sequence
<220> FEATURE:
<223> OTHER INFORMATION: recombinant protein

<400> SEQUENCE: 133

Met Lys Lys Thr Ala Ile Ala Ile Ala Val Ala Leu Ala Gly Phe Ala
 1               5                  10                  15

Thr Val Ala Gln Ala Ala Leu Thr Gln Pro Ser Ser Val Ser Ala Asn
                20                  25                  30

Pro Gly Glu Thr Val Lys Ile Thr Cys Ser Gly Asp Ser Ser Asp Tyr
            35                  40                  45

Gly Tyr Gly Trp Tyr Gln Gln Lys Ser Pro Gly Ser Ala Pro Val Thr
    50                  55                  60

Val Thr Tyr Ser Asn Asn Gln Arg Pro Pro Asn Ile Pro Ser Arg Phe
 65                  70                  75                  80

Ser Gly Ser Ala Ser Gly Ser Thr Ala Thr Leu Thr Ile Thr Gly Val
                85                  90                  95

Gln Val Glu Asp Glu Ala Val Tyr Tyr Cys Gly Ser Glu Asp Ser Thr
                100                 105                 110

Thr Asp Ala Val Phe Gly Ala Gly Thr Thr Leu Thr Val Leu Gly Gln
            115                 120                 125

```
Ser Ser Arg Ser Ser Ala Met Thr Leu Asp Glu Ser Gly Gly Gly Leu
        130                 135                 140

Gln Thr Pro Gly Gly Ala Leu Ser Leu Val Cys Lys Ala Ser Gly Phe
145                 150                 155                 160

Thr Phe Ser Ser Tyr Asp Met Gly Trp Val Arg Gln Ala Pro Gly Lys
                165                 170                 175

Gly Leu Glu Tyr Val Ala Gly Ile Thr Asn Asp Gly Arg Tyr Ala Ser
            180                 185                 190

Tyr Gly Ser Ala Val Asp Gly Arg Ala Thr Ile Ser Arg Asp Asn Gly
        195                 200                 205

Gln Ser Thr Val Arg Leu Gln Leu Asn Asn Leu Arg Ala Glu Asp Thr
    210                 215                 220

Gly Thr Tyr Tyr Cys Ala Arg Asp Asp Gly Ser Gly Trp Thr Gly Asn
225                 230                 235                 240

Thr Ile Asp Thr Trp Gly His Gly Thr Glu Val Ile Val Ser Ser Thr
                245                 250                 255

Ser Gly Gln Ala Gly Gln His His His His His Gly Ala Tyr Pro
            260                 265                 270

Tyr Asp Val Pro Asp Tyr Ala Ser
        275                 280

<210> SEQ ID NO 134
<211> LENGTH: 283
<212> TYPE: PRT
<213> ORGANISM: Artificial Sequence
<220> FEATURE:
<223> OTHER INFORMATION: recombinant protein

<400> SEQUENCE: 134

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Lys Ile Thr Cys Ser Gly Gly Gly Ser Tyr Ala
        35                  40                  45

Gly Ser Tyr Tyr Tyr Gly Trp Tyr Gln Gln Lys Ala Pro Gly Ser Ala
    50                  55                  60

Pro Val Thr Leu Ile Tyr Asp Asn Thr Asn Arg Pro Ser Asn Ile Pro
65                  70                  75                  80

Ser Arg Phe Ser Gly Ser Leu Ser Gly Ser Pro Gly Thr Leu Ala Ile
                85                  90                  95

Thr Gly Val Arg Ala Glu Asp Glu Ala Val Tyr Tyr Cys Gly Ser Phe
            100                 105                 110

His Ser Thr Asp Gly Gly Tyr Ala Ala Ile Phe Gly Ala Gly Thr
        115                 120                 125

Thr Leu Thr Val Leu Gly Gln Thr Ser Arg Ser Ser Ala Val Thr Leu
    130                 135                 140

Asp Glu Ser Gly Gly Gly Leu Gln Thr Pro Gly Gly Leu Ser Leu
145                 150                 155                 160

Leu Cys Lys Ala Ser Glu Phe Thr Ser Ile Ser Tyr Ala Met Glu Trp
                165                 170                 175

Val Arg Gln Ala Pro Gly Lys Gly Leu Glu Trp Val Ala Tyr Ile Asn
            180                 185                 190

Ser Asp Gly Ser Ser Thr Trp His Ala Pro Ala Val Lys Gly Arg Ala
        195                 200                 205
```

```
Thr Ile Ser Arg Asp Asn Gly Gln Ser Thr Val Arg Leu Gln Leu Asn
    210                 215                 220

Ser Leu Arg Ala Glu Asp Thr Ala Thr Tyr Tyr Cys Thr Ile Cys Ser
225                 230                 235                 240

Gly Gly Glu Asn Ile Tyr Thr Cys Cys His Gly Thr Glu Val Ile Val
                245                 250                 255

Ser Ser Thr Ser Gly Gln Asp Gly Gln His His His His His Gly
            260                 265                 270

Ala Tyr Pro Tyr Asp Val Pro Asp Tyr Ala Ser
            275                 280

<210> SEQ ID NO 135
<211> LENGTH: 281
<212> TYPE: PRT
<213> ORGANISM: Artificial Sequence
<220> FEATURE:
<223> OTHER INFORMATION: recombinant protein

<400> SEQUENCE: 135

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
                20                  25                  30

Leu Gly Gly Thr Val Lys Leu Thr Cys Ser Gly Gly Ser Ser Tyr Gly
            35                  40                  45

Tyr Ser Trp His Gln Gln Lys Ser Pro Gly Ser Ala Pro Val Thr Val
        50                  55                  60

Ile Tyr Ser Asn Asp Lys Arg Pro Ser Asp Ile Pro Ser Arg Phe Ser
65                  70                  75                  80

Gly Ser Ala Ser Gly Ser Thr Ala Thr Leu Thr Ile Thr Gly Val Gln
                85                  90                  95

Val Glu Asp Glu Ala Val Tyr Phe Cys Gly Ser Tyr Asp Ser Ser Ser
                100                 105                 110

Ile Ala Gly Ile Phe Gly Ala Gly Thr Thr Leu Thr Val Leu Gly Gln
            115                 120                 125

Ser Ser Arg Phe Ser Thr Val Thr Leu Asp Glu Ser Gly Gly Gly Leu
130                 135                 140

Gln Thr Pro Gly Gly Leu Ser Leu Val Cys Lys Ala Ser Gly Phe
145                 150                 155                 160

Thr Phe Ser Ser Tyr Gly Met Ala Trp Val Arg Gln Ala Pro Gly Lys
                165                 170                 175

Gly Leu Glu Trp Leu Ala Gly Ile Tyr Arg Asp Asp Asp Ser Thr Tyr
            180                 185                 190

Tyr Ala Pro Ala Val Lys Gly Arg Ala Thr Ile Ser Arg Asp Asn Gly
        195                 200                 205

Gln Ser Thr Val Arg Leu Gln Leu Asn Asn Leu Arg Thr Glu Asp Thr
    210                 215                 220

Ala Thr Tyr Tyr Cys Ala Lys Glu Ser Ala Ser Gly Gly Trp Asn Ala
225                 230                 235                 240

Gly Trp Ile Asp Ala Trp Gly His Gly Thr Glu Val Ile Val Ser Ser
                245                 250                 255

Thr Ser Gly Gln Ala Gly Gln His His His His His Gly Ala Tyr
            260                 265                 270

Pro Tyr Asp Val Pro Asp Tyr Ala Ser
        275                 280
```

<210> SEQ ID NO 136
<211> LENGTH: 280
<212> TYPE: PRT
<213> ORGANISM: Artificial Sequence
<220> FEATURE:
<223> OTHER INFORMATION: recombinant protein

<400> SEQUENCE: 136

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Lys Leu Thr Cys Ser Gly Asp Ser Ser Asp Tyr
        35                  40                  45

Gly Tyr Gly Trp Tyr Gln Gln Lys Ser Pro Gly Ser Ala Pro Val Thr
    50                  55                  60

Val Ile Tyr Asn Asn Asn Lys Arg Pro Ser Asp Ile Pro Ser Arg Phe
65                  70                  75                  80

Ser Gly Ser Lys Ser Gly Ser Thr Gly Thr Leu Thr Ile Ser Gly Val
                85                  90                  95

Gln Ala Glu Asp Glu Ala Val Tyr Phe Cys Gly Ser Glu Asp Ser Asn
            100                 105                 110

Thr Asp Ala Ile Phe Gly Ala Gly Thr Thr Leu Thr Val Leu Gly Gln
        115                 120                 125

Ser Ser Arg Ser Ser Ala Val Thr Leu Asp Glu Ser Gly Gly Gly Leu
    130                 135                 140

Gln Thr Pro Gly Gly Ala Leu Ser Leu Val Cys Glu Ala Ser Gly Phe
145                 150                 155                 160

Thr Phe Ser Ser Tyr Asp Met Gly Trp Ile Arg Gln Ala Pro Gly Lys
                165                 170                 175

Gly Leu Glu Tyr Val Ala Gly Ile Thr Ser Asn Gly Arg Tyr Ala Ser
            180                 185                 190

Tyr Gly Ser Ala Val Asp Gly Arg Ala Thr Ile Ser Arg Asp Asn Gly
        195                 200                 205

Gln Ser Thr Val Arg Leu Gln Leu Asn Asn Leu Arg Ala Glu Asp Thr
    210                 215                 220

Gly Thr Tyr Tyr Cys Ala Arg Asp Asp Gly Ser Gly Trp Thr Gly Asn
225                 230                 235                 240

Thr Ile Asp Ala Trp Gly His Gly Thr Glu Val Ile Val Ser Ser Thr
                245                 250                 255

Ser Gly Gln Ala Gly Gln His His His His His Gly Ala Tyr Pro
            260                 265                 270

Tyr Asp Val Pro Asp Tyr Ala Ser
        275                 280

<210> SEQ ID NO 137
<211> LENGTH: 280
<212> TYPE: PRT
<213> ORGANISM: Artificial Sequence
<220> FEATURE:
<223> OTHER INFORMATION: recombinant protein

<400> SEQUENCE: 137

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn

```
                    20                  25                  30
Leu Gly Gly Thr Val Lys Ile Thr Cys Ser Gly Gly Ser Gly Ser Tyr
                35                  40                  45
Gly Trp Tyr Gln Gln Lys Ser Pro Gly Ser Ala Pro Val Thr Val Ile
        50                  55                  60
Tyr Tyr Asn Asp Gln Arg Pro Ser Asp Ile Pro Ser Arg Phe Ser Gly
65                  70                  75                  80
Ser Lys Ser Gly Ser Thr Gly Thr Leu Thr Ile Thr Gly Val Gln Ala
                85                  90                  95
Glu Asp Glu Ala Val Tyr Tyr Cys Gly Gly Tyr Asp Ser Thr Tyr Val
                100                 105                 110
Gly Ile Phe Gly Ala Gly Thr Thr Leu Thr Val Leu Gly Gln Ser Ser
            115                 120                 125
Arg Ser Ser Ala Val Thr Leu Asp Glu Ser Gly Gly Gly Leu Gln Thr
        130                 135                 140
Pro Arg Gly Ala Leu Ser Leu Val Cys Lys Ala Ser Gly Phe Thr Phe
145                 150                 155                 160
Ser Ser Tyr Ser Met Ala Trp Val Arg Gln Ala Pro Gly Lys Gly Leu
                165                 170                 175
Glu Phe Val Ala Gly Ile Gln Asn Asp Gly Ser Ile Thr Asp Tyr Gly
                180                 185                 190
Ser Ala Val Asp Gly Arg Ala Thr Ile Ser Arg Asp Asp Gly Gln Ser
            195                 200                 205
Thr Val Arg Leu Gln Leu Asn Asn Leu Arg Thr Glu Asp Thr Ala Thr
        210                 215                 220
Tyr Tyr Cys Ala Lys Thr Thr Val Ala Asp Gly Val Ile Gly Ala Tyr
225                 230                 235                 240
Gly Ile Asp Ala Trp Gly His Gly Thr Glu Val Ile Val Ser Ser Thr
                245                 250                 255
Ser Gly Gln Ala Gly Gln His His His His His Gly Ala Tyr Pro
                260                 265                 270
Tyr Asp Val Pro Asp Tyr Ala Ser
            275                 280

<210> SEQ ID NO 138
<211> LENGTH: 280
<212> TYPE: PRT
<213> ORGANISM: Artificial Sequence
<220> FEATURE:
<223> OTHER INFORMATION: recombinant protein

<400> SEQUENCE: 138

Met Lys Lys Thr Ala Ile Ala Ile Ala Val Ala Leu Ala Gly Phe Ala
1               5                   10                  15
Thr Val Ala Gln Ala Ala Leu Thr Gln Pro Ser Ser Val Ser Ala Asn
                20                  25                  30
Pro Gly Glu Thr Val Lys Ile Thr Cys Ser Gly Asp Ser Ser Gly Tyr
                35                  40                  45
Gly Tyr Gly Trp Tyr Gln Gln Lys Ser Pro Gly Ser Ala Pro Val Thr
        50                  55                  60
Val Ile Tyr Asn Asn Asn Lys Arg Pro Ser Asp Ile Pro Ser Arg Phe
65                  70                  75                  80
Ser Gly Ser Lys Ser Gly Ser Thr Gly Thr Leu Thr Ile Thr Gly Val
                85                  90                  95
Gln Ala Glu Asp Glu Ala Val Tyr Phe Cys Gly Ser Glu Asp Ser Asn
```

```
            100                 105                 110
Thr Asp Ala Val Phe Gly Ala Gly Thr Thr Leu Thr Val Leu Gly Gln
        115                 120                 125
Ser Ser Arg Ser Ser Thr Val Thr Leu Asp Glu Ser Gly Gly Gly Leu
    130                 135                 140
Gln Thr Pro Gly Gly Thr Leu Ser Leu Ala Cys Lys Ala Ser Gly Phe
145                 150                 155                 160
Thr Phe Ser Gly Tyr Asp Met Gly Trp Val Arg Gln Ala Pro Gly Lys
                165                 170                 175
Gly Leu Glu Tyr Val Ala Gly Ile Thr Ser Asp Gly Arg Tyr Ala Ser
            180                 185                 190
Tyr Gly Ser Ala Val Asp Gly Arg Ala Ala Ile Trp Arg Asp Asn Gly
        195                 200                 205
Gln Ser Thr Val Arg Leu Gln Leu Lys Asn Leu Arg Thr Glu Asp Thr
    210                 215                 220
Ala Thr Tyr Tyr Cys Ala Arg Asp Asp Gly Ser Gly Trp Ser Gly Asn
225                 230                 235                 240
Asn Ile Asp Ala Trp Gly His Gly Thr Glu Val Ile Val Ser Ser Thr
                245                 250                 255
Ser Gly Gln Ala Gly Gln His His His His His Gly Ala Tyr Pro
            260                 265                 270
Tyr Asp Val Pro Asp Tyr Ala Ser
        275                 280

<210> SEQ ID NO 139
<211> LENGTH: 280
<212> TYPE: PRT
<213> ORGANISM: Artificial Sequence
<220> FEATURE:
<223> OTHER INFORMATION: recombinant protein

<400> SEQUENCE: 139

Met Lys Lys Thr Ala Ile Ala Ile Ala Val Ala Leu Ala Gly Phe Ala
1               5                   10                  15
Thr Val Ala Gln Ala Ala Leu Thr Gln Pro Ser Ser Val Ser Ala Asn
            20                  25                  30
Pro Gly Gly Thr Val Lys Ile Thr Cys Ser Gly Ser Ser Ser Ala Tyr
        35                  40                  45
Gly Tyr Gly Trp Tyr Gln Gln Lys Ser Pro Gly Ser Ala Pro Val Thr
    50                  55                  60
Val Ile Tyr Asn Asn Asn Lys Arg Pro Ser Asn Ile Pro Ser Arg Phe
65                  70                  75                  80
Ser Gly Ser Lys Ser Gly Ser Thr Gly Thr Leu Thr Ile Thr Gly Val
                85                  90                  95
Gln Ala Glu Asp Glu Ala Val Tyr Phe Cys Gly Ser Glu Asp Ser Ser
            100                 105                 110
Thr Asp Ala Ile Phe Gly Ala Gly Thr Thr Leu Thr Val Leu Gly Gln
        115                 120                 125
Ser Ser Arg Ser Ser Ala Val Thr Leu Asp Glu Ser Gly Gly Gly Leu
    130                 135                 140
Gln Thr Pro Gly Gly Ala Leu Ser Leu Val Cys Lys Ala Ser Gly Phe
145                 150                 155                 160
Thr Phe Ser Ser Tyr Asp Met Gly Trp Val Arg Gln Ala Pro Gly Lys
                165                 170                 175
Gly Leu Glu Tyr Val Ala Gly Ile Thr Asn Asp Gly Arg Tyr Ala Ser
```

```
                180                 185                 190
Tyr Gly Ser Ala Val Asp Gly Arg Ala Thr Ile Ser Arg Asp Asn Gly
            195                 200                 205

Gln Ser Thr Val Arg Leu Gln Leu Asn Asn Leu Arg Ala Glu Asp Thr
        210                 215                 220

Gly Thr Tyr Tyr Cys Ala Arg Asp Asp Gly Ser Gly Trp Thr Gly Asn
225                 230                 235                 240

Thr Ile Asp Thr Trp Gly His Gly Thr Glu Val Ile Val Ser Ser Thr
                245                 250                 255

Ser Gly Gln Ala Gly Gln His His His His His Gly Ala Tyr Pro
            260                 265                 270

Tyr Asp Val Pro Asp Tyr Ala Ser
            275                 280

<210> SEQ ID NO 140
<211> LENGTH: 280
<212> TYPE: PRT
<213> ORGANISM: Artificial Sequence
<220> FEATURE:
<223> OTHER INFORMATION: recombinant protein

<400> SEQUENCE: 140

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Glu Ile Thr Cys Ser Gly Ser Ser Gly Ser Tyr
        35                  40                  45

Gly Trp Tyr Gln Gln Lys Pro Pro Gly Ser Ala Pro Val Thr Val Ile
    50                  55                  60

Tyr Tyr Asn Asp Lys Arg Pro Ser Asp Ile Pro Ser Arg Phe Ser Gly
65                  70                  75                  80

Ser Lys Ser Gly Ser Thr Gly Thr Leu Thr Ile Thr Gly Val Gln Ala
                85                  90                  95

Glu Asp Glu Ala Val Tyr Tyr Cys Gly Gly Tyr Gly Ser Thr Tyr Leu
            100                 105                 110

Gly Ile Phe Gly Ala Gly Thr Thr Leu Thr Val Leu Gly Gln Ser Ser
        115                 120                 125

Arg Ser Ser Ala Val Thr Leu Asp Glu Ser Gly Gly Gly Leu Gln Met
    130                 135                 140

Pro Gly Gly Gly Leu Ser Leu Val Cys Lys Ala Ser Gly Phe Thr Phe
145                 150                 155                 160

Ser Ser Tyr Ala Met Gly Trp Met Arg Gln Ala Pro Gly Lys Gly Leu
                165                 170                 175

Glu Phe Val Ala Gly Ile Leu Asn Asp Gly Ser Ile Thr Asp Tyr Gly
            180                 185                 190

Ser Ala Val Lys Gly Arg Ala Thr Ile Ser Arg Asp Asp Gly Gln Ser
        195                 200                 205

Thr Val Arg Leu Gln Leu Ser Asn Leu Arg Thr Glu Asp Thr Ala Thr
    210                 215                 220

Tyr Tyr Cys Ala Lys Thr Thr Val Gly Asp Gly Val Ile Gly Ala Tyr
225                 230                 235                 240

Ala Ile Asp Ala Trp Gly His Gly Thr Glu Val Ile Val Ser Ser Thr
                245                 250                 255

Ser Gly Gln Ala Gly Gln His His His His His Gly Ala Tyr Pro
```

Tyr Asp Val Pro Asp Tyr Ala Ser
            275                 280

<210> SEQ ID NO 141
<211> LENGTH: 282
<212> TYPE: PRT
<213> ORGANISM: Artificial Sequence
<220> FEATURE:
<223> OTHER INFORMATION: recombinant protein

<400> SEQUENCE: 141

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Lys Ile Thr Cys Ser Gly Gly Gly Ser Tyr Ala
        35                  40                  45

Gly Ser Tyr Tyr Tyr Gly Trp Tyr Gln Gln Lys Ala Pro Gly Ser Ala
    50                  55                  60

Pro Val Thr Leu Ile Tyr Asp Asn Thr Asn Arg Pro Ser Asn Ile Pro
65                  70                  75                  80

Ser Arg Phe Ser Gly Ser Leu Ser Gly Ser Thr Gly Thr Leu Thr Ile
                85                  90                  95

Thr Gly Val Arg Ala Glu Asp Glu Ala Val Tyr Tyr Cys Gly Ser Phe
            100                 105                 110

Asp Ser Ser Thr Asp Ser Gly Tyr Ala Ala Ile Phe Gly Ala Gly Thr
        115                 120                 125

Thr Leu Thr Val Leu Gly Gln Ser Ser Arg Ser Ser Ala Val Thr Leu
130                 135                 140

Asp Glu Ser Gly Gly Gly Leu Gln Thr Pro Gly Gly Ala Leu Ser Leu
145                 150                 155                 160

Val Cys Arg Ala Ser Gly Ile Thr Phe Ser Thr Tyr Ala Met Glu Trp
                165                 170                 175

Val Arg Gln Ala Pro Gly Lys Gly Leu Glu Phe Val Ala Val Val Asn
            180                 185                 190

Ala Ala Gly Ser Thr Tyr Tyr Gly Ala Ala Val Lys Gly Arg Ala Thr
        195                 200                 205

Ile Ser Arg Asp Asn Gly Gln Ser Thr Val Arg Leu Gln Leu Asn Asn
    210                 215                 220

Leu Arg Ala Glu Asp Thr Gly Thr Tyr Tyr Cys Thr Arg Gly Ser Gly
225                 230                 235                 240

Gly Glu Asn Ile Asp Ala Trp Gly His Gly Thr Glu Val Ile Val Ser
                245                 250                 255

Ser Thr Ser Gly Gln Ala Gly Gln His His His His His His Gly Ala
            260                 265                 270

Tyr Pro Tyr Asp Val Pro Asp Tyr Ala Ser
        275                 280

<210> SEQ ID NO 142
<211> LENGTH: 280
<212> TYPE: PRT
<213> ORGANISM: Artificial Sequence
<220> FEATURE:
<223> OTHER INFORMATION: recombinant protein

<400> SEQUENCE: 142

```
Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Leu Gly Gly Thr Val Glu Ile Thr Cys Ser Gly Gly Ser Gly Ser Tyr
            35                  40                  45

Gly Trp Tyr Gln Gln Lys Ser Pro Gly Gly Ala Pro Val Thr Val Ile
        50                  55                  60

Tyr Tyr Asn Asp Lys Arg Pro Ser Asp Ile Pro Ser Arg Phe Ser Gly
65                  70                  75                  80

Ser Lys Ser Gly Ser Thr Ala Thr Leu Thr Ile Thr Gly Val Gln Val
                85                  90                  95

Glu Asp Glu Ala Val Tyr Tyr Cys Gly Ser Tyr Asp Ser Ser Tyr Val
            100                 105                 110

Gly Ile Phe Gly Val Gly Thr Thr Leu Thr Val Leu Gly Gln Ser Ser
        115                 120                 125

Arg Ser Ser Ala Val Thr Leu Asp Glu Ser Gly Gly Gly Leu Gln Thr
130                 135                 140

Pro Arg Gly Ala Leu Ser Leu Val Cys Lys Ala Ser Gly Phe Thr Phe
145                 150                 155                 160

Ser Ser Tyr Ser Met Ala Trp Val Arg Gln Ala Pro Gly Lys Gly Leu
                165                 170                 175

Glu Phe Val Ala Gly Ile Gln Asn Asp Gly Ser Ile Thr Asp Tyr Gly
            180                 185                 190

Ser Ala Val Asp Gly Arg Ala Thr Ile Ser Arg Asp Asp Gly Gln Ser
        195                 200                 205

Thr Val Arg Leu Gln Leu Asn Asn Leu Arg Thr Glu Asp Thr Ala Thr
210                 215                 220

Tyr Tyr Cys Ala Lys Thr Thr Val Ala Asp Gly Val Ile Gly Ala Tyr
225                 230                 235                 240

Gly Ile Asp Ala Trp Gly His Gly Thr Glu Val Ile Val Ser Ser Thr
                245                 250                 255

Ser Gly Gln Ala Gly Gln His His His His His Gly Ala Tyr Pro
            260                 265                 270

Tyr Asp Val Pro Asp Tyr Ala Ser
        275                 280

<210> SEQ ID NO 143
<211> LENGTH: 282
<212> TYPE: PRT
<213> ORGANISM: Artificial Sequence
<220> FEATURE:
<223> OTHER INFORMATION: recombinant protein

<400> SEQUENCE: 143

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Leu Gly Gly Thr Val Lys Ile Thr Cys Ser Gly Ser Ser Gly Ser Tyr
            35                  40                  45

Gly Trp Tyr Gln Gln Lys Ser Pro Gly Ser Ala Pro Val Thr Val Ile
        50                  55                  60

Tyr Arg Asn Asp Lys Arg Pro Ser Asn Ile Pro Ser Arg Phe Ser Gly
65                  70                  75                  80
```

```
Ala Leu Ser Gly Ser Thr Ala Thr Leu Thr Ile Thr Gly Val Gln Ala
                85                  90                  95

Glu Asp Glu Ala Val Tyr Phe Cys Gly Ser Ala Asp Ser Ser Gly Ala
            100                 105                 110

Ile Phe Gly Ala Gly Thr Thr Leu Thr Ala Leu Gly Gln Ser Ser Arg
        115                 120                 125

Ser Ser Thr Val Thr Leu Glu Glu Ser Gly Gly Gly Leu His Thr Pro
    130                 135                 140

Gly Gly Gly Leu Ile Leu Leu Cys Lys Gly Ser Gly Val Ser Phe Cys
145                 150                 155                 160

Asn Tyr Gly Met Gly Trp Met Arg Arg Asp Pro Gly Gly Gly Leu Glu
                165                 170                 175

Tyr Val Ala Gly Ile Ser Thr Gly Ser Tyr Thr Tyr Tyr Gly Pro Ala
            180                 185                 190

Val Lys Gly Arg Gly Thr Val Ser Arg Asp Asn Gly Gln Ser Thr Met
        195                 200                 205

Arg Leu Gln Leu Asn His Leu Arg Ala Glu Asp Glu Thr Ile Tyr Phe
    210                 215                 220

Cys Ala Arg Thr Asp Ala Ser Ser His Gly Cys Gly Ser Gly Thr Asp
225                 230                 235                 240

Leu Gly Ser Ile Asp Ala Trp Gly His Gly Thr Glu Val Leu Leu Ser
                245                 250                 255

Ser Thr Ser Gly Gln Ala Gly Gln His His His His His Gly Ala
            260                 265                 270

Tyr Pro Tyr Asp Val Pro Asp Tyr Ala Ser
        275                 280

<210> SEQ ID NO 144
<211> LENGTH: 280
<212> TYPE: PRT
<213> ORGANISM: Artificial Sequence
<220> FEATURE:
<223> OTHER INFORMATION: recombinant protein

<400> SEQUENCE: 144

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Lys Leu Thr Cys Ser Gly Asp Ser Ser Asp Tyr
        35                  40                  45

Gly Tyr Gly Trp Tyr Gln Gln Lys Ser Pro Gly Ser Ala Pro Val Thr
    50                  55                  60

Val Ile Tyr Asn Asn Asn Lys Arg Pro Ser Asp Ile Pro Ser Arg Phe
65                  70                  75                  80

Ser Gly Ser Lys Ser Gly Ser Thr Gly Thr Leu Thr Ile Ser Gly Val
                85                  90                  95

Gln Ala Glu Asp Glu Ala Val Tyr Phe Cys Gly Ser Glu Asp Ser Asn
            100                 105                 110

Ser Asp Ala Ile Phe Gly Ala Gly Thr Thr Leu Thr Val Leu Gly Gln
        115                 120                 125

Ser Ser Arg Ser Ser Ala Val Thr Leu Asp Glu Tyr Gly Gly Gly Leu
    130                 135                 140

Gln Thr Pro Gly Gly Ala Leu Ser Leu Val Cys Glu Ala Ser Gly Phe
145                 150                 155                 160
```

```
Thr Phe Ser Ser Tyr Asp Met Leu Arg Ile Pro His Ala Pro Gly Lys
                165                 170                 175

Gly Leu Glu Tyr Val Ala Gly Leu Thr Ser Asn Gly Tyr Ala Ser
            180                 185                 190

Tyr Gly Ser Ala Val Asp Gly Arg Ala Thr Ile Ser Arg Asp Asn Gly
            195                 200                 205

Gln Ser Thr Trp Arg Leu His Leu Asn Asn Leu Gly Ala Glu Asp Thr
        210                 215                 220

Gly Pro Tyr Tyr Cys Ala Gly Tyr Asp Gly Ser Gly Trp Thr Gly Asn
225                 230                 235                 240

Thr Ile Glu Ala Trp Gly His Arg Thr Glu Val Leu Val Ser Ser Thr
                245                 250                 255

Ser Gly Gln Ala Gly Gln His His His His His Gly Ala Tyr Pro
            260                 265                 270

Tyr Asp Val Pro Asp Tyr Ala Ser
            275                 280

<210> SEQ ID NO 145
<211> LENGTH: 286
<212> TYPE: PRT
<213> ORGANISM: Artificial Sequence
<220> FEATURE:
<223> OTHER INFORMATION: recombinant protein

<400> SEQUENCE: 145

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Leu Gly Gly Thr Val Lys Ile Thr Cys Ser Gly Gly Ser Ser Tyr Tyr
        35                  40                  45

Gly Trp Tyr Gln Gln Lys Ser Pro Gly Ser Ala Pro Val Thr Leu Ile
    50                  55                  60

Tyr Glu Asn Asn Asn Arg Pro Ser Asp Ile Pro Ser Arg Phe Ser Gly
65                  70                  75                  80

Ser Ala Ser Gly Ser Thr Ala Thr Leu Thr Ile Thr Gly Val Gln Ala
                85                  90                  95

Glu Asp Gly Ala Val Tyr Phe Cys Gly Ser Glu Asp Ser Thr Tyr Val
            100                 105                 110

Gly Ile Phe Gly Ala Gly Thr Thr Leu Thr Val Leu Gly Gln Ser Ser
        115                 120                 125

Arg Ser Ser Ala Val Thr Leu Asp Glu Ser Gly Gly Gly Leu Gln Thr
130                 135                 140

Pro Gly Arg Ala Leu Ser Leu Val Cys Lys Ala Ser Gly Phe Thr Phe
145                 150                 155                 160

Ser Ser Phe Asn Met Gly Trp Val Arg Gln Ala Pro Gly Lys Gly Leu
                165                 170                 175

Glu Tyr Val Ala Ser Ile Ser Ser Gly Ser Tyr Thr Ala Tyr Gly
            180                 185                 190

Ser Ala Val Lys Gly Arg Ala Thr Ile Ser Arg Asp Asn Gly Gln Ser
        195                 200                 205

Thr Val Arg Leu Gln Leu Asn Asn Leu Arg Ala Glu Asp Thr Ala Thr
    210                 215                 220

Tyr Tyr Cys Ala Lys Ala Ala Gly Ser Ala Tyr Tyr Tyr Thr Ala Val
225                 230                 235                 240
```

```
Thr Pro Ala Phe Ala Gly Ser Ile Asp Ala Trp Gly His Gly Thr Glu
                245                 250                 255

Val Ile Val Ser Ser Thr Ser Gly Gln Ala Gly Gln His His His His
            260                 265                 270

His His Gly Ala Tyr Pro Tyr Asp Val Pro Asp Tyr Ala Ser
        275                 280                 285

<210> SEQ ID NO 146
<211> LENGTH: 286
<212> TYPE: PRT
<213> ORGANISM: Artificial Sequence
<220> FEATURE:
<223> OTHER INFORMATION: recombinant protein

<400> SEQUENCE: 146

Met Lys Lys Thr Ala Ile Ala Ile Ala Val Ala Leu Ala Gly Phe Ala
1               5                  10                  15

Thr Val Ala Gln Ala Ala Leu Thr Gln Pro Ser Ser Val Ser Ala Asn
            20                  25                  30

Leu Gly Gly Thr Val Lys Ile Thr Cys Ser Gly Gly Ser Ser Tyr Tyr
        35                  40                  45

Gly Trp Tyr Gln Gln Lys Ser Pro Gly Ser Ala Pro Val Thr Leu Ile
    50                  55                  60

Tyr Glu Asn Asn Asn Arg Pro Ser Asp Ile Pro Ser Arg Phe Ser Gly
65                  70                  75                  80

Ser Ala Ser Gly Ser Thr Ala Pro Leu Thr Ile Thr Gly Val Gln Ala
                85                  90                  95

Glu Asp Gly Ala Val Tyr Phe Cys Gly Ser Glu Asp Ser Thr Tyr Val
            100                 105                 110

Gly Ile Phe Gly Ala Gly Thr Thr Leu Thr Val Leu Gly Gln Ser Ser
        115                 120                 125

Arg Ser Ser Ala Val Thr Leu Asp Glu Ser Gly Gly Gly Leu Gln Thr
    130                 135                 140

Pro Gly Arg Ala Leu Ser Leu Val Cys Lys Ala Ser Gly Phe Thr Phe
145                 150                 155                 160

Ser Ser Phe Asn Met Gly Trp Val Arg Gln Ala Pro Gly Lys Gly Leu
                165                 170                 175

Glu Tyr Val Ala Ser Ile Ser Ser Ser Gly Ser Tyr Thr Ala Tyr Gly
            180                 185                 190

Ser Ala Val Lys Gly Arg Ala Thr Ile Ser Arg Asp Asn Gly Gln Ser
        195                 200                 205

Thr Val Arg Leu Gln Leu Asn Asn Leu Arg Ala Glu Asp Thr Ala Thr
    210                 215                 220

Tyr Tyr Cys Ala Lys Ala Ala Gly Ser Ala Tyr Tyr Thr Ala Val
225                 230                 235                 240

Thr Pro Ala Phe Ala Gly Ser Ile Asp Ala Cys Gly His Gly Thr Glu
                245                 250                 255

Val Ile Val Ser Ser Thr Ser Gly Gln Ala Gly Gln His His His His
            260                 265                 270

His His Gly Ala Tyr Pro Tyr Asp Val Pro Asp Tyr Ala Ser
        275                 280                 285

<210> SEQ ID NO 147
<211> LENGTH: 280
<212> TYPE: PRT
<213> ORGANISM: Artificial Sequence
<220> FEATURE:
```

<223> OTHER INFORMATION: recombinant protein

<400> SEQUENCE: 147

```
Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Leu Gly Gly Thr Val Lys Ile Thr Cys Ser Gly Gly Ser Gly Ser Tyr
        35                  40                  45

Gly Trp Tyr Gln Gln Lys Ser Pro Gly Ser Ala Pro Val Thr Val Ile
    50                  55                  60

Tyr Tyr Asn Asp Gln Arg Pro Ser Asp Ile Pro Ser Arg Phe Ser Gly
65                  70                  75                  80

Ser Lys Ser Gly Ser Thr Gly Thr Leu Thr Ile Thr Gly Val His Ala
                85                  90                  95

Glu Asp Glu Ala Val Tyr Tyr Cys Gly Gly Tyr Asn Ser Thr Tyr Val
            100                 105                 110

Gly Ile Phe Gly Ala Gly Thr Thr Leu Thr Val Leu Gly Gln Ser Ser
        115                 120                 125

Arg Ser Ser Ala Val Thr Leu Asp Glu Ser Gly Gly Gly Leu His Thr
130                 135                 140

Pro Arg Gly Ala Leu Ser Leu Ile Cys Lys Ala Ser Gly Phe Thr Phe
145                 150                 155                 160

Ser Ser Tyr Ser Met Ala Trp Val Gln Gln Ala Pro Gly Lys Gly Leu
                165                 170                 175

Glu Phe Val Pro Gly Ile Leu Asn Asp Gly Ser Ile Thr Asp Tyr Gly
            180                 185                 190

Ser Ala Asp Asp Gly Arg Ala Thr Ile Ser Arg Asp Asp Gly Gln Ser
        195                 200                 205

Thr Val Arg Leu His Leu Ile Asn Leu Arg Thr Glu Asp Thr Ala Thr
    210                 215                 220

Tyr Tyr Cys Ala Lys Thr Thr Val Ala Asp Gly Val Ile Gly Ala Tyr
225                 230                 235                 240

Gly Ile Asp Ala Trp Gly His Gly Thr Glu Val Ile Val Ser Ser Thr
                245                 250                 255

Ser Gly Gln Ala Gly Gln His His His His His Gly Ala Tyr Pro
            260                 265                 270

Tyr Asp Val Pro Asp Tyr Ala Ser
    275                 280
```

<210> SEQ ID NO 148
<211> LENGTH: 282
<212> TYPE: PRT
<213> ORGANISM: Artificial Sequence
<220> FEATURE:
<223> OTHER INFORMATION: recombinant protein

<400> SEQUENCE: 148

```
Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Leu Gly Gly Thr Val Glu Ile Thr Cys Ser Gly Gly Ser Ser Ser Tyr
        35                  40                  45

Tyr Gly Trp Tyr Gln Gln Lys Ser Pro Gly Ser Ala Pro Val Thr Val
    50                  55                  60
```

```
Ile Tyr Trp Asn Asp Lys Arg Pro Ser Asp Ile Pro Ser Arg Phe Ser
 65                  70                  75                  80

Gly Ser Glu Ser Gly Ser Pro Ala Thr Leu Thr Ile Thr Gly Val Arg
                 85                  90                  95

Ala Glu Asp Glu Ala Val Tyr Phe Cys Gly Ser Gly Asp Ser Ser Gly
            100                 105                 110

Thr Gly Ile Phe Gly Ala Gly Thr Thr Leu Thr Val Leu Gly Gln Ser
        115                 120                 125

Ser Arg Ser Ser Ala Val Thr Leu Asp Glu Ser Gly Gly Gly Leu Gln
130                 135                 140

Thr Pro Gly Gly Gly Leu Ser Leu Val Cys Lys Ala Ser Gly Phe Ser
145                 150                 155                 160

Phe Ser Asp Tyr Thr Met Asn Trp Val Arg Gln Ala Pro Gly Lys Gly
                165                 170                 175

Leu Glu Trp Val Gly Gln Ile Ser Ser Asp Asn Gly Arg Tyr Thr Thr
            180                 185                 190

Tyr Gly Ala Ala Val Lys Gly Arg Ala Thr Ile Ser Arg Asp Asp Gly
        195                 200                 205

Gln Ser Thr Val Arg Leu Gln Leu Asn Asn Leu Lys Ala Glu Asp Thr
210                 215                 220

Ala Thr Tyr Tyr Cys Ala Lys Glu Ser Asp Gly Asp Tyr Asn Gly Gly
225                 230                 235                 240

Ala Gly Leu Ile Asp Ala Trp Gly His Gly Thr Glu Val Ile Val Ser
                245                 250                 255

Ser Thr Ser Gly Gln Ala Gly Gln His His His His His Gly Ala
            260                 265                 270

Tyr Pro Tyr Asp Val Pro Asp Tyr Ala Ser
        275                 280

<210> SEQ ID NO 149
<211> LENGTH: 282
<212> TYPE: PRT
<213> ORGANISM: Artificial Sequence
<220> FEATURE:
<223> OTHER INFORMATION: recombinant protein

<400> SEQUENCE: 149

Met Lys Lys Thr Ala Ile Ala Ile Ala Val Ala Leu Ala Gly Phe Ala
  1               5                  10                  15

Thr Val Ala Gln Ala Ala Leu Thr Gln Pro Ser Ser Val Ser Ala Asn
             20                  25                  30

Leu Gly Gly Thr Val Lys Ile Thr Cys Ser Gly Ser Ser Gly Ser Tyr
         35                  40                  45

Gly Trp Tyr Gln Gln Lys Ser Pro Gly Ser Ala Pro Val Thr Val Ile
     50                  55                  60

Tyr Trp Asn Asp Lys Arg Pro Ser Asn Ile Pro Ser Arg Phe Ser Gly
 65                  70                  75                  80

Ala Leu Ser Gly Ser Thr Ala Thr Leu Thr Ile Thr Gly Val Gln Ala
                 85                  90                  95

Glu Asp Glu Ala Val Tyr Phe Cys Gly Ser Ala Asp Ser Ser Gly Ala
            100                 105                 110

Ile Phe Gly Ala Gly Thr Thr Leu Thr Val Leu Gly Gln Ser Ser Arg
        115                 120                 125

Ser Ser Thr Val Thr Leu Asp Glu Ser Gly Gly Gly Leu Gln Thr Pro
130                 135                 140
```

Gly Gly Gly Leu Ser Leu Val Cys Lys Gly Ser Gly Phe Ala Phe Ser
145                 150                 155                 160

Asn Tyr Gly Met Gly Trp Met Arg Gln Ala Pro Gly Lys Gly Leu Glu
                165                 170                 175

Tyr Val Ala Gly Ile Ser Thr Gly Ser Tyr Thr Asp Tyr Gly Pro Ala
            180                 185                 190

Val Lys Gly Arg Ala Thr Ile Ser Arg Asp Asn Gly Gln Ser Thr Val
        195                 200                 205

Arg Leu Gln Leu Asn Asn Leu Arg Ala Glu Asp Ala Ala Ile Tyr Phe
    210                 215                 220

Cys Ala Lys Thr Ala Gly Ser Gly Tyr Gly Cys Gly Ser Gly Thr Asp
225                 230                 235                 240

Leu Gly Ser Ile Asp Ala Trp Gly His Gly Thr Glu Val Ile Val Ser
                245                 250                 255

Ser Thr Ser Gly Gln Ala Gly Gln His His His His His Gly Ala
            260                 265                 270

Tyr Pro Tyr Asp Val Pro Asp Tyr Ala Ser
        275                 280

<210> SEQ ID NO 150
<211> LENGTH: 22
<212> TYPE: PRT
<213> ORGANISM: Artificial Sequence
<220> FEATURE:
<223> OTHER INFORMATION: Recombinant protein

<400> SEQUENCE: 150

Met Lys Lys Thr Ala Ile Ala Ile Ala Val Ala Leu Ala Gly Phe Ala
1               5                   10                  15

Thr Val Ala Gln Ala Ala
            20

<210> SEQ ID NO 151
<211> LENGTH: 23
<212> TYPE: PRT
<213> ORGANISM: Artificial Sequence
<220> FEATURE:
<223> OTHER INFORMATION: Recombinant protein

<400> SEQUENCE: 151

Gly Gln Ala Gly Gln His His His His His His Gly Ala Tyr Pro Tyr
1               5                   10                  15

Asp Val Pro Asp Tyr Ala Ser
            20

<210> SEQ ID NO 152
<211> LENGTH: 4973
<212> TYPE: DNA
<213> ORGANISM: Artificial Sequence
<220> FEATURE:
<223> OTHER INFORMATION: recombinant plasmid

<400> SEQUENCE: 152
agagcgccca atacgcaaac cgcctctccc cgcgcgttgg ccgattcatt aatgcagctg      60
gcacgacagg tttcccgact ggaaagcggg cagtgagcgc aacgcaatta atgtgagtta    120
gctcactcat taggcacccc aggctttaca ctttatgctt ccggctcgta tgttgtgtgg    180
aattgtgagc ggataacaat tgaattcagg aggaatttaa aatgaaaaag acagctatcg    240
cgattgcagt ggcactggct ggtttcgcta ccgtggccca ggcggccgag ctcgccatgg    300

```
ctggttgggc agcgagtaat aacaatccag cggctgccgt aggcaatagg tatttcatta      360
tgactgtctc cttggcgact agctagttta gaattcgtaa tcatggtcat agctgtttcc      420
tgtgtgaaat tgttatccgc tcacaattcc acacaacata cgagccggaa gcataaagtg      480
taaagcctgg ggtgcctaat gagtgagcta actcacatta attgcgttgc gctcactgcc      540
cgctttccag tcgggaaacc tgtcgtgtta ctaatgatgg tgatggtgat ggctagtttt      600
gtcacaagat ttgggctcaa ctttcttgtc caccttggtg ttgctgggct tgtgattcac      660
gttgcagatg taggtctggg tgcccaagct gctggagggc acggtcacca cgctgctgag      720
ggagtagagt cctgaggact gtaggacagc cgggaaggtg tgcacgccgc tggtcagggc      780
gcctgagttc cacgacaccg tcgccggttc ggggaagtag tccttgacca ggcagcccag      840
ggccgctgtg cccccagagg tgctcttgga ggagggtgcc aggggaaga ccatgggcc       900 cttggtggag gctgcggaga cggtgaccgt ggtaccagca gaaacctggc caggctccca      960
ggctcctcat ctatggtaca tccagcaggg ccactggcat cccagacagg ttcagtggca     1020
gtgggtctgg gacagacttc actctcacca tcagcagact ggagcctgaa gattttgcag     1080
tgtactactg tcagcagtat ggtggctcac cgtggttcgg ccaagggacc aaggtggaac     1140
tcaaacgaac tgtggctgca ccatctgtct tcatcttccc gccatctgat gagcagttga     1200
aatctggaac tgcctctgtt gtgtgcctgc tgaataactt ctatcccaga gaggccaaag     1260
tacagtggaa ggtggataac gccctccaat cgggtaactc ccaggagagt gtcacagagc     1320
aggacagcaa ggacagcacc tacagcctca gcagcaccct gacgctgagc aaagcagact     1380
acgagaaaca caaagtctac gcctgcgaag tcacccatca gggcctgagc ttgcccgtca     1440
caaagagctt caacagggga gagtgttagt tctagataat taattaggag gaatttaaaa     1500
tgaaatacct attgcctacg gcagccgctg gattgttatt actcgctgcc caaccagcca     1560
tggccgaggt gcagctgctc gagatgagcg ataaaattat tcacctgact gacgacagtt     1620
ttgacacgga tgtactcaaa gcggacgggg cgatcctcgt cgatttctgg gcagagtggt     1680
gcggtccgtg caaaatgatc gccccgattc tggatgaaat cgctgacgaa tatcagggca     1740
aactgaccgt tgcaaaactg aacatcgatc aaaaccctgg cactgcgccg aaatatggca     1800
tccgtggtat cccgactctg ctgctgttca aaaacggtga agtggcggca accaaagtgg     1860
gtgcactgtc taaaggtcag ttgaaagagt tcctcgacgc taacctggcg tacccgtacg     1920
acgttccgga ctacggttct actagtggcc aggccggcca gcaccatcac catcaccatg     1980
gcgcataccc gtacgacgtt ccggactacg cttcttagga gggtggtggc tctgagggtg     2040
gcggttctga gggtggcggc tctgagggag cggttccgg tggtggctct ggttccggtg      2100
attttgatta tgaaaagatg gcaaacgcta ataaggggc tatgaccgaa aatgccgatg      2160
aaaacgcgct acagtctgac gctaaaggca aacttgattc tgtcgctact gattacggtg      2220
ctgctatcga tggtttcatt ggtgacgttt ccggccttgc taatggtaat ggtgctactg     2280
gtgattttgc tggctctaat cccaaatggc tcaagtcgg tgacggtgat aattcacctt      2340
taatgaataa tttccgtcaa tatttacctt ccctccctca atcggttgaa tgtcgccctt     2400
ttgtctttag cgctggtaaa ccatatgaat tttctattga ttgtgacaaa ataaacttat     2460
tccgtggtgt ctttgcgttt cttttatatg ttgccacctt tatgtatgta ttttctacgt     2520
ttgctaacat actgcgtaat aaggagtctt aagctagcta attaatttaa gcggccgcag     2580
atctgggaaa ttgtaagcgt taatattttg ttaaaattcg cgttaaattt ttgttaaatc     2640
```

-continued

```
agctcatttt ttaaccaata ggccgaaatc ggcaaaatcc cttataaatc aaaagaatag    2700
accgagatag ggttgagtgt tgttccagtt tggaacaaga gtccactatt aaagaacgtg    2760
gactccaacg tcaaagggcg aaaaaccgtc tatcagggcg atggcccact acgtgaacca    2820
tcaccctaat caagtttttt ggggtcgagg tgccgtaaag cactaaatcg aaccctaaa    2880
gggagccccc gatttagagc ttgacgggga agccggcga acgtggcgag aaaggaaggg    2940
aagaaagcga aaggagcggg cgctagggcg ctggcaagtg tagcggtcac gctgcgcgta    3000
accaccacac ccgccgcgct taatgcgccg ctacagggcg cgtcaggtgg cacttttcgg    3060
ggaaatgtgc gcggaacccc tatttgttta tttttctaaa tacattcaaa tatgtatccg    3120
ctcatgagac aataaccctg ataaatgctt caataatatt gaaaaaggaa gagtatgagt    3180
attcaacatt tccgtgtcgc ccttattccc ttttttgcgg cattttgcct tcctgttttt    3240
gctcacccag aaacgctggt gaaagtaaaa gatgctgaag atcagttggg tgcacgagtg    3300
ggttacatcg aactggatct caacagcggt aagatccttg agagttttcg ccccgaagaa    3360
cgttttccaa tgatgagcac ttttaaagtt ctgctatgtg gcgcggtatt atcccgtatt    3420
gacgccgggc aagagcaact cggtcgccgc atacactatt ctcagaatga cttggttgag    3480
tactcaccag tcacagaaaa gcatcttacg gatggcatga cagtaagaga attatgcagt    3540
gctgccataa ccatgagtga taacactgcg gccaacttac ttctgacaac gatcggagga    3600
ccgaaggagc taaccgcttt tttgcacaac atggggatc atgtaactcg ccttgatcgt    3660
tgggaaccgg agctgaatga agccatacca aacgacgagc gtgacaccac gatgcctgta    3720
gcaatggcaa caacgttgcg caaactatta actggcgaac tacttactct agcttcccgg    3780
caacaattaa tagactggat ggaggcggat aaagttgcag gaccacttct gcgctcggcc    3840
cttccggctg gctggtttat tgctgataaa tctggagccg gtgagcgtgg gtctcgcggt    3900
atcattgcag cactggggcc agatggtaag ccctcccgta tcgtagttat ctacacgacg    3960
gggagtcagg caactatgga tgaacgaaat agacagatcg ctgagatagg tgcctcactg    4020
attaagcatt ggtaactgtc agaccaagtt tactcatata tactttagat tgatttaaaa    4080
cttcattttt aatttaaaag gatctaggtg aagatccttt ttgataatct catgaccaaa    4140
atcccttaac gtgagttttc gttccactga gcgtcagacc ccgtagaaaa gatcaaagga    4200
tcttcttgag atccttttt tctgcgcgta atctgctgct tgcaaacaaa aaaaccaccg    4260
ctaccagcgg tggtttgttt gccggatcaa gagctaccaa ctcttttcc gaaggtaact    4320
ggcttcagca gagcgcagat accaaatact gtccttctag tgtagccgta gttaggccac    4380
cacttcaaga actctgtagc accgcctaca tacctcgctc tgctaatcct gttaccagtg    4440
gctgctgcca gtggcgataa gtcgtgtctt accgggttgg actcaagacg atagttaccg    4500
gataaggcgc agcggtcggg ctgaacgggg gttcgtgca cacagcccag cttggagcga    4560
acgacctaca ccgaactgag atacctacag cgtgagctat gagaaagcgc cacgcttccc    4620
gaagggagaa aggcggacag gtatccgta agcggcaggg tcggaacagg agagcgcacg    4680
agggagcttc caggggaaa cgcctggtat ctttatagtc ctgtcgggtt tcgccacctc    4740
tgacttgagc gtcgattttt gtgatgctcg tcagggggc ggagcctatg gaaaaacgcc    4800
agcaacgcgg cctttttacg gttcctggcc ttttgctggc cttttgctca catgttcttt    4860
cctgcgttat cccctgattc tgtggataac cgtattaccg cctttgagtg agctgatacc    4920
gctcgccgca gccgaacgac cgagcgcagc gagtcagtga gcgaggaagc gga    4973
```

```
<210> SEQ ID NO 153
<211> LENGTH: 282
<212> TYPE: PRT
<213> ORGANISM: Artificial sequence
<220> FEATURE:
<223> OTHER INFORMATION: recombinant protein

<400> SEQUENCE: 153

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Lys Ile Thr Cys Ser Gly Gly Ser Tyr Ser Tyr
        35                  40                  45

Gly Trp Tyr Gln Gln Lys Ser Pro Gly Ser Ala Pro Val Thr Val Ile
    50                  55                  60

Tyr Ser Ser Asp Lys Arg Pro Ser Asp Ile Pro Ser Arg Phe Ser Gly
65                  70                  75                  80

Ser Lys Ser Gly Ser Thr Ser Thr Leu Thr Ile Thr Gly Val Gln Ala
                85                  90                  95

Glu Asp Glu Ala Val Tyr Tyr Cys Gly Ser Arg Asp Ser Asn Tyr Val
            100                 105                 110

Gly Ile Phe Gly Ala Gly Thr Thr Leu Thr Val Leu Gly Gln Ser Ser
        115                 120                 125

Arg Ser Ser Thr Val Thr Leu Asp Glu Ser Gly Gly Gly Leu Gln Thr
    130                 135                 140

Pro Gly Gly Ala Leu Ser Leu Val Cys Lys Ala Ser Gly Phe Thr Phe
145                 150                 155                 160

Ser Ser Tyr Glu Met Gln Trp Val Arg Gln Ala Pro Gly Lys Gly Leu
                165                 170                 175

Glu Phe Val Ala Ala Ile Ser Ser Asp Gly Ser Tyr Thr Asn Tyr Gly
            180                 185                 190

Ala Ala Val Gln Gly Arg Ala Thr Ile Ser Arg Asp Asn Gly Gln Ser
        195                 200                 205

Thr Val Arg Leu Gln Leu Ser Asn Leu Arg Ala Glu Asp Thr Ala Thr
    210                 215                 220

Tyr Tyr Cys Ala Arg Ser Pro Gly Gly Tyr Thr Trp Trp Pro Gly Ala
225                 230                 235                 240

Ala Gly Gly Ile Asp Ala Trp Gly His Gly Thr Glu Val Ile Val Ser
                245                 250                 255

Ser Thr Ser Gly Gln Ala Gly Gln His His His His His His Gly Ala
            260                 265                 270

Tyr Pro Tyr Asp Val Pro Asp Tyr Ala Ser
        275                 280

<210> SEQ ID NO 154
<211> LENGTH: 283
<212> TYPE: PRT
<213> ORGANISM: Artificial sequence
<220> FEATURE:
<223> OTHER INFORMATION: recombinant protein

<400> SEQUENCE: 154

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30
```

Leu Gly Gly Thr Val Lys Ile Thr Cys Ser Gly Gly Asp Ser Ser Tyr
        35                  40                  45

Gly Trp Tyr Gln Gln Lys Ser Pro Gly Ser Ala Pro Val Thr Leu Ile
 50                  55                  60

Tyr Asp Asn Thr Asn Arg Pro Ser Asp Ile Pro Ser Arg Phe Ser Gly
 65                  70                  75                  80

Ser Lys Ser Gly Ser Thr Gly Thr Leu Thr Ile Thr Gly Val Gln Ala
                 85                  90                  95

Glu Asp Glu Ala Val Tyr Tyr Cys Gly Asn Ala Asp Ser Ser Ser Thr
            100                 105                 110

Ala Ala Phe Gly Ala Gly Thr Thr Leu Thr Val Leu Gly Gln Ser Ser
        115                 120                 125

Arg Ser Ser Thr Val Thr Leu Asp Glu Ser Gly Gly Gly Leu Gln Thr
130                 135                 140

Pro Gly Gly Ala Leu Ser Leu Val Cys Lys Ala Ser Gly Phe Thr Phe
145                 150                 155                 160

Ser Ser Tyr Ala Met Gly Trp Val Arg Gln Ala Pro Gly Lys Gly Leu
                165                 170                 175

Glu Tyr Val Ala Ala Ile Ser Ser Ala Gly Ser Thr Thr Asn Tyr Gly
            180                 185                 190

Ala Ala Val Lys Gly Arg Ala Thr Ile Ser Ser Asp Asn Gly Gln Ser
        195                 200                 205

Thr Val Arg Leu Gln Leu Asn Asn Leu Arg Ala Glu Asp Thr Ala Thr
210                 215                 220

Tyr Phe Cys Ala Lys Thr Ala Gly Ser Gly Tyr Tyr Val Trp Ser Ala
225                 230                 235                 240

Ile Ala Gly Asp Ile Tyr Ala Trp Gly His Gly Thr Glu Val Ile Val
                245                 250                 255

Ser Ser Thr Ser Gly Gln Ala Gly Gln His His His His His His Gly
            260                 265                 270

Ala Tyr Pro Tyr Asp Val Pro Asp Tyr Ala Ser
        275                 280

<210> SEQ ID NO 155
<211> LENGTH: 278
<212> TYPE: PRT
<213> ORGANISM: Artificial sequence
<220> FEATURE:
<223> OTHER INFORMATION: recombinant protein

<400> SEQUENCE: 155

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Pro Gly Glu Thr Val Glu Ile Thr Cys Ser Gly Gly Gly Ser Tyr
        35                  40                  45

Gly Trp Phe Gln Gln Lys Ser Pro Gly Ser Ala Pro Val Thr Val Ile
 50                  55                  60

Tyr Glu Ser Thr Lys Arg Pro Ser Asn Ile Pro Ser Arg Phe Ser Gly
 65                  70                  75                  80

Ser Gly Ser Gly Ser Thr Ser Thr Leu Thr Ile Thr Gly Val Arg Ala
                 85                  90                  95

Glu Asp Glu Ala Val Tyr Tyr Cys Gly Gly Tyr Asp Gly Ser Ser Asp
            100                 105                 110

```
Ala Ile Phe Gly Ala Gly Thr Thr Leu Thr Val Leu Gly Gln Ser Ser
            115                 120                 125

Arg Ser Ser Thr Val Thr Leu Asp Glu Ser Gly Gly Gly Leu Gln Thr
        130                 135                 140

Pro Gly Gly Ala Leu Ser Leu Val Cys Lys Ala Ser Gly Phe Thr Phe
145                 150                 155                 160

Ser Ser His Asp Met Gly Trp Val Arg Gln Ala Pro Gly Lys Gly Leu
                165                 170                 175

Glu Tyr Val Ala Gly Ile Thr Asp Gly Arg Tyr Ala Ser Tyr Gly
            180                 185                 190

Pro Ala Val Asp Gly Arg Ala Thr Ile Ser Arg Asp Asn Gly Gln Ser
            195                 200                 205

Thr Val Arg Leu Gln Leu Lys Asn Leu Arg Ala Glu Asp Thr Ala Thr
        210                 215                 220

Tyr Tyr Cys Ala Arg Asp Asp Gly Ser Gly Trp Ser Gly Asp Thr Ile
225                 230                 235                 240

Asp Thr Trp Gly His Gly Thr Glu Val Ile Val Ser Thr Ser Gly
                245                 250                 255

Gln Ala Gly Gln His His His His His Gly Ala Tyr Pro Tyr Asp
            260                 265                 270

Val Pro Asp Tyr Ala Ser
            275

<210> SEQ ID NO 156
<211> LENGTH: 280
<212> TYPE: PRT
<213> ORGANISM: Artificial sequence
<220> FEATURE:
<223> OTHER INFORMATION: recombinant protein

<400> SEQUENCE: 156

Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Leu Gly Gly Thr Val Glu Ile Thr Cys Ser Gly Gly Gly Ser Tyr Tyr
        35                  40                  45

Gly Trp Tyr Gln Gln Lys Ser Pro Gly Ser Ala Pro Val Thr Val Ile
    50                  55                  60

Tyr Ala Asn Thr Asn Gly Pro Ser Asp Ile Pro Ser Arg Phe Ser Gly
65                  70                  75                  80

Ser Thr Ser Gly Ser Thr Ala Thr Leu Thr Ile Thr Gly Val Gln Ala
                85                  90                  95

Asp Asp Glu Ala Val Tyr Ser Cys Gly Ser Tyr Asp Ser Ser Tyr Val
            100                 105                 110

Gly Ile Phe Gly Ala Gly Thr Thr Leu Thr Val Leu Gly Gln Ser Ser
        115                 120                 125

Arg Ser Ser Thr Val Thr Leu Asp Glu Ser Gly Gly Gly Leu Gln Thr
    130                 135                 140

Pro Gly Gly Ala Leu Ser Leu Val Cys Lys Ala Ser Gly Phe Thr Phe
145                 150                 155                 160

Asn Ser Tyr Ala Leu Glu Trp Val Arg Gln Ala Pro Gly Lys Gly Leu
                165                 170                 175

Glu Trp Val Ala Gly Ile Ser Gly Asp Gly Ser Tyr Arg His Tyr Gly
            180                 185                 190
```

```
Ser Ala Val Lys Gly Arg Ala Thr Ile Ser Arg Asp Ser Gly Gln Ser
        195                 200                 205

Thr Val Arg Leu Gln Leu Asn Asn Leu Arg Ala Glu Asp Thr Gly Thr
    210                 215                 220

Tyr Tyr Cys Ala Lys Ser Thr Gly Ser Gly Ala Gly Trp Gly Ala Ser
225                 230                 235                 240

Asn Ile Asp Ala Trp Gly His Gly Thr Glu Val Ile Val Ser Ser Thr
                245                 250                 255

Ser Gly Gln Ala Gly Gln His His His His His Gly Ala Tyr Pro
        260                 265                 270

Tyr Asp Val Pro Asp Tyr Ala Ser
    275                 280
```

<210> SEQ ID NO 157
<211> LENGTH: 282
<212> TYPE: PRT
<213> ORGANISM: Artificial Sequence
<220> FEATURE:
<223> OTHER INFORMATION: recombinant protein

<400> SEQUENCE: 157

```
Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Leu Gly Gly Thr Val Lys Ile Thr Cys Ser Gly Ser Ser Gly Ser Tyr
        35                  40                  45

Gly Trp Tyr Gln Gln Lys Ser Pro Gly Ser Ala Pro Val Thr Val Ile
    50                  55                  60

Tyr Trp Asn Asp Lys Arg Pro Ser Asn Ile Pro Ser Arg Phe Ser Gly
65                  70                  75                  80

Ala Leu Ser Gly Ser Thr Ala Thr Leu Thr Ile Thr Gly Val Gln Ala
                85                  90                  95

Glu Asp Glu Ala Val Tyr Phe Cys Gly Ser Ala Asp Ser Ser Gly Ala
            100                 105                 110

Ile Phe Gly Ala Gly Thr Thr Leu Thr Val Leu Gly Gln Ser Ser Arg
        115                 120                 125

Ser Ser Thr Val Thr Leu Asp Glu Ser Gly Gly Gly Leu Gln Thr Pro
130                 135                 140

Gly Gly Gly Leu Ser Leu Val Cys Lys Gly Ser Gly Phe Ala Phe Ser
145                 150                 155                 160

Asn Tyr Gly Met Gly Trp Met Arg Gln Ala Pro Gly Lys Gly Leu Glu
                165                 170                 175

Tyr Val Ala Gly Ile Ser Thr Gly Ser Tyr Thr Asp Tyr Gly Pro Ala
            180                 185                 190

Val Lys Gly Arg Ala Thr Ile Ser Arg Asp Asn Gly Gln Ser Thr Val
        195                 200                 205

Arg Leu Gln Leu Asn Asn Leu Arg Ala Glu Asp Ala Ala Ile Tyr Phe
    210                 215                 220

Cys Ala Lys Thr Ala Gly Ser Gly Tyr Gly Cys Gly Ser Gly Thr Asp
225                 230                 235                 240

Leu Gly Ser Ile Asp Ala Trp Gly His Gly Thr Glu Val Ile Val Ser
                245                 250                 255

Ser Thr Ser Gly Gln Ala Gly Gln His His His His His Gly Ala
                260                 265                 270
```

```
Tyr Pro Tyr Asp Val Pro Asp Tyr Ala Ser
        275                 280
```

<210> SEQ ID NO 158
<211> LENGTH: 280
<212> TYPE: PRT
<213> ORGANISM: Artificial sequence
<220> FEATURE:
<223> OTHER INFORMATION: recombinant protein

<400> SEQUENCE: 158

```
Met Lys Lys Thr Ala Ile Ala Ile Ala Val Ala Leu Ala Gly Phe Ala
1               5                   10                  15

Thr Val Ala Gln Ala Ala Leu Thr Gln Pro Ser Ser Val Ser Ala Asn
            20                  25                  30

Leu Gly Gly Thr Val Glu Ile Thr Cys Ser Gly Gly Gly Ser Tyr Tyr
        35                  40                  45

Gly Trp Tyr Gln Gln Lys Ser Pro Gly Ser Ala Pro Val Thr Val Ile
    50                  55                  60

Tyr Ala Asn Thr Asn Gly Pro Ser Asp Ile Pro Ser Arg Phe Ser Gly
65                  70                  75                  80

Ser Thr Ser Gly Ser Thr Ala Thr Leu Thr Ile Thr Gly Val Gln Ala
                85                  90                  95

Asp Asp Glu Ala Val Tyr Ser Cys Gly Ser Tyr Asp Ser Ser Tyr Val
            100                 105                 110

Gly Ile Phe Gly Ala Gly Thr Thr Leu Thr Val Leu Gly Gln Ser Ser
        115                 120                 125

Arg Ser Ser Thr Val Thr Leu Asp Glu Ser Gly Gly Gly Leu Gln Thr
130                 135                 140

Pro Gly Gly Ala Leu Ser Leu Val Cys Lys Ala Ser Gly Phe Thr Phe
145                 150                 155                 160

Asn Ser Tyr Ala Leu Glu Trp Val Arg Gln Ala Pro Gly Lys Gly Leu
                165                 170                 175

Glu Trp Val Ala Gly Ile Ser Gly Asp Gly Ser Tyr Arg His Tyr Gly
            180                 185                 190

Ser Ala Val Lys Gly Arg Ala Thr Ile Ser Arg Asp Ser Gly Gln Ser
        195                 200                 205

Thr Val Arg Leu Gln Leu Asn Asn Leu Arg Ala Glu Asp Thr Gly Thr
    210                 215                 220

Tyr Tyr Cys Ala Lys Ser Thr Gly Ser Gly Ala Gly Trp Gly Ala Ser
225                 230                 235                 240

Asn Ile Asp Ala Trp Gly His Gly Thr Glu Val Ile Val Ser Ser Thr
                245                 250                 255

Ser Gly Gln Ala Gly Gln His His His His His His Gly Ala Tyr Pro
            260                 265                 270

Tyr Asp Val Pro Asp Tyr Ala Ser
        275                 280
```

<210> SEQ ID NO 159
<211> LENGTH: 299
<212> TYPE: PRT
<213> ORGANISM: Artificial sequence
<220> FEATURE:
<223> OTHER INFORMATION: recombinant protein

<400> SEQUENCE: 159

```
Met Lys Lys Thr Ala Ile Ala Ile Ala Val Ala Leu Ala Gly Phe Ala
1               5                   10                  15
```

Thr Val Ala Gln Ala Ala Leu Thr Gln Pro Ser Ser Val Ser Ala Asn
            20                  25                  30

Pro Gly Gly Thr Val Lys Ile Thr Cys Ser Gly Ser Ser Gly Ser Tyr
        35                  40                  45

Tyr Gly Trp Tyr Gln Lys Ser Pro Gly Ser Ala Pro Val Thr Val
    50                  55                  60

Ile Tyr Asp Asn Asp Lys Arg Pro Ser Asp Val Pro Ser Arg Phe Ser
65                  70                  75                  80

Gly Ser Lys Ser Gly Pro Thr Ala Thr Leu Thr Ile Thr Gly Val Gln
                85                  90                  95

Ala Glu Asp Glu Ala Val Tyr Phe Cys Gly Ser Arg Asp Asn Ser Tyr
            100                 105                 110

Val Gly Ile Phe Gly Ala Gly Thr Thr Leu Thr Val Leu Gly Gln Ser
        115                 120                 125

Ser Arg Ser Ser Ala Val Thr Leu Asp Glu Ser Gly Gly Gly Leu Gln
    130                 135                 140

Thr Pro Gly Gly Ala Leu Ser Leu Val Cys Lys Ala Ser Gly Phe Thr
145                 150                 155                 160

Phe Ser Ser Tyr Asp Met Phe Trp Val Arg Gln Ala Pro Gly Lys Gly
                165                 170                 175

Leu Glu Phe Val Ala Gln Ile Asn Ser Ala Gly Ser Tyr Thr Asn Tyr
            180                 185                 190

Gly Ser Ala Val Lys Gly Arg Ala Thr Ile Ser Arg Asp Asp Gly Gln
        195                 200                 205

Ser Thr Val Arg Leu Gln Leu Asn Asn Leu Arg Ala Glu Asp Thr Gly
    210                 215                 220

Ile Tyr Phe Cys Ala Lys Ser Ala Ser Gly Tyr Tyr Tyr Ser Gly Ser
225                 230                 235                 240

Asp Ala Gly Asp Ile Asp Ala Trp Gly Thr Gly Pro Lys Ser Ser
                245                 250                 255

Pro Ser Thr Ser Gly Pro Gly Arg Pro Ala Pro Ser Pro Ser Pro Trp
        260                 265                 270

Arg Ile Pro Val Arg Arg Ser Gly Leu Arg Phe Leu Glu Arg Trp Ala
    275                 280                 285

Arg Asp Gln Leu Ser Cys Thr Lys Trp Leu Ile
290                 295

<210> SEQ ID NO 160
<211> LENGTH: 849
<212> TYPE: DNA
<213> ORGANISM: Artificial Sequence
<220> FEATURE:
<223> OTHER INFORMATION: recombinant polynucleotide

<400> SEQUENCE: 160
atgaaaaaga cagctatcgc gattgcagtg gcactggctg gtttcgctac cgtggcccag      60
gcggccctga ctcagccgtc ctcggtgtca gcaaacccag agaaaccgt caagatcacc      120 tgctctgggg gcagctatag ctatggctgg tatcagcaga agtcacctgg cagtgcccct     180
gtcactgtga tctatagcag cgacaagaga ccctcggaca tcccttcacg attctccggt     240
tccaaatccg gctccacaag cacattaacc atcactgggg tccaagccga ggacgaggct     300
gtctattact gtgggagcag ggacagcaac tatgttggta tatttggggc cgggacaacc     360
ctgaccgtcc taggtcagtc ctctagatct tccaccgtga cgttggacga gtccgggggc     420

| | |
|---|---:|
| ggcctccaga cgcccggagg agcgctcagc ctcgtctgca aggcctccgg attcaccttc | 480 |
| agcagttatg agatgcagtg ggtgcgacag gcgcccggca aggggctgga gttcgtcgca | 540 |
| gctattagca gtgatggcag ttacacaaac tacggggcgg cggtgcaggg ccgtgccacc | 600 |
| atctcgaggg acaacgggca gagcacagtg aggctgcagc tgagcaacct cagggctgag | 660 |
| gacaccgcca cctactactg cgccagaagt cctggtggtt acacttggtg gcctggagct | 720 |
| gctggtggta tcgacgcatg gggccacggg accgaagtca tcgtctcctc cactagtggc | 780 |
| caggccggcc agcaccatca ccatcaccat ggcgcatacc cgtacgacgt tccggactac | 840 |
| gcttcttag | 849 |

<210> SEQ ID NO 161
<211> LENGTH: 843
<212> TYPE: DNA
<213> ORGANISM: Artificial sequence
<220> FEATURE:
<223> OTHER INFORMATION: recombinant polynucleotide

<400> SEQUENCE: 161

| | |
|---|---:|
| atgaaaaaga cagctatcgc gattgcagtg gcactggctg gtttcgctac cgtggcccag | 60 |
| gcggccctga ctcagccgtc ctcggtgtca gcgaacccgg gaggaaccgt caagatcacc | 120 |
| tgctccggga gtagcagtgc ctatggttat ggctggtatc agcagaagtc acctggcagt | 180 |
| gcccctgtca ctgtgatcta taacaacaat aagagaccct caaacatccc ttcacgattc | 240 |
| tccggttcca aatccggctc cacgggcaca ttaaccatca ctggggtcca gccgaggac | 300 |
| gaggctgtct atttctgtgg gagtgaagac agcagcactg atgctatatt tggggccggg | 360 |
| acaaccctga ccgtcctagg tcagtcctct agatcttccg ccgtgacgtt ggacgagtcc | 420 |
| gggggcggcc tccagacgcc cggaggagcg ctcagcctcg tctgcaaggc ctccgggttc | 480 |
| accttcagca gttacgacat gggttgggtg cgacaggcgc ccggcaaggg actggaatac | 540 |
| gttgcgggta ttaccaatga tggtagatac gcatcatacg gtcggcggt ggatggccgt | 600 |
| gccaccatct cgagggacaa cgggcagagc acagtgaggc tgcagctgaa caacctcagg | 660 |
| gctgaggaca ccggcaccta ctactgcgcc agagatgatg gtagtggttg gactggtaat | 720 |
| actatcgaca catgggggcca cgggaccgaa gtcatcgtct cctccactag tggccaggcc | 780 |
| ggccagcacc atcaccatca ccatggcgca tacccgtacg acgttccgga ctacgcttct | 840 |
| tag | 843 |

<210> SEQ ID NO 162
<211> LENGTH: 834
<212> TYPE: DNA
<213> ORGANISM: Artificial sequence
<220> FEATURE:
<223> OTHER INFORMATION: recombinant polynucleotide

<400> SEQUENCE: 162

| | |
|---|---:|
| atgaaaaaga cagctatcgc gattgcagtg gcactggctg gtttcgctac cgtggcccag | 60 |
| gcggccctga ctcagccgtc ctcggtgtca gcgaacccgg gagaaaccgt caagatcacc | 120 |
| tgctccgggg gtagtggcag ctatggctgg tatcagcagg agtcacctgg cagcgctcct | 180 |
| gtcactgtga tctattacaa cgacaagaga ccctcggaca tcccttcacg attctccggt | 240 |
| tccgcatccg gctccacagc cacattaacc atcgctgggg tccgagccga ggacgaggct | 300 |
| gtctatttct gtgggagctg ggatagcagc actagtgctg gtatatttgg ggccgggaca | 360 |
| gccctgaccg tcctaggtca gtcctctaga tcttccgccg tgacgttgga cgagtccggg | 420 |

```
ggcggcctcc agacgcccgg aggagggctc agcctcgtct gcaaggcctc cggcttcagc    480
agcagccatg gcatgggctg gatgcgccag gcacctggca agggccttga attcgtcgcg    540
ggtattagaa gtgatggcag tagcacagca tacggggcgg cggtggatgg ccgcgccacc    600
atcacaaggg acgatgggca gagcacagtg acactgcagc tgaacaacct cagggctgag    660
gacaccgcca cctacttctg cgccaaaact aatagttaca atagcgctgg cataatcgac    720
gcatggggcc acgggaccga agtcatcgtc cctccactag tggccaggcc ggccagcac     780 catcaccatc accatggcgc ataccccgtac gacgttccgg actacgcttc ttag          834
```

<210> SEQ ID NO 163
<211> LENGTH: 843
<212> TYPE: DNA
<213> ORGANISM: Artificial sequence
<220> FEATURE:
<223> OTHER INFORMATION: recombinant polynucleotide

<400> SEQUENCE: 163

```
atgaaaaaga cagctatcgc gattgcagtg gcactggctg gtttcgctac cgtggcccag     60
gcggccctga ctcagccgtc ctcggtgtca gcaaacctgg aggaaccgt cgagatcacc     120 tgctccggga gtagtggcag ctatggctgg tatcagcaga agtcacctgg cagtgcccct    180
gtcactgtga tctattacaa cgacaagaga ccctcggaca tcccttcacg attctccggt    240
tccacatccg gctccacagc cacattaacc atcactgggg tccaagccga ggacgaggct    300
gtctatttct gtggtggcta cgacagcaac tatatcggta tatttggggc cgggacaacc    360
ctgaccgtcc taggtcagtc ctctagatct tccgccgtga cgttggacga gtccggggc     420 ggcctccaga cgccccgagg agcgctcagc ctcgtctgca aggcctccgg gttcaccttc    480
agcagttaca gcatggcctg ggtgcgacag gcgcccggca aggggctgga gttcgtcgcg    540
ggtattcaga atgatggtag tatcacagat tacgggtcgg cggtggatgg ccgtgccacc    600
atctcgaggg acgacgggca gagcacagtg aggctgcagc tgaacaacct caggactgag    660
gacaccgcca cctactactg cgccaaaact actgttgctg atggtgttat cggtgcttat    720
ggcatcgacg catggggcca cgggaccgaa gtcatcgtct cctccactag tggccaggcc    780
ggccagcacc atcaccatca ccatggcgca taccccgtacg acgttccgga ctacgcttct    840
tag                                                                    843
```

<210> SEQ ID NO 164
<211> LENGTH: 852
<212> TYPE: DNA
<213> ORGANISM: Artificial sequence
<220> FEATURE:
<223> OTHER INFORMATION: Recombinant polynucleotide

<400> SEQUENCE: 164

```
atgaaaaaga cagctatcgc gattgcagtg gcactggctg gtttcgctac cgtggcccag     60
gcggccctga ctcagccgtc ctcggtgtca gcaaacccag agaaaccgt caagatcacc     120 tgctccgggg gtggcagcta tgctggaagt tactattatg ctggtaccag gcagaaggca    180
cctggcagtg cccctgtcac tctgatctat gacaacacca cagaccctc gaacatccct    240 tcacgattct ccggttccct atccggctcc acgggcacat taaccatcac tggggtccga    300
gccgaggacg aggctgtcta ttactgtggg agcttcgaca gcagcactga tggtggatat    360
gctgccatat ttgggcccgg gacaaccctg accgtcctag gtcagtcctc tagatcttac    420
```

```
gccgtgacgt tggacgagtc cggggcggc ctccagacgc ccggaggagg gctcagcctc   480
gtctgcaagg cctccgagtt caccttcagc agttatgcca tggagtgggt gcgccaggca   540
cccggcaagg ggctggagtg ggtcgcctat attaacagtg atggtagtag cacatggtac   600
gcacctgcgg tgaagggccg tgccaccatc tcgaggaca acgggcagag cacagtgagg    660
ctgcagctga acagcctcag ggctgaagac accgccacct actactgcac cagaggttct   720
ggtggtgaaa atatagacac atggggccac gggaccgaag tcatcgtctc ctctactagt   780
ggccaggccg ccagcacca tcaccatcac catggcgcat acccgtacga cgttcccgac    840
tacgcttctt ag                                                       852

<210> SEQ ID NO 165
<211> LENGTH: 852
<212> TYPE: DNA
<213> ORGANISM: Artificial sequence
<220> FEATURE:
<223> OTHER INFORMATION: Recombinant polynucleotide

<400> SEQUENCE: 165
atgaaaaaga cagctatcgc gattgcagtg gcactggctg gtttcgctac cgtggcccag    60
gcggccctga ctcagccgtc ctcggtgtca gcaaacccag gagaaaccgt caagatcacc   120
tgctccgggg gtggcagcta tgctggaagt tactattatg ctggtacca gcagaaggca   180 cctggcagtg cccctgtcac tctgatctat gacaacacca cagaccctc gaacatccct   240 tcacgattct ccggttccct atccggctcc acgggcacat taaccatcac tggggtccga   300
gccgaggacg aggctgtcta ttactgtggg agcttcgaca gcagcactga tggtggatat   360
gctgccatat ttggggccgg gacaaccctg accgtcctag gtcagtcctc tagatcttcc   420
gccgtgacgt tggacgagtc cggggcggc ctccagacgc ccggaggagg gctcagcctc   480
gtctgcaagg cctccgagtt caccttcagc agttatgcca tggagtgggt gcgccaggca   540
cccggcaagg ggctggagtg ggtcgcctat attaacagtg atggtagtag cacatggtac   600
gcacctgcgg tgaagggccg tgccaccatc tcgagggaca acgggcagag cacagtgagg   660
ctgcagctga acagcctcag ggctgaggac accgccacct actactgcac cagaggttct   720
ggtggtgaaa atatagacac atggggccac gggaccgaag tcatcgtctc ctccactagt   780
ggccaggccg ccagcacca tcaccatcac catgccgcat acccgtacga cgttccagac    840
tacgcttctt ag                                                       852

<210> SEQ ID NO 166
<211> LENGTH: 843
<212> TYPE: DNA
<213> ORGANISM: Artificial Sequence
<220> FEATURE:
<223> OTHER INFORMATION: Recombinant polynucleotide

<400> SEQUENCE: 166
atgaaaaaga cagctatcgc gattgcagtg gcactggctg gtttcgctac cgtggcccag    60
gcggccctga ctcagccgtc ctcggtgtca gcaaacctgg aggaaccgt cgagatcacc   120 tgctccgggg gtagtggcag ctatggctgg tatcagcaga agtcacctgg cggtgccct    180 gtcactgtga tctattacaa cgacaagaga ccctcggaca tcccttcacg attctccggt    240
tccaaatccg gctccacagc cacattaacc atcactgggg tccaagtcga ggacgaggct   300
gtctattact gtgggagcta cgacagcagc tatgttggta tatttggggt cgggacaacc    360
ctgaccgtcc taggtcagtc ctctagatct tccgccgtga cgttggacga gtccgggggc   420
```

-continued

```
ggcctccaga cgccccgagg agcgctcagc ctcgtctgca aggcctccgg gttcaccttc      480
agcagttaca gcatggcctg ggtgcgacag gcgcccggca aggggctgga gttcgtcgcg      540
ggtattcaga atgatggtag tatcacagat tacgggtcgg cggtggatgg ccgtgccacc      600
atctcgaggg acgacgggca gagcacagtg aggctgcagc tgaacaacct caggactgag      660
gacaccgcca cctactactg cgccaaaact actgttgctg atggtgttat cggtgcttat      720
ggcatcgacg catggggcca cgggaccgaa gtcatcgtct cctccactag tggccaggcc      780
ggccagcacc atcaccatca ccatggcgca tacccgtacg acgttccgga ctacgcttct      840
tag                                                                   843
```